United States Patent
Usui et al.

(10) Patent No.: US 11,254,705 B2
(45) Date of Patent: Feb. 22, 2022

(54) CYCLIC PEPTIDE ANALOGS AND CONJUGATES THEREOF

(71) Applicant: Sirenas LLC, San Diego, CA (US)

(72) Inventors: Ippei Usui, San Diego, CA (US); Bryan Junn Lee, San Diego, CA (US); Steven Bruce Cohen, San Diego, CA (US); Venkat Rami Reddy Macherla, San Diego, CA (US); Jacob Neal Beverage, La Jolla, CA (US); Chung-Mao Pan, San Diego, CA (US); Farhana Barmare, San Diego, CA (US); Eduardo Esquenazi, La Jolla, CA (US)

(73) Assignee: SIRENAS LLC, San Diego, CA (US)

( * ) Notice: Subject to any disclaimer, the term of this patent is extended or adjusted under 35 U.S.C. 154(b) by 0 days.

(21) Appl. No.: 16/330,049

(22) PCT Filed: Aug. 31, 2017

(86) PCT No.: PCT/US2017/049764
§ 371 (c)(1),
(2) Date: Mar. 1, 2019

(87) PCT Pub. No.: WO2018/045245
PCT Pub. Date: Mar. 8, 2018

(65) Prior Publication Data
US 2019/0211060 A1    Jul. 11, 2019

Related U.S. Application Data

(60) Provisional application No. 62/383,330, filed on Sep. 2, 2016.

(51) Int. Cl.
| | | |
|---|---|---|
| *C07K 11/02* | (2006.01) | |
| *C07K 7/06* | (2006.01) | |
| *C07K 16/32* | (2006.01) | |
| *A61K 47/68* | (2017.01) | |
| *A61P 35/00* | (2006.01) | |
| *A61K 38/08* | (2019.01) | |
| *A61K 38/00* | (2006.01) | |
| *C07K 16/00* | (2006.01) | |

(52) U.S. Cl.
CPC ........... *C07K 7/06* (2013.01); *A61K 38/08* (2013.01); *A61K 47/6811* (2017.08); *A61K 47/6855* (2017.08); *A61K 47/6889* (2017.08); *A61P 35/00* (2018.01); *C07K 16/32* (2013.01); *A61K 38/00* (2013.01); *C07K 16/00* (2013.01); *C07K 2319/00* (2013.01)

(58) Field of Classification Search
None
See application file for complete search history.

(56) References Cited

U.S. PATENT DOCUMENTS

| | | |
|---|---|---|
| 4,542,225 A | 9/1985 | Blattler |
| 4,569,789 A | 2/1986 | Blattler et al. |
| 4,625,014 A | 11/1986 | Senter et al. |
| 4,764,368 A | 8/1988 | Blattler et al. |
| 4,816,567 A | 3/1989 | Cabilly et al. |
| 5,122,368 A | 6/1992 | Greenfield et al. |
| 5,208,020 A | 5/1993 | Chari et al. |
| 5,595,756 A | 1/1997 | Bally et al. |
| 5,622,929 A | 4/1997 | Willner et al. |
| 5,824,805 A | 10/1998 | King et al. |
| 6,214,345 B1 | 4/2001 | Firestone et al. |
| 2003/0083263 A1 | 5/2003 | Doronina et al. |
| 2005/0009751 A1 | 1/2005 | Senter et al. |
| 2005/0238649 A1 | 10/2005 | Doronina et al. |
| 2006/0024317 A1 | 2/2006 | Boyd et al. |
| 2006/0074008 A1 | 4/2006 | Senter et al. |
| 2017/0015710 A1 | 1/2017 | Macherla et al. |

FOREIGN PATENT DOCUMENTS

| | | |
|---|---|---|
| JP | 2003-64052 A | 3/2003 |
| JP | 2003-64097 A2 | 3/2003 |
| JP | 2008-266282 A | 11/2008 |
| JP | 2010-174004 A | 8/2010 |
| JP | 2010-174005 A | 8/2010 |
| WO | WO-1994/11026 A2 | 5/1994 |
| WO | WO-2004/010957 A2 | 2/2004 |
| WO | WO-2013/072813 A2 | 5/2013 |
| WO | WO-2015/095755 A1 | 6/2015 |

OTHER PUBLICATIONS

National Institute of Cancer—understanding and related topics, accessed Aug. 21, 2014 at URL: cancer.gov/cancertopics/understandingcancer, 63 pages (Year: 2014).*
Merck Manuals Lung Carcinoma accessed Mar. 12, 2017 at URL merckmanuals.com/professional/pulmonary-disorders/tumors-of-the-lungs/lung-carcinoma, 18 pages (Year: 2017).*
Merck Manual Colorectal Cancer accessed Aug. 21, 2014 at URL merckmanuals.com/home/digestive_disorders/tumors_of_the_digestive_system/colorectal_cancer.htm, 5 pages (Year: 2014).*
Merck Manual Bladder Cancer accessed Aug. 21, 2014 at URL: merckmanuals.com/home/kidney_and_urinary_tract_disorders/cancers_of_the_kidney_and_genitourinary_tract/bladder_cancer.html, 2 pages (Year: 2014).*
Thyroid cancer accessed Mar. 12, 2017 at URL www.merckmanuals.com/professional/endocrine-and-metabolic-disorders/thyroid-disorders/thyroid-cancers, 4 pages (Year: 2017).*
Renal cell carcinoma, accessed Mar. 12, 2017 at URL merckmanuals.com/professional/genitourinary-disorders/genitourinary-cancer/renal-cell-carcinoma, 6 pages (Year: 2017).*

(Continued)

*Primary Examiner* — Julie Ha
*Assistant Examiner* — Kristina M Hellman
(74) *Attorney, Agent, or Firm* — Morrison & Foerster LLP

(57) ABSTRACT

Provided are cyclic peptide analogs, conjugates comprising such compounds, and pharmaceutical compositions comprising such compounds and conjugates, and methods of treating cancer with such compounds and conjugates.

29 Claims, 9 Drawing Sheets

(56) References Cited

OTHER PUBLICATIONS

Merck Manual Prostate Cancer accessed Aug. 21, 2014 at URL: merckmanuals.com/home/kidney_and_urinary_tract_disorders/cancers_of_the_kidney_and_genitourinary_tract/prostate_cancer.html?qt=prostate cancer&alt=sh, 8 pages ( (Year: 2014).*
Merck Manuals Neuroblastoma accessed Mar. 12, 2017 at URL merckmanuals.com/professional/ pediatrics/pediatric-cancers/neuroblastoma, 4 pages (Year: 2017).*
Cholangiocarcinoma accessed Mar. 12, 2017 at URL surgery.usc.edu/divisions/tumor/pancreasdiseases/web%20pages/BILIARY%20SYSTEM/cholangiocarcinoma, 2 pages (Year: 2017).*
Bowie et al, "Deciphering the message in protein sequences: tolerance to amino acid substitutions," Science 247:1306-1310 (1990) ) (Year: 1990).*
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J. Cell Biol. 111:2129-2138 (1990) (Year: 1990).*
Aboud-Pirak, E. et al. (1989) "Cytotoxic Activity of a Daunorubicin or Vindesin Conjugated to a Monoclonal Antibody on Cultured MCF-7 Breast Carcinoma Cells," *Biochem. Pharmacol.* 38(4):641-648.
Auerbach, R. et al. (2000). "Angiogenesis Assays: Problems and Pitfalls," *Cancer and Metastasis Reviews* 19:167-172.
Badescu, G. et al. (May 3, 2014). "Bridging Disulfides for Stable and Defined Antibody Drug Conjugates," *Bioconjugate Chem.* 25(6):1124-1136.
Blättler, W.A. et al. (1985). "New Heterobifunctional Protein Crosslinking Reagent that Forms an Acid-Labile Link," *Biochemistry* 24(6) 1517-1524.
Bryant, P. et al. (Apr. 20, 2015). "In Vitro and In Vivo Evaluation of Cysteine Rebridged Trastuzumab—MMAE Antibody Drug Conjugates with Defined Drug-to-Antibody Ratios," *Mol. Pharmaceuticals* 12(6): 1872-1879.
Chabner, B.A. et al. (Last revision Aug. 2008). "Cellular and Molecular Basis of Cancer," Merck Manual, located at <http://www.merckmanuals.com/professional/print/hematology_and_oncology/overview_of . . . >, last visited on Nov. 7, 2012, 5 pages.
Clackson, T. et al. (1991). "Making Antibody Fragments Using Phage Display Libraries," *Nature* 352:624-628.
De Groot, F.M.H. et al. (2001, e-pub. Nov. 27, 2001). "Elongated Multiple Electronic Cascade and Cyclization Spacer Systems in Activatible Anticancer Prodrugs for Enhanced Drug Release," *J. Org. Chem* 66:8815-8830.
Doronina, S.O. et al. (2008; e-pub. Sep. 20, 2008). "Novel Peptide Linkers for Highly Potent Antibody—Auristatin Conjugate," *Bioconjugate Chem.* 19(10): 1960-1963.
Dubowchik, G.M. et al. (1999). "Receptor-Mediated and Enzyme-Dependent Targeting of Cytotoxic Anticancer Drugs," *Pharm. Therapeutics* 83:67-123.
Finniss, M.C. et al. (2014). "A Versatile Acid-Labile Linker for Antibody-Drug Conjugates," *Medicinal Chemistry Communications* 5(9): 1355-1358.
Gura, T. (Nov. 7, 1997). "Systems for Identifying New Drugs are Often Faulty," *Science* 278(5340):1041-1042.
Han, B. et al. (2006, e-pub. Feb. 11, 2006). "Aurilides B and C, Cancer Cell Toxins from a Papua New Guinea Collection of the Marine Cyanobacterium *Lyngbya majuscula*," *J. Nat. Prod.* 69:572-575.
Hermanson, G.T. (1996) "Introduction to Bioconjugation," Chapter 1 in *Bioconiuqate Techniques*, Academic Press, San Diego, CA, 125 pages.
Homer. (2008). "Failure Modes in the Discovery Process," Chapter 18 in *Cancer Drug Design and Discovery*, Neidle, Stephen, ed., Elsevier/Academic Press, pp. 427-431.
Karton-Lifshin, N. et al. (2012). "Exponential diagnostic signal amplification via dendritic chain reaction: the dendritic effect of a self-immolative amplifier component," *New J. Chem* 36(2):386-393.
Kern, J.C. et al. (Feb. 3, 2016; e-pub. Jan. 25, 2016). "Discovery of Pyrophosphate Diesters as Tunable, Soluble, and Bioorthogonal Linkers for Site-specific Antibody-Drug Conjugates," *J. Am. Chem. Soc.* 138(4):1430-1445.
Köhler, G. et al. (1975). "Continuous Cultures of Fused Cells Secreting Antibody of Predefined Specificity," *Nature* 256:495-497.
Laguzza, B.C. et al. (1989). "New Antitumor Monoclonal Antibody-Vinca Conjugates LY203725 and Related Compounds: Design, Preparation, and Representative in Vivo Activity," *J. Med. Chem.* 32:548-555.
Marks, J.D. et al. (1991). "By-passing Immunization, Human Antibodies from V-gene Libraries Displayed on Phage," *J. Mol. Biol.* 222:581-597.
Nakao, Y. et al. (2004, e-pub. Jul. 31, 2004). "Kulokekahilide-2, a Cytotoxic Depsipeptide from a Cephalaspidean Mollusk *Philinopsis speciosa,*" *J. Nat. Prod.* 67:1332-1340.
Neville, D.M. et al. (Sep. 5, 1989). "Enhancement of Immunotoxin Efficacy by Acid-cleavable Cross-linking Agents Utilizing Diphtheria Toxin and Toxin Mutants," *J Biol. Chem.* 264(25):14653-14661.
Queen, C. et al. (Dec. 1989). "A Humanized Antibody that Binds to the Interleukin 2 Receptor," *Proc. Nat'l Acad. Sci. USA* 86:10029-10033.
Sato, S. et al. (Jan. 28, 2011). "Marine Natural Product Aurilide Activates the OPA1-Mediated Apoptosis by Binding to Prohibition," Chemistry & Biology 18:131-139.
Seiche, W. et al. (Oct. 2005). "Bidentate Ligands by Self-Assembly through Hydrogen Bonding: A General Room Temperature/Ambient Pressure Regioselective Hydroformylation of Terminal Alkenes," *Advanced Synthesis & Catalysis* 347:1488-1494.
Senter, P.D. et al. (1985). "Novel Photocleavable Protein Crosslinking Reagents and their Use in the Preparation of Antibody-Toxin Conjugates," *Photochemistry and Photobiology* 42(3):231-237.
Sporn, M.B. et al. (2000). "Chemoprevention of Cancer," *Carcinogenesis* 21(3):525-530.
Suenaga, K. et al. (2008, e-pub. Jun. 14, 2008). "Synthesis and Cytotoxicity of Aurilide Analogs," *Bioorganic & Medicinal Chemistry Letters* 18: 3902-3905.
Takada, Y. et al. (2012; e-pub. Nov. 3, 2011). "The Total Synthesis and Structure-Activity Relationships of a Highly Cytotoxic Depsipeptide Kulokekahilide-2 and its Analogs," *Tetrahedron* 68(2):659-669.
Tan, L.T. (Feb. 23, 2010). "Filamentous Tropical Marine Cyanobacteria: A Rich Source of Natural Products for Anticancer Drug Discovery," *Journal of Applied Phycology* 22(5):659-676.
Tripathi, A. et al. (2010, e-pub. Oct. 11, 2010). "Lagunamides A and B: Cytotoxic and Antimalarial Cyclodepsipeptides from the Marine Cyanobacterium *Lyngbya majuscula,*" *J. Nat. Prod.* 73:1810-1814.
Tripathi, A. et al. (2011, e-pub. Sep. 6, 2011). "Lagunamide C, a Cytotoxic Cyclodepsipeptide from the Marine Cyanobacterium *Lyngbya majuscul,*" *Phytochemistry* 72 2369-2375.
Trouet, A. et al. (Jan. 1982). "A Covalent Linkage Between Daunorubicin and Proteins that is Stable in Serum and Reversible by Lysosomal Hydrolases, as Required for a Lysosomotropic Drug-carrier Conjugate: In vitro and in vivo studies," *Proc. Nat'l. Acad. Sci.* 79:626-629.
Umehara, M. et al. (2013, e-pub. Feb. 8, 2013). "Stereochemical analysis and cytotoxicity of kulokekahilide-2 and its analogues," *Tetrahedron* 69:3045-3053.
Umehara, M. et al. (2012, e-pub. Oct. 22, 2012). "Structure-Related Cytotoxic Activity of Derivatives from Kulokekahilide-2, a Cyclodepsipeptide in Hawaiin Marine Mollusk," *Bioorganic & Medicinal Chemistry Letters* 22(24)7422-7425.
Mtetta, E.S. et al. (1987). "Redesigning Nature's Poisons to Create Anti-Tumor Reagents," *Science* 238:1098; 11 pages.
Wang, G. et al. (2008; e-pub. Jul. 2, 2008). "Efficient and Selective Syntheses of (all-E)- and (6E,10Z)-2'-O-Methylmyxalamides D via Pd-Catalyzed Alkenylation-Carbonyl Olefination Synergy," *Organic Letters* 10(15):3223-3226.

(56) References Cited

OTHER PUBLICATIONS

Widdison, W.C. et al. (2015). "Development of Anilino-Maytansinoid ADCs that Efficiently Release Cytotoxic Metabolites in Cancer Cells and Induce High Levels of Bystander Killing," *Bioconjugate Chem* 26:2261-2278.

Williams, P.G. et al. (2003, e-pub. Nov. 19, 2003). "The Structure of Palau'amide, a Potent Cytotoxin from a Species of the Marine *Cyanobacterium Lyngbya*," *J. Nat. Prod.* 66:1545-1549.

International Preliminary Report on Patentability dated Mar. 14, 2019 for PCT Application No. PCT/US2017/049764, filed on Aug. 31, 2017, 8 pages.

International Preliminary Report on Patentability dated Sep. 14, 2017 for PCT Application No. PCT/US2016/020763 filed on Mar. 3, 2016, twelve pages.

International Search Report and Written Opinion dated Jul. 19, 2016 for PCT/US2016/020763, filed on Mar. 3, 2016, seventeen pages.

International Search Report and Written Opinion dated Nov. 17, 2017, for PCT Application No. PCT/US2017/049764, filed on Aug. 31, 2017, 14 pages.

Invitation to Pay Additional Fees and, where Applicable, Protest Fee, mailed May 9, 2016, for PCT Application No. PCT/US2016/020763 filed on Mar. 3, 2016, ten pages.

\* cited by examiner

CYCLIC PEPTIDE ANALOGS AND CONJUGATES THEREOF

CROSS-REFERENCE TO RELATED APPLICATIONS

This application is a national stage application under 35 U.S.C. § 371 of International Application No. PCT/US2017/049764, filed internationally on Aug. 31, 2017, which claims priority to U.S. Provisional Application No. 62/383,330, filed Sep. 2, 2016, which are hereby incorporated by reference in their entirety.

FIELD

Provided herein are cyclic peptide analogs, pharmaceutical compositions comprising such compounds, and methods of treating cancer with such compounds.

BACKGROUND

Cancer is a serious and debilitating disease brought on by abnormal and unchecked cell division in a patient. Current treatment strategies include chemotherapy, radiation therapy, and surgery. These treatment options may be singular treatments or combined for a more effective regimen. Unfortunately, many patients do not respond well to current chemotherapeutic regimens or develop resistance after prolonged treatment. In addition, for many chemotherapeutics, there is a maximal lifetime level of drug that a patient may be administered. In this case, new drugs must be tried. Thus, there is a need for development of new and varied chemotherapeutic compounds to assist in the treatment of cancer.

An important aspect of cancer, as opposed to infection caused by an exogenous pathogen for example, is that the disease is caused by cells already existing in the patient. These cells are similar in many ways to healthy tissue and reside among healthy cells in the patient. Thus, chemotherapeutic compounds, even if directly administered to a tumor, run the risk of entering and affecting healthy tissue in addition to cancerous tissue. This non-specific delivery can cause systemic and serious side effects in a patient including nausea, weakness, bleeding problems, infection, and hair loss. To avoid these systemic effects, chemotherapeutic compounds may be conjugated to a targeting molecule that assists with the specific and direct delivery of a chemotherapeutic compound to cancerous tissue only, preventing delivery to healthy tissue. These drugs may be associated with fewer and less severe side effects than traditional therapy, and so there is a need to develop chemotherapeutics that are effective in isolation, but are also suitable for conjugation to a targeting molecule.

Various types of agents have been described for use in treatment of cancer. Many of these compounds pose challenges. For instance, many compounds described for use in treatment of cancer have problems associated with toxicity. Some compounds present challenges related to their chemical synthesis. There are also challenges associated with finding appropriate permutations of therapeutic agents for combination therapy. Furthermore, only a minority of agents identified for use in treatment of cancer are suitable for conjugation to a targeting moiety. Accordingly, there remains a need for new compounds and conjugates for use in treatment of cancer.

SUMMARY

In one aspect, provided is a compound of Formula (I):

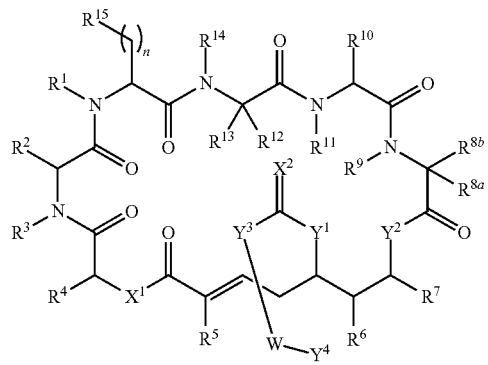

or a salt thereof, wherein $R^1$, $R^2$, $R^3$, $R^{8a}$, $R^9$, $R^{11}$, $R^{12}$, $R^{13}$, and $R^{14}$ are each independently H, substituted or unsubstituted alkyl, substituted or unsubstituted alkenyl, substituted or unsubstituted alkynyl, substituted or unsubstituted cycloalkyl, or substituted or unsubstituted cycloalkenyl;

$R^4$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or substituted or unsubstituted heterocyclyl;

$R^5$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, halo, or perhaloalkyl;

$R^6$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, halo, or perhaloalkyl;

$R^7$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or substituted or unsubstituted heterocyclyl;

$R^{15}$ is substituted or unsubstituted aryl, substituted or unsubstituted heteroaryl, substituted or unsubstituted cycloalkyl, substituted or unsubstituted heterocyclyl, or substituted or unsubstituted alkyl;

n is 0, 1, or 2;

$X^1$ is —N($R^d$)— or —O—;

$X^2$ is O or S;

$Y^1$ and $Y^2$ are each independently —N($R^d$)—, —O—, or —S—;

$Y^3$ is —N($R^d$)—, —O—, —S—, or substituted or unsubstituted heterocycloalkyl;

$Y^4$ is —$OR^a$, —$NR^bR^c$, or —$SR^a$;

each $R^a$, $R^b$, $R^c$, and $R^d$ is independently H, substituted or unsubstituted alkyl, substituted or unsubstituted alkenyl, substituted or unsubstituted alkynyl, substituted or unsubstituted cycloalkyl, or substituted or unsubstituted cycloalkenyl;

W is $(CH_2)_m$—Z—$(CH_2)_p$;

Z is substituted or unsubstituted alkyl, substituted or unsubstituted substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or $(CH_2CH_2O)_q$;

m, and p are each independently an integer from 0-12, inclusive; and q is an integer from 1-12, inclusive;

provided that i) when $Y^4$ is —OH, W is not —$(CH_2)_2$— or —$(CH_2CH_2O)_3(CH_2)_2$—; and ii) when $Y^4$ is —$NHR^c$ or —$N(CH_3)R^c$, W is not —$(CH_2)_2$—, —$(CH_2)_6$—, or —$CH_2(CH_2CH_2O)_3(CH_2)_3$—.

In some embodiments of Formula (I) or any variation thereof, $R^1$, $R^3$, $R^4$, $R^5$, $R^6$, $R^{8a}$, $R^{8b}$, $R^9$, $R^{10}$, $R^{11}$, $R^{12}$, $R^{13}$ and $R^{14}$ are each independently H or $C_1$-$C_6$ alkyl. In some embodiments, $R^2$ is H or $C_1$-$C_6$ alkyl optionally substituted with $NH_2$. In some embodiments, $R^1$, $R^5$, $R^6$, $R^{8a}$, and $R^{14}$ are each methyl; $R^2$ is methyl or —$(CH_2)_4NH_2$; $R^3$, $R^{8b}$, $R^9$, $R^{11}$, $R^{12}$, and $R^{13}$ are each H; $R^4$ is iso-butyl; and $R^{10}$ is sec-butyl.

In some embodiments of Formula (I) or any variation thereof, $R^{15}$ is phenyl optionally substituted with halo, hydroxy, alkoxy, $C_1$-$C_6$ alkyl, or $C_1$-$C_6$ perhaloalkyl; and n is 1.

In some embodiments of Formula (I) or any variation thereof, $X^1$ is —O— or —$N(R^d)$—, and $R^d$ is H or $C_1$-$C_6$ alkyl.

In some embodiments of Formula (I) or any variation thereof, $R^7$ is H, $C_1$-$C_6$ alkyl, $C_1$-$C_6$ alkenyl, or $C_1$-$C_6$ alkynyl.

In some embodiments of Formula (I) or any variation thereof, $Y^1$ is —O—. In some embodiments, $Y^2$ is —O—. In some embodiments, $X^2$ is —O—. In some embodiments, $Y^1$, $Y^2$, and $X^2$ are each —O—, and $Y^3$ is —$N(R^d)$—. In some embodiments, $Y^4$ is —$OR^a$ or —$NR^bR^c$. In some embodiments, each $R^a$, $R^b$, $R^c$, and $R^d$ is independently H or —$CH_3$.

In some embodiments of Formula (I) or any variation thereof, m and p are each 0. In some embodiments. Z is $C_3$-$C_{12}$ alkyl. In some embodiments, Z is selected from the group consisting of substituted or unsubstituted $C_3$-$C_{12}$ cycloalkyl, substituted or unsubstituted $C_3$-$C_{12}$ cycloalkenyl, substituted or unsubstituted $C_5$-$C_{12}$ aryl, substituted or unsubstituted $C_5$-$C_{12}$ heteroaryl. In some embodiments, Z is $C_3$-$C_{12}$ alkyl or $(CH_2CH_2O)_q$, wherein q is an integer from 1-8, inclusive. In some embodiments, q is 1 or 2.

Provided in some embodiments are compounds selected from the group consisting of compounds of Table 1, or a salt thereof.

Provided in some aspects is a conjugate containing a compound of Formula (I) or any variation thereof bonded to a ligand, wherein the ligand is a polypeptide, a nucleic acid, or a targeting moiety. In some embodiments, the ligand is an antibody. In some embodiments, the compound is bonded to the ligand via a linker.

Provided in some aspects is a conjugate containing a compound of Formula (I) or any variation thereof bonded to a linker. In some embodiments, the linker is a cleavable linker. In some embodiments, the linker is a non-cleavable linker.

Provided in some aspects is a conjugate of Formula (III):

(III)

or a salt thereof, wherein $R^1$, $R^2$, $R^3$, $R^{8a}$, $R^{8b}$, $R^9$, $R^{10}$, $R^{11}$, $R^{12}$, $R^{13}$, and $R^{14}$ are each independently H, substituted or unsubstituted alkyl, substituted or unsubstituted alkenyl, substituted or unsubstituted alkynyl, substituted or unsubstituted cycloalkyl, or substituted or unsubstituted cycloalkenyl;

$R^4$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or substituted or unsubstituted heterocyclyl;

$R^5$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, halo, or perhaloalkyl;

$R^6$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, halo, or perhaloalkyl;

$R^7$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or substituted or unsubstituted heterocyclyl;

$R^{15}$ is substituted or unsubstituted aryl, substituted or unsubstituted heteroaryl, substituted or unsubstituted cycloalkyl, substituted or unsubstituted heterocyclyl, or substituted or unsubstituted alkyl;

n is 0, 1, or 2;

$X^1$ is —$N(R^d)$— or —O—;

$X^2$ is O or S;

$Y^1$ and $Y^2$ are each independently —$N(R^d)$—, —O—, or —S—;

$Y^3$ is —$N(R^d)$—, —O—, —S—, or substituted or unsubstituted heterocycloalkyl;

$Y^{4a}$ is —O—, —$NR^b$—, or —S—;

each $R^b$ and $R^d$ is independently H, substituted or unsubstituted alkyl, substituted or unsubstituted alkenyl, substituted or unsubstituted alkynyl, substituted or unsubstituted cycloalkyl, or substituted or unsubstituted cycloalkenyl;

W is $(CH_2)_m$—Z—$(CH_2)_p$;

Z is substituted or unsubstituted alkyl, substituted or unsubstituted substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or $(CH_2CH_2O)_q$;

m, and p are each independently an integer from 0-12, inclusive;
q is an integer from 1-12, inclusive;
a, b, c, and d are each independently 0, 1, or 2;
each $L_1$ is independently

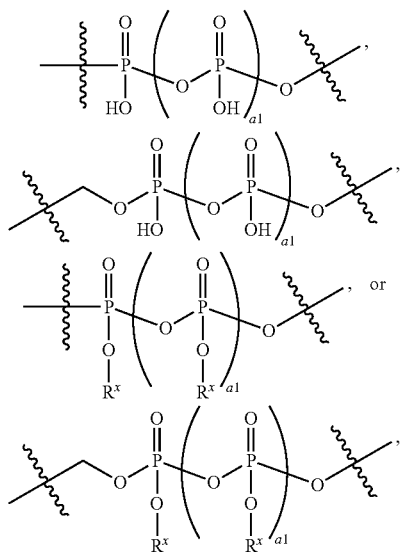

wherein a1 is 0, 1, or 2, and each $R^x$ is unsubstituted or substituted alkyl;
each $L_2$ is independently

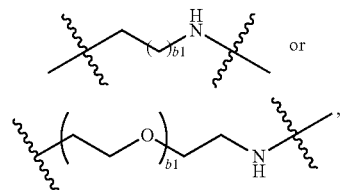

wherein b1 is an integer from 0 to 12, inclusive;
each $L_3$ is independently wherein each AA is an amino acid, c1 is an integer from 0-12, inclusive, and c2 is an integer from 0-10, inclusive;
each $L_4$ is independently

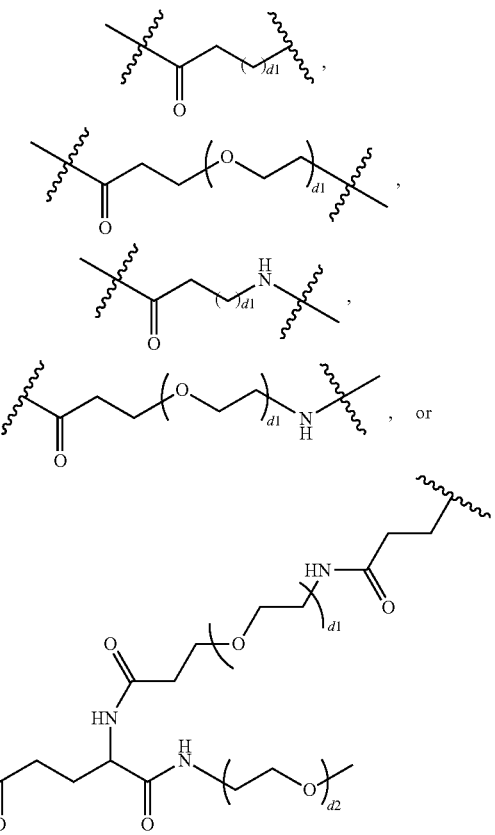

wherein d1 is an integer from 0-12, inclusive, and d2 is an integer from 0-30, inclusive; and
Fn is selected from the group consisting of H unsubstituted or substituted alkyl,

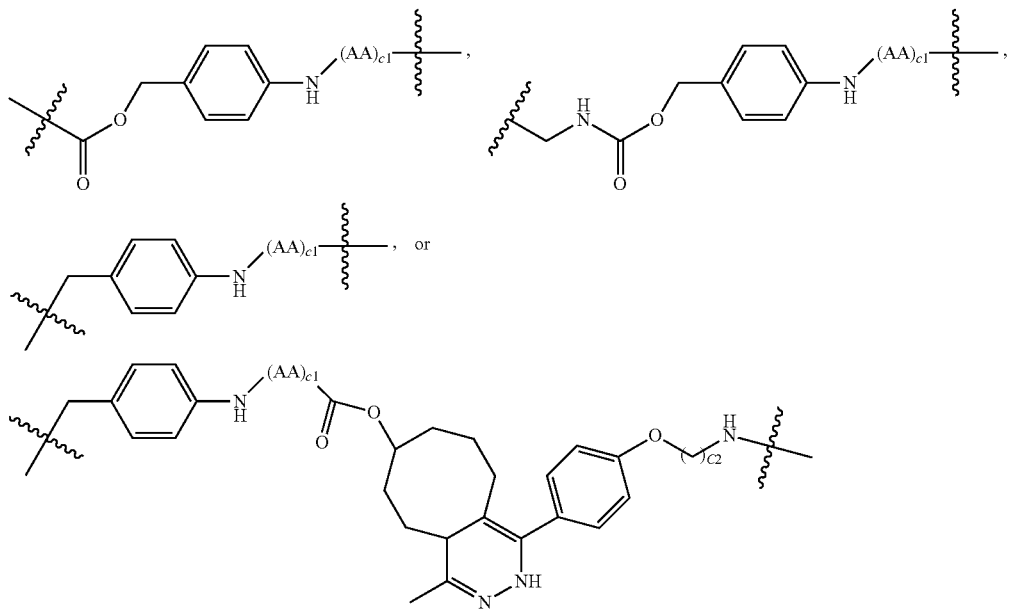

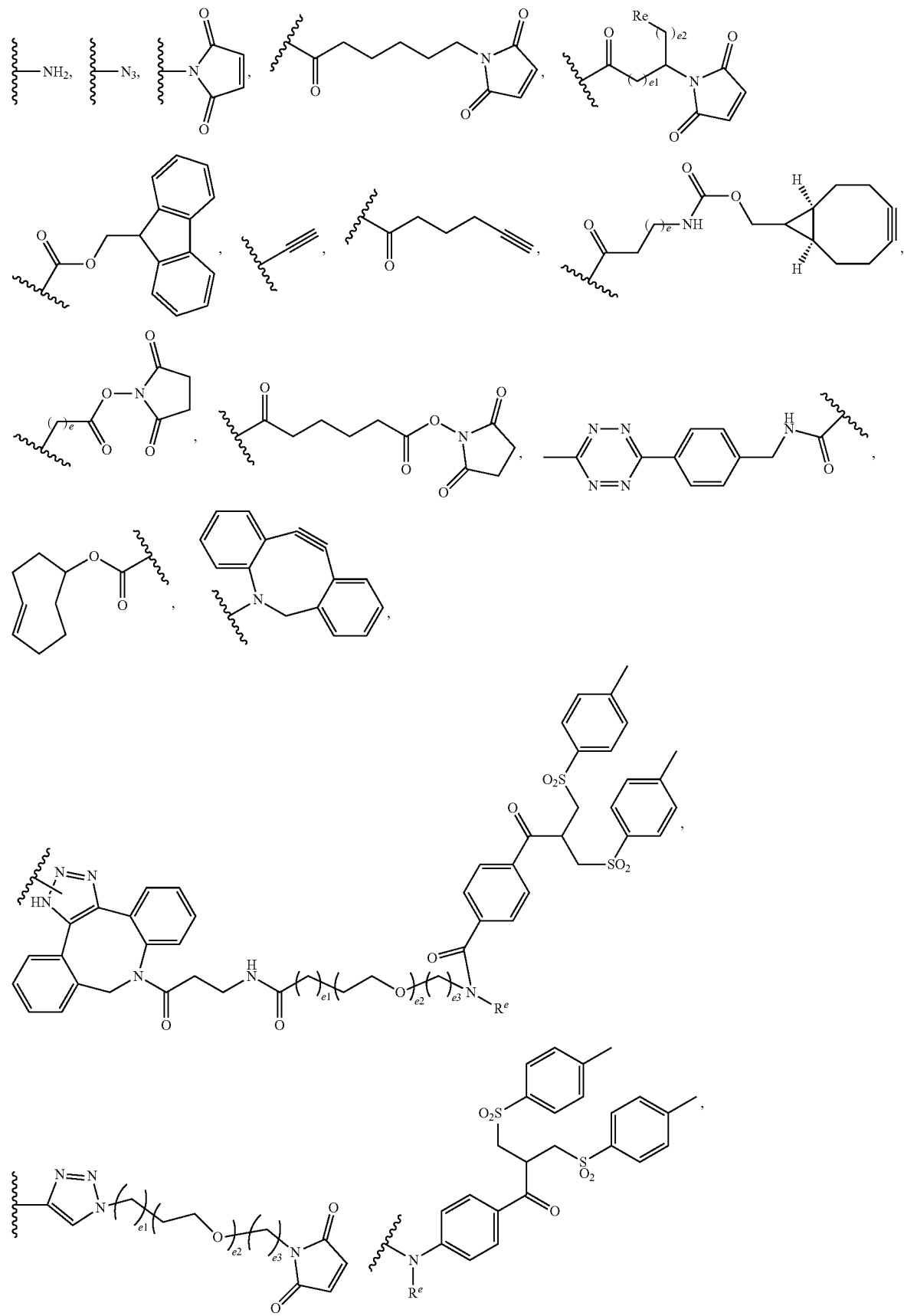

-continued

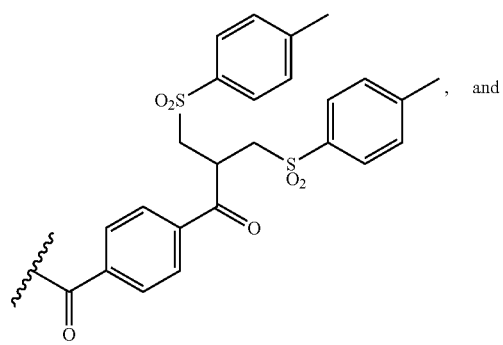, and 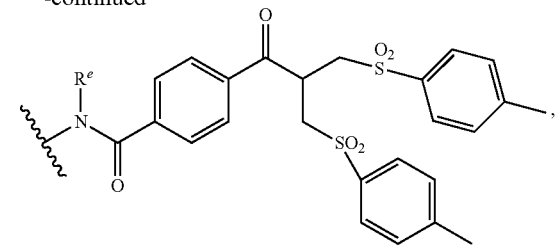, wherein e1, e2, and e3 are each independently an integer from 0-12, inclusive, and $R^e$ is H or alkyl.

Provided in some aspects is a conjugate of Formula (IV):

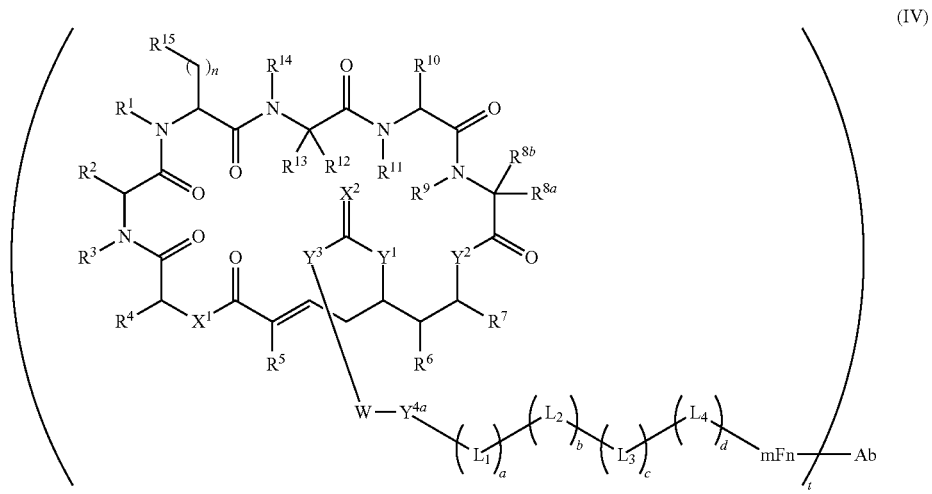

(IV)

or a salt thereof, wherein $R^1$, $R^2$, $R^3$, $R^{8a}$, $R^{8b}$, $R^9$, $R^{10}$, $R^{11}$, $R^{12}$, $R^{13}$, and $R^{14}$ are each independently H, substituted or unsubstituted alkyl, substituted or unsubstituted alkenyl, substituted or unsubstituted alkynyl, substituted or unsubstituted cycloalkyl, or substituted or unsubstituted cycloalkenyl;

$R^4$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or substituted or unsubstituted heterocyclyl;

$R^5$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, halo, or perhaloalkyl;

$R^6$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, halo, or perhaloalkyl;

$R^7$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or substituted or unsubstituted heterocyclyl;

$R^{15}$ is substituted or unsubstituted aryl, substituted or unsubstituted heteroaryl, substituted or unsubstituted cycloalkyl, substituted or unsubstituted heterocyclyl, or substituted or unsubstituted alkyl;

n is 0, 1, or 2;

$X^1$ is —N($R^d$)— or —O—;

$X^2$ is O or S;

$Y^1$ and $Y^2$ are each independently —N($R^d$)—, —O—, or —S—;

$Y^3$ is —N($R^d$)—, —O—, —S—, or substituted or unsubstituted heterocycloalkyl;

$Y^{4a}$ is —O—, —N$R^b$—, or —S—;

each $R^b$ and $R^d$ is independently H, substituted or unsubstituted alkyl, substituted or unsubstituted alkenyl, substituted or unsubstituted alkynyl, substituted or unsubstituted cycloalkyl, or substituted or unsubstituted cycloalkenyl;

W is $(CH_2)_m$—Z—$(CH_2)_p$;

Z is substituted or unsubstituted alkyl, substituted or unsubstituted substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or $(CH_2CH_2O)_q$;

m and p are each independently an integer from 0-12, inclusive;

q is an integer from 1-12, inclusive;

a, b, c, and d are each independently 0, 1, or 2;

each L₁ is independently

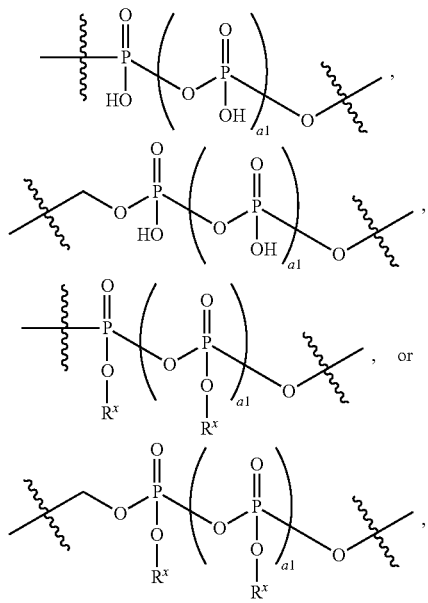

wherein a1 is 0, 1, or 2, and each $R^x$ is unsubstituted or substituted alkyl;

each L₂ is independently

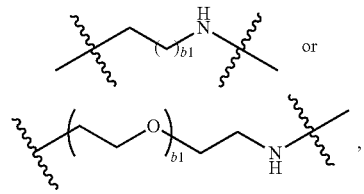

wherein b1 is an integer from 0 to 12, inclusive;

each L₃ is independently

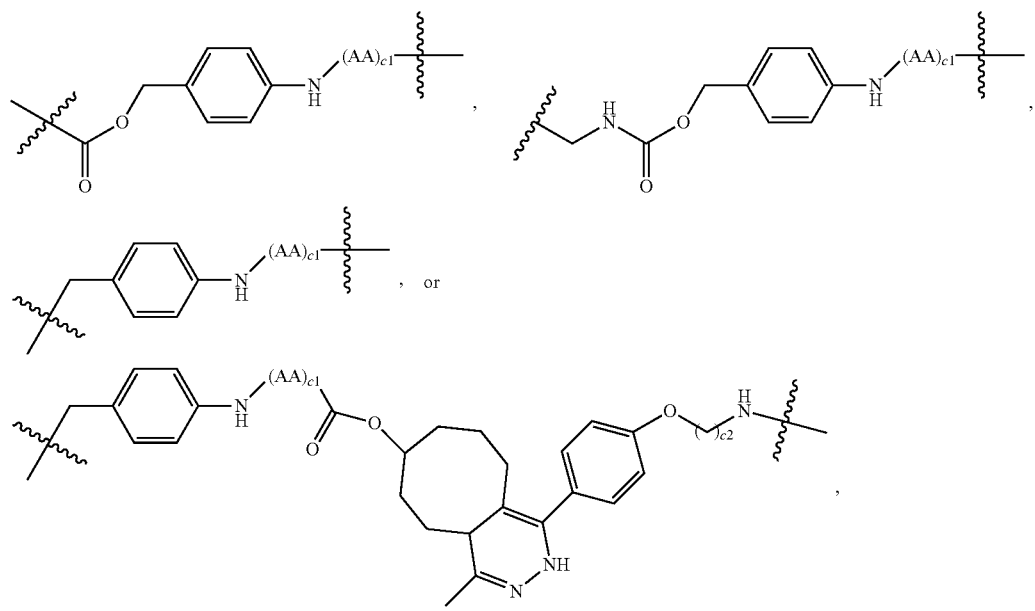

wherein each AA is an amino acid, c1 is an integer from 0-12, inclusive, and c2 is an integer from 0-10, inclusive;

each L₄ is independently

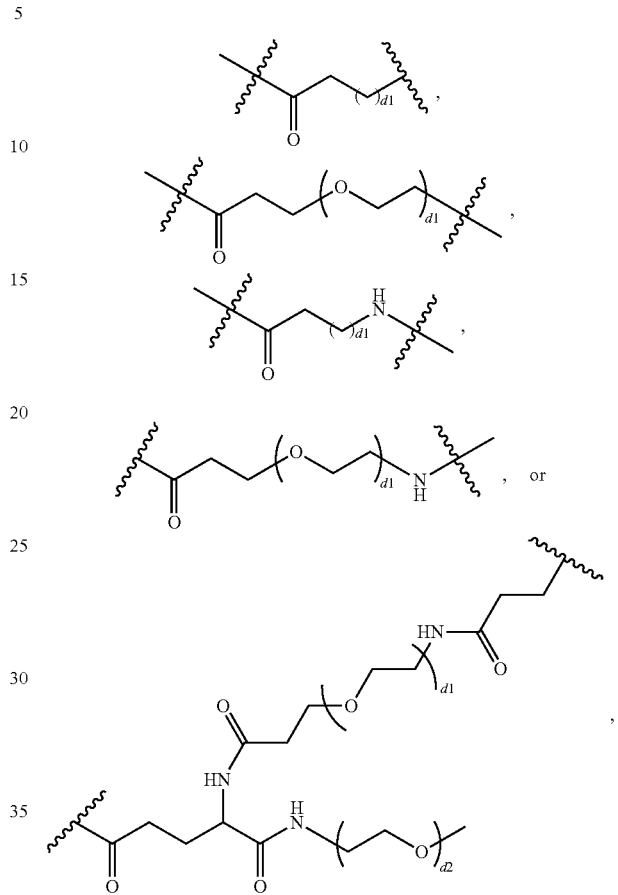

wherein d1 is an integer from 0-12, inclusive, and d2 is an integer from 0-30, inclusive;

mFn is selected from the group consisting of a bond, unsubstituted or substituted alkyl,
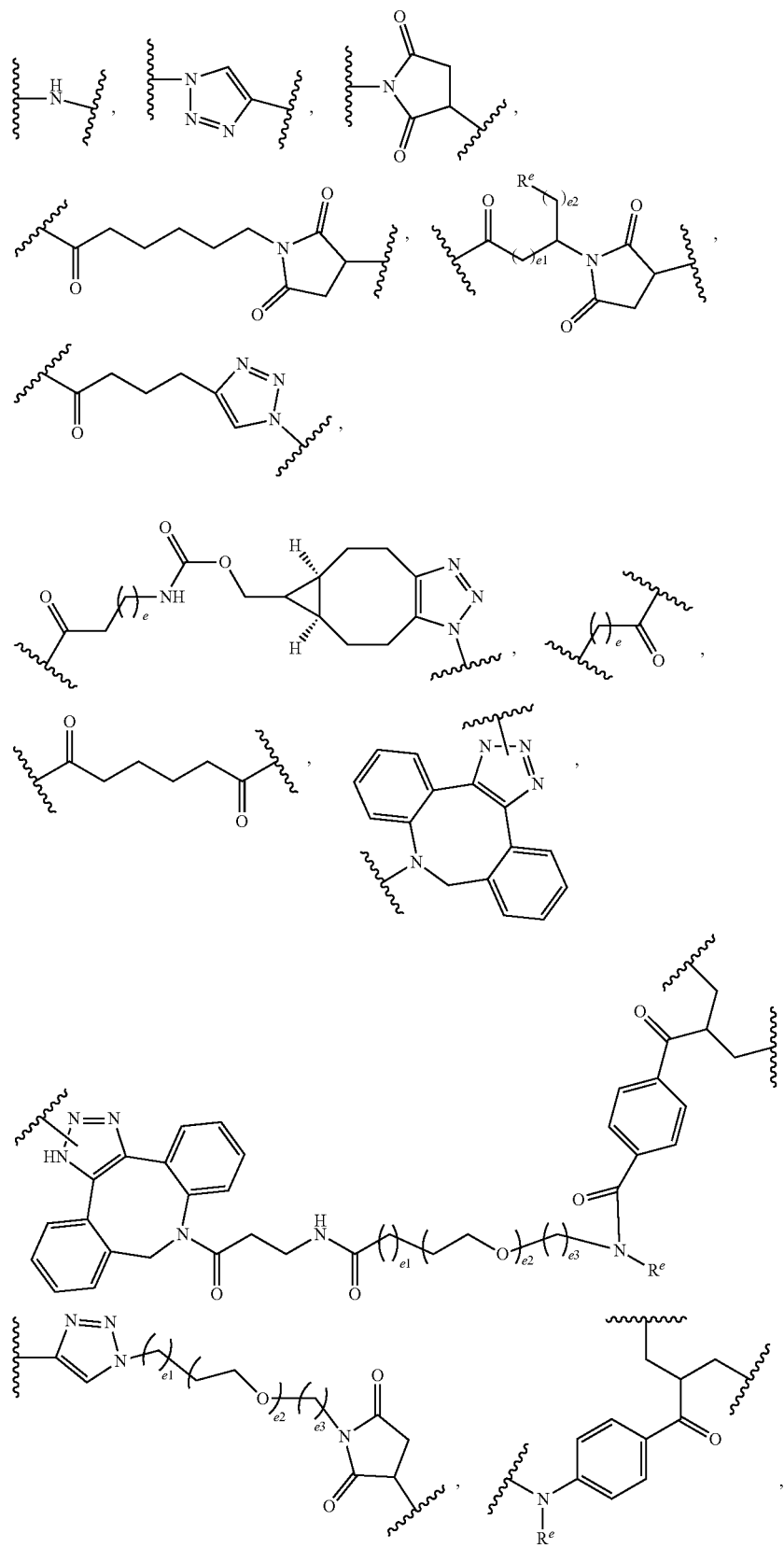

-continued

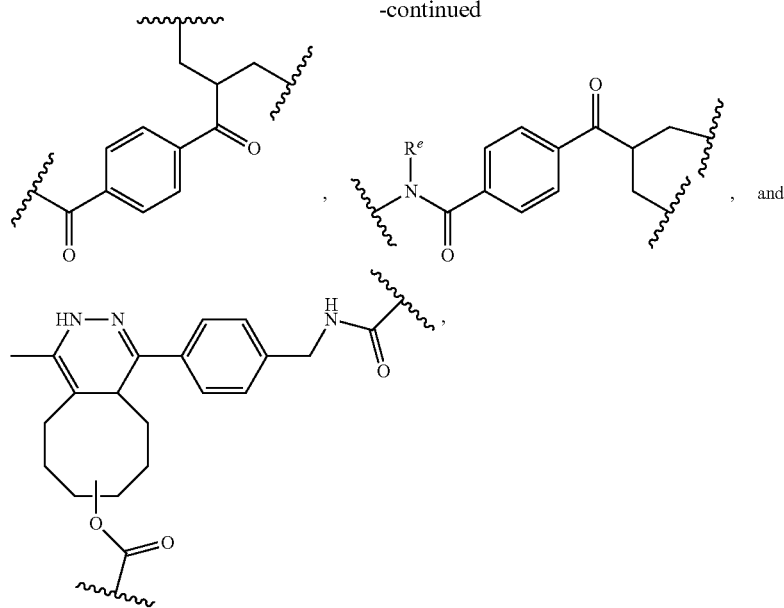

wherein e1, e2, and e3 are each independently an integer from 0-12, inclusive, and $R^e$ is H or alkyl;

t is an integer from 1-12, inclusive; and

Ab is an antibody.

In some embodiments of Formulae (III) or (IV), i) when $Y^{4a}$ is —O—, W is not —$(CH_2)_2$— or —$(CH_2CH_2O)_3(CH_2)_2$—; and ii) when $Y^{4a}$ is —NH— or —N(CH$_3$)—, W is not —$(CH_2)_2$—, —$(CH_2)_6$—, or —$CH_2(CH_2CH_2O)_3(CH_2)_3$—.

In some embodiments of Formulae (III) or (IV) or any variation thereof, $R^1$, $R^3$, $R^4$, $R^5$, $R^6$, $R^{8a}$, $R^{8b}$, $R^9$, $R^{10}$, $R^{11}$, $R^{12}$, $R^{13}$ and $R^{14}$ are each independently H or $C_1$-$C_6$ alkyl. In some embodiments, $R^2$ is H or $C_1$-$C_6$ alkyl optionally substituted with NH$_2$. In some embodiments, $R^1$, $R^5$, $R^6$, $R^{8a}$, and $R^{14}$ are each methyl; $R^2$ is methyl or —$(CH_2)_4NH_2$; $R^3$, $R^{8b}$, $R^9$, $R^{11}$, $R^{12}$, and $R^{13}$ are each H; $R^4$ is iso-butyl; and $R^{10}$ is sec-butyl.

In some embodiments of Formulae (III) or (IV) or any variation thereof, $R^{15}$ is phenyl optionally substituted with halo, hydroxy, $C_1$-$C_6$ alkoxy, $C_1$-$C_6$ alkyl, or $C_1$-$C_6$ perhaloalkyl; and n is 1.

In some embodiments of Formulae (III) or (IV) or any variation thereof; $X^1$ is —O— or —N($R^d$)—, and $R^d$ is H or $C_1$-$C_6$ alkyl.

In some embodiments of Formulae (III) or (IV) or any variation thereof, $R^7$ is H, $C_1$-$C_6$ alkyl, $C_1$-$C_6$ alkenyl, or $C_1$-$C_6$ alkynyl.

In some embodiments of Formulae (III) or (IV) or any variation thereof, $Y^1$ is —O—. In some embodiments, $Y^2$ is —O—. In some embodiments, $X^2$ is —O—. In some embodiments, $Y^1$, $Y^2$, and $X^2$ are each —O—, and $Y^3$ is —N($R^d$)—. In some embodiments, $Y^{4a}$ is —O— or —$NR^b$—. In some embodiments, each $R^b$ and $R^d$ is independently H or —CH$_3$.

In some embodiments of Formulae (III) or (IV) or any variation thereof, m and p are each 0. In some embodiments, Z is $C_3$-$C_{12}$ alkyl. In some embodiments, Z is selected from the group consisting of substituted or unsubstituted $C_3$-$C_{12}$ cycloalkyl, substituted or unsubstituted $C_3$-$C_{12}$ cycloalkenyl, substituted or unsubstituted $C_5$-$C_{12}$ aryl, substituted or unsubstituted $C_5$-$C_{12}$ heteroaryl. In some embodiments, Z is $C_3$-$C_{12}$ alkyl or $(CH_2CH_2O)_q$, wherein q is an integer from 1-8, inclusive. In some embodiments, q is 1 or 2.

In some embodiments of Formulae (III) or (IV) or any variation thereof, $L_1$ is

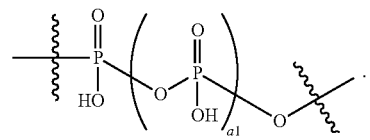

In some embodiments, $L_1$ is

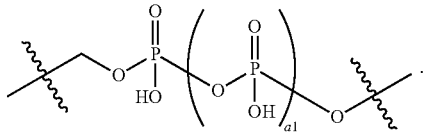

In some embodiments, $L_1$ is

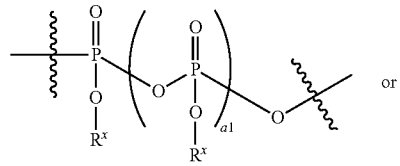

or

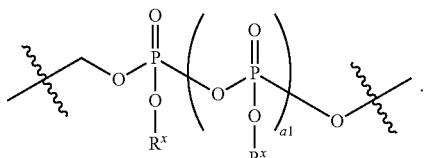

In some embodiments, a1 is 0 or 1. In some embodiments, each $R^x$ is $C_1$-$C_4$ alkyl. In some embodiments, each $R^x$ is $C_1$-$C_4$ alkyl, substituted with halo. In some embodiments, each $R^x$ is trichloroethyl.

In some embodiments of Formulae (III) or (IV) or any variation thereof, $L_2$ is

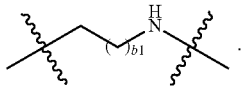

In some embodiments, b1 is an integer from 1-8, inclusive.

In some embodiments of Formulae (III) or (IV) or any variation thereof, $L_3$ is

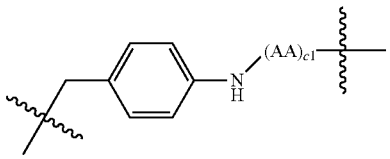

In some embodiments, $L_3$ is

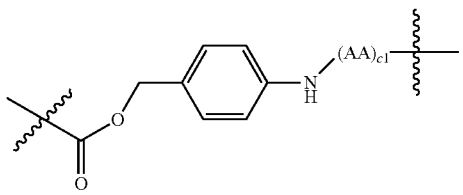

In some embodiments, $L_3$ is

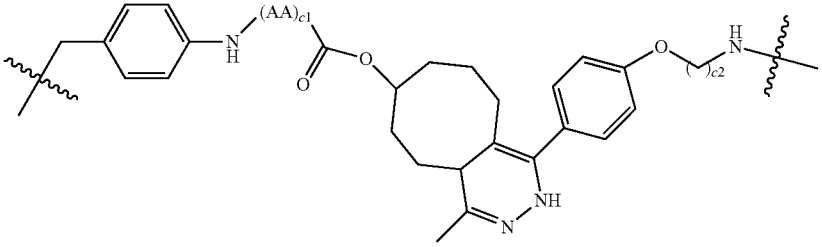

In some embodiments, c1 is 2. In some embodiments, c2 is 3. In some embodiments, $(AA)_{c1}$ is -Cit-Val- or -Ala-Val-.

In some embodiments of Formulae III or (IV) or any variation thereof, $L_4$ is

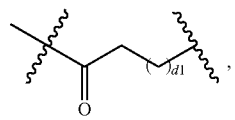

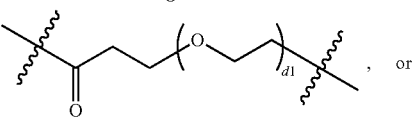, or

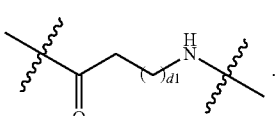

In some embodiments, d1 is any integer from 2-7, inclusive.

In some embodiments of Formulae (III) or (IV) or any variation thereof, a, b, c, and d are each independently 0 or 1.

In some embodiments,

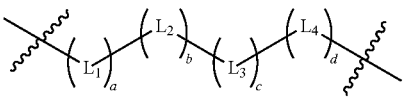

is selected from the group consisting of:

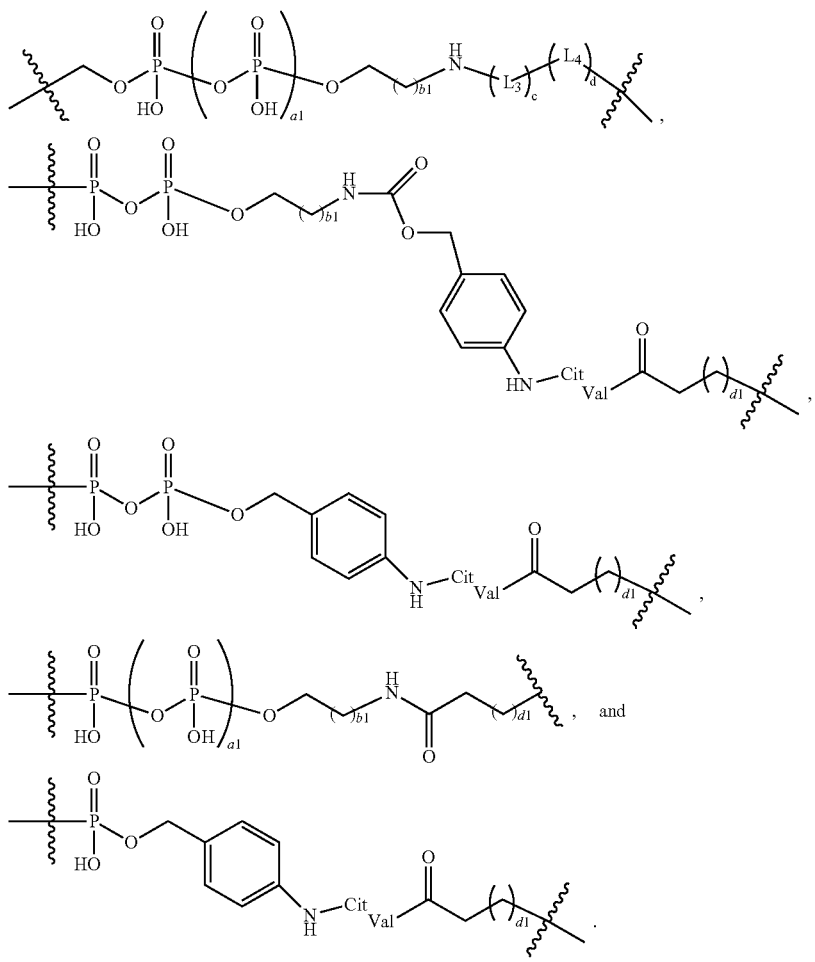

Provided in some embodiments are conjugates selected from the group consisting of conjugates of Table 2, or a salt thereof.

In some embodiments, the conjugate is selected from the group consisting of conjugates of Table 3, or a salt thereof. In some embodiments, b is an integer from 1-12, inclusive, and Ab is an antibody.

In some aspects, provided are pharmaceutical compositions containing a compound of Formula (I), or a pharmaceutically acceptable salt thereof, and a pharmaceutically acceptable carrier. Provided in other embodiments are pharmaceutical compositions containing a conjugate of Formulae (III) or (IV), or a pharmaceutically acceptable salt thereof, and a pharmaceutically acceptable carrier. In some embodiments, the pharmaceutical composition contains one or more compounds of Table 1, or a pharmaceutically acceptable salt thereof. In other embodiments, the pharmaceutical composition contains one or more conjugates of Table 2 or Table 3, or a pharmaceutically acceptable salt thereof.

Provided in some aspects are methods of treating cancer in an individual in need thereof, the method including administering to the individual a therapeutically effective amount of a compound of Formula (I), or a pharmaceutically acceptable salt thereof. In other aspects, provided are methods of treating cancer in an individual in need thereof, the method including administering to the individual a therapeutically effective amount of a conjugate of Formulae (III) or (IV), or a pharmaceutically acceptable salt thereof. In some embodiments, the method includes administering to the individual a therapeutically effect amount of one or more compounds of Table 1, or a pharmaceutically acceptable salt thereof. In other embodiments, the method includes administering to the individual a therapeutically effect amount of one or more conjugates of Table 2 or 3, or a pharmaceutically acceptable salt thereof.

In some aspects, provided are kits containing a compound of Formula (I), or a pharmaceutically acceptable salt thereof, and instructions for use in treatment of cancer in an individual in need thereof. Provided in other embodiments are kits containing a conjugate of Formulae (III) or (IV), or a pharmaceutically acceptable salt thereof, and instructions for use in treatment of cancer in an individual in need thereof. In some embodiments, the kits contain one or more compounds of Table 1, or a pharmaceutically acceptable salt thereof. In other embodiments, the kits contain one or more conjugates of Tables 2 or 3, or a pharmaceutically acceptable salt thereof.

DETAILED DESCRIPTION

Definitions

Figure 1:
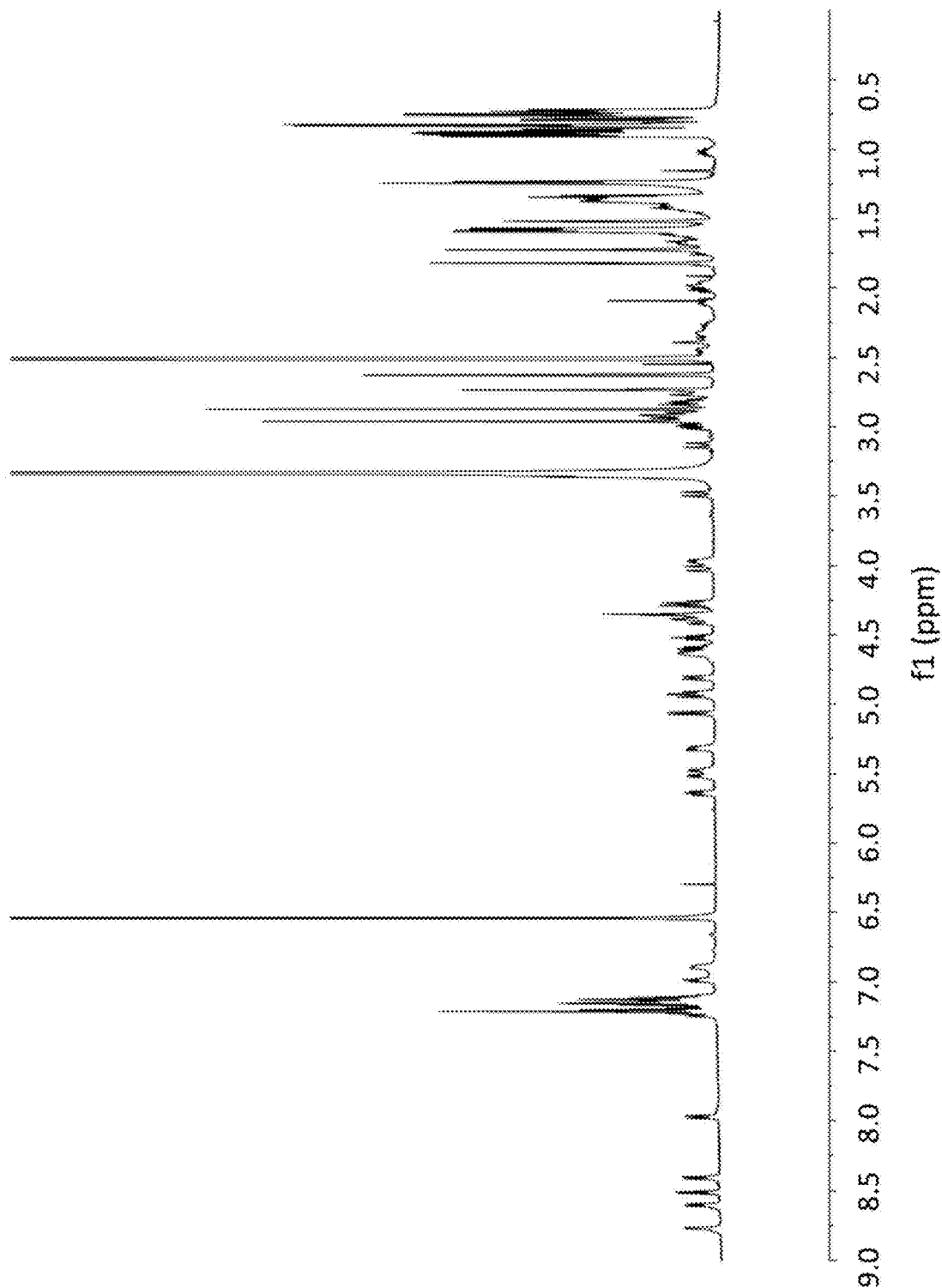
FIG. 1 is a $^1$H NMR spectrum of Compound 2 in DMSO-d6.

As used herein, reference to "about" a value or parameter herein includes (and describes) embodiments that are directed to that value or parameter per se. For example, description referring to "about X" includes description of "X".

Unless clearly indicated otherwise, "an individual" as used herein intends a mammal, including but not limited to a human, bovine, primate, equine, canine, feline, porcine, and ovine animals. Thus, the compositions and methods provided herein have use in both human medicine and in the veterinary context, including use in agricultural animals and domestic pets. The individual may be a human who has been diagnosed with or is suspected of having a condition described herein, such as cancer. The individual may be a human who exhibits one or more symptoms associated with a condition described herein, such as cancer. The individual may be a human who has a mutated or abnormal gene associated with a condition described herein, such as cancer. The individual may be a human who is genetically or otherwise predisposed to or at risk of developing a condition described herein, such as cancer.

As used herein, "treatment" or "treating" is an approach for obtaining beneficial or desired results including clinical results. For purposes of the compositions and methods provided herein, beneficial or desired clinical results include, but are not limited to, one or more of the following: decreasing one or more symptoms resulting from the condition, diminishing the extent of the condition, stabilizing the condition (e.g., preventing or delaying the worsening of the condition), preventing or delaying the spread (e.g., metastasis) of the condition, delaying or slowing the progression of the condition, ameliorating a disease state, providing a remission (whether partial or total) of a disease, decreasing the dose of one or more other medications required to treat the condition, enhancing the effect of another medication used to treat the condition, increasing the quality of life of an individual having the condition, and/or prolonging survival. A method of treating cancer encompasses a reduction of the pathological consequence of cancer. The methods described herein contemplate any one or more of these aspects of treatment.

As used herein, an "at risk" individual is an individual who is at risk of developing a disease or condition described herein, such as cancer. An individual "at risk" may or may not have detectable disease, and may or may not have displayed detectable disease prior to the treatment methods described herein. "At risk" denotes that an individual has one or more so-called risk factors, which are measurable parameters that correlate with development of a disease or condition described herein, such as cancer. An individual having one or more of these risk factors has a higher probability of developing the disease or condition than an individual without these risk factor(s).

As used herein, by "combination therapy" is meant a therapy that includes two or more different compounds. Thus, in one aspect, a combination therapy comprising a compound detailed herein and another compound is provided. In some variations, the combination therapy optionally includes one or more pharmaceutically acceptable carriers or excipients, non-pharmaceutically active compounds, and/or inert substances. In various embodiments, treatment with a combination therapy may result in an additive or even synergistic (e.g., greater than additive) result compared to administration of a single compound provided herein alone. In some embodiments, a lower amount of each compound is used as part of a combination therapy compared to the amount generally used for individual therapy. Preferably, the same or greater therapeutic benefit is achieved using a combination therapy than by using any of the individual compounds alone. In some embodiments, the same or greater therapeutic benefit is achieved using a smaller amount (e.g., a lower dose or a less frequent dosing schedule) of a compound in a combination therapy than the amount generally used for individual compound or therapy. Preferably, the use of a small amount of compound results in a reduction in the number, severity, frequency, and/or duration of one or more side-effects associated with the compound.

As used herein, the term "effective amount" intends such amount of a compound provided herein which in combination with its parameters of efficacy and toxicity, should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds. In various embodiments, an effective amount of the composition or therapy may (i) reduce the number of cancer cells; (ii) reduce tumor size; (iii) inhibit, retard, slow to some extent, and preferably stop cancer cell infiltration into peripheral organs; (iv) inhibit (e.g., slow to some extent and preferably stop) tumor metastasis; (v) inhibit tumor growth; (vi) prevent or delay occurrence and/or recurrence of a tumor; and/or (vii) relieve to some extent one or more of the symptoms associated with the cancer. In various embodiments, the amount is sufficient to ameliorate, palliate, lessen, and/or delay one or more of symptoms of a disease or condition described herein, such as cancer.

As is understood in the art, an "effective amount" may be in one or more doses, i.e., a single dose or multiple doses may be required to achieve the desired treatment endpoint. An effective amount may be considered in the context of administering one or more therapeutic agents, and a compound, or pharmaceutically acceptable salt thereof, may be considered to be given in an effective amount if, in conjunction with one or more other agents, a desirable or beneficial result may be or is achieved.

A "therapeutically effective amount" refers to an amount of a compound or salt thereof sufficient to produce a desired therapeutic outcome (e.g., reducing the severity or duration of, stabilizing the severity of, or eliminating one or more symptoms of a disease or condition described herein, such as cancer). For therapeutic use, beneficial or desired results include, e.g., decreasing one or more symptoms resulting from the disease (biochemical, histologic and/or behavioral), including its complications and intermediate pathological phenotypes presenting during development of the disease or condition, increasing the quality of life of those suffering from the disease or condition, decreasing the dose of other medications required to treat the disease or condition, enhancing effect of another medication, delaying the progression of the disease or condition, and/or prolonging survival of patients.

It is understood that an effective amount of a compound or pharmaceutically acceptable salt thereof, including a prophylactically effective amount, may be given to an individual in the adjuvant setting, which refers to a clinical setting in which an individual has had a history of cancer, and generally (but not necessarily) has been responsive to therapy, which includes, but is not limited to, surgery (e.g., surgical resection), radiotherapy, and chemotherapy. However, because of their history of cancer, these individuals are considered at risk of developing cancer. Treatment or administration in the "adjuvant setting" refers to a subsequent mode of treatment.

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Pharmaceutically acceptable salts can be prepared in situ in the manufacturing process, or by separately reacting a purified compound provided herein in its free acid or base form with a suitable organic or inorganic base or acid, respectively, and isolating the salt thus formed during subsequent purification.

The term "excipient" as used herein means an inert or inactive substance that may be used in the production of a drug or pharmaceutical, such as a tablet containing a compound provided herein as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

"Alkyl" refers to and includes saturated linear or branched univalent hydrocarbon structures and combinations thereof. Particular alkyl groups are those having 1 to 20 carbon atoms (a "$C_1$-$C_{20}$ alkyl"). More particular alkyl groups are those having 1 to 8 carbon atoms (a "$C_1$-$C_8$ alkyl") or 1 to 6 carbon atoms (a "$C_1$-$C_6$ alkyl"). When an alkyl residue having a specific number of carbons is named, all geometric isomers having that number of carbons are intended to be encompassed and described; thus, for example, "butyl" is meant to include n-butyl, sec-butyl, iso-butyl, and tert-butyl; "propyl" includes n-propyl and iso-propyl. This term is exemplified by groups such as methyl, t-butyl, n-heptyl, octyl, and the like.

"Cycloalkyl" refers to and includes cyclic univalent hydrocarbon structures. Cycloalkyl can consist of one ring, such as cyclohexyl, or multiple rings, such as adamantyl. A cycloalkyl comprising more than one ring may be fused, spiro or bridged, or combinations thereof. A preferred cycloalkyl is a saturated cyclic hydrocarbon having from 3 to 13 annular carbon atoms. A more preferred cycloalkyl is a saturated cyclic hydrocarbon having from 3 to 8 annular carbon atoms (a "$C_3$-$C_8$ cycloalkyl"). Examples of cycloalkyl groups include adamantyl, decahydronaphthalenyl, cyclopropyl, cyclobutyl, cyclopentyl, cyclohexyl, and the like.

"Alkenyl" refers to an unsaturated hydrocarbon group having at least one site of olefinic unsaturation (i.e., having at least one moiety of the formula C=C) and preferably having from 2 to 10 carbon atoms and more preferably 2 to 8 carbon atoms. Examples of alkenyl include but are not limited to —$CH_2$—CH=CH—$CH_3$ and —CH=CH—CH=$CH_2$.

"Cyclolkenyl" refers to an unsaturated hydrocarbon group within a cycloalkyl having at least one site of olefinic unsaturation (i.e., having at least one moiety of the formula C=C). Cycloalkenyl can consist of one ring, such as cyclohexyl, or multiple rings, such as norbornenyl. A more preferred cycloalkenyl is an unsaturated cyclic hydrocarbon having from 3 to 8 annular carbon atoms (a "$C_3$-$C_8$ cycloalkenyl"). Examples of cycloalkenyl groups include cyclopropenyl, cyclobutenyl, cyclopentenyl, cyclohexenyl, and the like.

"Alkynyl" refers to an unsaturated hydrocarbon group having at least one site of acetylenic unsaturation (i.e., having at least one moiety of the formula C≡C) and preferably having from 2 to 10 carbon atoms and more preferably 2 to 8 carbon atoms and the like.

The term "alkoxy" refers to an —O-alkyl group, where the O is the point of attachment to the rest of the molecule, and alkyl is as defined above.

"Heterocycle", "heterocyclic", or "heterocyclyl" refers to a saturated or an unsaturated non-aromatic group having a single ring or multiple condensed rings, and having from 1 to 10 annular carbon atoms and from 1 to 4 annular heteroatoms, such as nitrogen, sulfur or oxygen, and the like. A heterocycle comprising more than one ring may be fused, spiro or bridged, or any combination thereof. In fused ring systems, one or more of the rings can be aryl or heteroaryl. A heterocycle having more than one ring where at least one ring is aromatic may be connected to the parent structure at either a non-aromatic ring position or at an aromatic ring position. In one variation, a heterocycle having more than one ring where at least one ring is aromatic is connected to the parent structure at a non-aromatic ring position.

"Aryl" or "Ar" refers to an unsaturated aromatic carbocyclic group having a single ring (e.g., phenyl) or multiple condensed rings (e.g., naphthyl or anthryl) which condensed rings may or may not be aromatic. In one variation, the aryl group contains from 6 to 14 annular carbon atoms. An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Heteroaryl" or "HetAr" refers to an unsaturated aromatic carbocyclic group having from 1 to 10 annular carbon atoms and at least one annular heteroatom, including but not limited to heteroatoms such as nitrogen, oxygen and sulfur. A heteroaryl group may have a single ring (e.g., pyridyl, furyl) or multiple condensed rings (e.g., indolizinyl, benzothienyl) which condensed rings may or may not be aromatic. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position.

The term "halogen" represents chlorine, fluorine, bromine, or iodine. The term "halo" represents chloro, fluoro, bromo, or iodo.

The term "substituted" means that the specified group or moiety bears one or more substituents including, but not limited to, substituents such as alkoxy, acyl, acyloxy, carbonylalkoxy, acylamino, amino, aminoacyl, aminocarbonylamino, aminocarbonyloxy, cycloalkyl, cycloalkenyl, aryl, heteroaryl, aryloxy, cyano, azido, halo, hydroxyl, nitro, carboxyl, thiol, thioalkyl, cycloalkyl, cycloalkenyl, alkyl, alkenyl, alkynyl, heterocyclyl, aralkyl, aminosulfonyl, sulfonylamino, sulfonyl, oxo, carbonylalkylenealkoxy and the like. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

A composition of "substantially pure" compound means that the composition contains no more than 15% or preferably no more than 10% or more preferably no more than 5% or even more preferably no more than 3% and most preferably no more than 1% impurity, which impurity may be the compound in a different stereochemical form. For instance, a composition of substantially pure (S) compound means that the composition contains no more than 15% or no more than 10% or no more than 5% or no more than 3% or no more than 1% of the (R) form of the compound.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof in any ratio, are considered within the scope of the formula. Thus, any formula given herein is intended to represent a racemate, one or more enantiomeric forms, one or more diastereomeric forms, one or more atropisomeric forms, and mixtures thereof in any ratio. Furthermore, certain structures may exist as geometric isomers (i.e., cis and trans isomers), as tautomers, or as atropisomers. Additionally, any formula given herein is intended to refer also to any one of hydrates, solvates, and amorphous and polymorphic forms of such compounds, and mixtures thereof, even if such forms are not listed explicitly. In some embodiments, the solvent is water and the solvates are hydrates.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds described herein include isotopes of hydrogen, carbon, nitrogen, oxygen, phosphorous, fluorine, chlorine, and iodine, such as $^{2}H$, $^{3}H$ $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Substitution with heavier isotopes such as deuterium (i.e., $^{2}H$) may afford certain therapeutic advantages resulting from greater metabolic stability, for example increased in vivo half-life or reduced dosage requirements. Isotopically labeled compounds described herein and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

Compounds

Compounds and salts thereof (such as pharmaceutically acceptable salts) are detailed herein, including in the Brief Summary and in the appended claims. Also provided are the use of all of the compounds described herein, including any and all stereoisomers, including geometric isomers (cis/trans), E/Z isomers, enantiomers, diastereomers, and mixtures thereof in any ratio including racemic mixtures, salts and solvates of the compounds described herein, as well as methods of making such compounds. Any compound described herein may also be referred to as a drug.

In one aspect, provided are compounds of Formula (I):

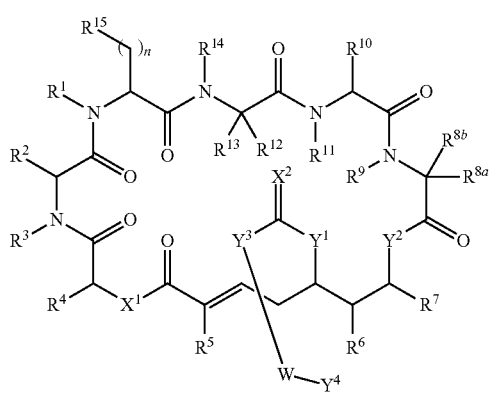

(I)

or a salt thereof, wherein $R^1$, $R^2$, $R^3$, $R^{8a}$, $R^{8b}$, $R^9$, $R^{10}$, $R^{11}$, $R^{12}$, $R^{13}$, and $R^{14}$ are each independently H, substituted or unsubstituted alkyl, substituted or unsubstituted alkenyl, substituted or unsubstituted alkynyl, substituted or unsubstituted cycloalkyl, or substituted or unsubstituted cycloalkenyl;

$R^4$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or substituted or unsubstituted heterocyclyl;

$R^5$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, halo, or perhaloalkyl;

$R^6$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, halo, or perhaloalkyl;

$R^7$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or substituted or unsubstituted heterocyclyl;

$R^{15}$ is substituted or unsubstituted aryl, substituted or unsubstituted heteroaryl, substituted or unsubstituted cycloalkyl, substituted or unsubstituted heterocyclyl, or substituted or unsubstituted alkyl;

n is 0, 1, or 2;

$X^1$ is —N($R^d$)— or —O—;

$X^2$ is O or S;

$Y^1$ and $Y^2$ are each independently —N($R^d$)—, —O—, or —S—;

$Y^3$ is —N($R^d$)—, —O—, —S—, or substituted or unsubstituted heterocycloalkyl;

$Y^4$ is —$OR^a$, —$NR^bR^c$, or —$SR^a$;

each $R^a$, $R^b$, $R^c$, and $R^d$ is independently H, substituted or unsubstituted alkyl, substituted or unsubstituted alkenyl, substituted or unsubstituted alkynyl, substituted or unsubstituted cycloalkyl, or substituted or unsubstituted cycloalkenyl;

W is $(CH_2)_m$—Z—$(CH_2)_p$;

Z is substituted or unsubstituted alkyl, substituted or unsubstituted substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or $(CH_2CH_2O)_q$;

m, and p are each independently an integer from 0-12, inclusive; and q is an integer from 1-12, inclusive;

provided that i) when $Y^4$ is —OH, W is not —$(CH_2)_2$— or —$(CH_2CH_2O)_3(CH_2)_2$—; and ii) when $Y^4$ is —$NHR^c$ or —$N(CH_3)R^c$, W is not —$(CH_2)_2$—, —$(CH_2)_6$—, or —$CH_2(CH_2CH_2O)_3(CH_2)_3$—.

In any variation of Formula (I) described herein, $X^1$ may be —O—. In other embodiments of Formula (I), $X^1$ is —N($R^d$)—, where $R^d$ is H, substituted or unsubstituted alkyl, substituted or unsubstituted alkenyl, substituted or unsubstituted alkynyl, substituted or unsubstituted cycloalkyl, or substituted or unsubstituted cycloalkenyl. In some of these embodiments, $X^1$ is —N($R^d$)— where $R^d$ is $C_1$-$C_6$ unsubstituted alkyl, such as methyl or ethyl. In some of these embodiments, $X^1$ is —N($R^d$)— where $R^d$ is H or $C_1$-$C_6$ alkyl. In some of these embodiments, $X^1$ is —NH—.

In some embodiments of Formula (I), $X^2$ is O. In other embodiments of Formula (I), $X^2$ is S.

In some embodiments of Formula (I), $Y^1$, $Y^2$, and $Y^3$ are each independently —N($R^d$)—, —O—, or —S—.

In some embodiments of Formula (I), $Y^1$ is —O—. In other embodiments of Formula (I), $Y^1$ is —S—. In yet other embodiments of Formula (I), $Y^1$ is —N($R^d$)—, where $R^d$ is H, substituted or unsubstituted alkyl, substituted or unsubstituted alkenyl, substituted or unsubstituted alkynyl, substituted or unsubstituted cycloalkyl, or substituted or unsubstituted cycloalkenyl. In some of these embodiments, $Y^1$ is —N($R^d$)—, where $R^d$ is H or $C_1$-$C_6$ alkyl, such as methyl or ethyl. In some embodiments, $Y^1$ is —NH—. In any of the foregoing embodiments of Formula (I), the carbon bearing $Y^1$ may be in the (R) stereochemical configuration. In any of the foregoing embodiments of Formula (I), the carbon bearing $Y^1$ may be in the (S) stereochemical configuration.

In some embodiments, $Y^2$ is —O—. In some embodiments, $Y^2$ is —S—. In some embodiments of Formula (I), $Y^2$ is —N($R^d$)— where $R^d$ is H, substituted or unsubstituted alkyl, substituted or unsubstituted alkenyl, substituted or unsubstituted alkynyl, substituted or unsubstituted cycloalkyl, or substituted or unsubstituted cycloalkenyl. In some of these embodiments, $Y^2$ is —N($R^d$)—, where $R^d$ is H or $C_1$-$C_6$ alkyl, such as methyl or ethyl. In some embodiments, $Y^2$ is —NH—. In any of the foregoing embodiments of Formula (I), the carbon bearing $Y^2$ may be in the (R) stereochemical configuration. In any of the foregoing embodiments of Formula (I), the carbon bearing $Y^2$ may be in the (S) stereochemical configuration. In any of the foregoing embodiments of Formula (I), the carbon bearing $Y^1$ may be in the (R) stereochemical configuration. In any of the foregoing embodiments of Formula (I), the carbon bearing $Y^1$ may be in the (S) stereochemical configuration.

In some embodiments of Formula (I), $Y^3$ is —N($R^d$)— where $R^d$ is H, substituted or unsubstituted alkyl, substituted or unsubstituted alkenyl, substituted or unsubstituted alkynyl, substituted or unsubstituted cycloalkyl, or substituted or unsubstituted cycloalkenyl. In some of these embodiments, $Y^3$ is —N($R^d$)—, where $R^d$ is H or $C_1$-$C_6$ alkyl, such as methyl or ethyl. In some embodiments, $Y^3$ is —NH—. In some embodiments, $Y^3$ is —O—. In some embodiments, $Y^3$ is —S—. In some embodiments, $Y^3$ is substituted or unsubstituted heterocycloalkyl. In some embodiments, $Y^3$ is substituted or unsubstituted pyrrolidinyl, pyrazolidinyl, imidazolidinyl, tetrahydrofuranyl, 1,3-dioxolanyl, tetrahydrothiophenyl, oxathiolanyl, sulfolanyl, piperidinyl, piperazinyl, tetrahydropyranyl, dioxanyl, thienyl, dithianyl, trithianyl, morpholinyl, thiomorpholinyl. In some embodiments, $Y^3$ is piperazinyl.

In some embodiments of Formula (I), $Y^4$ is —OR$^a$— where $R^a$ is H, substituted or unsubstituted alkyl, substituted or unsubstituted alkenyl, substituted or unsubstituted alkynyl, substituted or unsubstituted cycloalkyl, or substituted or unsubstituted cycloalkenyl. In some of these embodiments, $Y^4$ is —OR$^a$—, where $R^a$ is H or $C_1$-$C_6$ alkyl, such as methyl or ethyl. In some of these embodiments, $Y^4$ is —NHR$^c$, where $R^c$ is substituted or unsubstituted $C_1$-$C_6$ alkyl. In some embodiments, $Y^4$ is —OH. In some embodiments of Formula (I), $Y^4$ is —NR$^b$R$^c$, where $R^b$, and $R^c$ is each independently H, substituted or unsubstituted alkyl, substituted or unsubstituted alkenyl, substituted or unsubstituted alkynyl, substituted or unsubstituted cycloalkyl, or substituted or unsubstituted cycloalkenyl. In some of these embodiments, $Y^4$ is —NR$^b$R$^c$, where $R^b$, and $R^c$ is each independently H or $C_1$-$C_6$ alkyl, such as methyl or ethyl. In some of these embodiments, $Y^4$ is —NHR$^c$, where $R^c$ is substituted or unsubstituted $C_1$-$C_6$ alkyl. In some embodiments, $Y^4$ is —NH$_2$. In some embodiments of Formula (I), $Y^4$ is —SR$^a$— where $R^a$ is H, substituted or unsubstituted alkyl, substituted or unsubstituted alkenyl, substituted or unsubstituted alkynyl, substituted or unsubstituted cycloalkyl, or substituted or unsubstituted cycloalkenyl. In some of these embodiments, $Y^4$ is —SR$^a$—, where $R^a$ is H or $C_1$-$C_6$ alkyl, such as methyl or ethyl. In some of these embodiments, $Y^4$ is —NHR$^c$, where $R^c$ is substituted or unsubstituted $C_1$-$C_6$ alkyl. In some embodiments, $Y^4$ is —NHR$^c$, where $R^c$ is $C_1$-$C_6$ alkyl substituted with oxo. In some embodiments, $Y^4$ is —SH.

In some embodiments of Formula (I), each $R^a$, $R^b$, $R^c$, and $R^d$ is independently H, or substituted or unsubstituted alkyl. In some embodiments, each $R^a$, $R^b$, $R^c$, and $R^d$ is independently H or —CH$_3$. In some embodiments, $R^a$ and $R^b$ are independently H or —$C_1$-$C_6$ alkyl. In some embodiments, $R^b$ and $R^c$ are independently H or —$C_1$-$C_6$ alkyl. In some embodiments, $R^b$ and $R^c$ are each —$C_1$-$C_6$ alkyl. In some embodiments, one of $R^b$ and $R^c$ is H or —$C_1$-$C_6$ alkyl, and the other is —$C_1$-$C_6$ alkyl substituted with oxo. In some embodiments, one of $R^b$ or $R^c$ is —$C_1$-$C_6$ alkyl and the other is acetyl.

In some embodiments of Formula (I), W is (CH$_2$)$_m$—Z—(CH$_2$)$_p$, where Z is selected from the group consisting of substituted or unsubstituted $C_3$-$C_{12}$ cycloalkyl, substituted or unsubstituted $C_3$-$C_{12}$ cycloalkenyl, substituted or unsubstituted $C_5$-$C_{12}$ aryl, and substituted or unsubstituted $C_5$-$C_{12}$ heteroaryl. In some embodiments, Z is $C_3$-$C_{12}$ alkyl. In some embodiments, Z is substituted or unsubstituted aryl. In some embodiments, Z is phenyl. In some embodiments, Z is substituted or unsubstituted heteroaryl. In some embodiments, Z is substituted or unsubstituted cycloalkyl. In some embodiments, Z is cyclohexyl. In some embodiments, Z is substituted or unsubstituted heterocycloalkyl. In other embodiments, Z is (CH$_2$CH$_2$O)$_q$. In some embodiments of Formula (I), q is an integer from 1-12, inclusive. In some embodiments, q is an integer from 4-8, inclusive. In other embodiments, q is 1 or 2. In some embodiments of Formula (I), m and p are each independently an integer from 0-12, inclusive. In some embodiments, in is an integer from 0-8, inclusive. In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, in is 7. In some embodiments, m is 8. In some embodiments of Formula (I), p is an integer from 0-8, inclusive. In some embodiments, p is 0. In some embodiments, p is 1. In some embodiments, p is 2. In some embodiments, p is 3. In some embodiments, p is 4. In some embodiments, p is 5. In some embodiments, p is 6. In some embodiments, p is 7. In some embodiments, p is 8. In some embodiments, m and p are each 0.

In some embodiments, W is —$C_2$-$C_{12}$ alkyl-, wherein —$C_2$-$C_{12}$ alkyl- is optionally substituted. In some embodiments, W is —$C_2$-$C_{12}$ alkyl-. In some embodiments, W is —(CH$_2$)$_2$—. In some embodiments, W is —(CH$_2$)$_3$—. In some embodiments, W is —(CH$_2$)$_4$—. In some embodiments, W is —(CH$_2$)$_5$—. In some embodiments, W is —(CH$_2$)$_6$—. In some embodiments, W is —(CH$_2$)$_7$—. In some embodiments, W is —$C_3$-$C_{12}$ alkyl-, wherein —$C_3$-$C_{12}$ alkyl- is optionally substituted. In some embodiments, W is —$C_3$-$C_{12}$ alkyl-.

In some embodiments of Formula (I), $R^1$, $R^2$, $R^3$, $R^4$, $R^{8a}$, $R^{8b}$, $R^9$, $R^{10}$, $R^{11}$, $R^{12}$, $R^{13}$, and $R^{14}$ are each independently H or substituted or unsubstituted alkyl, such as unsubstituted $C_1$-$C_6$ alkyl. In some embodiments, $R^1$ is H. In other embodiments, $R^1$ is $C_1$-$C_6$ alkyl, such as methyl. In some embodiments, $R^2$ is H. In some embodiments, $R^2$ is substituted or unsubstituted alkyl. In some embodiments, $R^2$ is $C_1$-$C_6$ alkyl, such as methyl. In some embodiments, $R^2$ is $C_1$-$C_6$ alkyl optionally substituted with NH$_2$. In yet other embodiments, $R^2$ is —(CH$_2$)$_4$NH$_2$ which is optionally substituted. In some embodiments, $R^3$ is H. In other embodiments, $R^3$ is $C_1$-$C_6$ alkyl, such as methyl. In some embodiments, $R^4$ is H. In other embodiments, $R^4$ is $C_1$-$C_6$ alkyl, such as methyl. In particular embodiments, $R^4$ is isobutyl. In some embodiments, $R^{8a}$ and $R^{8b}$ are both H. In other embodiments, $R^{8a}$ and $R^{8b}$ are each independently $C_1$-$C_6$ alkyl, such as methyl. In some embodiments, $R^{8a}$ and $R^{8b}$ are both methyl. In yet other embodiments, one of $R^{8a}$ and $R^{8b}$ is H and the other is $C_1$-$C_6$ alkyl, such as methyl. In yet other embodiments, one of $R^{8a}$ and $R^{8b}$ is H and the other is —(CH$_2$)$_4$NH$_2$, which is optionally substituted. In some embodiments, $R^9$ is H. In other embodiments, $R^9$ is $C_1$-$C_6$ alkyl, such as methyl. In some embodiments, $R^{10}$ is H. In other embodiments, $R^{10}$ is $C_1$-$C_6$ alkyl, such as methyl. In particular embodiments, $R^{10}$ is sec-butyl. In some embodiments, $R^9$ is H. In other embodiments, $R^9$ is $C_1$-$C_6$ alkyl, such as methyl. In some embodiments, $R^{12}$ and $R^{13}$ are both H. In other embodiments, $R^{12}$ and $R^{13}$ are each independently $C_1$-$C_6$ alkyl, such as methyl. In yet other embodiments, one of $R^{12}$ and $R^{13}$ is H and the other is $C_1$-$C_6$ alkyl, such as methyl. In some embodiments, $R^{14}$ is H. In other embodiments, $R^{14}$ is $C_1$-$C_6$ alkyl, such as methyl.

In some embodiments, $R^1$, $R^3$, $R^4$, $R^5$, $R^6$, $R^{8a}$, $R^{8b}$, $R^9$, $R^{10}$, $R^{11}$, $R^{12}$, $R^{13}$, and $R^{14}$ are each independently H or $C_1$-$C_6$ alkyl. In some embodiments, $R^1$, $R^5$, $R^6$, $R^{8a}$, and $R^{14}$ are each methyl.

In some embodiments of Formula (I), $R^1$ is methyl, $R^2$ is methyl, $R^3$ is H, and $R^4$ is isobutyl. In some of these embodiments, $X^1$ is —O—. In some of these embodiments, $R^{15}$ is substituted or unsubstituted aryl and n is 1. In particular embodiments, $R^{15}$ is substituted or unsubstituted phenyl, and n is 1. The substituted phenyl may be a phenyl substituted at the para position. The substituted phenyl may be a phenyl substituted at the meta position. The substituted phenyl may be phenyl substituted with one or more fluoro, chloro, trifluoromethyl, or hydroxyl groups. In particular embodiments, the substituted phenyl is 4-fluorophenyl, 4-chlorophenyl, 4-(trifluoromethyl)phenyl, or 4-hydroxyphenyl. In some embodiments, the substituted phenyl is 4-cyanophenyl. In any of the foregoing embodiments of Formula (I), n may be 0. In any of the foregoing embodiments of Formula (I), n may be 1. In any of the foregoing embodiments of Formula (I), n may be 2.

In some embodiments of Formula (I), $R^5$ is H or $C_1$-$C_6$ alkyl, such as methyl. In other embodiments of Formula (I), $R^5$ is halo. In some such embodiments, $R^5$ is fluoro. In other such embodiments, $R^5$ is chloro. In yet other embodiments of Formula (I), $R^5$ is perhaloalkyl. In some such embodiments, $R^5$ is trifluoromethyl.

In some embodiments of Formula (I), $R^6$ is H or $C_1$-$C_6$ alkyl. In some such embodiments, $R^6$ is H. In other such embodiments, $R^6$ is methyl. In other embodiments of Formula (I) embodiments, $R^6$ is halo. In some such embodiments, $R^6$ is fluoro. In some such embodiments, $R^6$ is chloro. In yet other embodiments of Formula (I), $R^6$ is substituted or unsubstituted aryl. In particular embodiments, $R^6$ is substituted phenyl. In other particular embodiments, $R^6$ is unsubstituted phenyl.

In some embodiments of Formula (I), $R^7$ is H, $C_1$-$C_6$ alkyl, $C_1$-$C_6$ alkenyl, or $C_1$-$C_6$ alkynyl. In some embodiments of Formula (I), $R^7$ is H or $C_1$-$C_6$ alkyl. In some such embodiments, $R^7$ is methyl. In other such embodiments, $R^7$ is H. In particular embodiments, $R^7$ is

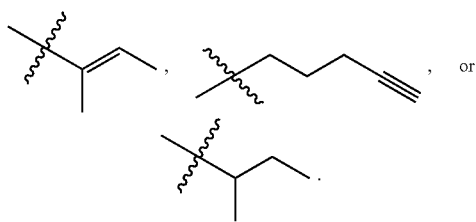

When $R^7$ is sec-butyl, it may be (S)-sec-butyl or (R)-sec-butyl. In some embodiments, $R^7$ is substituted or unsubstituted aryl, such as phenyl.

In some embodiments of Formula (I), $R^5$, $R^6$, and $R^7$ are all substituted or unsubstituted alkyl. In particular embodiments of Formula (I), $R^5$ and $R^6$ are both methyl, and $R^7$ is

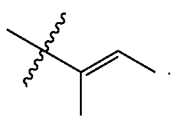 [SMILES: */C(C)=C/C]

In other particular embodiments of Formula (I), $R^5$ and $R^6$ are both methyl, and $R^7$ is

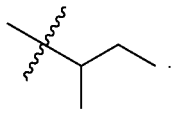 [SMILES: *C(C)CC]

In other particular embodiments of Formula (I), $R^5$ is methyl, and $R^6$ and $R^7$ are both hydrogen. In yet other particular embodiments of Formula (I), $R^5$ and $R^6$ are both methyl, and $R^7$ is hydrogen.

In some embodiments of Formula (I), $R^{15}$ is substituted or unsubstituted aryl, substituted or unsubstituted heteroaryl, substituted or unsubstituted cycloalkyl, or substituted or unsubstituted heterocyclyl. In any variation of Formula (I) described herein, $R^{15}$ may be substituted or unsubstituted aryl, substituted or unsubstituted heteroaryl, or substituted or unsubstituted heterocyclyl. In some embodiments of Formula (I), $R^{15}$ is substituted or unsubstituted aryl, such as phenyl. In some embodiments, $R^{15}$ is phenyl optionally substituted with halo, hydroxy, $C_1$-$C_6$ alkoxy, $C_1$-$C_6$ alkyl, or $C_1$-$C_6$ perhaloalkyl. In some embodiments, $R^{15}$ is phenyl substituted with halo, such as fluoro or chloro. In other embodiments, $R^{15}$ is phenyl substituted with hydroxyl. In other embodiments, $R^{15}$ is phenyl substituted with alkoxy. In other embodiments, $R^{15}$ is phenyl substituted with cyano. In other embodiments, $R^{15}$ is phenyl substituted with perhalomethyl. In some embodiments, $R^{15}$ is phenyl which is substituted at the para position. In some embodiments, $R^{15}$ is 4-chlorophenyl. In other embodiments, $R^{15}$ is 4-cyanophenyl. In yet other embodiments, $R^{15}$ is unsubstituted phenyl. In any of the foregoing embodiments, n may be 1. In any of the foregoing embodiments, n may be 2. In any of the foregoing embodiments, n may be 0.

In some embodiments, the carbon bearing $R^2$ may be in the (S) stereochemical configuration. In some embodiments, the carbon bearing $R^2$ may be in the (R) stereochemical configuration. In some embodiments, the carbon bearing $R^4$ may be in the (S) stereochemical configuration. In some embodiments, the carbon bearing $R^4$ may be in the (R) stereochemical configuration. In some embodiments, the carbon bearing $R^6$ may be in the (S) stereochemical configuration. In some embodiments, the carbon bearing $R^6$ may be in the (R) stereochemical configuration. In some embodiments, the carbon bearing $R^7$ may be in the (S) stereochemical configuration. In some embodiments, the carbon bearing $R^7$ may be in the (R) stereochemical configuration. In some embodiments, the carbon bearing $R^{8a}$ and $R^{8b}$ may be in the (S) stereochemical configuration. In some embodiments, the carbon bearing $R^{8a}$ and $R^{8b}$ may be in the (R) stereochemical configuration. In some embodiments, the carbon bearing $R^{10}$ may be in the (S) stereochemical configuration. In some embodiments, the carbon bearing $R^{10}$ may be in the (R) stereochemical configuration. In some embodiments, the carbon bearing $R^{12}$ and $R^{13}$ may be in the (S) stereochemical configuration. In some embodiments, the carbon bearing $R^{12}$ and $R^{13}$ may be in the (R) stereochemical configuration. In any of the foregoing embodiments of Formula (I), the carbon bearing $Y^1$ may be in the (R) stereochemical configuration. In any of the foregoing embodiments of Formula (I), the carbon bearing $Y^1$ may be in the (S) stereochemical configuration.

In some variations of any of the embodiments of Formula (I) provided herein, $Y^1$, $Y^2$, and $Y^3$ are each independently —N($R^d$)—, —O—, or —S—. In some variations of any of the embodiments of Formula (I) provided herein, $Y^1$ is —O— and $Y^2$ is —O—. In some variations, $Y^1$ is —S— and $Y^2$ is —O—. In some variations, $Y^1$ is —O— and $Y^2$ is —S—. In some variations, $Y^1$ is —S— and $Y^2$ is —S—. In some variations, $Y^1$ and $Y^2$ are each —N($R^d$)—, where each $R^d$ is independently H, or substituted or unsubstituted alkyl, substituted or unsubstituted alkenyl, substituted or unsubstituted alkynyl, substituted or unsubstituted cycloalkyl, or substituted or unsubstituted cycloalkenyl. In some variations, $Y^1$ is —O— and $Y^2$ is —N($R^d$)—, where each $R^d$ is independently H, or substituted or unsubstituted alkyl, substituted or unsubstituted alkenyl, substituted or unsubstituted alkynyl, substituted or unsubstituted cycloalkyl, or substituted or unsubstituted cycloalkenyl. In some variations, $Y^1$ is —S— and $Y^2$ is —N($R^d$)—, where each $R^d$ is independently H, or substituted or unsubstituted alkyl, substituted or unsubstituted alkenyl, substituted or unsubstituted alkynyl, substituted or unsubstituted cycloalkyl, or substituted or unsubstituted cycloalkenyl. In some variations, $Y^1$ is —N($R^d$)—, where each $R^d$ is independently H, or substituted or unsubstituted alkyl, substituted or unsubstituted alkenyl, substituted or unsubstituted alkynyl, substituted or unsubstituted cycloalkyl, or substituted or unsubstituted cycloalkenyl, and $Y^2$ is —O—. In any of the foregoing embodiments of Formula (I), the compound may contain one of the following features: (i) $Y^3$ is —N($R^d$)— and $Y^4$ is —N$R^bR^c$; (ii) $Y^3$ is —N($R^d$)— and $Y^4$ is —O$R^a$; (iii) $Y^3$ is —N($R^d$)— and $Y^4$ is —S$R^a$; (iv) $Y^3$ is —O— and $Y^4$ is —N$R^bR^c$; (v) $Y^3$ is —O— and $Y^4$ is —O$R^a$; (vi) $Y^3$ is —O— and $Y^4$ is —S$R^a$; (vii) $Y^3$ is —S— and $Y^4$ is —N$R^bR^c$; (viii) $Y^3$ is —S— and $Y^4$ is —O$R^a$; (ix) $Y^3$ is —S— and $Y^4$ is —S$R^a$; (x) $Y^3$ is substituted or unsubstituted heterocycloalkyl and $Y^4$ is —O$R^a$; (xi) $Y^3$ is substituted or unsubstituted heterocycloalkyl and $Y^4$ is —N$R^bR^c$; or (xii) $Y^3$ is substituted or unsubstituted heterocycloalkyl and $Y^4$ is —S$R^a$. In any of the foregoing embodiments of Formula (I), the compound may further contain one of the following features: (i) $X^1$ is —O— and $X^2$ is O; (ii) $X^1$ is —O— and $X^2$ is S; (iii) $X^1$ is —N($R^d$)— and $X^2$ is O; or (iv) $X^1$ is —N($R^d$)— and $X^2$ is S. In any of the foregoing embodiments of Formula (I) may be $(CH_2)_m$—Z—$(CH_2)_p$; where Z is selected from the group consisting of substituted or unsubstituted $C_3$-$C_{12}$ cycloalkyl, substituted or unsubstituted $C_3$-$C_{12}$ cycloalkenyl, substituted or unsubstituted $C_5$-$C_{12}$ aryl, and substituted or unsubstituted $C_5$-$C_{12}$ heteroaryl. In some embodiments, Z is $C_3$-$C_{12}$ alkyl. In some embodiments, Z is substituted or unsubstituted aryl. In some embodiments, Z is phenyl. In some embodiments, Z is substituted or unsubstituted heteroaryl. In some embodiments, Z is substituted or unsubstituted cycloalkyl. In some embodiments, Z is cyclohexyl. In some embodiments, Z is substituted or unsubstituted heterocycloalkyl. In other embodiments, Z is $(CH_2CH_2O)_q$. In some embodiments of Formula (I), q is an integer from 1-12, inclusive. In some embodiments, q is an integer from 4-8, inclusive. In other embodiments, q is 1 or 2. In some embodiments of Formula (I), m and p are each independently an integer from 0-12, inclusive. In some embodiments, in is an integer from 0-8, inclusive. In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments of Formula (I), p is an integer from 0-8, inclusive. In some embodiments, p is 2. In some embodiments, p is 5. In some embodiments, p is 7. In some embodiments, m and p are each 0. In any of the foregoing embodiments of Formula (I), W is —$C_2$-$C_{12}$ alkyl-, wherein —$C_2$-$C_{12}$ alkyl- is optionally substituted. In some embodiments, W is —$C_2$-$C_{12}$ alkyl-. In some embodiments, W is —$(CH_2)_2$—. In some embodiments, W is —$(CH_2)_4$—. In some embodiments, W is —$(CH_2)_5$—. In some embodiments, W is —$(CH_2)_6$—. In some embodiments, W is —$(CH_2)_7$—.

In any of the foregoing embodiments of Formula (I), the carbon bearing $Y^1$ may be in the (R) stereochemical configuration. In any of the foregoing embodiments of Formula (I), the carbon bearing $Y^1$ may be in the (S) stereochemical configuration. In any of the foregoing embodiments of Formula (Ib), $Y^2$ may be in the (R) stereochemical configuration. In any of the foregoing embodiments of Formula (Ib), $Y^2$ may be in the (S) stereochemical configuration.

In some embodiments, $Y^1$, and $Y^2$ are each —O—, $X^2$ is O, and $Y^3$ is —N($R^d$)—.

In another aspect, the compound of Formula (I) is a compound of Formula (Ia):

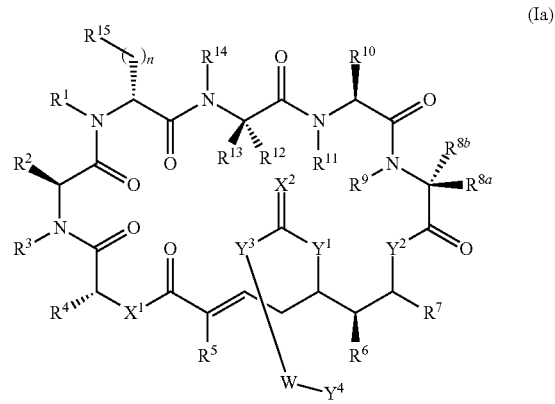

(Ia)

or a salt thereof, wherein $R^1$, $R^2$, $R^3$, $R^4$, $R^5$, $R^6$, $R^7$, $R^{8a}$, $R^{8b}$, $R^9$, $R^{10}$, $R^{11}$, $R^{12}$, $R^{13}$, $R^{14}$, $R^{15}$, n, $X^1$, $X^2$, W, $Y^1$, $Y^2$, $Y^3$ and $Y^4$ are as defined for Formula (I) and any variation or embodiment thereof, provided that i) when $Y^4$ is —OH, W is not —$(CH_2)_2$— or —$(CH_2CH_2O)_3(CH_2)_2$—; and ii) when $Y^4$ is —NH$R^c$ or —N(CH$_3$)$R^c$, W is not —$(CH_2)_2$—, —$(CH_2)_6$—, or —CH$_2$(CH$_2$CH$_2$O)$_3$(CH$_2$)$_3$—.

In another aspect, the compound of Formula (I) is a compound of Formula (Ib):

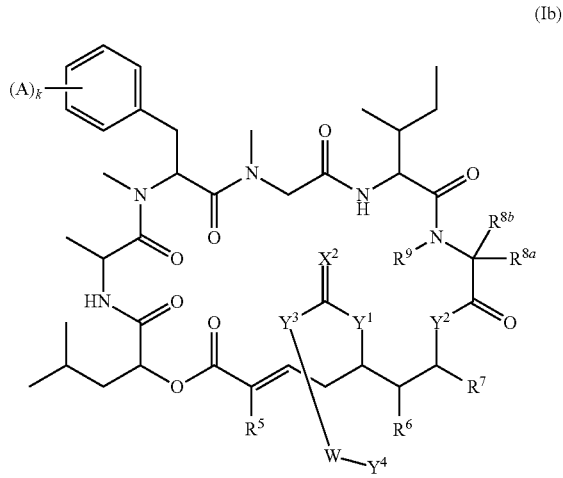

(Ib)

or a salt thereof, wherein
$R^5$, $R^6$, $R^7$, $R^{8a}$, $R^{8b}$, $R^9$, $X^2$, W, $Y^1$, $Y^2$, $Y^3$, and $Y^4$ are defined as for Formula (I) or any variation or embodiment thereof.

A is halo, perhalomethyl, cyano, nitro, amino, hydroxy, or alkoxy; and k is 0, 1, 2, 3, 4, or 5, provided that i) when $Y^4$ is —OH, W is not —$(CH_2)_2$— or —$(CH_2CH_2O)_3(CH_2)_2$—; and ii) when $Y^4$ is —$NHR^c$ or —$N(CH_3)R^c$, W is not —$(CH_2)_2$—, —$(CH_2)_6$—, or —$CH_2(CH_2CH_2O)_3(CH_2)_3$—.

In some embodiments of Formula (Ib), $R^{8a}$ is H and $R^{8b}$ is methyl. In some embodiments, $R^{8a}$ and $R^{8b}$ are both H. In some embodiments, $R^{8a}$ is H and $R^{8b}$ is ethyl. In some embodiments, $R^{8a}$ and $R^{8b}$ are both methyl. In any of these embodiments, $R^9$ may be H. In any of these embodiments, $R^9$ may be methyl.

In some of the aforementioned embodiments of Formula (Ib), k is 1. In some such embodiments, A is halo. In some such embodiments, A is fluoro. In some such embodiments, A is chloro. In some such embodiments, A is trifluoromethyl. In some such embodiments, A is hydroxy. In some embodiments, A is cyano. In particular embodiments where k is 1. A is fluoro, chloro, trifluoromethyl, or hydroxy and is attached at the para position on the phenyl ring. In some embodiments where k is 1, A is cyano and is attached at the para position on the phenyl ring. In some embodiments where k is 1, A is cyano and is attached at the meta position on the phenyl ring. In other particular embodiments where k is 1, A is fluoro, chloro, trifluoromethyl, or hydroxy and is attached at the meta position on the phenyl ring. In any of the foregoing embodiments of Formula (Ib), the compound may contain one of the following features: i) $Y^1$ and $Y^2$ are each —O—; ii) $Y^1$ is —O—, and $Y^2$ is —S—; iii) $Y^1$ is —O—, and $Y^2$ is —$N(R^d)$—; (iv) $Y^1$ is —O—, and $Y^2$ is —NH—; and (v) $Y^1$ is —O—, and $Y^2$ is —$N(CH_3)$—. In any of the foregoing embodiments of Formula (Ib), the compound may contain one of the following features: i) $Y^1$ and $Y^2$ are each —S—; ii) $Y^1$ is —S—, and $Y^2$ is —O—; iii) $Y^1$ is —S—, and $Y^2$ is —$N(R^d)$—; (iv) $Y^1$ is —S—, and $Y^2$ is —NH—; and (v) $Y^1$ is —S—, and $Y^2$ is —$N(CH_3)$—. In any of the foregoing embodiments of Formula (Ib), the compound may contain one of the following features: i) $Y^1$ and $Y^2$ are each —$N(R^d)$—; ii) $Y^1$ is —$N(R^d)$—, and $Y^2$ is —S—; iii) $Y^1$ is —$N(R^d)$—, and $Y^2$ is —O—; (iv) $Y^1$ is —$N(R^d)$—, and $Y^2$ is —NH—; (v) $Y^1$ is —$N(R^d)$—, and $Y^2$ is —$N(CH_3)$—; (vi) $Y^1$ is —$N(CH_3)$—, and $Y^2$ is —$N(CH_3)$—; (vii) $Y^1$ is —NH—, and $Y^2$ is —$N(CH_3)$—; (viii) $Y^1$ is —$N(CH_3)$—, and $Y^2$ is —NH—; and $Y^1$ is —NH—, and $Y^2$ is —NH—. In any of the foregoing embodiments of Formula (Ib), the compound may contain one of the following features: (i) $Y^3$ is —$N(R^d)$— and $Y^4$ is —$NR^bR^c$; (ii) $Y^3$ is —$N(R^d)$— and $Y^4$ is —$OR^a$; (iii) $Y^3$ is —$N(R^d)$— and $Y^4$ is —$SR^a$; (iv) $Y^3$ is —O— and $Y^4$ is —$NR^bR^c$; (v) $Y^3$ is —O— and $Y^4$ is —$OR^a$; (vi) $Y^3$ is —O— and $Y^4$ is —$SR^a$; (vii) $Y^3$ is —S— and $Y^4$ is —$NR^bR^c$; (viii) $Y^3$ is —S— and $Y^4$ is —$OR^a$; (ix) $Y^3$ is —S— and $Y^4$ is —$SR^a$; (x) $Y^3$ is substituted or unsubstituted heterocycloalkyl and $Y^4$ is —$OR^a$; (xi) $Y^3$ is substituted or unsubstituted heterocycloalkyl and $Y^4$ is —$NR^bR^c$; or (xii) $Y^3$ is substituted or unsubstituted heterocycloalkyl and $Y^4$ is —$SR^a$. In any of the foregoing embodiments of Formula (Ib), the compound may further contain one of the following features: (i) $X^1$ is —O— and $X^2$ is O; (ii) $X^1$ is —O— and $X^2$ is S; (iii) $X^1$ is —$N(R^d)$— and $X^2$ is O; or (iv) $X^1$ is —$N(R^d)$— and $X^2$ is S. In any of the foregoing embodiments of Formula (Ib), W may be $(CH_2)_m$—Z—$(CH_2)_p$, where Z is selected from the group consisting of substituted or unsubstituted $C_3$-$C_{12}$ cycloalkyl, substituted or unsubstituted $C_3$-$C_{12}$ cycloalkenyl, substituted or unsubstituted $C_5$-$C_{12}$ aryl, and substituted or unsubstituted $C_5$-$C_{12}$ heteroaryl. In some embodiments, Z is $C_3$-$C_{12}$ alkyl. In some embodiments, Z is substituted or unsubstituted aryl. In some embodiments, Z is phenyl. In some embodiments, Z is substituted or unsubstituted heteroaryl. In some embodiments, Z is substituted or unsubstituted cycloalkyl. In some embodiments, Z is cyclohexyl. In some embodiments, Z is substituted or unsubstituted heterocycloalkyl. In other embodiments, Z is $(CH_2CH_2O)_q$. In some embodiments of Formula (Ib), q is an integer from 1-12, inclusive. In some embodiments, q is an integer from 4-8, inclusive. In other embodiments, q is 1 or 2. In some embodiments of Formula (Ib), m and p are each independently an integer from 0-12, inclusive. In some embodiments, m is an integer from 0-8, inclusive. In some embodiments, m is 2. In some embodiments, in is 5. In some embodiments, m is 7. In some embodiments of Formula (Ib), p is an integer from 0-8, inclusive. In some embodiments, p is 2. In some embodiments, p is 5. In some embodiments, p is 7. In some embodiments, m and p are each 0. In any of the foregoing embodiments of Formula (Ib), W is —$C_2$-$C_{12}$ alkyl-, wherein —$C_2$-$C_{12}$ alkyl- is optionally substituted. In some embodiments, W is —$C_2$-$C_{12}$ alkyl-. In some embodiments, W is —$(CH_2)_2$—. In some embodiments, W is —$(CH_2)_4$—. In some embodiments, W is —$(CH_2)_5$—. In some embodiments, W is —$(CH_2)_6$—. In some embodiments, W is —$(CH_2)_7$—. In any of the foregoing embodiments of Formula (Ib), $Y^1$ may be in the (R) stereochemical configuration. In any of the foregoing embodiments of Formula (Ib), $Y^1$ may be in the (S) stereochemical configuration. In any of the foregoing embodiments of Formula (Ib), $Y^2$ may be in the (R) stereochemical configuration. In any of the foregoing embodiments of Formula (Ib), $Y^2$ may be in the (S) stereochemical configuration.

In some embodiments of Formula (Ib), k is 0. In some of these embodiments of Formula (Ib), the compound may contain one of the following features: i) $Y^1$ and $Y^2$ are each —O—; ii) $Y^1$ is —O—, and $Y^2$ is —S—; iii) $Y^1$ is —O—, and $Y^2$ is —$N(R^d)$—; (iv) $Y^1$ is —O—, and $Y^2$ is —NH—; and (v) $Y^1$ is —O—, and $Y^2$ is —$N(CH_3)$—. In some of these embodiments of Formula (Ib), the compound may contain one of the following features: i) $Y^1$ and $Y^2$ are each —S—; ii) $Y^1$ is —S—, and $Y^2$ is —O—; iii) $Y^1$ is —S—, and $Y^2$ is —$N(R^d)$—; (iv) $Y^1$ is —S—, and $Y^2$ is —NH—; and (v) $Y^1$ is —S—, and $Y^2$ is —$N(CH_3)$—. In some of these embodiments of Formula (Ib), the compound may contain one of the following features: i) $Y^1$ and $Y^2$ are each —$N(R^d)$—; ii) $Y^1$ is —$N(R^d)$—, and $Y^2$ is —S—; iii) $Y^1$ is —$N(R^d)$—, and $Y^2$ is —O—; (iv) $Y^1$ is —$N(R^d)$—, and $Y^2$ is —NH—; (v) $Y^1$ is —$N(R^d)$—, and $Y^2$ is —$N(CH_3)$—; (vi) $Y^1$ is —$N(CH_3)$—, and $Y^2$ is —$N(CH_3)$—; (vii) $Y^1$ is —NH—, and $Y^2$ is —$N(CH_3)$—; (viii) $Y^1$ is —$N(CH_3)$—, and $Y^2$ is —NH—; and $Y^1$ is —NH—, and $Y^2$ is —NH—. In any of the foregoing embodiments of Formula (Ib), the compound may contain one of the following features: (i) $Y^3$ is —$N(R^d)$— and $Y^4$ is —$NR^bR^c$; (ii) $Y^3$ is —$N(R^d)$— and $Y^4$ is —$OR^a$; (iii) $Y^3$ is —$N(R^d)$— and $Y^4$ is —$SR^a$; (iv) $Y^3$ is —O— and $Y^4$ is —$NR^bR^c$; (v) $Y^3$ is —O— and $Y^4$ is —$OR^a$; (vi) $Y^3$ is —O— and $Y^4$ is —$SR^a$; (vii) $Y^3$ is —S— and $Y^4$ is —$NR^bR^c$; (viii) $Y^3$ is —S— and $Y^4$ is —$OR^a$; (ix) $Y^3$ is —S— and $Y^4$ is —$SR^a$; (x) $Y^3$ is substituted or unsubstituted heterocycloalkyl and $Y^4$ is —$OR^a$; (xi) $Y^3$ is substituted or unsubstituted heterocycloalkyl and $Y^4$ is —$NR^bR^c$; or (xii) $Y^3$ is substituted or unsubstituted heterocycloalkyl and $Y^4$ is —$SR^a$. In any of the foregoing embodiments of Formula (Ib), the compound may further contain one of the following features: (i) $X^1$ is —O— and $X^2$ is O; (ii) $X^1$ is —O— and $X^2$ is S; (iii) $X^1$ is —$N(R^d)$— and $X^2$ is O; or (iv) $X^1$ is —N($R^d$)— and $X^2$ is S. In any of the foregoing embodiments of Formula (Ib), W may be $(CH_2)_m$—Z—$(CH_2)_p$, where Z is selected from the group consisting of substituted or unsubstituted $C_3$-$C_{12}$ cycloalkyl, substituted or unsubstituted $C_3$-$C_{12}$ cycloalkenyl, substituted or unsubstituted $C_5$-$C_{12}$ aryl, and substituted or unsubstituted $C_5$-$C_{12}$ heteroaryl. In some embodiments, Z is $C_3$-$C_{12}$ alkyl. In some embodiments, Z is substituted or unsubstituted aryl. In some embodiments, Z is phenyl. In some embodiments, Z is substituted or unsubstituted heteroaryl. In some embodiments, Z is substituted or unsubstituted cycloalkyl. In some embodiments, Z is cyclohexyl. In some embodiments, Z is substituted or unsubstituted heterocycloalkyl. In other embodiments, Z is $(CH_2CH_2O)_q$. In some embodiments of Formula (Ib), q is an integer from 1-12, inclusive. In some embodiments, q is an integer from 4-8, inclusive. In other embodiments, q is 1 or 2. In some embodiments of Formula (Ib), m and p are each independently an integer from 0-12, inclusive. In some embodiments, m is an integer from 0-8, inclusive. In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments of Formula (Ib), p is an integer from 0-8, inclusive. In some embodiments, p is 0. In some embodiments, p is 1. In some embodiments, p is 2. In some embodiments, p is 3. In some embodiments, p is 4. In some embodiments, p is 5. In some embodiments, p is 6. In some embodiments, p is 7. In some embodiments, p is 8. In some embodiments, m and p are each 0. In any of the foregoing embodiments of Formula (Ib), W is —$C_2$-$C_{12}$ alkyl-, wherein —$C_2$-$C_{12}$ alkyl- is optionally substituted. In some embodiments, W is —$C_2$-$C_{12}$ alkyl-. In some embodiments, W is —$(CH_2)_2$—. In some embodiments, W is —$(CH_2)_3$—. In some embodiments, W is —$(CH_2)_4$—. In some embodiments, W is —$(CH_2)_5$—. In some embodiments, W is —$(CH_2)_6$—. In some embodiments, W is —$(CH_2)_7$—. In some embodiments, W is —$C_3$-$C_{12}$ alkyl-, wherein —$C_3$-$C_{12}$ alkyl- is optionally substituted. In come embodiments, W is —$C_3$-$C_{12}$ alkyl-. In any of the foregoing embodiments of Formula (Ib), $Y^1$ may be in the (R) stereochemical configuration. In any of the foregoing embodiments of Formula (Ib), $Y^1$ may be in the (S) stereochemical configuration. In any of the foregoing embodiments of Formula (Ib), $Y^2$ may be in the (R) stereochemical configuration. In any of the foregoing embodiments of Formula (Ib), $Y^2$ may be in the (S) stereochemical configuration.

In some embodiments of Formula (Ib), $R^5$ is H or $C_1$-$C_6$ alkyl, such as methyl. In other embodiments of Formula (Ib), $R^5$ is halo. In some such embodiments, $R^5$ is fluoro. In other such embodiments, $R^5$ is chloro. In yet other embodiments of Formula (Ib), $R^5$ is perhaloalkyl. In some such embodiments, $R^5$ is trifluoromethyl.

In some embodiments of Formula (Ib), $R^6$ is H or $C_1$-$C_6$ alkyl. In some such embodiments, $R^6$ is H. In other such embodiments, $R^6$ is methyl. In other embodiments of Formula (Ib) embodiments, $R^6$ is halo. In some such embodiments, $R^6$ is fluoro. In some such embodiments, $R^6$ is chloro. In yet other embodiments of Formula (Ib), $R^6$ is substituted or unsubstituted aryl. In particular embodiments, $R^6$ is substituted phenyl. In other particular embodiments, $R^6$ is unsubstituted phenyl.

In some embodiments of Formula (Ib), R is H or $C_1$-$C_6$ alkyl. In some such embodiments, $R^7$ is methyl. In other such embodiments, $R^7$ is H. In particular embodiments, $R^7$ is

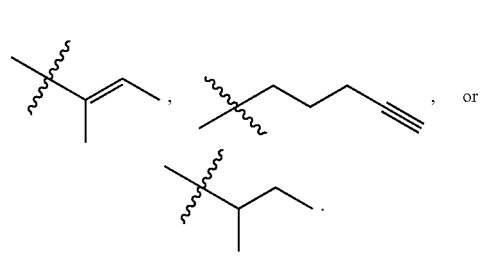

When $R^7$ is sec-butyl, it may be (S)-sec-butyl or (R)-sec-butyl. In some embodiments, $R^7$ is substituted or unsubstituted aryl, such as phenyl.

In some embodiments of Formula (Ib), $R^5$, $R^6$, and $R^7$ are all substituted or unsubstituted alkyl. In particular embodiments of Formula (Ib), $R^5$ and $R^6$ are both methyl, and $R^7$ is

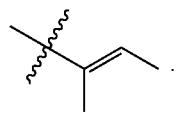 [SMILES: */C(C)=C/C]

In other particular embodiments of Formula (Ib), $R^5$ and $R^6$ are both methyl, and $R^7$ is

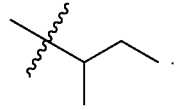 [SMILES: *C(C)CC]

In other particular embodiments of Formula (Ib), $R^5$ is methyl, and $R^6$ and $R^7$ are both hydrogen. In yet other particular embodiments of Formula (Ib), $R^5$ and $R^6$ are both methyl, and $R^7$ is hydrogen.

In some variations of Formula (Ib), $R^{8a}$ and $R^{8b}$ are independently selected from H and methyl, $R^9$ is H, $R^5$ and $R^6$ are both methyl. In some variations, $Y^1$ is —O— and $Y^2$ is —O—. In any of the foregoing embodiments, the compound may contain one of the following features: (i) $Y^3$ is —N($R^d$)— and $Y^4$ is —$NR^bR^c$; (ii) $Y^3$ is —N($R^d$)— and $Y^4$ is —$OR^a$; (iii) $Y^3$ is —N($R^d$)— and $Y^4$ is —$SR^a$; (iv) $Y^3$ is —O— and $Y^4$ is —$NR^bR^c$; (v) $Y^3$ is —O— and $Y^4$ is —$OR^a$; (vi) $Y^3$ is —O— and $Y^4$ is —$SR^a$; (vii) $Y^3$ is —S— and $Y^4$ is —$NR^bR^c$; (viii) $Y^3$ is —S— and $Y^4$ is —$OR^a$; (ix) $Y^3$ is —S— and $Y^4$ is —$SR^a$; (x) $Y^3$ is substituted or unsubstituted heterocycloalkyl and $Y^4$ is —$OR^a$; (xi) $Y^3$ is substituted or unsubstituted heterocycloalkyl and $Y^4$ is —$NR^bR^c$; or (xii) $Y^3$ is substituted or unsubstituted heterocycloalkyl and $Y^4$ is —$SR^a$. In any of the foregoing embodiments of Formula (I), the compound may further contain one of the following features: (i) $X^1$ is —O— and $X^2$ is O; (ii) $X^1$ is —O— and $X^2$ is S; (iii) $X^1$ is —N($R^d$)— and $X^2$ is O; or (iv) $X^1$ is —N($R^d$)— and $X^2$ is S. In any of the foregoing embodiments of Formula (Ib), W may be $(CH_2)_m$—Z—$(CH_2)_p$, where Z is selected from the group consisting of substituted or unsubstituted $C_3$-$C_{12}$ cycloalkyl, substituted or unsubstituted $C_3$-$C_{12}$ cycloalkenyl, substituted or unsubstituted $C_5$-$C_{12}$ aryl, and substituted or unsubstituted $C_5$-$C_{12}$ heteroaryl. In some embodiments, Z is $C_3$-$C_{12}$ alkyl. In some embodiments, Z is substituted or unsubstituted aryl. In some embodiments, Z is phenyl. In some embodiments, Z is substituted or unsubstituted heteroaryl. In some embodiments, Z is substituted or unsubstituted cycloalkyl. In some embodiments, Z is cyclohexyl. In some embodiments, Z is substituted or unsubstituted heterocycloalkyl. In other embodiments, Z is $(CH_2CH_2O)_q$. In some embodiments of Formula (Ib), q is an integer from 1-12, inclusive. In some embodiments, q is an integer from 4-8, inclusive. In other embodiments, q is 1 or 2. In some embodiments of Formula (Ib), m and p are each independently an integer from 0-12, inclusive. In some embodiments, m is an integer from 0-8, inclusive. In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments of Formula (Ib), p is an integer from 0-8, inclusive. In some embodiments, p is 0. In some embodiments, p is 1. In some embodiments, p is 2. In some embodiments, p is 3. In some embodiments, p is 4. In some embodiments, p is 5. In some embodiments, p is 6. In some embodiments, p is 7. In some embodiments, p is 8. In some embodiments, m and p are each 0. In any of the foregoing embodiments of Formula (Ib), W is —$C_2$-$C_{12}$ alkyl-, wherein —$C_2$-$C_{12}$ alkyl- is optionally substituted. In some embodiments, W is —$C_2$-$C_{12}$ alkyl-. In some embodiments, W is —$(CH_2)_2$—. In some embodiments, W is —$(CH_2)_3$—. In some embodiments, W is —$(CH_2)_4$—. In some embodiments, W is —$(CH_2)_5$—. In some embodiments, W is —$(CH_2)_6$—. In some embodiments, W is —$(CH_2)_7$—. In some embodiments, W is —$C_3$-$C_{12}$ alkyl-, wherein —$C_3$-$C_{12}$ alkyl- is optionally substituted. In some embodiments, W is —$C_3$-$C_{12}$ alkyl-. In any of the foregoing embodiments of Formula (Ib), $Y^1$ may be in the (R) stereochemical configuration. In any of the foregoing embodiments of Formula (Ib), $Y^1$ may be in the (S) stereochemical configuration. In any of the foregoing embodiments of Formula (Ib), $Y^2$ may be in the (R) stereochemical configuration. In any of the foregoing embodiments of Formula (Ib), $Y^2$ may be in the (S) stereochemical configuration. In any of the foregoing variations, the compound of Formula (Ib) is further defined by having k=1. In any of the foregoing variations, the compound of Formula (Ib) is further defined by having k=0.

In another aspect, the compound of Formula (I) is a compound of Formula (Ic):

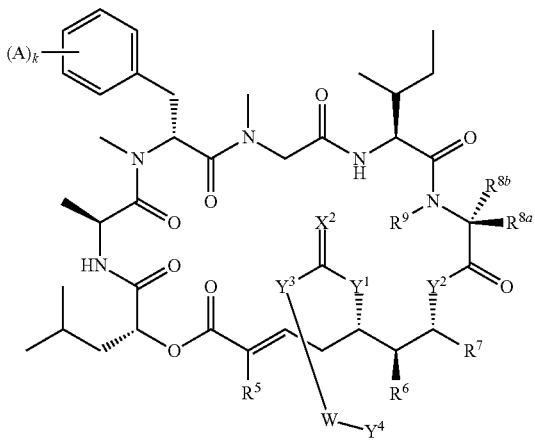

(Ic)

or a salt thereof, wherein $R^5$, $R^6$, $R^{8a}$, $R^{8b}$, $R^9$, $X^2$, W, $Y^1$, $Y^2$, $Y^3$, $Y^4$, A, and k are defined as for Formula (Ib) or any variation or embodiment thereof, provided that i) when $Y^4$ is —OH, W is not —$(CH_2)_2$— or —$(CH_2CH_2O)_3(CH_2)_2$—;

and ii) when $Y^4$ is —$NHR^c$ or —$N(CH_3)R^c$, W is not —$(CH_2)_2$—, —$(CH_2)_6$—, or —$CH_2(CH_2CH_2O)_3(CH_2)_3$—.

In some embodiments of Formula (Ic), $R^{8a}$ is H and $R^{8b}$ is methyl. In some embodiments, $R^{8a}$ and $R^{8b}$ are both H. In some embodiments, $R^{8a}$ is H and $R^{8b}$ is ethyl. In some embodiments, $R^{8a}$ and $R^{8b}$ are both methyl. In any of these embodiments, $R^9$ may be H. In any of these embodiments, $R^9$ may be methyl.

In some of the aforementioned embodiments of Formula (Ic), k is 1. In some such embodiments, A is halo. In some such embodiments, A is fluoro. In some such embodiments, A is chloro. In some such embodiments, A is trifluoromethyl. In some such embodiments, A is hydroxy. In some embodiments, A is cyano. In particular embodiments where k is 1, A is fluoro, chloro, trifluoromethyl, or hydroxy and is attached at the para position on the phenyl ring. In some embodiments where k is 1, A is cyano and is attached at the para position on the phenyl ring. In some embodiments where k is 1, A is cyano and is attached at the meta position on the phenyl ring. In other particular embodiments where m is 1, A is fluoro, chloro, trifluoromethyl or hydroxy and is attached at the meta position on the phenyl ring. In any of the foregoing embodiments of Formula (Ic), the compound may contain one of the following features: i) $Y^1$ and $Y^2$ are each —O—; ii) $Y^1$ is —O—, and $Y^2$ is —S—; iii) $Y^1$ is —O—, and $Y^2$ is —$N(R^d)$—; (iv) $Y^1$ is —O—, and $Y^2$ is —NH—; and (v) $Y^1$ is —O—, and $Y^2$ is —$N(CH_3)$—. In any of the foregoing embodiments of Formula (Ic), the compound may contain one of the following features: i) $Y^1$ and $Y^2$ are each —S—; ii) $Y^1$ is —S—, and $Y^2$ is —O—; iii) $Y^1$ is —S—, and $Y^2$ is —$N(R^d)$—; (iv) $Y^1$ is —S—, and $Y^2$ is —NH—; and (v) $Y^1$ is —S—, and $Y^2$ is —$N(CH_3)$—. In any of the foregoing embodiments of Formula (Ic), the compound may contain one of the following features: i) $Y^1$ and $Y^2$ are each —$N(R^d)$—; ii) $Y^1$ is —$N(R^d)$—, and $Y^2$ is —S—; iii) $Y^1$ is —$N(R^d)$—, and $Y^2$ is —O—; (iv) $Y^1$ is —$N(R^d)$—, and $Y^2$ is —NH—; (v) $Y^1$ is —$N(R^d)$—, and $Y^2$ is —$N(CH_3)$—; (vi) $Y^1$ is —$N(CH_3)$—, and $Y^2$ is —$N(CH_3)$—; (vii) $Y^1$ is —NH—, and $Y^2$ is —$N(CH_3)$—; (viii) $Y^1$ is —$N(CH_3)$—, and $Y^2$ is —NH—; and $Y^1$ is —NH—, and $Y^2$ is —NH—. In any of the foregoing embodiments, the compound may contain one of the following features: (i) $Y^3$ is —$N(R^d)$— and $Y^4$ is —$NR^bR^c$; (ii) $Y^3$ is —$N(R^d)$— and $Y^4$ is —$OR^a$; (iii) $Y^3$ is —$N(R^d)$— and $Y^4$ is —$SR^a$; (iv) $Y^3$ is —O— and $Y^4$ is —$NR^bR^c$; (v) $Y^3$ is —O— and $Y^4$ is —$OR^a$; (vi) $Y^3$ is —O— and $Y^4$ is —$SR^a$; (vii) $Y^3$ is —S— and $Y^4$ is —$NR^bR^c$; (viii) $Y^3$ is —S— and $Y^4$ is —$OR^a$; (ix) $Y^3$ is —S— and $Y^4$ is —$SR^a$; (x) $Y^3$ is substituted or unsubstituted heterocycloalkyl and $Y^4$ is —$OR^a$; (xi) $Y^3$ is substituted or unsubstituted heterocycloalkyl and $Y^4$ is —$NR^bR^c$; or (xii) $Y^3$ is substituted or unsubstituted heterocycloalkyl and $Y^4$ is —$SR^a$. In any of the foregoing embodiments of Formula (I), the compound may further contain one of the following features: (i) $X^1$ is —O— and $X^2$ is O; (ii) $X^1$ is —O— and $X^2$ is S; (iii) $X^1$ is —$N(R^d)$— and $X^2$ is O; or (iv) $X^1$ is —$N(R^d)$— and $X^2$ is S. In any of the foregoing embodiments of Formula (Ic), W may be $(CH_2)_m$—Z—$(CH_2)_p$, where Z is selected from the group consisting of substituted or unsubstituted $C_3$-$C_{12}$ cycloalkyl, substituted or unsubstituted $C_3$-$C_{12}$ cycloalkenyl, substituted or unsubstituted $C_5$-$C_{12}$ aryl, and substituted or unsubstituted $C_5$-$C_{12}$ heteroaryl. In some embodiments, Z is $C_3$-$C_{12}$ alkyl. In some embodiments, Z is substituted or unsubstituted aryl. In some embodiments, Z is phenyl. In some embodiments, Z is substituted or unsubstituted heteroaryl. In some embodiments, Z is substituted or unsubstituted cycloalkyl. In some embodiments, Z is cyclohexyl. In some embodiments, Z is substituted or unsubstituted heterocycloalkyl. In other embodiments, Z is $(CH_2CH_2O)_q$. In some embodiments of Formula (Ic), q is an integer from 1-12, inclusive. In some embodiments, q is an integer from 4-8, inclusive. In other embodiments, q is 1 or 2. In some embodiments of Formula (Ic), m and p are each independently an integer from 0-12, inclusive. In some embodiments, m is an integer from 0-8, inclusive. In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments of Formula (Ic), p is an integer from 0-8, inclusive. In some embodiments, p is 0. In some embodiments, p is 1. In some embodiments, p is 2. In some embodiments, p is 3. In some embodiments, p is 4. In some embodiments, p is 5. In some embodiments, p is 6. In some embodiments, p is 7. In some embodiments, p is 8. In some embodiments, m and p are each 0. In any of the foregoing embodiments of Formula (Ic), W is —$C_2$-$C_{12}$ alkyl-, wherein —$C_2$-$C_{12}$ alkyl- is optionally substituted. In some embodiments, W is —$C_2$-$C_{12}$ alkyl-. In some embodiments, W is —$(CH_2)_2$—. In some embodiments, W is —$(CH_2)_3$—. In some embodiments, W is —$(CH_2)_4$—. In some embodiments, W is —$(CH_2)_5$—. In some embodiments, W is —$(CH_2)_6$—. In some embodiments, W is —$(CH_2)_7$—. In some embodiments, W is —$C_3$-$C_{12}$ alkyl-, wherein —$C_3$-$C_{12}$ alkyl- is optionally substituted. In some embodiments, W is —$C_3$-$C_{12}$ alkyl-. In any of the foregoing embodiments of Formula (Ic), $Y^1$ may be in the (R) stereochemical configuration. In any of the foregoing embodiments of Formula (Ic), $Y^1$ may be in the (S) stereochemical configuration. In any of the foregoing embodiments of Formula (Ib), $Y^2$ may be in the (R) stereochemical configuration. In any of the foregoing embodiments of Formula (Ic), $Y^2$ may be in the (S) stereochemical configuration.

In some embodiments of Formula (Ic), k is 0. In some of these embodiments of Formula (Ic), the compound may contain one of the following features: i) $Y^1$ and $Y^2$ are each —O—; ii) $Y^1$ is —O—, and $Y^2$ is —S—; iii) $Y^1$ is —O—, and $Y^2$ is —N($R^d$)—; (iv) $Y^1$ is —O—, and $Y^2$ is —NH—; and (v) $Y^1$ is —O—, and $Y^2$ is —N($CH_3$)—. In some of these embodiments of Formula (Ic), the compound may contain one of the following features: i) $Y^1$ and $Y^2$ are each —S—; ii) $Y^1$ is —S—, and $Y^2$ is —O—; iii) $Y^1$ is —S—, and $Y^2$ is —N($R^d$)—; (iv) $Y^1$ is —S—, and $Y^2$ is —NH—; and (v) $Y^1$ is —S—, and $Y^2$ is —N($CH_3$)—. In some of these embodiments of Formula (Ic), the compound may contain one of the following features: i) $Y^1$ and $Y^2$ are each —N($R^d$)—; ii) $Y^1$ is —N($R^d$)—, and $Y^2$ is —S—; iii) $Y^1$ is —N($R^d$)—, and $Y^2$ is —O—; (iv) $Y^1$ is —N($R^d$)—, and $Y^2$ is —NH—; (v) $Y^1$ is —N($R^d$)—, and $Y^2$ is —N($CH_3$)—; (vi) $Y^1$ is —N($CH_3$)—, and $Y^2$ is —N($CH_3$)—; (vii) $Y^1$ is —NH—, and $Y^2$ is —N($CH_3$)—; (viii) $Y^1$ is —N($CH_3$)—, and $Y^2$ is —NH—; and $Y^1$ is —NH—, and $Y^2$ is —NH—. In any of the foregoing embodiments, the compound may contain one of the following features: (i) $Y^3$ is —N($R^d$)— and $Y^4$ is —N$R^bR^c$; (ii) $Y^3$ is —N($R^d$)— and $Y^4$ is —O$R^a$; (iii) $Y^3$ is —N($R^d$)— and $Y^4$ is —S$R^a$; (iv) $Y^3$ is —O— and $Y^4$ is —N$R^bR^c$; (v) $Y^3$ is —O— and $Y^4$ is —O$R^a$; (vi) $Y^3$ is —O— and $Y^4$ is —S$R^a$; (vii) $Y^3$ is —S— and $Y^4$ is —N$R^bR^c$; (viii) $Y^3$ is —S— and $Y^4$ is —O$R^a$; (ix) $Y^3$ is —S— and $Y^4$ is —S$R^a$; (x) $Y^3$ is substituted or unsubstituted heterocycloalkyl and $Y^4$ is —O$R^a$; (xi) $Y^3$ is substituted or unsubstituted heterocycloalkyl and $Y^4$ is —N$R^bR^c$; or (xii) $Y^3$ is substituted or unsubstituted heterocycloalkyl and $Y^4$ is —S$R^a$. In any of the foregoing embodiments of Formula (Ic), the compound may further contain one of the following features: (i) $X^1$ is —O— and $X^2$ is O; (ii) $X^1$ is —O— and $X^2$ is S; (iii) is —N($R^d$)— and $X^2$ is O; or (iv) $X^1$ is —N($R^d$)— and $X^2$ is S. In any of the foregoing embodiments of Formula (Ic), W may be $(CH_2)_m$—Z—$(CH_2)_p$, where Z is selected from the group consisting of substituted or unsubstituted $C_3$-$C_{12}$ cycloalkyl, substituted or unsubstituted $C_3$-$C_{12}$ cycloalkenyl, substituted or unsubstituted $C_5$-$C_{12}$ aryl, and substituted or unsubstituted $C_5$-$C_{12}$ heteroaryl. In some embodiments, Z is $C_3$-$C_{12}$ alkyl. In some embodiments, Z is substituted or unsubstituted aryl. In some embodiments, Z is phenyl. In some embodiments, Z is substituted or unsubstituted heteroaryl. In some embodiments, Z is substituted or unsubstituted cycloalkyl. In some embodiments, Z is cyclohexyl. In some embodiments, Z is substituted or unsubstituted heterocycloalkyl. In other embodiments, Z is $(CH_2CH_2O)_q$. In some embodiments of Formula (Ic), q is an integer from 1-12, inclusive. In some embodiments, q is an integer from 4-8, inclusive. In other embodiments, q is 1 or 2. In some embodiments of Formula (Ic), m and p are each independently an integer from 0-12, inclusive. In some embodiments, m is an integer from 0-8, inclusive. In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments of Formula (Ic), p is an integer from 0-8, inclusive. In some embodiments, p is 0. In some embodiments, p is 1. In some embodiments, p is 2. In some embodiments, p is 3. In some embodiments, p is 4. In some embodiments, p is 5. In some embodiments, p is 6. In some embodiments, p is 7. In some embodiments, p is 8. In some embodiments, m and p are each 0. In any of the foregoing embodiments of Formula (Ic), W is —$C_2$-$C_{12}$ alkyl-, wherein —$C_2$-$C_{12}$ alkyl- is optionally substituted. In some embodiments, W is —$C_2$-$C_{12}$ alkyl-. In some embodiments, W is —$(CH_2)_2$—. In some embodiments, W is —$(CH_2)_3$—. In some embodiments, W is —$(CH_2)_4$—. In some embodiments, W is —$(CH_2)_5$—. In some embodiments, W is —$(CH_2)_6$—. In some embodiments, W is —$(CH_2)_7$—. In some embodiments, W is —$C_3$-$C_{12}$ alkyl-, wherein —$C_3$-$C_{12}$ alkyl- is optionally substituted. In some embodiments, W is —$C_3$-$C_{12}$ alkyl-. In any of the foregoing embodiments of Formula (Ic), $Y^1$ may be in the (R) stereochemical configuration. In any of the foregoing embodiments of Formula (Ic), $Y^1$ may be in the (S) stereochemical configuration. In any of the foregoing embodiments of Formula (Ic), $Y^2$ may be in the (R) stereochemical configuration. In any of the foregoing embodiments of Formula (Ic), $Y^2$ may be in the (S) stereochemical configuration.

In some embodiments of Formula (Ic), $R^5$ is H or $C_1$-$C_6$ alkyl, such as methyl. In other embodiments of Formula (Ic), $R^5$ is halo. In some such embodiments, $R^5$ is fluoro. In other such embodiments, $R^5$ is chloro. In yet other embodiments of Formula (Ic), $R^5$ is perhaloalkyl. In some such embodiments, $R^5$ is trifluoromethyl.

In some embodiments of Formula (Ic), $R^6$ is H or $C_1$-$C_6$ alkyl. In some such embodiments, $R^6$ is H. In other such embodiments, $R^6$ is methyl. In other embodiments of Formula (Ic) embodiments, $R^6$ is halo. In some such embodiments, $R^6$ is fluoro. In some such embodiments, $R^6$ is chloro. In yet other embodiments of Formula (Ic), $R^6$ is substituted or unsubstituted aryl. In particular embodiments, $R^6$ is substituted phenyl. In other particular embodiments, $R^6$ is unsubstituted phenyl.

In some embodiments of Formula (Ic), $R^7$ is H or $C_1$-$C_6$ alkyl. In some such embodiments, $R^7$ is methyl. In other such embodiments, $R^7$ is H. In particular embodiments, $R^7$ is

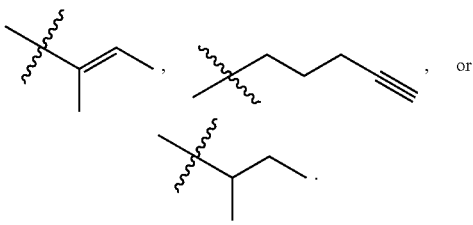

When $R^7$ is sec-butyl, it may be (S)-sec-butyl or (R)-sec-butyl. In some embodiments, $R^7$ is substituted or unsubstituted aryl, such as phenyl.

In some embodiments of Formula (Ic), $R^5$, $R^6$, and $R^7$ are all substituted or unsubstituted alkyl. In particular embodiments of Formula (Ic), $R^5$ and $R^6$ are both methyl, and $R^7$ is

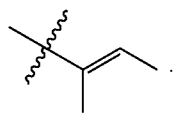 [SMILES: */C(C)=C/C]

In other particular embodiments of Formula (Ic), $R^5$ and $R^6$ are both methyl, and $R^7$ is

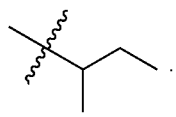 [SMILES: *C(C)CC]

In other particular embodiments of Formula (Ic), $R^5$ is methyl, and $R^6$ and $R^7$ are both hydrogen. In yet other particular embodiments of Formula (Ic), $R^5$ and $R^6$ are both methyl, and $R^7$ is hydrogen.

In some variations of Formula (Ic), $R^{8a}$ and $R^{8b}$ are independently selected from H and methyl, $R^9$ is H, and $R^5$ and $R^6$ are both methyl. In some embodiments, $R^{8a}$ and $R^{8b}$ are both methyl. In any of the foregoing variations, the compound of Formula (Ic) is further defined by having k=1. In any of the foregoing variations, the compound of Formula (Ic) is further defined by having k=0.

In some variations of Formula (I), the compound is of Formula (Id):

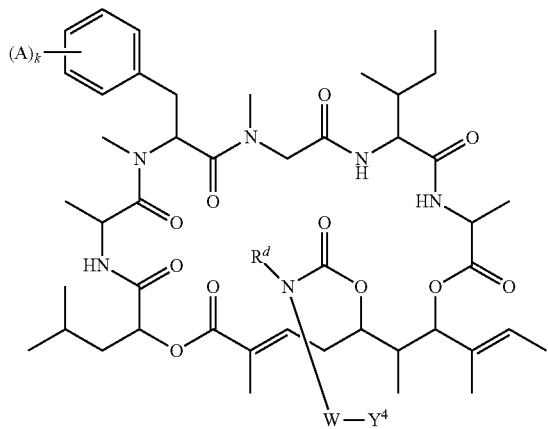

(Id)

or a salt thereof, wherein $Y^4$ is —$OR^a$, —$NR^bR^c$, or —$SR^a$;

each $R^a$, $R^b$, $R^c$, and $R^d$ is independently H, substituted or unsubstituted alkyl, substituted or unsubstituted alkenyl, substituted or unsubstituted alkynyl, substituted or unsubstituted cycloalkyl, or substituted or unsubstituted cycloalkenyl;

W is $(CH_2)_m$—Z—$(CH_2)_p$;

Z is substituted or unsubstituted alkyl, substituted or unsubstituted substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or $(CH_2CH_2O)_q$;

m, and p are each independently an integer from 0-12, inclusive; and q is an integer from 1-12, inclusive;

A is H, halo, perhalomethyl, cyano, nitro, amino, hydroxy, or alkoxy; and k is 0, 1, 2, 3, 4, or 5;

provided that i) when $Y^4$ is —OH, W is not —$(CH_2)_2$— or —$(CH_2CH_2O)_3(CH_2)_2$—; and ii) when $Y^4$ is —$NHR^c$ or —$N(CH_3)R^c$, W is not —$(CH_2)_2$—, —$(CH_2)_6$—, or —$CH_2(CH_2CH_2O)_3(CH_2)_3$—.

In some embodiments of Formula (Id), $R^d$ is H, Z is substituted or unsubstituted alkyl, and $Y^4$ is OH. In some embodiments of Formula (Id), $R^d$ is H, Z is substituted or unsubstituted aryl, and $Y^4$ is OH. In some embodiments of Formula (Id), $R^d$ is H, Z is substituted or unsubstituted cycloalkyl, and $Y^4$ is OH. In any of the foregoing embodiments, A is H, halo, perhalomethyl, cyano, nitro, amino, hydroxy, or alkoxy, and k is an integer from 1 to 3. In some embodiments, A is H, halo, or cyano. In some embodiments, A is connected at the para position of the phenyl ring, and k is 1. In some embodiments, k is 0.

In some variations of Formula (I), the compound is of Formula (Ie):

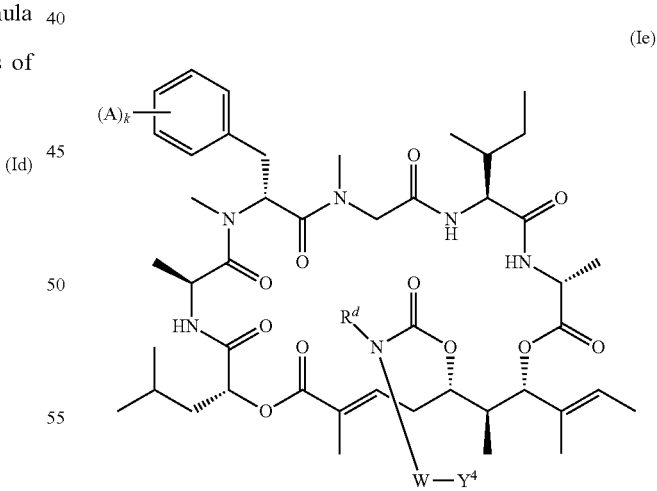

(Ie)

or a salt thereof wherein $Y^4$ is —$OR^a$, —$NR^bR^c$, or —$SR^a$;

each $R^a$, $R^b$, $R^c$, and $R^d$ is independently H, substituted or unsubstituted alkyl, substituted or unsubstituted alkenyl, substituted or unsubstituted alkynyl, substituted or unsubstituted cycloalkyl, or substituted or unsubstituted cycloalkenyl;

W is $(CH_2)_m$—Z—$(CH_2)_p$;

Z is substituted or unsubstituted alkyl, substituted or unsubstituted substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or $(CH_2CH_2O)_q$;

m, and p are each independently an integer from 0-12, inclusive; and q is an integer from 1-12, inclusive;

A is H, halo, perhalomethyl, cyano, nitro, amino, hydroxy, or alkoxy; and k is 0, 1, 2, 3, 4, or 5;

provided that i) when $Y^4$ is —OH, W is not —$(CH_2)_2$— or —$(CH_2CH_2O)_3(CH_2)_2$—; and ii) when $Y^4$ is —$NHR^c$ or —$N(CH_3)R^c$, W is not —$(CH_2)_2$—, —$(CH_2)_6$—, or —$CH_2(CH_2CH_2O)_3(CH_2)_3$—.

In some embodiments of Formula (Ie), $R^d$ is H, Z is substituted or unsubstituted alkyl, and $Y^4$ is OH. In some embodiments of Formula (Ie); $R^d$ is H, Z is substituted or unsubstituted aryl, and $Y^4$ is OH. In some embodiments of Formula (Ie), $R^d$ is H, Z is substituted or unsubstituted cycloalkyl, and $Y^4$ is OH. In any of the foregoing embodiments, A is H, halo, perhalomethyl, cyano, nitro, amino, hydroxy, or alkoxy, and k is an integer from 1 to 3. In some embodiments, A is H, halo, or cyano. In some embodiments, A is connected at the para position of the phenyl ring, and k is 1. In some embodiments, k is 0. In some embodiments, A is 4-chlorophenyl. In some embodiments, A is 4-cyanophenyl. In some embodiments, A is H.

In some embodiments, provided herein are compounds and salts thereof described in Table 1, and uses thereof.

TABLE 1

| Compound No. | Structure |
|---|---|
| 1 | |
| 2 | 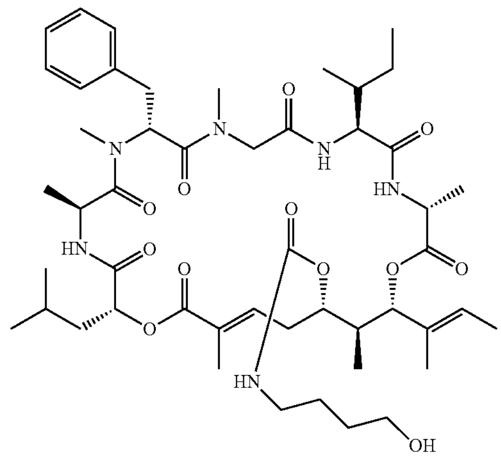 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCCO)[C@@H]1C] |
| 3 | 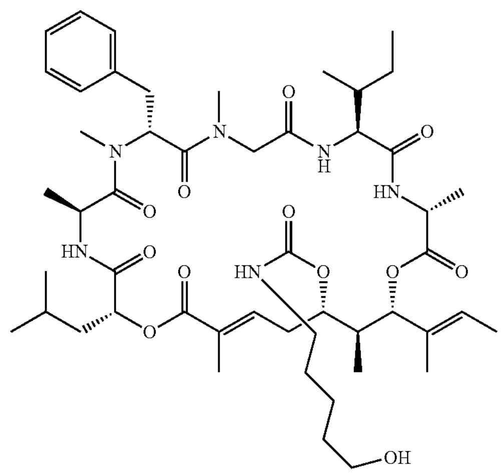 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCCCO)[C@@H]1C] |
| 4 | 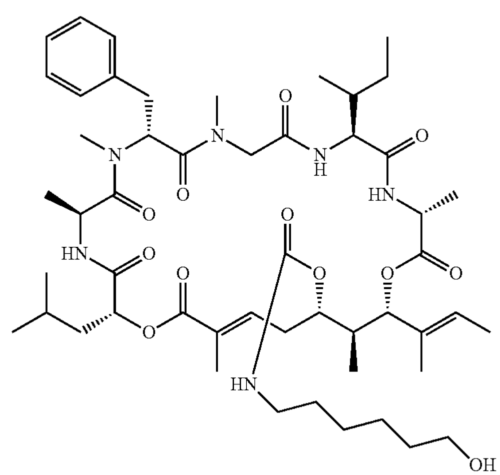 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCCCCO)[C@@H]1C] |

TABLE 1-continued

| Compound No. | Structure |
|---|---|
| 5 | (structure) |
| 6 | (structure) |
| 7 | (structure) |
| 8 | (structure) |
| 9 | (structure) |

TABLE 1-continued

| Compound No. | Structure |
|---|---|
| 10 | (structure) |
| 11 | (structure) |
| 12 | (structure) |
| 13 | (structure) |
| 14 | (structure) |
| 15 | (structure) |

TABLE 1-continued
| Compound No. | Structure |
|---|---|
| 16 | 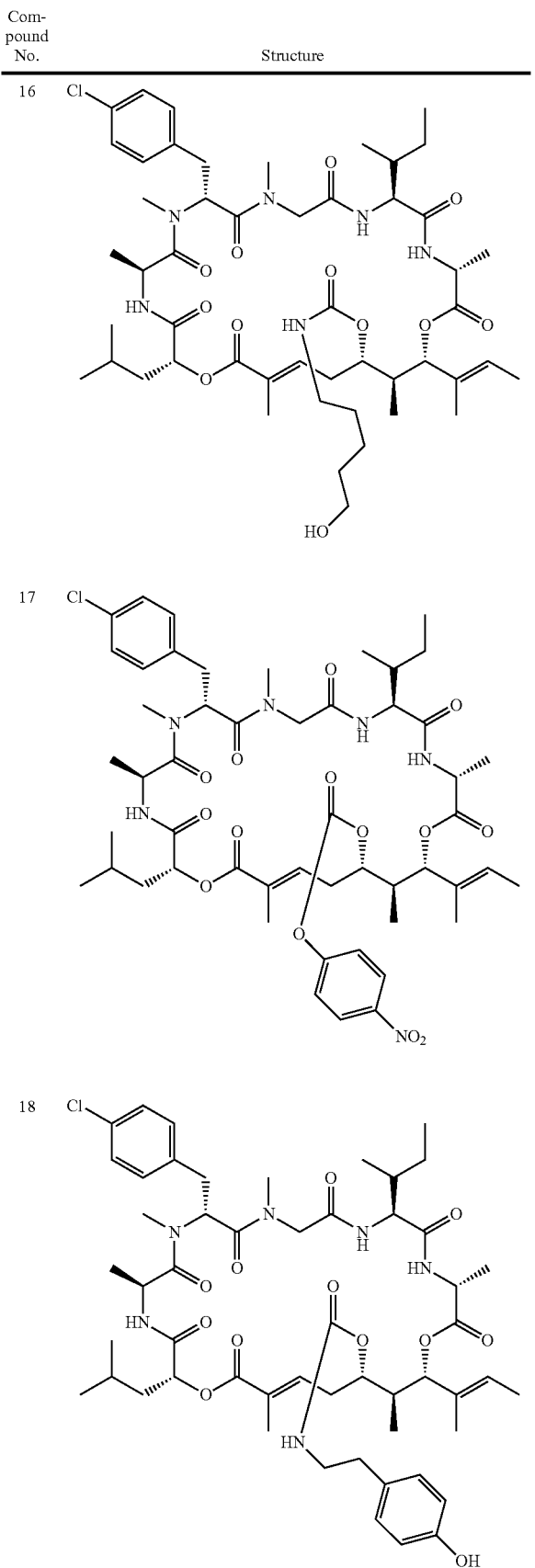 |
| 17 | 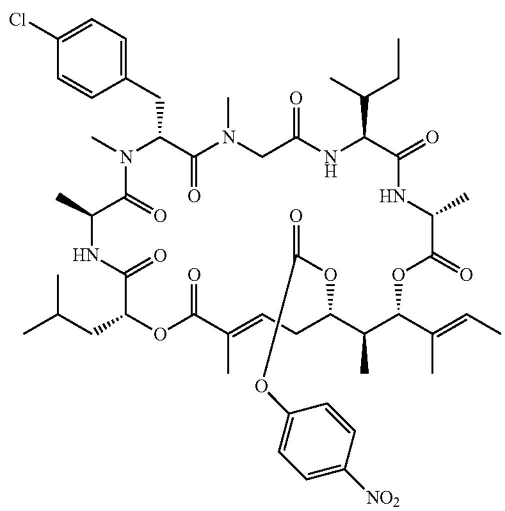 [SMILES: C/C=C(\C)[C@H]1OC(=O)[C@@H](C)NC(=O)[C@H](C(C)CC)NC(=O)CN(C)C(=O)[C@@H](Cc2ccc(Cl)cc2)N(C)C(=O)[C@H](C)NC(=O)[C@@H](CC(C)C)OC(=O)/C(C)=C/C[C@H](OC(=O)Oc2ccc([N+](=O)[O-])cc2)[C@@H]1C] |
| 18 | 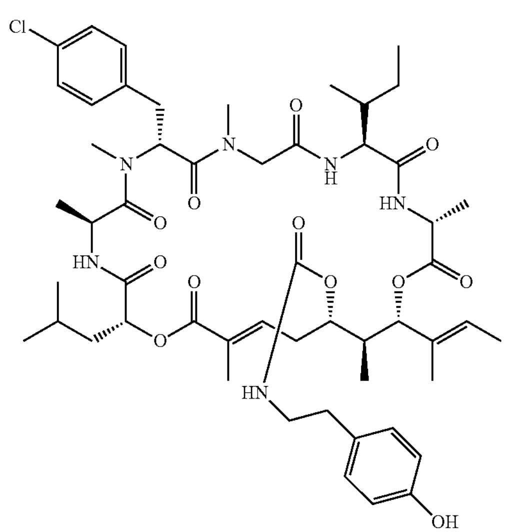 [SMILES: C/C=C(\C)[C@H]1OC(=O)[C@@H](C)NC(=O)[C@H](C(C)CC)NC(=O)CN(C)C(=O)[C@@H](Cc2ccc(Cl)cc2)N(C)C(=O)[C@H](C)NC(=O)[C@@H](CC(C)C)OC(=O)/C(C)=C/C[C@H](OC(=O)NCCc2ccc(O)cc2)[C@@H]1C] |
TABLE 1-continued
| Compound No. | Structure |
|---|---|
| 19 | 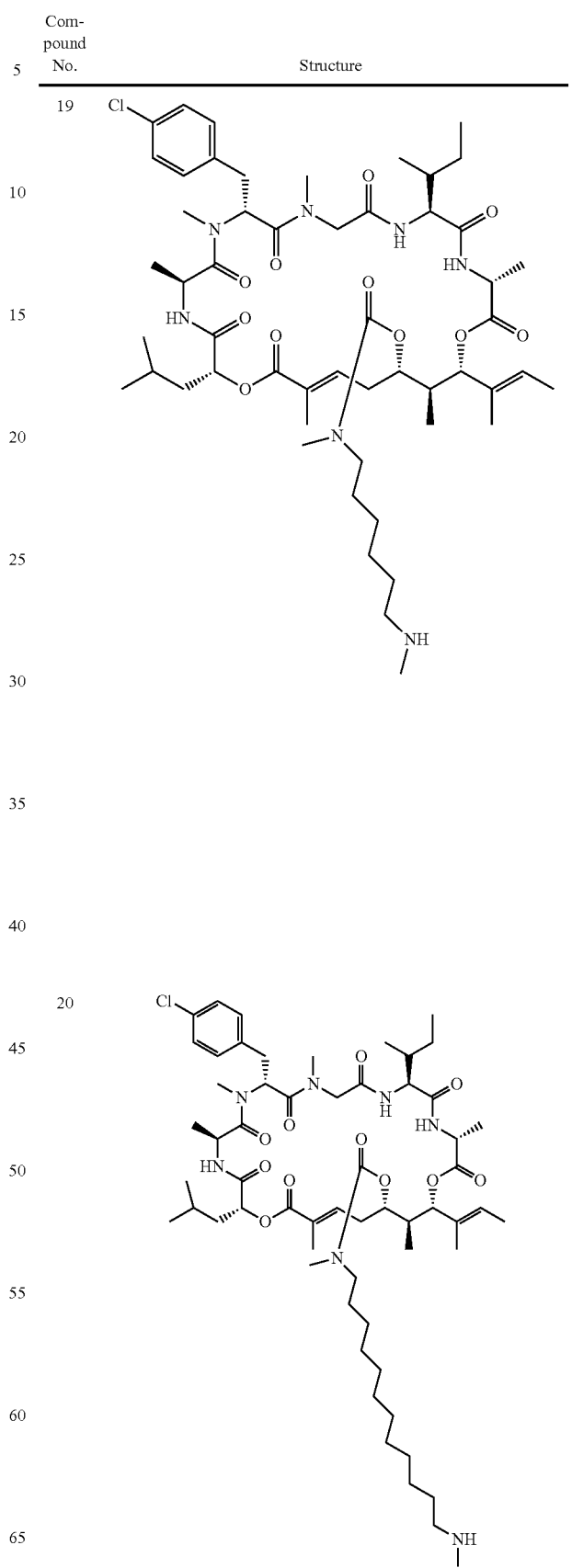 |
| 20 | 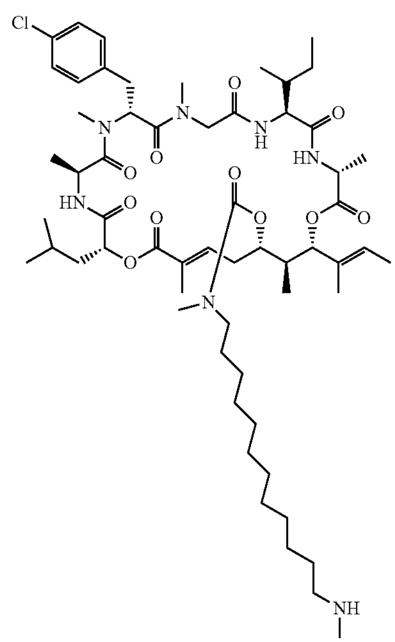 [SMILES: C/C=C(\C)[C@H]1OC(=O)[C@@H](C)NC(=O)[C@H](C(C)CC)NC(=O)CN(C)C(=O)[C@@H](Cc2ccc(Cl)cc2)N(C)C(=O)[C@H](C)NC(=O)[C@@H](CC(C)C)OC(=O)/C(C)=C/C[C@H](OC(=O)N(C)CCCCCCCCCCCCNC)[C@@H]1C] |

TABLE 1-continued
| Compound No. | Structure |
|---|---|
| 21 | 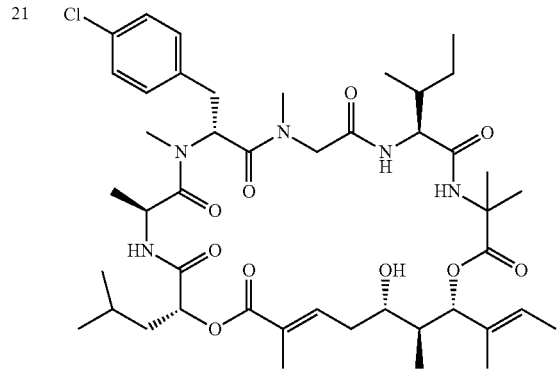 |
| 22 | 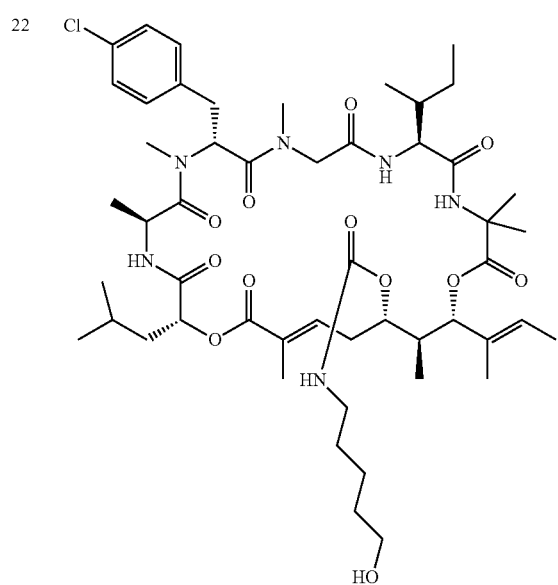 |
| 23 | 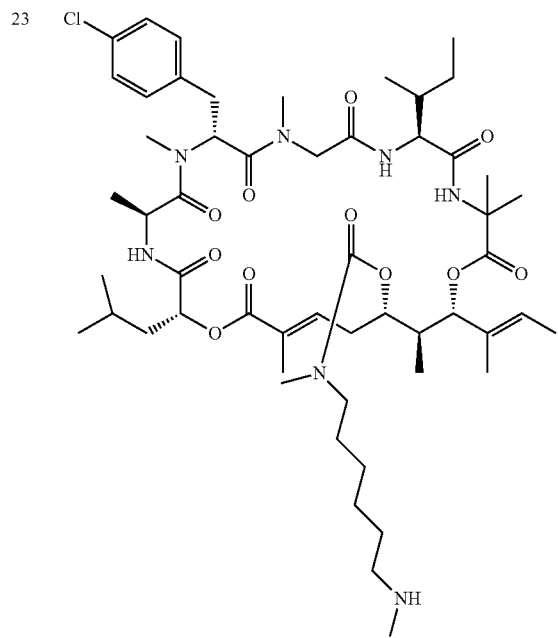 |
| 24 | 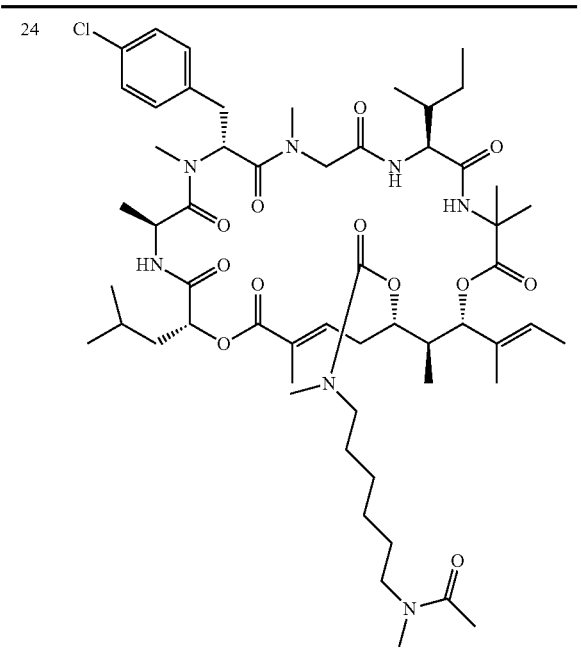 |
| 25 | 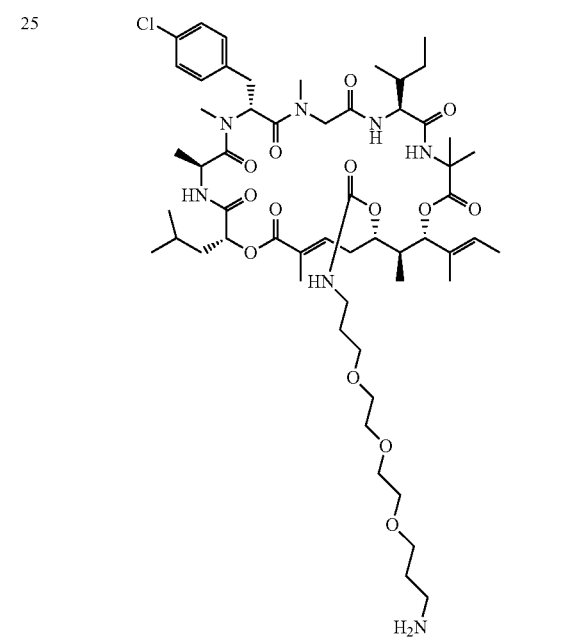 |

TABLE 1-continued
| Compound No. | Structure |
|---|---|
| 26 | 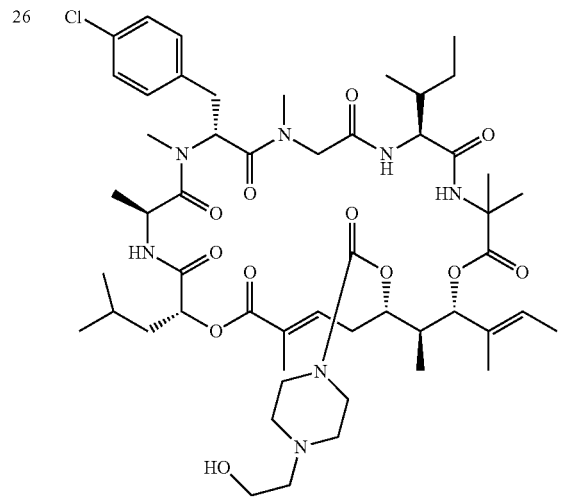 |
| 27 | 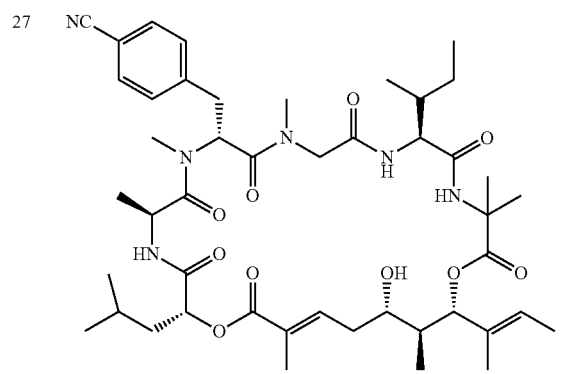 |
| 28 | 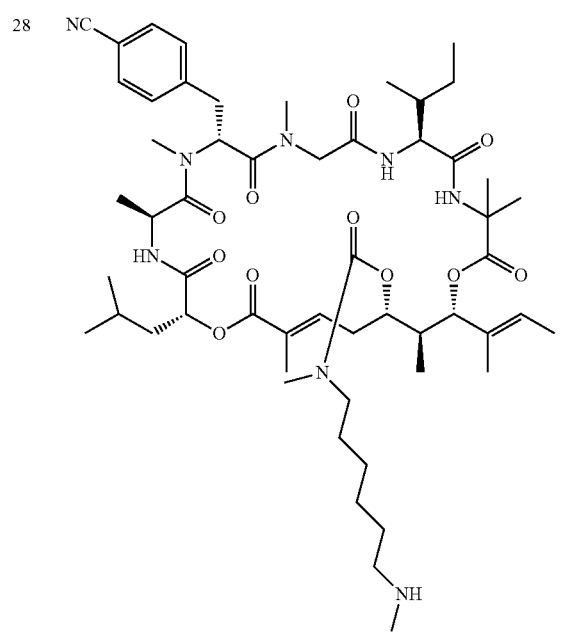 |
| 29 | 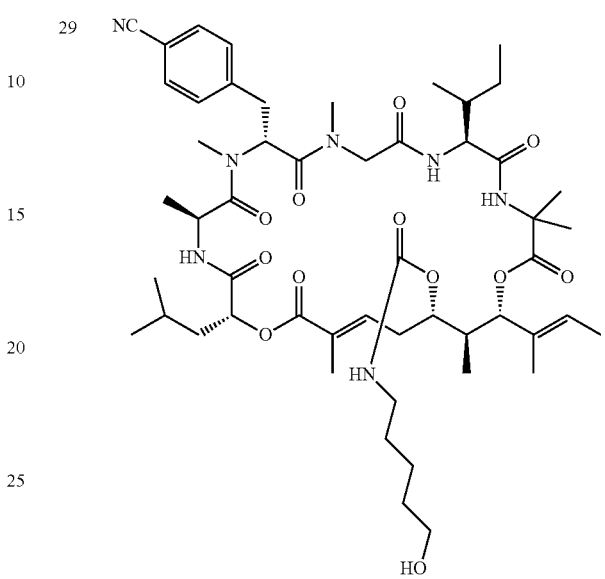 |
| 30 | 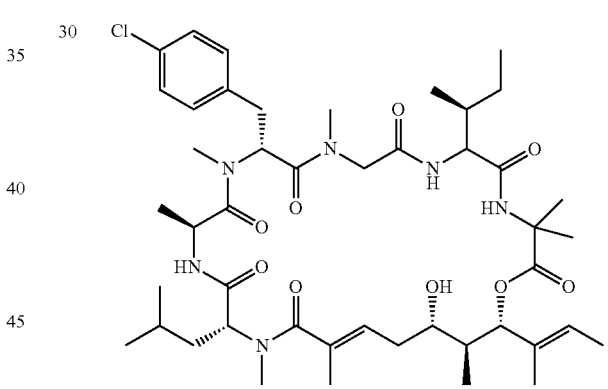 |
| 31 | 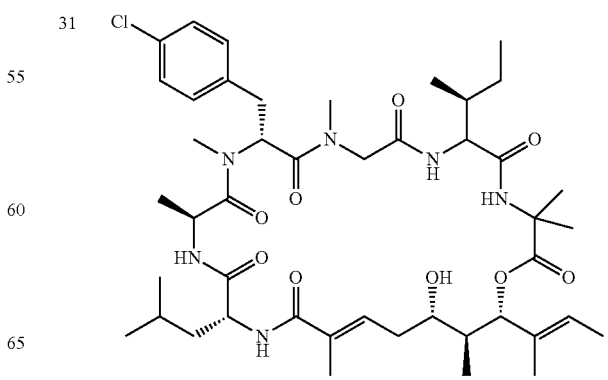 |

TABLE 1-continued

| Compound No. | Structure |
|---|---|
| 32 | 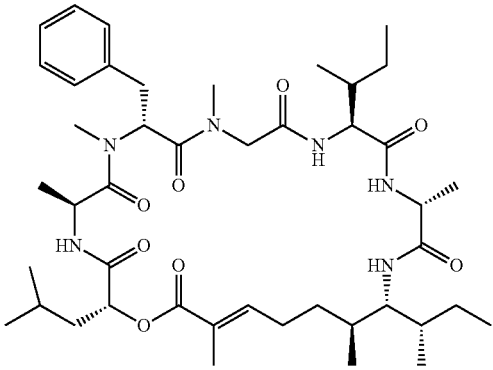 [SMILES: CCC(C)[C@@H]1NC(=O)CN(C)C(=O)[C@@H](Cc2ccccc2)N(C)C(=O)[C@H](C)NC(=O)[C@@H](CC(C)C)OC(=O)/C(C)=C/CC[C@H](C)[C@@H]([C@@H](C)CC)NC(=O)[C@@H](C)NC1=O] |
| 33 | 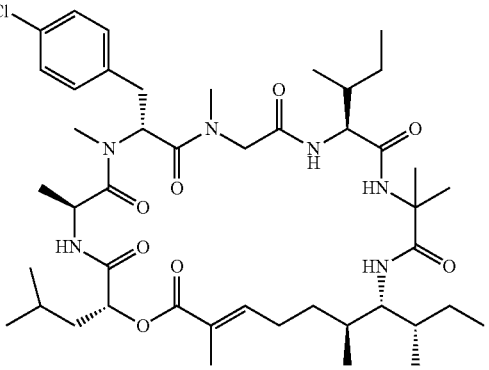 |

In some variations, any of the compounds described herein, such as a compound of Formula (I), (Ia), (Ib), (Ic), (Id), or (Ie), or any variation thereof, or a compound of Table 1, may be deuterated (e.g., a hydrogen atom is replaced by a deuterium atom). In some of these variations, the compound is deuterated at a single site. In other variations, the compound is deuterated at multiple sites. Deuterated compounds can be prepared from deuterated starting materials in a manner similar to the preparation of the corresponding non-deuterated compounds. Hydrogen atoms may also be replaced with deuterium atoms using other methods known in the art.

Representative examples of compounds detailed herein, including intermediates and final compounds, are depicted in the tables and elsewhere herein. It is understood that in one aspect, any of the compounds may be used in the methods detailed herein, including, where applicable, intermediate compounds that may be isolated and administered to an individual.

The compounds depicted herein may be present as salts even if salts are not depicted, and it is understood that the compositions and methods provided herein embrace all salts and solvates of the compounds depicted here, as well as the non-salt and non-solvate form of the compound, as is well understood by the skilled artisan. In some embodiments, the salts of the compounds provided herein are pharmaceutically acceptable salts.

In one variation, the compounds herein are synthetic compounds prepared for administration to an individual. In another variation, compositions are provided containing a compound in substantially pure form. In another variation, provided are pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

Any variation or embodiment of $R^1$, $R^2$, $R^3$, $R^4$, $R^5$, $R^6$, $R^7$, $R^{8a}$, $R^{8b}$, $R^9$, $R^{10}$, $R^{11}$, $R^{12}$, $R^{13}$, $R^{14}$, $R^{15}$, n, $X^1$, $X^2$, W, $Y^1$, $Y^2$, $Y^3$ and $Y^4$ provided herein can be combined with every other variation or embodiment of $R^1$, $R^2$, $R^3$, $R^4$, $R^5$, $R^6$, $R^7$, $R^{8a}$, $R^{8b}$, $R^9$, $R^{10}$, $R^{11}$, $R^{12}$, $R^{13}$, $R^{14}$, $R^{15}$, n, $X^1$, $X^2$, W, $Y^1$, $Y^2$, $Y^3$ and $Y^4$, as if each combination had been individually and specifically described.

Conjugates

The compounds described herein may be conjugated to one or more linkers and/or ligands. A ligand may be directly bound to a compound of Formula (I), (Ia), (Ib), (Ic), (Id), or (Ie) or any variation thereof, including any compound listed in Table 1. Alternatively, a ligand may be bound to a compound of Formula (I), (Ia), (Ib), (Ic), (Id), or (Ie) or any variation thereof, including any compound listed in Table 1, via one or more linkers. In some variations, the ligand is a polypeptide. In some variations, the ligand is a nucleic acid. In some variations, the ligand is a targeting moiety. In some variations, the ligand is an antibody. In some variations, the antibody binds to a receptor. In some variations, the antibody binds to a receptor on the surface of a cell.

Accordingly, in one aspect, provided herein are conjugates of the compounds described herein. In some variations, provided is a conjugate containing a compound of Formula (I), (Ia), (Ib), (Ic), (Id), or (Ie), or any variation thereof, or any compound listed in Table 1, bonded to a ligand. In some variations, the compound of Formula (I), (Ia), (Ib), (Ic), (Id), or (Ie), or any variation thereof, or any compound listed in Table 1, is directly bonded to the ligand (i.e., no linker is present). In other variations, the compound of Formula (I), (Ia), (Ib), (Ic), (Id), or (Ie), or any variation thereof, or any compound listed in Table 1, is bonded to the ligand via a linker. Any suitable ligand and/or linker can be used in the foregoing compositions, including, but not limited to, any of the linkers or ligands described herein.

In any of the conjugates provided herein, the ratio of compound to ligand may be 1:1, 2:1, 3:1, 4:1, 5:1, 6:1, 7:1, 8:1, 9:1, 10:1, 11:1, or 12:1. In any of the conjugates provided herein, the ratio of compound to ligand may be 1:1 or 1:2. In any of the conjugates provided herein, the ratio of linker to ligand may be 1:1, 2:1, 3:1, 4:1, 5:1, 6:1, 7:1, 8:1, 9:1, 10:1, 11:1, or 12:1.

Also provided herein are conjugates containing a compound described herein bonded to a linker. The ratio of compound to linker may be 1:1, 2:1, 3:1, 1:2, or 1:3. In some embodiments, the linker is additionally bonded to a ligand. In other embodiments, the linker is not bonded to a ligand. In some such embodiments, the linker contains one or more functional groups suitable for bonding to a ligand.

In some variations, provided is a conjugate containing a compound of Formula (I), (Ia), (Ib), (Ic), (Id), or (Ie), or any variation thereof, or any compound listed in Table 1, bonded to a linker. Any suitable linker can be used in the foregoing compositions, including, but not limited to, any of the linkers described herein. The linker may be suitable for attachment to a ligand.

One or more linkers and/or ligands may be bonded to a compound described herein via a functional group including, but not limited to —NHR, —NHNH$_2$, —ONH$_2$, —N$_3$, —OH, —SH, or —CO$_2$H located at any chemically feasible position on the compound. In some embodiments, the conjugation site on the compound is an —OH or —NH₂ group. In particular embodiments, the conjugation site on the compound is an —OH or —NH₂ group located at the position corresponding to $Y^4$. In other embodiments, the conjugation site on the compound is a phenyl ring substituted with —NHR, —NH₂, or OH. In particular embodiments, the functional group for conjugation is at the para position on the phenyl ring. In yet other embodiments, an amino acid unit of the compound has been replaced with a lysine unit as a site for conjugation.

Provided herein are compounds of Formula (I), (Ia), (Ib), (Ic), (Id), or (Ie), or any variation thereof, or any compound listed in Table 1, or a salt thereof, wherein the compound is substituted at any chemically feasible position with a moiety suitable for attachment to a linker and/or ligand. In some variations, provided are compounds of Formula (I), (Ia), (Ib), (Ic), (Id), or (Ie), or any variation thereof, or any compound listed in Table 1, or a salt thereof, wherein the compound is substituted at any chemically feasible position with a functional group which is —NHR, —NHNH₂, —ONH₂, —N₃, —OH, —SH, or —CO₂H. In any of the foregoing embodiments, the functional group suitable for attachment to a linker and/or ligand is bonded to a protecting group, which may be removed prior to reaction with a linker and/or ligand.

In some aspects, provided are conjugates of Formula (II):

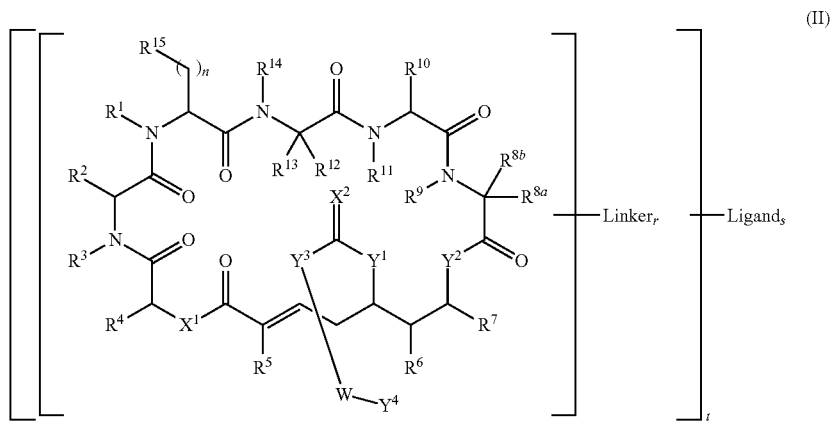

(II)

and salts thereof, wherein $R^1$, $R^2$, $R^3$, $R^4$, $R^5$, $R^6$, $R^7$, $R^{8a}$, $R^{8b}$, $R^9$, $R^{10}$, $R^{11}$, $R^{12}$, $R^{13}$, $R^{14}$, $R^{15}$, n, W, $X^1$, $X^2$, $Y^1$, $Y^2$, $Y^3$, and $Y^4$ are as defined for Formula (I) or any variation thereof;
r is 0, 1, or 2;
s is 0, 1, or 2; and
t is an integer from 1-12, inclusive.

In other aspects, provided are conjugates of Formula (IIa):

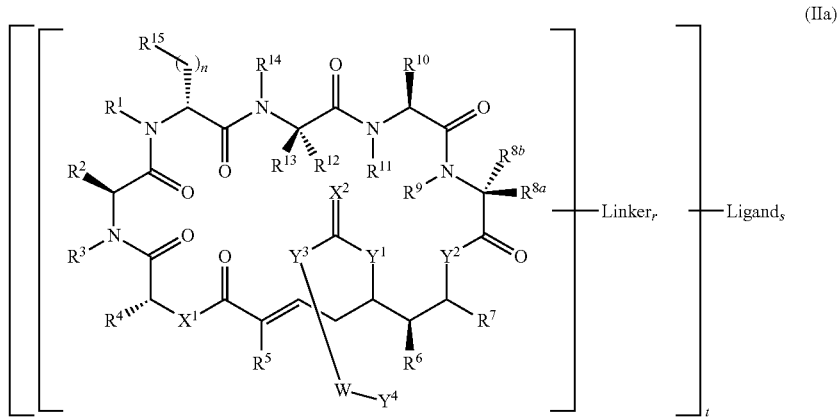

(IIa)

and salts thereof, wherein $R^1$, $R^2$, $R^3$, $R^4$, $R^5$, $R^6$, $R^7$, $R^{8a}$, $R^{8b}$, $R^9$, $R^{10}$, $R^{11}$, $R^{12}$, $R^{13}$, $R^{14}$, $R^{15}$, n, W, $X^1$, $X^2$, $Y^1$, $Y^2$, $Y^3$, and $Y^4$ are as defined for Formula (Ia) or any variation thereof;
r is 0, 1, or 2;
s is 0, 1, or 2; and
t is an integer from 1-12, inclusive.

In other aspects, provided are conjugates of Formula (IIb):

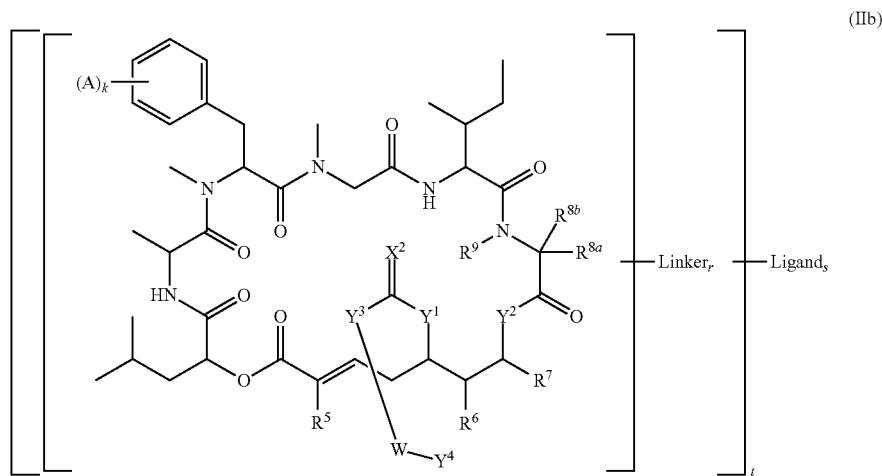

(IIb)

and salts thereof, wherein $R^5$, $R^6$, $R^7$, $R^{8a}$, $R^{8b}$, $R^9$, W, $X^2$, $Y^1$, $Y^2$, $Y^3$, $Y^4$, A and k are as defined for Formula (Ib) or any variation thereof;

r is 0, 1, or 2;
s is 0, 1, or 2; and
t is an integer from 1-12, inclusive.

In other aspects, provided are conjugates of Formula (IIc):

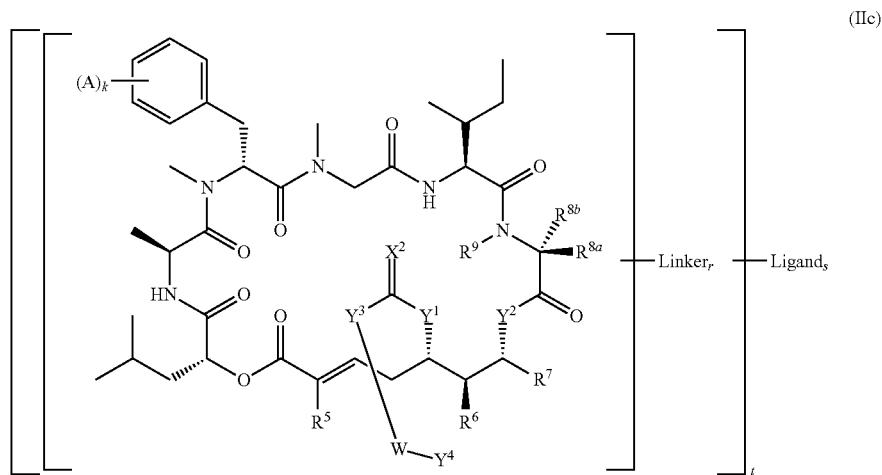

(IIc)

and salts thereof, wherein $R^5$, $R^6$, $R^7$, $R^{8a}$, $R^{8b}$, $R^9$, W, $X^2$, $Y^1$, $Y^2$, $Y^3$, $Y^4$, A and k are as defined for Formula (Ic) or any variation thereof;

r is 0, 1, or 2;
s is 0, 1, or 2; and
t is an integer from 1-12, inclusive.

In other aspects, provided are conjugates of Formula (IId):


and salts thereof, wherein $R^d$, W, $Y^4$, A and k are as defined for Formula (Id) or any variation thereof:
  r is 0, 1, or 2;
  s is 0, 1, or 2; and
  t is an integer from 1-12, inclusive.

In other aspects, provided are conjugates of Formula (IIe):


and salts thereof, wherein $R^d$, W, $Y^4$, A and k are as defined for Formula (Id) or any variation thereof;
  q is 0, 1, or 2;
  p is 0, 1, or 2; and
  t is an integer from 1-12, inclusive.

In some embodiments of any of Formulae (II), (IIa), (IIb), (IIc), (IId), and (IIe), one or both of the following conditions apply: i) when $Y^4$ is —OH, W is not —$(CH_2)_2$— or —$(CH_2CH_2O)_3(CH_2)_2$—; and ii) when $Y^4$ is —$NHR^c$ or —$N(CH_3)R^c$, W is not —$(CH_2)_2$—, —$(CH_2)_6$—, or —$CH_2$ $(CH_2CH_2O)_3(CH_2)_3$—.

In any variations of conjugates having Formulae (II), (IIa), (IIb), (IIc), (IId), and (IIe), chemically appropriate valences and chemical bonding are present in the compound at the site of conjugation to the linker and/or ligand. For example, an atom on the compound is replaced by the linker or ligand such that a chemically appropriate number of bonds is maintained for all atoms. In particular examples, an —OH moiety on the compound is replaced with an —O-linker-ligand moiety in the conjugate, or an —$NH_2$— moiety on the compound is replaced with an —NH-linker-ligand moiety in the conjugate.

In some variations of any of the conjugates of Formulae (II), (IIa), (IIb), (IIc), (IId), and (IIe), one or more linkers and/or ligands may be bonded to a compound described herein via a functional group including, but not limited to —OH, —NHR, —$NHNH_2$, —$ONH_2$, —$N_3$, —SH, or —$CO_2H$ located at any chemically feasible position on the compound. In some embodiments, the conjugation site on the compound is an —OH or —$NH_2$ group. In particular embodiments, the conjugation site on the compound is an —OH or —$NH_2$ group located at the position corresponding to —$Y^4$. In other embodiments, the conjugation site on the compound is a phenyl ring substituted with —NHR, —$NH_2$, or OH. In particular embodiments, the substitution is at the para position on the phenyl ring. In yet other embodiments, an amino acid unit of the compound has been replaced with a lysine unit as a site for conjugation.

In some variations of any of the conjugates of Formula (II), (IIa), (IIb), (IIc), (IId), or (IIe), one or more linkers and/or ligands may be bonded to a compound described herein via a hydroxyl group (—OH). In some variations, the linkers can be carbamate linkers, silyl linkers, pyrophosphate linkers, p-aminobenzyl (PAB) linkers, denditric-type linkers or any combinations of such linkers thereof. In some embodiments, the linkers and/or ligands may be conjugated to a compound described herein via a primary or secondary hydroxyl group. In particular embodiments, the conjugation site on the compound is a primary or secondary hydroxyl group located at the position corresponding to —$Y^4$. In some embodiments, the conjugation site on the compound is a primary or secondary hydroxyl group located at the position corresponding to $R^2$. In some embodiments, the conjugation site on the compound is a primary or secondary hydroxyl group located at the position corresponding to $R^{8a}$ or $R^{8b}$. In some embodiments, the conjugation site on the compound is a primary or secondary hydroxyl group located at the position corresponding to $R^{15}$. In other embodiments, the conjugation site on the compound is a primary or secondary hydroxyl group located at the position corresponding to $R^4$. In some embodiments, the conjugation site on the compound is a phenyl ring substituted with —OH. In particular embodiments, the substitution is at the para position on the phenyl ring.

Ligands

The term "ligand" as used herein refers to any molecule or moiety connected to the compounds described herein. "Ligand" may refer to one or more ligands attached to a compound. Likewise, multiple compounds may be attached to a single ligand.

Ligands may serve a number of purposes including facilitating uptake of the conjugate into a target cell or tissue and directing the conjugate to a particular cell or tissue (also referred to as conjugate targeting). A ligand may also serve to enhance the efficacy of the compounds by, for example, inhibiting or interacting with cellular factors that may inhibit or reduce the efficacy of the compounds described herein. The compound as described herein may be conjugated to one or more ligands. The term "ligand" as used herein refers to one or more ligands.

In some embodiments, a ligand is an antibody, or fragment thereof. In other embodiments, the ligand is a peptide or protein. In yet other embodiments, the ligand is another moiety useful for directing the compounds described herein to a target cell or tissue.

Antibody ligands include monoclonal antibodies, polyclonal antibodies, multispecific antibodies (e.g. bispecific antibodies) formed from at least two intact antibodies, multivalent antibodies, humanized antibodies, and antibody fragments. Examples of antibody fragments include Fab, Fab', F(ab')$_2$ and Fv fragments; diabodies; linear antibodies; single chain antibody molecules; and multispecific antibodies formed from antibody fragment(s). In one embodiment the term "antibody" encompasses a molecule comprising at least one variable region from a light chain immunoglobulin molecule and at least one variable region from a heavy chain molecule that in combination form a specific binding site for the target antigen. In one embodiment, the antibody is an IgG antibody. For example, the antibody is an IgG1, IgG2, IgG3, or IgG4 antibody.

The term "monoclonal antibody," as used herein, refers to an antibody obtained from a population of substantially homogeneous antibodies. A monoclonal antibody composition typically displays a single binding specificity and affinity for a particular epitope. In contrast, polyclonal antibody compositions typically include a multitude of antibodies that may be directed against different epitopes of the same target molecule. A polyclonal antibody composition may contain a plurality of monoclonal antibodies with different epitope specificities, affinities, or avidities within a single antigen that contains multiple antigenic epitopes. The term "monoclonal" indicates the character of the antibody as being obtained from a substantially homogeneous population of antibodies, and is not to be construed as requiring production of the antibody by any particular method. For example, the monoclonal antibodies to be used in accordance with any of the compositions, uses, or methods described herein may be made by the hybridoma method first described by Kohler et al. (1975) Nature 256: 495, or may be made by recombinant DNA methods (see, e.g., U.S. Pat. No. 4,816,567). The "monoclonal antibodies" may also be isolated from phage antibody libraries using the techniques described in Clarkson et al. (1991) Nature 352: 624-628 and Marks et al. (1991) J. Mol. Biol. 222: 581-597, for example.

As used herein, the term "humanized antibody" refers to forms of antibodies that contain sequences from non-human (e.g., murine) antibodies as well as human antibodies. These antibodies retain the activity of a non-human antibody while being less immunogenic in humans. Humanized antibodies are chimeric antibodies which contain at least part of its sequence derived from non-human immunoglobulin. In general, the humanized antibody will comprise substantially all the non-human CDR regions, while the remaining parts of the antibody may be replaced by the corresponding human counterparts. In some embodiments, the humanized antibody retains at least one complete non-human variable domain. The humanized antibody optionally also will comprise at least a portion of an immunoglobulin constant region (Fc), typically that of a human immunoglobulin. See e.g., U.S. Pat. No. 4,816,567; Queen et al. (1989) Proc. Nat'l Acad. Sci. USA 86:10029-10033; and Antibody Engineering: A Practical Approach (Oxford University Press 1996).

The term "recombinant antibody", as used herein, includes all human and non-human antibodies that are prepared, expressed, created or isolated by recombinant means, such as antibodies isolated from an animal (e.g., a mouse) or a hybridoma prepared therefrom, antibodies isolated from a host cell transformed to express the antibody, e.g., from a transfectoma, antibodies isolated from a recombinant, combinatorial antibody library, and antibodies prepared, expressed, created or isolated by any other means that involve splicing of all or a portion of a human immunoglobulin gene, sequences to other DNA sequences.

Exemplary peptide or protein ligands include receptor ligands for targeting delivery of the conjugate to a particular cell. Receptor ligands may engage with their target receptor and provide specific targeting to a tissue or cell type that expresses that receptor. This receptor engagement may also facilitate cellular uptake of the conjugate. Exemplary peptides may also include targeting peptides to facilitate passage across the cell membrane or intracellular targeting including, but not limited to, targeting to organelles such as the nucleus, Golgi apparatus, lysosome, and mitochondria.

In some embodiments, the ligand is an antibody that is specific for a cancer cell antigen. A "cancer cell antigen" is a peptide or molecular moiety expressed by a cancer cell that is recognized by an antibody. Antibodies specific for a cancer cell antigen can be obtained commercially or produced by any method known to one of skill in the art such as, e.g., chemical synthesis or recombinant expression techniques.

In additional embodiments, the peptide ligand is an interferon, a lymphokine, or a hormone.

Additional exemplary ligands include nucleic acids (e.g. DNA, RNA, PNA, etc.) or other molecules known in the art that would be useful for conjugation to the presently described compounds.

Linkers

In one embodiment, the compounds described herein comprise one or more linker or linking group. The term "linker", "linker molecule", "linking group", or "linker moiety" as used herein refers to a chemical moiety comprising a covalent bond and/or a chain of atoms that covalently attaches a ligand to a drug moiety or other molecule. For example, exemplary linkers, including their structure and synthesis, are described in WO 2004/010957, U.S. Pat. Publ. No. 2006/0074008, U.S. Pat. Publ. No. 2005/0238649, and U.S. Pat. Publ. No. 2006/0024317, U.S. Pat. Publ. Nos. 2003/0083263, 2005/0238649 and 2005/0009751, WO 2015/095755, W. C. Widdison et al., *Bioconjugate Chem.*, 2015, 26, 2261; D. Shabat et al., *New J. Chem.*, 2012, 36, 386; F. M. H. de Groot et al., *J. Org. Chem.*, 2001, 66, 8815; J. M. DeSimone et al., *Med. Chem. Comm.*, 2014, 5, 1355; and R. M. Garbaccio et al., *J. Amer. Chem. Soc.*, 2016, 138(4), 1430, each of which is incorporated herein by reference in its entirety and for all purposes.

The linker may be cleavable or non-cleavable. Cleavable linkers are typically cleavable under intracellular conditions, such that the linker itself is degraded and releases the compound from the ligand. Non-cleavable linkers do not degrade intracellularly and in this embodiment, the compound is released from the ligand via degradation of the ligand.

A conjugate as described herein may or may not comprise a linker molecule or moiety. A person of skill in the art could determine the appropriate type of linker based on the type of treatment or tissue being targeted by the conjugate. Exemplary linking moieties include hydrazones, peptides, chelating agents, maleimides, disulfide groups, thioether groups, acid labile groups, photolabile groups, peptidase labile groups, or esterase labile groups, as known to one of skill in the art. Linker moieties may comprise a divalent radical such as an alkyldiyl, an arylene, a heteroarylene, moieties such as: —$(CR_2)_nO(CR_2)_n$—, repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide.

Cleavable linkers may be cleaved or degraded by a cleaving agent (e.g. a protease or reducing agent) present in the intracellular environment. In some embodiments, the linker is a peptidyl linker that is cleaved by an intracellular peptidase or protease enzyme, including, but not limited to, a lysosomal or endosomal protease. In some embodiments, the peptidyl linker is at least two amino acids long. Protein and peptide cleaving agents can include cathepsins B and D and plasmin, all of which are known to cleave dipeptides resulting in the release of active drug inside target cells (see, e.g., Dubowchik and Walker (1999) *Pharm. Therapeutics* 83:67-123). For example, a peptidyl linker that is cleavable by the thiol-dependent protease cathepsin-B, which is highly expressed in cancerous tissue, can be used (e.g., a Phe-Leu containing linker). Other examples of such linkers are described, e.g., in U.S. Pat. No. 6,214,345, incorporated herein by reference in its entirety and for all purposes. In a specific embodiment, the peptidyl linker cleavable by an intracellular protease is a Val-Cit linker or a Phe-Lys linker (see, e.g., U.S. Pat. No. 6,214,345, which describes the synthesis of doxorubicin with the val-cit linker).

A cleavable linker may be fully cleaved by a cleaving agent to release the compound to which it is bound. Alternatively, a cleavable linker may be partially cleaved, such that a portion of the linker remains bound to the compound. For example, if a linker is bound to a compound via a group —C(O)N(CH$_3$)CH$_2$CH$_2$N(CH$_3$)—, the linker may be partially cleaved such that group —C(O)N(CH$_3$)CH$_2$CH$_2$NHCH$_3$ remains bound to the compound.

In other embodiments, the cleavable linker is pH-sensitive. Typically, the pH-sensitive linker is unstable and degrades under acidic conditions. For example, an acid-labile linker that is cleavable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker (1999) *Pharm. Therapeutics* 83:67-123; Neville et al. (1989) *Biol. Chem.* 264:14653-14661.) Such linkers are relatively stable under neutral pH conditions, such as those in the blood, but are unstable at below pH 5.5 or 5.0, the approximate pH of the lysosome.

Typically, the linker is not substantially sensitive to the extracellular environment. As used herein, "not substantially sensitive to the extracellular environment," in the context of a linker, means that no more than about 20%, 15%, 10%, 5%, or 1% of the linkers, in a sample of compound-ligand conjugate compound, are cleaved when the antibody-drug conjugate compound is in an extracellular environment. Whether a linker is not substantially sensitive to the extracellular environment can be determined using methods known to those of skill in the relevant art.

In some embodiments, the linker contains a spacer unit. In some embodiments, the spacer unit contains a para-aminobenzoate (PAB) moiety. In some embodiments, the linker contains a stretcher unit. In some embodiments, the stretcher unit contains a maleimide moiety.

In some embodiments, the linking groups will be bifunctional, meaning they comprise two reactive sites, wherein a first reactive site may be bound to the compounds described herein and the second reactive site may be bound to the ligand. The linker may be hetero-bifunctional, indicating that the binding moieties on either end of the linker moiety are different.

In some embodiments, conjugates of the ligand and compound are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidoberizoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al (1987) Science, 238: 1098. Carbon-14-labeled 1-isothiocyanatobenzyl-3-methyl-diethylene triaminepentaacetic acid (MX-DTPA) is an exemplary chelating agent for conjugation of radionucleotide to the compound or ligand (WO94/11026).

The compounds described herein can be linked to ligands via an acid labile linker as previously described (Blattler et al, 24 Biochemistry, 1517-1524 (1985), U.S. Pat. Nos. 4,542,225, 4,569,789 and 4,764,368).

The compounds described herein can be linked to ligands via a photolabile linker as previously described (Senter et al, 42 Photochemistry and Photobiology, 231-237 (1985), U.S. Pat. No. 4,625,014).

The compounds described herein can be linked to a ligand to produce a conjugate that can be cleaved by intracellular esterases to liberate free drug. (For examples see: U.S. Pat. No. 5,208,020 and Aboud-Pirak et al, 38 Biochem. Pharmacol., 641-648 (1989), Laguzza et al, 32 J. Med. Chem., 549-555 (1989)).

The compounds described herein can also be linked to ligands via peptide spacer linkers. It has been previously shown that short peptide spacers between drugs and macromolecular carriers are stable in serum but are readily hydrolyzed by intracellular lysosomal peptidases (Trouet et al, 79 Proc. Nat'l. Acad. Sci. 626-629 (1982)).

Functional groups on the compound that can serve as a handle for attachment of a linker or ligand using the coupling methods described herein include, without limitation, —OH, —NHR, —NHNH$_2$, —ONH$_2$, —SH, —CO$_2$H, and other functional groups. In any of the variations of Formulae (I), (Ia), (Ib), (Ic), (Id), and (Ie) described herein, the compound may be modified to contain one or more functional groups that can serve as a handle for attachment of a linker or ligand at any chemically feasible position. In some embodiments, any of the variations of Formulae (I), (Ia), (Ib), (Ic), (Id), and (Ic) may contain one or more moieties selected from the group consisting of —OH, —NHR, —NHNH$_2$, —ONH$_2$, —N$_3$, —SH, —CO$_2$H at any chemically feasible position. In some embodiments, a handle for attachment of a linker or ligand can be located on an amino acid side chain. In other embodiments, a handle for attachment of a linker or ligand can be located at position Y$^4$. In other embodiments, a handle for attachment of a linker or ligand can be located at positions R$^2$, R$^{8a}$, R$^{8b}$, R$^{15}$, or R$^4$.

In some variations the linker is of formula (L-Fn), where the linker is bonded to a compound provided herein via the bond shown as

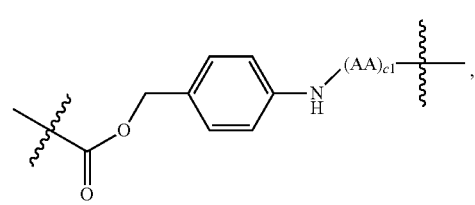

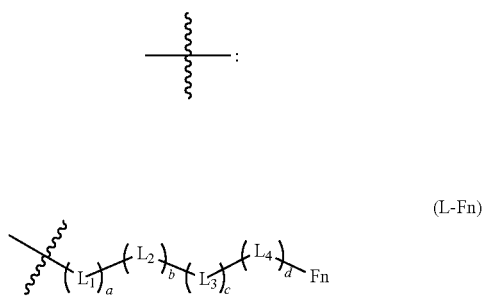

(L-Fn)

wherein
a, b, c, and d are independently 0, 1, or 2;
each L$_1$ is independently

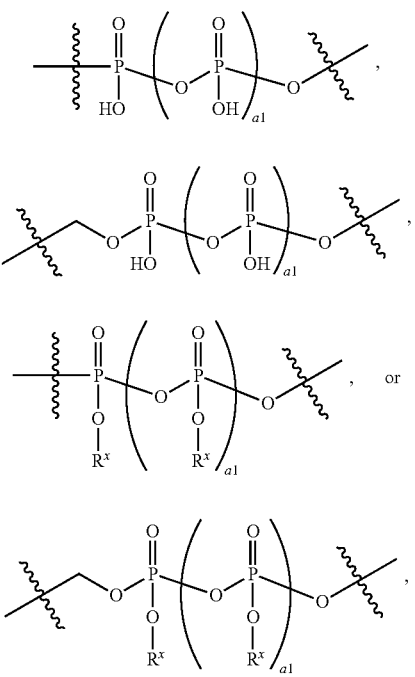

wherein a1 is 0, 1, or 2, and each R$^8$ is unsubstituted or substituted alkyl;

each L$_2$ is independently

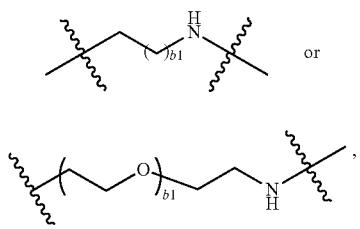

wherein b1 is an integer from 0 to 12, inclusive;
each L$_3$ is independently

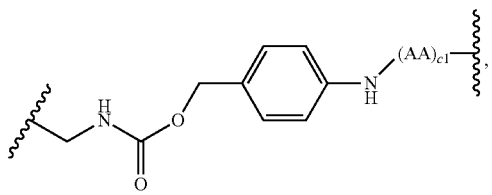

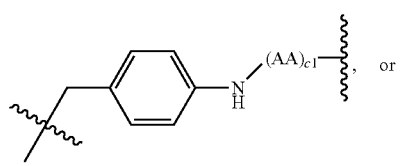

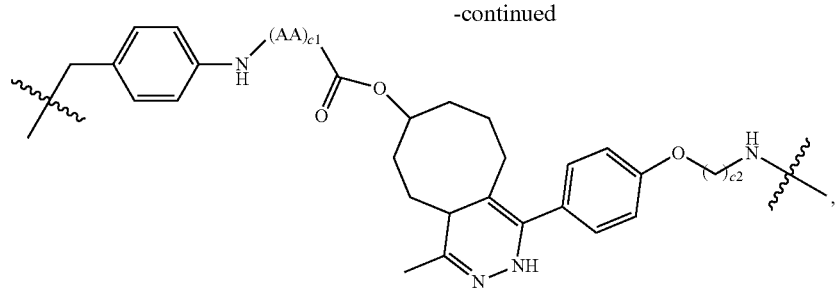
wherein each AA is an amino acid, c1 is an integer from 0-12, inclusive, and c2 is an integer from 0-10, inclusive; each $L_4$ is independently
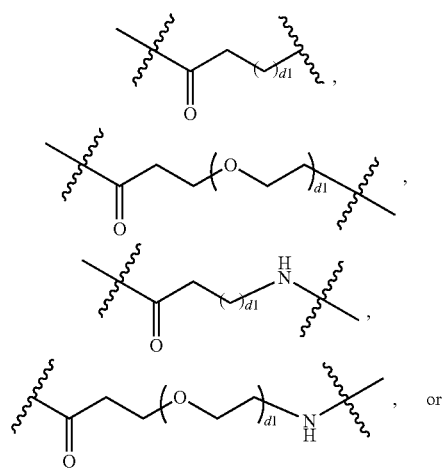
, or
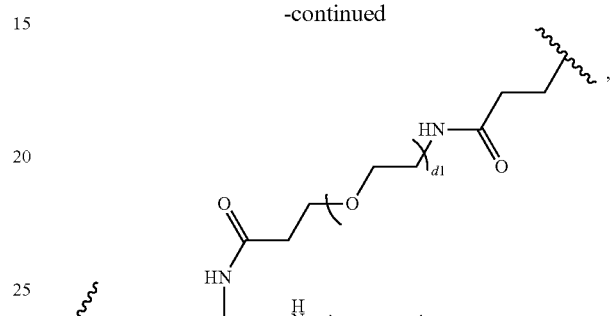
wherein d1 is an integer from 0-12, inclusive, and d2 is an integer from 0-30, inclusive; and
Fn is selected from the group consisting of H, unsubstituted or substituted alkyl,
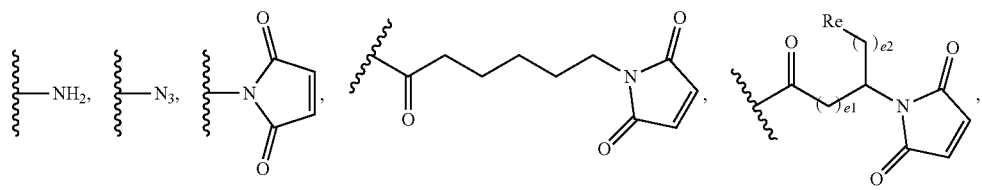
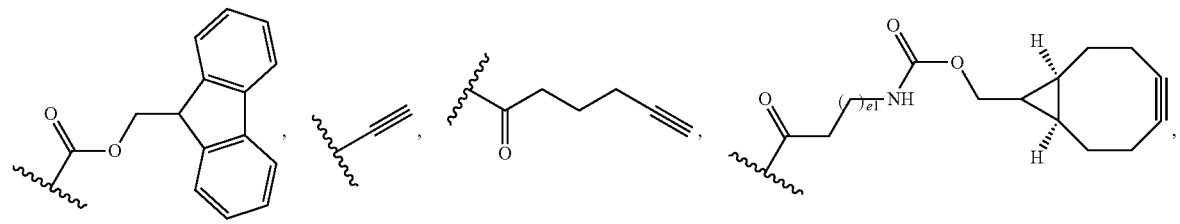
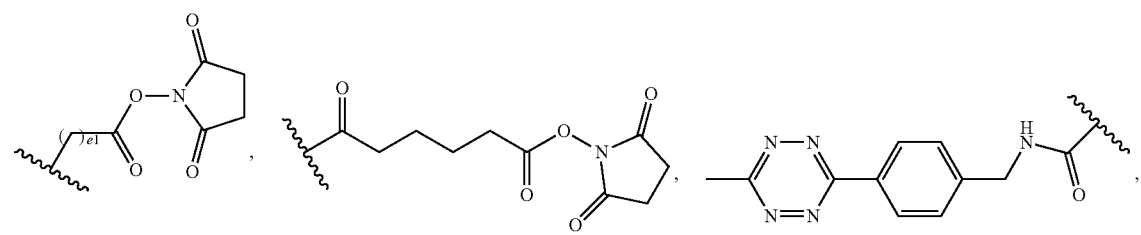

-continued
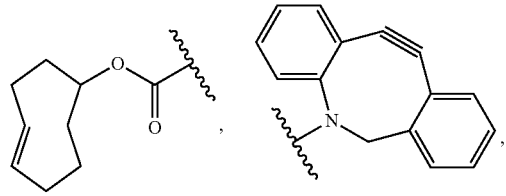
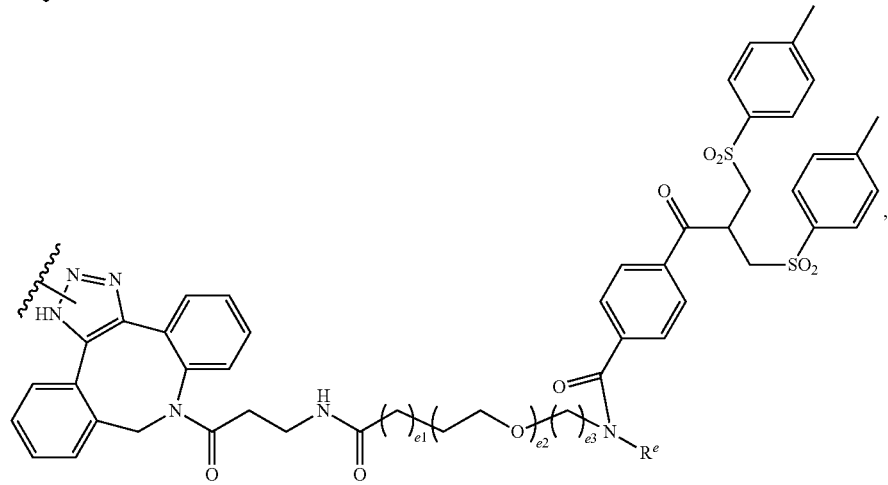
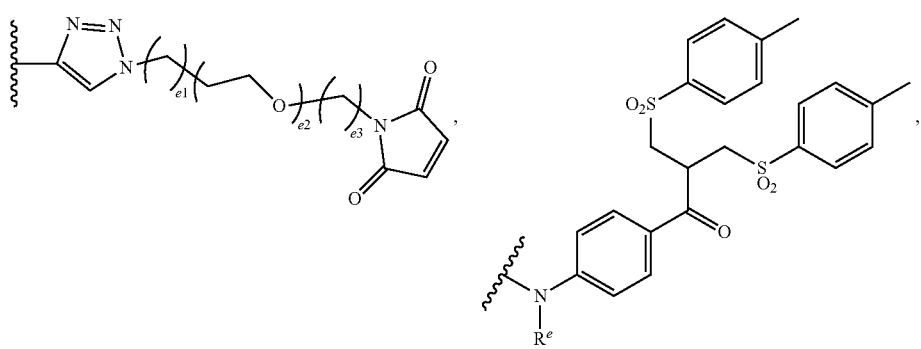
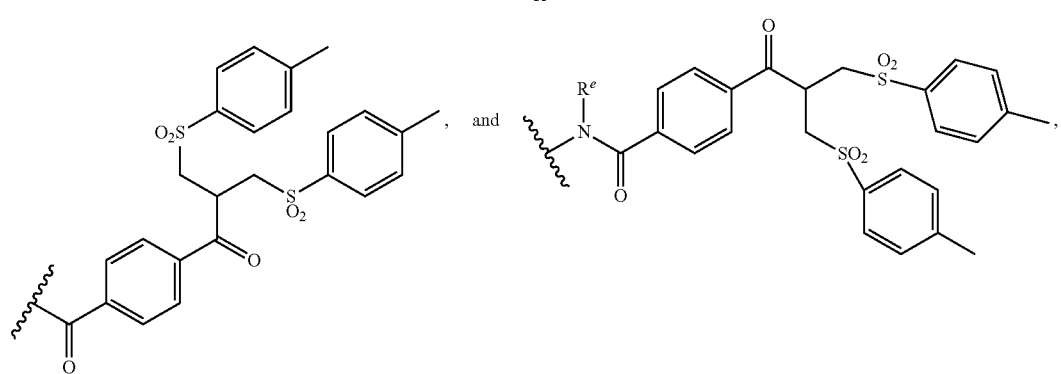
wherein e1, e2, and e3 are each independently an integer from 0-12, inclusive, and $R^e$ is H or alkyl.
In some embodiments of Formula (L-Fn), $L_1$ is independently
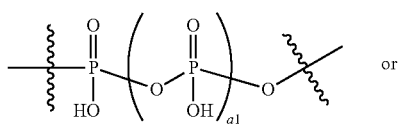 or
-continued
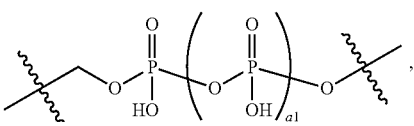
wherein a1 is 0, 1, or 2. In some embodiments of Formula (L-Fn), $L_3$ is independently

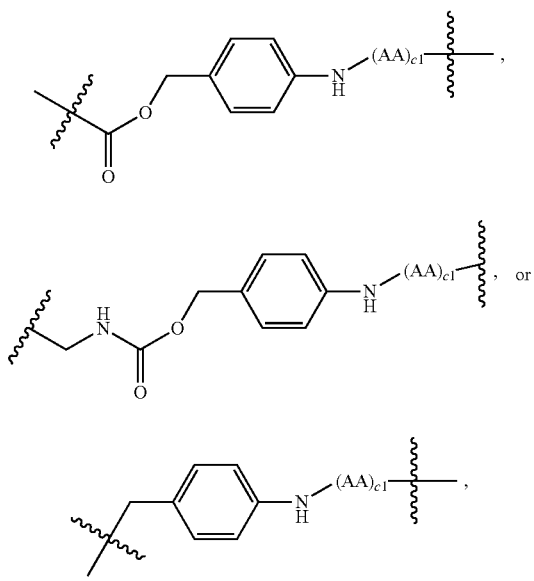
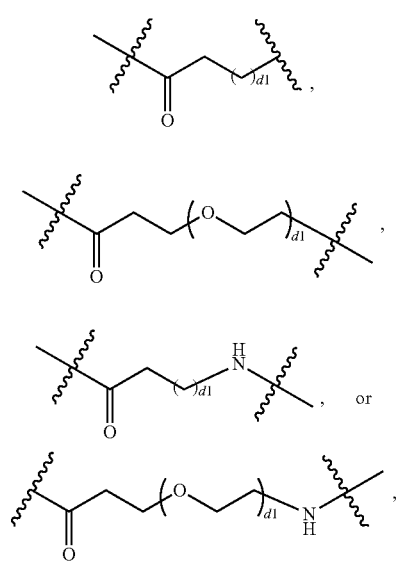
wherein each AA is an amino acid and c1 is an integer from 0-12 inclusive. In some embodiments of Formula (L-Fn), $L_4$ is independently
wherein d1 is an integer from 0-12, inclusive. In some embodiments of Formula (L-Fn), Fn is selected from the group consisting of H,
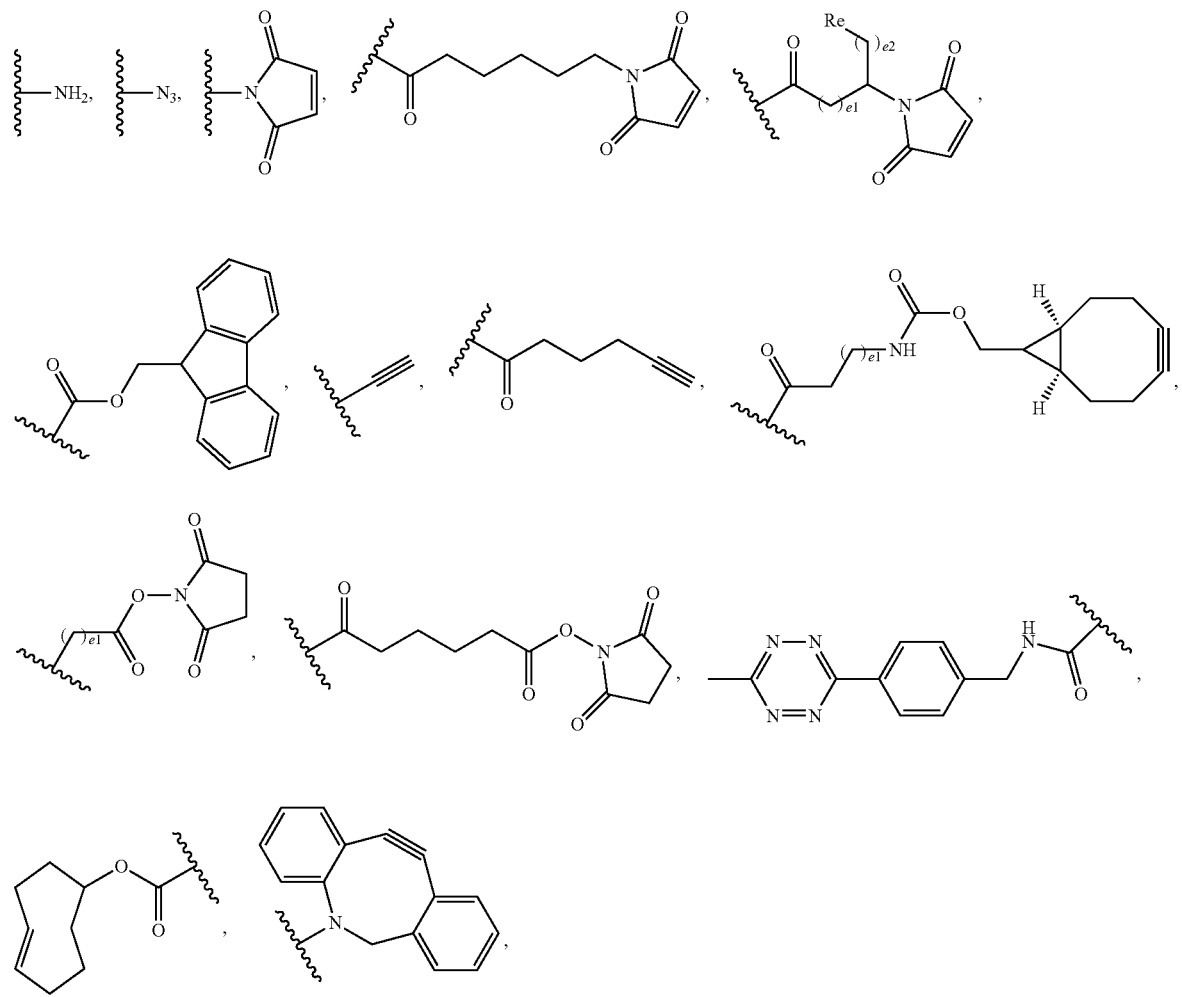

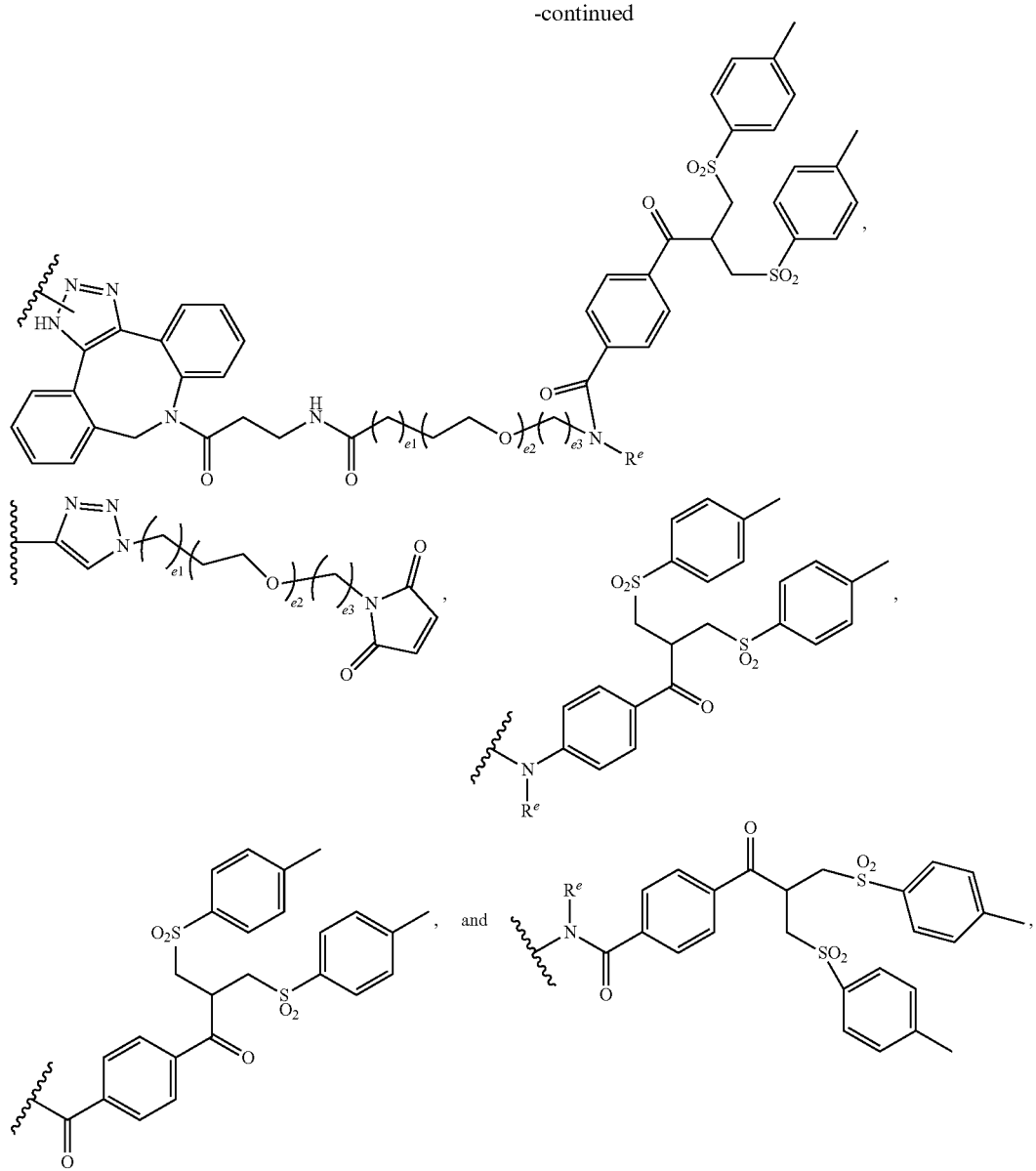

wherein e1, e2, and e3 are each independently an integer from 0-12, inclusive, and $R^e$ is H or alkyl.

In some embodiments of Formula (L-Fn), a1 is 0. In some embodiments, a1 is 1. In some embodiments of Formula (L-Fn) b1 is 1 to 8. In some embodiments, b1 is 1. In some embodiments, b1 is 2. In some embodiments, b1 is 3. In some embodiments, b1 is 4. In some embodiments, b1 is 5. In some embodiments, $L_3$ is

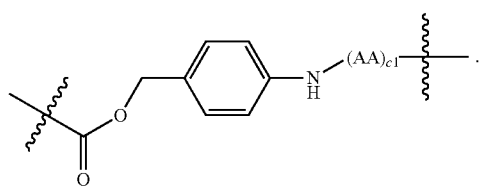

In some embodiments, a and b are both 0 and $L_3$ is

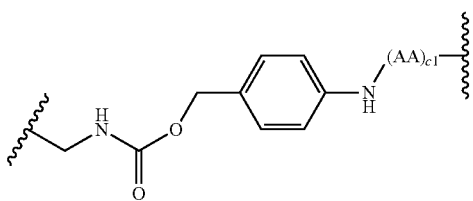

In some embodiments, b is 0 and $L_3$ is

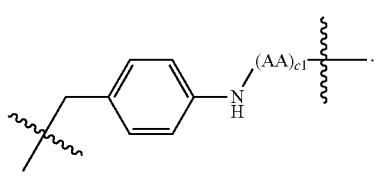

In some embodiments, $L_3$ is

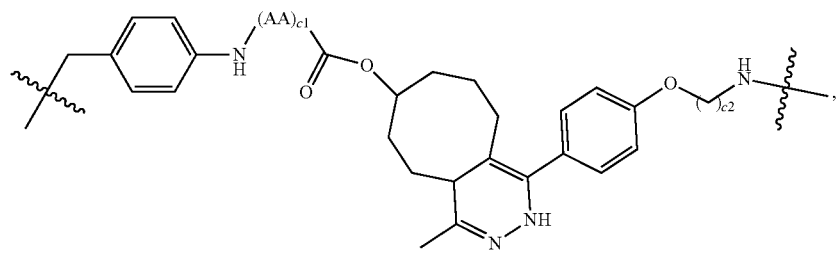

wherein c2 is 3. In some embodiments, AA may be a natural amino acid. In some embodiments, AA may be an unnatural amino acid. In some embodiments $(AA)_{c1}$ may comprise natural amino acids, unnatural amino acids, or both natural and unnatural amino acids. In some embodiments $(AA)_{c1}$ is -Cit-Val-. In some embodiments, $(AA)_{c1}$ is -Ala-Val-. In some embodiments, c1 is 0-8. In some embodiments, c1 is 0. In some embodiments, c1 is 1. In some embodiments, c1 is 2. In some embodiments, c1 is 3. In some embodiments, c1 is 4. In some embodiments, $L_4$ is

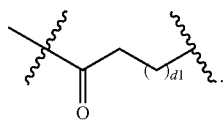

In some embodiments, $L_4$ is

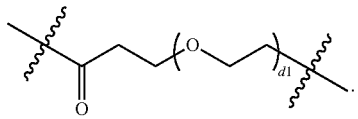

In some embodiments, $L_4$ is

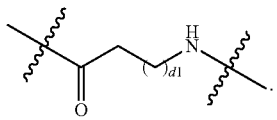

In some embodiments, $L_4$ is

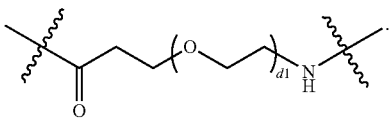

In other embodiments, $L_4$ is

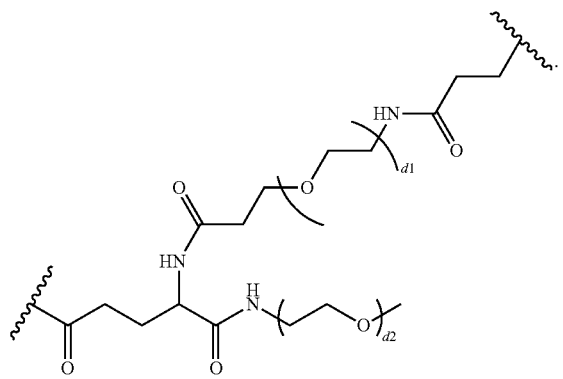

In some embodiments, d1 is 1-8. In some embodiments, d1 is 1. In some embodiments, d1 is 2. In some embodiments, d1 is 3. In some embodiments, d1 is 4. In some embodiments, d1 is 5. In some embodiment, d2 is 1-30. In some embodiments, d2 is 12-28. In some embodiments, d2 is 24. In some embodiments, Fn is unsubstituted or substituted alkyl. In some embodiments, Fn is alkyl substituted with halo. In some embodiments, Fn is trichloroethyl (Tce). In some embodiments, Fn is

In some embodiments, Fn is

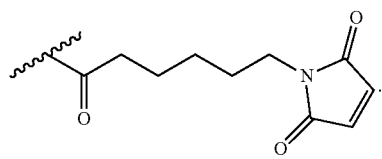 [SMILES: *C(=O)CCCCCN1C(=O)C=CC1=O]

In some embodiments, Fn is

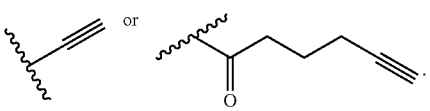

In some embodiments, Fn is

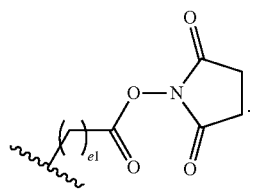

In some embodiments, Fn is

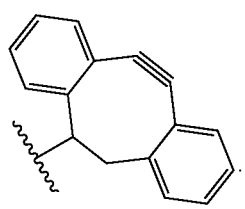 [SMILES: *C1Cc2ccccc2C#Cc2ccccc21]

In some embodiments, Fn is

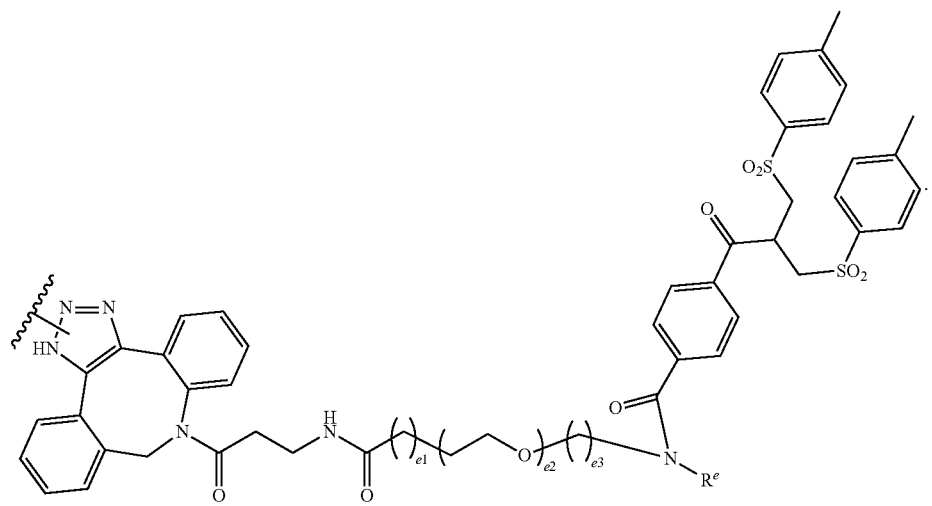

In other embodiments, Fn is

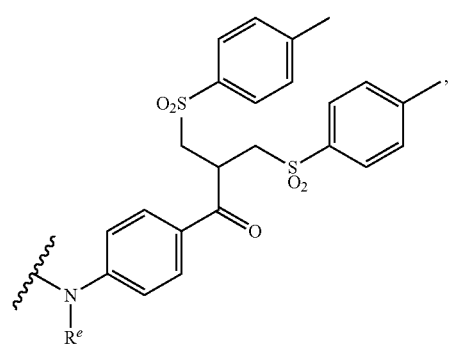

or

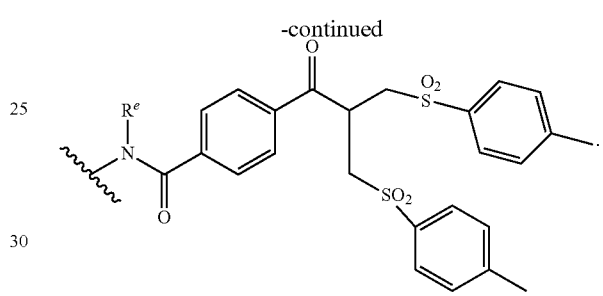

-continued

In some variations, the linker is of Formula (La-Fn):

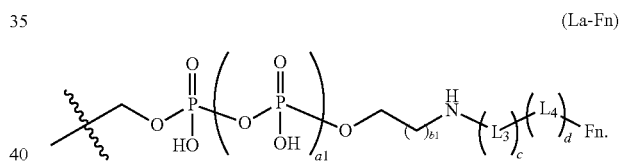

(La-Fn)

In some embodiments of Formula (La-Fn), a1 is 0. In some embodiments, a1 is 1. In some embodiments of Formula La, b1 is 1 to 8. In some embodiments, b1 is 1. In some embodiments, b1 is 2. In some embodiments, b1 is 3. In some embodiments, b1 is 4. In some embodiments, b1 is 5. In some embodiments, $L_3$ is

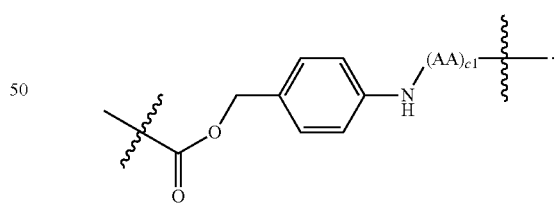

In some embodiments, $L_3$ is

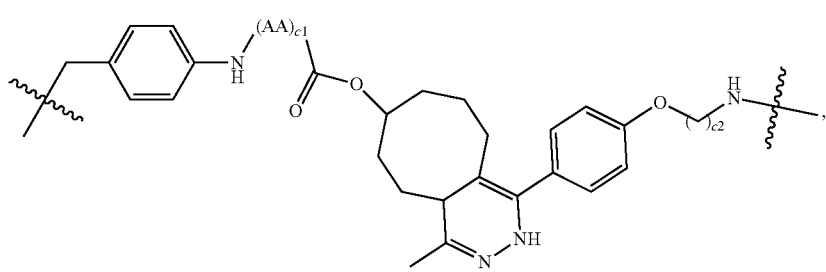

wherein c2 is 0-10. In some embodiments, c2 is 3. In some embodiments, AA may be a natural amino acid. In some embodiments, AA may be an unnatural amino acid. In some embodiments $(AA)_{c1}$ may comprise natural amino acids, unnatural amino acids, or both natural and unnatural amino acids. In some embodiments $(AA)_{c1}$ is -Cit-Val-. In some embodiments, $(AA)_{c1}$ is -Ala-Val-. In some embodiments, c1 is 0-8. In some embodiments, c1 is 0. In some embodiments, c1 is 1. In come embodiments, c1 is 2. In some embodiments, c1 is 3. In some embodiments, c1 is 4. In some embodiments, $L_4$ is

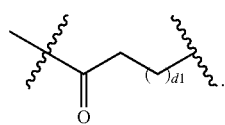

In some embodiments, $L_4$ is

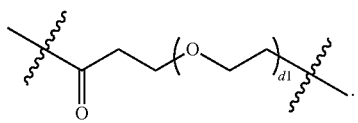

In some embodiments, $L_4$ is

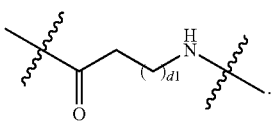

In some embodiments, $L_4$ is

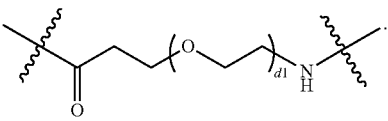

In other embodiments, $L_4$ is

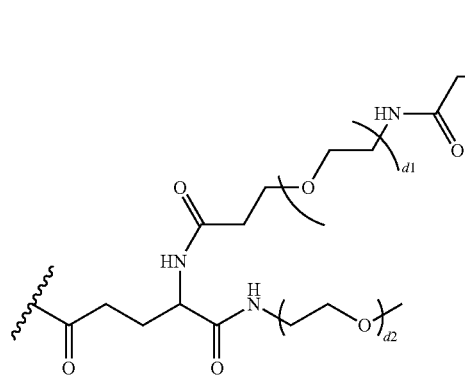

In some embodiments, d1 is 1-8. In some embodiments, d1 is 1. In some embodiments, d1 is 2. In some embodiments, d1 is 3. In some embodiments, d1 is 4. In some embodiments, d1 is 5. In some embodiment, d2 is 1-30. In some embodiments, d2 is 12-28. In some embodiments, d2 is 24. In some embodiments of Formula (La-Fn), Fn is unsubstituted or substituted alkyl. In some embodiments, Fn is alkyl substituted with halo. In some embodiments, Fn is trichloroethyl (Tce). In some embodiments of Formula (La-Fn), Fn is

In some embodiments, Fn is

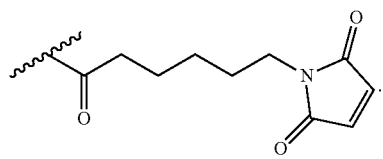 [SMILES: *C(=O)CCCCCN1C(=O)C=CC1=O]

In some embodiments, Fn is

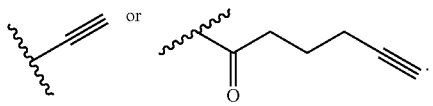

In some embodiments, Fn is

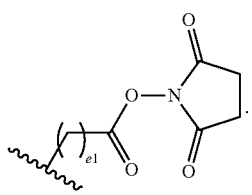

In some embodiments, Fn is

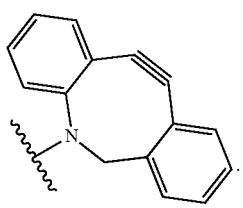 [SMILES: *N1Cc2ccccc2C#Cc2ccccc21]

In some embodiments, Fn is

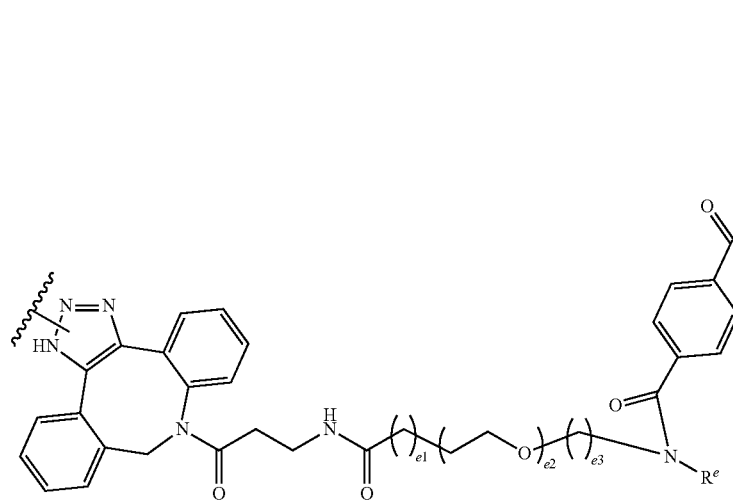

In other embodiments, Fn is

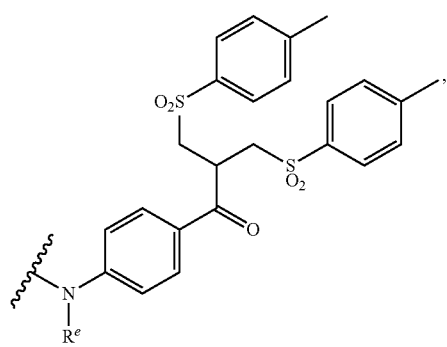

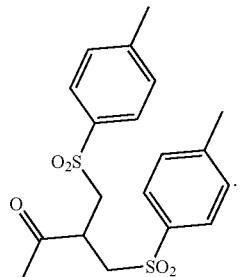

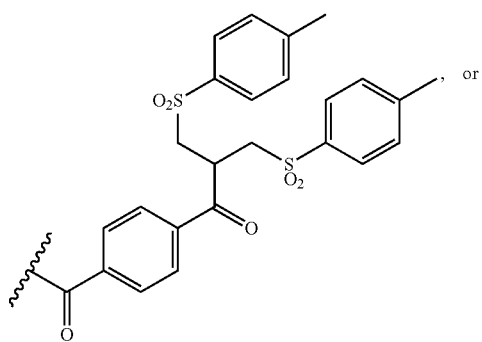

or

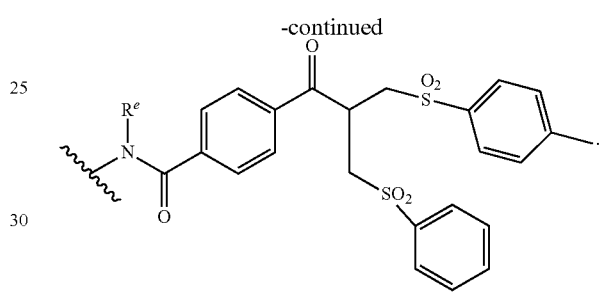

In some variations, the linker is of Formula (Lb-Fn):

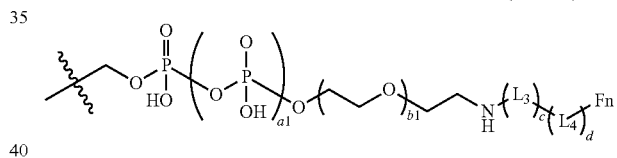

In some embodiments of Formula (Lb-Fn), a1 is 0. In some embodiments, a1 is 1. In some embodiments of Formula (Lb-Fn), b1 is 1 to 8. In some embodiments, b1 is 1. In some embodiments, b1 is 2. In some embodiments, b1 is 3. In some embodiments, b1 is 4. In some embodiments, b1 is 5. In some embodiments, $L_3$ is

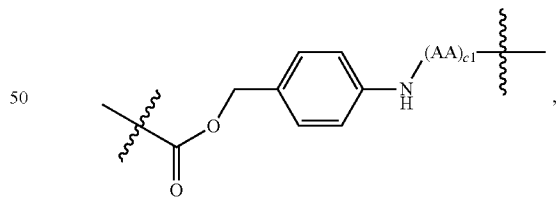

In some embodiments, $L_3$ is

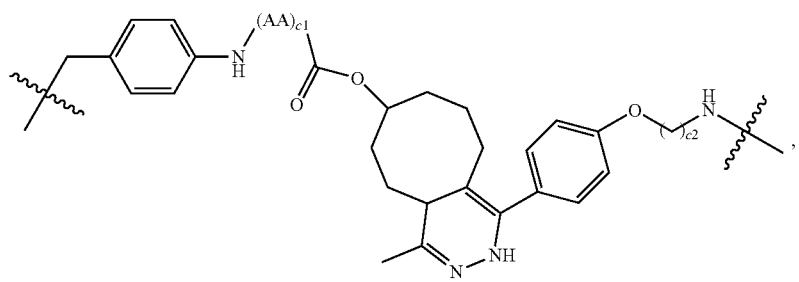

wherein c2 is 0-10. In some embodiments, c2 is 3. In some embodiments, AA may be a natural amino acid. In some embodiments, AA may be an unnatural amino acid. In some embodiments $(AA)_{c1}$ may comprise natural amino acids, unnatural amino acids, or both natural and unnatural amino acids. In some embodiments $(AA)_{c1}$ is -Cit-Val-. In some embodiments, $(AA)_{c1}$ is -Ala-Val-. In some embodiments, c1 is 0-8. In some embodiments, c1 is 0. In some embodiments, c1 is 1. In some embodiments, c1 is 2. In some embodiments, c1 is 3. In some embodiments, c1 is 4. In some embodiments, $L_4$ is

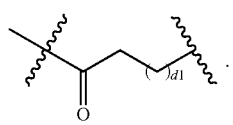

In some embodiments, $L_4$ is

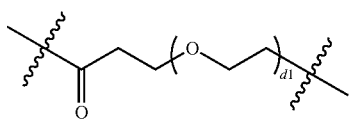

In some embodiments, $L_4$ is

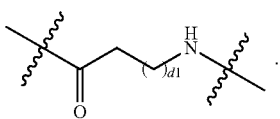

In some embodiments, $L_4$ is

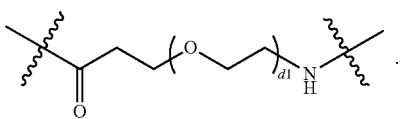

In other embodiments, $L_4$ is

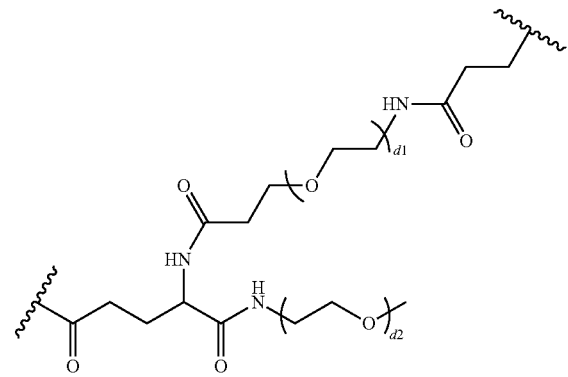

In some embodiments, d1 is 1-8. In some embodiments, d1 is 1. In some embodiments, d1 is 2. In some embodiments, d1 is 3. In some embodiments, d1 is 4. In some embodiments, d1 is 5. In some embodiment, d2 is 1-30. In some embodiments, d2 is 12-28. In some embodiments, d2 is 24. In some embodiments of Formula (Lb-Fn), Fn is unsubstituted or substituted alkyl. In some embodiments, Fn is alkyl substituted with halo. In some embodiments, Fn is trichloroethyl (Tce). In some embodiments of Formula (Lb-Fn), Fn is

$N_3$. In some embodiments, Fn is

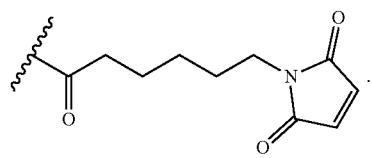 [SMILES: *C(=O)CCCCCN1C(=O)C=CC1=O ; "."]

In some embodiments, Fn is

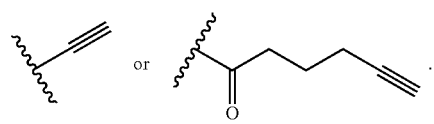

In some embodiments, Fn is

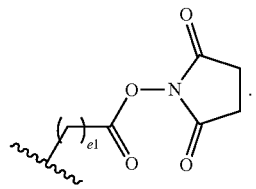

In some embodiments, Fn is

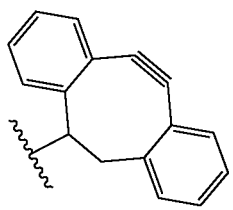

In some embodiments, Fn is

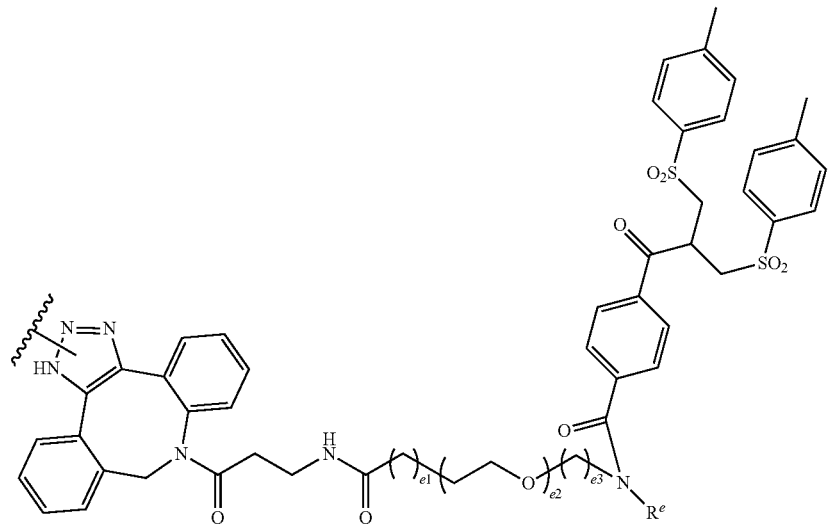

In other embodiments, Fn is

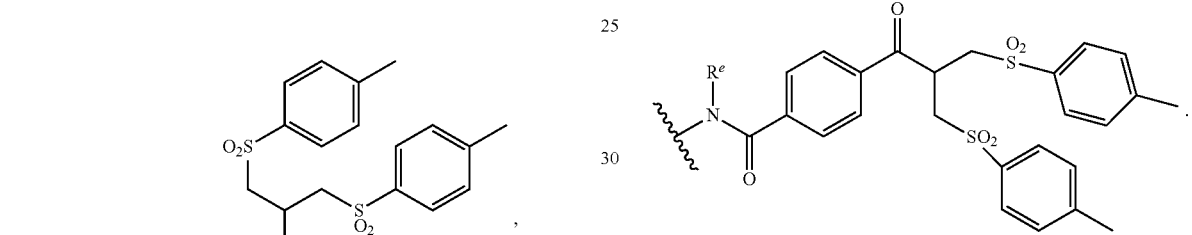

-continued

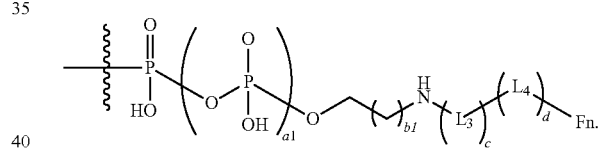

In some variations, the linker is of Formula (Lc-Fn):

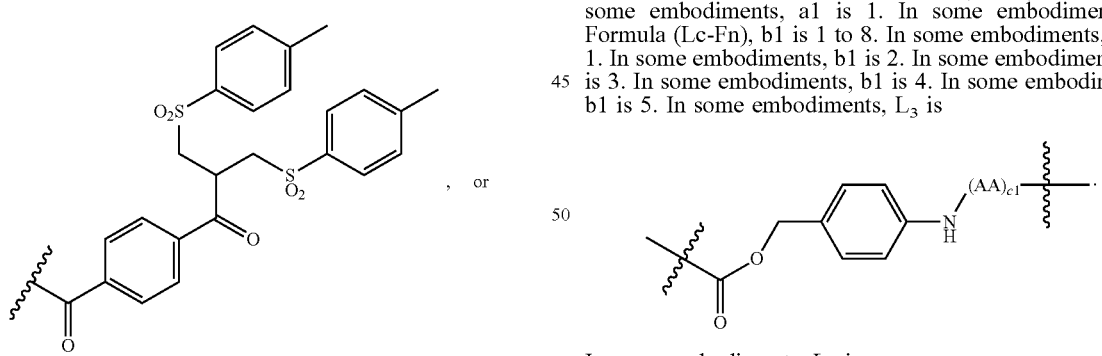

In some embodiments of Formula (Lc-Fn), a1 is 0. In some embodiments, a1 is 1. In some embodiments of Formula (Lc-Fn), b1 is 1 to 8. In some embodiments, b1 is 1. In some embodiments, b1 is 2. In some embodiments, b1 is 3. In some embodiments, b1 is 4. In some embodiments, b1 is 5. In some embodiments, $L_3$ is

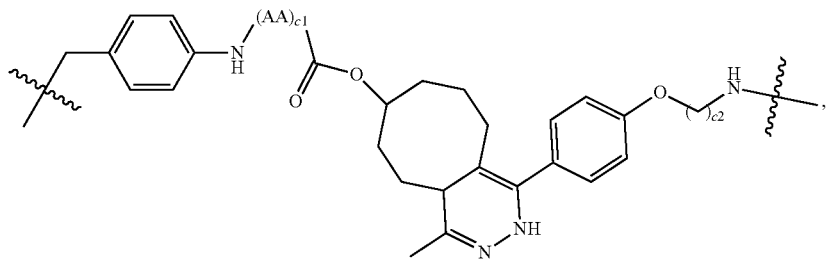

In some embodiments, $L_3$ is wherein c2 is 0-10. In some embodiments, c2 is 3. In some embodiments, AA may be a natural amino acid. In some embodiments, AA may be an unnatural amino acid. In some embodiments $(AA)_{c1}$ may comprise natural amino acids, unnatural amino acids, or both natural and unnatural amino acids. In some embodiments $(AA)_{c1}$ is -Cit-Val-. In some embodiments, $(AA)_{c1}$ is -Ala-Val-. In some embodiments, c1 is 0-8. In some embodiments, c1 is 0. In some embodiments, c1 is 1. In some embodiments, c1 is 2. In some embodiments, c1 is 3. In some embodiments, c1 is 4. In some embodiments, $L_4$ is

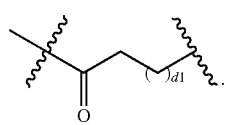

In some embodiments, $L_4$ is

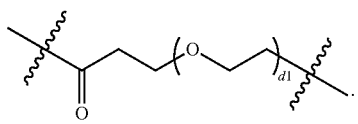

In some embodiments, $L_4$ is

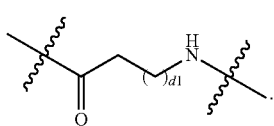

In some embodiments, $L_4$ is

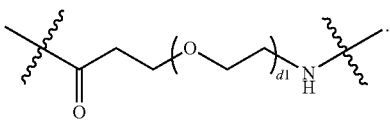

In other embodiments, $L_4$ is

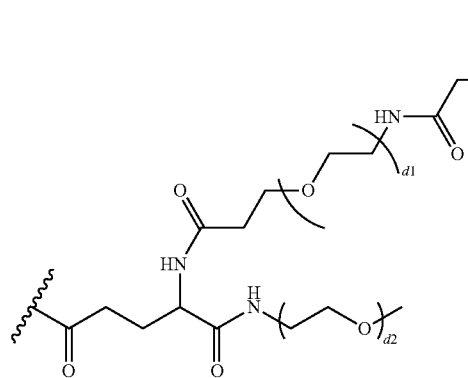

In some embodiments, d1 is 1-8. In some embodiments, d1 is 1. In some embodiments, d1 is 2. In some embodiments, d1 is 3. In some embodiments, d1 is 4. In some embodiments, d1 is 5. In some embodiment, d2 is 1-30. In some embodiments, d2 is 12-28. In some embodiments, d2 is 24. In some embodiments of Formula (Le-Fn), Fn is unsubstituted or substituted alkyl. In some embodiments, Fn is alkyl substituted with halo. In some embodiments, Fn is trichloroethyl (Tce). In some embodiments of Formula (Lc-Fn), Fn is

In some embodiments, Fn is

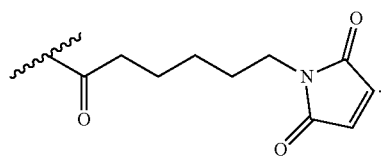 [SMILES: *C(=O)CCCCCN1C(=O)C=CC1=O]

In some embodiments, Fn is

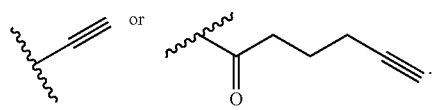

In some embodiments, Fn is

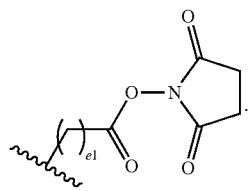

In some embodiments, Fn is

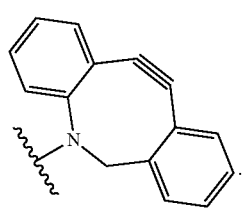 [SMILES: *N1Cc2ccccc2C#Cc2ccccc21]

In some embodiments, Fn is

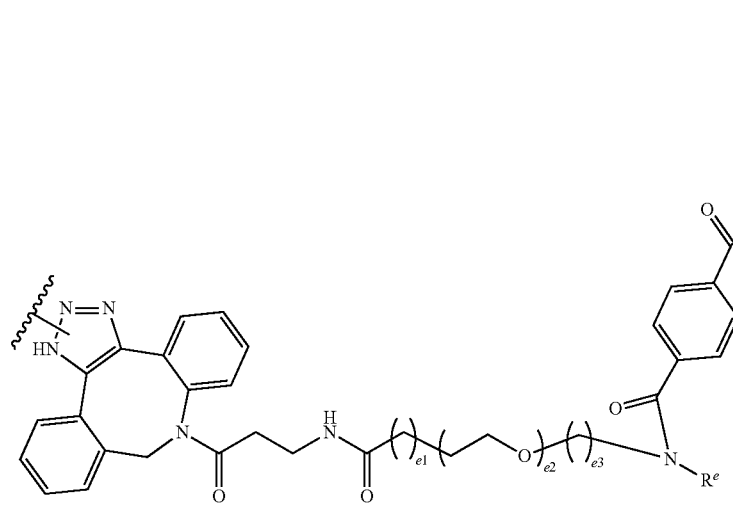

In other embodiments, Fn is

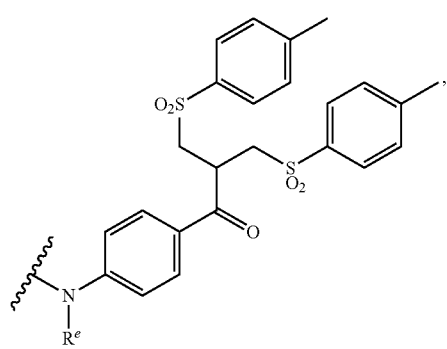

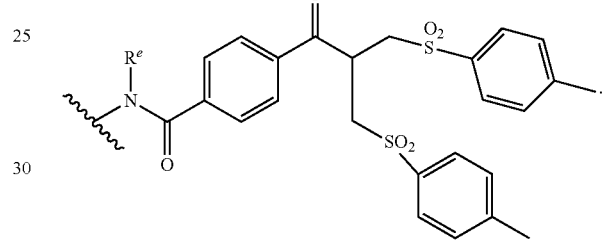

In some variations, the linker is of Formula (Ld-Fn):

(Ld-Fn)

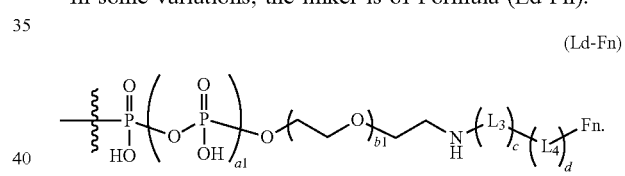

In some embodiments of Formula (Ld-Fn), a1 is 0. In some embodiments, a1 is 1. In some embodiments of Formula (Ld-Fn), b1 is 1 to 8. In some embodiments, b1 is 1. In some embodiments, b1 is 2. In some embodiments, b1 is 3. In some embodiments, b1 is 4. In some embodiments, b1 is 5. In some embodiments, $L_3$ is

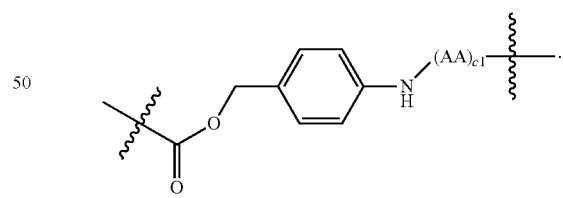

In some embodiments, $L_3$ is

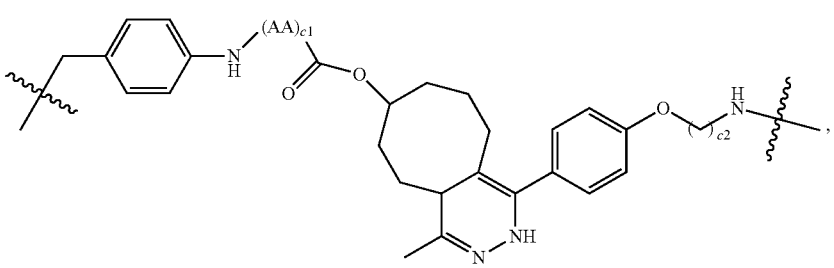

wherein c2 is 0-10. In some embodiments, c2 is 3. In some embodiments, AA may be a natural amino acid. In some embodiments, AA may be an unnatural amino acid. In some embodiments $(AA)_{c1}$ may comprise natural amino acids, unnatural amino acids, or both natural and unnatural amino acids. In some embodiments $(AA)_{c1}$ is -Cit-Val-. In some embodiments, $(AA)_{c1}$ is -Ala-Val-. In some embodiments, c1 is 0-8. In some embodiments, c1 is 0. In some embodiments, c1 is 1. In some embodiments, c1 is 2. In some embodiments, c1 is 3. In some embodiments, c1 is 4. In some embodiments, $L_4$ is

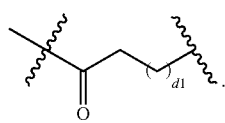

In some embodiments, $L_4$ is

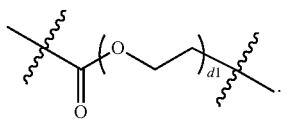

In some embodiments, $L_4$ is

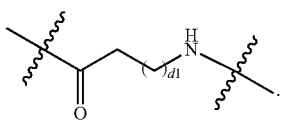

In some embodiments, $L_4$ is

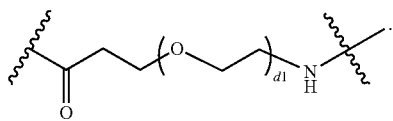

In other embodiments, $L_4$ is

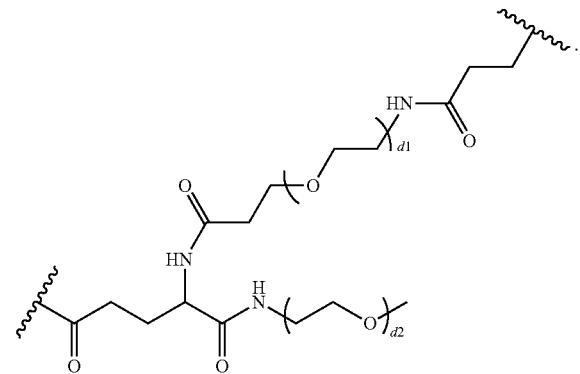

In some embodiments, d1 is 1-8. In some embodiments, d1 is 1. In some embodiments, d1 is 2. In some embodiments, d1 is 3. In some embodiments, d1 is 4. In some embodiments, d1 is 5. In some embodiment, d2 is 1-30. In some embodiments, d2 is 12-28. In some embodiments, d2 is 24. In some embodiments of Formula (Ld-Fn), Fn is unsubstituted or substituted alkyl. In some embodiments, Fn is alkyl substituted with halo. In some embodiments, Fn is trichloroethyl (Tce). In some embodiments of Formula (Ld-Fn), Fn is

In some embodiments, Fn is

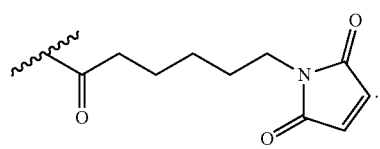 [SMILES: *C(=O)CCCCCN1C(=O)C=CC1=O]

In some embodiments, Fn is

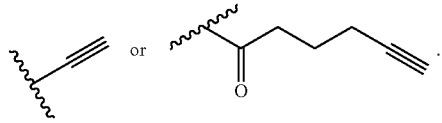

In some embodiments, Fn is

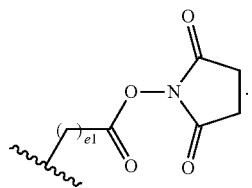

In some embodiments, Fn is

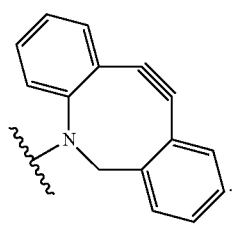 [SMILES: *N1Cc2ccccc2C#Cc2ccccc21]

In some embodiments, Fn is
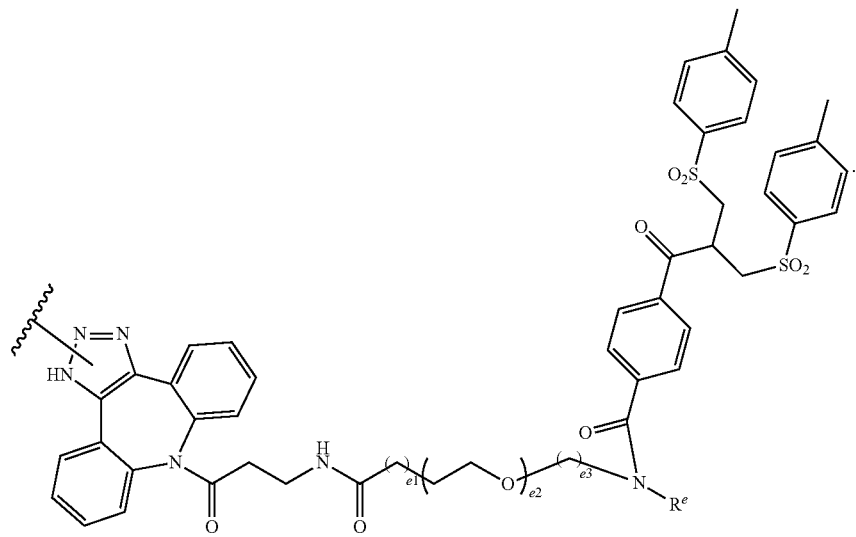
In other embodiments, Fn is
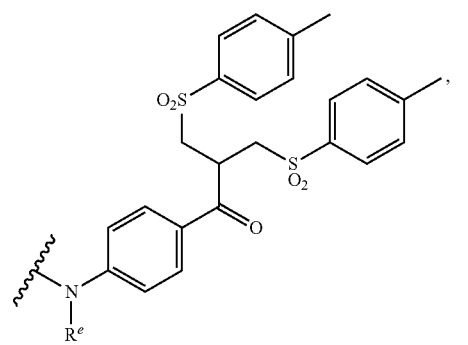
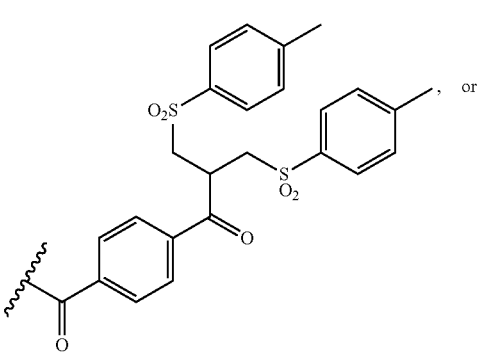
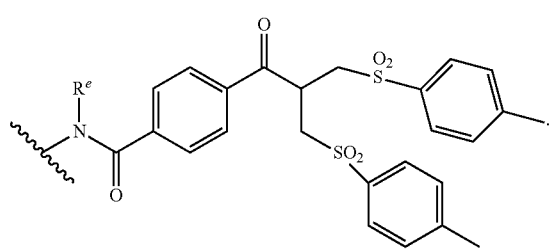
In some embodiments, the linker is
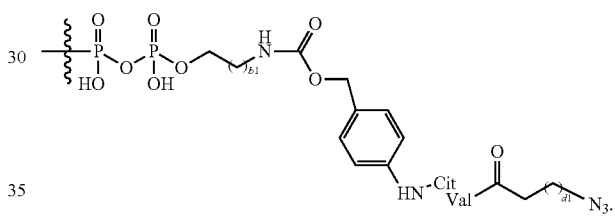
In some embodiments, the linker is
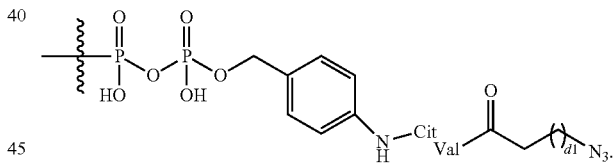
In some embodiments, the linker is
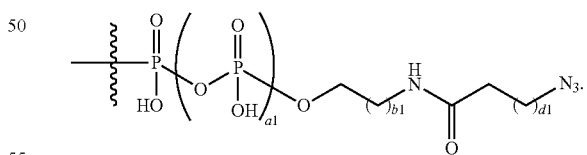
In some embodiments, the linker is
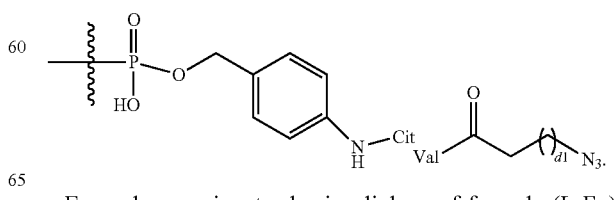
Exemplary conjugates having linkers of formula (L-Fn) include the following conjugates of Formula (III):

(III)

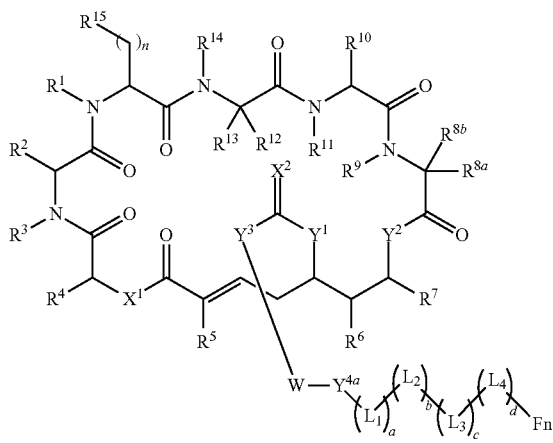

and salts thereof.

wherein $R^1, R^2, R^3, R^4, R^5, R^6, R^7, R^{8a}, R^{8b}, R^9, R^{10}, R^{11}, R^{12}, R^{13}, R^{14}, R^{15}$, n, W, $X^1, X^2, Y^1, Y^2$, and $Y^3$ are as defined for Formula (I) or any variation thereof;

$Y^{4a}$ —O—, —$NR^b$—, or —S—, wherein $R^b$ is H, substituted or unsubstituted alkyl, substituted or unsubstituted alkenyl, substituted or unsubstituted alkynyl, substituted or unsubstituted cycloalkyl, or substituted or unsubstituted cycloalkenyl; and $L_1, L_2, L_3, L_4$, a, b, c, d, and Fn are as defined for Formula (L-Fn) or any variation thereof.

In some aspects, provided are conjugates of Formula (IIIa):

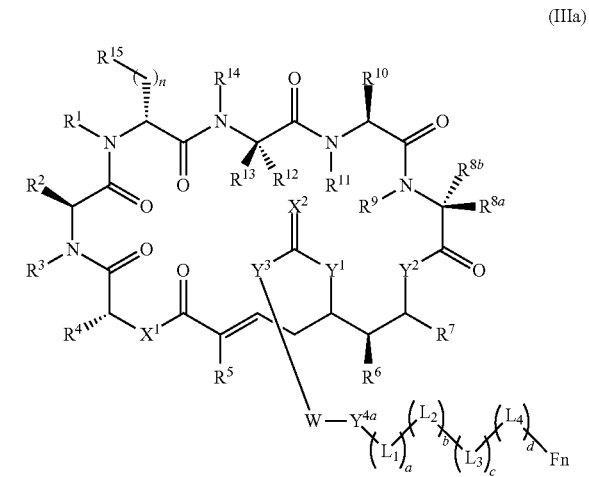

(IIIa)

and salts thereof, wherein $R^1, R^2, R^3, R^4, R^5, R^6, R^7, R^{8a}, R^{8b}, R^9, R^{10}, R^{11}, R^{12}, R^{13}, R^{14}$, n, W, $X^1, X^2, Y^1, Y^2$, and $Y^3$ are as defined for Formula (Ia) or any variation thereof;

$Y^{4a}$ is —O—, —$NR^b$—, or —S—, wherein $R^b$ is H, substituted or unsubstituted alkyl, substituted or unsubstituted alkenyl, substituted or unsubstituted alkynyl, substituted or unsubstituted cycloalkyl, or substituted or unsubstituted cycloalkenyl; and $L_1, L_2, L_3, L_4$, a, b, c, d, and Fn are as defined for Formula (L-Fn) or any variation thereof.

In some aspects, provided are conjugates of Formula (IIIb):

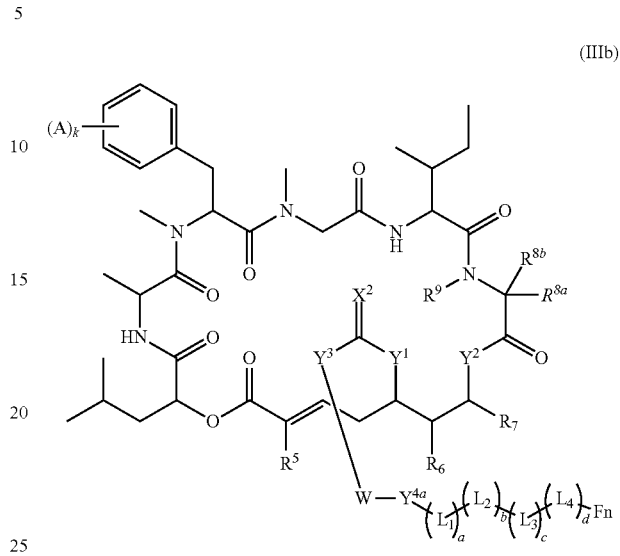

(IIIb)

and salts thereof.

wherein $R^5, R^6, R^7, R^{8a}, R^{8b}, R^9$, W, $X^2, Y^1, Y^2, Y^3$, A and k are as defined for Formula (Ib) or any variation thereof;

$Y^{4a}$ is —O—, or —S—, wherein $R^b$ is H, substituted or unsubstituted alkyl, substituted or unsubstituted alkenyl, substituted or unsubstituted alkynyl, substituted or unsubstituted cycloalkyl, or substituted or unsubstituted cycloalkenyl; and $L_1, L_2, L_3, L_4$, a, b, c, d, and Fn are as defined for Formula (L-Fn) or any variation thereof.

In some aspects, provided are conjugates of Formula (IIIc):

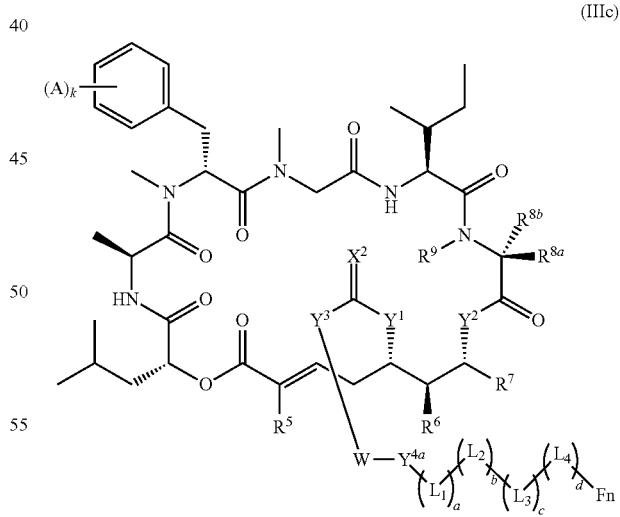

(IIIc)

and salts thereof, wherein $R^5, R^6, R^7, R^{8a}, R^{8b}, R^9$, W, $X^2, Y^1, Y^2, Y^3$, A and k are as defined for Formula (Ic) or any variation thereof;

$Y^{4a}$ is —O—, —$NR^b$—, or —S—, wherein $R^b$ is H, substituted or unsubstituted alkyl, substituted or unsubstituted alkenyl, substituted or unsubstituted alkynyl, substituted or unsubstituted cycloalkyl, or substituted or unsubstituted cycloalkenyl; and $L_1$, $L_2$, $L_3$, $L_4$, a, b, c, d, and Fn are as defined for Formula (L-Fn) or any variation thereof.

In some aspects, provided are conjugates of Formula (IIId):

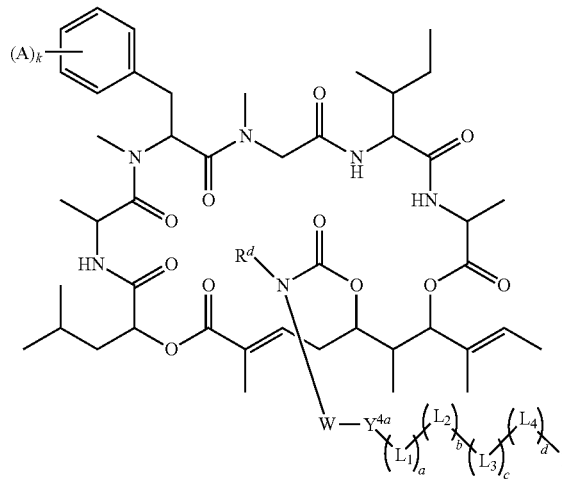

(IIId)

and salts thereof, wherein $R^d$, W, A and k are as defined for Formula (Id) or any variation thereof;

$Y^{4a}$ is —O—, —$NR^b$—, or —S—, wherein $R^b$ is H, substituted or unsubstituted alkyl, substituted or unsubstituted alkenyl, substituted or unsubstituted alkynyl, substituted or unsubstituted cycloalkyl, or substituted or unsubstituted cycloalkenyl; and $L_1$, $L_2$, $L_3$, $L_4$, a, b, c, d, and Fn are as defined for Formula (L-Fn) or any variation thereof.

In some aspects, provided are conjugates of Formula (IIIe):

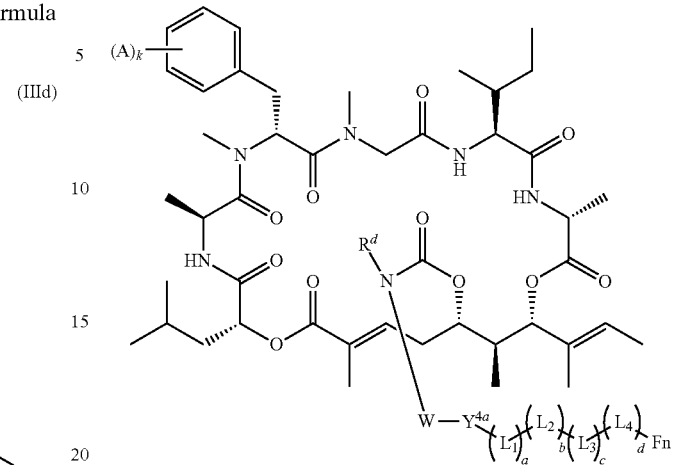

(IIIe)

and salts thereof, wherein $R^d$, W, A and k are as defined for Formula (Id) or any variation thereof;

$Y^{4a}$ is —O—, —$NR^b$—, or —S—, wherein $R^b$ is H, substituted or unsubstituted alkyl, substituted or unsubstituted alkenyl, substituted or unsubstituted alkynyl, substituted or unsubstituted cycloalkyl, or substituted or unsubstituted cycloalkenyl; and $L_1$, $L_2$, $L_3$, $L_4$, a, b, c, d, and Fn are as defined for Formula (L-Fn) or any variation thereof.

In some embodiments of any of Formulae (III), (IIIa), (IIIb), (IIIc), (IIId), and (IIIe), one or both of the following conditions apply: i) when $Y^{4a}$ is —O—, W is not —$(CH_2)_2$— or —$(CH_2CH_2O)_3(CH_2)_2$—; and ii) when $Y^{4a}$ is —NH— or —N($CH_3$), W is not —$(CH_2)_2$—, —$(CH_2)_6$—, or —$CH_2(CH_2CH_2O)_3(CH_2)_3$—.

Exemplary conjugates are shown in Table 2. Also provided herein are salts of any of the conjugates shown in Table 2. In some embodiments, a conjugate shown in Table 2, or a salt thereof, is a precursor compound in which the linker portion may be further modified, e.g., to insert a functional group suitable for bonding to a ligand.

TABLE 2

| Conjugate | Structure |
|---|---|
| L1 | 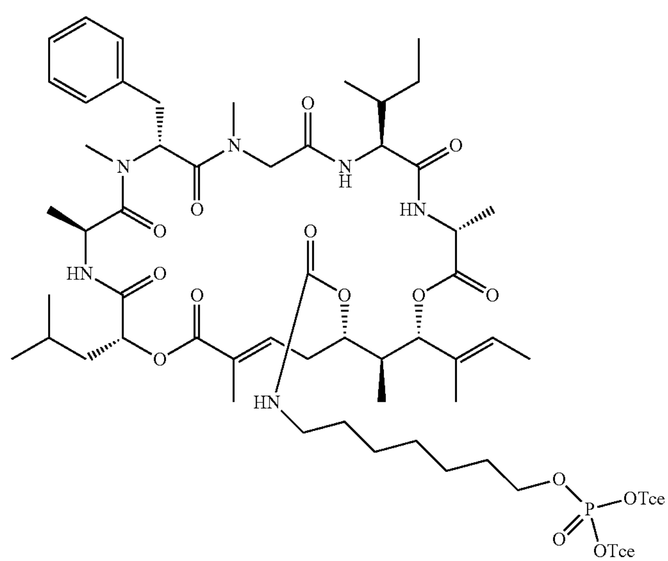 |

TABLE 2-continued

| Conjugate | Structure |
|---|---|
| L2 | 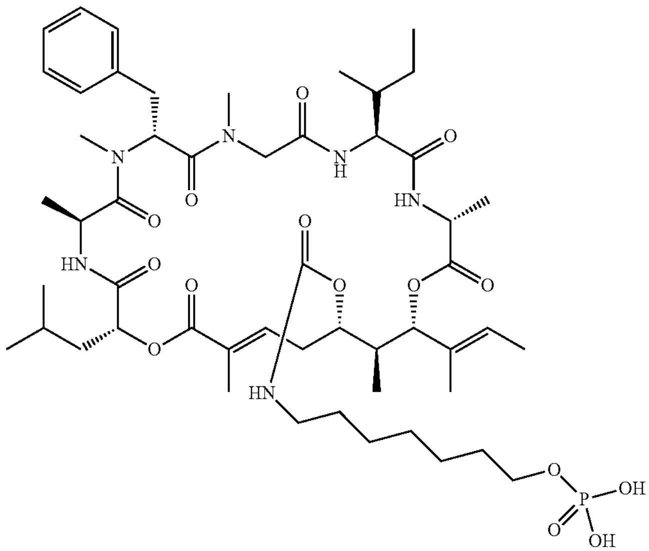 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCCCCCOP(=O)(O)O)[C@@H]1C] |
| L3 | 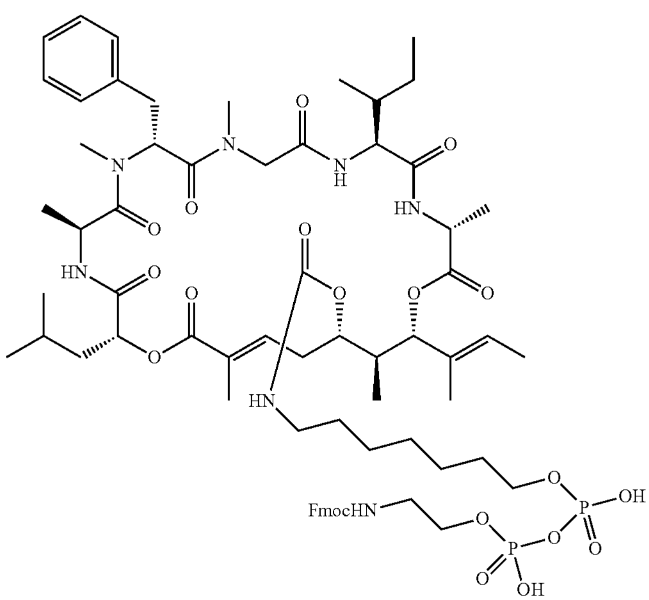 |

TABLE 2-continued
| Conjugate | Structure |
|---|---|
| L4 | 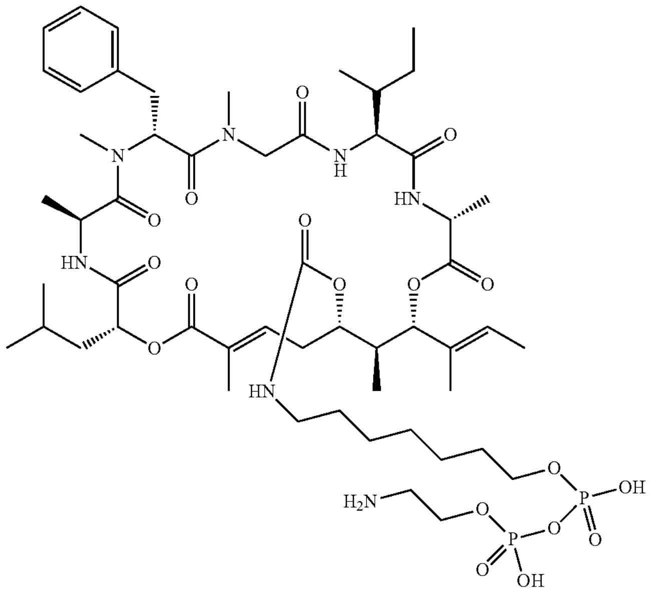 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCCCCCOP(=O)(O)OP(=O)(O)OCCN)[C@@H]1C] |
| L5 | 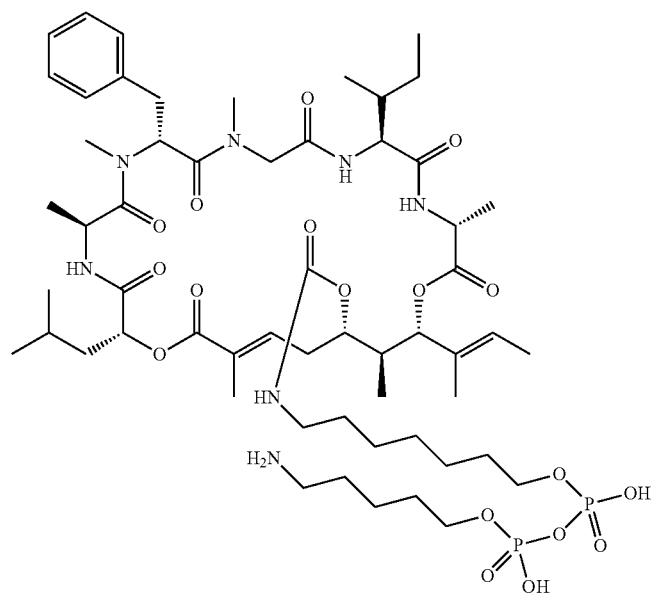 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCCCCCOP(=O)(O)OP(=O)(O)OCCCCCN)[C@@H]1C] |

TABLE 2-continued
| Conjugate | Structure |
|---|---|
| L6 | 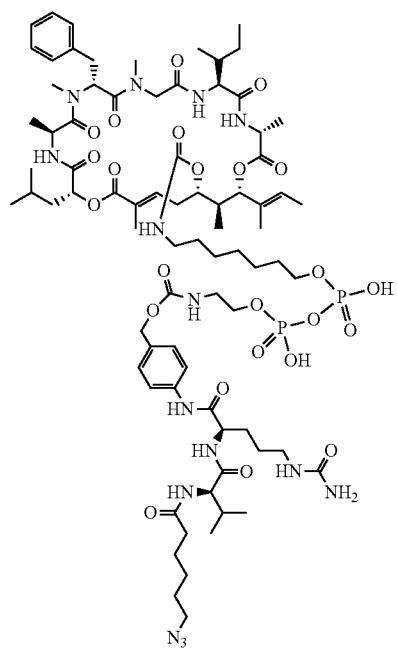 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCCCCCOP(=O)(O)OP(=O)(O)OCCNC(=O)OCc2ccc(NC(=O)[C@@H](CCCNC(N)=O)NC(=O)[C@H](NC(=O)CCCCCN=[N+]=[N-])C(C)C)cc2)[C@@H]1C] |
| L7 | 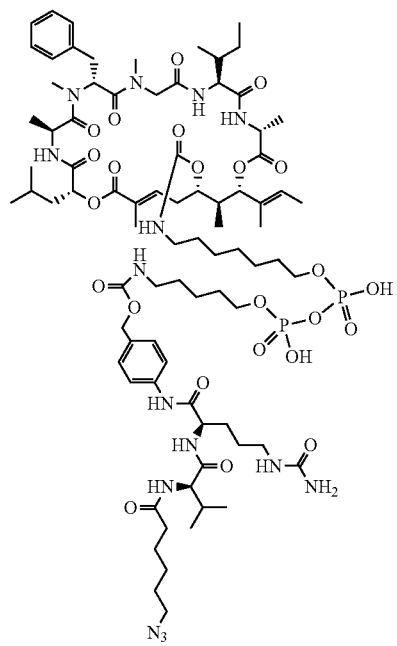 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCCCCCOP(=O)(O)OP(=O)(O)OCCCCCNC(=O)OCc2ccc(NC(=O)[C@@H](CCCNC(N)=O)NC(=O)[C@H](NC(=O)CCCCCN=[N+]=[N-])C(C)C)cc2)[C@@H]1C] |

TABLE 2-continued
| Conjugate | Structure |
|---|---|
| L8 | 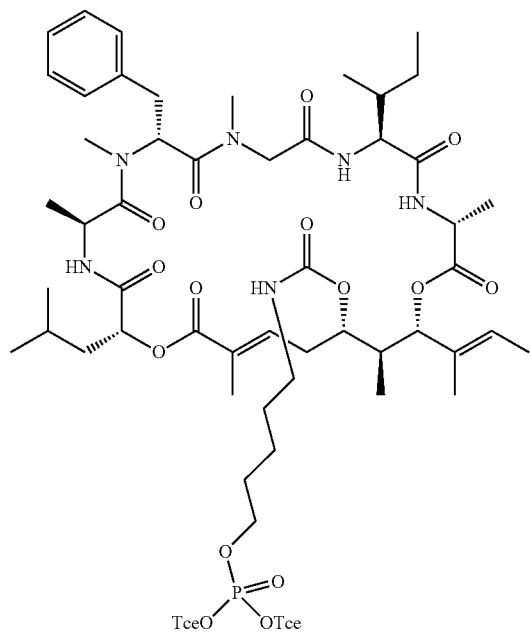 |
| L9 | 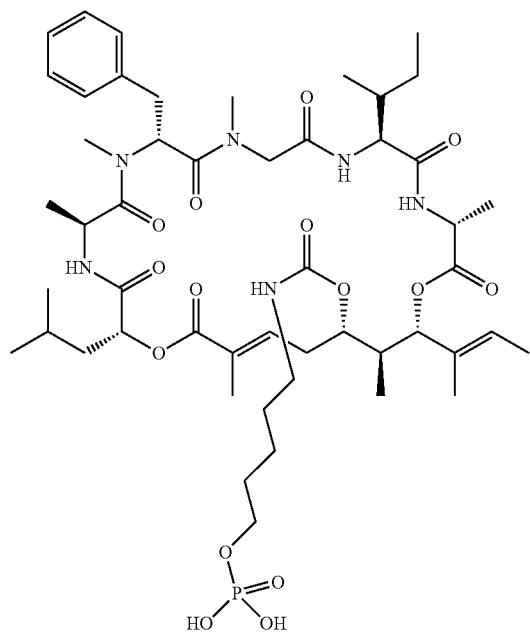 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCCCOP(=O)(O)O)[C@@H]1C] |

TABLE 2-continued
| Conjugate | Structure |
|---|---|
| L10 | 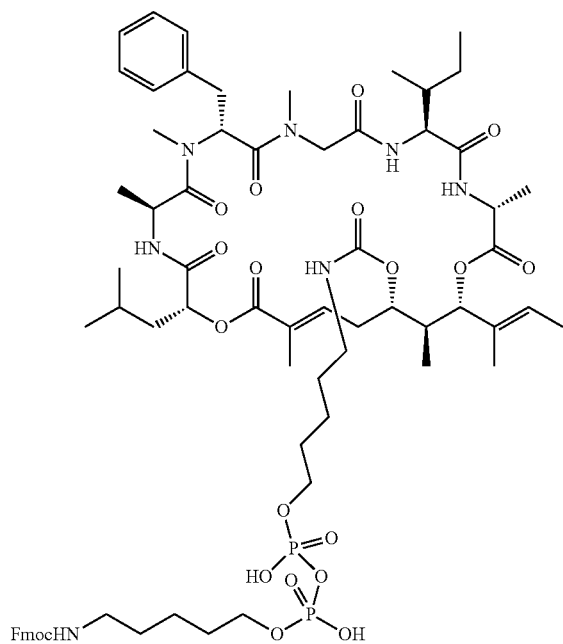 |
| L11 | 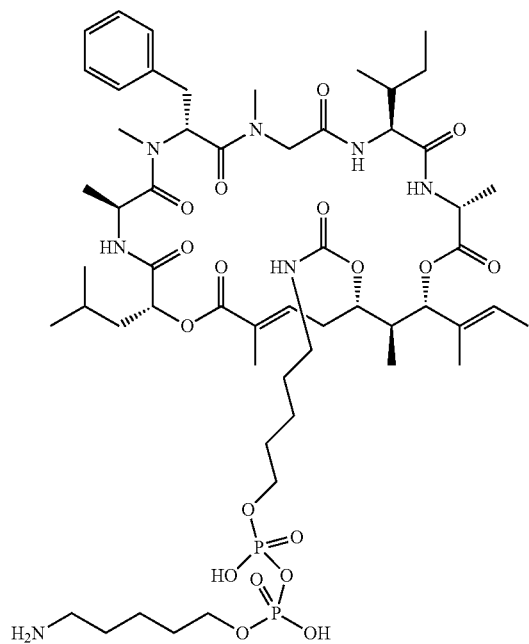 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCCCOP(=O)(O)OP(=O)(O)OCCCCCN)[C@@H]1C] |

TABLE 2-continued
| Conjugate | Structure |
|---|---|
| L12 | 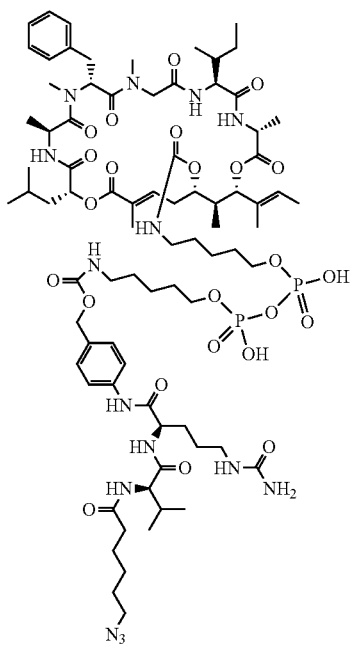 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCCCOP(=O)(O)OP(=O)(O)OCCCCCNC(=O)OCc2ccc(NC(=O)[C@@H](CCCNC(N)=O)NC(=O)[C@H](NC(=O)CCCCCN=[N+]=[N-])C(C)C)cc2)[C@@H]1C] |
| L13 | 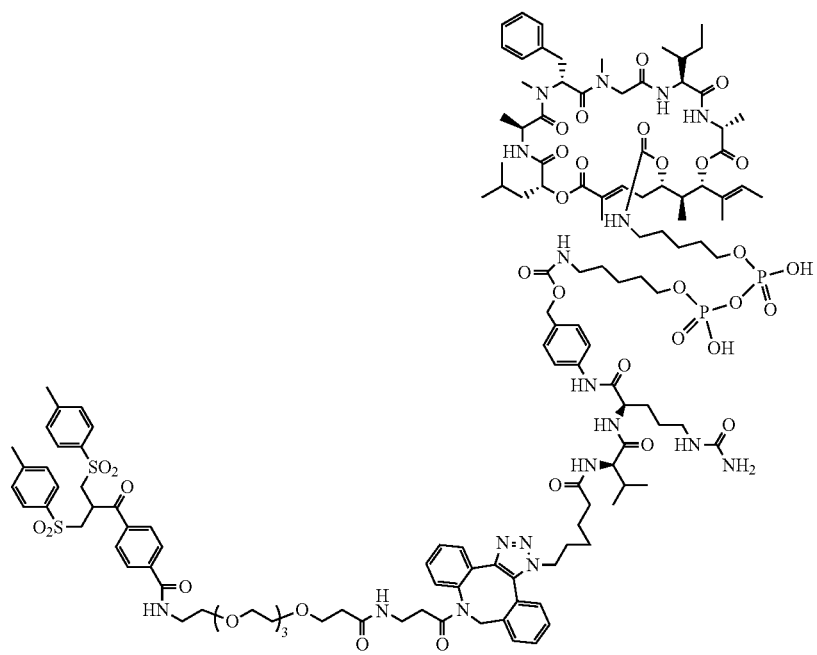 |

TABLE 2-continued
| Conjugate | Structure |
|---|---|
| L14 | 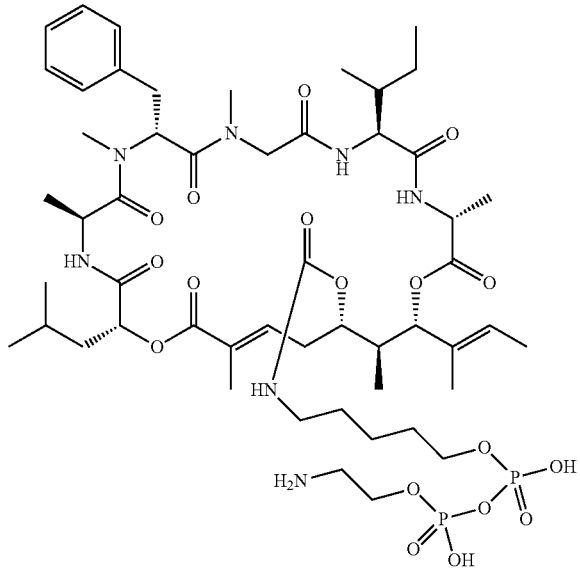 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCCCOP(=O)(O)OP(=O)(O)OCCN)[C@@H]1C] |
| L15 | 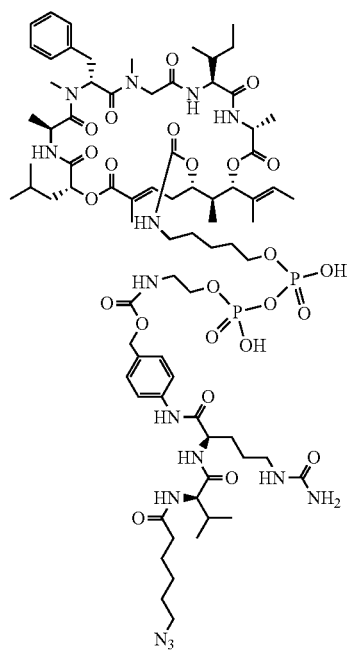 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCCCOP(=O)(O)OP(=O)(O)OCCNC(=O)OCc2ccc(NC(=O)[C@@H](CCCNC(N)=O)NC(=O)[C@H](NC(=O)CCCCCN=[N+]=[N-])C(C)C)cc2)[C@@H]1C] |

TABLE 2-continued
| Conjugate | Structure |
|---|---|
| L16 | 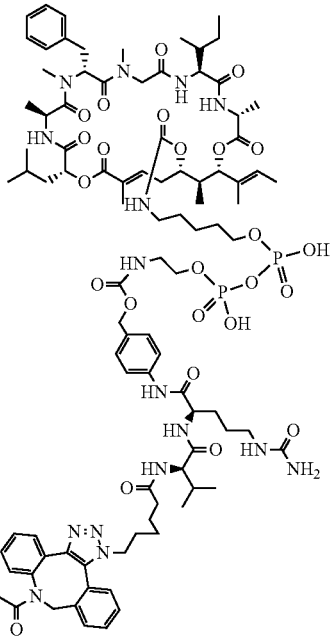 |
| L17 | 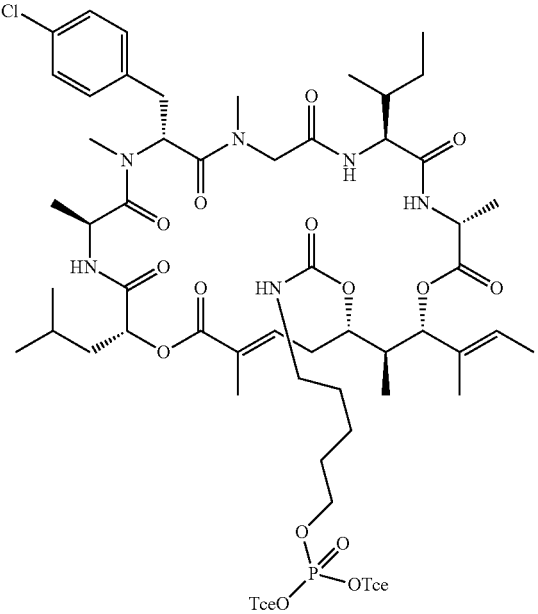 |

TABLE 2-continued
| Conjugate | Structure |
|---|---|
| L18 | 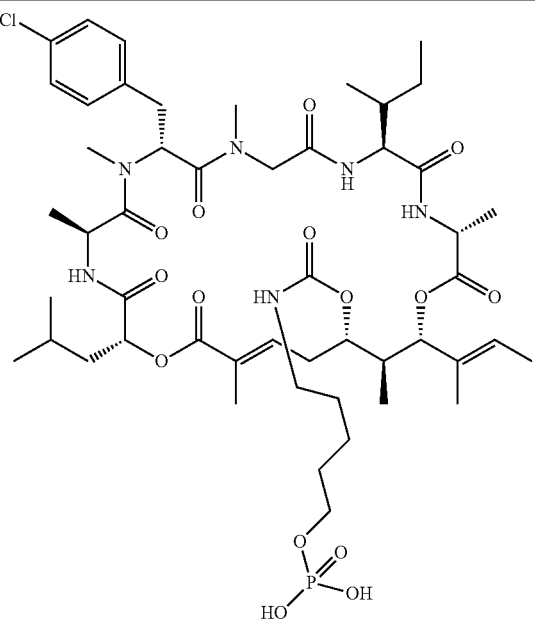 |
| L19 | 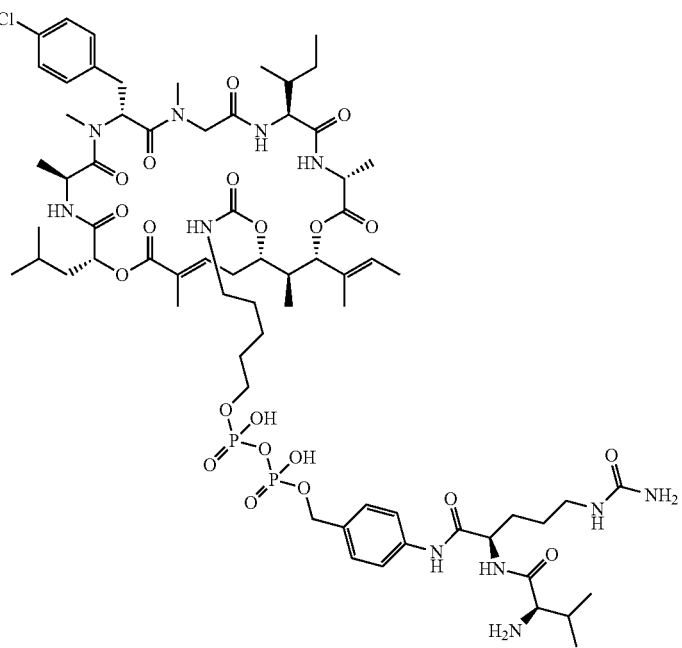 [SMILES: C/C=C(\C)[C@H]1OC(=O)[C@@H](C)NC(=O)[C@H](C(C)CC)NC(=O)CN(C)C(=O)[C@@H](Cc2ccc(Cl)cc2)N(C)C(=O)[C@H](C)NC(=O)[C@@H](CC(C)C)OC(=O)/C(C)=C/C[C@H](OC(=O)NCCCCCOP(=O)(O)OP(=O)(O)OCc2ccc(NC(=O)[C@@H](CCCNC(N)=O)NC(=O)[C@H](N)C(C)C)cc2)[C@@H]1C] |

TABLE 2-continued
| Conjugate | Structure |
|---|---|
| L20 | 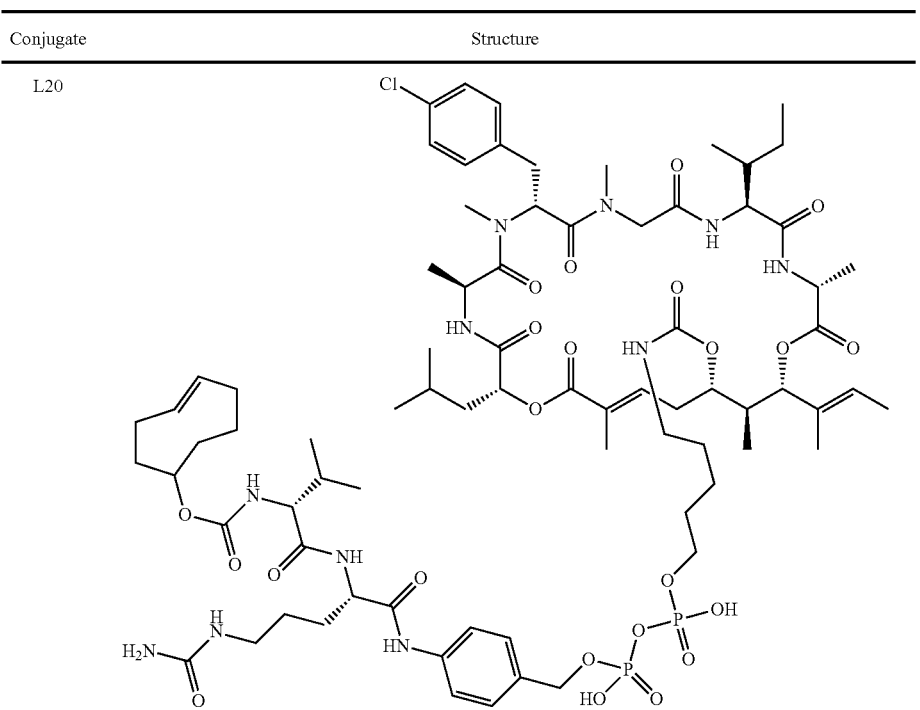 |
| L21 | 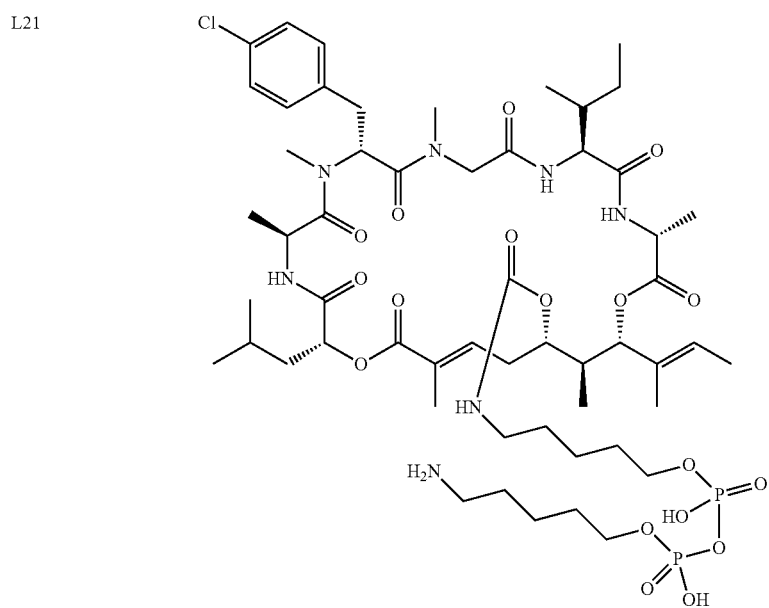 |

TABLE 2-continued
| Conjugate | Structure |
|---|---|
| L22 | 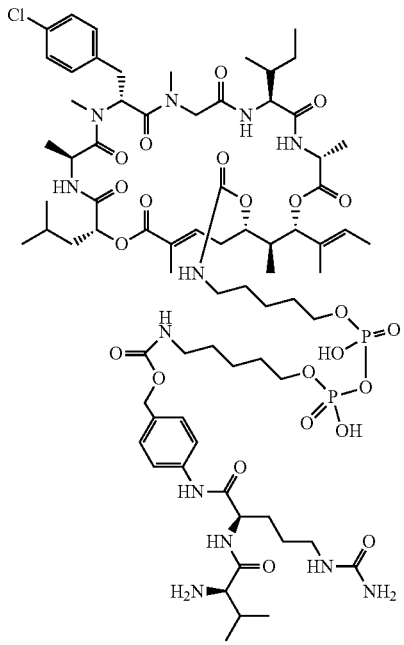 [SMILES: C/C=C(\C)[C@H]1OC(=O)[C@@H](C)NC(=O)[C@H](C(C)CC)NC(=O)CN(C)C(=O)[C@@H](Cc2ccc(Cl)cc2)N(C)C(=O)[C@H](C)NC(=O)[C@@H](CC(C)C)OC(=O)/C(C)=C/C[C@H](OC(=O)NCCCCCOP(=O)(O)OP(=O)(O)OCCCCCNC(=O)OCc2ccc(NC(=O)[C@@H](CCCNC(N)=O)NC(=O)[C@H](N)C(C)C)cc2)[C@@H]1C] |
| L23 | 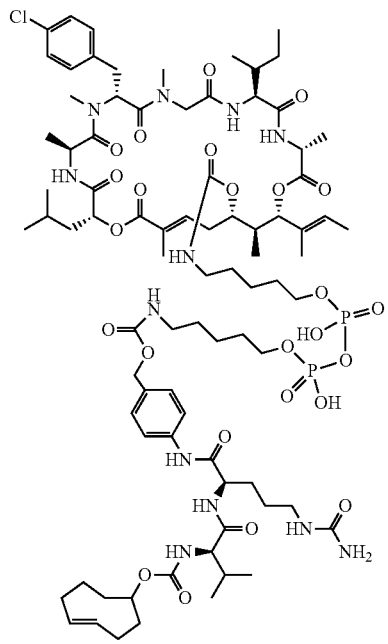 [SMILES: C/C=C(\C)[C@H]1OC(=O)[C@@H](C)NC(=O)[C@H](C(C)CC)NC(=O)CN(C)C(=O)[C@@H](Cc2ccc(Cl)cc2)N(C)C(=O)[C@H](C)NC(=O)[C@@H](CC(C)C)OC(=O)/C(C)=C/C[C@H](OC(=O)NCCCCCOP(=O)(O)OP(=O)(O)OCCCCCNC(=O)OCc2ccc(NC(=O)[C@@H](CCCNC(N)=O)NC(=O)[C@H](NC(=O)OC3CC/C=C/CCC3)C(C)C)cc2)[C@@H]1C] |

TABLE 2-continued
| Conjugate | Structure |
|---|---|
| L24 | 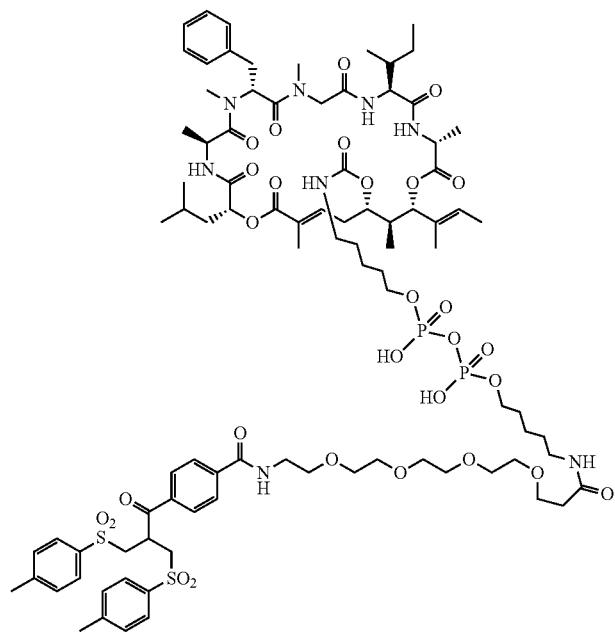 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCCCOP(=O)(O)OP(=O)(O)OCCCCCNC(=O)CCOCCOCCOCCOCCNC(=O)c2ccc(C(=O)C(CS(=O)(=O)c3ccc(C)cc3)CS(=O)(=O)c3ccc(C)cc3)cc2)[C@@H]1C] |
| L25 | 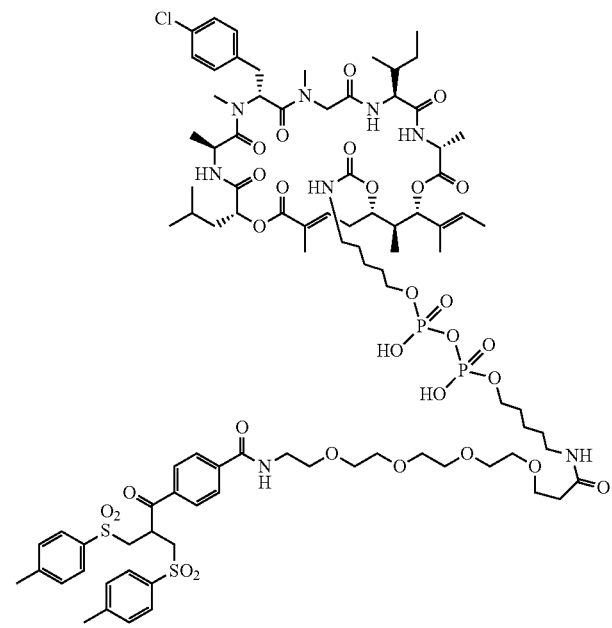 [SMILES: C/C=C(\C)[C@H]1OC(=O)[C@@H](C)NC(=O)[C@H](C(C)CC)NC(=O)CN(C)C(=O)[C@@H](Cc2ccc(Cl)cc2)N(C)C(=O)[C@H](C)NC(=O)[C@@H](CC(C)C)OC(=O)/C(C)=C/C[C@H](OC(=O)NCCCCCOP(=O)(O)OP(=O)(O)OCCCCCNC(=O)CCOCCOCCOCCOCCNC(=O)c2ccc(C(=O)C(CS(=O)(=O)c3ccc(C)cc3)CS(=O)(=O)c3ccc(C)cc3)cc2)[C@@H]1C] |

TABLE 2-continued
| Conjugate | Structure |
|---|---|
| L26 | 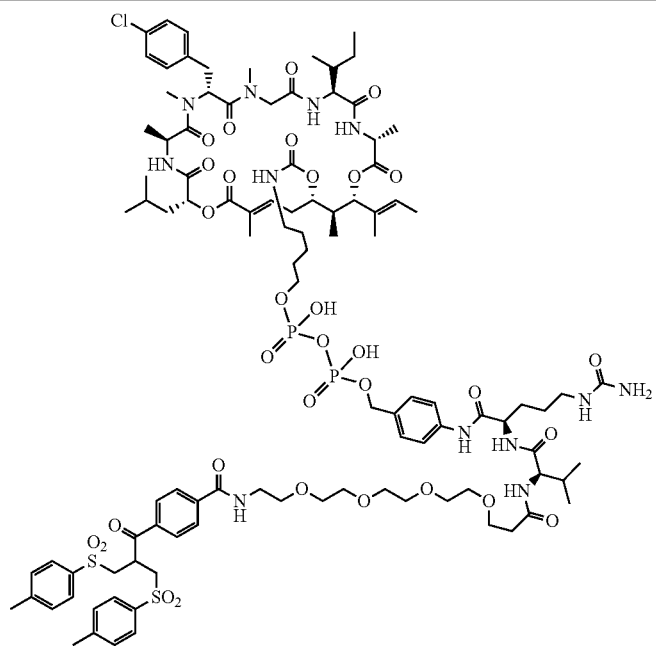 [SMILES: C/C=C(\C)[C@H]1OC(=O)[C@@H](C)NC(=O)[C@H](C(C)CC)NC(=O)CN(C)C(=O)[C@@H](Cc2ccc(Cl)cc2)N(C)C(=O)[C@H](C)NC(=O)[C@@H](CC(C)C)OC(=O)/C(C)=C/C[C@H](OC(=O)NCCCCCOP(=O)(O)OP(=O)(O)OCc2ccc(NC(=O)[C@@H](CCCNC(N)=O)NC(=O)[C@H](NC(=O)CCOCCOCCOCCOCCNC(=O)c3ccc(C(=O)C(CS(=O)(=O)c4ccc(C)cc4)CS(=O)(=O)c4ccc(C)cc4)cc3)C(C)C)cc2)[C@@H]1C] |
| L27 | 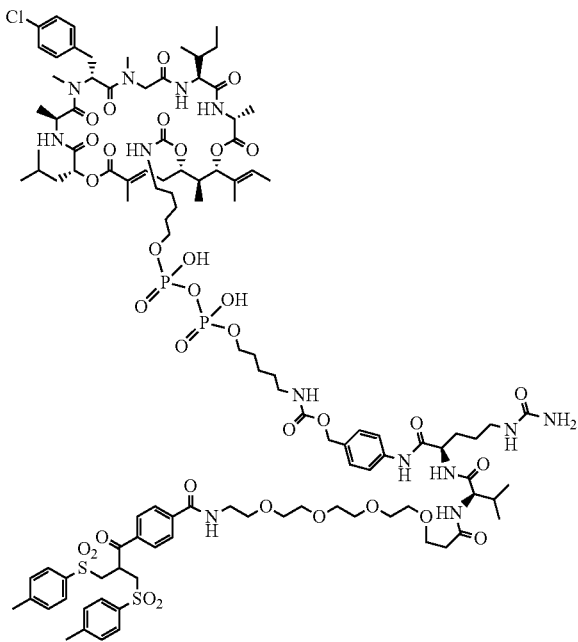 [SMILES: C/C=C(\C)[C@H]1OC(=O)[C@@H](C)NC(=O)[C@H](C(C)CC)NC(=O)CN(C)C(=O)[C@@H](Cc2ccc(Cl)cc2)N(C)C(=O)[C@H](C)NC(=O)[C@@H](CC(C)C)OC(=O)/C(C)=C/C[C@H](OC(=O)NCCCCCOP(=O)(O)OP(=O)(O)OCCCCCNC(=O)OCc2ccc(NC(=O)[C@@H](CCCNC(N)=O)NC(=O)[C@H](NC(=O)CCOCCOCCOCCOCCNC(=O)c3ccc(C(=O)C(CS(=O)(=O)c4ccc(C)cc4)CS(=O)(=O)c4ccc(C)cc4)cc3)C(C)C)cc2)[C@@H]1C] |

TABLE 2-continued
| Conjugate | Structure |
|---|---|
| L28 | 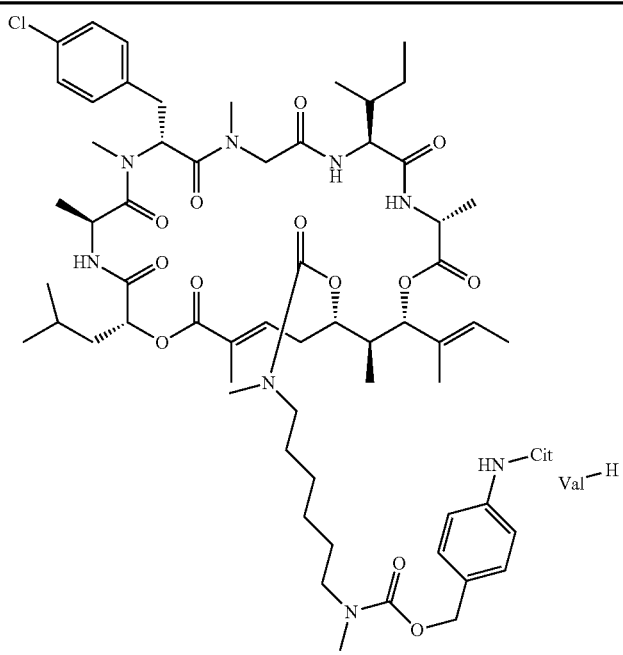 |
| L29 | 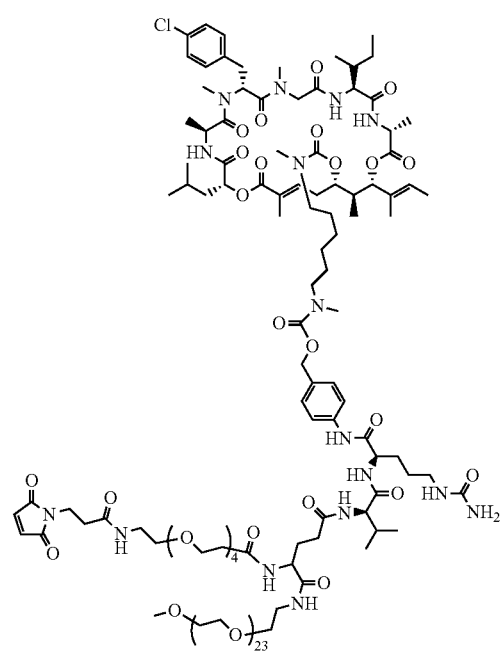 |

TABLE 2-continued
| Conjugate | Structure |
|---|---|
| L30 | 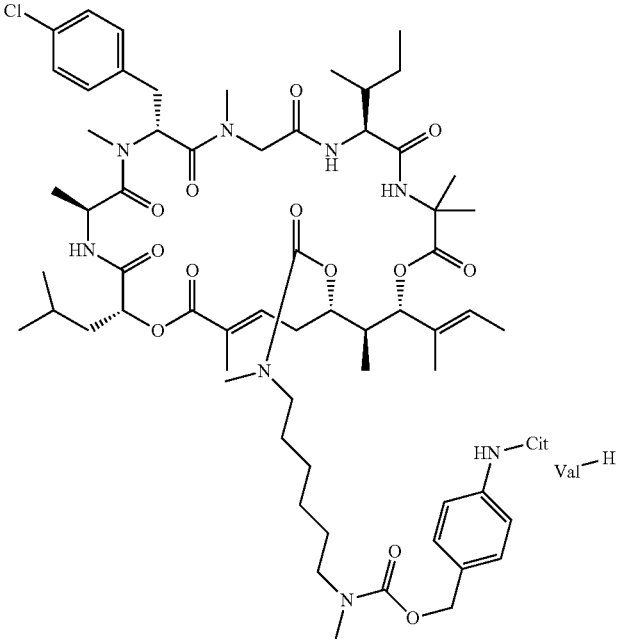 |
| L31 | 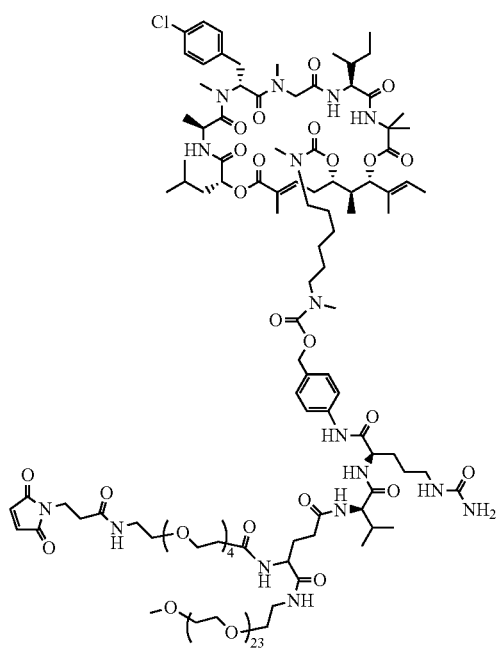 |

In some variations, a conjugate of Table 2 is further bonded to a ligand, such as an antibody. In some variations, the ligand is bonded via an azide moiety on the linker. In some variations, the ligand is bonded via an alkyne moiety on the linker. In some variations, the ligand is bonded via a maleimide moiety on the linker. In some variations, the ligand is bonded via an amine moiety on the linker. In some variations, the ligand is bonded via a hydroxyl moiety on the linker. In some variations, the ligand is bonded via a sulfonyl moiety on the linker. In other variations, the ligand is bonded via a thiol moiety on the linker.

In some aspects, provided are conjugates of Formula (IV):

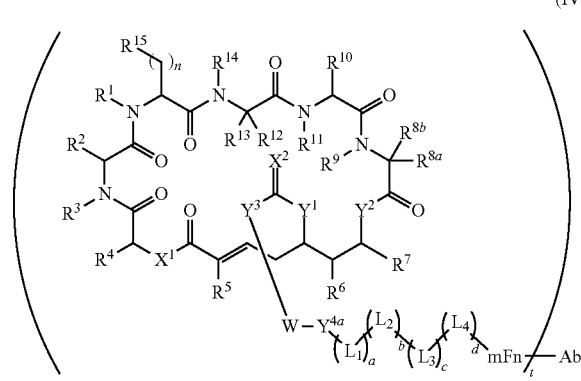

(IV)

and salts thereof, wherein $R^1$, $R^2$, $R^3$, $R^4$, $R^5$, $R^6$, $R^7$, $R^{8a}$, $R^{8b}$, $R^9$, $R^{10}$, $R^{11}$, $R^{12}$, $R^{13}$, $R^{14}$, $R^{15}$, n, W, $X^1$, $X^2$, $Y^1$, $Y^2$, and $Y^3$ are as defined for Formula (I) or any variation thereof;

$Y^{4a}$ is —O—, —NR$^b$—, or —S—, wherein $R^b$ is H, substituted or unsubstituted alkyl, substituted or unsubstituted alkenyl, substituted or unsubstituted alkynyl, substituted or unsubstituted cycloalkyl, or substituted or unsubstituted cycloalkenyl;

$L_1$, $L_2$, $L_3$, $L_4$, a, b, c, and d are as defined for Formula (L-Fn) or any variation thereof;

mFn is a modified form of functional group Fn as defined in Formula (L-Fn) with a valence suitable for bonding to an antibody;

t is an integer from 1-12, inclusive; and

Ab is an antibody.

In some aspects, provided are conjugates of Formula (IVa):

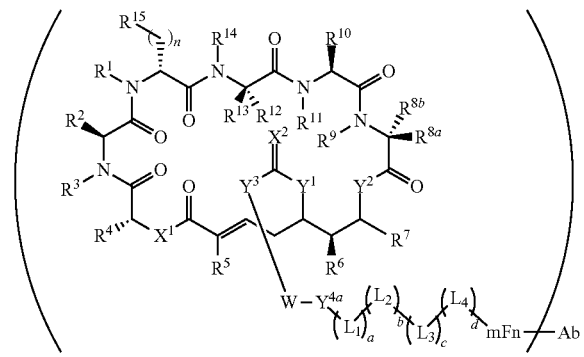

(IVa)

and salts thereof, wherein $R^1$, $R^2$, $R^3$, $R^4$, $R^5$, $R^6$, $R^7$, $R^{8a}$, $R^{8b}$, $R^9$, $R^{10}$, $R^{11}$, $R^{12}$, $R^{13}$, $R^{14}$, $R^{15}$, n, W, $X^1$, $X^2$, $Y^1$, $Y^2$, and $Y^3$ are as defined for Formula (Ia) or any variation thereof;

$Y^{4a}$ is —O—, —NR$^b$—, or —S—, wherein $R^b$ is H, substituted or unsubstituted alkyl, substituted or unsubstituted alkenyl, substituted or unsubstituted alkynyl, substituted or unsubstituted cycloalkyl, or substituted or unsubstituted cycloalkenyl;

$L_1$, $L_2$, $L_3$, $L_4$, a, b, c, and d are as defined for Formula (L-Fn) or any variation thereof;

mFn is a modified form of functional group Fn as defined in Formula (L-Fn) with a valence suitable for bonding to an antibody;

t is an integer from 1-12, inclusive; and

Ab is an antibody.

In some aspects, provided are conjugates of Formula (IVb):

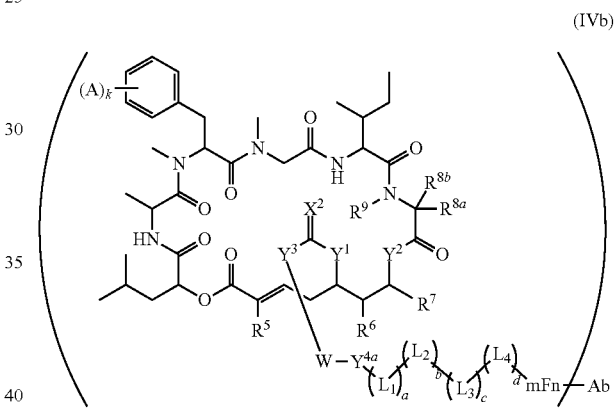

(IVb)

and salts thereof, wherein $R^5$, $R^6$, $R^7$, $R^{8a}$, $R^{8b}$, $R^9$, W, $X^2$, $Y^1$, $Y^2$, $Y^3$, A, and k are as defined for Formula (Ib) or any variation thereof;

$Y^{4a}$ is —O—, —NR$^b$—, or —S—, wherein $R^b$ is H, substituted or unsubstituted alkyl, substituted or unsubstituted alkenyl, substituted or unsubstituted alkynyl, substituted or unsubstituted cycloalkyl, or substituted or unsubstituted cycloalkenyl;

$L_1$, $L_2$, $L_3$, $L_4$, a, b, c, and d are as defined for Formula (L-Fn) or any variation thereof;

mFn is a modified form of functional group Fn as defined in Formula (L-Fn) with a valence suitable for bonding to an antibody;

t is an integer from 1-12, inclusive; and

Ab is an antibody.

In some aspects, provided are conjugates of Formula (IVc):

(IVc)

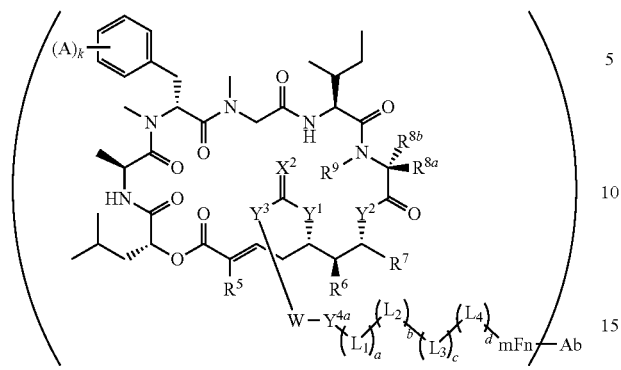

and salts thereof, wherein $R^5$, $R^6$, $R^7$, $R^{8a}$, $R^{8b}$, $R^9$, W, $X^2$, $Y^1$, $Y^2$, $Y^3$, A and k are as defined for Formula (Ic) or any variation thereof;

$Y^{4a}$ is —O—, —$NR^b$—, or —S—, wherein $R^b$ is H, substituted or unsubstituted alkyl, substituted or unsubstituted alkenyl, substituted or unsubstituted alkynyl, substituted or unsubstituted cycloalkyl, or substituted or unsubstituted cycloalkenyl;

$L_1$, $L_2$, $L_3$, $L_4$, a, b, c, and d are as defined for Formula (L-Fn) or any variation thereof;

mFn is a modified form of functional group Fn as defined in Formula (L-Fn) with a valence suitable for bonding to an antibody;

t is an integer from 1-12, inclusive; and

Ab is an antibody.

In some aspects, provided are conjugates of Formula (IVd):

(IVd)

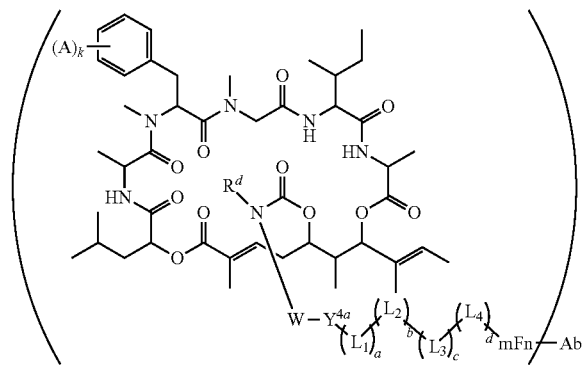

and salts thereof, wherein $R^d$, W, A and k are as defined for Formula (Id) or any variation thereof;

$Y^{4a}$ is —O—, —$NR^b$—, or —S—, wherein $R^b$ is H, substituted or unsubstituted alkyl, substituted or unsubstituted alkenyl, substituted or unsubstituted alkynyl, substituted or unsubstituted cycloalkyl, or substituted or unsubstituted cycloalkenyl;

$L_1$, $L_2$, $L_3$, $L_4$, a, b, c, and d are as defined for Formula (L-Fn) or any variation thereof;

mFn is a modified form of functional group Fn as defined in Formula (L-Fn) with a valence suitable for bonding; to an antibody;

t is an integer from 1-12, inclusive; and

Ab is an antibody.

In some aspects, provided are conjugates of Formula (IVe):

(IVe)

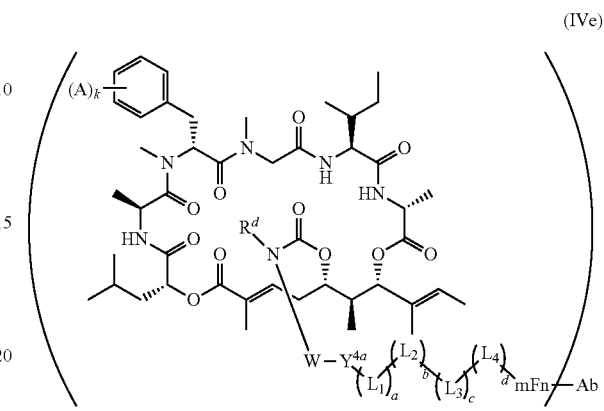

and salts thereof, wherein $R^d$, W, A and k are as defined for Formula (Id) or any variation thereof;

$Y^{4a}$ is —O—, —$NR^b$—, or —S—, wherein $R^b$ is H, substituted or unsubstituted alkyl, substituted or unsubstituted alkenyl, substituted or unsubstituted alkynyl, substituted or unsubstituted cycloalkyl, or substituted or unsubstituted cycloalkenyl;

$L_1$, $L_2$, $L_3$, $L_4$, a, b, c, and d are as defined for Formula (L-Fn) or any variation thereof;

mFn is a modified form of functional group Fn as defined in Formula (L-Fn) with a valence suitable for bonding to an antibody;

t is an integer from 1-12, inclusive; and

Ab is an antibody.

In some embodiments of any of Formulae (IV), (IVa), (IVb), (IVc), (IVd), and (IVe), one or both of the following conditions apply: i) when $Y^{4a}$ is —O—, W is not —$(CH_2)_2$— or —$(CH_2CH_2O)_3(CH_2)_2$—; and ii) when $Y^{4a}$ is —NH or —$N(CH_3)$, W is not —$(CH_2)_2$, —$(CH_2)_6$—, or —$CH_2(CH_2CH_2O)_3(CH_2)_3$—.

In some embodiments, t is an integer from 1-8, inclusive. In some embodiments, t is 1. In some embodiments, t is 2. In some embodiments, t is 3. In some embodiments, t is 4. In some embodiments, t is 5. In other embodiments, t is 6. In some embodiments, mFn is selected from the group consisting of a bond, unsubstituted or substituted alkylene,

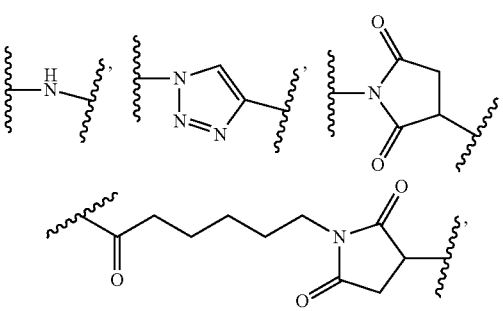

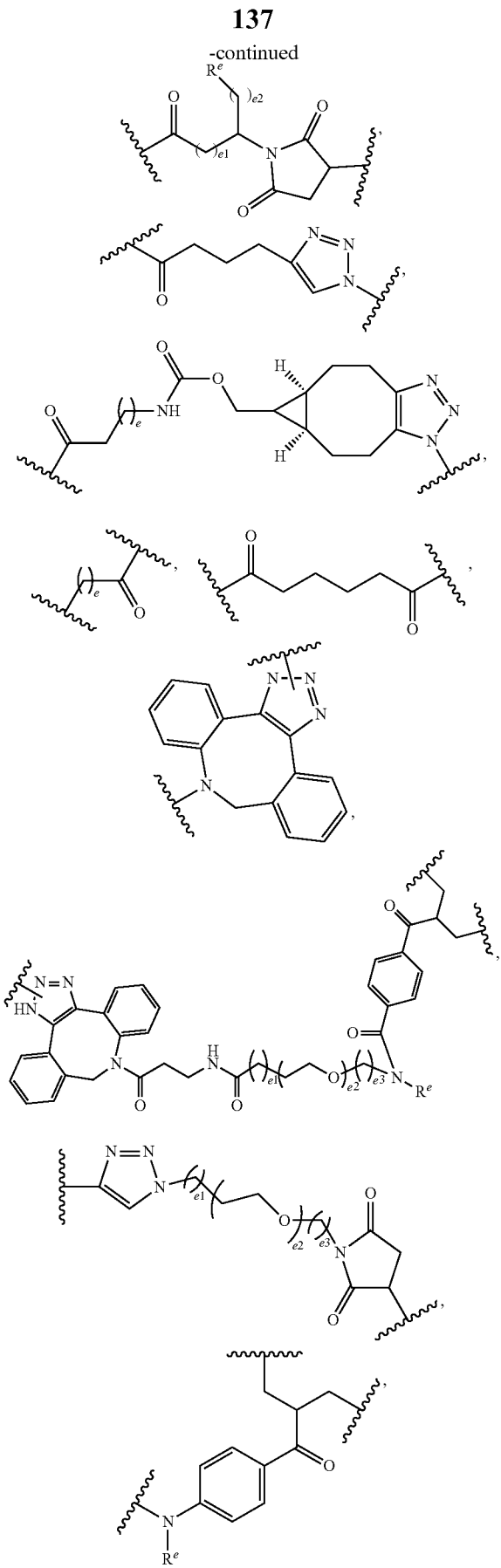
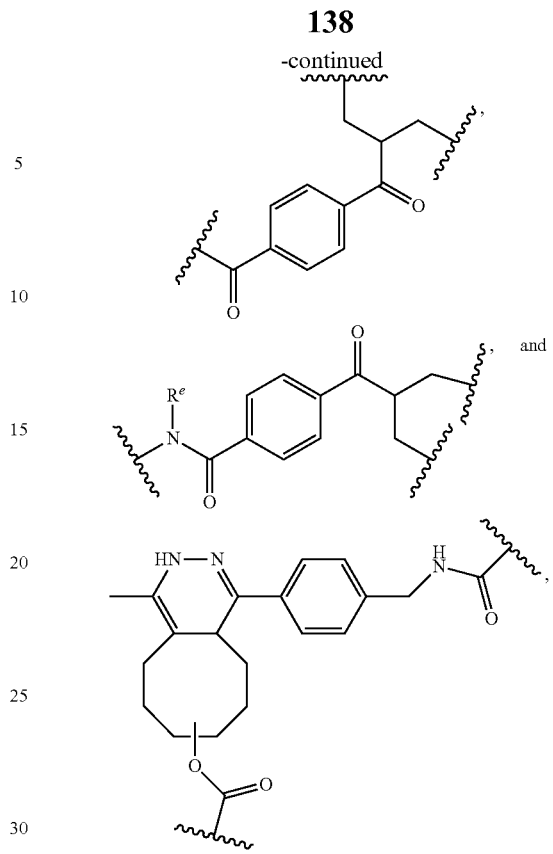

wherein e1, e2, and e3 are each independently an integer from 0-12, inclusive, and $R^e$ is H or alkyl.

Figure 9:
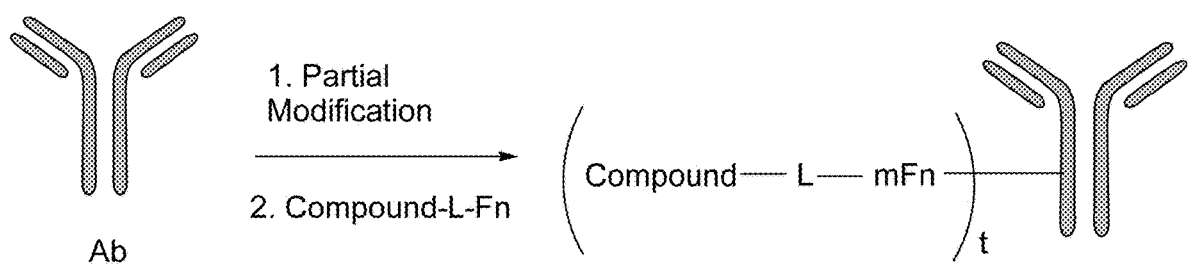
FIG. 9 is a general scheme showing preparation of conjugates containing an antibody.

Conjugates containing an antibody can be prepared by the general scheme as shown in FIG. 9, wherein Compound denotes any compound provided herein, including any compound of Formula (I), (Ia), (Ib), (Ic), (Id), or (Ie) or any variation thereof, or any compound listed in Table 1, or a salt thereof. The partial modification of the antibody can be carried out by any method known in the art. In some embodiments, the partial modification is partial or full reduction of disulfide bonds in the antibody, for example, by any method known in the art. In other embodiments, the partial modification is attachment of one or more suitable chemical moieties by conjugation via a chemically feasible functional group. In some embodiments, the chemically feasible functional group is bonded to the sidechain of an amino acid within the antibody. In some embodiments, the chemically feasible functional group is a maleimide. In some embodiments, the partial modification is the installation of one or more chemical moieties containing an alkynyl or azide group, for example, by any method known in the art. In some embodiments, the linker bonds to a cysteine side chain of the antibody. In some embodiments, the linker bonds to a lysine side chain of the antibody.

Exemplary conjugates containing an antibody are shown in Table 3. In any of the conjugates of Table 3, t is an integer from 1-12, inclusive, and Ab is an antibody. In some variations, the antibody binds to a receptor. In some variations, the antibody binds to a receptor on the surface of a cell. In some embodiments, t is 1. In some embodiments, t is 2. In some embodiments, t is 3. In some embodiments, t is 4. In some embodiments, t is 5 in some embodiments, t is 6. In some embodiments, t is 7. In some embodiments, t is 8. In some embodiments, t is 9. In some embodiments, t is 10. In some embodiments, t is 11. In some embodiments, t is 12. In some variations, the antibody in any of the conjugates of Table 3 is replaced with any other suitable ligand. Also provided are salts of any of the conjugates shown in Table 3 or any variation thereof.
TABLE 3
| Conjugate | Structure |
|---|---|
| C6 | 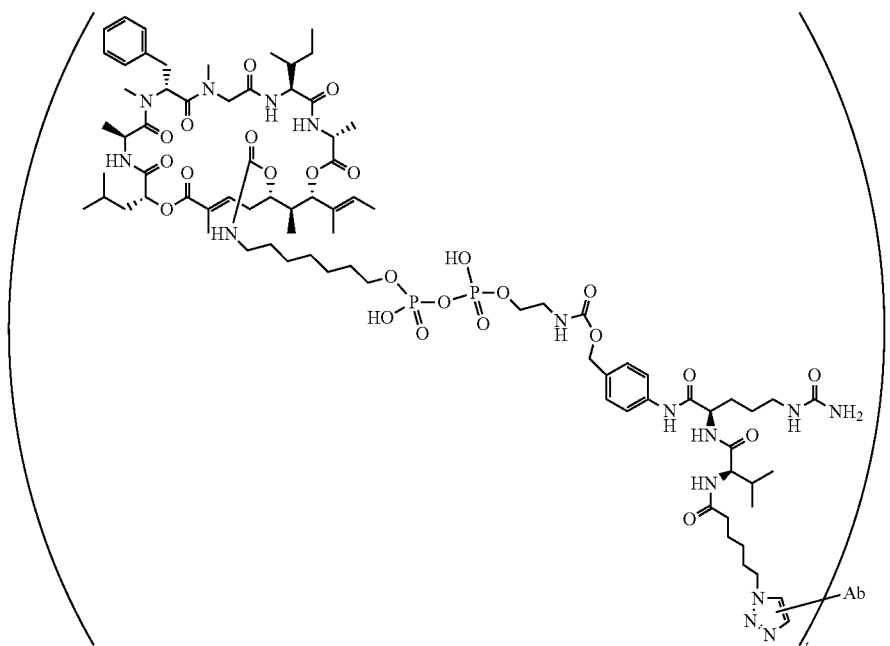 |
| C7 | 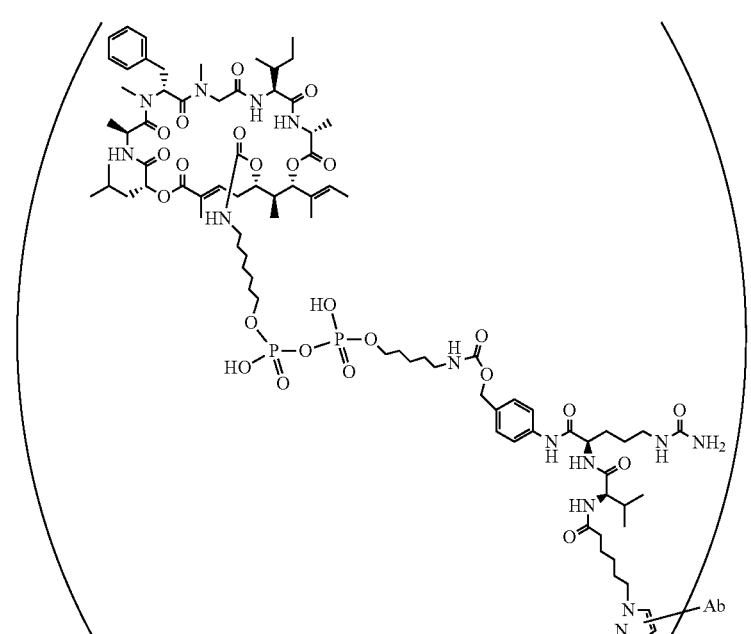 |

TABLE 3-continued
| Conjugate | Structure |
|---|---|
| C12 | 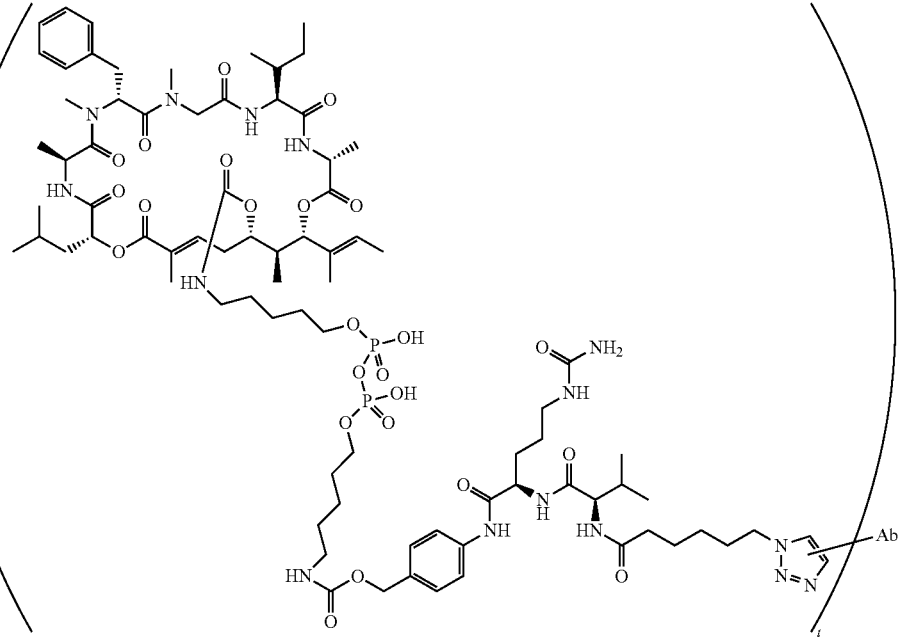 |
| C13 | 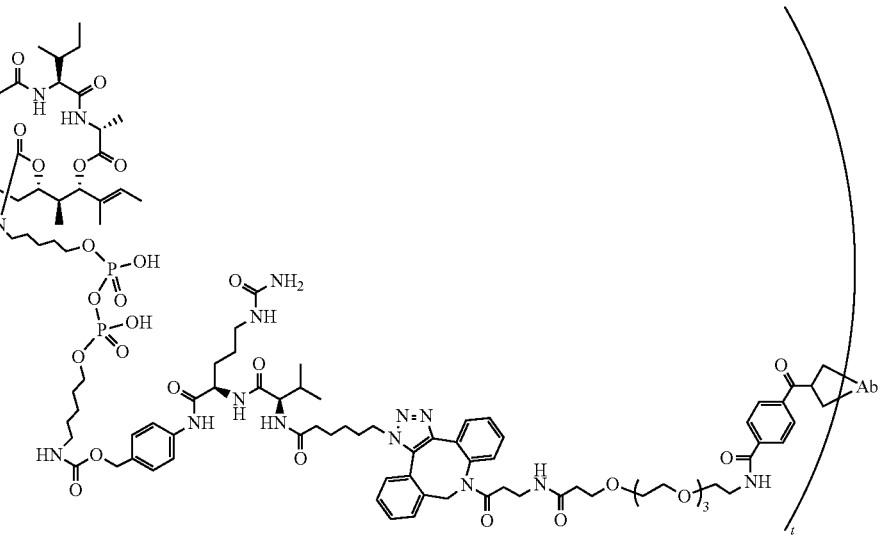 |

TABLE 3-continued
| Conjugate | Structure |
|---|---|
| C15 | 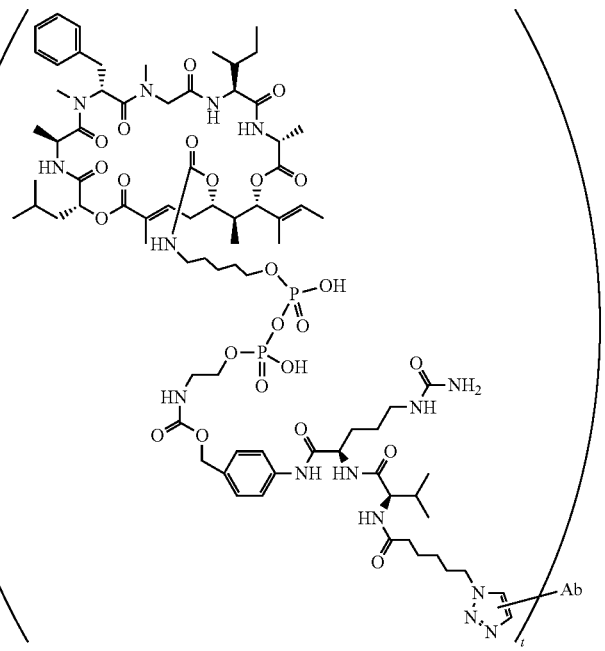 |
| C16 | 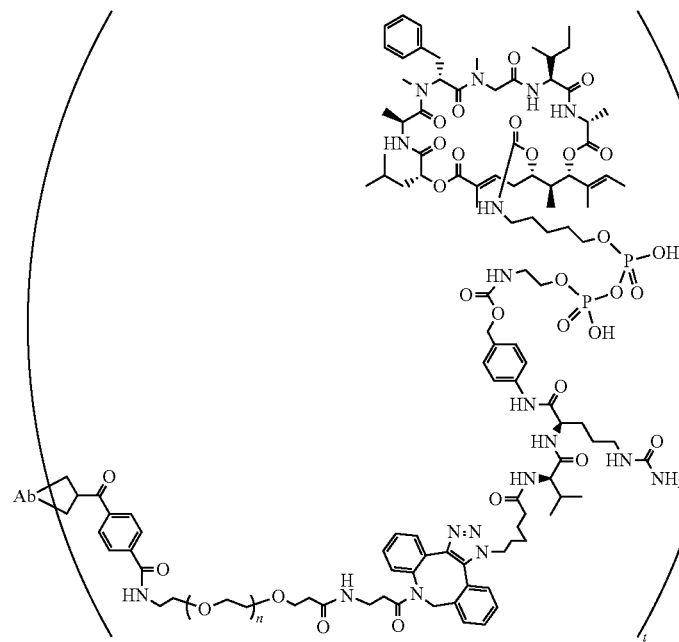 |

TABLE 3-continued
| Conjugate | Structure |
|---|---|
| C20 | 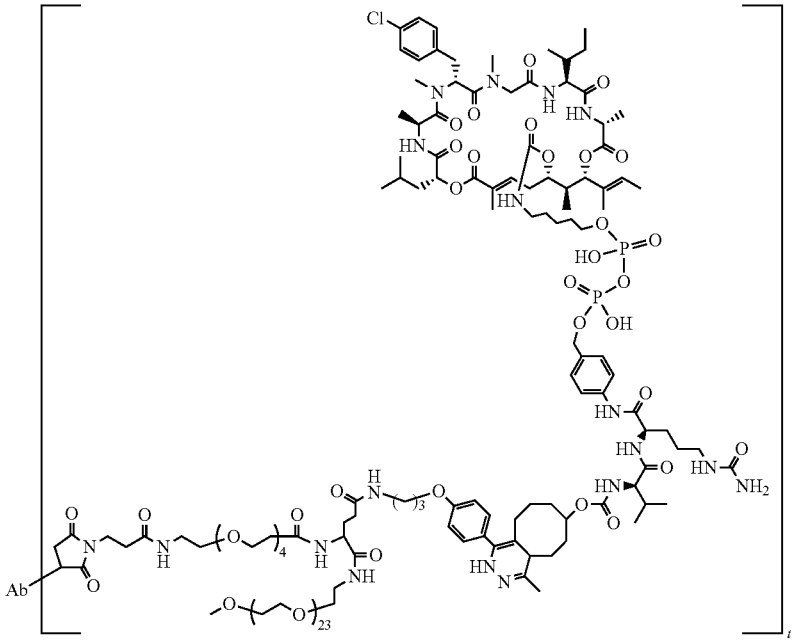 |
| C23 | 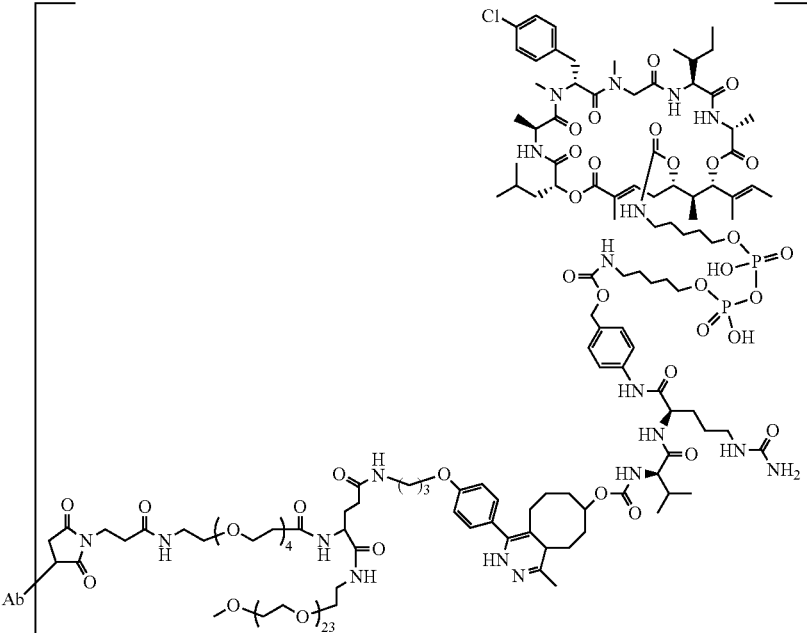 |

TABLE 3-continued
| Conjugate | Structure |
|---|---|
| C24 | 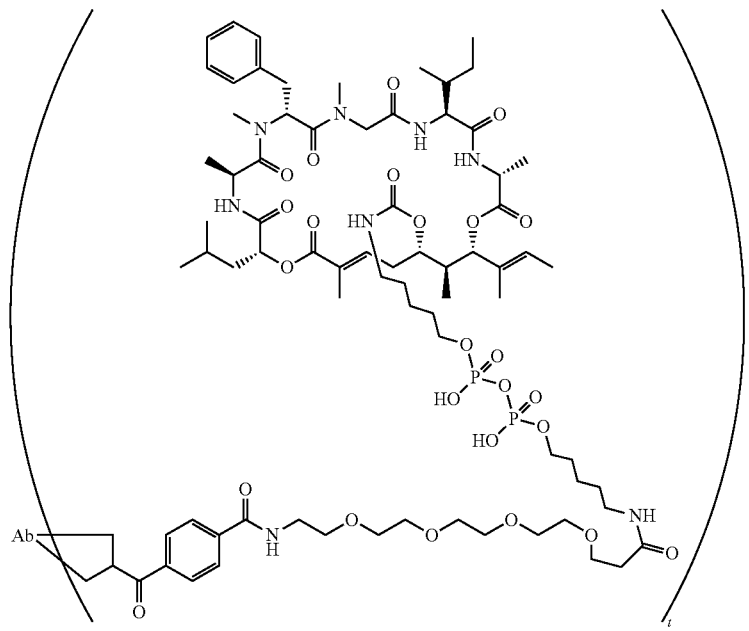 |
| C25 | 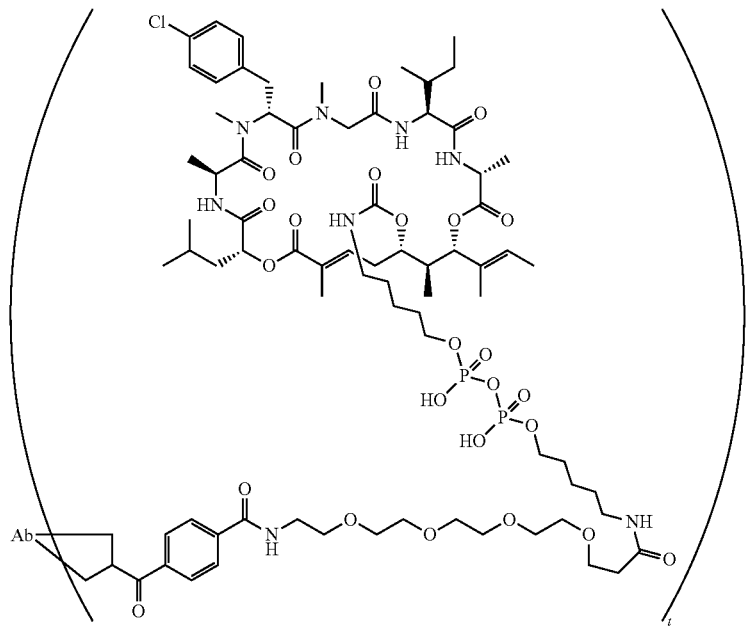 |

TABLE 3-continued
| Conjugate | Structure |
|---|---|
| C26 | 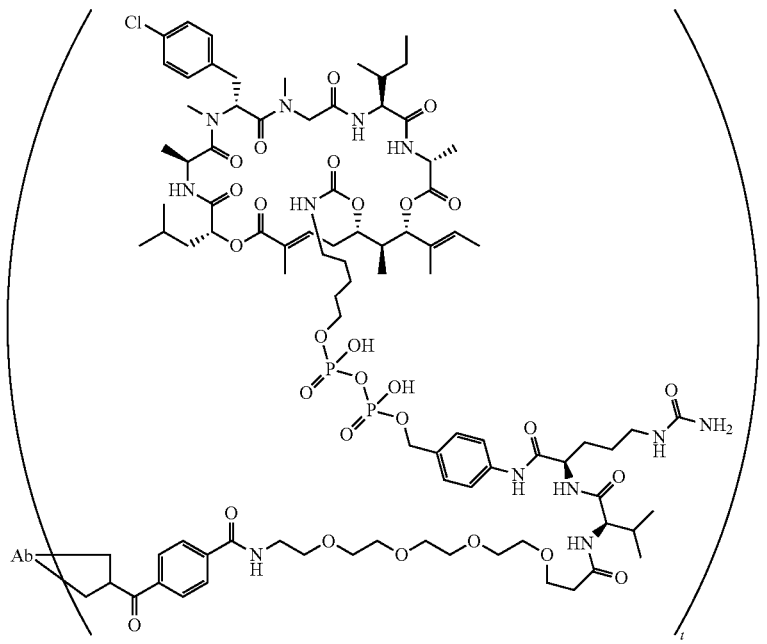 |
| C27 | 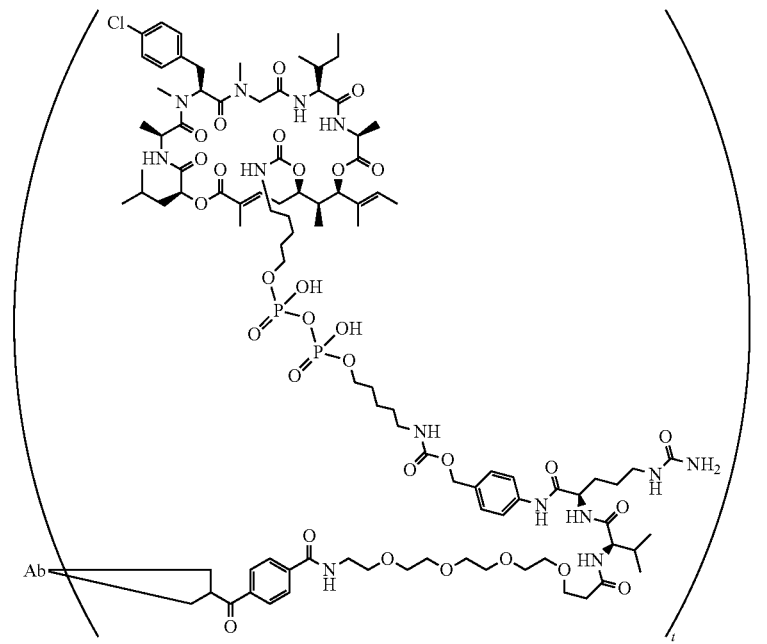 |

TABLE 3-continued

| Conjugate | Structure |
|---|---|
| C29 | 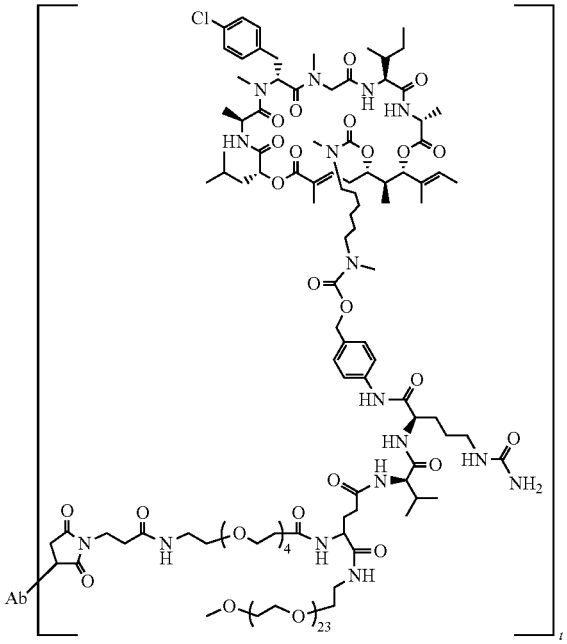 |
| C31 | 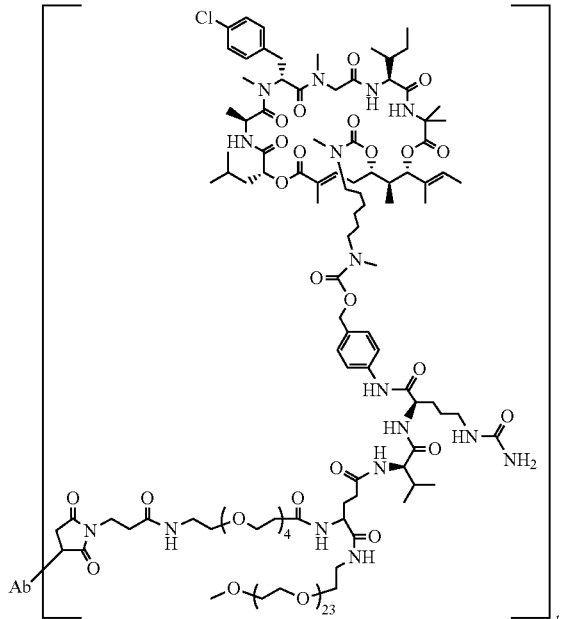 |

Compositions

The present disclosure also provides a composition, e.g., a pharmaceutical composition, containing one or more of the compounds or conjugates described herein. The composition may be a pharmaceutical composition. The composition may be an intermediate for use in preparation of a pharmaceutical compositions. Compositions may contain one or more compounds or conjugates described herein. In some aspects, a composition may contain a synthetic intermediate that may be used in the preparation of a compound or conjugate described herein. The compositions described herein may contain any other suitable active or inactive agents.

Any of the compositions described herein may be sterile or contain components that are sterile. Sterilization can be achieved by methods known in the art. Any of the compositions described herein may contain one or more compounds or conjugates that are substantially pure.

In any composition containing a conjugate, wherein the conjugate comprises a ligand, the average ratio of drug to ligand in the composition is from 1 to 12, inclusive, where the ratio may be an integral or non-integral value. In some such compositions, the conjugate comprises an antibody, and the average drug to antibody ratio (DAR) is from 1 to 12, inclusive, where the ratio may be an integral or non-integral value.

Pharmaceutical Formulations

The present disclosure also provides a composition, e.g., a pharmaceutical composition, containing one or more of the compounds described herein, formulated together with a pharmaceutically acceptable carrier. Pharmaceutical compositions of the invention also can be administered in combination therapy, i.e., combined with other agents. For example, the combination therapy can include a conjugate as described herein combined with at least one other active agent.

Pharmaceutically acceptable carriers may include any and all carriers, excipients, stabilizers, solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., the conjugate described herein, may be coated in a material to protect the compound from the action of acids and other natural conditions that may inactivate the compound.

Acceptable carriers, excipients, or stabilizers are nontoxic to recipients at standard dosages and concentrations to be administered, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone, amino acids such as glycine, glutamine, asparagine, histidine, arginine, or lysine; monosaccharides, disaccharides, and other carbohydrates including glucose, mannose, or dextrins, chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™ or polyethylene glycol (PEG).

The pharmaceutical compositions of the invention may include one or more pharmaceutically acceptable salts. A pharmaceutically acceptable salt retains the desired biological activity of the parent compound and does not impart any undesired toxicological effects. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like. Examples of suitable aqueous and non-aqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Dosages and Dosage Forms

For the prevention or treatment of disease, the appropriate dosage of conjugates and compounds described herein will depend on the type of disease to be treated, the severity and course of the disease, whether the compound or conjugate is administered for preventive or therapeutic purposes, mode of delivery, previous therapy, and the subject's clinical history. The compounds and conjugates described herein are suitably administered to a subject at one time or over a series of treatments. Depending on the type and severity of the disease, a typical daily dosage might range from about 0.0001 mg/kg to 100 mg/kg or more, depending on the factors mentioned above. For repeated administrations over several days or longer, depending on the condition, the treatment is sustained until a desired suppression of disease symptoms occurs.

For example dosages can be 0.3 mg/kg body weight, 1 mg/kg body weight, 3 mg/kg body weight, 5 mg/kg body weight or 10 mg/kg body weight or within the range of 1-10 mg/kg. Treatment regimens may comprise administration once per week, once every two weeks, once every three weeks, once every four weeks, once per month, once every 3 months or once every three to 6 months. In other embodiments, sustained release formulations are administered, which would result in less frequent administration compared to non-sustained release formulations.

The amount of active ingredient which can be combined with a carrier material to produce a single dosage form will generally be that amount of the composition which produces a therapeutic effect, without being toxic to the subject. Generally, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Administration

A composition described herein can be administered via one or more routes of administration using one or more of a variety of methods known in the art. As will be appreciated by the skilled artisan, the route and/or mode of administration will vary depending upon the desired results. Routes of administration for the compounds and compositions described herein include oral, sublingual, buccal, intranasal, topical, rectal, intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Methods of Treatment

In one embodiment, the disease or condition to be treated or prevented is cancer. The term "cancer" refers to precancerous conditions, non-malignant, low-grade, high-grade, and malignant cancer. Cancer of any tissue type is contemplated for treatment or prevention by the compounds disclosed herein. Exemplary types of cancer include carcinoma, lymphoma, blastoma, sarcoma, leukemia, and lymphoid malignancies. More specifically, in certain embodiments the cancer is squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Provided herein is a method of treating cancer in an individual in need thereof by administering to the individual a therapeutically effective amount of a compound, conjugate, or composition described herein. Also provided herein is the use of a compound, conjugate, or composition described herein in the manufacture of a medicament for treatment of cancer in an individual in need thereof. Also provided herein is the use of a compound, conjugate, or composition described herein for treatment of cancer in an individual in need thereof. Also provided herein is a compound, conjugate, or composition described herein for use in treatment of cancer in an individual in need thereof.

In one aspect, provided herein are kits containing a compound, conjugate, or composition described herein and instructions for use. The kits may contain instructions for use in the treatment of cancer in an individual in need thereof. A kit may additionally contain any materials or equipment that may be used in the administration of the compound, conjugate, or composition, such as vials, syringes, or IV bags. A kit may also contain sterile packaging.

General Synthetic Methods

Compounds of Formula (I) will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. In addition, one of skill in the art will recognize that protecting groups may be used to protect certain functional groups (amino, carboxy, or side chain groups) from reaction conditions, and that such groups are removed under standard conditions when appropriate. Unless otherwise specified, the variables are as defined above in reference to Formula (I).

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g. a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

General methods of preparing compounds described herein are depicted in exemplified methods below. Variable groups in the schemes provided herein are defined as for Formula (I), (Ia), (Ib), (Ic), (Id), (Ie), (II), (IIa), (IIb), (IIc), (IId), (IIe), (III), (IIIa), (IIIb), (IIIc), (IIId), (IIIe), (IV), (IVa), (IVb), (IVc), (IVd), (IVe), or any variation thereof. Other compounds described herein may be prepared by similar methods. For example, Scheme 1b is an exemplified synthesis of the method detailed in Scheme 1a, but other compounds described herein may be prepared by similar methods.

Peptide coupling, esterification, and deprotection reactions referred to herein can be carried out using methods known in the art.

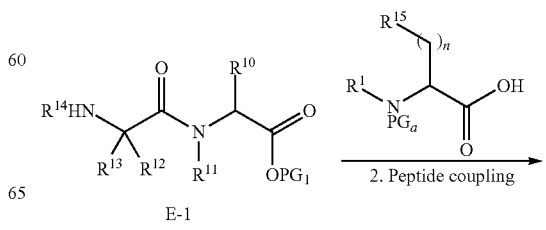

Scheme 1a.

157
-continued

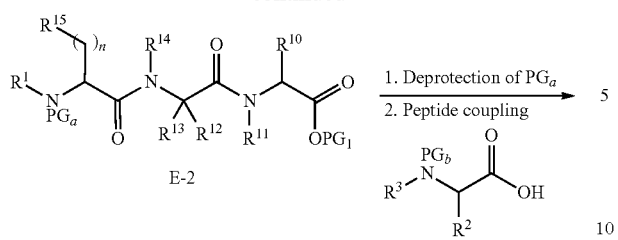

E-2

1. Deprotection of PG$_a$
2. Peptide coupling

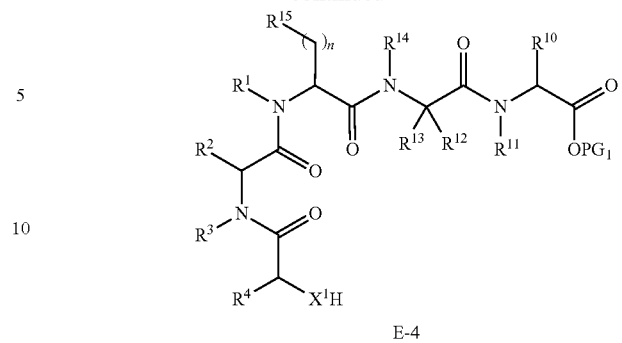

158
-continued

E-4

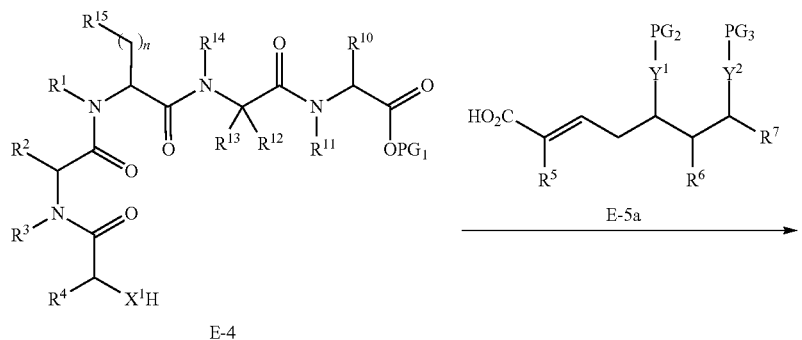

E-3

1. Deprotection of PG$_b$
2. Peptide coupling

Protected di-peptide E-1 is subjected to a peptide coupling reaction to form protected tri-peptide E-2. Protecting group PG$_a$ is removed, followed by a further peptide coupling reaction to afford compound E-3. Protecting group PG$_b$ is then removed, followed by a further peptide coupling reaction to afford compound E-4.

Scheme 2a.

E-4

E-5a

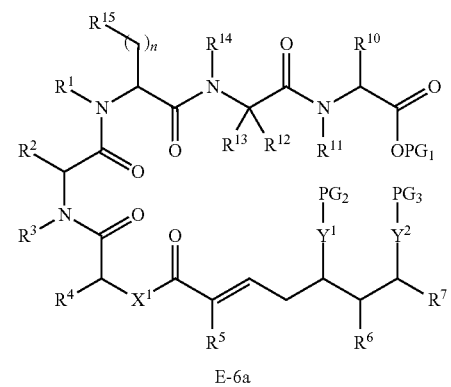

E-6a

Compound E-4 is reacted with compound E-5a under suitable conditions to afford compound E-6a.

PG$_4$, cyclization via a peptide coupling reaction, and removal of protecting group PG$_2$ afford compounds of Formula E-9b.

Exemplified syntheses according to Schemes 1a through 5a are described in Schemes 1b through 3b.

Scheme 3a.

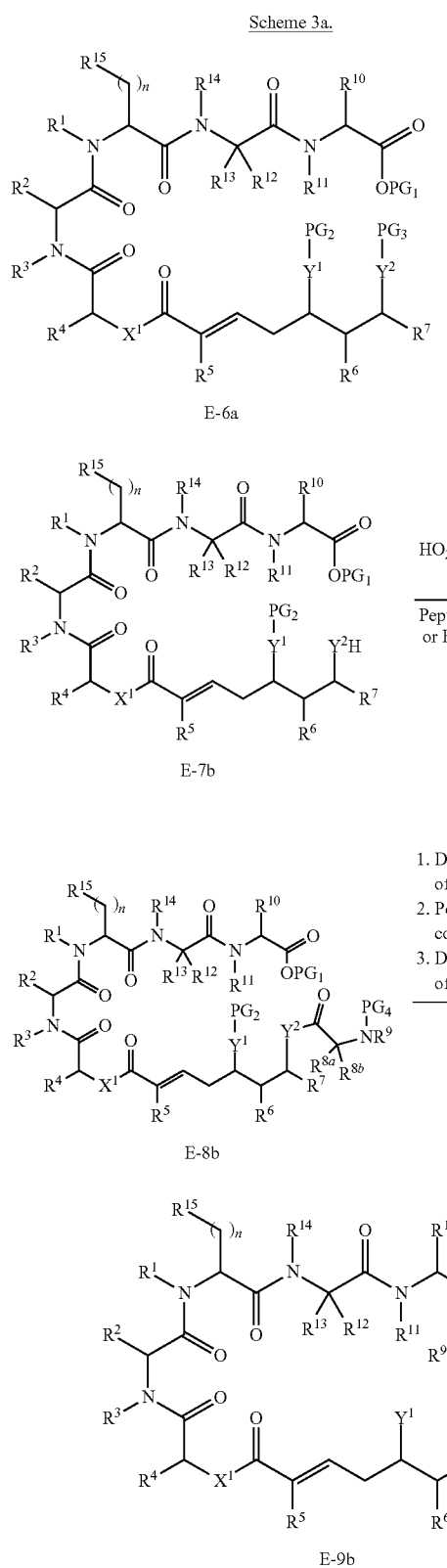

Scheme 1b.

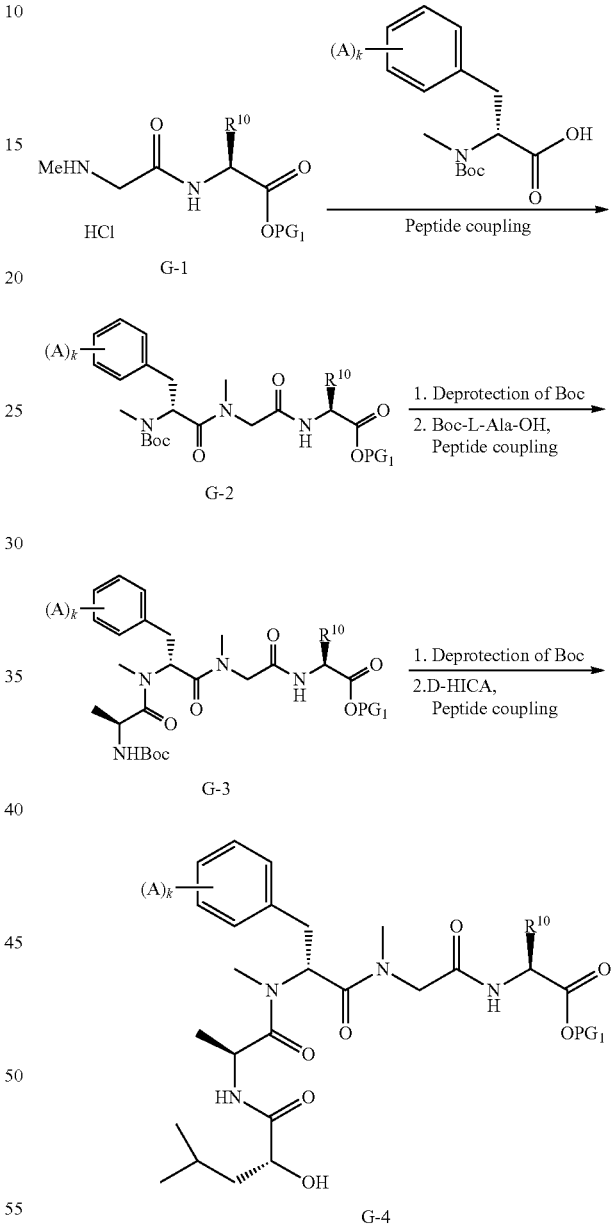

Selective deprotection of compound E-6a to remove protecting group PG$_3$ affords compound E-7b. This compound is subject to peptide coupling or esterification to afford compound E-8b. Removal of protecting groups PG$_1$ and In exemplified synthesis, the hydrochloride salt of protected di-peptide G-1 is subjected to a peptide coupling reaction to a Boc-protected phenylalanine or substituted phenylalanine to afford tri-peptide G-2. The Boc group is removed, followed by a peptide coupling reaction to Boc-protected alanine to afford compound G-3. The Boc-group is removed, and the compound is further reacted with D-2-hydroxyisocaproic acid (D-HICA) via a peptide coupling reaction to afford compound G-4.

Scheme 2b.
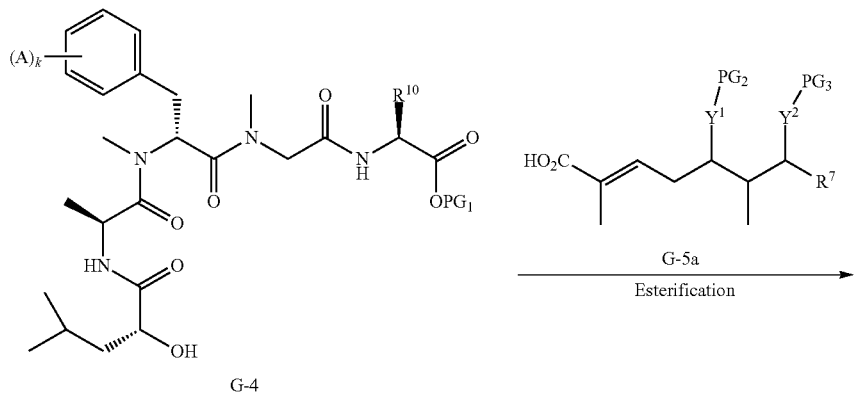
G-4
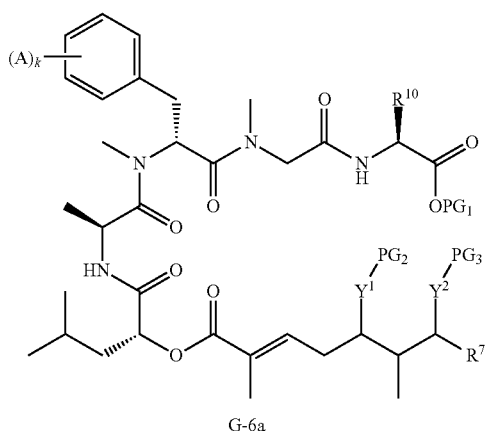
G-6a
Compound G-4 is reacted with compound G-5a under suitable esterification conditions to afford compound G-6a.
Scheme 3b.
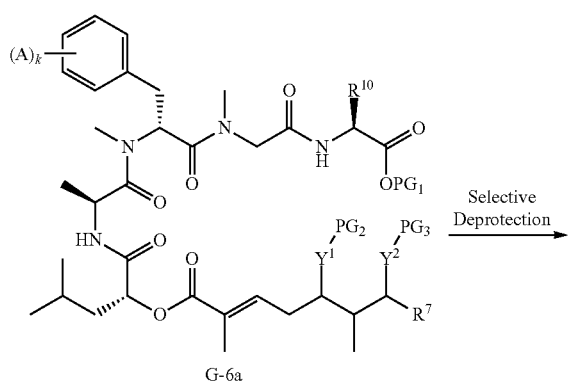
G-6a
-continued
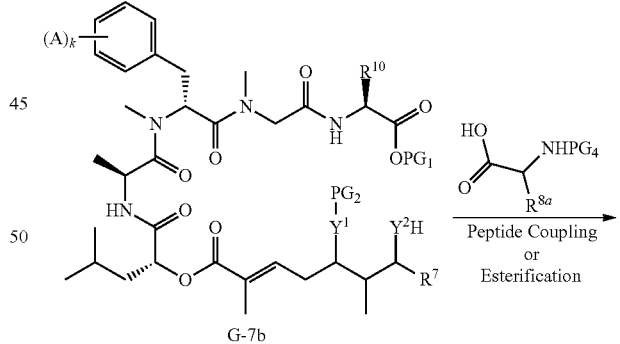
G-7b
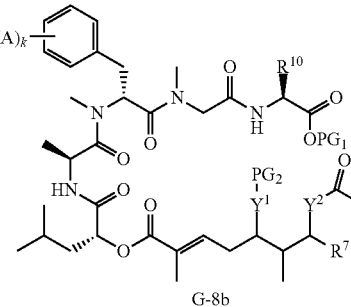
G-8b
1. Deprotection of PG$_1$ and PG$_4$
2. Peptide coupling
3. Deprotection of PG$_2$ -continued

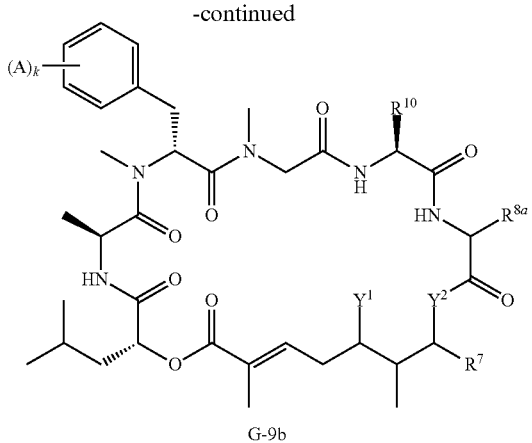

G-9b

Compound G-6a is selectively deprotected to remove PG$_3$, resulting in compound G-7b. G-7b is subject to peptide coupling or esterification to afford compound G-8b. Removal of protecting groups PG$_1$ and PG$_4$, cyclization via a peptide coupling reaction, and removal of protecting group PG$_2$ affords compound G-9a.

In another exemplified synthesis shown in Scheme 4, compound G-10 is reacted with chloro p-nitrophenylformate to form compound G-11, which is coupled with H$_2$N—(CH$_2$)$_m$—Z—(CH$_2$)$_p$—Y$^4$ to form compound G-12.

Scheme 4

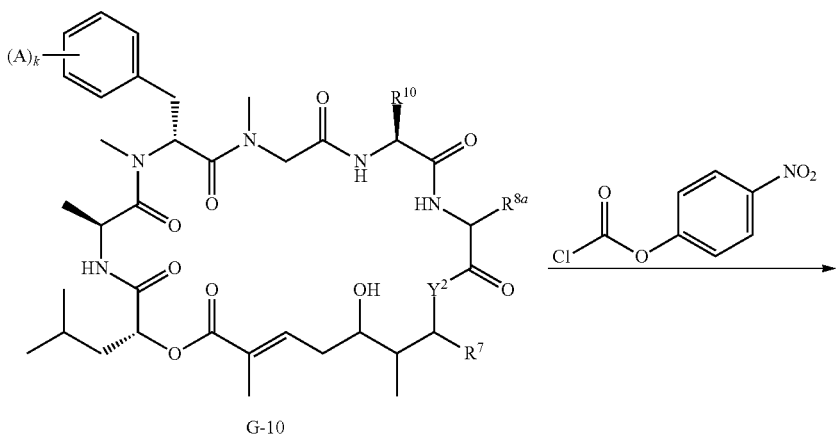

G-10

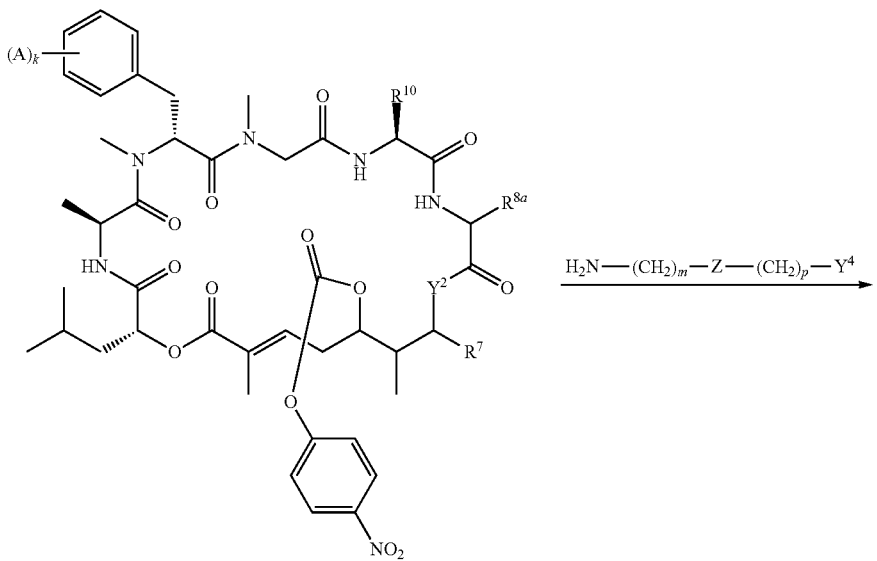

G-11

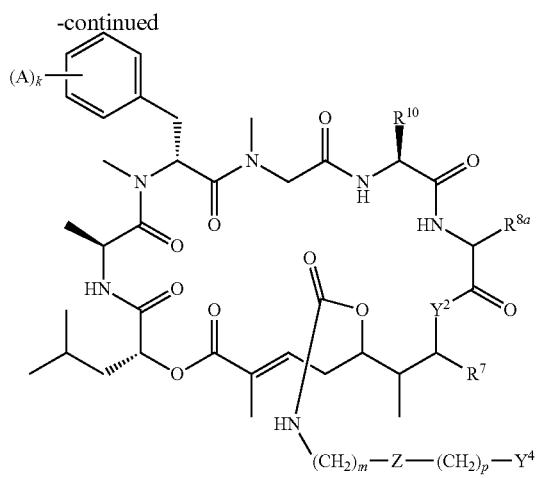

G-12

Another exemplified synthesis is shown in Scheme 5. Compound G13 is coupled to G14 to form G15, which is selectively deprotected to remove $PG_3$. The resulting compound G16 is coupled with compound G17 to form G18, which is selectively deprotected to remove $PG_2$, resulting in compound G-19. G-19 is then coupled with G-20 to form G21, which undergoes selective deprotection of $PG_4$ to form G-22. Deprotection of $PG_5$ affords G-23, which undergoes a cyclization via a peptide coupling reaction to form G-24. G24 is deprotected to remove $PG_1$ to afford G-25.

Scheme 5

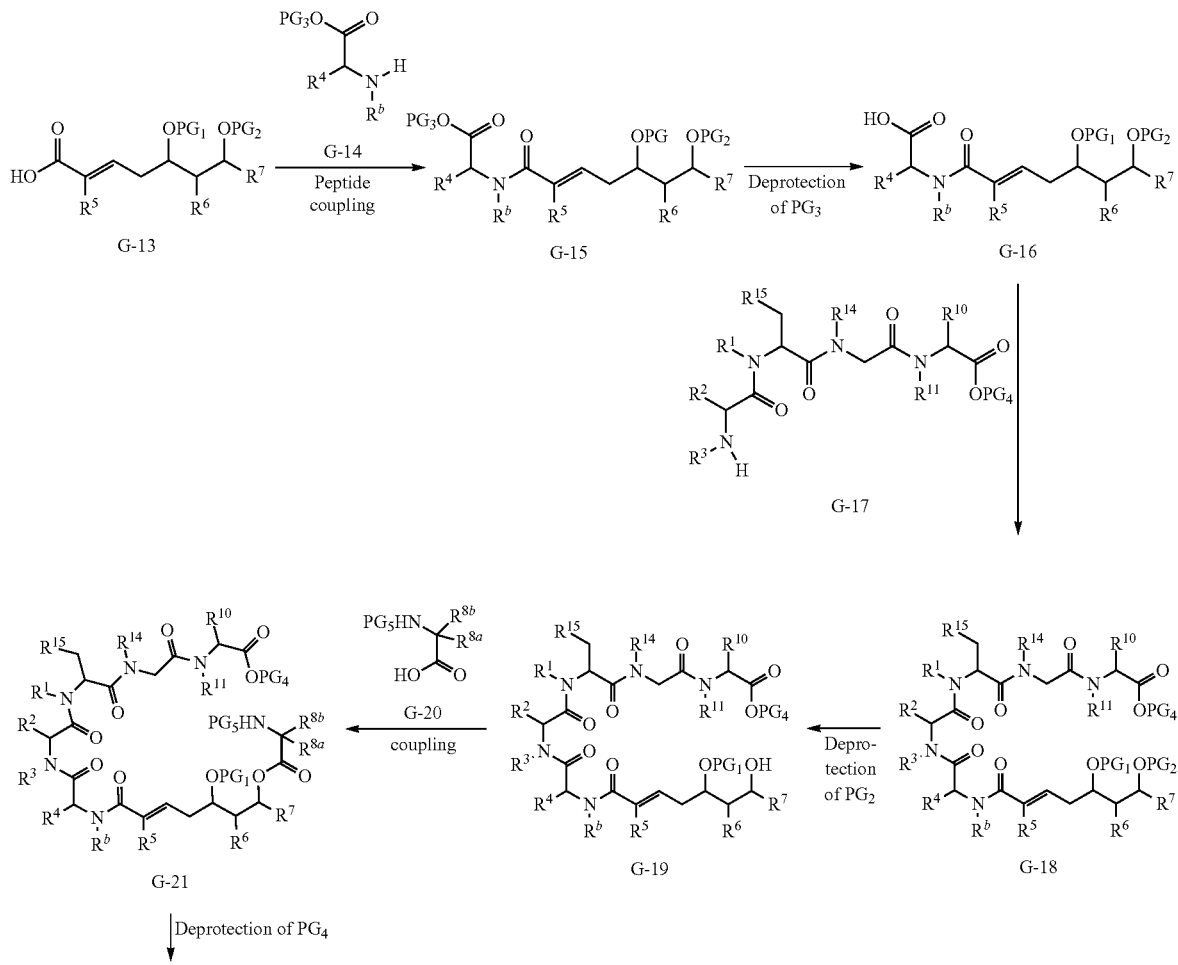

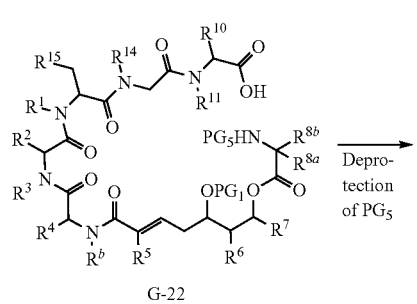

G-22

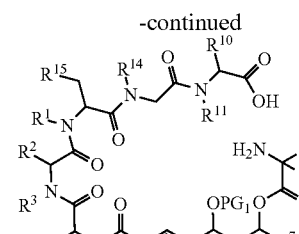

-continued

G-23

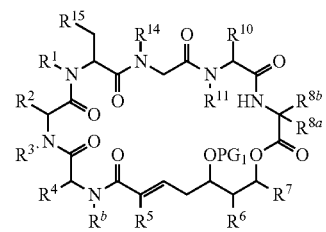

G-24

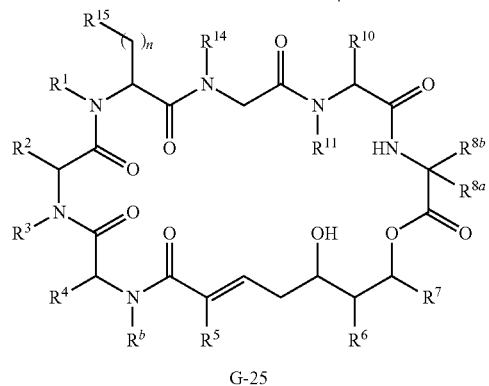

G-25

Another exemplified synthesis is shown in Scheme 6. Compound H-1 is reacted with n-BuLi followed by (+)-B-methoxydiisopinocamphenyl borane, boron tifluoride etherate, and H-2 to form compound H-3. Reaction with methanesulfonyl chloride in DMAP and trimethylamine and methylene chloride affords compound H-4. Compound H-4 is treated with sodium azide to produce compound H-5. Compound H-5 is treated with Dicarbonylacetylacetonato rhodium and Biphephos, followed by $NaBH_4$ at −40° C. to produce compound H-6, which is further reduced to compound H-7 using $NaBH_4$. Compound H-7 is reduced to compound H-8 using palladium on carbon in methanol. Compound H-8 is coupled with compound H-9 using DIPEA and HATU in methylene chloride to form compound H-10. Compound H-11 is formed by reacting compound H-10 with DMP in methylene chloride. Compound H-11 is reacted with compound H-12 to form compound H-13. Compound H-13 is treated with TFA in methylene chloride to form compound H-14, which is coupled with compound H-15 to form compound H-16. Compound H-16 is deprotected using $NH_4OAc$ and zinc followed by diethylamine and MeCN to form compound H-17, which undergoes a cyclization via coupling to form H-18.

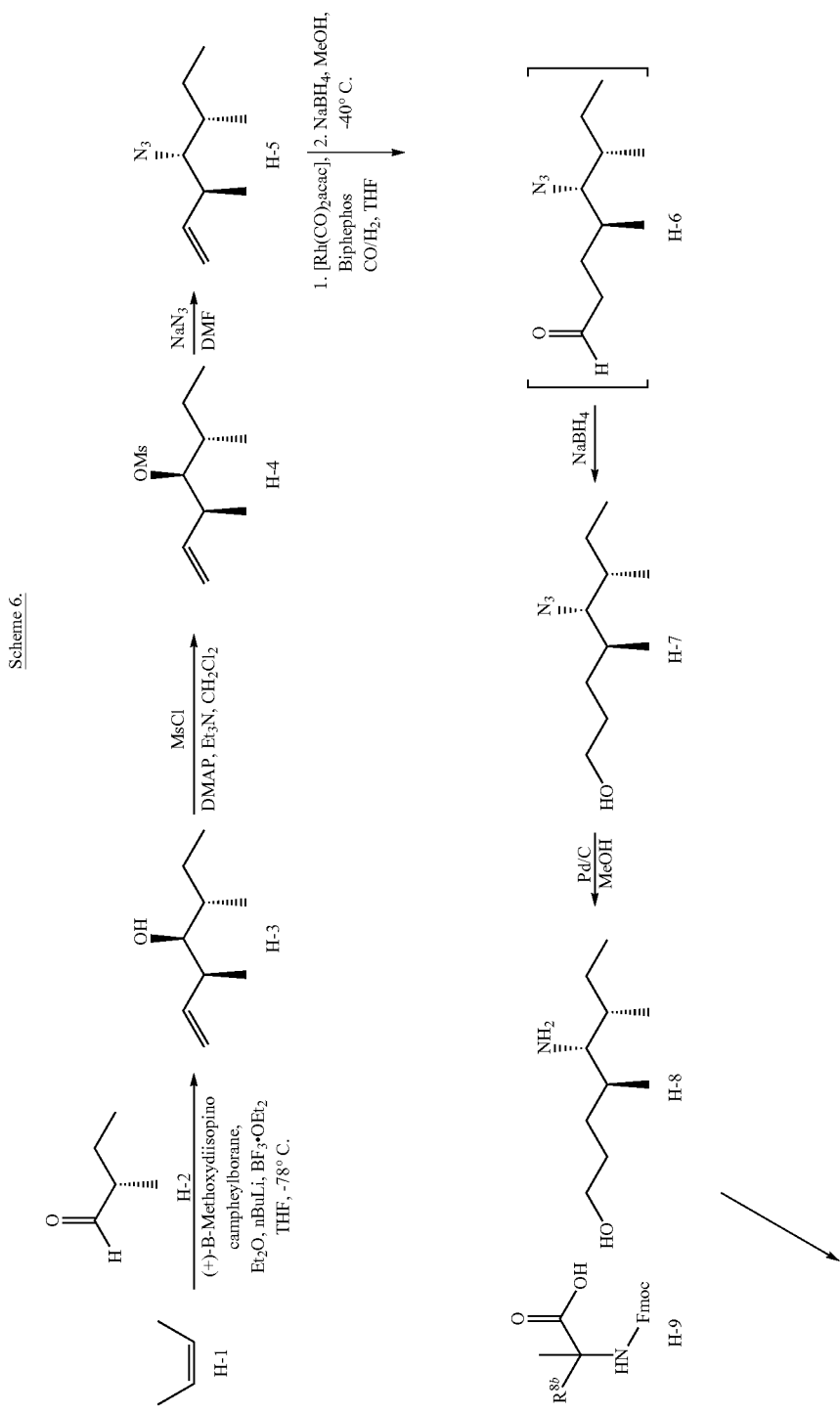

-continued
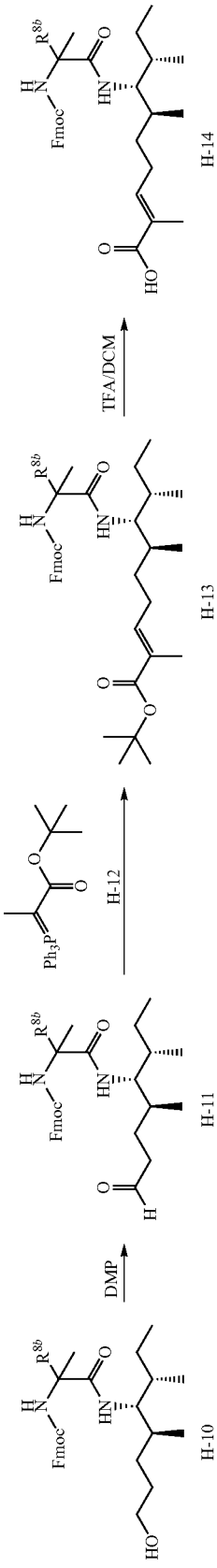
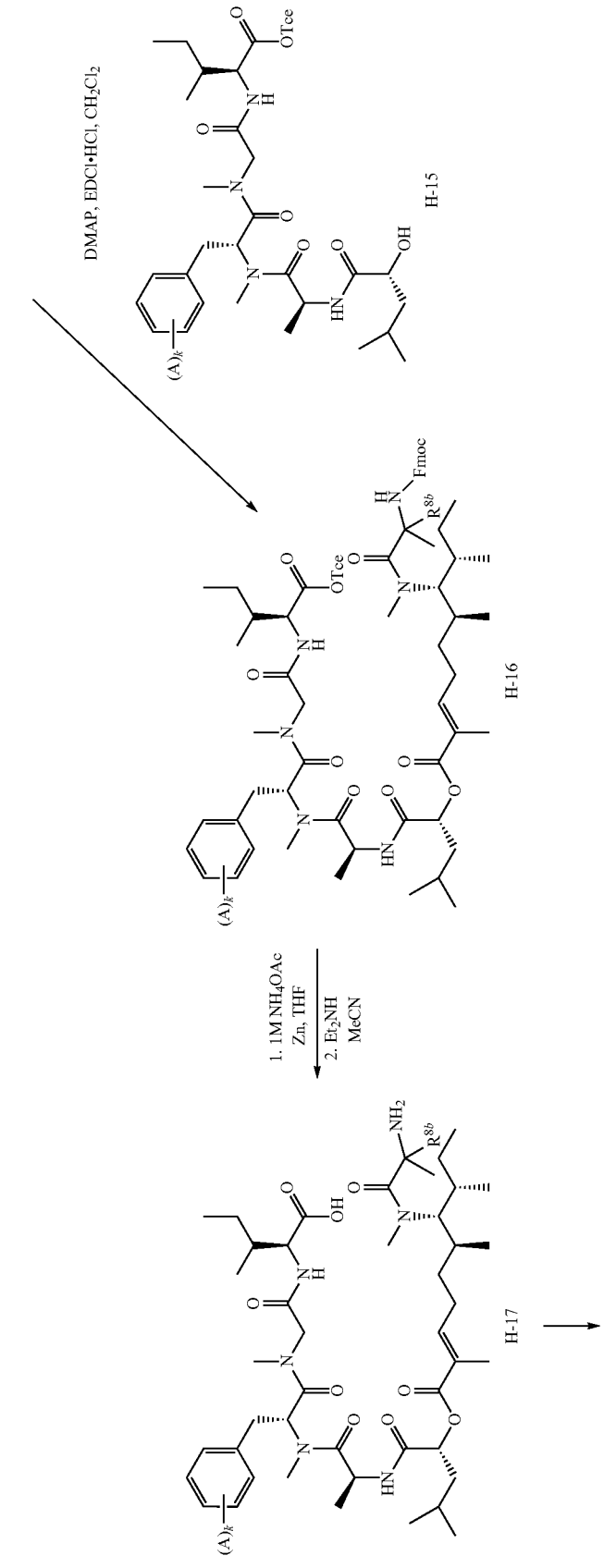

-continued
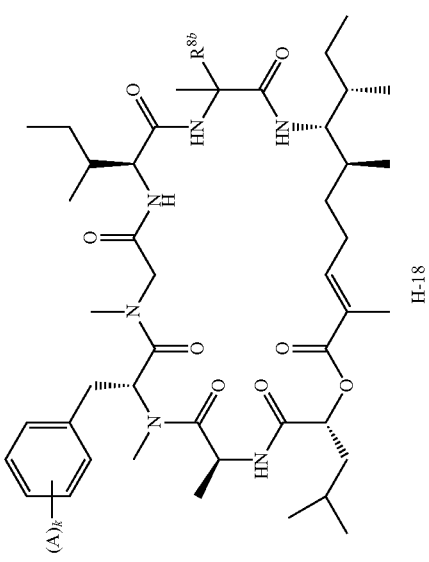

Certain intermediates useful in the preparation of the compounds and conjugates described herein may be synthesized according to any of the following schemes or variations theref.

Compound I-1a is reacted with aldehyde I-2a in the presence of Bu$_2$BOTf in methylene chloride at −78° C. to form compound I-3a. Reaction with trimethylaluminum and MeNHOMeHCl in methylene chloride followed by treatment with TBSCl and imidazole in DMF affords compound I-4a. Compound I-4a is treated with diisobutylaluminum hydride in methylene chloride at −78° C. to afford aldehyde I-5a. Compound I-5a is reacted with compound I-5z in the presence of boron trifluoride diethyl etherate in methylene chloride at −78° C. to afford compound I-6a. Compound I-6a can be subjected to a Dess-Martin reaction in methylene chloride at 23° C. to afford ketone I-7a. Further reaction with sodium borohydride in methanol at −40° C. affords compound I-8a. Compound I-8a is treated with acetic acid, acetic anhydride, and DMSO, followed by treatment with lithium hydroxide to afford compound I-9a. Compound I-9a can be further reacted as described herein to afford a 5-hydroxy-26-membered intone compound provided herein.

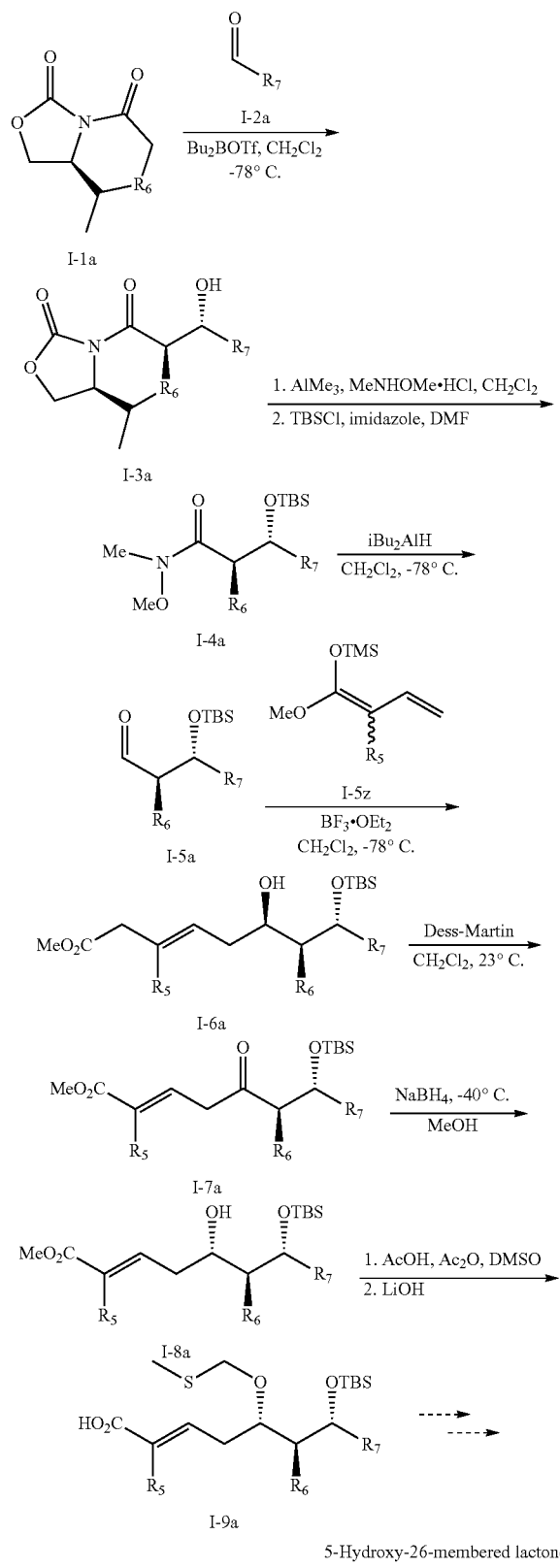

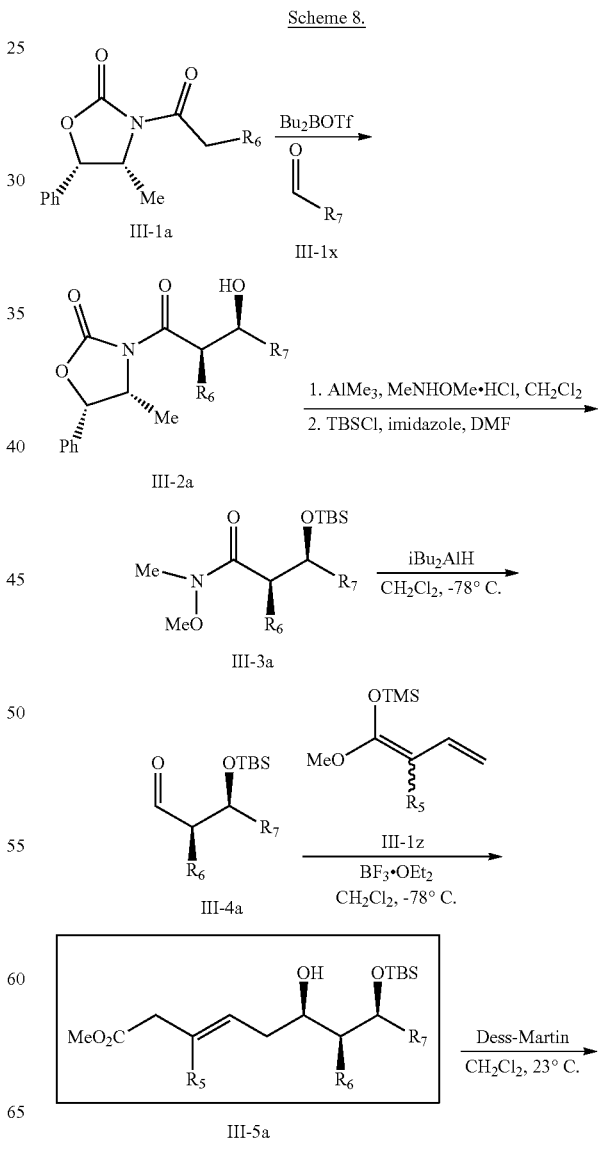

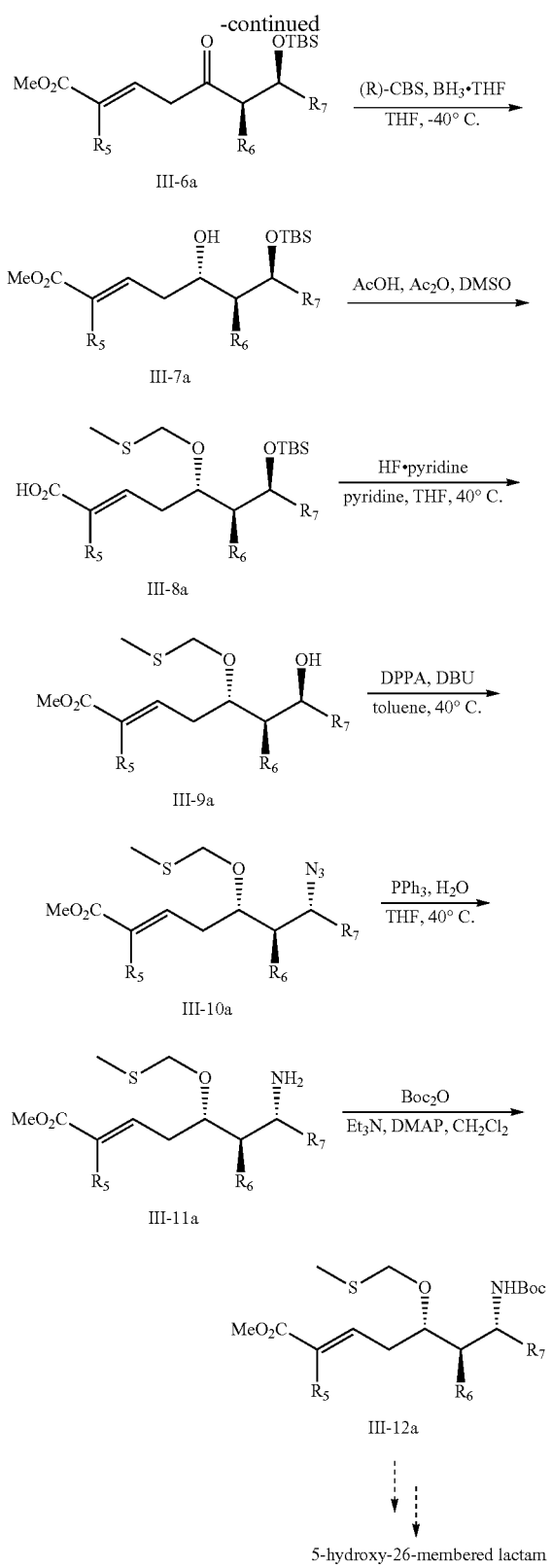

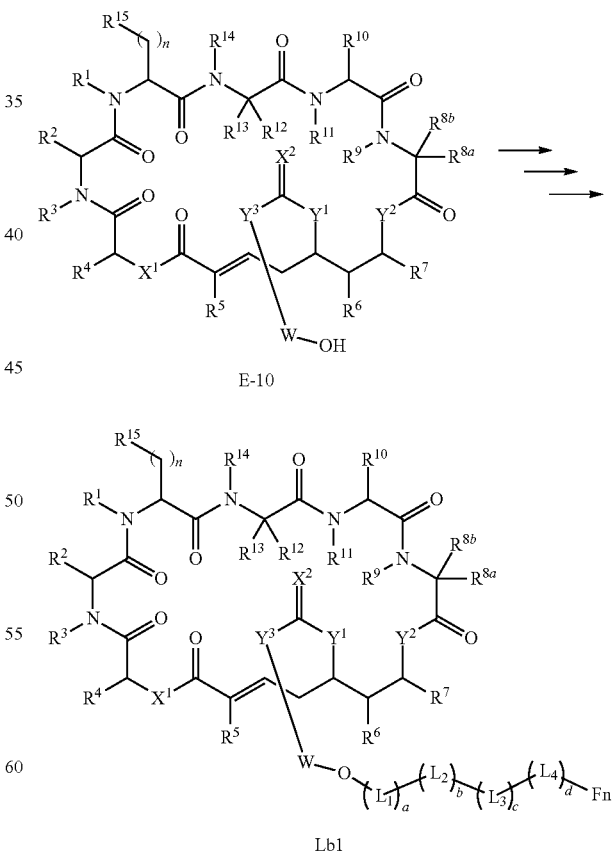

DMF affords compound III-3a. Compound III-3a is treated with diisobutylaluminum hydride in methylene chloride at −78° C. to afford aldehyde III-4a. Compound III-4a is reacted with compound in the presence of boron trifluoride diethyl etherate in methylene chloride at −78° C. to afford compound III-5a. Compound III-5a can be subjected to a Dess-Martin reaction in methylene chloride at 23° C. to afford ketone III-6a. Further reaction with (R)-CBS and sodium borohydride in THF at −40° C. affords compound III-7a. Compound III-7a is treated with acetic acid, acetic anhydride, and DMSO to afford compound III-8a. Treatment with HF pyridine in pyridine and THF at 40° C. affords compound III-9a. Compound III-9a is reacted with DPPA and DBU in toluene at 40° C. to afford compound III-10a. Further reaction with triphenylphosphine in water and THF at 40° C. results in compound III-1a. Treatment with Boc anhydride, trimethylamine, and DMAP in methylene chloride affords compound III-12a. Compound III-12a can be further reacted as described herein to afford a 5-hydroxy-26-membered lactam compound provided herein.

Compounds containing linkers as described herein can be obtain from appropriate precursor compounds and may be prepared using methods known in the art. In some variations, linker-containing compounds of Formula (Lb1) may be prepared in accordance with the general procedure of Scheme 9.

Compound III-1a is reacted with aldehyde III-1x in the presence of $Bu_2BOTf$ to form compound III-2a. Reaction with trimethylaluminum and MeNHOMeHCl in methylene chloride followed by treatment with TBSCl and imidazole in Compounds of Formula (Ib2) may be prepared in accordance with Schemes 10-14, below.

Scheme 10
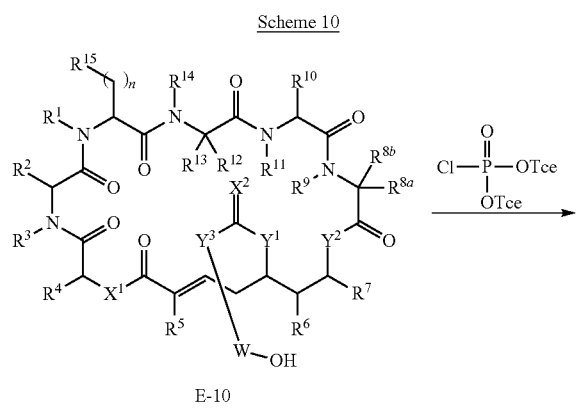
E-10
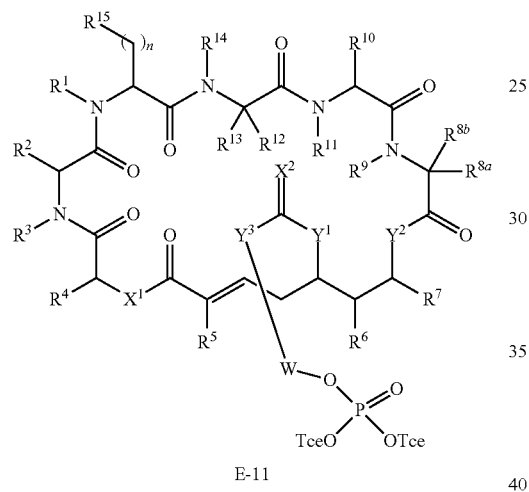
E-11
Compound E-10 may be reacted with bis (2,2,2-trichloroethyl)phosphorochloridate under suitable conditions to afford a compound of E-11.
Scheme 11.
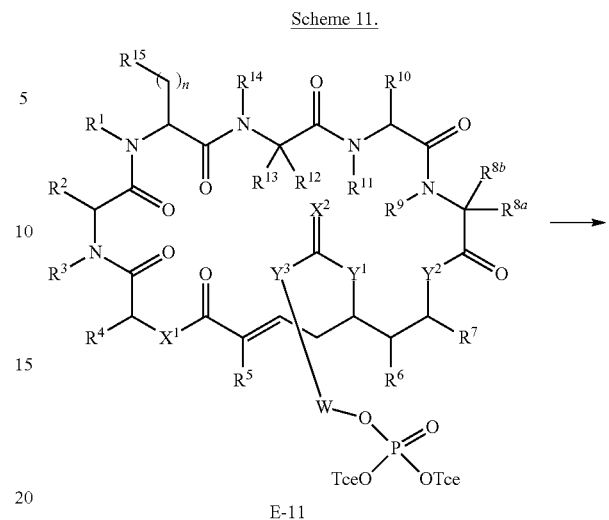
E-11
E-12
Compound E-11 may be converted to compound E-12.
Scheme 12.
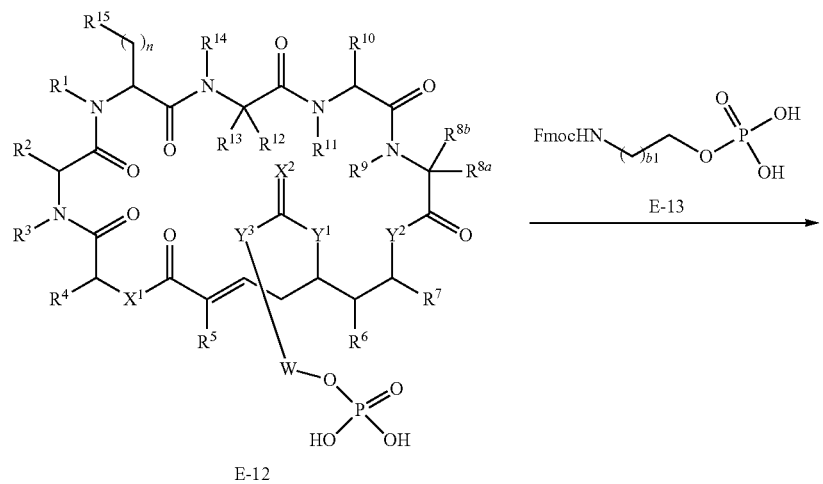
E-12

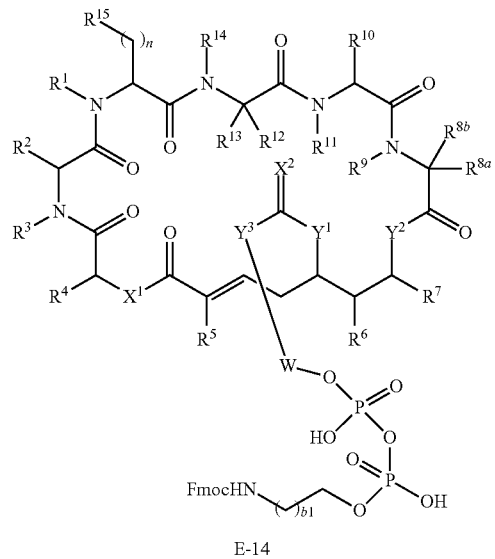
E-14
Compound E-12 may be coupled with compound E-13 to form compound E-14.
Scheme 13
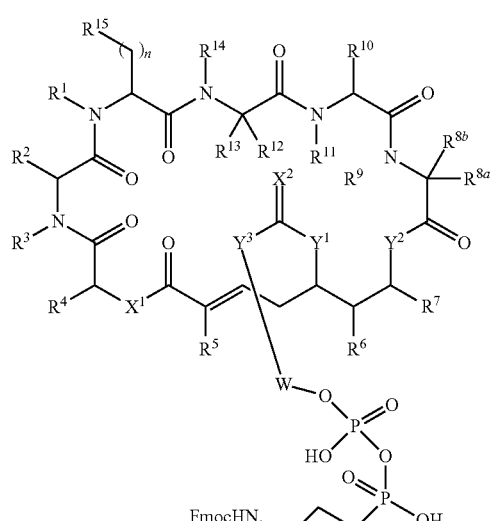
E-14
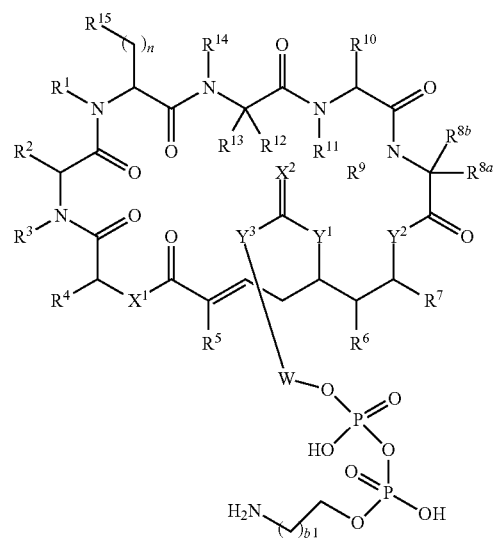
E-15
Compound E-14 may be deprotected to form compound E-15.

Scheme 14

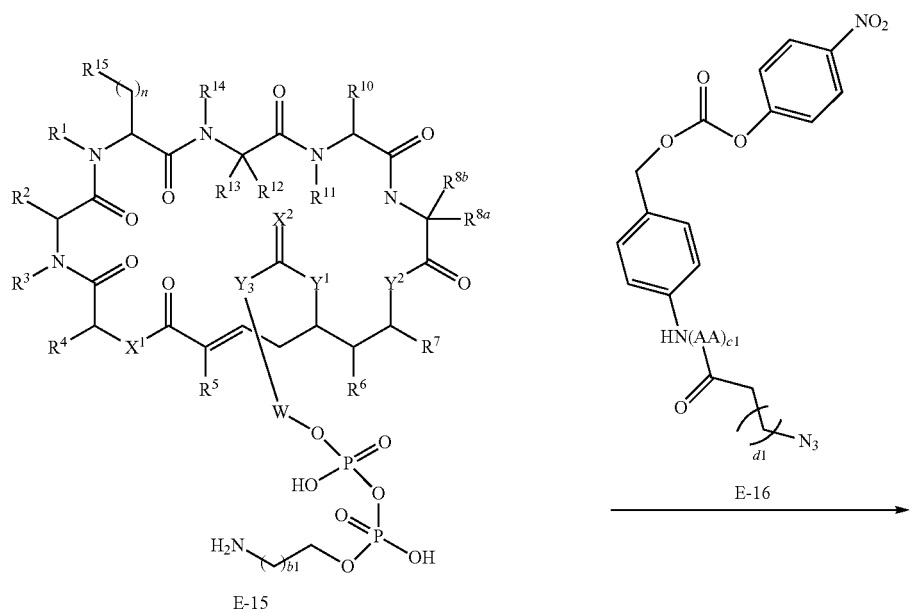

E-15

E-16

Compound E-15 may be coupled with compound E-16 to from compounds of Formula (Ib2). Compounds of Formula (Ib2) may be coupled to a ligand.

As shown in Scheme 15, the compound may be reacted with a linker (L-Fn) at any position on the compound suitable for reaction with a linker to produce the compound-linker conjugate compound-L-Fn using suitable methods known in the art. In some embodiments, linker is attached via the $Y^4$ group of the compound. In Scheme 13, Compound-L-Fn may comprise any compound or conjugate described herein.

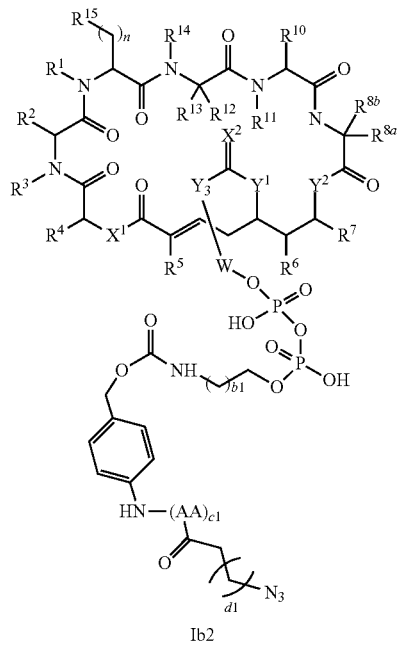

Ib2

Scheme 15

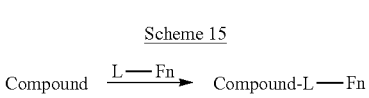

A compound of Formula (I), wherein $Y^4$ is OH, may be reacted using suitable methods to produce a conjugate containing the compound of Formula (I) bonded to a azide-containing linker, such as compounds of Formula (Ib2).

Azide-containing compound-L-Fn conjugates provided herein can be conjugated to an antibody comprising an alkyne functional group (wherein U represents any suitable portion of a linker moiety) using methods known in the art, such as using click chemistry, as shown in Scheme 16.

Scheme 16

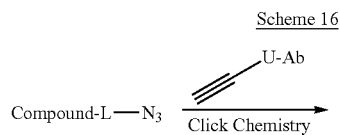

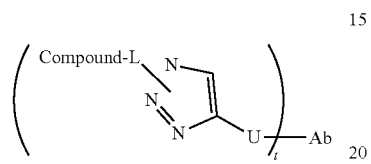

Similarly, antibodies containing an azide functional group may be conjugated with alkyne-containing compound-L-Fn conjugates using click chemistry methods.

Compounds of Formula (I), may also be reacted using suitable methods to produce a conjugate containing the compound of Formula (I) bonded to a maleimide-containing linker. In some embodiments, the linker is attached via the $Y^4$ group of the compound, wherein $Y^4$ is —OH. More generally, any of the compounds described herein can be coupled to a maleimide-containing linker at a suitable position, as shown in Scheme 17.

Scheme 17.

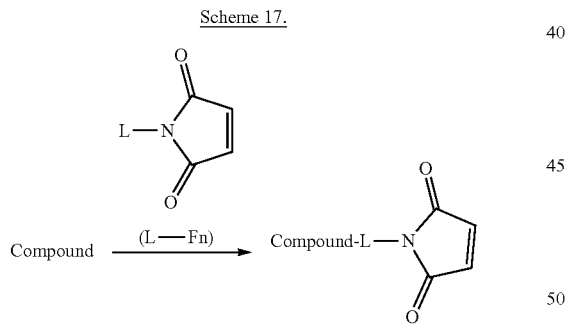

Compounds or conjugates comprising maleimide groups can be conjugated to an antibody using methods known in the art, such as those described in Greg T. Hermanson, *Bioconjugate Techniques*, Academic Press 19, page 60. An exemplary method is provided in Scheme 18. The antibody is first subjected to reducing conditions for partial or full reduction of disulfide bonds. The modified antibody is then conjugated to the compound-L-Fn via maleimide-sulfhydryl conjugation techniques, upon which the maleimide of the compound-L-Fn is directly conjugated to the sulfur atom of a cysteine side chain in the antibody.

Scheme 18.

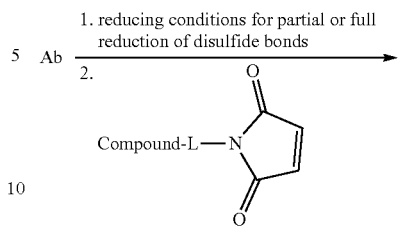

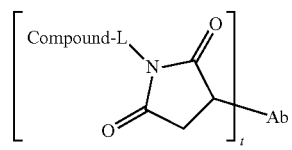

Bis-sulfone containing compounds can also be coupled to thiol-modified antibodies (bridged disulfide antibodies) via alkene group (ref: Badescu, G. et al., Bioconjugate Chem. 2014, 25, 1124-1136). An exemplary method is provided in Scheme 17. After subjecting the antibody to reducing conditions for partial or full reduction of disulfide bonds, the modified antibody is conjugated to the compound-L-Fn via two sulfide bonds, one via each of two geometrically close cysteine side chains within the antibody.

Scheme 19

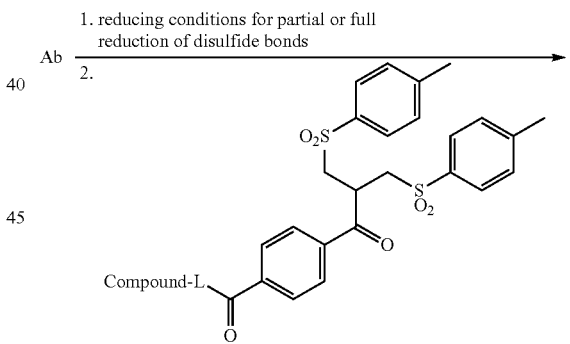

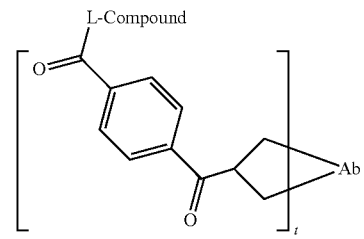

Alternatively, conjugation of compound-L-Fn to the antibody can be performed using a combination of the methods discussed above, such as shown in Schemes 20-23.

Scheme 20

1. reducing conditions for partial or full reduction of disulfide bonds
Ab ─────────────────────────────────→
2.

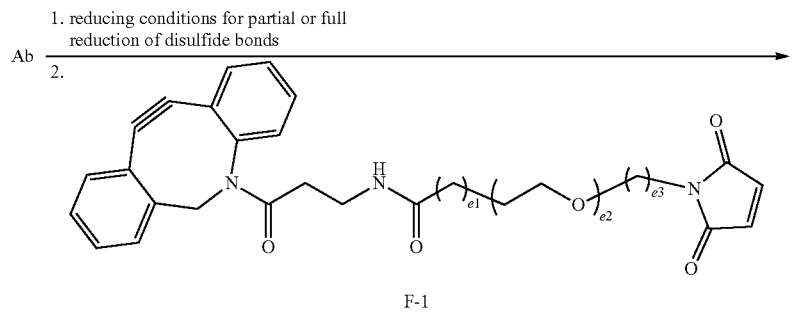

F-1

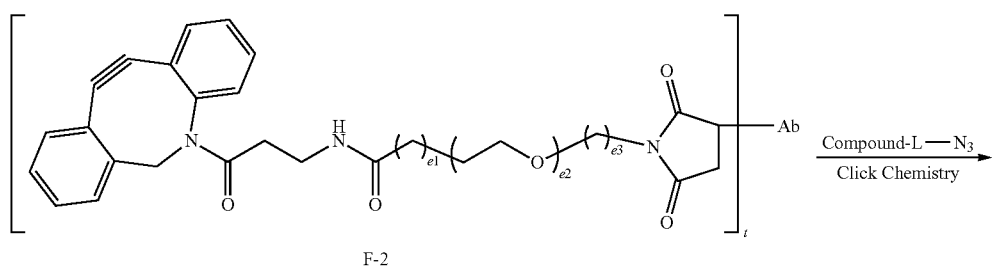

F-2

Compound-L—N₃
Click Chemistry

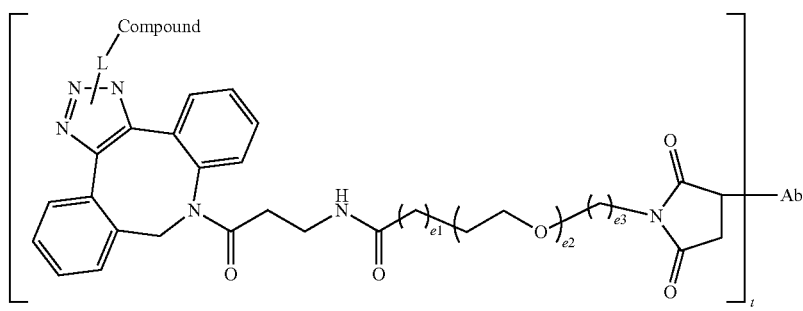

In Scheme 20, the maleimide moiety of each compound F-1 may be bound to the sulfur atom of a cysteine residue on the antibody. The modified antibody F-2 can be coupled to an azide-containing compound-L-Fn via click chemistry.

Scheme 21

1. reducing conditions for partial or full reduction of disulfide bonds
Ab ─────────────────────────────────→
2.

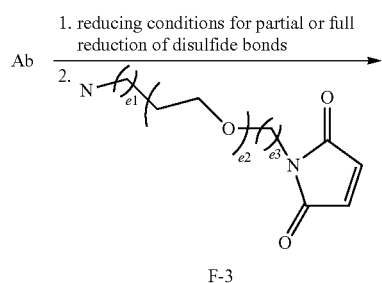

F-3

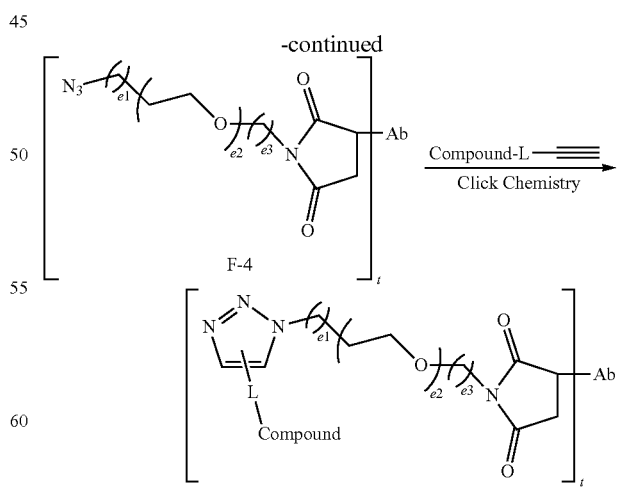

F-4

Compound-L≡≡≡
Click Chemistry

In Scheme 21, the maleimide moiety of each compound F-3 may be bound to the sulfur atom of a cysteine residue on the antibody. The modified antibody F-4 can be coupled to an azide-containing compound-L-Fn via click chemistry.

Scheme 22
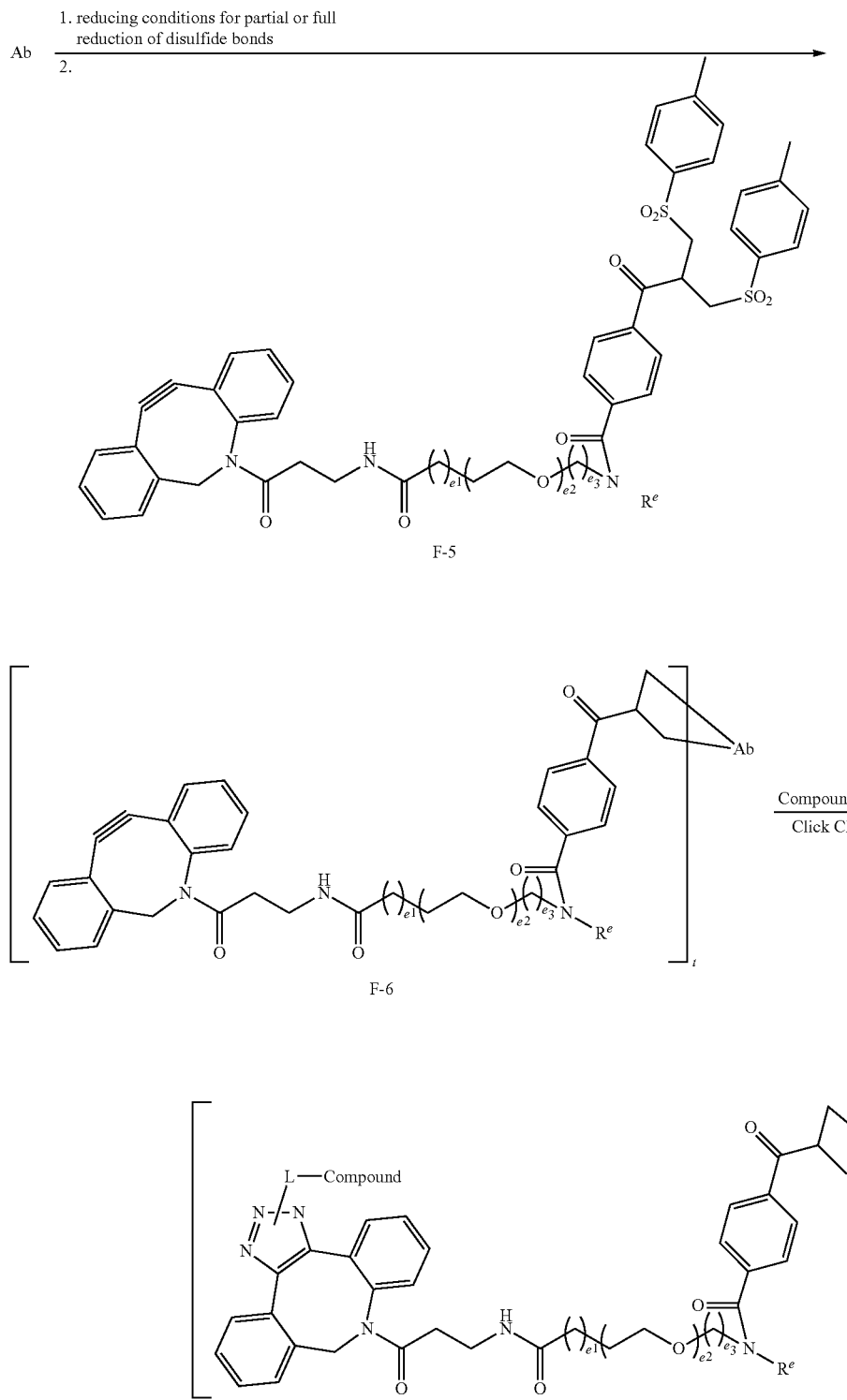
In Scheme 22, compound F-5 is first conjugated to the antibody to form bridged disulfide antibody (F-6) via two sulfide bonds. The bridged disulfide antibody F-6 is then coupled to an azide-containing compound-L-Fn via click chemistry.

Scheme 23
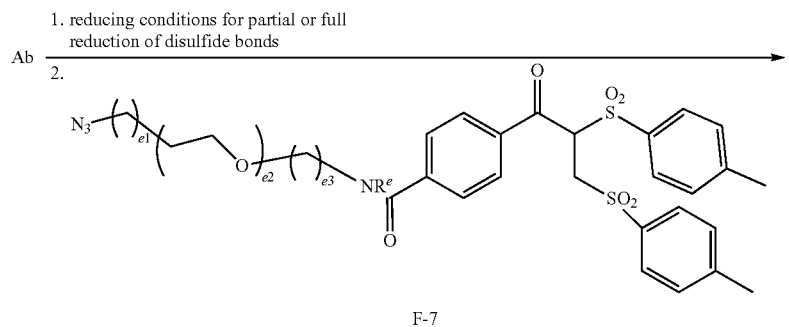
F-7
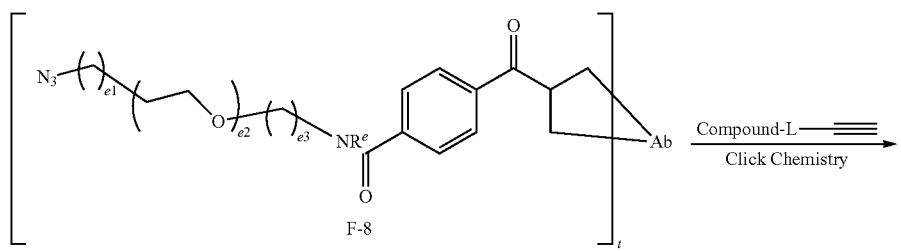
F-8
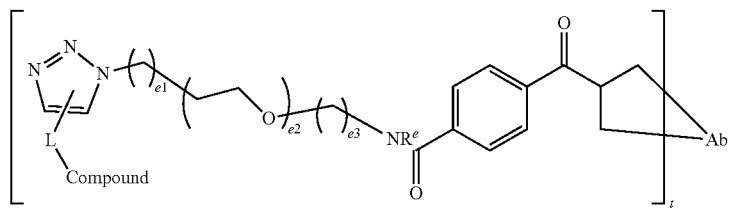
In Scheme 23, compound F-7 is first conjugated to the antibody to form bridged disulfide antibody (F-8) via two sulfide bonds. The bridged disulfide antibody F-8 is then coupled to an alkyne-containing compound-L-Fn via click chemistry.
Scheme 23a:
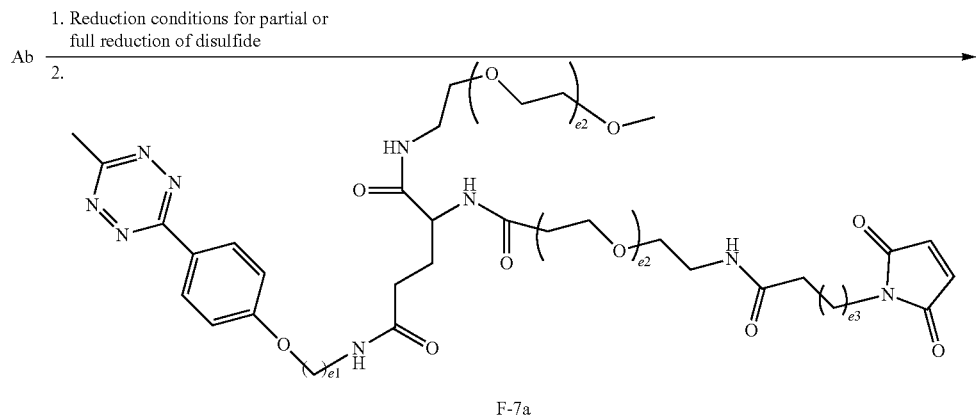
F-7a

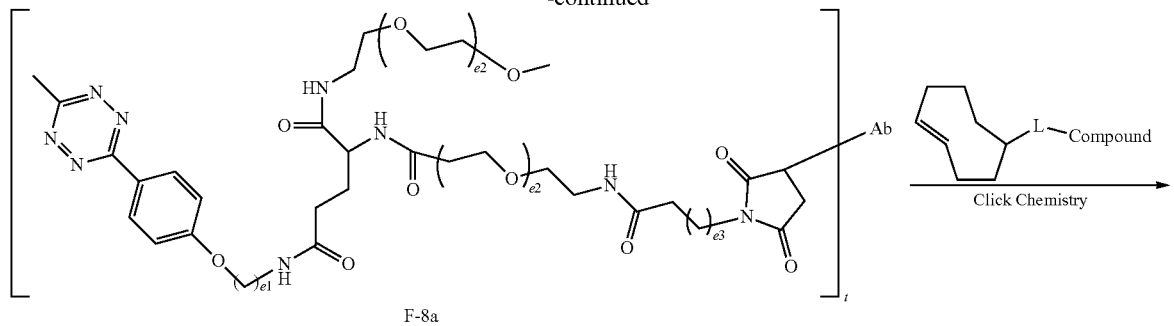

F-8a

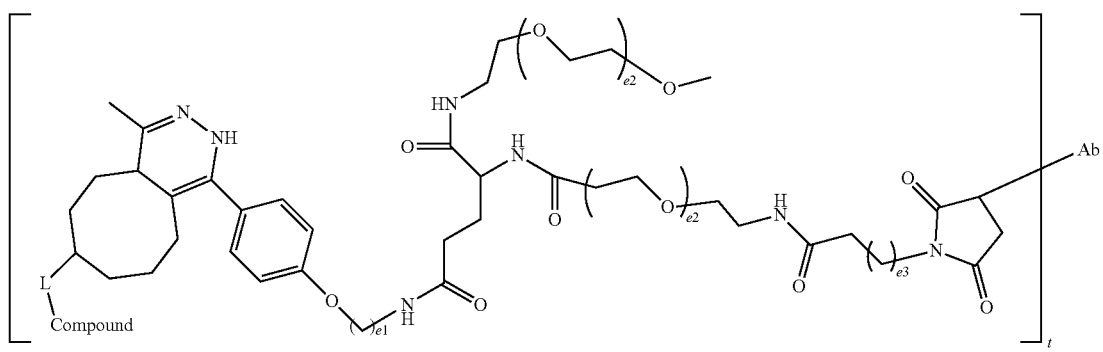

In Scheme 23a, the maleimide moiety of each compound F-7a may be bound to the sulfur atom of a cysteine residue on the antibody. The modified antibody F-8a can be coupled to an cyclooctene-containing compound-L-Fn via click chemistry.

EXAMPLES

The following examples are offered to illustrate but not to limit the compositions, uses, and methods provided herein. The compounds are prepared using the general methods described above.

The following chemical abbreviations are used throughout the Examples: CDI (1,1'-carbonyldiimidazole), DCM (dichloromethane), DMAP (4-dimethylaminopyridine), DMF (dimethylformamide), DMP (Dess-Martin periodinane), EDC (1-Ethyl-3-(3-dimethylaminopropyl)carbodiimide), ESI (electrospray ionization), Fmoc (Fluorenylmethyloxycarbonyl), HATU (1-[Bis(dimethylamino)methylene]-1H-1,2,3-triazolo[4,5-b]pyridinium 3-oxid hexafluorophosphate), HRMS (High Resolution Mass Spectrometry), Hünig's base (DIPEA, or N,N-Diisopropylethylamine), LRMS (Low Resolution Mass Spectrometry), MeCN (acetonitrile), MeOH (methanol), RP (Reversed Phase), rt (room temperature), THF (tetrahydrofuran), and TLC (thin layer chromatography).

Example 1

Synthesis of Intermediate 1

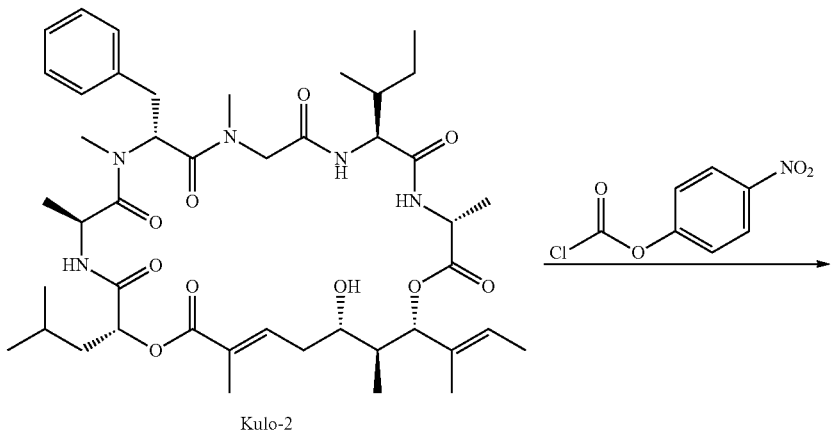

Kulo-2

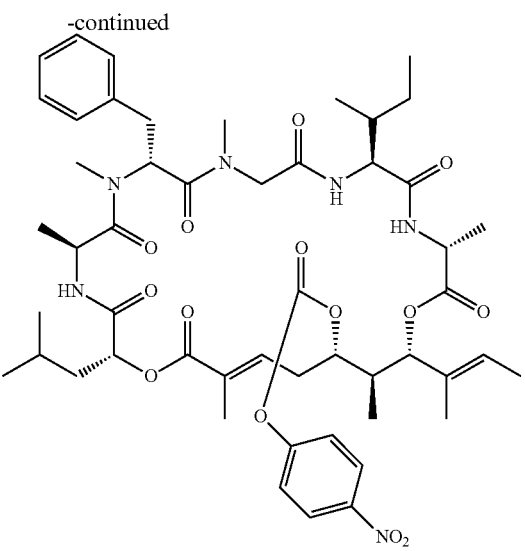

Intermediate 1

To a solution of kulo-2 (48 mg, 58 μmol) in DCM (5 mL) was added DMAP (6 mg, 50 μmol), chloro p-nitrophenylformate (160 mg, 793 μmol) and diisopropylethylamine (0.5 mL). The reaction mixture was stirred for 4 h at rt, then diluted with ethyl acetate and washed with 10% citric acid solution. The aqueous layer was extracted with ethyl acetate and the combined organic layer was washed with sodium bicarbonate solution and brine, then dried over NaSO₄ and concentrated in vacuo. The crude material was subjected to column chromatography to yield Intermediate 1.

Example 2

Synthesis of Compound 1

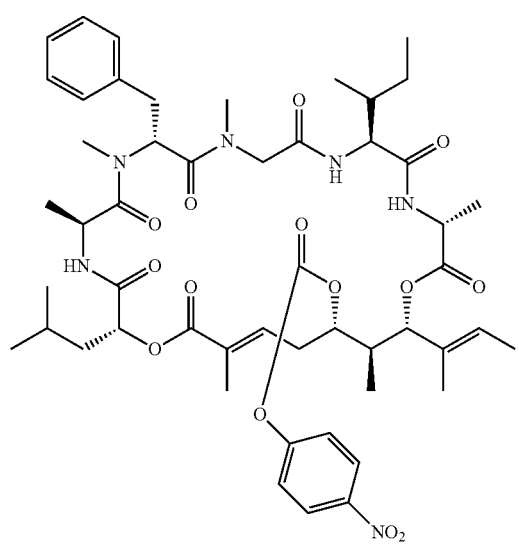

→

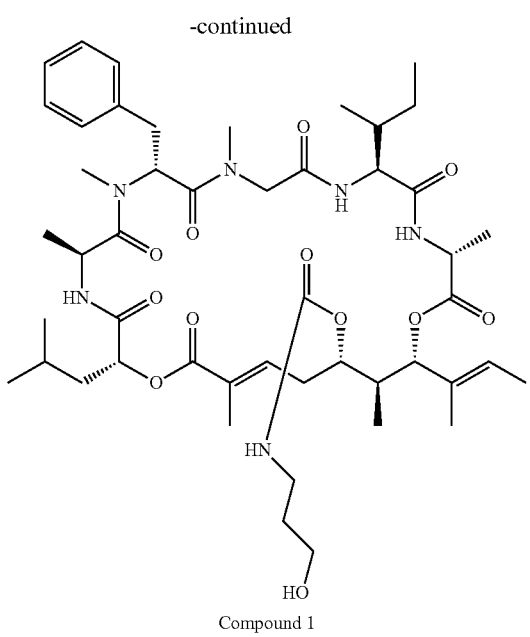

Compound 1

To the solution of (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl(4-nitrophenyl) carbonate (2.018 μmol, 2 mg) in DCM (4.66 mmol, 0.3 mL) was added 3-aminopropan-1-ol (2.018 μmol, 1.4 μL) and Hünig's base (0.020 mmol, 3.5 μL). The mixture was stirred overnight and the volatile was removed. The residue was purified with RP-flash to afford (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (3-hydroxypropyl)carbamate (0.7 mg, 37.4%). Observed HRMS (ESI) m/z: 927.5473 [M+H]+.

Example 3

Synthesis of Compound 2

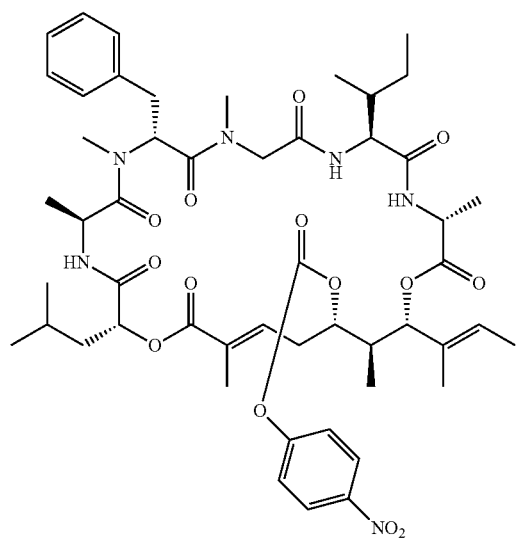

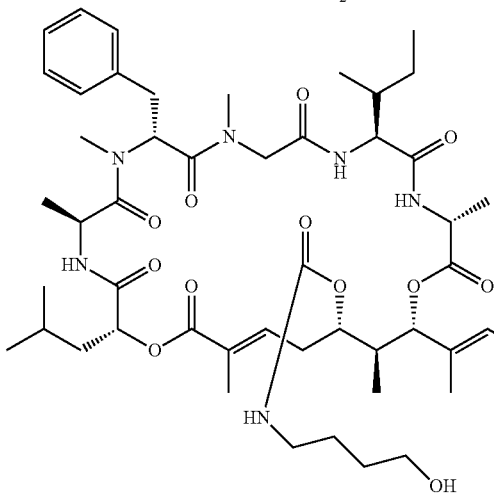

Compound 2

To the solution of (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (4-nitrophenyl) carbonate (2.018 μmol, 2 mg) in DCM (7.77 mmol, 0.5 mL) was added 4-aminobutan-1-ol (0.168 mmol, 15 mg) and Hünig's base (0.286 mmol, 50 μL). The mixture was stirred overnight and the volatile was removed. The residue was purified with Rp-flash to afford (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (4-hydroxybutyl) carbamate (1.7 mg, 90%). Observed HRMS (ESI) m/z: 941.562 [M+H]+. The $^1$H NMR spectrum of Compound 2 is shown in FIG. 1.

Example 4

Synthesis of Compound 3

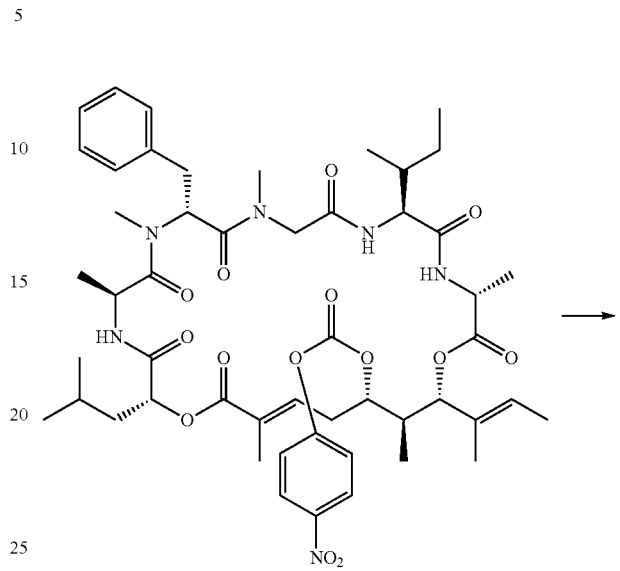

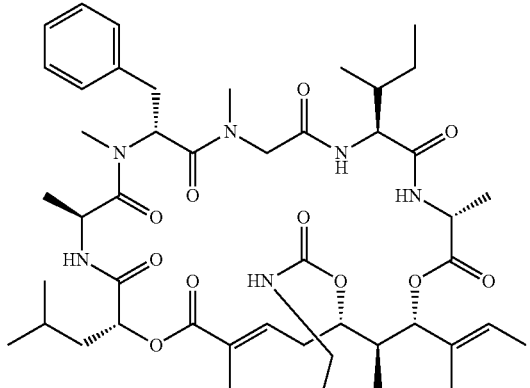

Compound 3

To the solution of (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (4-nitrophenyl) carbonate (5.04 μmol, 5 mg) in DCM (15.54 mmol, 1 mL) was added 5-aminopentan-1-ol (0.048 mmol, 5 mg) and Hünig's base (0.252 mmol, 0.044 mL). The mixture was stirred ovrernight, and the volatile was removed. The residue was purified with rp-flash to afford (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxa-4,7,10,13,16-pentaazacyclohexacos-24-en-22-yl (5-hydroxypentyl)carbamate (4.19 μmol, 4 mg, 83%). Observed HRMS (ESI) m/z: 955.5842 [M+H]+.

Example 5

Synthesis of Compound 4

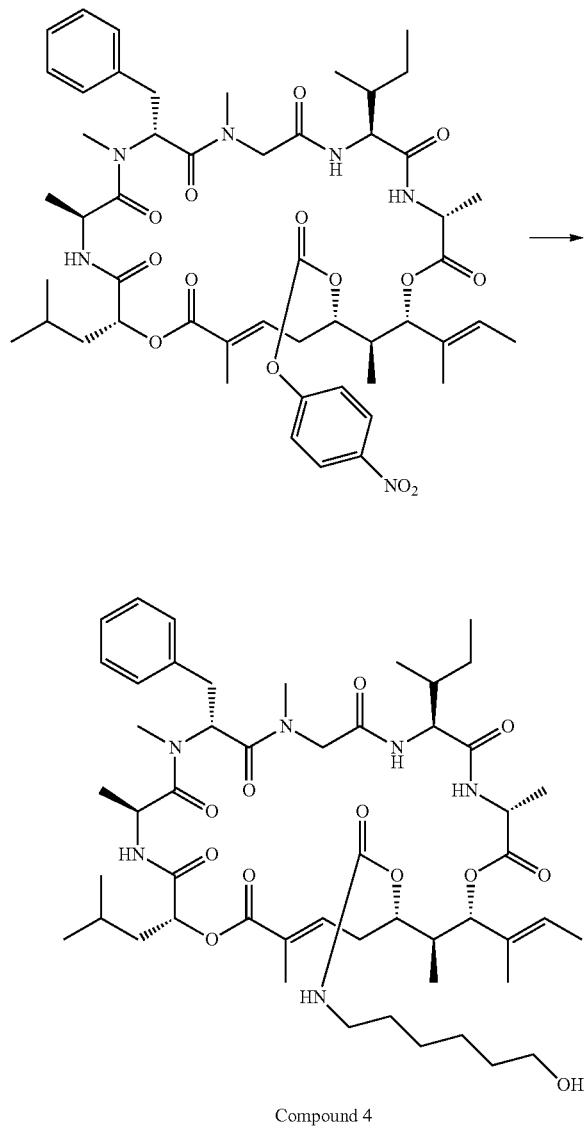

Compound 4

Figure 2:
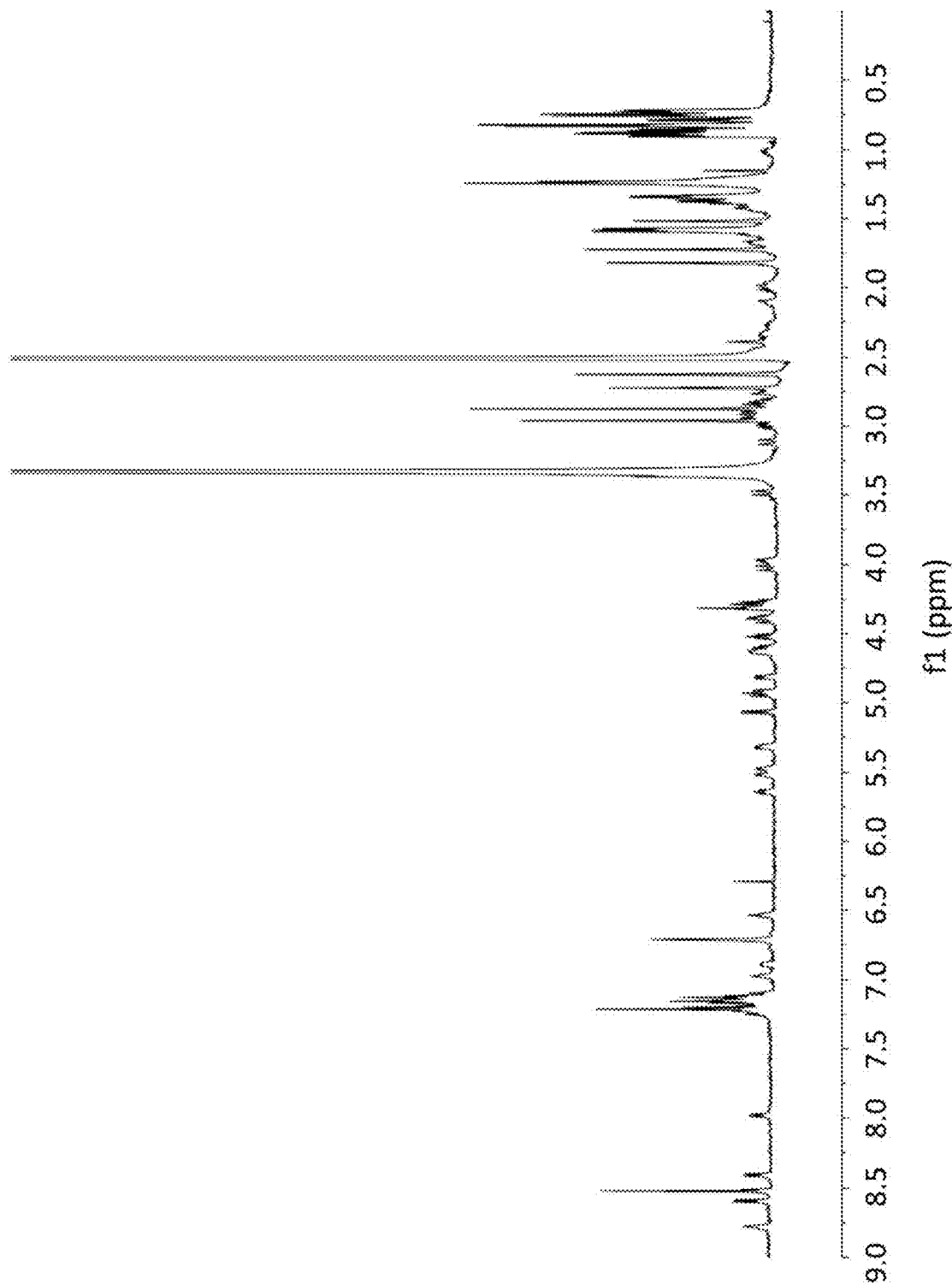
FIG. 2 is a $^1$H NMR spectrum of Compound 4 in DMSO-d6.

To the solution of (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl(4-nitrophenyl) carbonate (2.018 μmol, 2 mg) in DCM (7.77 mmol, 0.5 mL) was added 6-aminohexan-1-ol (0.017 mmol, 2 mg) and Hünig's base (0.286 mmol, 50 μL). The mixture was stirred overnight and the volatile was removed. The residue was purified with RP-flash to afford (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl(6-hydroxyhexyl) carbamate (2 mg, 102%). Observed HRMS (ESI) m/z: 969.599 [M+H]+. The $^1$H NMR spectrum of Compound 4 is shown in FIG. 2.

Example 6

Synthesis of Compound 5

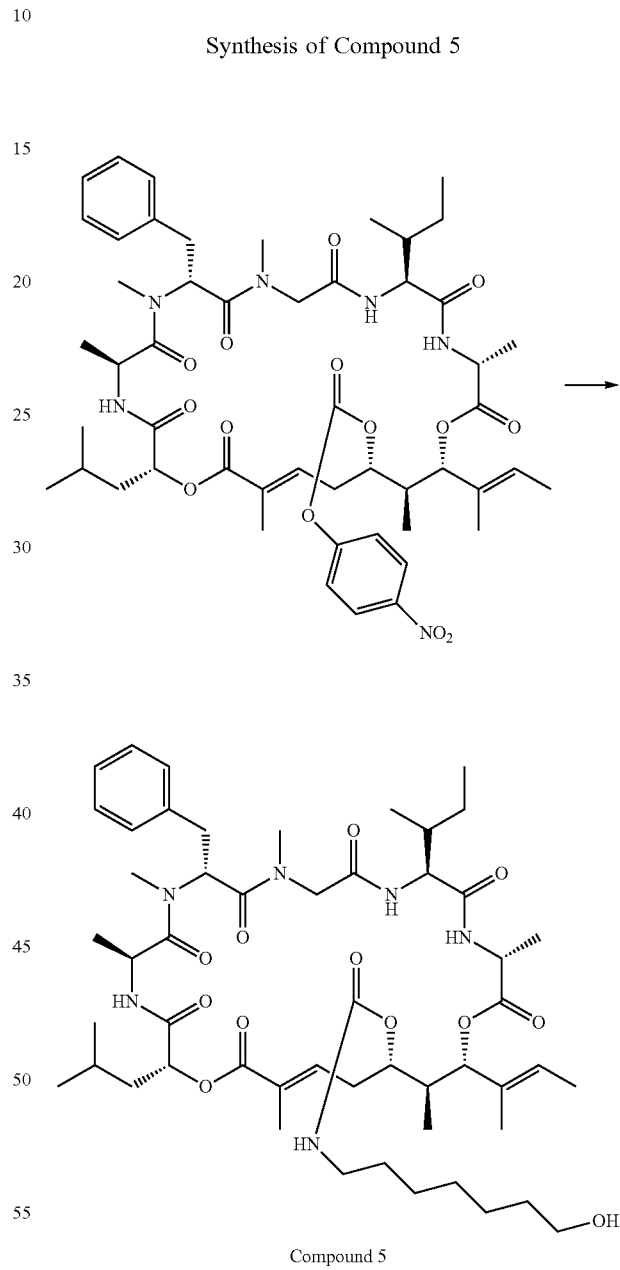

Compound 5

To the solution of (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl(4-nitrophenyl) carbonate (1.01 μmol, 1 mg) in DCM (1.554 mmol, 0.1 mL) was added 7-aminoheptan-1-ol (9.91 μmol, 1.3 mg) and Hünig's base (0.0103 mmol, 1.8

μL). The mixture was stirred overnight and the volatile was removed. The residue was purified with RP-flash to afford (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl(7-hydroxyheptyl) carbamate (0.6 mg, 60.5%). Observed (ESI) m/z: 983.6125 [M+H]+.

Example 7

Synthesis of Compound 6

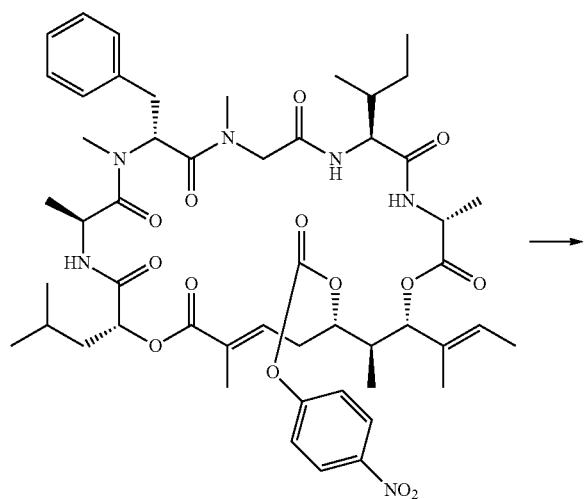

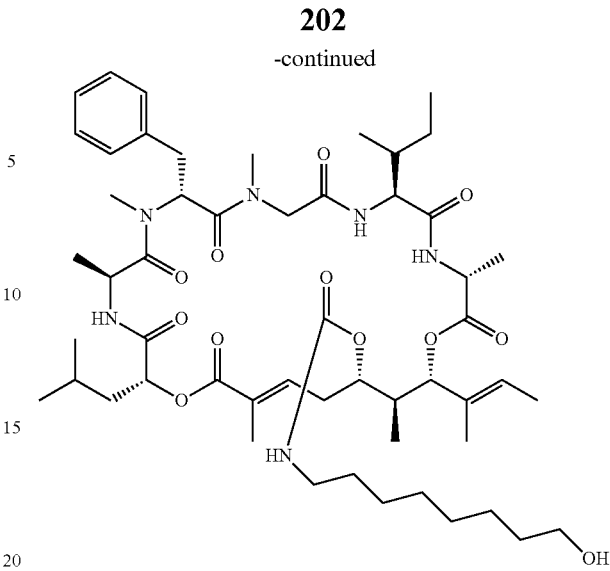

To the solution of (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (4-nitrophenyl) carbonate (1.009 μmol, 1 mg) in DCM (3.11 mmol, 0.2 mL) was added Hünig's base (0.0103 mmol, 1.8 μL) and 8-aminooctan-1-ol (0.0103 mmol, 1.5 mg). The mixture was stirred overnight, and the volatile was removed. The residue was purified with RP-flash to afford (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (8-hydroxyoctyl) carbamate (0.3 mg, 29.8%). Observed HRMS (ESI) m/z: 997.6288 [M+H]+.

Example 8

Synthesis of Compound 8

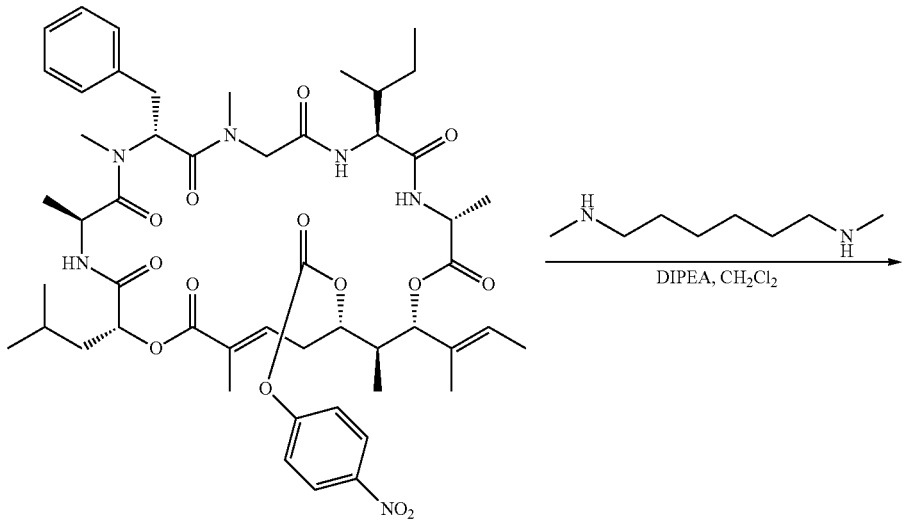

-continued

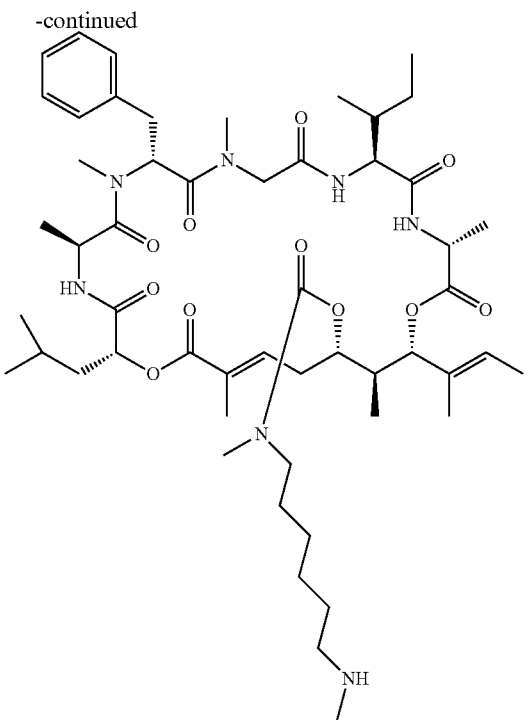

To a solution of (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl(4-nitrophenyl) carbonate (0.002 g, 2.018 µmol; Intermediate 1 from example 1) in DCM (4.66 mmol, 0.3 mL) was added N1,N6-dimethylhexane-1,6-diamine (1.455 mg, 0.010 mmol) and DIPEA (2.608 mg, 3.524 µL, 0.020 mmol) and stirred for 4 hours. The solvent was removed, and the residue was purified with reverse phase flash (MeCN+ 0.1% formic acid and H$_2$+0.1% formic acid) to afford (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl methyl(6-(methylamino)hexyl)carbamate (0.970 mg, 48.2% 0.974 µmol). Observed HRMS (ESI) m/z: 996.642 [M+H]+.

Example 9

Synthesis of Compound 9

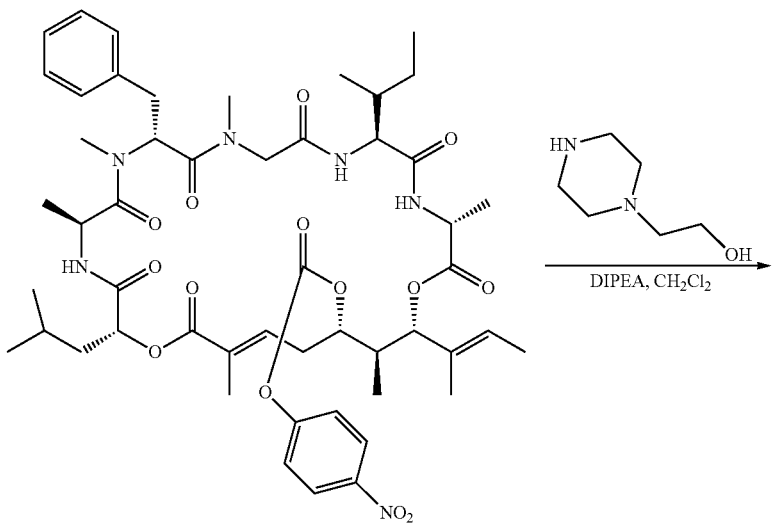

-continued

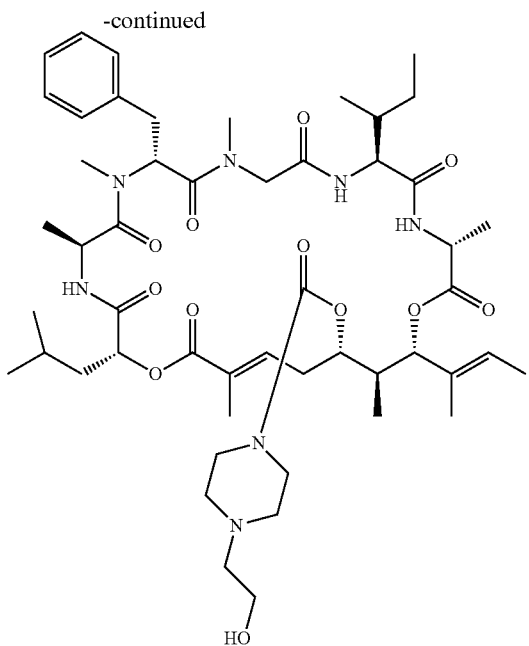

To a solution of (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl(4-nitrophenyl) carbonate (0.005 g, 5.04 µmol; Intermediate 1 from Example 1) in DCM (7.77 mmol, 0.5 mL) was added 2-(piperazin-1-yl)ethan-1-ol (6.567 mg, 6.190 µL, 0.050 mmol) and DIPEA (6.52 mg, 8.81 µL, 0.050 mmol) and stirred for 4 hours. The solvent was removed, and the residue was purified with reverse phase flash (MeCN+ 0.1% formic acid|H$_2$O+0.1% formic acid) to afford (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl-4-(2-hydroxyethyl)piperazine-1-carboxylate (4 mg, 4.07 µmol, 81%). Observed HRMS (ESI) m/z: 982.5882 [M+H]$^+$.

Example 10

Synthesis of Compound 10

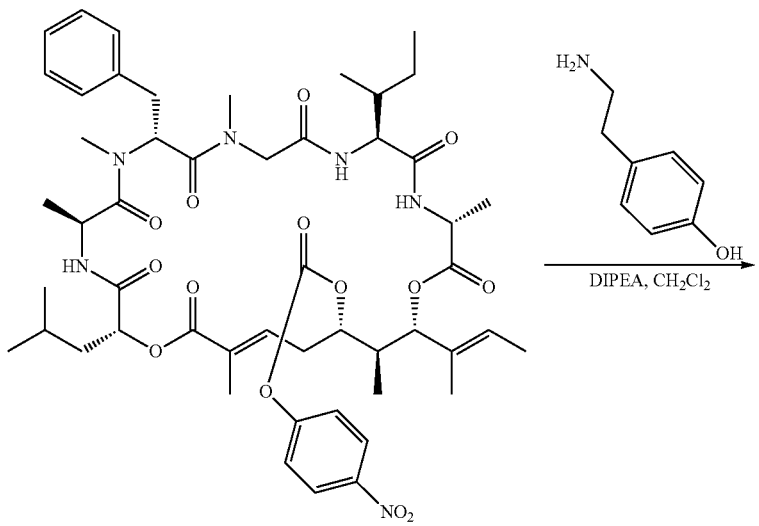

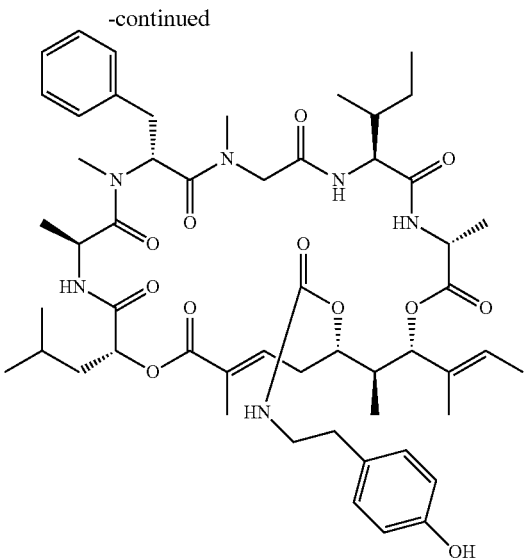

To a solution of (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (4-nitrophenyl) carbonate (5.0 mg, 5.044 μmol, 1.0 eq; Intermediate 1 from Example 1) in DCM (0.1 mL, 5.04 μmol) was added 4-(2-aminoethyl)phenol (3.460 mg, 0.025 mmol, 5.0 eq) and DIPEA (4.41 μL, 0.025 mmol, 5.0 eq) and stirred overnight. The reaction was monitored by reverse phase HPLC. The reaction mixture was concentrated on the rotavap and the crude residue obtained was purified by reverse phase flash chromatography (acetonitrile with 0.1% formic acid/H$_2$O with 0.1% formic acid) to afford (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (4-hydroxyphenethyl)carbamate (2.140 mg, 2.16 μmol, 42.9%). Observed HRMS (ESI) m/z: 989.5665 [M+H]$^+$.

Example 11

Synthesis of Compound 11

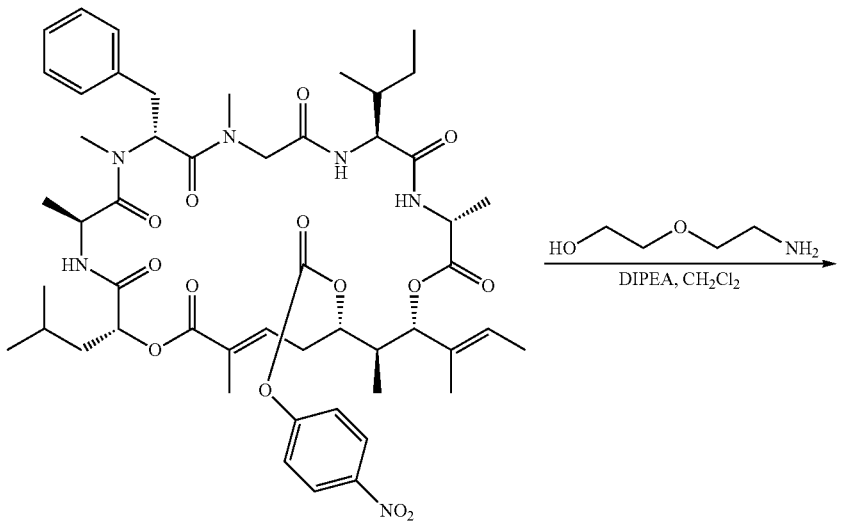

-continued

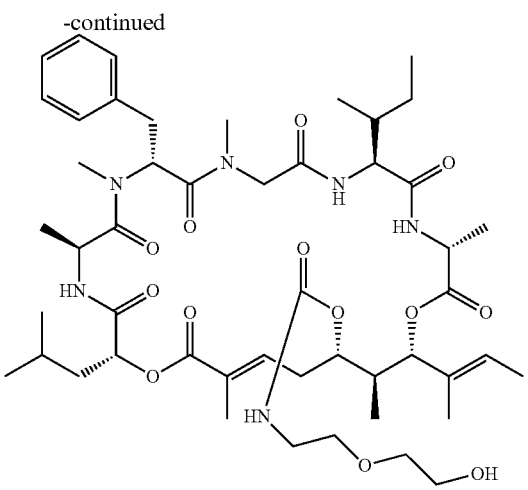

To a solution of (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (4-nitrophenyl) carbonate (5.0 mg, 5.044 μmol, 1.0 eq; Intermediate 1 from Example 1) in DCM (0.1 mL, 5.04 μmol) was added 2-(2-aminoethoxy)ethan-1-ol (5.3 mg, 0.050 mmol, 10.0 eq) and DIPEA (8.81 μL, 0.050 mmol, 10.0 eq) and stirred for 2 h. The reaction was monitored by reverse phase HPLC. The reaction mixture was concentrated on the rotavap and the crude residue obtained was purified by reverse phase flash chromatography (acetonitrile with 0.1% formic acid/H$_2$O with 0.1% formic acid) to afford (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (2-(2-hydroxyethoxy)ethyl)carbamate (3.25 mg, 3.40 μmol, 67.3%). Observed HRMS (ESI) m/z: 957.554 [M+H]$^+$.

Example 12

Synthesis of Compound 12

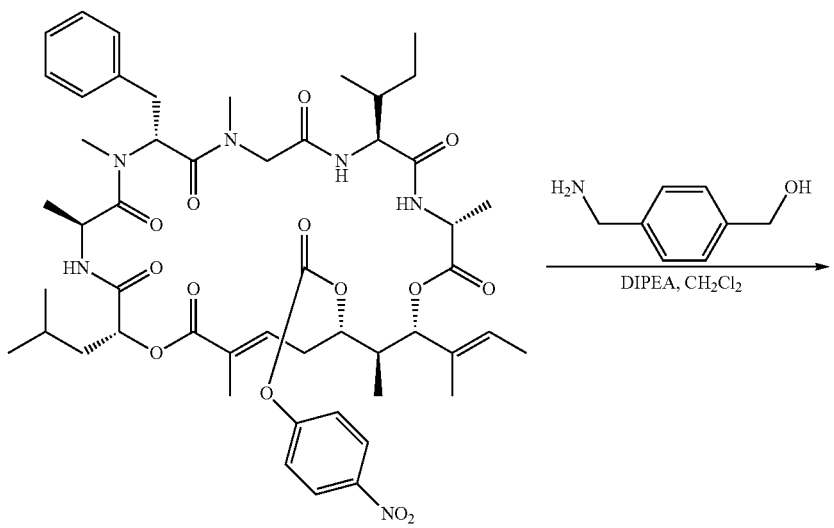

-continued

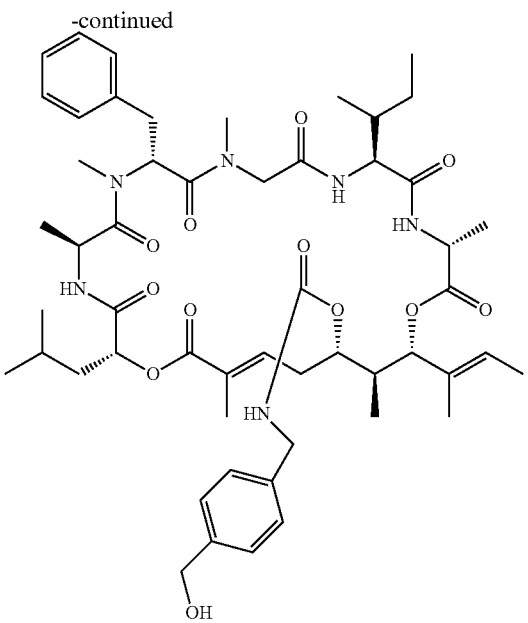

To a solution of (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl(4-nitrophenyl) carbonate (5.0 mg, 5.044 µmol, 1.0 eq; Intermediate 1 from Example 1) in DCM (0.1 mL, 5.04 µmol) was added (4-(aminomethyl)phenyl)methanol (3.46 mg, 0.025 mmol, 5.0 eq) and DIPEA (8.81 µL, 0.050 mmol, 10.0 eq) and stirred overnight. The reaction was monitored by reverse phase HPLC. The reaction mixture was concentrated on the rotavap and the crude residue obtained was purified by reverse phase flash chromatography (acetonitrile with 0.1% formic acid/H$_2$O with 0.1% formic acid) to afford (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (4-(hydroxymethyl)benzyl)carbamate (2.75 mg, 2.78 µmol, 55.1%). Observed HRMS (ESI) m/z: 989.565 [M+H]$^+$.

Example 13

Synthesis of Compound 13

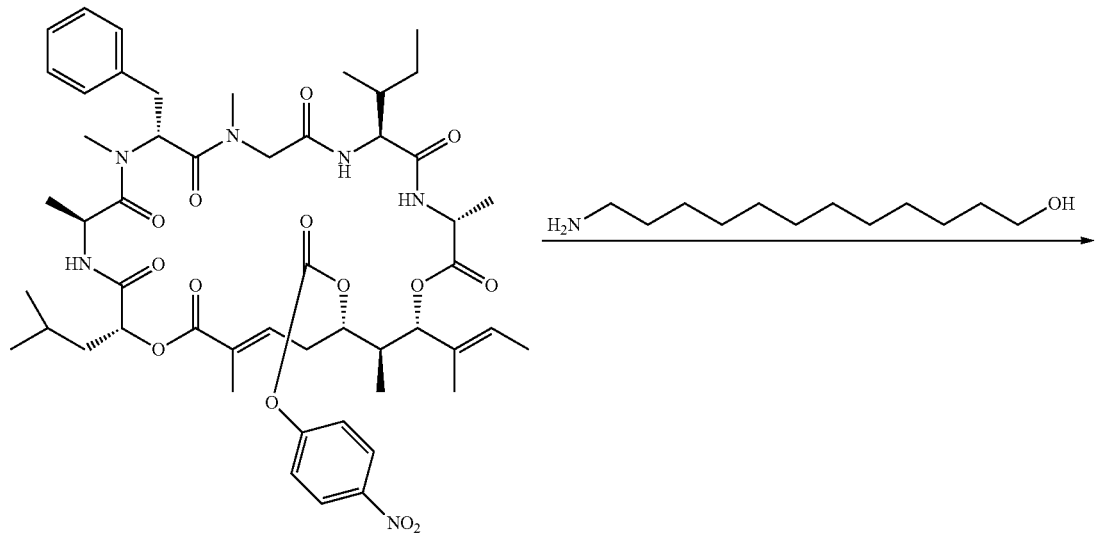

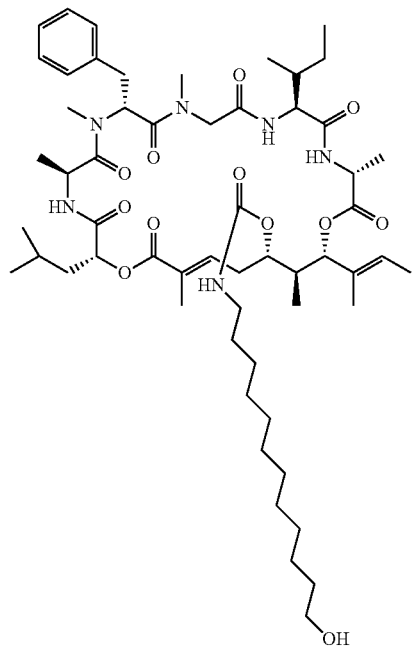

To a solution of (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (4-nitrophenyl) carbonate (0.007 g, 7.06 μmol; Intermediate 1 from Example 1) in DCM (10.88 mmol, 0.7 mL) was added 12-aminododecan-1-ol (0.014 g, 0.070 mmol) and DIPEA (9.13 mg, 12 μL, 0.071 mmol) and stirred for 5 hours. The solvent was removed and the residue was purified with reverse phase flash (MeCN+0.1% formic acid|H$_2$O+0.1% formic acid) to afford (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (12-hydroxydodecyl) carbamate (0.004 g, 53.8%, 7.06 μmol). Observed HRMS (ESI) m/z: 1053.6864 [M+H]$^+$.

Example 14

Synthesis of Compound 15

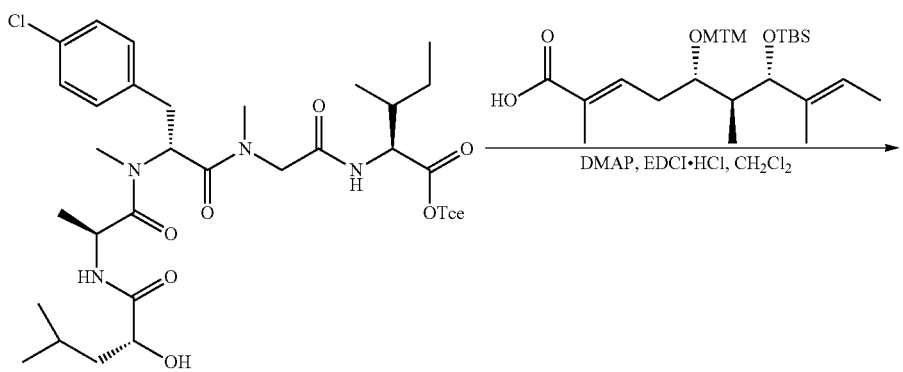

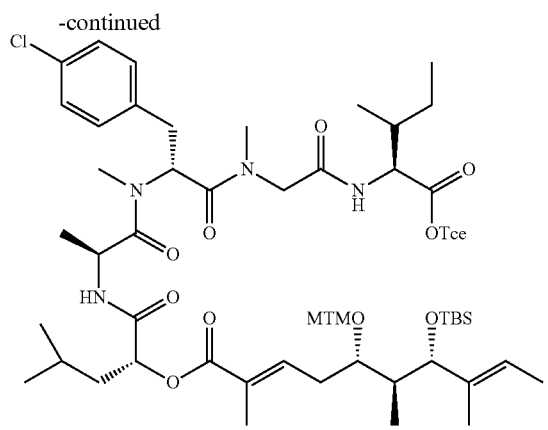

Step 1: To the solution of (2E,5S,6S,7S,8E)-7-((tert-butyldimethylsilyl)oxy)-2,6,8-trimethyl-5-((methylthio)methoxy)deca-2,8-dienoic acid (100 mg, 0.239 mmol), 2,2,2-trichloroethyl N—((R)-3-(4-chlorophenyl)-2-((S)-2-((R)-2-hydroxy-4-methylpentanamido)-N-methylpropanamido)propanoyl)-N-methylglycyl-L-alloisoleucinate (0.205 g, 0.287 mmol), DMAP (0.029 g, 0.239 mmol) in DCM (1.32 g, 1 mL, 15.542 mmol) was added EDC (0.115 g, 0.599 mmol) at 0° C. The mixture was warmed up to rt and stirred overnight. After the completion of the reaction, the solution was diluted with citric acid solution and EtOAc. The organic phase was washed with NaHCO₃ aq and brine, dried over Na₂SO₄ and concentrated in vacuo. The residue was purified with flash to afford 2,2,2-trichloroethyl (2S,8R,11S,14R)-2-((R)-sec-butyl)-14-(((2E,5S,6S,7S,8E)-7-((tert-butyldimethylsilyl)oxy)-2,6,8-trimethyl-5-((methylthio)methoxy)deca-2,8-dienoyl)oxy)-8-(4-chlorobenzyl)-6,9,11,16-tetramethyl-4,7,10,13-tetraoxo-3,6,9,12-tetraazaheptadecanoate (0.192 g, 71.91%).

butyldimethylsilyl)oxy)-2,6,8-trimethyl-5-((methylthio)methoxy)deca-2,8-dienoyl)oxy)-8-(4-chlorobenzyl)-6,9,11,16-tetramethyl-4,7,10,13-tetraoxo-3,6,9,12-tetraazaheptadecanoate (0.192 g, 0.172 mmol) in 0.05M solution (3.46 mL) of 1:1:6 (HF pyridine, pyridine, THF) was stirred at 60° C. for 12 h. After the completion of the reaction through TLC, the mixture was diluted with EtOAc and NaHCO₃ aq. The organic phase was washed with brine, dried over Na₂SO₄ and concentrated in vacuo. The residue was purified with flash to afford 2,2,2-trichloroethyl (2S,8R,11S,14R)-2-((R)-sec-butyl)-8-(4-chlorobenzyl)-14-(((2E,5S,6R,7S,8E)-7-hydroxy-2,6,8-trimethyl-5-((methylthio)methoxy)deca-2,8-dienoyl)oxy)-6,9,11,16-tetramethyl-4,7,10,13-tetraoxo-3,6,9,12-tetraazaheptadecanoate (148 mg, 85.86%).

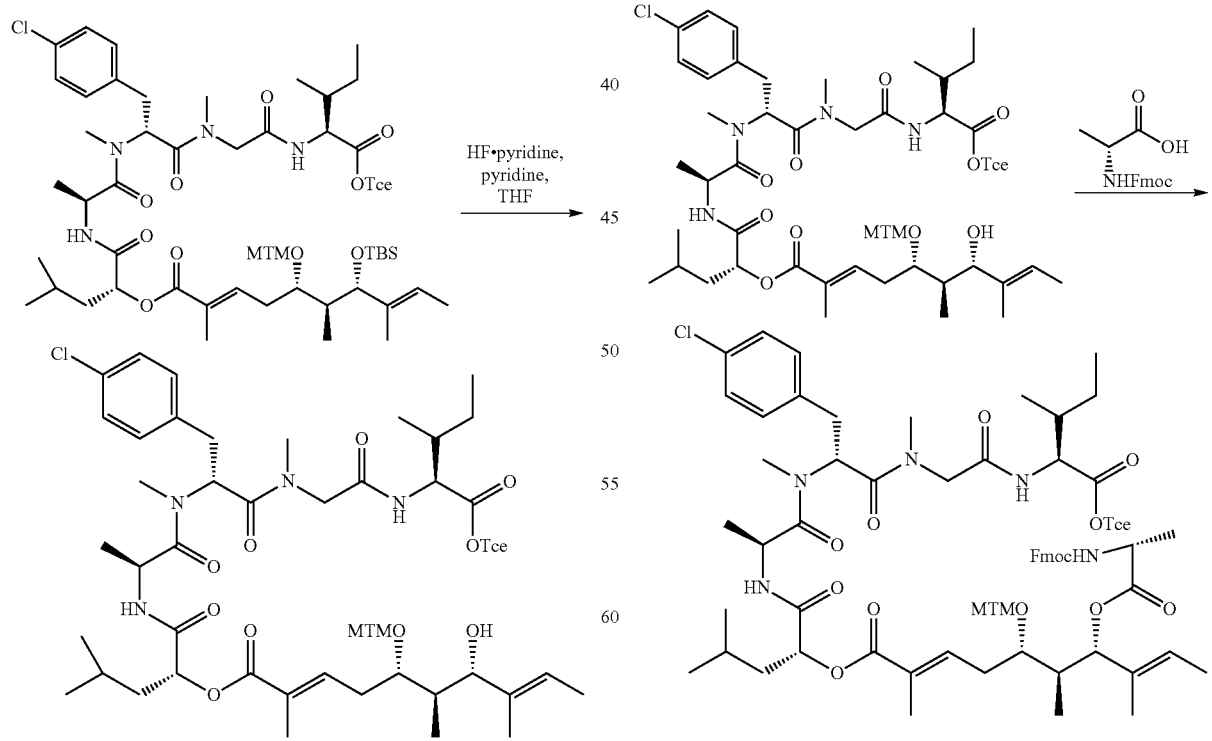

Step 2: To a solution of 2,2,2-trichloroethyl (2S,8R,11S,14R)-2-((R)-sec-butyl) 14-(((2E,5S,6S,7S,8E)-7-((tert- Step 3: To the solution of (((9H-fluoren-9-yl)methoxy)carbonyl)-D-alanine (0.763 g, 2.453 mmol), 2,2,2-trichloroethyl (2S,8R,11S,14R)-2-((R)-sec-butyl)-8-(4-chlorobenzyl)-14-(((2E,5S,6R,7S,8E)-7-hydroxy-2,6,8-trimethyl-5-((methylthio)methoxy)deca-2,8-dienoyl)oxy)-6,9,11,16-tetramethyl-4,7,10,13-tetraoxo-3,6,9,12-tetraazaheptadecanoate (817 mg, 0.817 mmol) and DMAP (0.099 g, 0.817 mmol) in DCM (4.224 g, 3.2 mL, 49.736 mmol) was added EDC (0.470 g, 2.453 mmol) at 0° C. After stirring at 0° C. for 3 h, the mixture was warmed to rt and stirred overnight, diluted with EtOAc and citric acid solution. The organic phase was washed with NaHCO₃ and brine, dried over Na₂SO₄ and concentrated in vacuo. The residue was purified with flash to afford 2,2,2-trichloroethyl (2S,8R,11S,14R)-14-(((2E,5S,6S,7S,8E)-7-(((((9H-fluoren-9-yl)methoxy)carbonyl)-D-alanyl)oxy)-2,6,8-trimethyl-5-((methylthio)methoxy)deca-2,8-dienoyl)oxy)-2-((R)-sec-butyl)-8-(4-chlorobenzyl)-6,9,11,16-tetramethyl-4,7,10,13-tetraoxo-3,6,9,12-tetraazaheptadecanoate (1 g, 94.62%) with some Fmoc ala impurity.

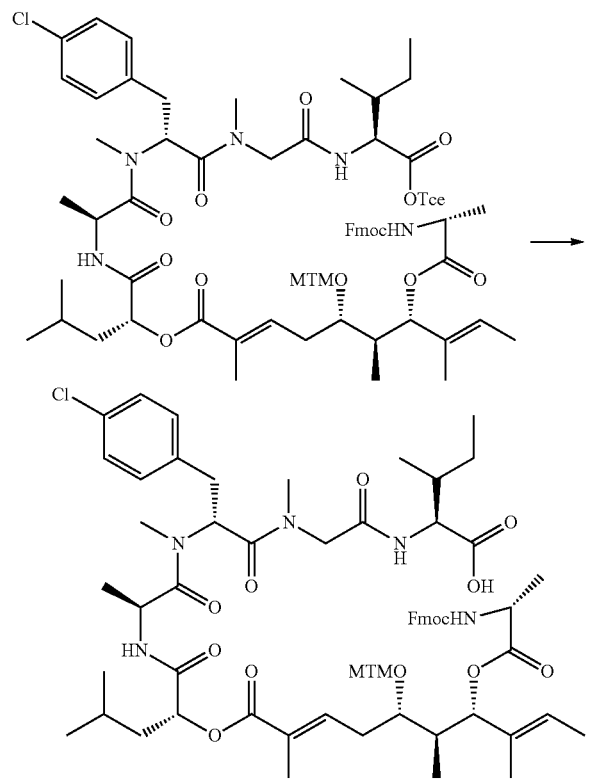

Step 4: To the solution of 2,2,2-trichloroethyl (2S,8R,11S,14R)-14-(((2E,5S,6S,7S,8E)-7-(((((9H-fluoren-9-yl)methoxy)carbonyl)-D-alanyl)oxy)-2,6,8-trimethyl-5-((methylthio)methoxy)deca-2,8-dienoyl)oxy)-2-((R)-sec-butyl)-8-(4-chlorobenzyl)-6,9,11,16-tetramethyl-4,7,10,13-tetraoxo-3,6,9,12-tetraazaheptadecanoate (1 g, 0.773 mmol) in THF (17.6 g, 20 mL, 244.081 mmol) and ammonium acetate (0.308 g, 4 mL, 4 mmol) was added zinc (5 g, 76.475 mmol) at rt. The mixture was stirred for 6 h. The mixture was added citric acid solution and filtered over celite (EtOAc). The aq phase was extracted with EtOAc and the organic phase was washed with brine, dried over Na₂SO₄ and concentrated in vacuo to use in next step.

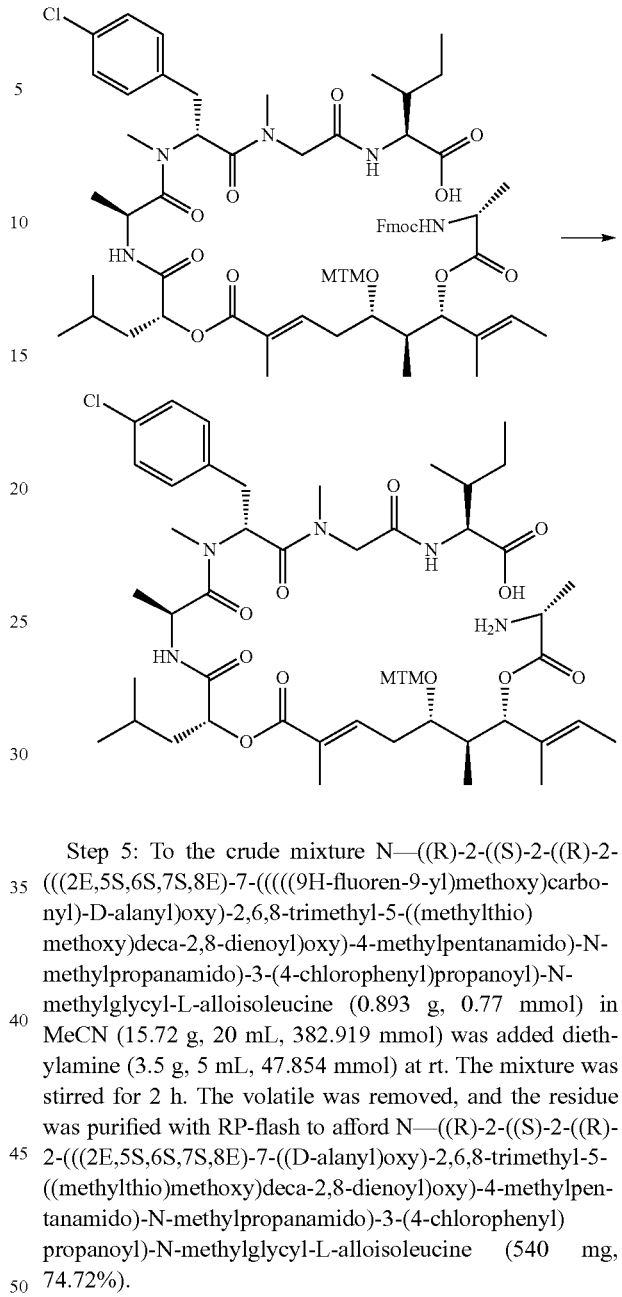

Step 5: To the crude mixture N—((R)-2-((S)-2-((R)-2-(((2E,5S,6S,7S,8E)-7-(((((9H-fluoren-9-yl)methoxy)carbonyl)-D-alanyl)oxy)-2,6,8-trimethyl-5-((methylthio)methoxy)deca-2,8-dienoyl)oxy)-4-methylpentanamido)-N-methylpropanamido)-3-(4-chlorophenyl)propanoyl)-N-methylglycyl-L-alloisoleucine (0.893 g, 0.77 mmol) in MeCN (15.72 g, 20 mL, 382.919 mmol) was added diethylamine (3.5 g, 5 mL, 47.854 mmol) at rt. The mixture was stirred for 2 h. The volatile was removed, and the residue was purified with RP-flash to afford N—((R)-2-((S)-2-((R)-2-(((2E,5S,6S,7S,8E)-7-((D-alanyl)oxy)-2,6,8-trimethyl-5-((methylthio)methoxy)deca-2,8-dienoyl)oxy)-4-methylpentanamido)-N-methylpropanamido)-3-(4-chlorophenyl)propanoyl)-N-methylglycyl-L-alloisoleucine (540 mg, 74.72%).

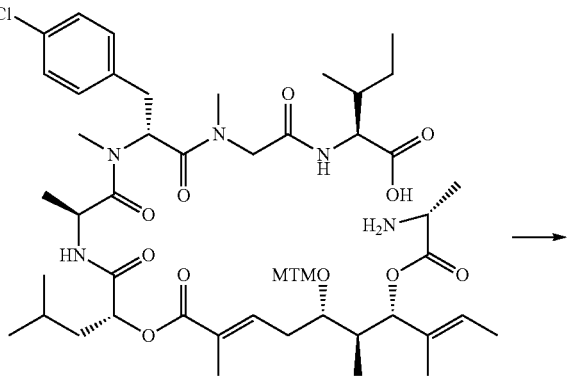

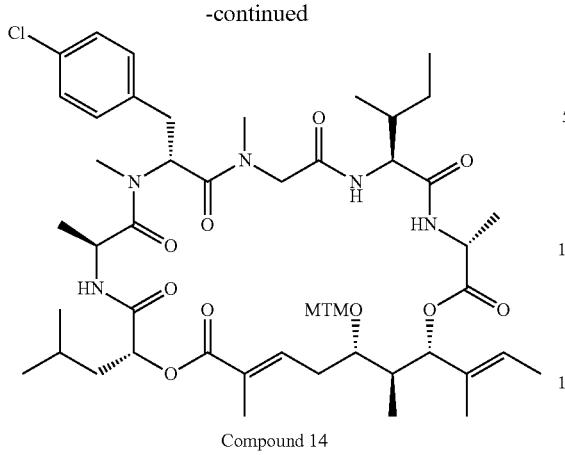

Compound 14

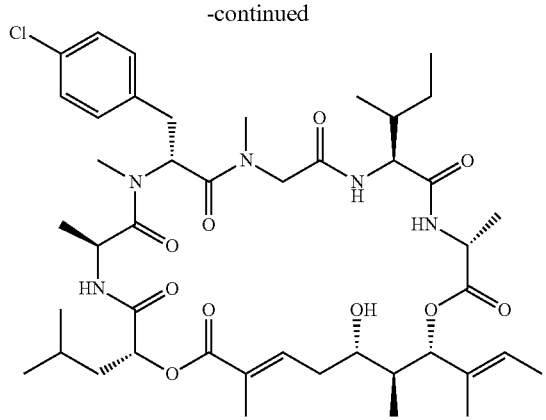

Compound 15

Figure 7:
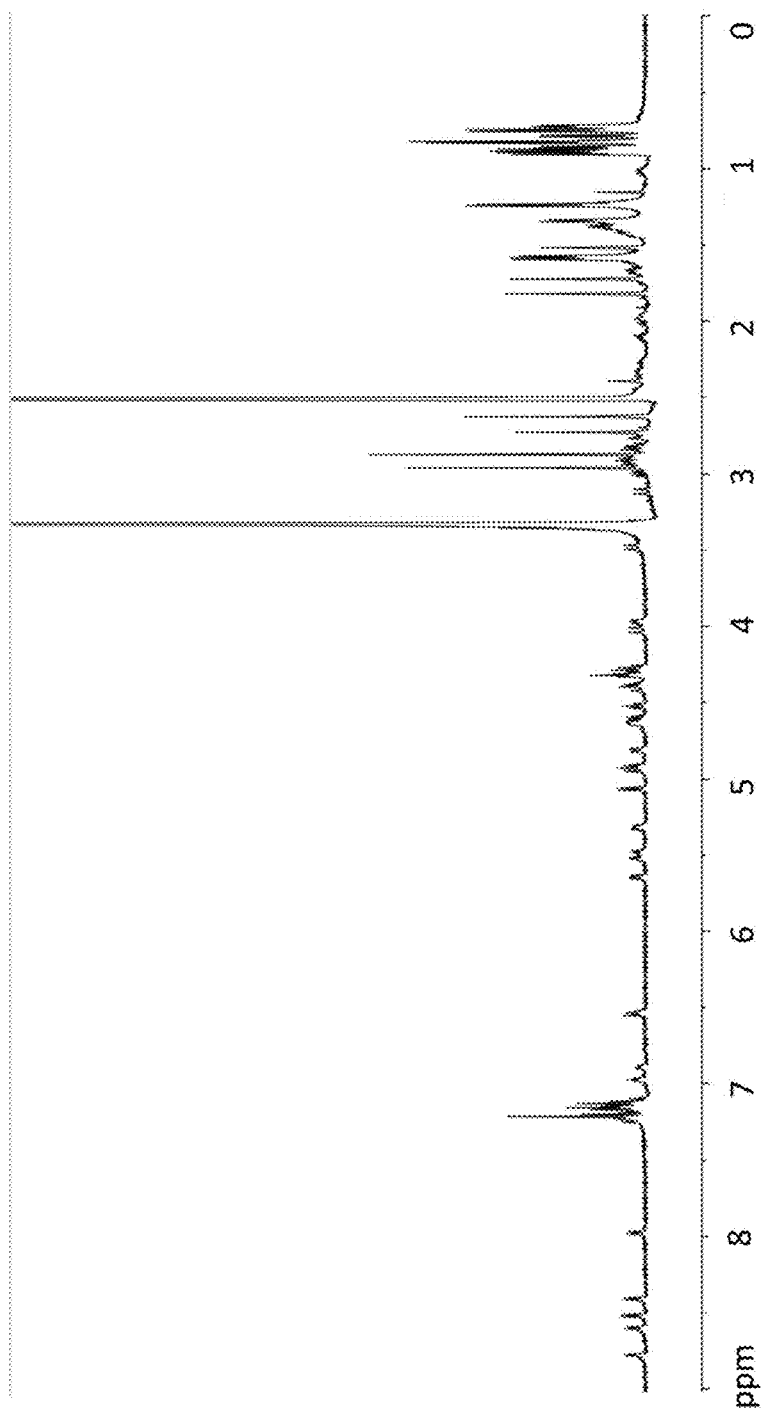
FIG. 7 is a $^1$H NMR spectrum of Compound 14 in DMSO-d6.

Step 6: To the solution of N—((R)-2-((S)-2-((R)-2-(((2E,5S,6S,7S,8E)-7-((D-alanyl)oxy)-2,6,8-trimethyl-5-((methylthio)methoxy)deca-2,8-dienoyl)oxy)-4-methylpentanamido)-N-methylpropanamido)-3-(4-chlorophenyl)propanoyl)-N-methylglycyl-L-alloisoleucine (0.54 g, 0.575 mmol) in DCM (1.188 kg, 900 mL, 13.988 mol) and DMF (94.399 g, 100 mL, 1.291 mol) was added HOAt (0.783 g, 5.753 mmol) and EDC (1.102 g, 5.753 mmol) at 0° C. The mixture was warmed up to rt slowly and stirred overnight. The solvent was removed and diluted with EtOAc and citric acid solution. The organic phase was washed with NaHCO$_3$ aq and brine, dried over Na$_2$SO$_4$, concentrated in vacuo. The residue was purified with flash to afford (3R,6S,12R,15S,18R,24S,25S,26S,E)-26-((E)-but-2-en-2-yl)-6-((R)-sec-butyl)-12-(4-chlorobenzyl)-18-isobutyl-3,10,13,15,21,25-hexamethyl-24-((methylthio)methoxy)-1,19-dioxa-4,7,10,13,16-pentaazacyclohexacos-21-ene-2,5,8,11,14,17,20-heptaone (365 mg, 68.92%). Observed HRMS (ESI) m/z: 920.4605 [M+H]$^+$. The $^1$H NMR spectrum of Chloro-Kulo2-OMTM in DMSO-d6 is shown in FIG. 7.

Step 7: To the solution of (3R,6S,12R,15S,18R,24S,25S,26S,E)-26-((E)-but-2-en-2-yl)-6-((R)-sec-butyl)-12-(4-chlorobenzyl)-18-isobutyl-3,10,13,15,21,25-hexamethyl-24-((methylthio)methoxy)-1,19-dioxa-4,7,10,13,16-pentaazacyclohexacos-21-ene-2,5,8,11,14,17,20-heptaone (0.368 g, 0.4 mmol) in THF (8.447 g, 9.6 mL, 117.159 mmol) and water (2.4 g, 2.4 ml, 133.222 mmol) was added 2,6-lutidine (0.857 g, 0.931 mL, 8 mmol) and silver nitrate (2.717 g, 16 mmol). The mixture was heated at 65° C. overnight. The mixture was cooled to rt and diluted with EtOAc and 1N HCl, then filtered over celite. The aqueous phase was extracted with EtOAc and the organic phase was washed with NaHCO$_3$ aq and brine, dried over NaSO4 and concentrated and in vacuo. The residue was purified with rp-flash to afford (3R,6S,12R,15S,18R,24S,25S,26S,E)-26-((E)-but-2-en-2-yl)-6-((R)-sec-butyl)-12-(4-chlorobenzyl)-24-hydroxy-18-isobutyl-3,10,13,15,21,25-hexamethyl-1,19-dioxa-4,7,10,13,16-pentaazacyclohexacos-21-ene-2,5,8,11,14,17,20-heptaone (257 mg, 74.67%).

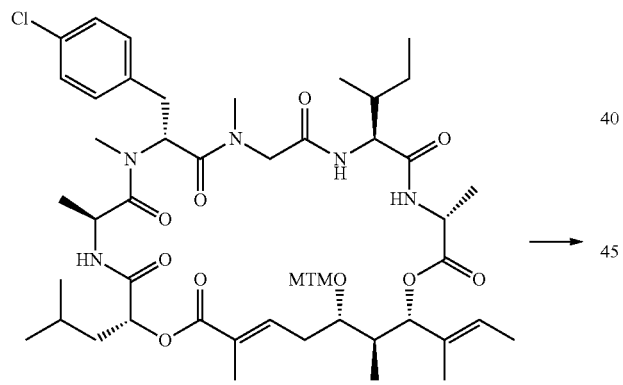

Example 15

Synthesis of intermediate 2

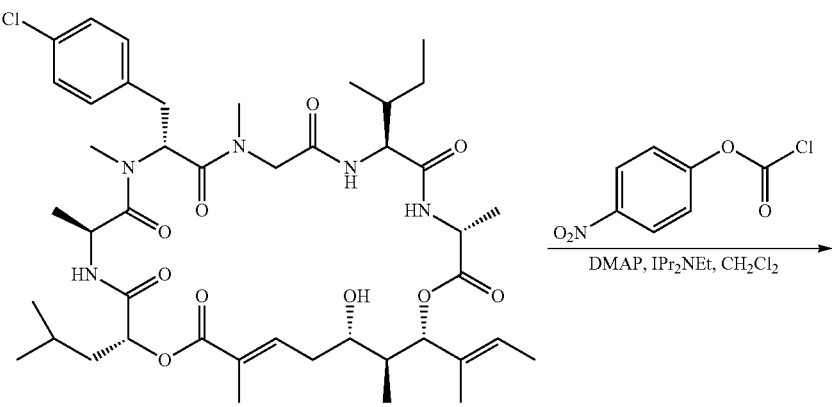

-continued

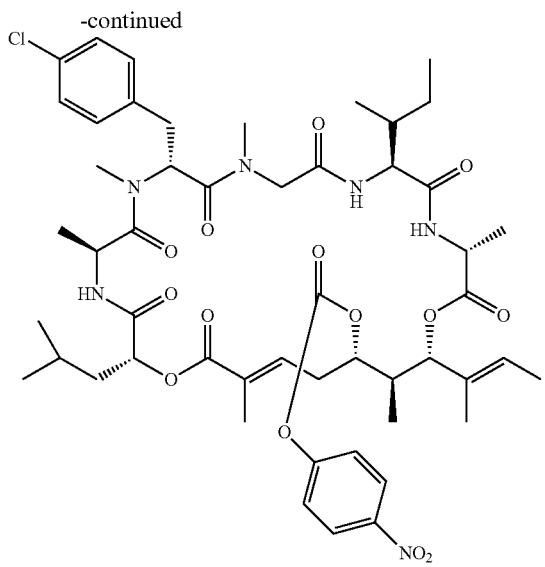

Intermediate 2

To a solution of (3R,6S,12R,15S,18R,24S,25S,26S,E)-26-((E)-but-2-en-2-yl)-6-((R)-sec-butyl)-12-(4-chlorobenzyl)-24-hydroxy-18-isobutyl-3,10,13,15,21,25-hexamethyl-1,19-dioxa-4,7,10,13,16-pentaazacyclohexacos-21-ene-2,5,8,11,14,17,20-heptaone (0.13 g, 0.151 mmol) in DCM (1 mL, 15.54 mmol) was added DMAP (0.018 g, 0.151 mmol), DIPEA (0.976 g, 1.319 mL, 7.553 mmol) and 4-nitrophenyl carbonochloridate (0.305 g, 1.511 mmol). The reaction was stirred for 6 h and diluted with EtOAc and citric acid solution. The organic phase was washed with NaHCO$_3$ aq and brine, dried over Na$_2$SO$_4$, concentrated in vacuo. The residue was purified with flash to afford (2R,5S,8R,14S,17R,20S,21S,22S,E)-20-((E)-but-2-en-2-yl)-14-((R)-sec-butyl)-8-(4-chlorobenzyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (4-nitrophenyl) carbonate (0.11 g, 71%, 0.107 mmol).

Example 16

Synthesis of Compound 16

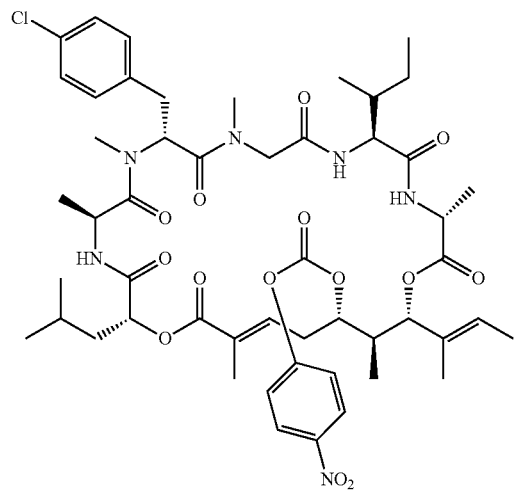

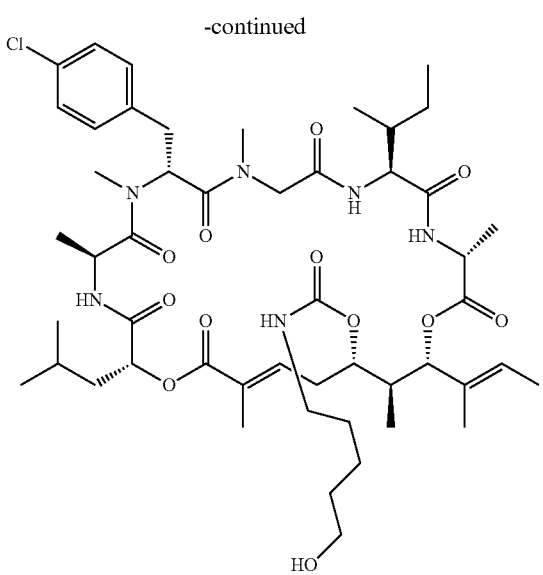

Figure 8:
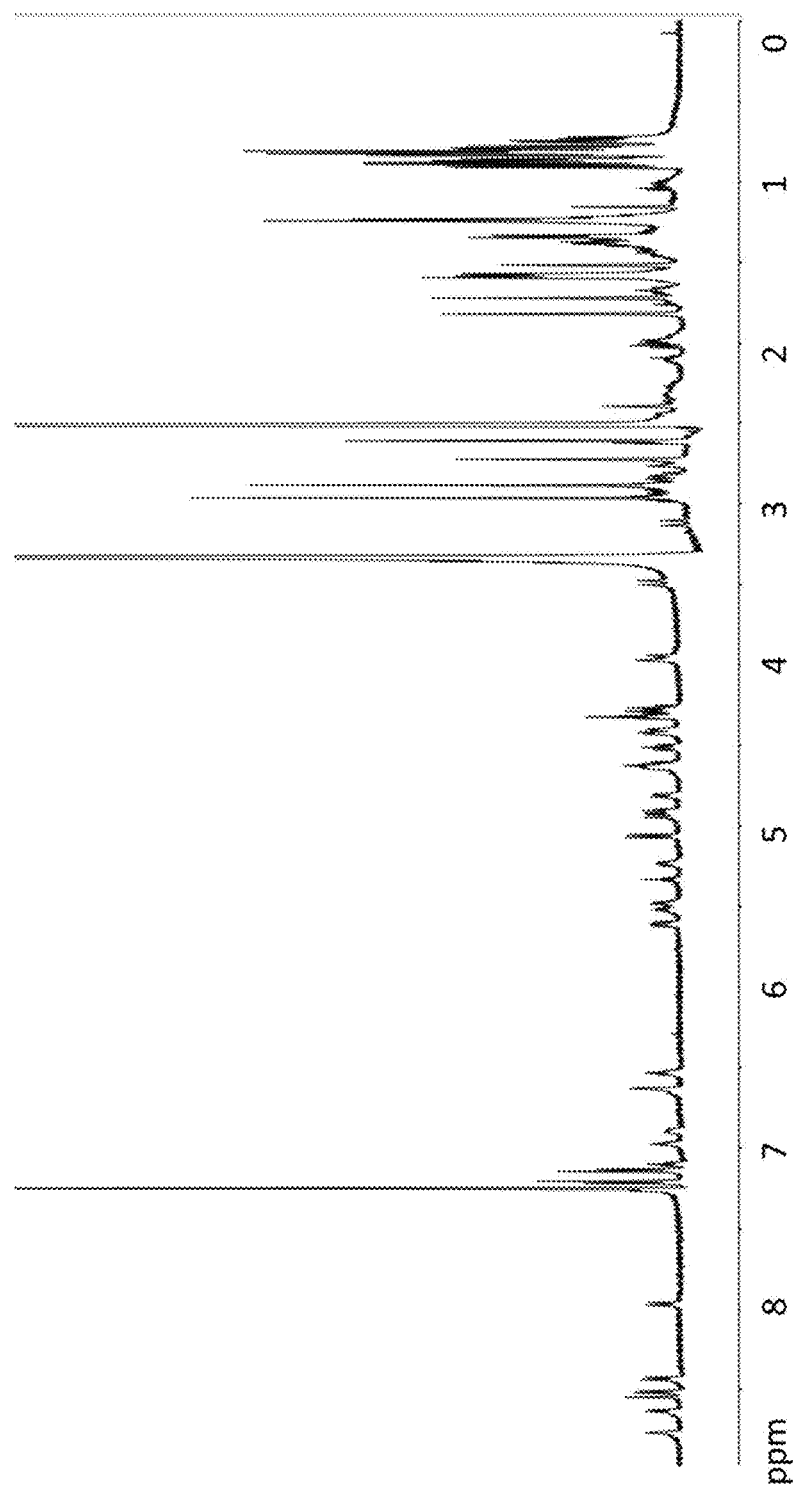
FIG. 8 is a $^1$H NMR spectrum of Compound 16 in DMSO-d6.

To the solution of (2R,5S,8R,14S,17R,20S,21S,22S,E)-20-((E)-but-2-en-2-yl)-14-((R)-sec-butyl)-8-(4-chlorobenzyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (4-nitrophenyl) carbonate (59 mg, 0.060 mmol) in DCM (6.600 g, 5 mL, 77.713 mmol) was added 5-aminopentan-1-ol (50 mg, 0.484 mmol) and Hunig's base (0.148 g, 0.2 mL, 1.145 mmol) at rt and the mixture was stirred overnight. The volatile was removed and the residue was purified with RP-flash to afford (2R,5S,8R,14S,17R,20S,21S,22S,E)-20-((E)-but-2-en-2-yl)-14-((R)-sec-butyl)-8-(4-chlorobenzyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (5-hydroxypentyl)carbamate (52 mg, 91.45%). Observed HRMS (ESI) m/z: 989.5447 [M+H]$^+$. The $^1$H NMR spectrum of Compound 16 in DMSO-d is shown in FIG. 8.

Example 17

Synthesis of Compound 17

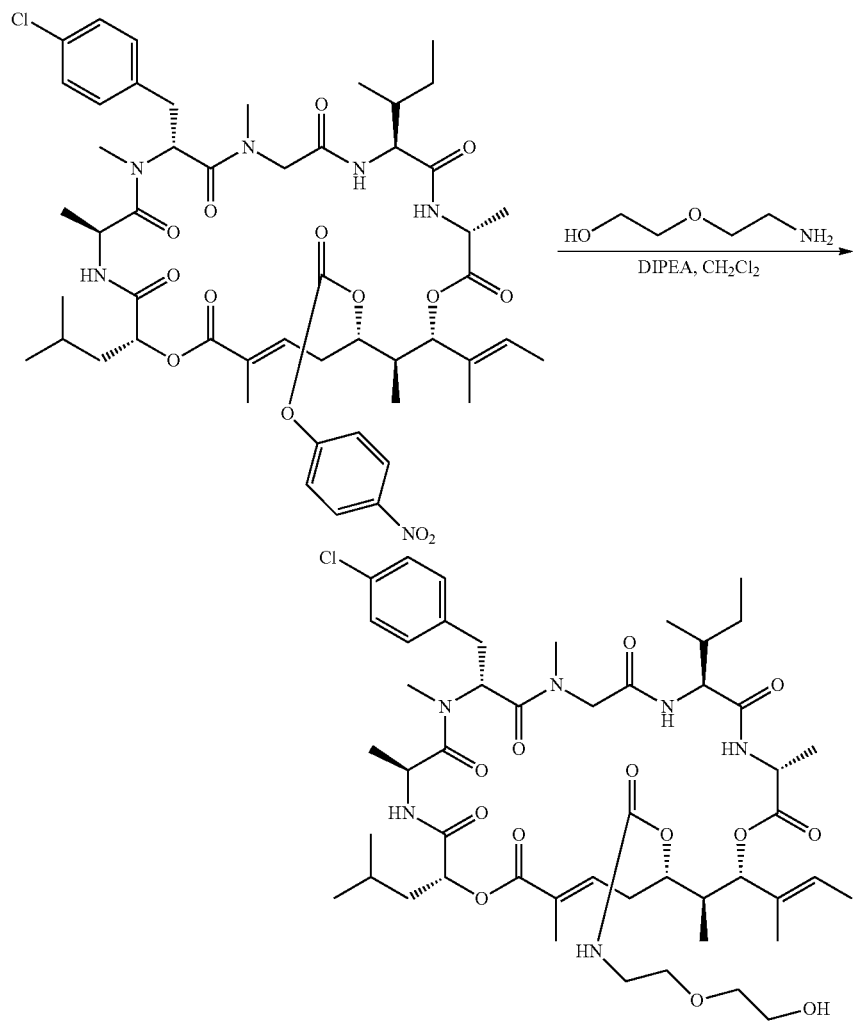

To a solution of (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl(4-nitrophenyl) carbonate (3.0 mg, 2.93 μmol, 1.0 eq; Intermediate 2) in DCM (0.1 mL, 5.04 μmol) was added 2-(2-aminoethoxy)ethan-1-ol (3.08 mg, 0.029 mmol, 10.0 eq) and DIPEA (5.11 μL, 0.029 mmol, 10.0 eq) and stirred for 4 h. The reaction was monitored by reverse phase HPLC. The reaction mixture was concentrated on the rotavap and the crude residue obtained was purified by reverse phase flash chromatography (acetonitrile with 0.1% formic acid/H$_2$O with 0.1% formic acid) to afford (2R,5S,8R,14S,17R,20S,21S,22S,E)-20-((E)-but-2-en-2-yl)-14-((R)-sec-butyl)-8-(4-chlorobenzyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (2-(2-hydroxyethoxy)ethyl)carbamate (1.72 mg, 1.735 μmol, 59.3%). Observed HRMS (ESI) m/z: 991.518 [M+H]$^+$.

Example 18

Synthesis of Compound 18

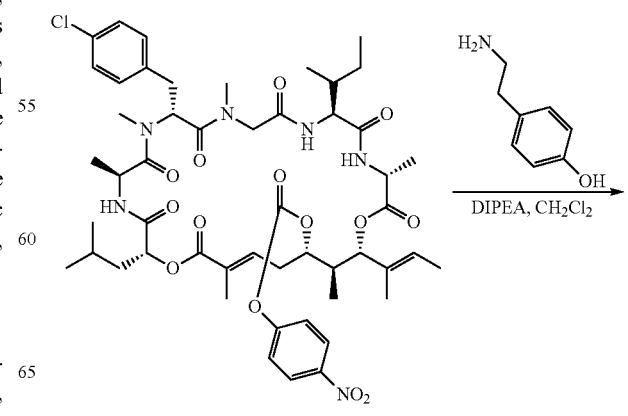

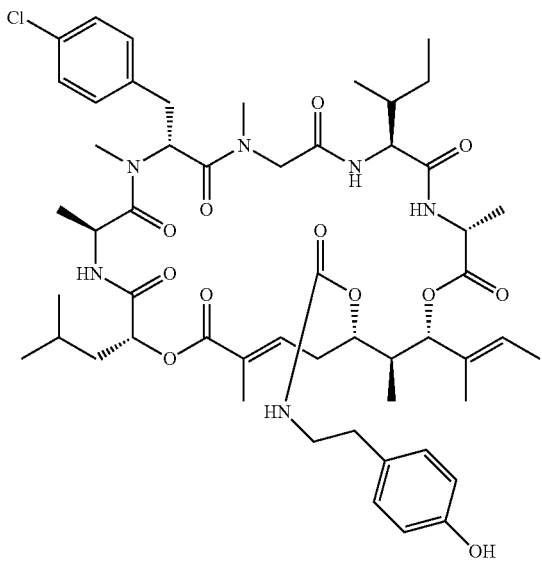

To a solution of (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl(4-nitrophenyl) carbonate (3.0 mg, 2.93 µmol, 1.0 eq) in DCM (0.1 mL, 5.04 µmol; Intermediate 2) was added 4-(2-aminoethyl)phenol (4.01 mg, 0.029 mmol, 10.0 eq) and DIPEA (5.11 µL, 0.029 mmol, 10.0 eq) and stirred overnight. The reaction was monitored by reverse phase HPLC. The reaction mixture was concentrated on the rotavap and the crude residue obtained was purified by reverse phase flash chromatography (acetonitrile with 0.1% formic acid/H₂O with 0.1% formic acid) to afford (2R,5S,8R,14S,17R,20S,21S,22S,E)-20-((E)-but-2-en-2-yl)-14-((R)-sec-butyl)-8-(4-chlorobenzyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (4-hydroxyphenethyl)carbamate (1.64 mg, 1.602 µmol, 54.8%). Observed HRMS (ESI) m/z: 1023.523 [M+H]⁺.

Example 19

Synthesis of Compound 19

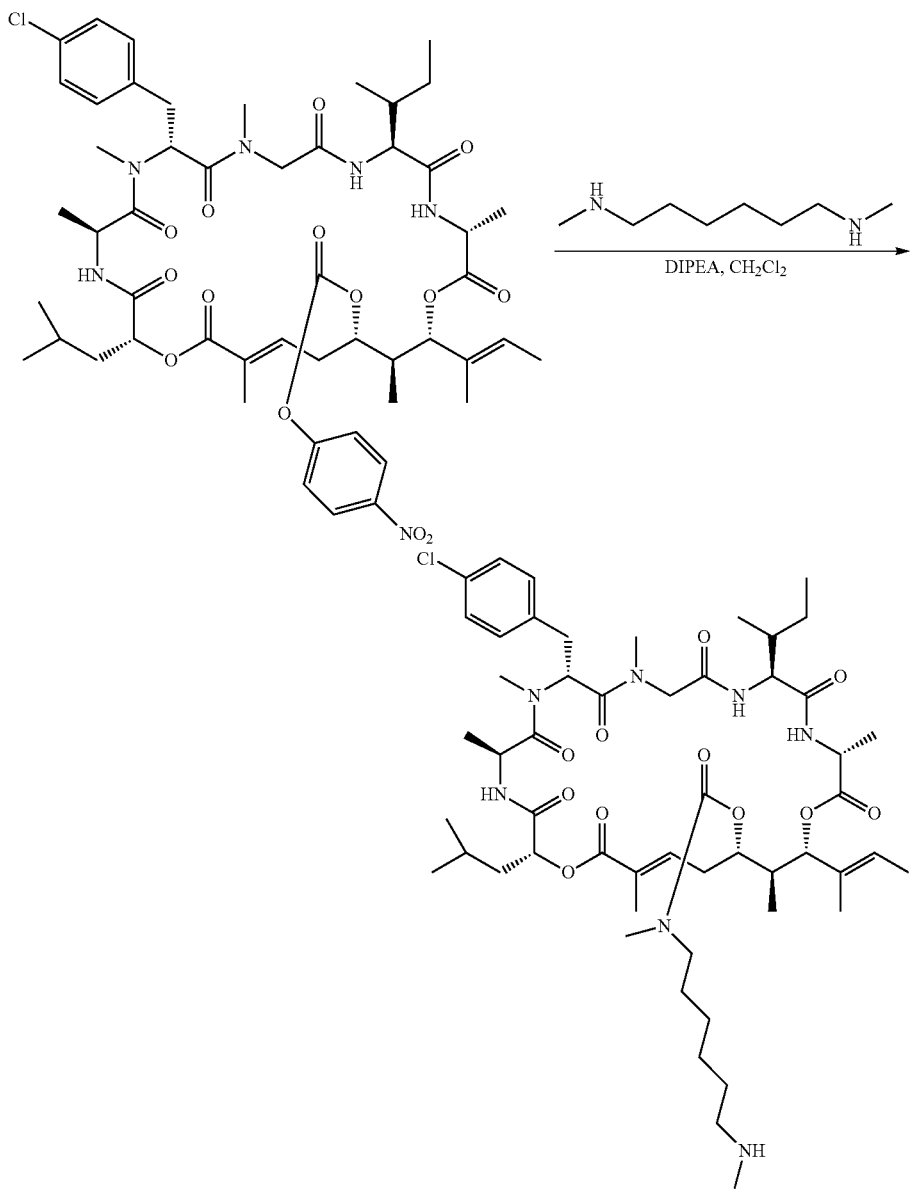

To a solution of ((2R,5S,8R,14S,17R,20S,21S,22S,E)-20-((E)-but-2-en-2-yl)-14-((R)-sec-butyl)-8-(4-chlorobenzyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl(4-nitrophenyl) carbonate (0.0035 g, 3.41 µmol) in DCM (4.66 mmol, 0.3 mL) was added N1,N6-dimethyl-hexane-1,6-diamine (4.923 mg, 0.034 mmol) and DIPEA (4.410 mg, 5.960 µL, 0.034 mmol) and stirred for 3 hours. The solvent was removed and the residue was purified with C18 reverse chromatography (MeCN+0.1% formic acid|H$_2$O+0.1% formic acid) to afford (2R,5S,8R,14S,17R,20S,21S,22S,E)-20-((E)-but-2-en-2-yl)-14-((R)-sec-butyl)-8-(4-chlorobenzyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl methyl (6-(methylamino)hexyl)carbamate (0.002 g, 57%, 3.41 µmol). Observed HRMS (ESI) m/z: 1030.6007 [M+H]$^+$.

Example 20

Synthesis of Compound 20

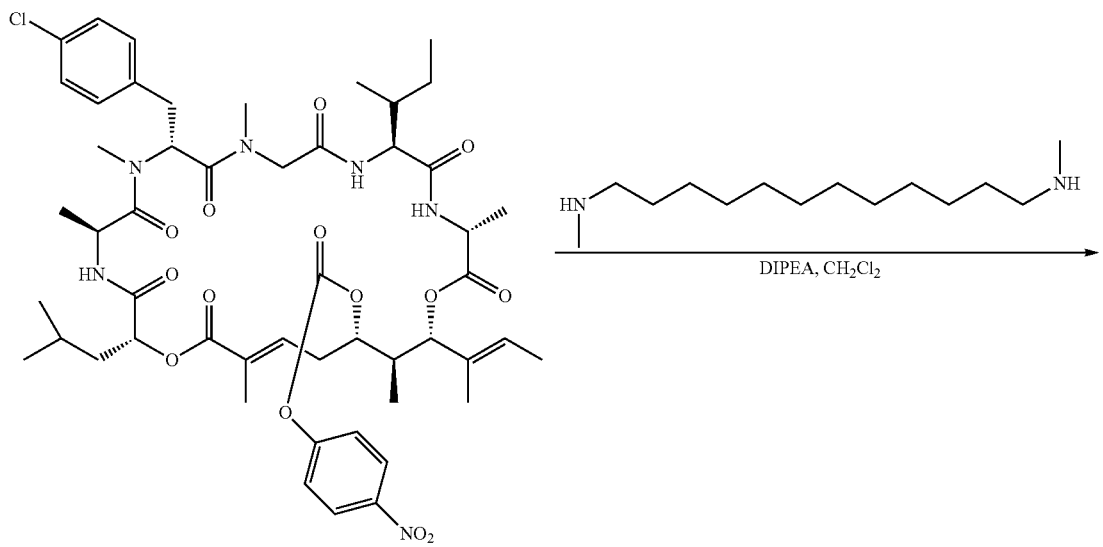

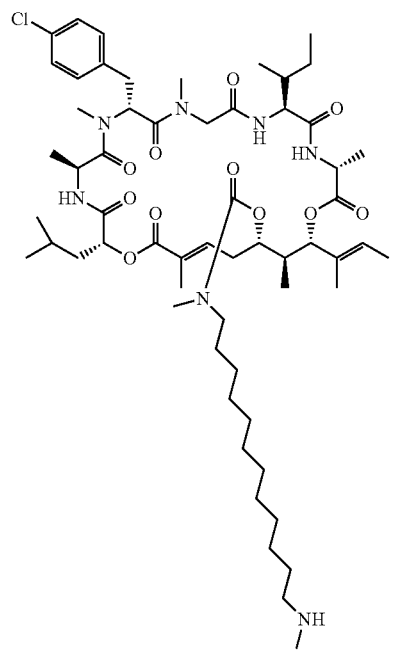

To a solution of ((2R,5S,8R,14S,17R,20S,21S,22S,E)-20-((E)-but-2-en-2-yl)-14-((R)-sec-butyl)-8-(4-chlorobenzyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (4-nitrophenyl) carbonate (0.003 g, 2.93 μmol; Intermediate 2) in DCM (4.66 mmol, 0.3 mL) was added N1,N12-dimethyldodecane-1,12-diamine (6.681 mg, 0.029 mmol) and DIPEA (3.780 mg, 5.108 μL, 0.029 mmol) and stirred for 3 hours. The solvent was removed and the residue was purified with C18 reverse chromatography (MeCN+ 0.1% formic acid| H$_2$O+0.1% formic acid) to afford (2R,5S,8R,14S,17R,20S,21S,22S,E)-20-((E)-but-2-en-2-yl)-14-((R)-sec-butyl)-8-(4-chlorobenzyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl methyl(12-(methylamino)dodecyl)carbamate (0.685 mg, 21%, 2.93 μmol). Observed HRMS (ESI) m/z: 1114.7044 [M+H]$^+$.

Example 21

Synthesis of Compound 21

7-hydroxy-2,6,8-trimethyl-5-((methylthio)methoxy)deca-2,8-dienoyl)oxy)-6,9,11,16-tetramethyl-4,7,10,13-tetraoxo-3,6,9,12-tetraazaheptadecanoate (151.7 mg, 0.151 mmol; Intermediate from Example 14) and DMAP (0.018 g, 0.151 mmol) in DCM (4.224 g, 3.2 mL, 49.736 mmol) was added EDC (0.087 g, 0.455 mmol) at 0° C. After stirring at 0° C. for 3 h, the mixture was warmed to rt and stirred overnight, diluted with EtOAc and citric acid solution. The organic phase was washed with NaHCO$_3$ and brine, dried over Na$_2$SO$_4$ and concentrated in vacuo. The residue was purified with flash to afford 2,2,2-trichloroethyl (2S,8R,11S,14R)-14-(((2E,5S,6S,7S,8E)-7-((2-((((9H-fluoren-9-yl)methoxy)carbonyl)amino)-2-methylpropanoyl)oxy)-2,6,8-trimethyl-5-((methylthio)methoxy)deca-2,8-dienoyl)oxy)-2-((R)-sec-butyl)-8-(4-chlorobenzyl)-6,9,11,16-tetramethyl-4,7,10,13-tetraoxo-3,6,9,12-tetraazaheptadecanoate (0.196 g, 99.05%) with some Fmoc-Isobutyric acid impurity.

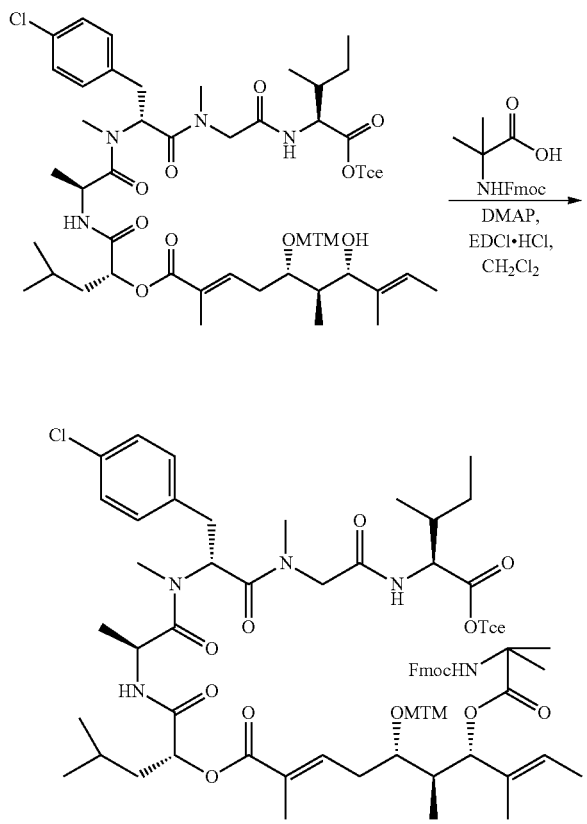

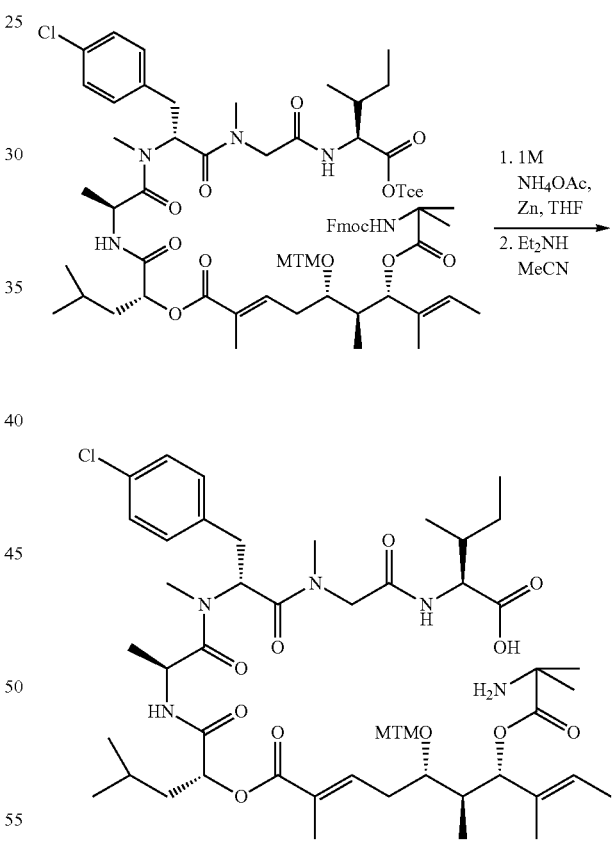

Step 1: To the solution of 2-(((((9H-fluoren-9-yl)methoxy)carbonyl)amino)-2-methylpropanoic acid (0.148 g, 0.455 mmol), 2,2,2-trichloroethyl (2S,8R,11S,14R)-2-((R)-sec-butyl)-8-(4-chlorobenzyl)-14-(((2E,5S,6R,7S,8E)-

Step 2: To a solution of 2,2,2-trichloroethyl (2S,8R,11S,14R)-14-(((2E,5S,6S,7S,8E)-7-((2-((((9H-fluoren-9-yl)methoxy)carbonyl)amino)-2-methylpropanoyl)oxy)-2,6,8-trimethyl-5-((methylthio)methoxy)deca-2,8-dienoyl)oxy)-2-((R)-sec-butyl)-8-(4-chlorobenzyl)-6,9,11,16-tetramethyl-4,7,10,13-tetraoxo-3,6,9,12-tetraazaheptadecanoate (0.196 g, 0.150 mmol) in 0.025 M of THF (6 mL), and 0.113 M of 1 M NH$_4$OAc (1.3 mL) was added zinc (2.753 g, 42.120 mmol) and stirred for 4 h. The reaction was complete through TLC was filtered through celite concentrated. The resulting residue was dissolved in MeCN (2 mL) and diethyl amine was added (2 mL). After 3 h the reaction was concentrated in vacuo. The residue was purified with reverse phase flash to afford N—((R)-2-((S)-2-((R)-2-(((2E,5S,6S,7S,8E)-7-((2-amino-2-methylpropanoyl)oxy)-2,6,8-trimethyl-5-((methylthio)methoxy)deca-2,8-dienoyl)oxy)-4-methylpentanamido)-N-methylpropanamido)-3-(4-chlorophenyl)propanoyl)-N-methylglycyl-L-alloisoleucine (0.1124 g, 78%, 0.118 mmol).

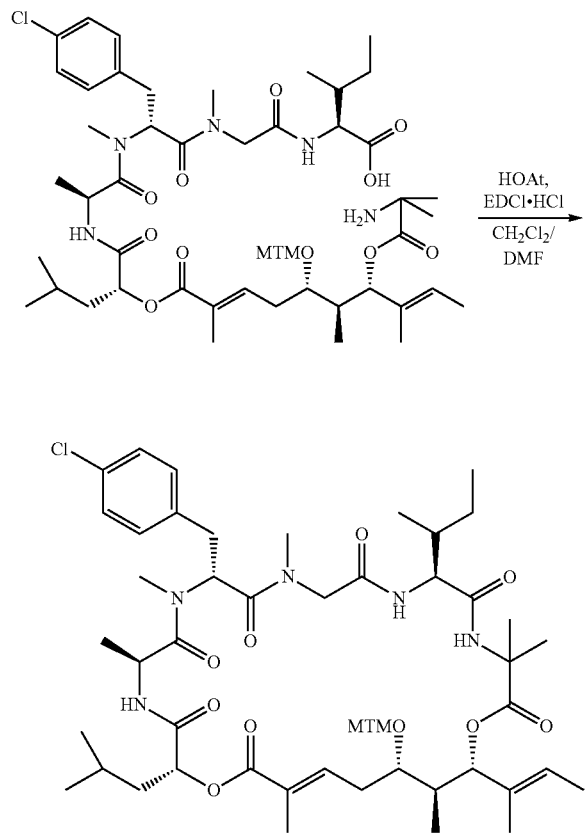

Step 3: To the solution of N—((R)-2-((S)-2-((R)-2-(((2E,5S,6S,7S,8E)-7-((2-amino-2-methylpropanoyl)oxy)-2,6,8-trimethyl-5-((methylthio)methoxy)deca-2,8-dienoyl)oxy)-4-methylpentanamido)-N-methylpropanamido)-3-(4-chlorophenyl)propanoyl)-N-methylglycyl-L-alloisoleucine (0.112 g, 0.117 mmol) in 0.000996M of 1:10 (DMF 18 mL:DCM 100 mL) was added HOAt (0.160 g, 1.179 mmol) and EDC (0.226 g, 1.179 mmol). The solvent was removed and diluted with EtOAc and citric acid solution. The organic phase was washed with aqueous NaHCO$_3$ and brine, dried over NaSO$_4$, concentrated in vacuo. The residue was purified with flash to afford (6S,12R,15S,18R,24S,25S,26S,E)-26-((E)-but-2-en-2-yl)-6-((R)-sec-butyl)-12-(4-chlorobenzyl)-18-isobutyl-3,3,10,13,15,21,25-heptamethyl-24-((methylthio)methoxy)-1,19-dioxa-4,7,10,13,16-pentaazacyclohexacos-21-ene-2,5,8,11,14,17,20-heptaone (0.036 g, 32.74%).

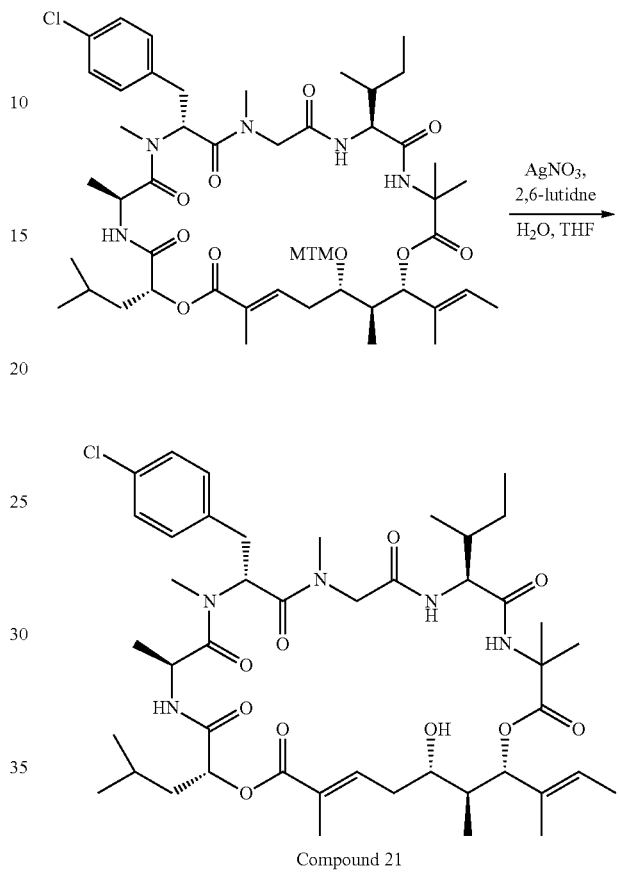

Compound 21

Step 4: To the solution of (6S,12R,15S,18R,24S,25S,26S,E)-26-((E)-but-2-en-2-yl)-6-((R)-sec-butyl)-12-(4-chlorobenzyl)-18-isobutyl-3,3,10,13,15,21,25-heptamethyl-24-((methylthio)methoxy)-1,19-dioxa-4,7,10,13,16-pentaazacyclohexacos-21-ene-2,5,8,11,14,17,20-heptaone (0.036 g, 0.038 mmol) in THF (0.816 g, 0.927 mL, 11.317 mmol) and water (0.231 g, 0.231 mL, 12.862 mmol) was added 2,6-lutidine (0.082 g, 0.089 mL, 0.772 mmol) and silver nitrate (0.262 g, 1.544 mmol). The mixture was heated at 65° C. for 3-4 hours. The mixture was cooled to rt and diluted with EtOAc and 1 N HCl, then filtered over celite. The aq phase was extracted with EtOAc and the organic phase was washed with aqueous NaHCO$_3$ and brine, dried over NaSO$_4$ and concentrated and in vacuo. The residue was purified with reverse phase flash to afford (6S,12R,15S,18R,24S,25S,26S,E)-26-((E)-but-2-en-2-yl)-6-((R)-sec-butyl)-12-(4-chlorobenzyl)-24-hydroxy-18-isobutyl-3,3,10,13,15,21,25-heptamethyl-1,19-dioxa-4,7,10,13,16-pentaazacyclohexacos-21-ene-2,5,8,11,14,17,20-heptaone (0.022 g, 65.1%, 0.025 mmol). Observed HRMS (ESI) m/z: 874.4734 [M+H]$^+$.

Example 22

Synthesis of Intermediate 3

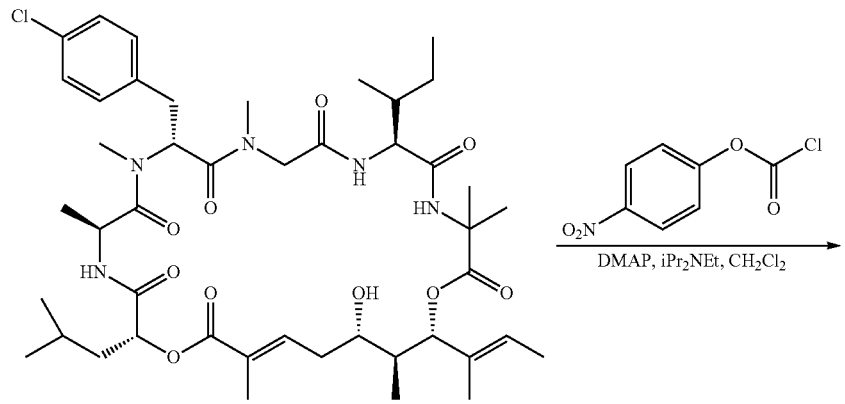

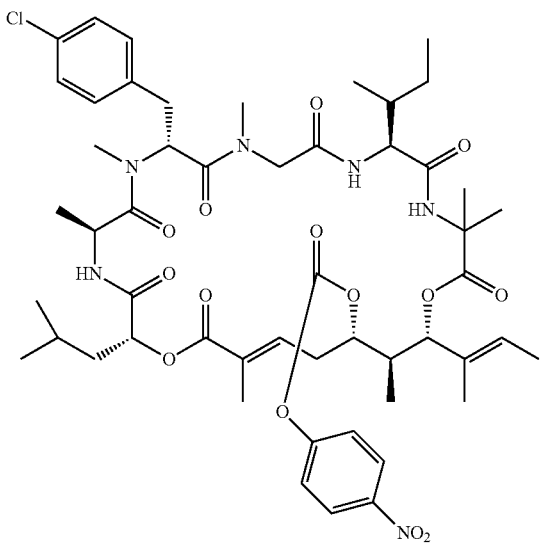

Intermediate 3

To a solution of (6S,12R,15S,18R,24S,25S,26S,E)-26-((E)-but-2-en-2-yl)-6-((R)-sec-butyl)-12-(4-chlorobenzyl)-24-hydroxy-18-isobutyl-3,3,10,13,15,21,25-heptamethyl-1,19-dioxa-4,7,10,13,16-pentaazacyclohexacos-21-ene-2,5,8,11,14,17,20-heptaone (0.007 g, 8.00 μmol) in DCM (400 μL, 6.22 mmol) was added N,N-dimethylpyridin-4-amine (0.977 mg, 8.004 μmol), DIPEA (0.051 g, 0.069 mL, 0.400 mmol), and 4-nitrophenyl carbonochloridate (0.007 g, 8.00 μmol). The reaction was stirred for 6 h and diluted with EtOAc and citric acid solution. The organic phase was washed with NaHCO$_3$ aq and brine, dried over Na$_2$SO$_4$, concentrated in vacuo. The residue was purified with flash to afford (2R,5S,8R,14S,20S,21S,22S,E)-20-((E)-but-2-en-2-yl)-14-((R)-sec-butyl)-8-(4-chlorobenzyl)-2-isobutyl-5,7,10,17,17,21,25-heptamethyl-3,6,9,12,15,18,26-heptaoxo-1,19-dioxa-4,7,10,13,16-pentaazacyclohexacos-24-en-22-yl (4-nitrophenyl) carbonate (0.0048 g, 57.7%, 4.62 μmol).

Example 23

Synthesis of Compound 22

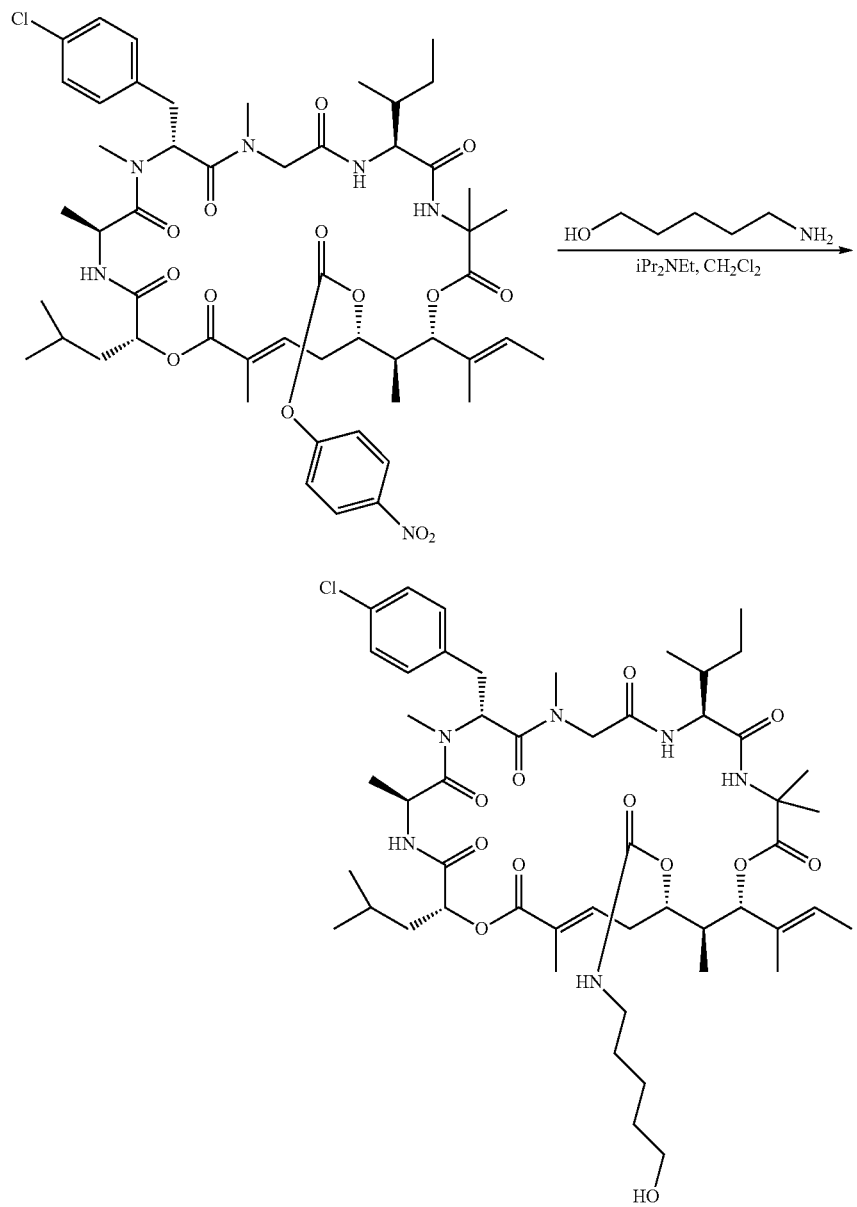

To a solution of (2R,5S,8R,14S,20S,21S,22S,E)-20-((E)-but-2-en-2-yl)-14-((R)-sec-butyl)-8-(4-chlorobenzyl)-2-isobutyl-5,7,10,17,17,21,25-heptamethyl-3,6,9,12,15,18,26-heptaoxo-1,19-dioxa-4,7,10,13,16-pentaazacyclohexacos-24-en-22-yl(4-nitrophenyl) carbonate (0.0048 g, 4.62 µmol) in DCM (0.7 mL, 10.88 mmol) was added 5-aminopentan-1-ol (0.00476 g, 0.046 mmol) and DIPEA (5.97 mg, 8.06 µL, 0.046 mmol) and stirred for 4 hours. The solvent was removed and the residue was purified with C18 reverse phase chromatography chromatography (MeCN+0.1% formic acid|H$_2$O+0.1% formic acid) to afford (2R,5S,8R,14S,20S,21S,22S,E)-20-((E)-but-2-en-2-yl)-14-((R)-sec-butyl)-8-(4-chlorobenzyl)-2-isobutyl-5,7,10,17,17,21,25-heptamethyl-3,6,9,12,15,18,26-heptaoxo-1,19-dioxa-4,7,10,13,16-pentaazacyclohexacos-24-en-22-yl(5-hydroxypentyl) carbamate (0.002 g, 43.2%, 4.62 µmol). Observed HRMS (ESI) m/z: 1003.5538 [M+H]$^+$.

Example 24

Synthesis of Compound 23

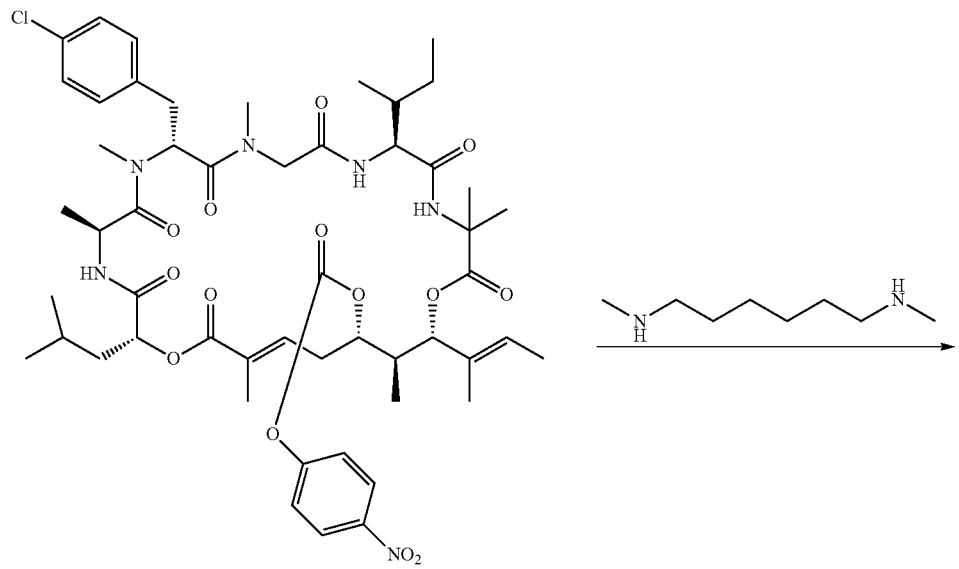

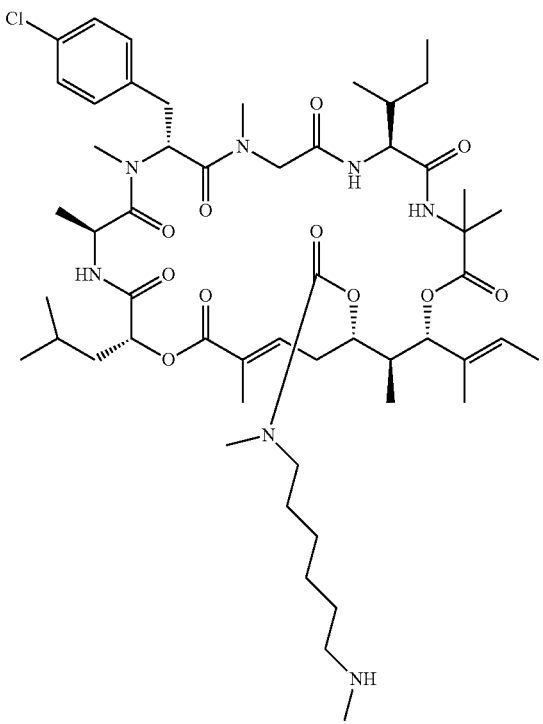

To a solution of (2R,5S,8R,14S,20S,21S,22S,E)-20-((E)-but-2-en-2-yl)-14-((R)-sec-butyl)-8-(4-chlorobenzyl)-2-isobutyl-5,7,10,17,17,21,25-heptamethyl-3,6,9,12,15,18,26-heptaoxo-1,19-dioxa-4,7,10,13,16-pentaazacyclohexacos-24-en-22-yl (4-nitrophenyl) carbonate (0.0035 g, 3.37 μmol) in DCM (3.11 mmol, 0.2 mL) was added N1,N6-dimethylhexane-1,6-diamine (4.856 mg, 6.070 μL, 0.033 mmol) and DIPEA (4.351 mg, 5.880 μL, 0.033 mmol) and stirred for 3 hours. The solvent was removed and the residue was purified with C18 reverse phase chromatography (MeCN+0.1% formic acid|H₂O+0.1% formic acid) to afford (2R,5S,8R,14S,20S,21S,22S,E)-20-((E)-but-2-en-2-yl)-14-((R)-sec-butyl)-8-(4-chlorobenzyl)-2-isobutyl-5,7,10,17,17,21,25-heptamethyl-3,6,9,12,15,18,26-heptaoxo-1,19-dioxa-4,7,10,13,16-pentaazacyclohexacos-24-en-22-yl methyl(6-(methylamino)hexyl)carbamate (1.1 mg, 31%, 3.37 µmol). Observed HRMS (ESI) m/z: 1044.6156 [M+H]⁺.

Example 25

Synthesis of Compound 24

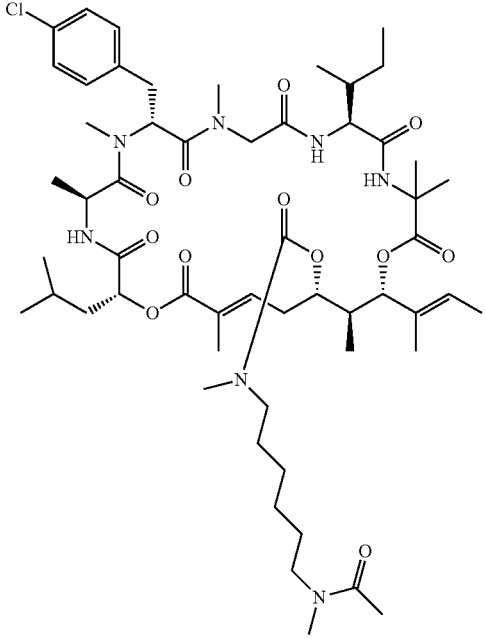

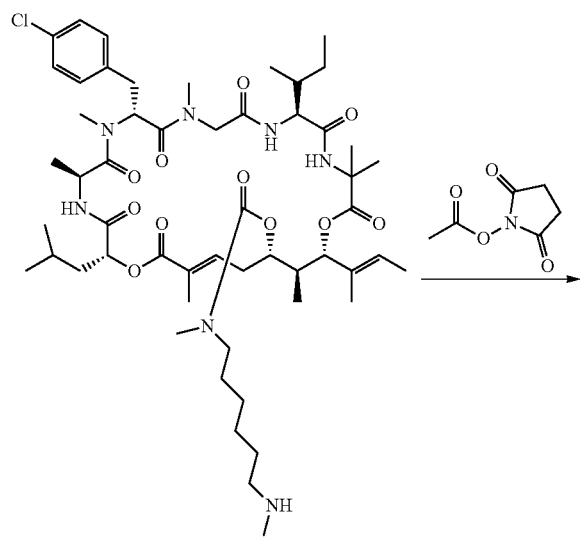

To a solution of (2R,5S,8R,14S,20S,21S,22S,E)-20-((E)-but-2-en-2-yl)-14-((R)-sec-butyl)-8-(4-chlorobenzyl)-2-isobutyl-5,7,10,17,17,21,25-heptamethyl-3,6,9,12,15,18,26-heptaoxo-1,19-dioxa-4,7,10,13,16-pentaazacyclohexacos-24-en-22-yl methyl(6-(methylamino)hexyl)carbamate (0.002 g, 1.914 µmol) in DCM (4.66 mmol, 300 µL) was added 2,5-dioxopyrrolidin-1-yl acetate (3.007 mg, 0.019 mmol) and DIPEA (2.474 mg, 3.343 µL, 0.019 mmol) and stirred for 5 hours. The solvent was removed and the residue was purified with C18 reverse phase chromatography (MeCN+0.1% formic acid|H₂O+0.1% formic acid) to afford (2R,5S,8R,14S,20S,21S,22S,E)-20-((E)-but-2-en-2-yl)-14-((R)-sec-butyl)-8-(4-chlorobenzyl)-2-isobutyl-5,7,10,17,17,21,25-heptamethyl-3,6,9,12,15,18,26-heptaoxo-1,19-dioxa-4,7,10,13,16-pentaazacyclohexacos-24-en-22-yl methyl(6-(N-methylacetamido)hexyl)carbamate (1.1 mg, 53%, 1.012 µmol). Observed HRMS (ESI) m/z: 1086.6287 [M+H]⁺.

Example 26

Synthesis of Compound 25

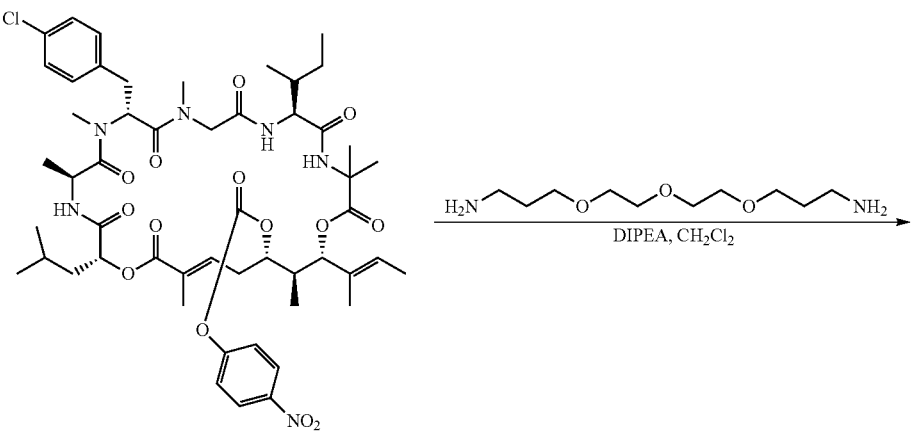

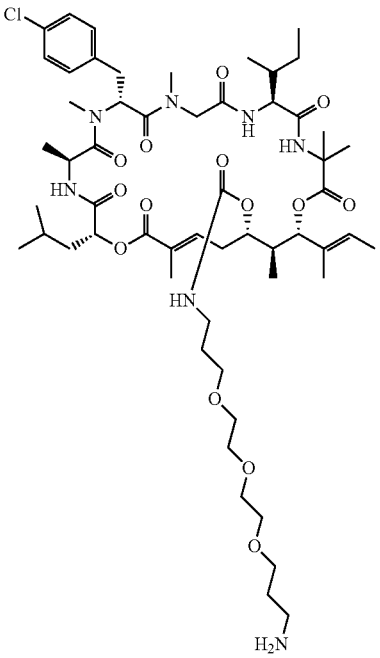

To a solution of (2R,5S,8R,14S,20S,21S,22S,E)-20-((E)-but-2-en-2-yl)-1-((R)-sec-butyl)-8-(4-chlorobenzyl)-2-isobutyl-5,7,10,17,17,21,25-heptamethyl-3,6,9,12,15,18,26-heptaoxo-1,19-dioxa-4,7,10,13,16-pentaazacyclohexacos-24-en-22-yl (4-nitrophenyl) carbonate (0.005 g, 4.81 μmol) in DCM (700 μL) was added 3,3'-((oxybis(ethane-2,1-diyl))bis(oxy))bis(propan-1-amine) (0.010 g, 0.010 mL, 0.048 mmol) and DIPEA (6.216 mg, 8.400 μL, 0.048 mmol) and stirred for 3 h. The solvent was removed and the residue was purified on reverse phase flash to afford (2R,5S,8R,14S,20S,21S,22S,E)-20-((E)-but-2-en-2-yl)-14-((R)-sec-butyl)-8-(4-chlorobenzyl)-2-isobutyl-5,7,10,17,17,21,25-heptamethyl-3,6,9,12,15,18,26-heptaoxo-1,19-dioxa-4,7,10,13,16-pentaazacyclohexacos-24-en-22-yl (3-(2-(2-(3-aminopropoxy)ethoxy)ethoxy)propyl)carbamate (0.00097 g, 18%, 0.865 μmol). Observed HRMS (ESI) m/z: 1120.6394 [M+H]$^-$.

Example 27

Synthesis of Compound 26

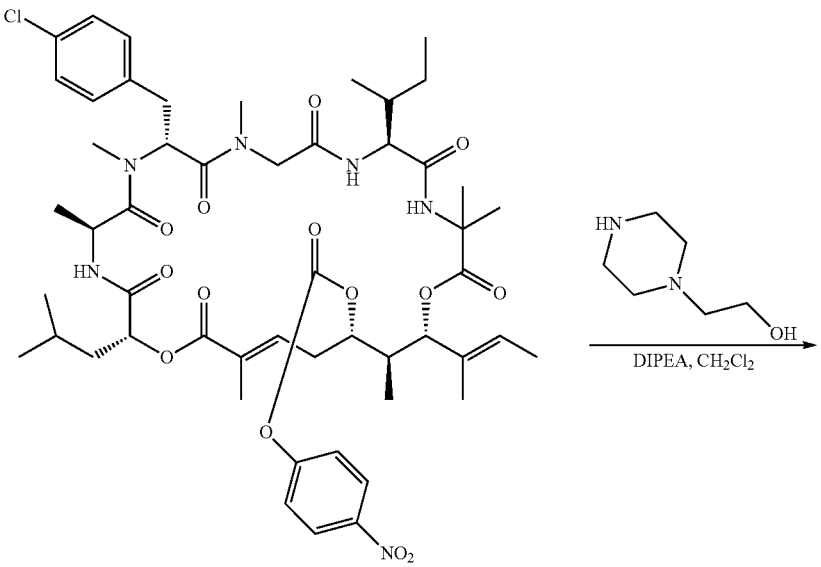

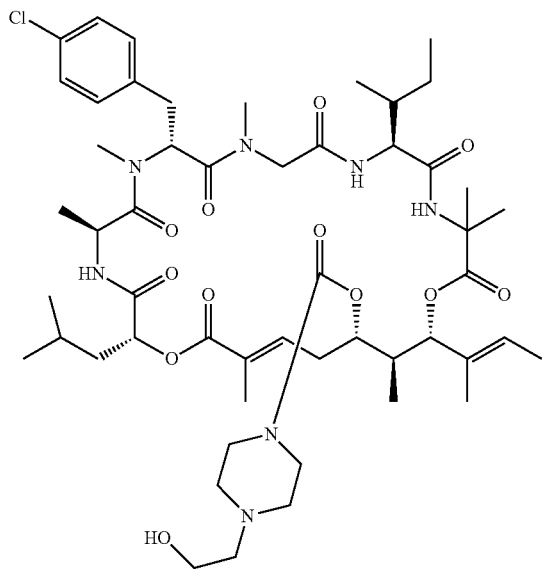

To a solution of (2R,5S,8R,14S,20S,21S,22S,E)-20-((E)-but-2-en-2-yl)-14-((R)-sec-butyl)-8-(4-chlorobenzyl)-2-isobutyl-5,7,10,17,17,21,25-heptamethyl-3,6,9,12,15,18,26-heptaoxo-1,19-dioxa-4,7,10,13,16-pentaazacyclohexacos-24-en-22-yl (4-nitrophenyl) carbonate (0.005 g, 4.81 μmol) in DCM (0.263 g, 200 μL, 3.108 mmol) was added 2-(piperazin-1-yl)ethan-1-ol (6.261 mg, 5.901 μL, 0.048 mmol) and DIPEA (6.216 mg, 8.400 μL, 0.048 mmol) and stirred for 3 h. The solvent was removed and the residue was purified with reverse phase flash to afford (2R,5S,8R,14S,20S,21S,22S,E)-20-((E)-but-2-en-2-yl)-14-((R)-sec-butyl)-8-(4-chlorobenzyl)-2-isobutyl-5,7,10,17,17,21,25-heptamethyl-3,6,9,12,15,18,26-heptaoxo-1,19-dioxa-4,7,10,13,16-pentaazacyclohexacos-24-en-22-yl 4-(2-hydroxyethyl)piperazine-1-carboxylate (0.002 g, 40.3%, 4.81 μmol). Observed HRMS (ESI) m/z: 1130.5647 [M+H]$^+$.

Example 28

Synthesis of Compound 27

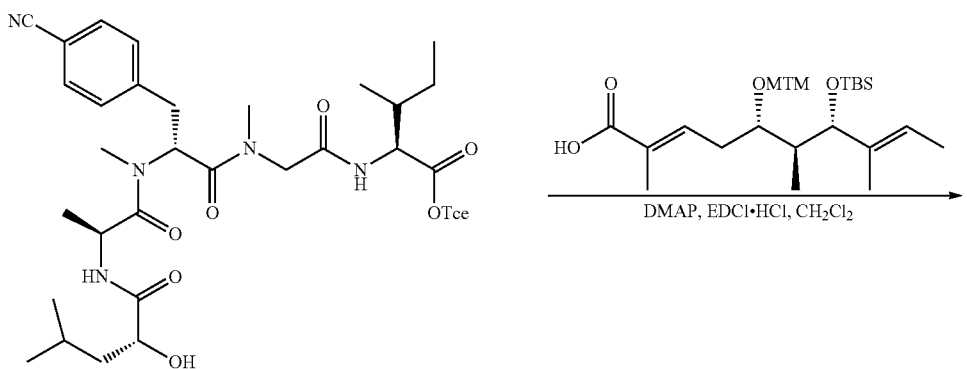

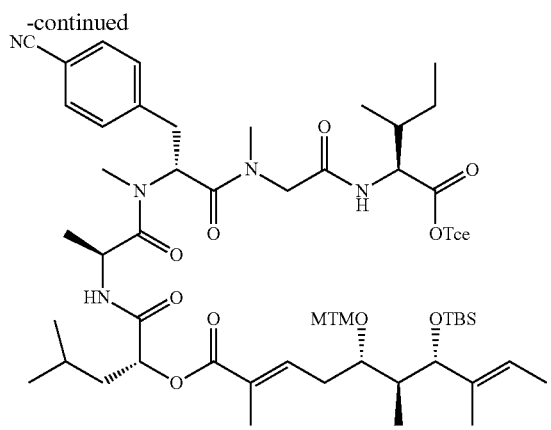

Step 1: To a stirring solution of 2,2,2-trichloroethyl N—((R)-3-(4-cyanophenyl)-2-((S)-2-((R)-2-hydroxy-4-methylpentanamido)-N-methylpropanamido)propanoyl)-N-methylglycyl-L-alloisolencinate (0.456 g, 0.647 mmol) and (2E,5S,6S,7S,8E)-7-((tert-butyldimethylsilyl)oxy)-2,6,8-trimethyl-5-((methylthio)methoxy)deca-2,8-dienoic acid (0.225 g, 0.539 mmol) in DCM (1 mL) was added DMAP (0.065 g, 0.539 mmol) and EDC (0.258 g, 1.349 mmol) at 0° C. The reaction was stirred for 36 h and diluted with EtOAc and citric acid solution. The organic phase was washed with NaHCO₃ aq and brine, and dried over Na₂SO₄, concentrated in vacuo. The residue was purified with flash to afford 2,2,2-trichloroethyl (2S,8R,11S,14R)-2-((R)-sec-butyl)-14-(((2E,5S,6S,7S,8E)-7-((tert-butyldimethylsilyl)oxy)-2,6,8-trimethyl-5-((methylthio)methoxy)deca-2,8-dienoyl)oxy)-8-(4-cyanobenzyl)-6,9,11,16-tetramethyl-4,7,10,13-tetraoxo-3,6,9,12-tetraazaheptadecanoate (0.5658 g, 95%, 0.513 mmol).

butyldimethylsilyl)oxy)-2,6,8-trimethyl-5-((methylthio)methoxy)deca-2,8-dienoyl)oxy)-8-(4-cyanobenzyl)-6,9,11,16-tetramethyl-4,7,10,13-tetraoxo-3,6,9,12-tetraazaheptadecanoate (0.565 g, 0.512 mmol) was dissolved in THF (6.77 mL), pyridine (1.615 mL) and HF pyridine (1.615 mL). The reaction was stirred overnight at 60° C. After the completion of the reaction through TLC, the mixture was diluted with EtOAc and NaHCO₃ aq. The organic phase was washed with brine, dried over Na₂SO₄ and concentrated in vacuo. The residue was purified with flash to afford 2,2,2-trichloroethyl (2S,8R,11S,14R)-2-((R)-sec-butyl)-8-(4-cyanobenzyl)-14-(((2E,5S,6R,7S,8E)-7-hydroxy-2,6,8-trimethyl-5-((methylthio)methoxy)deca-2,8-dienoyl)oxy)-6,9,11,16-tetramethyl-4,7,10,13-tetraoxo-3,6,9,12-tetraazaheptadecanoate (0.4 g, 0.404 mmol, 79%).

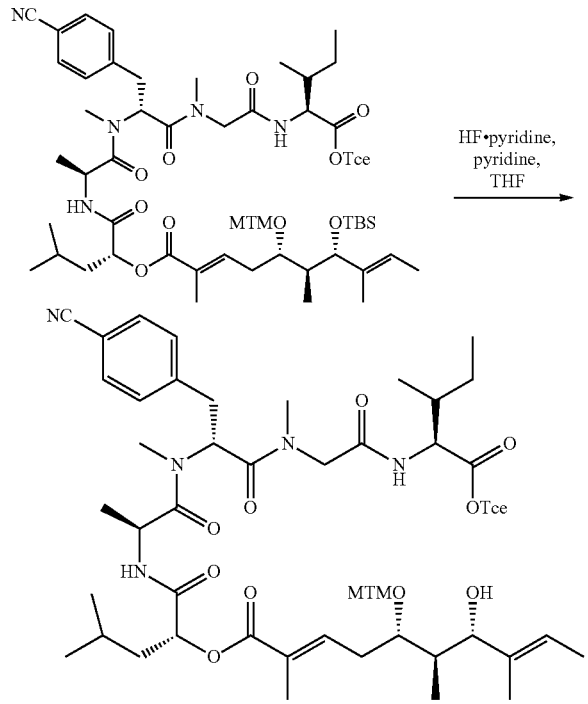

Step 2: To a solution of 2,2,2-trichloroethyl (2S,8R,11S,14R)-2-((R)-sec-butyl)-14-(((2E,5S,6S,7S,8E)-7-((tert-

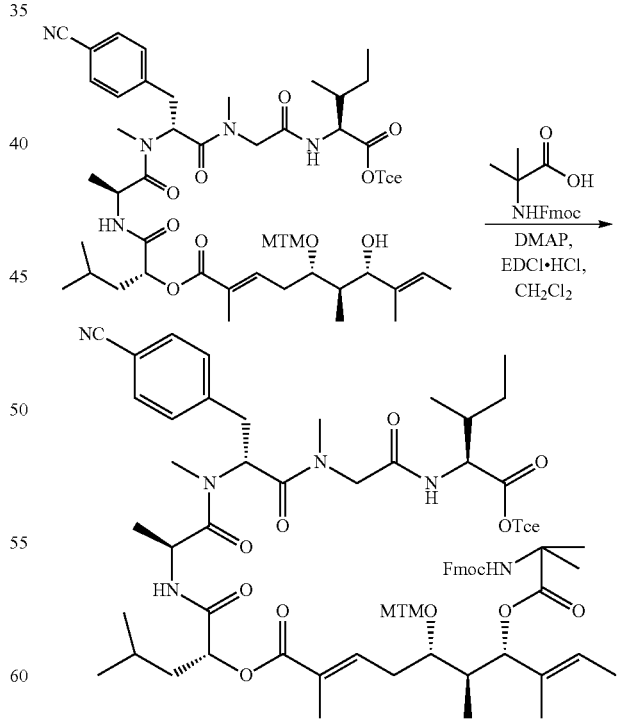

Step 3: To a solution of 2,2,2-trichloroethyl (2S,8R,11S,14R)-2-((R)-sec-butyl)-8-(4-cyanobenzyl)-14-(((2E,5S,6R,7S,8E)-7-hydroxy-2,6,8-trimethyl-5-((methylthio)methoxy)deca-2,8-dienoyl)oxy)-6,9,11,16-tetramethyl-4,7,10,13- tetraoxo-3,6,9,12-tetraazaheptadecanoate (0.2 g, 0.202 mmol) in DCM (0.7 mL) was added 2-((((9H-fluoren-9-yl)methoxy)carbonyl)amino)-2-methylpropanoic acid (0.197 g, 0.606 mmol), DMAP (0.024 g, 0.202 mmol) and EDC (0.116 g, 0.606 mmol) at 0° C. The solution was stirred overnight, diluted with EtOAc and citric acid solution. The organic phase was washed with NaHCO$_3$ and brine, dried over Na$_2$SO$_4$ and concentrated in vacuo. The residue was purified with flash to afford 2,2,2-trichloroethyl (2S,8R,11S,14R)-14-(((2E,5S,6S,7S,8E)-7-((2-((((9H-fluoren-9-yl)methoxy)carbonyl)amino)-2-methylpropanoyl)oxy)-2,6,8-trimethyl-5-((methylthio)methoxy)deca-2,8-dienoyl)oxy)-2-((R)-sec-butyl)-8-(4-cyanobenzyl)-6,9,11,16-tetramethyl-4,7,10,13-tetraoxo-3,6,9,12-tetraazaheptadecanoate (0.2495 g, 94%, 0.190 mmol).

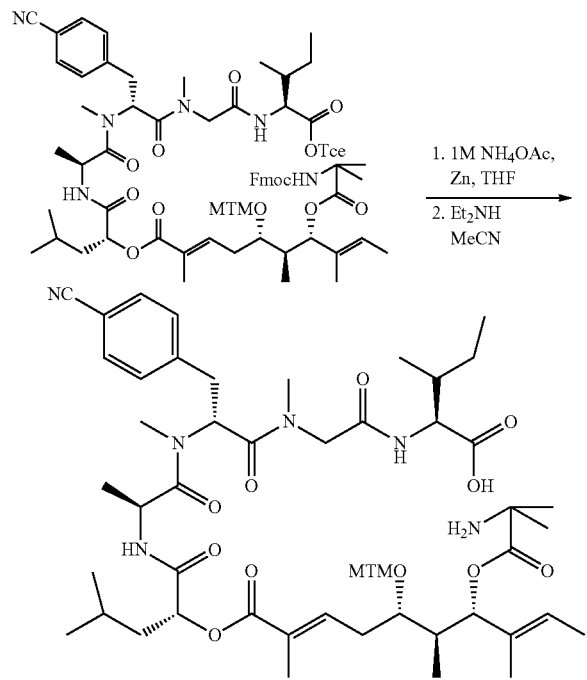

Step 4: To a stirring solution of 2,2,2-trichloroethyl (2S,8R,11S,14R)-14-(((2E,5S,6S,7S,8E)-7-((2-((((9H-fluoren-9-yl)methoxy)carbonyl)amino)-2-methylpropanoyl)oxy)-2,6,8-trimethyl-5-((methylthio)methoxy)deca-2,8-dienoyl)oxy)-2-((R)-sec-butyl)-8-(4-cyanobenzyl)-6,9,11,16-tetramethyl-4,7,10,13-tetraoxo-3,6,9,12-tetraazaheptadecanoate (0.2459 g, 0.190 mmol) in THF (7.58 mL, 0.025 M) and 1 M NH$_4$OAC (1.7 mL, 0.113 M) was added zinc (3.471 g, 53.092 mmol) and stirred for 3 h, filtered through a pad of celite using MeCN and concentrated in vacuo. The resulting residue was dissolved in MeCN (3 mL) and diethylamine (3 mL) was added. After 1 h, the reaction was concentrated in vacuo. The residue was purified with reverse phase to afford N—((R)-2-((S)-2-((R)-2-(((2E,5S,6S,7S,8E)-7-((2-amino-2-methylpropanoyl)oxy)-2,6,8-trimethyl-5-((methylthio)methoxy)deca-2,8-dienoyl)oxy)-4-methylpentanamido)-N-methylpropanamido)-3-(4-cyanophenyl)propanoyl)-N-methylglycyl-L-alloisoleucine with a quantitative yield.

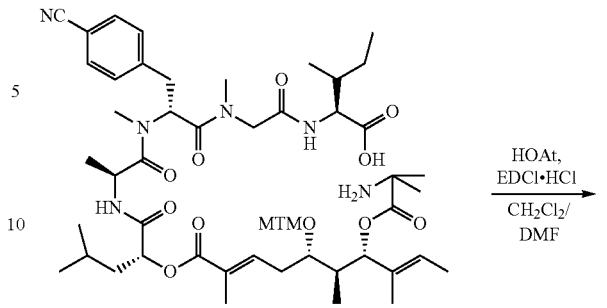

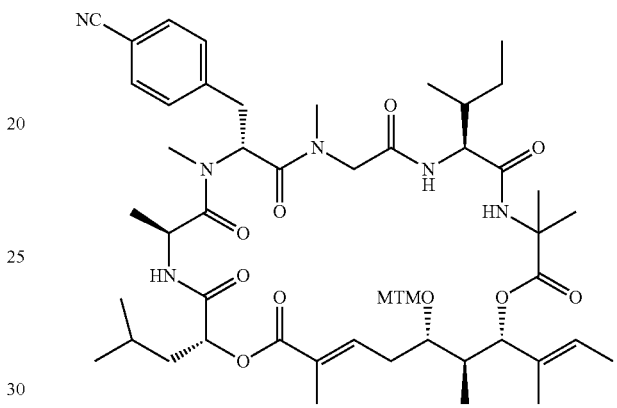

Step 5: To a solution of N—((R)-2-((S)-2-((R)-2-(((2E,5S,6S,7S,8E)-7-((2-amino-2-methylpropanoyl)oxy)-2,6,8-trimethyl-5-((methylthio)methoxy)deca-2,8-dienoyl)oxy)-4-methylpentanamido)-N-methylpropanamido)-3-(4-cyanophenyl)propanoyl)-N-methylglycyl-L-alloisoleucine (0.195 g, 0.206 mmol) in 0.000996 M solution of 1:10 (DMF 20 mL:DCM 180 mL) was added 1-hydroxy-7-azabenzotriazole (0.281 g, 2.067 mmol) and EDC (0.396 g, 2.067 mmol) and stirred for 24 h, the solvent was removed and diluted with EtOAc and citric acid solution. The organic phase was washed with NaHCO$_3$ aq and brine, dried over Na$_2$SO$_4$, concentrated in vacuo. The residue was purified with reverse phase flash to afford (4-(((2R,5S,8R,14S,20S,21S,22S,E)-20-((E)-but-2-en-2-yl)-14-((R)-sec-butyl)-2-isobutyl-5,7,10,17,17,21,25-heptamethyl-22-((methylthio)methoxy)-3,6,9,12,15,18,26-heptaoxo-1,19-dioxa-4,7,10,13,16-pentaazacyclohexacos-24-en-8-yl)methyl)benzonitrile (0.1081 g, 56.5%, 0.117 mmol).

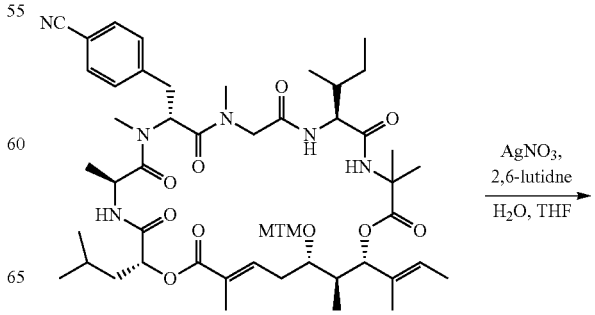

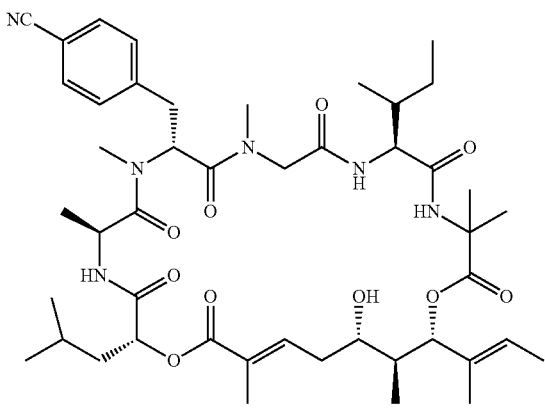

Compound 27

Step 6: To a stirring solution of 4-((((2R,5S,8R,14S,20S,21S,22S,E)-20-((E)-but-2-en-2-yl)-14-((R)-sec-butyl)-2-isobutyl-5,7,10,17,17,21,25-heptamethyl-22-((methylthio)methoxy)-3,6,9,12,15,18,26-heptaoxo-1,19-dioxa-4,7,10,13,16-pentaazacyclohexacos-24-en-8-yl)methyl)

benzonitrile (0.108 g, 0.116 mmol) in THF (2.426 g, 2.757 mL, 33.649 mmol) and water (0.690 g, 0.690 mL, 38.323 mmol) was added 2,6-lutidine (0.250 g, 0.272 mL, 2.336 mmol) and silver nitrate (0.793 g, 4.673 mmol). The reaction was then heated to 60° C. for 1.5-2 hours. After the completion of the reaction. The mixture was cooled to rt and diluted with EtOAc and 1 N HCl, then filtered over celite. The aqueous phase was extracted with EtOAc and the organic phase was washed with aqueous NaHCO₃ and brine, dried over NaSO₄ and concentrated and in vacuo. The residue was purified with rp-flash to afford 4-(((2R,5S,8R,14S,20S,21S,22S,E)-20-((E)-but-2-en-2-yl)-14-((R)-sec-butyl)-22-hydroxy-2-isobutyl-5,7,10,17,17,21,25-heptamethyl-3,6,9,12,15,18,26-heptaoxo-1,19-dioxa-4,7,10,13,16-pentaazacyclohexacos-24-en-8-yl)methyl)benzonitrile (0.03 g, 29.7%, 0.035 mmol).

Example 29

Synthesis of Intermediate 4

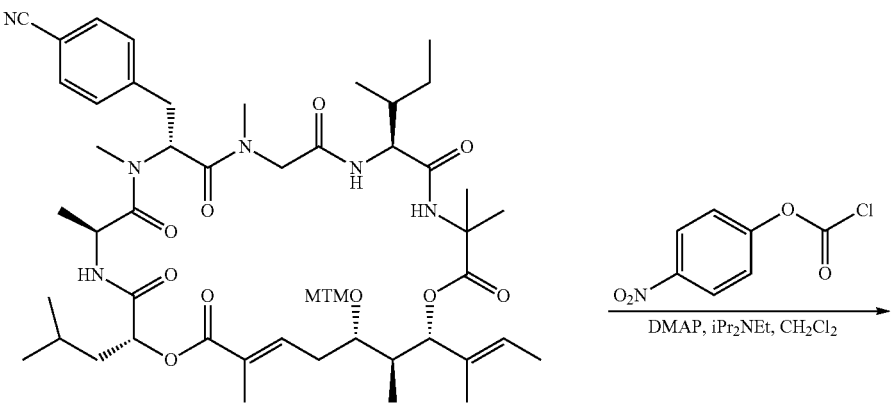

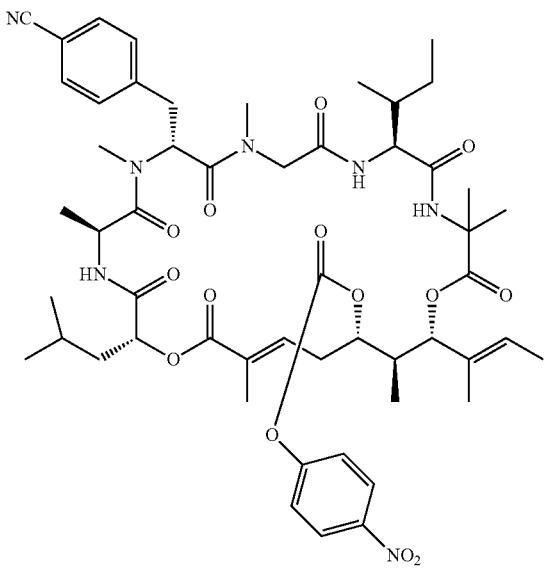

Intermediate 4

To a stirring solution of 4-(((2R,5S,8R,14S,20S,21S,22S,E)-20-((E)-but-2-en-2-yl)-14-((R)-sec-butyl)-22-hydroxy-2-isobutyl-5,7,10,17,17,21,25-heptamethyl-3,6,9,12,15,18,26-heptaoxo-1,19-dioxa-4,7,10,13,16-pentaazacyclohexacos-24-en-8-yl)methyl)benzonitrile (0.005 g, 6.820 μmol) in DCM (300 μL) was added DMAP (0.833 mg, 6.820 μmol), DIPEA (0.044 g, 0.059 mL, 0.341 mmol) and 4-nitrophenyl carbonochloridate (0.013 g, 0.068 mmol) and stirred for 6 h. After the completion of the reaction, the solution was diluted with EtOAc and citric acid solution. The organic phase was washed with NaHCO₃ (aq) and brine, dried over Na₂SO₄, concentrated in vacuo. The residue was purified with reverse phase flash to afford (2R,5S,8R,14S,20S,21S,22S,E)-20-((E)-but-2-en-2-yl)-14-((R)-sec-butyl)-8-(4-cyanobenzyl)-2-isobutyl-5,7,10,17,17,21,25-heptamethyl-3,6,9,12,15,18,26-heptaoxo-1,19-dioxa-4,7,10,13,16-pentaazacyclohexacos-24-en-22-yl (4-nitrophenyl) carbonate (0.0025 g, 35.6%, 6.82 μmol).

Example 30

Synthesis of Compound 28

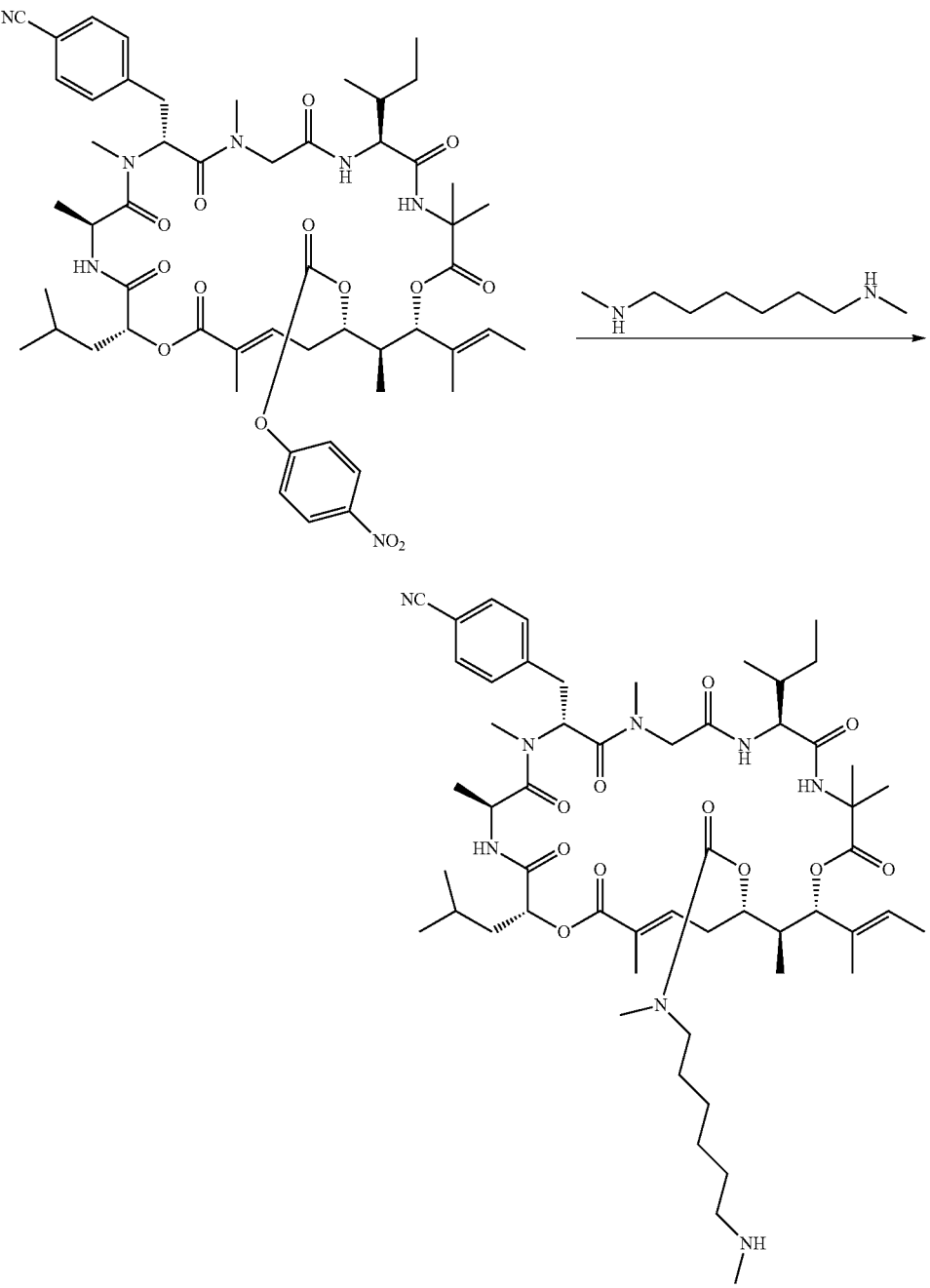

To a stirring solution of (2R,5S,8R,14S,20S,21S,22S,E)-20-((E)-but-2-en-2-yl)-14-((R)-sec-butyl)-8-(4-cyanobenzyl)-2-isobutyl-5,7,10,17,17,21,25-heptamethyl-3,6,9,12,15,18,26-heptaoxo-1,19-dioxa-4,7,10,13,16-pentaazacyclohexacos-24-en-22-yl (4-nitrophenyl) carbonate (0.0012 g, 1.165 µmol) in DCM (200 µL) was added N1,N6-dimethylhexane-1,6-diamine (1.680 mg, 0.011 mmol) and DIPEA (1.505 mg, 2.034 µL, 0.011 mmol). The reaction was stirred for 2 h, and the solvent was removed. The residue was purified with reverse phase flash to afford ((2R,5S,8R,14S,20S,21S,22S,E)-20-((E)-but-2-en-2-yl)-14-((R)-sec-butyl)-8-(4-cyanobenzyl)-2-isobutyl-5,7,10,17,17,21,25-heptamethyl-3,6,9,12,15,18,26-heptaoxo-1,19-dioxa-4,7,10,13,16-pentaazacyclohexacos-24-en-22-yl methyl(6-(methylamino)hexyl)carbamate (0.0011 g, 91%, 1.062 µmol). Observed HRMS (ESI) m/z: 1035.6547 [M+H]$^+$.

Example 31

Synthesis of Compound 29

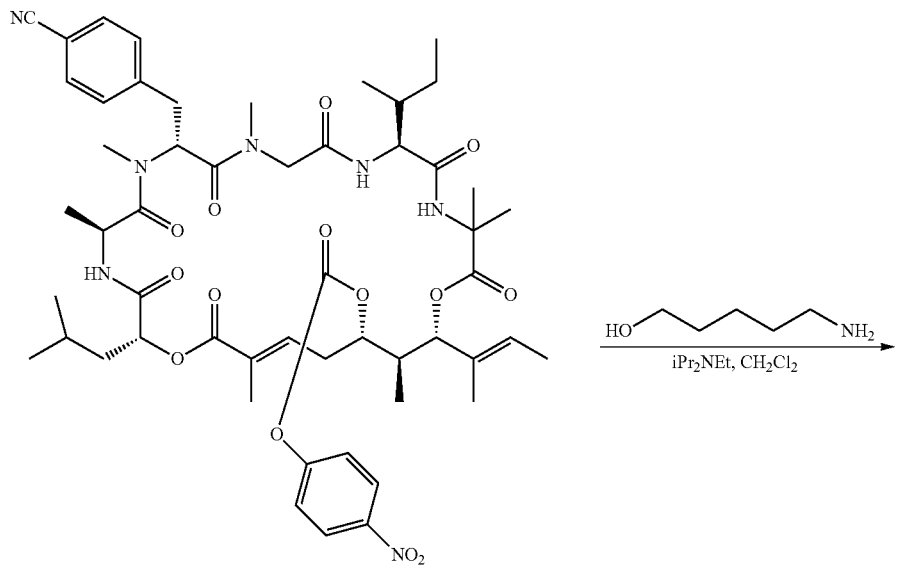

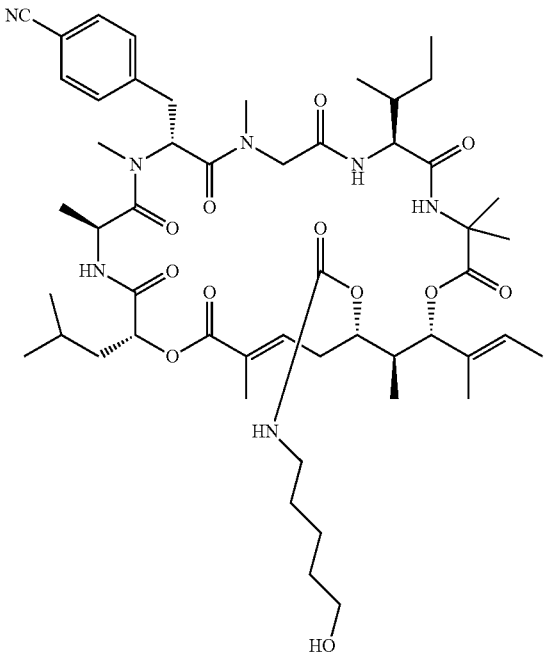

To a stirring solution of (2R,5S,8R,14S,20S,21S,22S,E)-20-((E)-but-2-en-2-yl)-14-((R)-sec-butyl)-8-(4-cyanobenzyl)-2-isobutyl-5,7,10,17,17,21,25-heptamethyl-3,6,9,12,15,18,26-heptaoxo-1,19-dioxa-4,7,10,13,16-pentaazacyclohexacos-24-en-22-yl (4-nitrophenyl) carbonate (0.002 g, 2.426 µmol) in DCM ((0.263 g, 200 µL, 3.108 mmol) was added 5-aminopentan-1-ol (2.503 mg, 0.024 µmol) and DIPEA (3.136 mg, 4.238 µL, 0.024 mmol) and stirred for 2 h. The solvent was removed and the residue was purified with reverse phase to afford (2R,5S,8R,14S,20S,21S,22S,E)-20-((E)-but-2-en-2-yl)-14-((R)-sec-butyl)-8-(4-cyanobenzyl)-2-isobutyl-5,7,10,17,17,21,25-heptamethyl-3,6,9,12,15,18,26-heptaoxo-1,19-dioxa-4,7,10,13,16-pentaazacyclohexacos-24-en-22-yl (5-hydroxypentyl) carbamate (0.00107 g, 44.3%, 2.427 µmol). Observed HRMS (ESI) m/z: 994.58 [M+H]$^+$.

Example 32

Synthesis of Compound 30

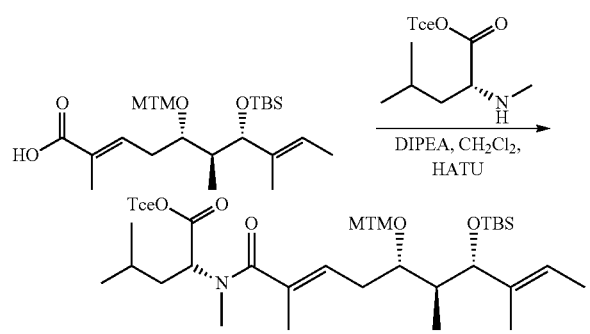

Step 1: To a reaction chamber equipped with stir bar (2E,5S,6S,7S,8E)-7-((tert-butyldimethylsilyl)oxy)-2,6,8-trimethyl-5-((methylthio)methoxy)deca-2,8-dienoic acid (0.053 g, 0.127 mmol) and 2,2,2-trichloroethyl methyl-D-leucinate (0.42 g, 0.153 mmol) were charged and dissolved in methylene chloride (1.27 mL, 0.1 M) followed by N,N-diisopropylethylamine (DIPEA, 0.044 mL, 0.254 mmol) addition. The reaction was cooled to 0° C. using an ice bath followed by 1-Hydroxy-7-azabenzotriazole (HOAt, 0.022 g, 0.140 mmol) and 1-Ethyl-3-(3-dimethylaminopropyl)carbodiimide (EDC, 0.027 g, 0.140 mmol) addition. The reaction was stir at 0° C. for 10 min before allowed warmed up to room-temperature for additional 2 hours and was monitored via LC/MS. Upon completion, the reaction was diluted with methylene chloride and washed with 1 N Hydrochloric acid solution, saturated NaHCO$_3$ solution, and brine. Combined organic layers were dried over Na$_2$SO$_4$, filtered through a filter paper, and the filtrate was concentrated in vacuo. The crude material was purified via silica gel chromatography using hexanes and ethyl acetate as eluents to yield 2,2,2-trichloroethyl N-((2E,5S,6S,7S,8E)-7-((tert-butyldimethylsilyl)oxy)-2,6,8-trimethyl-5-((methylthio)methoxy)deca-2,8-dienoyl)-N-methyl-D-leucinate as white solid (0.036 g, 0.-53 mmol, 42%).

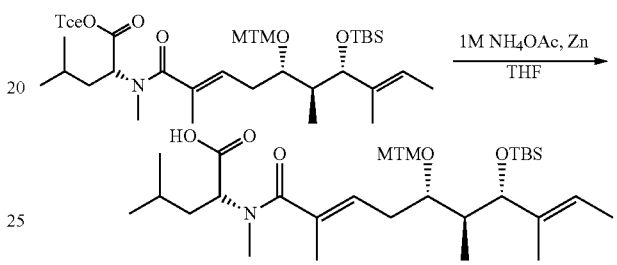

Step 2: To a reaction chamber equipped with stir bar 2,2,2-trichloroethyl N-((2E,5S,6S,7S,8E)-7-((tert-butyldimethylsilyl)oxy)-2,6,8-trimethyl-5-((methylthio)methoxy)deca-2,8-dienoyl)-N-methyl-D-leucinate (0.036 g, 0.053 mmol) and zinc dust (6-9 mesh, 0.976 g, 14.93 mmol) were charged. The material was suspended in tetrahydrofuran (THF, 1.06 mL, 0.25 M) followed by 1.06 mL of 1 M NH$_4$OAc solution addition. The reaction was allowed to stir at room-temperature for 8 h and monitored via LC/MS. Upon completion, the reaction was diluted with ethyl acetate and 1 N Hydrochloric acid solution and the reaction was filtered through a pad of celite. Filtrate was washed with 1 N Hydrochloric acid solution, saturated NaHCO$_3$ solution, and brine. Combined organic layers were dried over Na$_2$SO$_4$, filtered and concentrated in vacuo. Crude material was purified via reverse-phase C-18 column using water (with 0.1% formic acid) and acetonitrile (with 0.1% formic acid) as eluents to yield: N-((2E,5S,6S,7S,8E)-7-((tert-butyldimethylsilyl)oxy)-2,6,8-trimethyl-5-((methylthio)methoxy)deca-2,8-dienoyl)-N-methyl-D-leucine as white solid (0.011 g, 0.020 mmol, 37.9%)

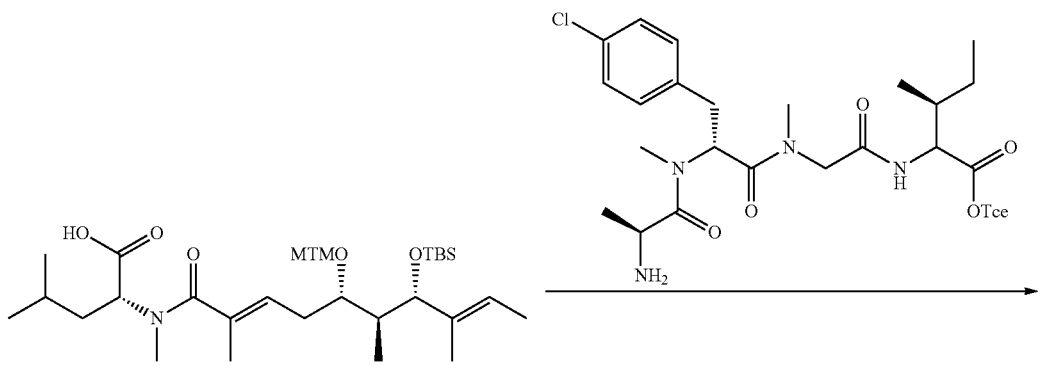

-continued

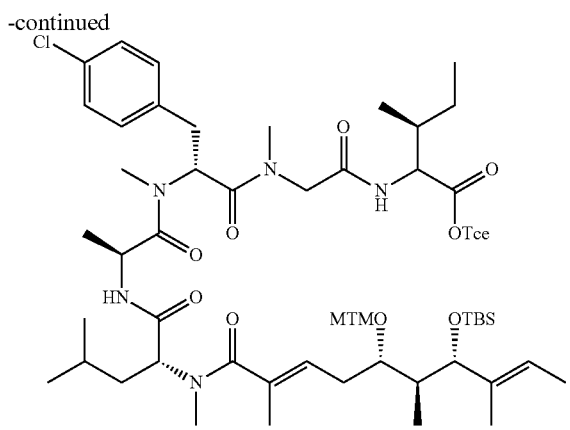

Step 3: To a reaction chamber equipped with stir bar 2,2,2-trichloroethyl N—((R)-2-((S)-2-amino-N-methylpropanamido)-3-(4-chlorophenyl)propanoyl)-N-methylglycyl-L-alloisoleucinate (0.036 g, 0.061 mmol) and N-((2E,5S,6S,7S,8E)-7-((tert-butyldimethylsilyl)oxy)-2,6,8-trimethyl-5-((methylthio)methoxy)deca-2,8-dienoyl)-N-methyl-D-leucine (0.011 g, 0.020 mmol) were charged and dissolved in 0.202 mL methylene chloride. The reaction was cooled to 0° C. using an ice bath followed by N, N-diisopropylethylamine (DIPEA, 0.014 mL, 0.081 mmol) addition then 1-Hydroxy-7-azabenzotriazole (HOAt, 0.0094 g, 0.061 mmol) and 1-Ethyl-3-(3-dimethylaminopropyl)carbodiimide (EDC, 0.012 g, 0.061 mmol) addition. The reaction was stir at 0° C. for 4 h before warmed up to room-temperature for additional 8 h stirring and monitored via LC/MS. Upon completion, the reaction was diluted with methylene chloride and washed with 1 N Hydrochloric acid solution, saturated NaHCO₃ solution, and brine. Combined organic layers were dried over Na₂SO₄, filtered, and concentrated in vacuo. The crude material was purified via silica gel chromatography using hexanes and ethyl acetate as eluents to yield 2,2,2-trichloroethyl N—((R)-2-((S)-2-((R)-2-((2E,5S,6S,7S,8E)-7-((tert-butyldimethylsilyl)oxy)-N,2,6,8-tetramethyl-5-((methylthio)methoxy)deca-2,8-dienamido)-4-methylpentanamido)-N-methylpropanamido)-3-(4-chlorophenyl)propanoyl)-N-methylglycyl-L-alloisoleucinate (0.015 g, 0.013 mmol, yield: 66%) as white solid.

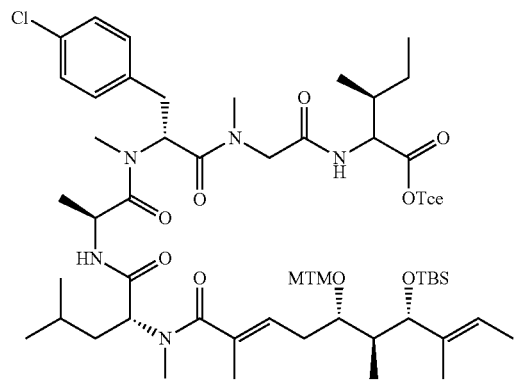

-continued

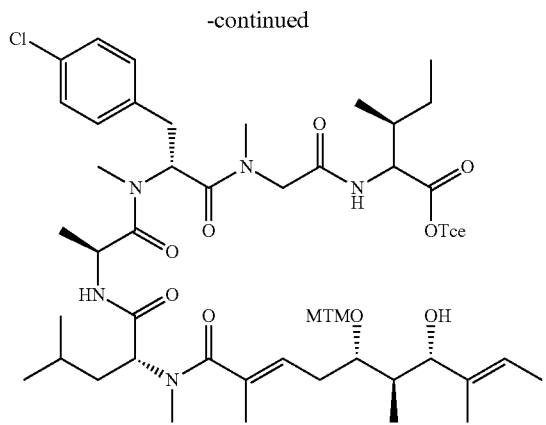

Step 4: To a reaction chamber equipped with stir bar 2,2,2-trichloroethyl N—((R)-2-((S)-2-((R)-2-((2E,5S,6S,7S,8E)-7-((tert-butyldimethylsilyl)oxy)-N,2,6,8-tetramethyl-5-((methylthio)methoxy)deca-2,8-dienamido)-4-methylpentanamido)-N-methylpropanamido)-3-(4-chlorophenyl)propanoyl)-N-methylglycyl-L-alloisoleucinate (0.014 g, 0.012 mmol) was charged and dissolved in a solution of 500 µL of THF/HF-pyridine/pyridine mixture (ratio: 4 to 1 to 1). The reaction chamber was sealed with Teflon and allowed to stir at 65° C. for 8 h and monitored via thin-layer-chromatography. Upon completion, the reaction was diluted with ethyl acetate followed by slow addition of saturated NaHCO₃ solution until gas evolution completed. The reaction was washed with saturated NaHCO₃ solution and brine. Combined organic layers were washed with 1N Hydrochloric acid solution then brine. Combined organic layers were dried over Na₂SO₄, filtered and concentrated in vacuo. The crude material was purified via silica gel chromatography using hexanes and ethyl acetate as eluents to yield 2,2,2-trichloroethyl N—((R)-3-(4-chlorophenyl)-2-((S)-2-((R)-2-((2E,5S,6R,7S,8E)-7-hydroxy-N,2,6,8-tetramethyl-5-((methylthio)methoxy)deca-2,8-dienamido)-4-methylpentanamido)-N-methylpropanamido)propanoyl)-N-methylglycyl-L-alloisoleucinate as white solid (0.005 g, 4.94 µmol, yield: 39.7%).

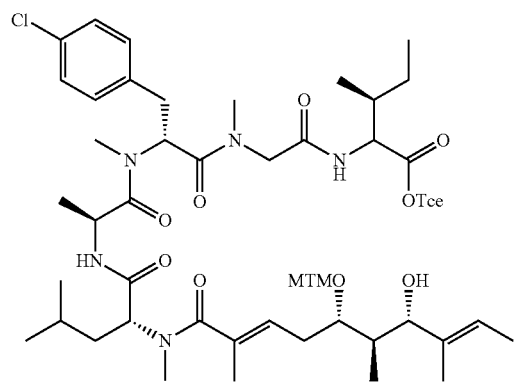

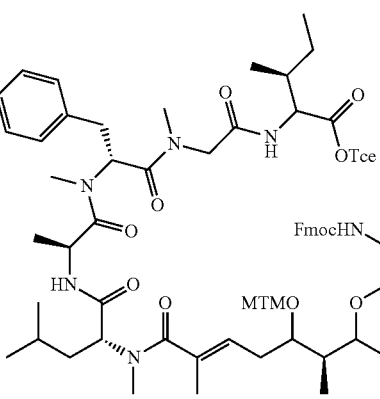

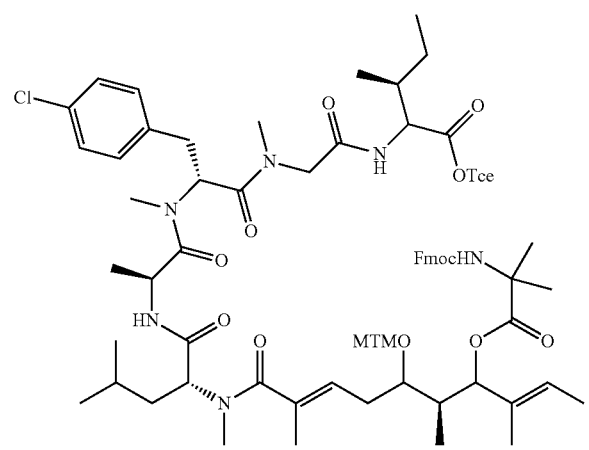

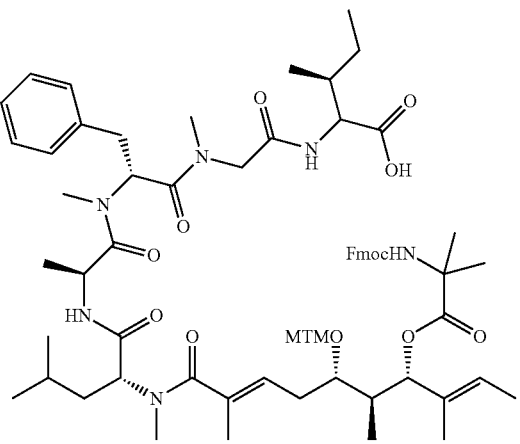

Step 5: To a reaction chamber equipped with stir bar 2,2,2-trichloroethyl N—((R)-3-(4-chlorophenyl)-2-((S)-2-((R)-2-((2E,5S,6R,7S,8E)-7-hydroxy-N,2,6,8-tetramethyl-5-((methylthio)methoxy)deca-2,8-dienamido)-4-methylpentanamido)-N-methylpentanamido)propanoyl)-N-methylglycyl-L-alloisoleucinate (0.01 g, 0.01 mmol) and 2-((((9H-fluoren-9-yl)methoxy)carbonyl)amino)-2-methylpropanoic acid (0.0064 g, 0.02 mmol) were charged and dissolved in 0.099 mL methylene chloride followed by 4-dimethylaminopyridine (DMAP, 0.00133 g, 0.011 mmol). The reaction was cooled to 0° C. followed by 1-Ethyl-3-(3-dimethylaminopropyl)carbodiimide (EDC, 0.016 g, 0.081 mmol) addition. The reaction was kept at 0° C., and monitored via Thin-Layer-Chromatography for 4 h before it reached completion. Upon completion, the reaction was diluted with ethyl acetate and washed with 1 N Hydrochloric acid solution, saturated NaHCO₃ solution and brine. Combined organic layers were dried over Na₂SO₄, filtered, and concentrated in vacuo. Crude material was purified via silica gel chromatography using hexanes and ethyl acetate as eluents to yield 2,2,2-trichloroethyl N—((R)-2-((S)-2-((8S,9S,10S,16S,E)-8-((E)-but-2-en-2-yl)-1-(9H-fluoren-9-yl)-16-isobutyl-5,5,9,13,15-pentamethyl-10-((methylthio)methoxy)-3,6,14-trioxo-2,7-dioxa-4,15-diazaheptadec-12-en-17-amido)-N-methylpropanamido)-3-(4-chlorophenyl)propanoyl)-N-methylglycyl-L-alloisoleucinate as white solid (0.002 g, 1.592 µmol, yield: 16.1%).

Step 6: To a reaction chamber equipped with stir bar, 2,2,2-trichloroethyl N—((R)-2-((S)-2-((8S,9S,10S,16R,E)-8-((E)-but-2-en-2-yl)-1-(9H-fluoren-9-yl)-16-isobutyl-5,5,9,13,15-pentamethyl-10-((methylthio)methoxy)-3,6,14-trioxo-2,7-dioxa-4,15-diazaheptadec-12-en-17-amido)-N-methylpropanamido)-3-(4-chlorophenyl)propanoyl)-N-methylglycyl-L-alloisoleucinate (0.002 g, 1.592 µmol) and zinc dust (6-9 mesh, 0.031 g, 0.478 mmol) were charged and suspended in 400 µL THF and 400 µL of 1 M NH₄OAc. The reaction was allowed to stir at room-temperature for 3 h and monitored via LC/MS. Upon completion, the reaction diluted with ethyl acetate and 1 N Hydrochloric acid then filtered through a pad of celite. The filtrate was washed with 1 N Hydrochloric acid, saturated NaHCO₃ solution, and brine. Combined organic layers were dried over Na₂SO₄, filtered, and the filtrate was concentrated in vacuo. The crude material was purified via reverse-phase C-18 column using water (with 0.1% formic acid) and acetonitrile (with 0.1% formic acid) as eluent to yield N—((R)-2-((S)-2-((8S,9S,10S,16R,E)-8-((E)-but-2-en-2-yl)-1-(9H-fluoren-9-yl)-16-isobutyl-5,5,9,13,15-pentamethyl-10-((methylthio)methoxy)-3,6,14-trioxo-2,7-dioxa-4,15-diazaheptadec-12-en-17-amido)-N-methylpropanamido)-3-(4-chlorophenyl)propanoyl)-N-methylglycyl-L-alloisoleucine (0.0008 g, 0.673 µmol, yield: 42.3%).

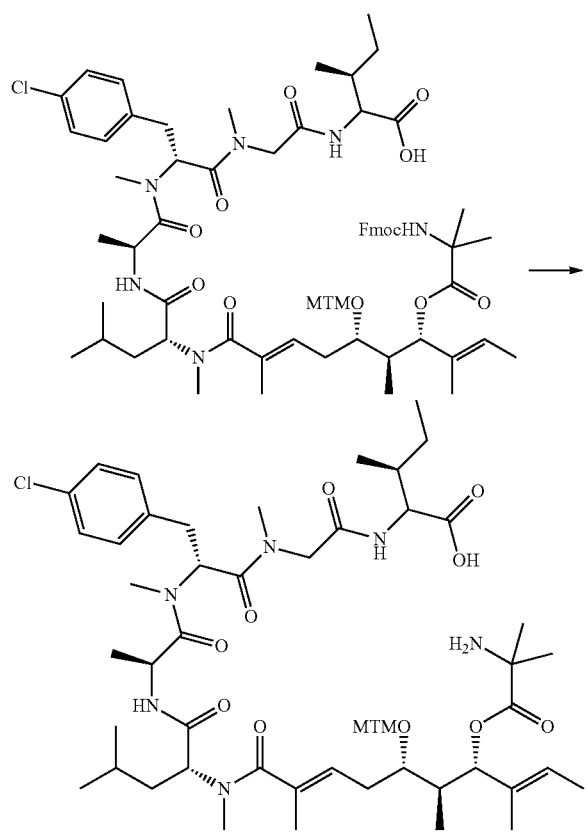

Step 7: To a reaction chamber equipped with stir bar N—((R)-2-((S)-2-((R)-2-((2E,5S,6S,7S,8E)-7-((2-((((9H-fluoren-9-yl)methoxy)carbonyl)amino)-2-methylpropanoyl)oxy)-2,6,8-trimethyl-5-((methylthio)methoxy)deca-2,8-dienamido)-4-methylpentanamido)-N-methylpropanamido)-3-(4-chlorophenyl)propanoyl)-N-methylglycyl-L-alloisoleucine (0.00019 g, 1.592 μmol) was charged and dissolved in 0.159 mL of a diethylamine/acetonitrile solution mixture (ratio: 1 to 9). The reaction was allowed to stir at room-temperature for 30 min and monitored via LC/MS. Upon completion the reaction was concentrated using a Argon stream then purified via reverse-phase C-18 column using water (with 0.1% formic acid) and acetonitrile (with 0.1% formic acid) as eluent to yield N—((R)-2-((S)-2-((R)-2-((2E,5S,6S,7S,8E)-7-((2-amino-2-methylpropanoyl)oxy)-N,2,6,8-tetramethyl-5-((methylthio)methoxy)deca-2,8-dienamido)-4-methylpentanamido)-N-methylpropanamido)-3-(4-chlorophenyl)propanoyl)-N-methylglycyl-L-alloisoleucine as an amorphous solid. The material was free-based by dissolving sample in saturated NaHCO₃ solution and extracted with a solution of methylene chloride/methanol mixture (ratio: 9 to 1). Combined organic layers were dried over Na₂SO₄, filtered, and the filtrate was concentrated in vacuo. The crude material was purified via reverse-phase C-18 column using water (with 0.1% formic acid) and acetonitrile (with 0.1% formic acid) as eluents to yield N—((R)-2-((S)-2-((R)-2-((2E,5S,6S,7S,8E)-7-((2-amino-2-methylpropanoyl)oxy)-N,2,6,8-tetramethyl-5-((methylthio)methoxy)deca-2,8-dienamido)-4-methylpentanamido)-N-methylpropanamido)-3-(4-chlorophenyl)propanoyl)-N-methylglycyl-L-alloisoleucine as free base as an amorphous solid (0.00084 g, 0.8 μmol, yield: 50.5%).

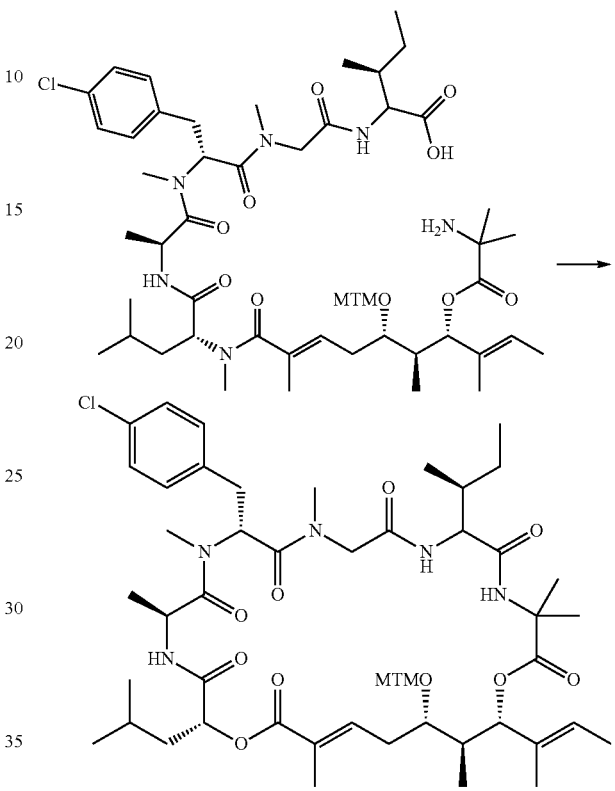

Step 8: To a reaction chamber equipped with stir bar N—((R)-2-((S)-2-((R)-2-((2E,5S,6S,7S,8E)-7-((2-amino-2-methylpropanoyl)oxy)-N,2,6,8-tetramethyl-5-((methylthio)methoxy)deca-2,8-dienamido)-4-methylpentanamido)-N-methylpropanamido)-3-(4-chlorophenyl)propanoyl)-N-methylglycyl-L-alloisoleucine (0.002 g, 2.18 μmol) was charged and dissolved in 2.18 mL methylene chloride and cooled to 0° C. using an ice bath 1-Hydroxy-7-azabenzotriazole (HOAt, 0.0034 g, 0.022 mmol) was added to the reaction mixture followed by 1-Ethyl-3-(3-dimethylaminopropyl)carbodiimide (EDC, 0.0042 g, 0.022 mmol) addition. The reaction was allowed to stir at 0° C. for 4 h before warm up to room-temperature for additional 12 h stirring and was monitored via LC/MS. Upon completion, the reaction was diluted with ethyl acetate and washed with 1 M citric acid solution, saturated NaHCO₃, and brine. The crude material was purified via reverse-phase C-18 column using water (with 0.1% formic acid) and acetonitrile (with 0.1% formic acid) as eluent to yield (6S,12R,15S,18R,24S,25S,26S,E)-26-((E)-but-2-en-2-yl)-6-((R)-sec-butyl)-12-(4-chlorobenzyl)-18-isobutyl-3,3,10,13,15,19,21,25-octamethyl-24-((methylthio)methoxy)-1-oxa-4,7,10,13,16,19-hexaazacyclohexacos-21-ene-2,5,8,11,14,17,20-heptaone as an amorphous solid (0.0008 g, 0.844 μmol, yield: 38.8%).

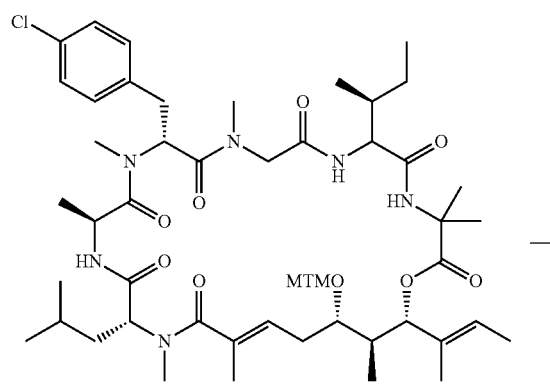

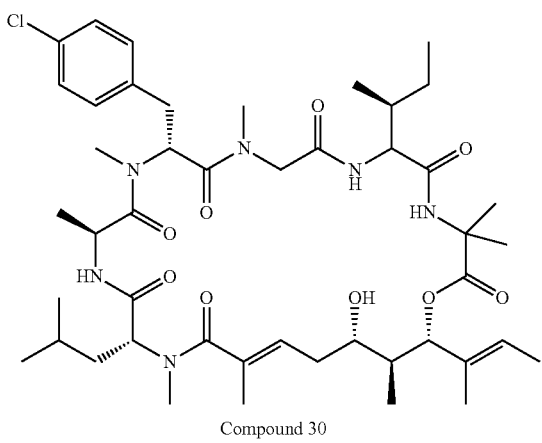

Compound 30

Step 9: To a reaction chamber equipped with stir bar (6S,12R,15S,18R,24S,25S,26S,E)-26-((E)-but-2-en-2-yl)-6-((R)-sec-butyl)-12-(4-chlorobenzyl)-18-isobutyl-3,3,10,13,15,19,21,25-octamethyl-24-((methylthio)methoxy)-1-oxa-4,7,10,13,16,19-hexaazacyclohexacos-21-ene-2,5,8,11,14,17,20-heptaone (0.0008 g, 0.844 μmol) was charged and dissolved in 0.350 mL of water/THF mixture (ratio: 3 to 2) followed by Silver nitrate (AgNO$_3$, 0.0057 g, 0.034 mmol), 2,6-lutidine (1.97 μL, 0.017 mmol). The reaction was sealed with Teflon and heated to 65° C. for 2 h and monitored via LC/MS. Upon completion, the reaction was diluted with ethyl acetate and 1 N hydrochloric acid solution and filtered through a pad of celite. The filtrate was washed with 1 N Hydrochloric acid solution, saturated NaHCO$_3$, and brine. Combined organic layers were dried over Na$_2$SO$_4$, filtered, and the filtrate was concentrated in vacuo. The crude material was purified via reverse phase C-18 column using water (with 0.1% formic acid) and acetonitrile (with 0.1% formic acid) as eluents to yield (6S,12R,15S,18R,24S,25S,26S,E)-26-((E)-but-2-en-2-yl)-6-((R)-sec-butyl)-12-(4-chlorobenzyl)-24-hydroxy-18-isobutyl-3,3,10,13,15,19,21,25-octamethyl-1-oxa-4,7,10,13,16,19-hexaazacyclohexacos-21-ene-2,5,8,11,14,17,20-heptaone as a white solid (0.0002 g, 0.237 μmol, yield: 28.0%). Observed HRMS (ESI) m/z: 887.5075 [M+H]$^+$.

Example 33

Synthesis of Compound 31

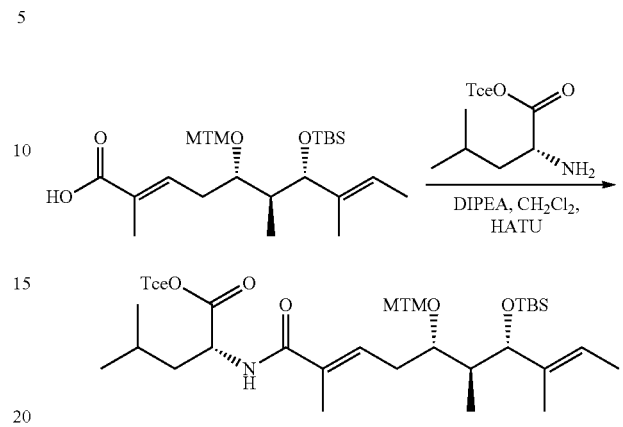

Step 1: To a reaction chamber equipped with stir bar (2E,5S,6S,7S,8E)-7-((tert-butyldimethylsilyl)oxy)-2,6,8-trimethyl-5-((methylthio)methoxy)deca-2,8-dienoic acid (0.055 g, 0.132 mmol) and 2,2,2-trichloroethyl D-leucinate (0.104 g, 0.396 mmol) were charged and dissolved in methylene chloride (1.32 mL, 0.1 M) followed by N, N-diisopropylethylamine (DIPEA, 0.092 mL, 0.528 mmol) addition. The reaction was cooled to 0° C. using an ice bath followed by (1-[Bis(dimethylamino)methylene]-1H-1,2,3-triazolo[4,5-b]pyridinium 3-oxid hexafluorophosphate) (HATU, 0.151 g, 0.396 mmol) addition. The reaction was stir at 0° C. for 10 min before warmed up to room-temperature for additional 2 h stirring and was monitored via LC/MS. Upon completion, the reaction was diluted with methylene chloride and washed with 1 M citric acid solution, saturated NaHCO$_3$ solution, and brine. Combined organic layers were dried over Na$_2$SO$_4$, filtered, and the filtrate was concentrated in vacuo. The crude material was purified via silica gel chromatography using hexanes and ethyl acetate as eluents to yield 2,2,2-trichloroethyl ((2E,5S,6S,7S,8E)-7-((tert-butyldimethylsilyl)oxy)-2,6,8-trimethyl-5-((methylthio)methoxy)deca-2,8-dienoyl)-D-leucinate as white solid (0.069 g, 0.105 mmol, 79%).

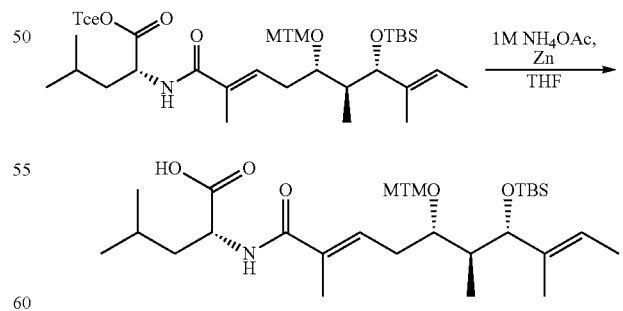

Step 2: To a reaction chamber equipped with stir bar 2,2,2-trichloroethyl ((2E,5S,6S,7S,8E)-7-((tert-butyldimethylsilyl)oxy)-2,6,8-trimethyl-5-((methylthio)methoxy) deca-2,8-dienoyl)-D-leucinate (0.08 g, 0.121 mmol) and zinc dust (6-9 mesh, 2.215 g, 33.90 mmol) were charged. The materials were suspended in tetrahydrofuran (THF, 1.20 mL, 0.2 M) followed by 1.20 mL of 1 M NH₄OAc solution addition. The reaction was allowed to stir at room-temperature for 2 h and monitored via LC/MS. Upon completion, the reaction was diluted with ethyl acetate and 1 M citric acid solution then filtered through a pad of celite. Filtrate was washed with 1 M citric acid solution, saturated NaHCO₃ solution, and brine. Combined organic layers were dried over Na₂SO₄, filtered and the filtrate was concentrated in vacuo. Crude material was purified via reverse-phase C-18 column using water (with 0.1% formic acid) and acetonitrile (with 0.1% formic acid) as eluents to yield ((2E,5S,6S,7S,8E)-7-((tert-butyldimethylsilyl)oxy)-2,6,8-trimethyl-5-((methylthio)methoxy)deca-2,8-dienoyl)-D-leucine as white solid (0.046 g, 0.087 mmol, 71.8%).

tion was diluted with methylene chloride and washed with 1 M citric acid solution, saturated NaHCO₃ solution, and brine. Combined organic layers were dried over Na₂SO₄, filtered, and the filtrate was concentrated in vacuo. The crude material was purified via silica gel chromatography using hexanes and ethyl acetate as eluents to yield 2,2,2-trichloroethyl N—((R)-2-((S)-2-((R)-2-((2E,5S,6S,7S,8E)-7-((tert-butyldimethylsilyl)oxy)-2,6,8-trimethyl-5-((methylthio)methoxy)deca-2,8-dienamido)-4-methylpentanamido)-N-methylpropanamido)-3-(4-chlorophenyl)propanoyl)-N-methylglycyl-L-alloisoleucinate as white solid (0.09 g, 0.081 mmol, yield: 93%).

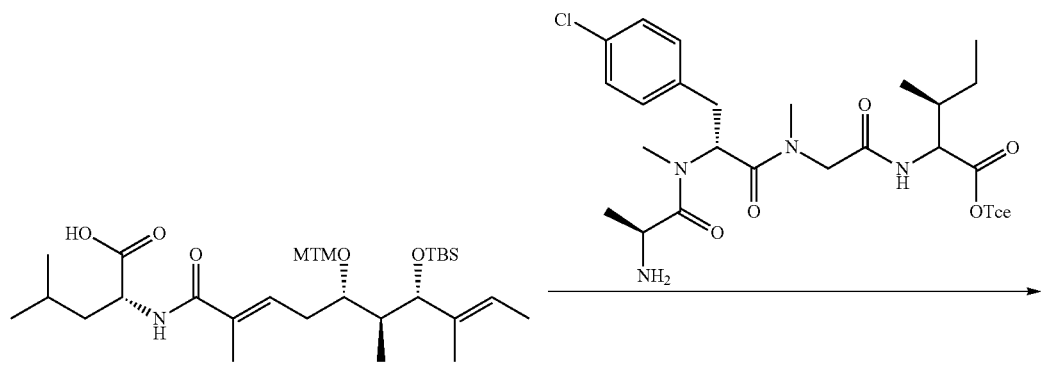

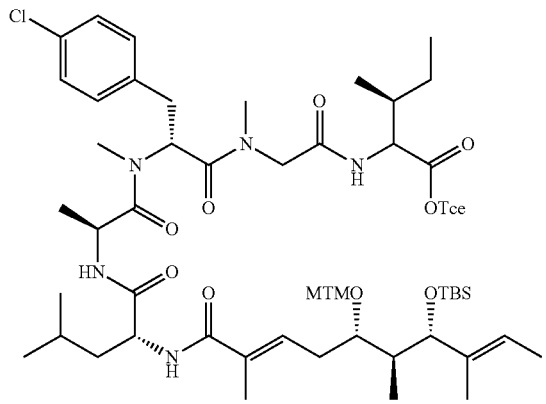

Step 3: To a reaction chamber equipped with stir bar 2,2,2-trichloroethyl N—((R)-2-((S)-2-amino-N-methylpropanamido)-3-(4-chlorophenyl)propanoyl)-N-methylglycyl-L-alloisoleucinate (0.078 g, 0.130 mmol) and ((2E,5S,6S,7S,8E)-7-((tert-butyldimethylsilyl)oxy)-2,6,8-trimethyl-5-((methylthio)methoxy)deca-2,8-dienoyl)-D-leucine (0.046 g, 0.087 mmol) were charged and dissolved in 0.347 mL methylene chloride. The reaction was cooled to 0° C. using an ice bath followed by N, N-diisopropylethylamine (DIPEA, 0.061 mL, 0.347 mmol) and (1-[Bis(dimethylamino)methylene]-1H-1,2,3-triazolo[4,5-b]pyridinium 3-oxid hexafluorophosphate) (HATU, 0.099 g, 0.260 mmol) addition. The reaction was stir at 0° C. for 10 min before warmed up to room-temperature for additional 4 h stirring and was monitored via LC/MS. Upon completion, the reac-

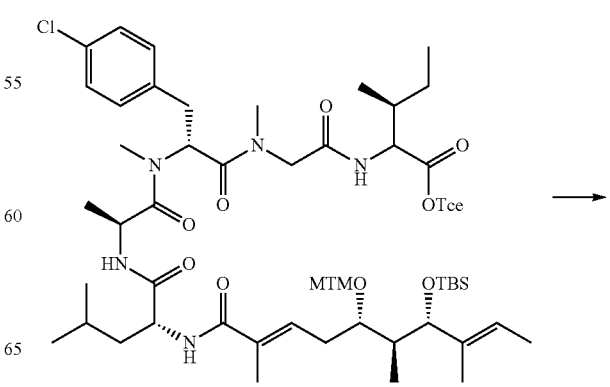

267

-continued

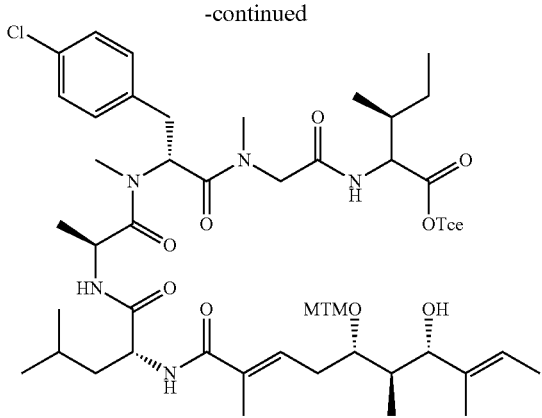

Step 4: To a reaction chamber equipped with stir bar 2,2,2-trichloroethyl N—((R)-2-((S)-2-((R)-2-((2E,5S,6S,7S,8E)-7-((tert-butyldimethylsilyl)oxy)-2,6,8-trimethyl-5-((methylthio)methoxy)deca-2,8-dienamido)-4-methylpentanamido)-N-methylpropanamido)-3-(4-chlorophenyl)propanoyl-N-methylglycyl-L-alloisoleucinate (0.09 g, 0.081 mmol) was charged and dissolved in a solution of 810 µL of THF/HF-pyridine/pyridine mixture (ratio: 4 to 1 to 1). The reaction chamber was sealed with Teflon and allowed to stir at 65° C. for 8 h and monitored via thin-layer-chromatography. Upon completion, the reaction was diluted with ethyl acetate followed by slow addition of saturated NaHCO$_3$ solution until gas evolution was completed. The reaction was washed with saturated NaHCO$_3$ solution and brine. Combined organic layers were dried over Na$_2$SO$_4$, filtered and the filtrate was concentrated in vacuo. The crude material was purified via silica gel chromatography using hexanes and ethyl acetate as eluents to yield 2,2,2-trichloroethyl N—((R)-3-(4-chlorophenyl)-2-((S)-2-((R)-2-((2E,5S,6R,7S,8E)-7-hydroxy-2,6,8-trimethyl-5-((methylthio)methoxy)deca-2,8-dienamido)-4-methylpentanamido)-N-methylpropanamido)propanoyl)-N-methylglycyl-L-alloisoleucinate as white solid (0.027 g, 0.027 mmol, yield: 33.4%).

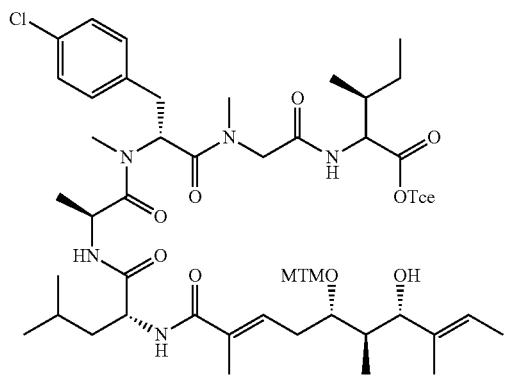

268

-continued

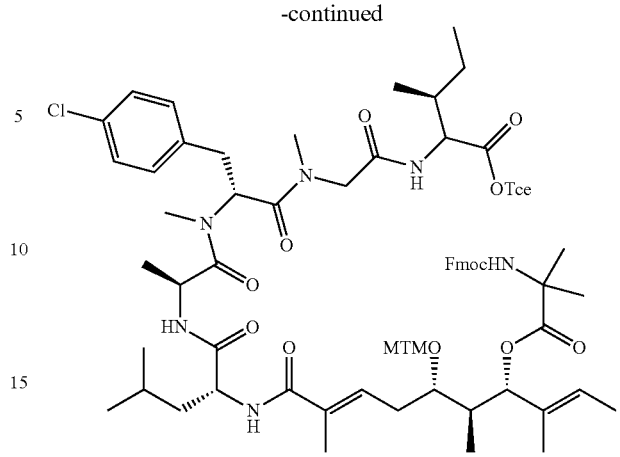

Step 5: To a reaction chamber equipped with stir bar 2,2,2-trichloroethyl N—((R)-3-(4-chlorophenyl)-2-((S)-2-((R)-2-((2E,5S,6R,7S,8E)-7-hydroxy-2,6,8-trimethyl-5-((methylthio)methoxy)deca-2,8-dienamido)-4-methylpentanamido)-N-methylpropanamido)propanoyl)-N-methylglycyl-L-alloisoleucinate (0.027 g, 0.027 mmol) and 2-(((((9H-fluoren-9-yl)methoxy)carbonyl)amino)-2-methylpropanoic acid (0.026 g, 0.081 mmol) were charged and dissolved in 0.135 mL methylene chloride followed by 4-dimethylaminopyridine (DMAP, 0.00331 g, 0.027 mmol). The reaction was cooled to 0° C. followed by 1-Ethyl-3-(3-dimethylaminopropyl)carbodiimide (EDC, 0.016 g, 0.081 mmol) addition. The reaction was kept at 0° C. and monitored via Thin-Layer-Chromatography for 6 h before it reached completion. Upon completion, the reaction was diluted with ethyl acetate and washed with 1 M citric acid solution and brine. Combined organic layers were dried over Na$_2$SO$_4$, filtered, and concentrated in vacuo. Crude material was purified via silica gel chromatography using hexanes and ethyl acetate as eluents to yield 2,2,2-trichloroethyl N—((R)-2-((S)-2-((R)-2-((2E,5S,6S,7S,8E)-7-((2-((((9H-fluoren-9-yl)methoxy)carbonyl)amino)-2-methylpropanoyl)oxy)-2,6,8-trimethyl-5-((methylthio)methoxy)deca-2,8-dienamido)-4-methylpentanamido)-N-methylpropanamido)-3-(4-chlorophenyl)propanoyl)-N-methylglycyl-L-alloisoleucinate (0.02 g, 0.027 µmol, yield: 56.6%) as white solid.

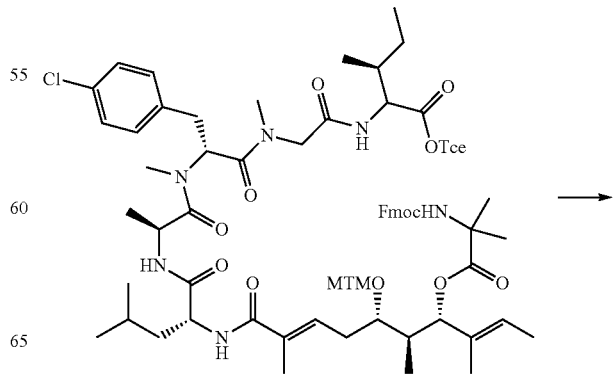

269
-continued

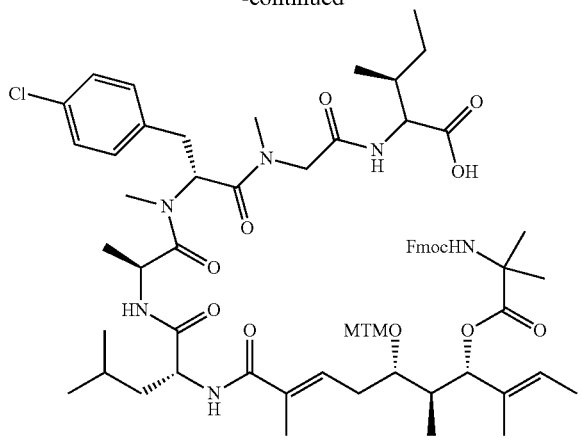

Step 6: To a reaction chamber equipped with stir bar, 2,2,2-trichloroethyl N—((R)-2-((S)-2-((R)-2-((2E,5S,6S,7S,8E)-7-((2-((((9H-fluoren-9-yl)methoxy)carbonyl)amino)-2-methylpropanoyl)oxy)-2,6,8-trimethyl-5-((methylthio)methoxy)deca-2,8-dienamido)-4-methylpentanamido)-N-methylpropanamido)-3-(4-chlorophenyl)propanoyl)-N-methylglycyl-L-alloisoleucinate (0.014 g, 0.0107 mmol) and zinc dust (6-9 mesh, 0.196 g, 3.00 mmol) were charged and suspended in 880 µL THF and 880 µL of 1 M NH₄OAc. The reaction was allowed to stir at room-temperature for 3 h and monitored via LC/MS. Upon completion, the reaction was diluted with ethyl acetate and 1 M citric acid then filtered through a pad of celite. The filtrate was washed with 1 M citric acid and brine. Combined organic layers were dried over Na₂SO₄, filtered, and the filtrate was concentrated in vacuo. The crude material was purified via reverse-phase C-18 column using water (with 0.1% formic acid) and acetonitrile (with 0.1% formic acid) as eluents to yield N—((R)-2-((S)-2-((R)-2-((2E,5S,6S,7S,8E)-7-((2-((((9H-fluoren-9-yl)methoxy)carbonyl)amino)-2-methylpropanoyl)oxy)-2,6,8-trimethyl-5-((methylthio)methoxy)deca-2,8-dienamido)-4-methylpentanamido)-N-methylpropanamido)-3-(4-chlorophenyl)propanoyl)-N-methylglycyl-L-alloisoleucine as white solid (0.01 g, 8.52 µmol, yield: 79%).

270
-continued

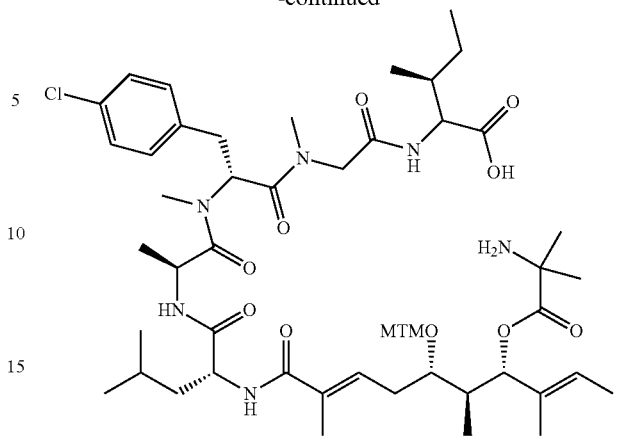

Step 7: To a reaction chamber equipped with stir bar N—((R)-2-((S)-2-((R)-2-((2E,5S,6S,7S,8E)-7-((2-((((9H-fluoren-9-yl)methoxy)carbonyl)amino)-2-methylpropanoyl)oxy)-2,6,8-trimethyl-5-((methylthio)methoxy)deca-2,8-dienamido)-4-methylpentanamido)-N-methylpropanamido)-3-(4-chlorophenyl)propanoyl)-N-methylglycyl-L-alloisoleucine (0.0072 g, 6.13 µmol) was charged and dissolved in 0.123 of a diethylamine/CH₃CN solution mixture (ratio: 1 to 9). The reaction was allowed to stir at room-temperature for 30 min and monitored via LC/MS. Upon completion the reaction was concentrated using a Argon stream then purified via reverse-phase C-18 column using water (with 0.1% formic acid) and acetonitrile (with 0.1% formic acid) as eluents to yield N—((R)-2-((S)-2-((R)-2-((2E,5S,6S,7S,8E)-7-((2-amino-2-methylpropanoyl)oxy)-2,6,8-trimethyl-5-((methylthio)methoxy)deca-2,8-dienamido)-4-methylpentanamido)-N-methylpropanamido)-3-(4-chlorophenyl)propanoyl)-N-methylglycyl-L-alloisoleucine as amorphous solid. The material was free-based by dissolving sample in saturated NaHCO₃ solution and extracted with a solution of methylene chloride/methanol mixture (ratio: 9 to 1). Combined organic layers were dried over Na₂SO₄, filtered, and the filtrate was concentrated in vacuo. The crude material was purified via reverse-phase C-18 column using water (with 0.1% formic acid) and acetonitrile (with 0.1% formic acid) as eluent to yield free base as amorphous solid (0.00584 g, 6.13 µmol, yield: 68.5%).

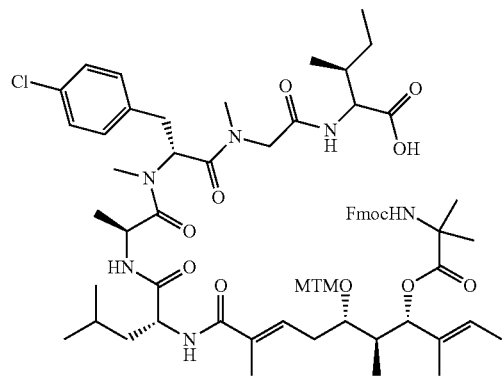

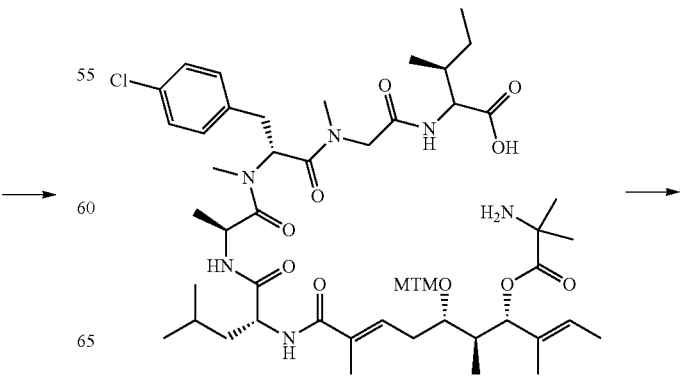

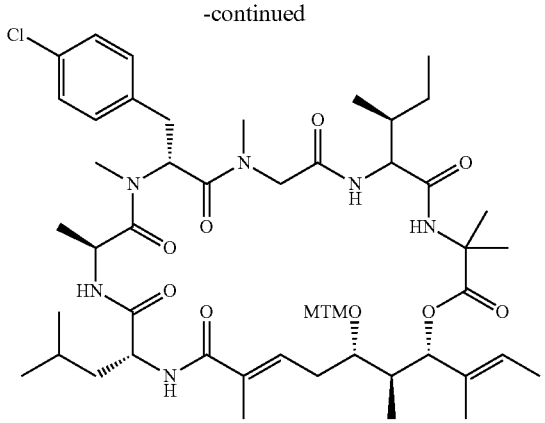

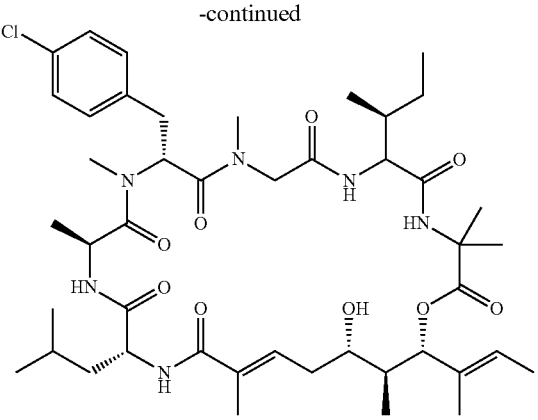

Compound 31

Step 8: To a reaction chamber equipped with stir bar N—((R)-2-((S)-2-((R)-2-((2E,5S,6S,7S,8E)-7-((2-amino-2-methylpropanoyl)oxy)-2,6,8-trimethyl-5-((methylthio)methoxy)deca-2,8-dienamido)-4-methylpentanamido)-N-methylpropanamido)-3-(4-chlorophenyl)propanoyl)-N-methylglycyl-L-alloisoleucine (0.00584 g, 6.14 μmol) was charged and dissolved in 6.14 mL methylene chloride and cooled to 0° C. using an ice bath. 1-Hydroxy-7-azabenzotriazole (HOAt, 9.46 mg, 0.061 mmol) was added to the reaction mixture followed by 1-Ethyl-3-(3-dimethylaminopropyl)carbodiimide (EDC, 0.012 g, 0.061 mmol) addition. The reaction was allowed to stir at 0° C. for 6 h before warm up to room-temperature for additional 12 h stirring and was monitored via LC/MS. Upon completion, the reaction was diluted with ethyl acetate and washed with 1 M citric acid solution, saturated NaHCO₃, and brine. The crude material was purified via reverse-phase C-18 column using water (with 0.1% formic acid) and acetonitrile (with 0.1% formic acid) as eluents to yield (6S,12R,15S,18R,24S,25S,26S,E)-26-((E)-but-2-en-2-yl)-6-((R)-sec-butyl)-12-(4-chlorobenzyl)-18-isobutyl-3,3,10,13,15,21,25-heptamethyl-24-((methylthio)methoxy)-1-oxa-4,7,10,13,16,19-hexaazacyclohexacos-21-ene-2,5,8,11,14,17,20-heptaone as an amorphous solid (0.0038 g, 6.14 μmol, yield: 66.3%).

Step 9: To a reaction chamber equipped with stir bar (6S,12R,15S,18R,24S,25S,26S,E)-26-((E)-but-2-en-2-yl)-6-((R)-sec-butyl)-12-(4-chlorobenzyl)-18-isobutyl-3,3,10,13,15,21,25-heptamethyl-24-((methylthio)methoxy)-1-oxa-4,7,10,13,16,19-hexaazacyclohexacos-21-ene-2,5,8,11,14,17,20-heptaone (0.0038 g, 4.07 μmol) was charged and dissolved in 0.122 mL of water/THF mixture (ratio: 1 to 4) followed by Silver nitrate (AgNO₃, 0.028 g, 0.163 mmol), 2,6-lutidine (9.48 μL, 0.081 mmol). The reaction was sealed with Teflon and heated to 65° C. for 2 h and monitored via LC/MS. Upon completion, the reaction was diluted with 0.05 N hydrochloric acid solution and filtered through a pad of celite. The filtrate was washed with 1 M citric acid solution, saturated NaHCO₃, and brine. Combined organic layers were dried over Na₂SO₄, filtered, the filtrate was concentrated in vacuo. The crude material was purified via reverse phase C-18 column using water (with 0.1% formic acid) and acetonitrile (with 0.1% formic acid) as eluents to yield (6S,12R,15S,18R,24S,25S,26S,E)-26-((E)-but-2-en-2-yl)-6-((R)-sec-butyl)-12-(4-chlorobenzyl)-24-hydroxy-18-isobutyl-3,3,10,13,15,21,25-heptamethyl-1-oxa-4,7,10,13,16,19-hexaazacyclohexacos-21-ene-2,5,8,11,14,17,20-heptaone as a white solid (0.002 g, 4.07 μmol, yield: 56.3%). Observed HRMS (ESI) m/z: 873.4887 [M+H]⁺.

Example 34

Synthesis of Compound 32

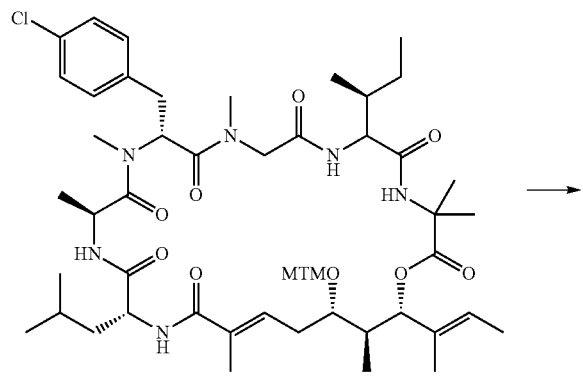

Step 1: To a stirring −78° C. solution of t-BuOK (3.4 g, 30.3 mmol) in THF (9.5 mL) was added cis-2-butene (3.39 g, 37.1783 mmol) followed by the addition of n-BuLi (15.8 mL, 1.915 M in hexanes). The resultant yellow suspension was stirred at −78° C. for 30 mins, subsequently at −45° C. for 60 min and cooled to −78° C. again. (+)-B-methoxydi-isopinocamphenyl borane (11.52 g, 36.41 mmol) in THF (21.1615 mL) was added slowly. After the addition was completed, the mixture was stirred at −78° C. for 1 hour and boron tifluoride etherate (10.67 mL, 48%) was added dropwise. Immediately afterwards, a solution of isobutyraldehyde (7.178 mL, 74 mmol) was added dropwise. The mixture was kept at −78° C. for 3 h. The reaction was quenched with saturated NaOAc and 30% $H_2O_2$. The resulting solution was stirred at −78° C. for 30 mins and warmed to room temperature over 12 h. The aqueous layer was extracted with $Et_2O$, and the combined organic layers were dried over $MgSO_4$, and concentrated under reduced pressure yielding a colorless liquid. The liquid was purified by flash chromatography (EtOAc/n-hexane) and the colorless alcohol. A2 was obtained as a colorless liquid. (2.5 g, 58%, 17.58 mmol). (Ref. Organic Letters, 10(15); 3223-3226; 2008)

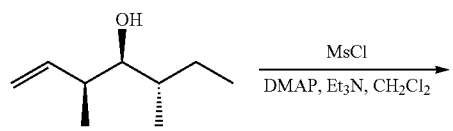

Step 2: To a stirring solution of (3S,4S,5S)-3,5-dimethylhept-1-en-4-ol (0.9 g, 6.33 mmol) in DCM (31.6 mL, 6.33 mmol, 0.2 M) was added triethylamine (0.768 g, 1.058 mL, 7.592 mmol) followed by methanesulfonyl chloride (0.869 g, 0.591 mL, 7.592 mmol) at 0° C. The reaction was allowed to stir at 0° C. for 30 min before warming to RT. After stirring for 1 h, the solvent was removed and the residue was purified with flash to afford (3S,4S,5S)-3,5-dimethylhept-1-en-4-yl methanesulfonate (0.5032 g, 36.1%, 2.284 mmol).

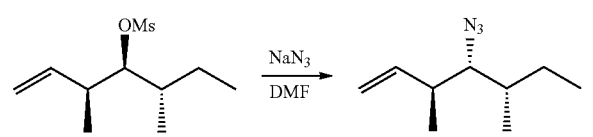

Step 3: To a stirring solution of (3S,4S,5S)-3,5-dimethylhept-1-en-4-yl methanesulfonate (1.424 g, 6.46 mmol) in DMF (6.31 mL, 6.46 mmol) was added sodium azide (1.260 g, 19.389 mmol) and heated at 65° C. overnight. After stirring overnight, the reaction was diluted with saturated sodium chloride and ethyl acetate. The organic phase was washed with brine, dried over $Na_2SO_4$ and concentrated in vacuo. The residue was purified with flash to afford (3S,4R,5S)-4-azido-3,5-dimethylhept-1-ene (0.451 g, 42%, 2.7 mmol).

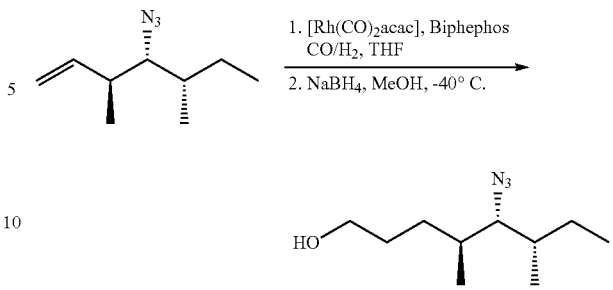

Step 4: To a stirring solution of Dicarbonylacetylacetonato rhodium (I) (2.071 mg, 7.998 μmol) in THF (3.058 g, 3.476 mL, 0.597 mmol) was added Biphephos (14 mg, 0.24 μmol) and (3S,4R,5S)-4-azido-3,5-dimethylhept-1-ene (0.1 g, 0.597 mmol) in THF (5 mL). The reaction was vacumn flushed with carbon/monoxide/hydrogen gas and stirred for 48 hours. After 48 hours, workup/purification was not necessary and carried forward to $NaBH_4$ reaction. (Ref. Adv. Synth. Catal. 2005, 347, 1488-1494)

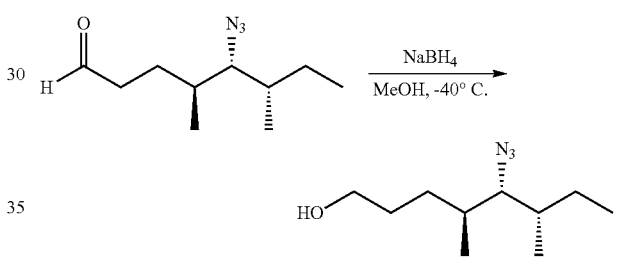

Step 5: To a stirring solution of 5-azido-4,6-dimethyloctanal (0.714 g, 3.619 mmol) in MeOH (23.87 mL, 590 mmol) was added $NaBH_4$ (0.684 g, 18.095 mmol) at −40° C. and stirred for 2 h. The solvent was removed and the residue was purified with flash to afford (4S,5R,6S)-5-azido-4,6-dimethyloctan-1-ol (0.42 g, 58.2%, 2.107 mmol).

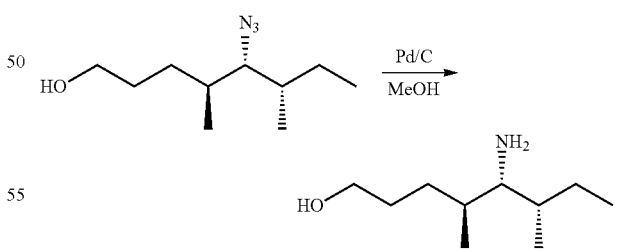

Step 6: To a stirring solution of palladium on Carbon (0.027 g, 0.251 mmol) in MeOH (0.5 mL, 12.36 mmol) was added (4S,5R,6S)-5-azido-4,6-dimethyloctan-1-ol in MeOH (0.5 mL, 12.36 mmol). The reaction was stirred for 30 min and filtered through a pad of celite using methanol to afford (4S,5R,6S)-5-amino-4,6-dimethyloctan-1-ol (0.0487 g, 88%, 0.281 mmol)

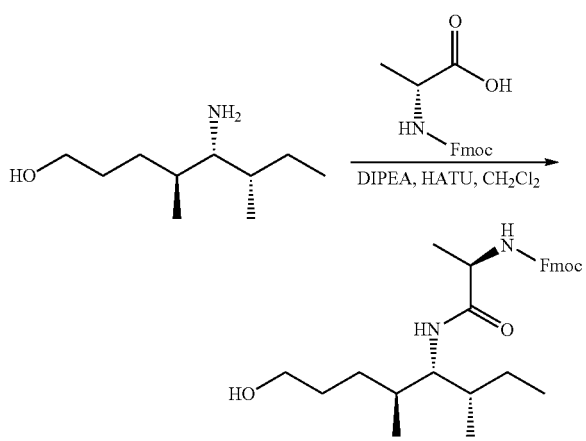

Step 7: To a stirring solution of (4S,5R,6S)-5-amino-4,6-dimethyloctan-1-ol (0.0487 g, 0.281 mmol) in DCM (0.7 mL, 10.88 mmol) was added (((9H-fluoren-9-yl)methoxy)carbonyl)-D-alanine (0.262 g, 0.843 mmol), DIPEA (0.145 g, 0.196 mL, 1.124 mmol) and HATU (0.128 g, 0.337 mmol). The reaction was stirred for 1 h, the solution was diluted with citric acid solution and EtOAc. The organic phase was washed with aqueous $NaHCO_3$ and brine, dried over $Na_2SO_4$ and concentrated in vacuo. The residue was purified with flash to afford (9H-fluoren-9-yl)methyl ((R)-1-(((3S,4R,5S)-8-hydroxy-3,5-dimethyloctan-4-yl)amino)-1-oxopropan-2-yl)carbamate (0.0432 g, 33%, 0.093 mmol).

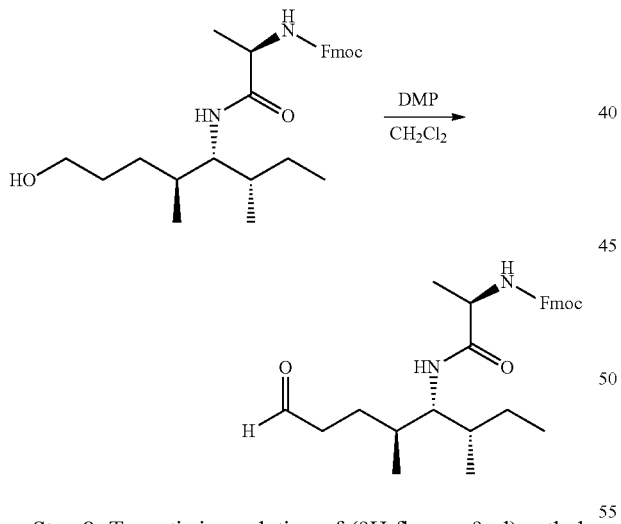

Step 8: To a stirring solution of (9H-fluoren-9-yl)methyl ((R)-1-(((3S,4R,5S)-8-hydroxy-3,5-dimethyloctan-4-yl)amino)-1-oxopropan-2-yl)carbamate (0.0434 g, 0.093 mmol) in DCM (1.098 g, 0.832 mL, 12.93 mmol) was added DMP (0.051 g, 0.120 mmol) at 0° C. The reaction was stirred for (h), the solution was diluted with pH 7.4 buffer, sodium thiosulfate, and $Et_2O$. The organic phase was washed with saturated sodium bicarbonate solution, brine, and $Na_2SO_4$ and concentrated in vacuo. The residue was purified with flash to afford (9H-fluoren-9-yl)methyl ((R)-1-(((3S,4R,5S)-3,5-dimethyl-8-oxooctan-4-yl)amino)-1-oxopropan-2-yl)carbamate (0.043 g, 100%, 0.093 mmol).

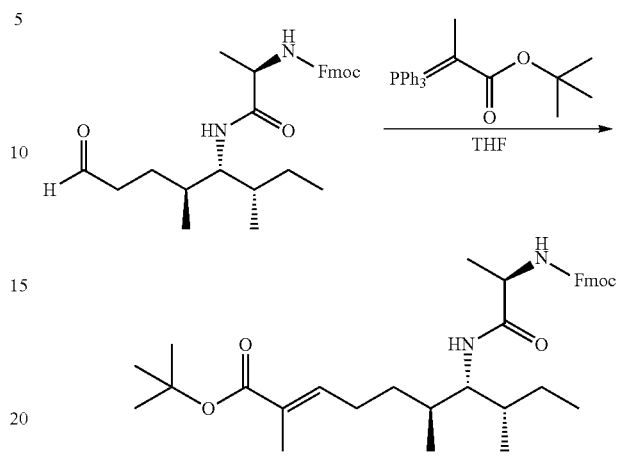

Step 9: To a stirring solution of (9H-fluoren-9-yl)methyl (1-(((3S,4R,5S)-3,5-dimethyl-8-oxooctan-4-yl)amino)-1-oxopropan-2-yl)carbamate (0.043 g, 0.093 mmol) in THF (3 mL, 36.6 mmol) was added tert-butyl 2-(triphenyl-$\lambda^5$-phosphanylidene)propanoate (0.108 g, 0.278 mmol) and stirred for 3 hours, the solvent was removed and the residue was purified with flash to afford tert-butyl (6S,7R,8S,E)-7-((R)-2-((((9H-fluoren-9 yl)methoxy)carbonyl)amino)propanamido)-2,6,8-trimethyldec-2-enoate (0.0415 g, 78%, 0.072 mmol).

Step 10: To a stirring solution of tert-butyl (6S,7R,8S,E)-7-(2-((((9H-fluoren-9-yl)methoxy)carbonyl)amino)propanamido)-2,6,8-trimethyldec-2-enoate (0.04 g, 0.069 mmol) in DCM (1 mL, 15.54 mmol) was added TFA (1 mL, 12.98 mmol) and stirred for 30 min. The solvent was removed and the residue was purified with flash to afford (6S,7R,8S,E)-7-((R)-(2-((((9H-fluoren-9-yl)methoxy)carbonyl)amino)propanamido)-2,6,8-trimethyldec-2-enoic acid in quantitative yield.

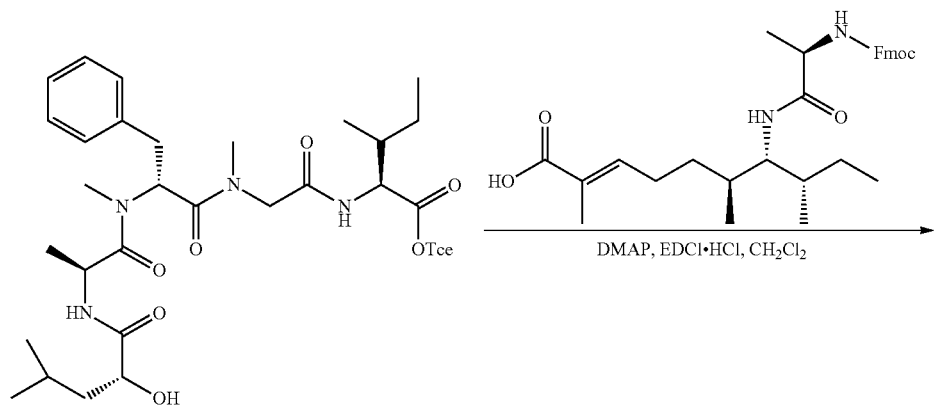

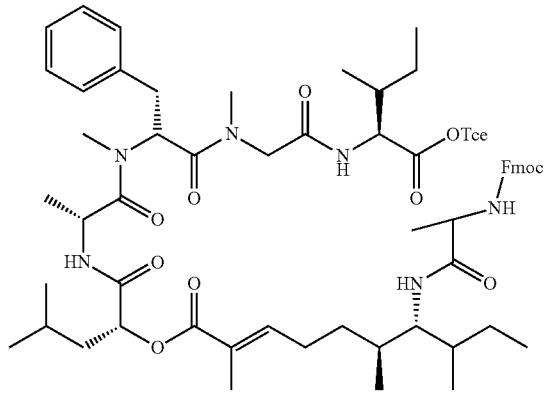

Step 11: To a stirring solution of (6S,7R,8S,E)-7-((R)-2-((((9H-fluoren-9-yl)methoxy)carbonyl)amino)propanamido)-2,6,8-trimethyldec-2-enoic acid (0.045 g, 0.086 mmol) in DCM (1 mL, 15.54 mmol) was added 2,2,2-trichloroethyl N—(N—(((R)-2-hydroxy-4-methylpentanoyl)-D-alanyl)-N-methyl-D-phenylalanyl)-N-methyl-glycyl-L-alloisoleucinate (0.070 g, 0.103 mmol), DMAP (0.010 g, 0.086 mmol) and EDC (0.049 g, 0.259 mmol) and stirred for 18 h. The reaction was diluted with citric acid solution and EtOAc. The organic phase was washed with aqueous NaHCO₃ and brine, dried over Na₂SO₄ and concentrated in vacuo. The residue was purified with flash to afford 2,2,2-trichloroethyl (2S,8R,11R,14R)-14-(((6S,7R,E)-7-(2-((((9H-fluoren-9-yl)methoxy)carbonyl)amino)propanamido)-2,6,8-trimethyldec-2-enoyl)oxy)-8-benzyl-2-((R)-sec-butyl)-6,9,11,16-tetramethyl-4,7,10,13-tetraoxo-3,6,9,12-tetraazaheptadecanoate (0.0623 g, 61%, 0.053 mmol).

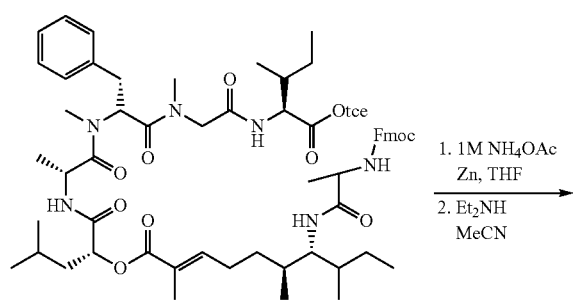

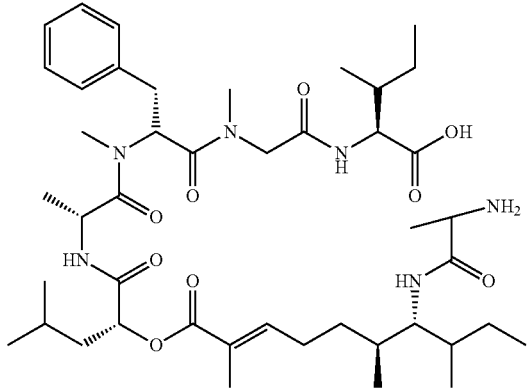

Step 12: To a solution of 2,2,2-trichloroethyl (2S,8R,11R,14R)-14-(((6S,7R,E)-7-(2-((((9H-fluoren-9-yl)methoxy)carbonyl)amino)propanamido)-2,6,8-trimethyldec-2-enoyl)oxy)-8-benzyl-2-((R)-sec-butyl)-6,9,11,16-tetramethyl-4,7,10,13-tetraoxo-3,6,9,12-tetraazaheptadecanoate (0.062 g, 0.052 mmol) In THF (1.854 g, 2.107 mL, 0.052 mmol) was added 1M NH₄OAc (0.113M, 470 µL) and zinc (0.964 g, 14.749 mmol) and stirred for 4 h. The reaction was then filtered through a pad of celite using acetonitrile and concentrated in vacuo. The residue was dissolved in MeCN (0.5 mL) and diethylamine (0.5 mL), and stirred for 1 h, and the solvent was removed. the residue was purified with C18 reverse chromatography (MeCN+0.1% formic acid|H₂O+ 0.1% formic acid to afford N—(N-(((2R)-2-(((6S,7R,E)-7-

(2-aminopropanamido)-2,6,8-trimethyldec-2-enoyl)oxy)-4-methylpentanoyl)-D-alanyl)-N-methyl-D-phenylalanyl)-N-methylglycyl-L-alloisoleucine (0.065 g, 149%, 0.078 mmol).

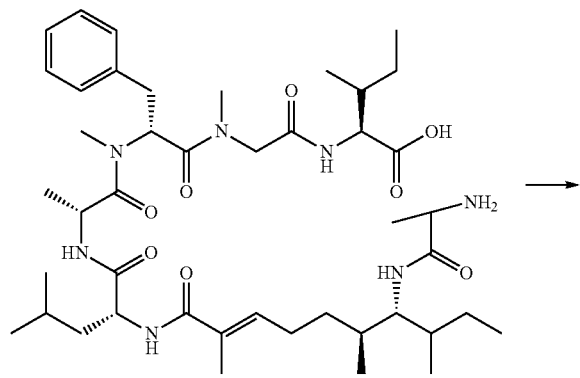

Step 13: To a solution of N—(N-(((2R)-2-(((6S,7R,E)-7-(2-aminopropanamido)-2,6,8-trimethyldec-2-enoyl)oxy)-4-methylpentanoyl)-D-alanyl)-N-methyl-D-phenylalanyl)-N-methylglycyl-L-alloisoleucine (0.065 g, 0.078 mmol) in DCM/DMF was added 1-hydroxy-7-azabenzotriazole (0.106 g, 0.783 mmol), and EDC (0.150 g, 0.783 mmol), and stirred for 18 h. The solvent was removed and the diluted with EtOAc and citric acid solution. The organic phase was washed with NaHCO₃, brine, dried over sodium sulfate and concentrated in vacuo. The residue was purified with flash to afford (2R,5S,8R,14S,17R,20R,21S,E)-8-benzyl-14-((R)-sec-butyl)-20-((S)-sec-butyl)-2-isobutyl-5,7,10,17,21,25-hexamethyl-1-oxa-4,7,10,13,16,19-hexaazacyclohexacos-24-ene-3,6,9,12,15,18,26-heptaone (0.0166 g, 26.2%, 0.021 mmol).

Example 35

Synthesis of Compound 33

Preparation of Compound 33 is very similar to the synthesis of Compound 32 with the replacement of one amino acid from Fmoc-D-Ala to Fmoc-Isobutylic Acid. The pentapeptide has also been replaced with a halogenated pentapeptide (X=Cl). The last step in the synthesis is described below.

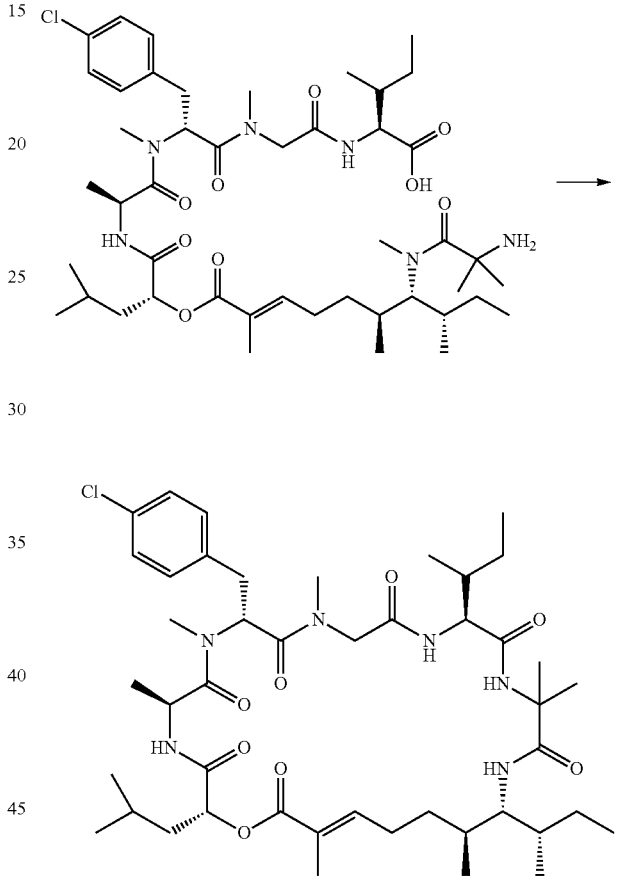

To a solution of N-((2R)-2-((2R)-2-((2R)-2-(((6S,7R,E)-7-(2-amino-2-methylpropanamido)-2,6,8-trimethyldec-2-enoyl)oxy)-4-methylpentanamido)-N-methylpropanamido)-3-(4-chlorophenyl)propanoyl)-N-methylglycyl-L-alloisoleucine (0.063 g, 0.072 mmol) in DCM/DMF was added 1-hydroxy-7-azabenzotriazole (0.098 g, 0.718 mmol) and EDC (0.138 g, 0.718 mmol) and stirred for 18 h. The solvent was removed and the diluted with EtOAc and citric acid solution. The organic phase was washed with NaHCO₃, brine, dried over sodium sulfate and concentrated in vacuo. The residue was purified with flash to afford (2R,5S,8R,14S,20S,21S,E)-20-((E)-but-2-en-2-yl)-14-((R)-sec-butyl)-8-(4-chlorobenzyl)-2-isobutyl-5,7,10,17,17,21,25-heptamethyl-1-oxa-4,7,10,13,16,19-hexaazacyclohexacos-24-ene-3,6,9,12,15,18,26-heptaone (0.008 g, 13%, 9.33 μmol).

Example 36

Synthesis of Conjugate L1

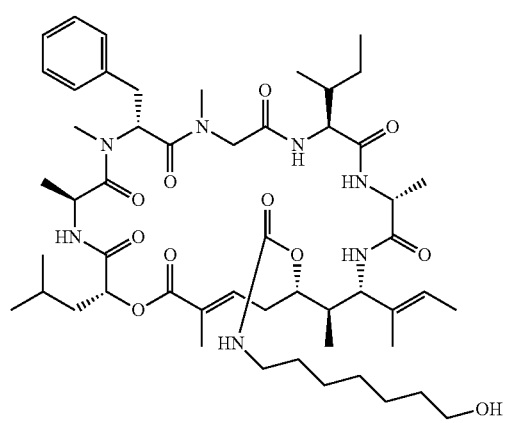

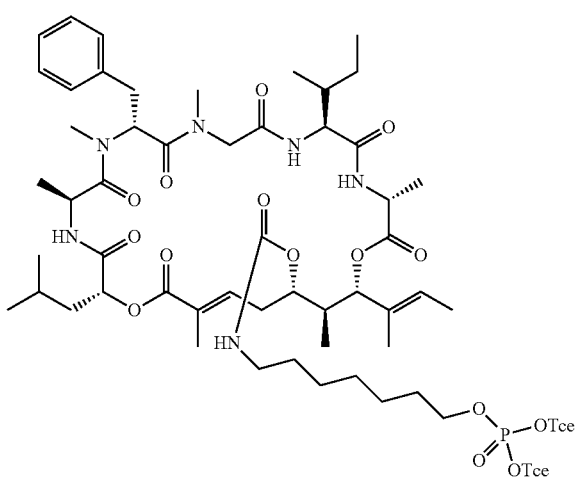

To the solution of (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (7-hydroxyheptyl)carbamate (0.053 mmol, 52 mg) in pyridine (12.36 mmol, 1 mL) was added Bis(2,2,2-trichloroethyl) phosphorochloridate (0.212 mmol 0.080 g). The mixture was stirred for 4 h and purified with RP-flash to afford (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (7-((bis(2,2,2-trichloroethoxy)phosphoryl)oxy)heptyl)carbamate (37 mg, 52.8%). Observed LRMS (ESI) m/z: 1323.3 [M+H]+.

Example 37

Synthesis of Conjugate L2

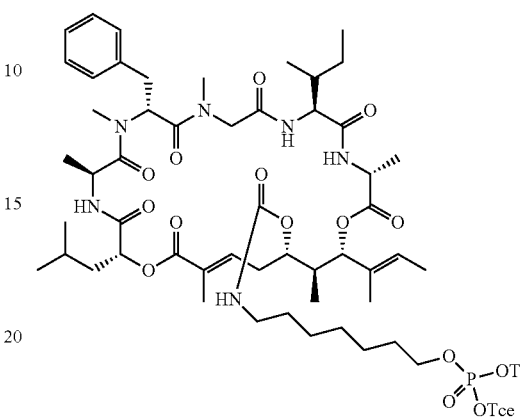

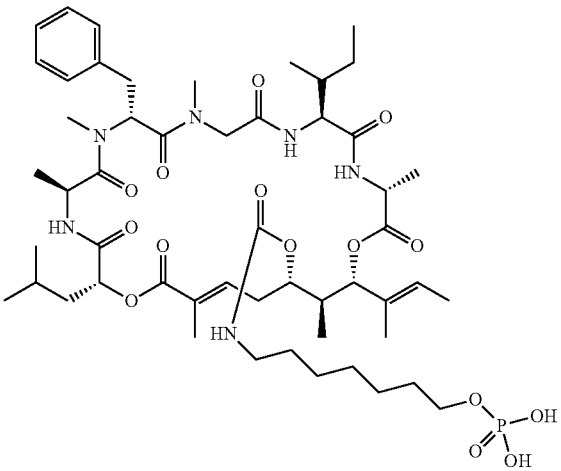

To the solution of (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl(7-((bis(2,2,2-trichloroethoxy)phosphoryl)oxy)heptyl)carbamate (0.028 mmol, 37 mg) in THF (24.41 mmol, 2 mL) and ammonium acetate (0.400 mmol, 0.4 mL) was added zinc (2.79 mmol, 0.182 g). The mixture was stirred overnight and filtered over celite. The volatile was removed and the residue was purified with RP-flash to afford (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (7-(phosphonooxy)heptyl)carbamate (24 mg, 81%). Observed LRMS (ESI) m/z: 1063.5 [M+H]+.

Example 38

Synthesis of Conjugate L3

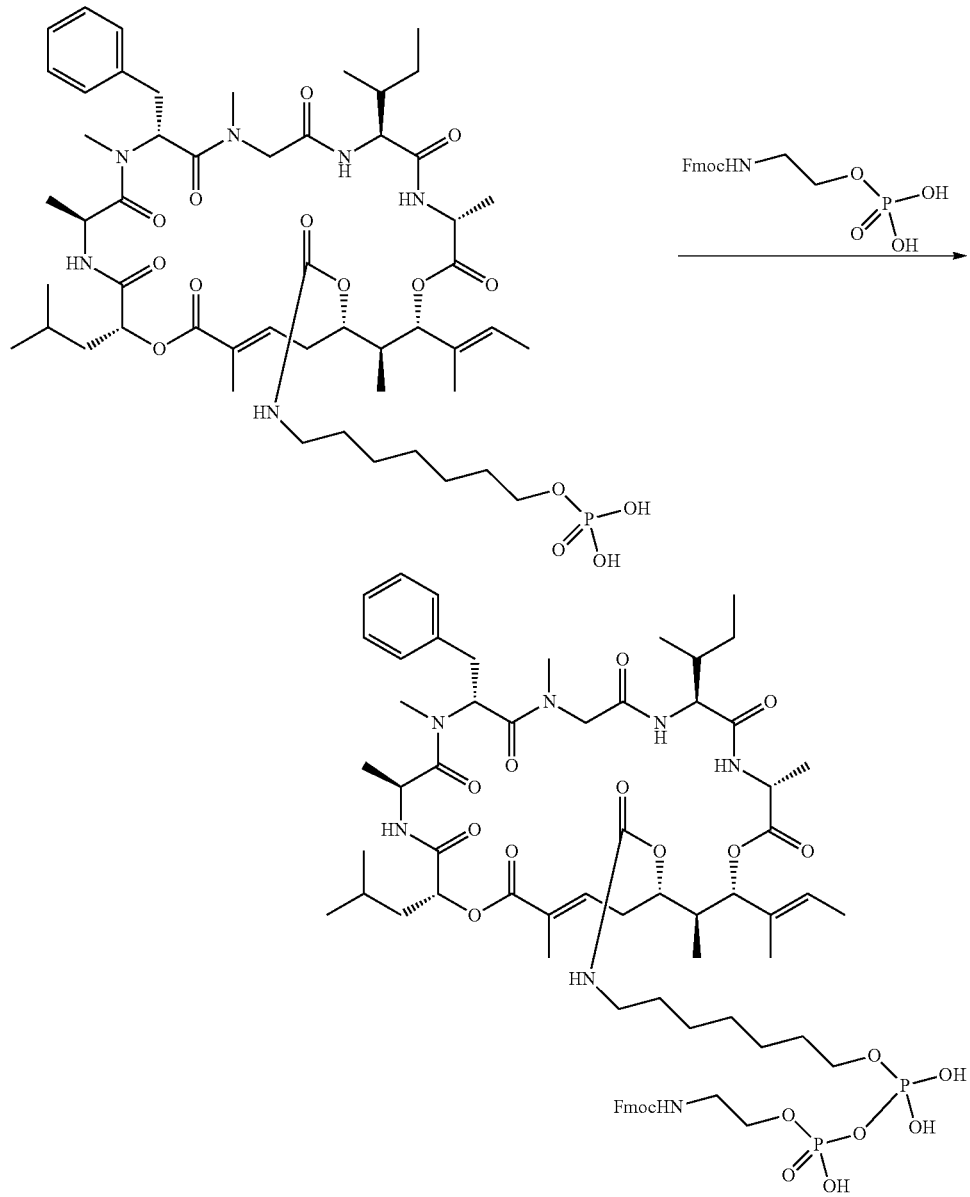

To the solution of (9H-fluoren-9-yl)methyl (2-(phosphonooxy)ethyl)carbamate (0.056 mmol, 0.021 g) in DMF (6.46 mmol, 0.5 mL) was added CDI (0.113 mmol, 0.018 g) and triethylamine (0.056 mmol, 7.87 μL). The mixture was stirred for 4 h and MeOH was added, then the volatile was removed. The residue was added DMF (6.46 mmol, 0.5 mL), zinc chloride (0.169 mmol, 0.023 g) and (2R,5S,8R,14S, 17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (7-(phosphonooxy) heptyl)carbamate (5.64 μmol, 6 mg) and stirred at 37 degree overnight. The mixture was purified with RP-flash to afford (9H-fluoren-9-yl)methyl (2-((((((7-(((((2R,5S,8R,14S,17R, 20S,21S,22S,E)-8-benzyl-20-((E)-but-2-en-2-yl)-14-((R)-sec-butyl)-2-isobutyl-5,7,10,17,21,25-hexamethyl-3,6,9,12, 15,18,26-heptaoxo-1,19-dioxa-4,7,10,13,16-pentaazacyclohexacos-24-en-22-yl)oxy)carbonyl)amino) heptyl)oxy)(hydroxy)phosphoryl)oxy)(hydroxy) phosphoryl)oxy)ethyl) carbamate (7.95 mg, 100%) with some impurity. Observed LRMS (ESI) m/z: 1408.5 [M+H]+.

Example 39

Synthesis of Conjugate L4

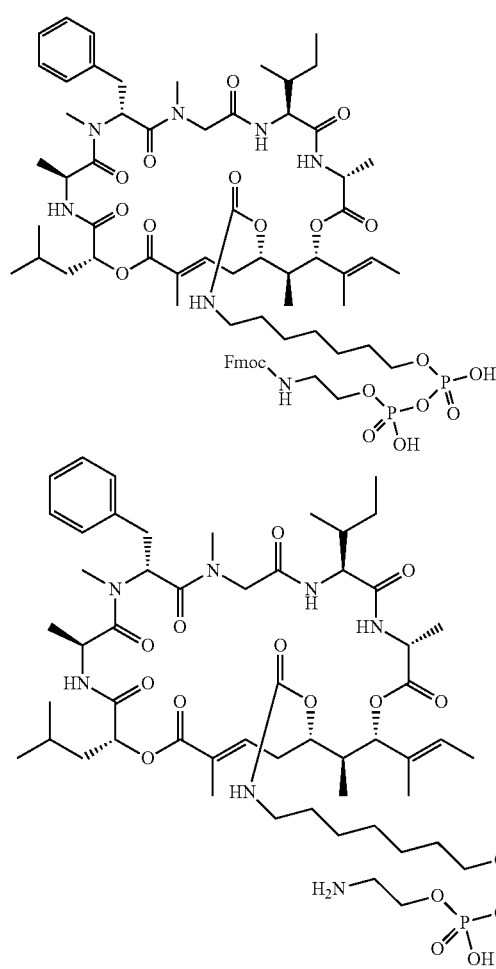

Figure 3:
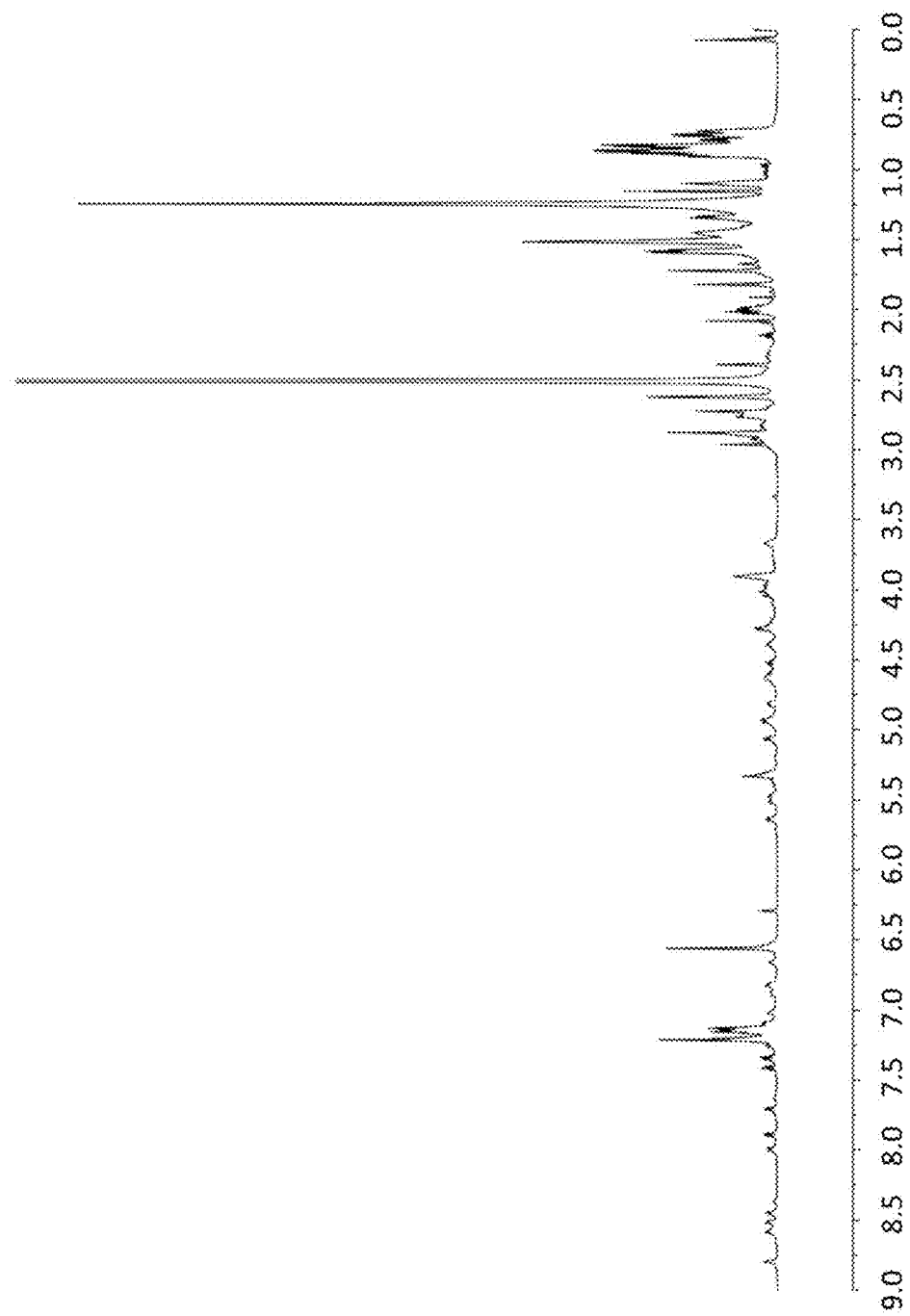
FIG. 3 is a $^1$H NMR spectrum of Conjugate L4 in DMSO-d6.

The solution of (9H-fluoren-9-yl)methyl (2-((((((7-(((((2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl)oxy)carbonyl)amino)heptyl)oxy)(hydroxy)phosphoryl)oxy)(hydroxy)phosphoryl)oxy)ethyl) carbamate (1.420 µmol, 2 mg) in DMF (12.91 mmol, 1 mL) and diethylamine (0.957 mmol, 0.1 mL) was stirred overnight and the volatile was removed. The residue was purified with RP-flash to afford (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (7-(((((2-aminoethoxy)(hydroxy)phosphoryl)oxy)(hydroxy)phosphoryl)oxy)heptyl)carbamate (1.2 mg, 71.2%). Observed HRMS (ESI) m/z: 1186.5698 [M+H]+. The $^1$H NMR spectrum of Conjugate L4 is shown in FIG. 3.

Example 40

Synthesis of Conjugate L5

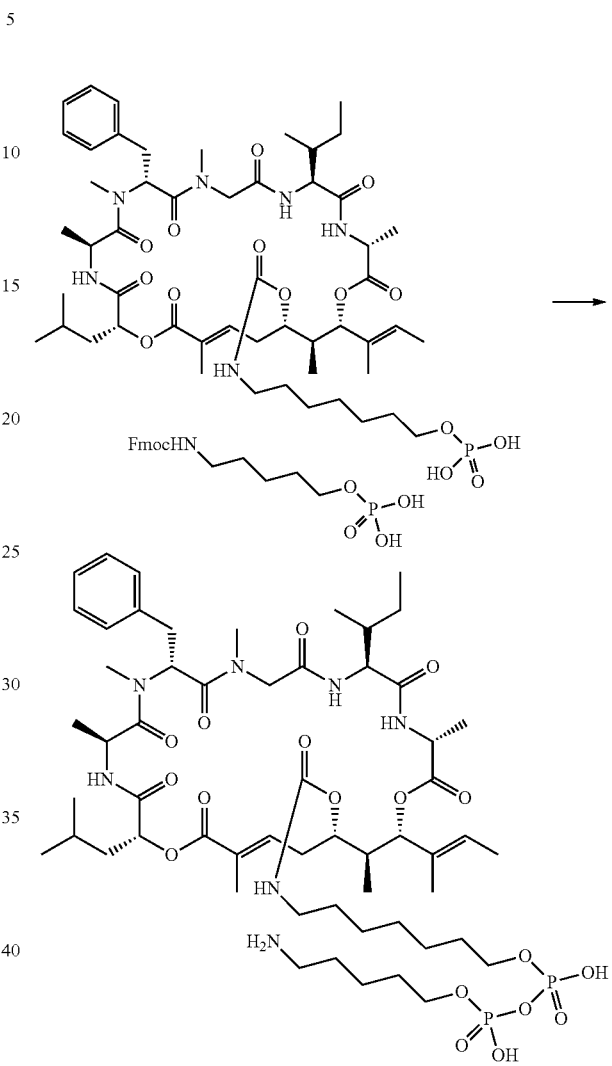

Figure 4:
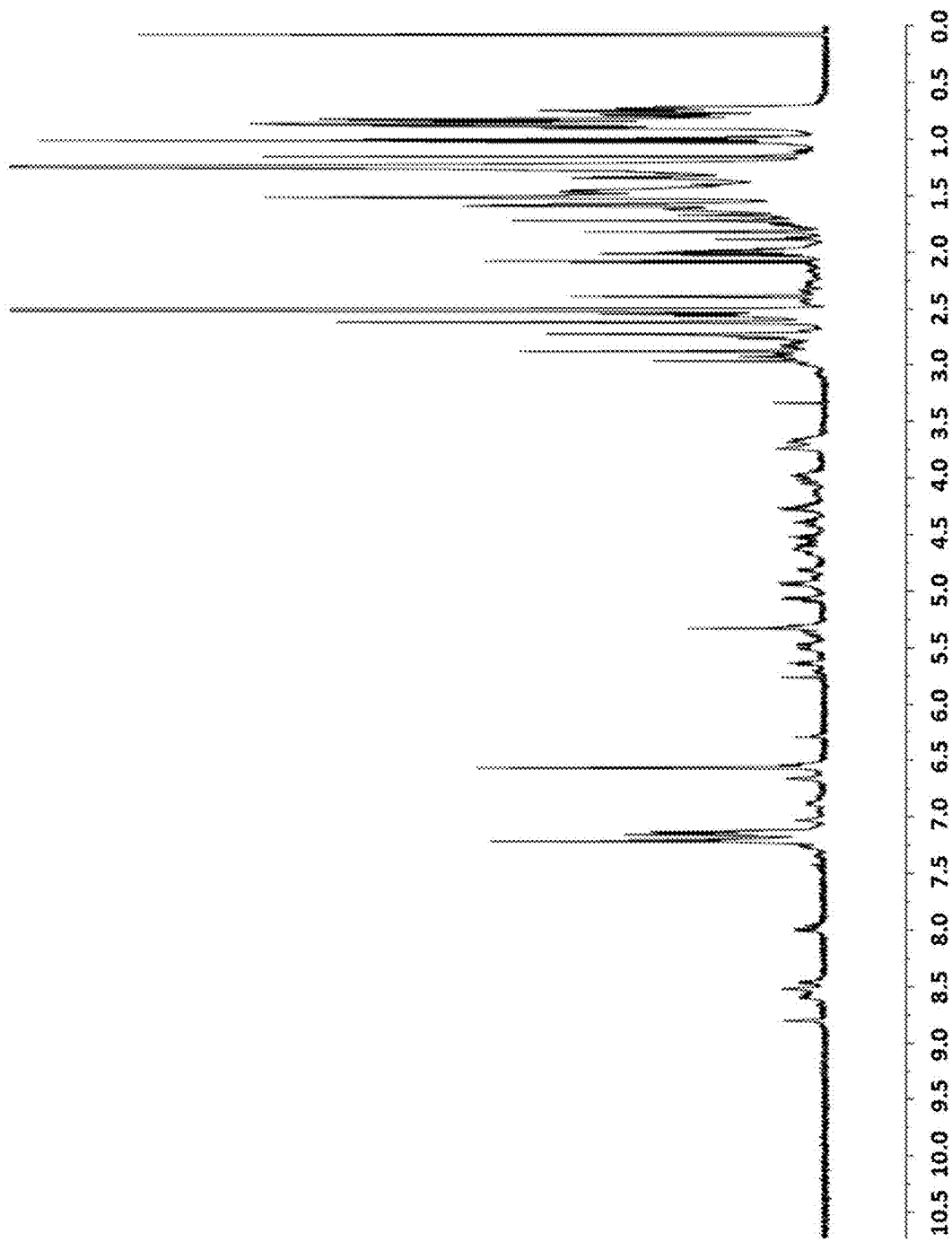
FIG. 4 is a $^1$H NMR spectrum of Conjugate L5 in DMSO-d6.

To the solution of (9H-fluoren-9-yl)methyl (5-(phosphonooxy)pentyl)carbamate (0.019 mmol, 7.63 mg) in DMF (6.46 mmol, 0.5 mL) was added CDI (0.038 mmol, 6.10 mg) and triethylamine (0.019 mmol, 2.62 µL). The mixture was stirred for 4 h and MeOH was added, then the volatile was removed. The residue was added DMF (6.46 mmol, 0.5 mL), zinc chloride (0.188 mmol, 0.026 g) and (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (7-(phosphonooxy)heptyl)carbamate (1.881 µmol, 2 mg) and stirred at 37 degree overnight. The mixture was purified with RP-flash to afford an intermediate, which was treated with MeCN (9.57 mmol, 0.5 ml) and diethylamine (0.957 mmol, 0.1 mL) for overnight and the volatile was removed and the residue was purified with RP-flash to afford (2R,5S,8R,14S,17R,20S,21S,22S,E)-8-benzyl-20-((E)-but-2-en-2-yl)-14-((R)-secbutyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (7-((((((5-aminopentyl)oxy)(hydroxy)phosphoryl)oxy)(hydroxy)phosphoryl)oxy)heptyl)carbamate (1.5 mg, 64.9%). Observed LRMS (ESI) m/z: 1228.5 [M+H]+. The 1H NMR spectrum of Conjugate L5 is shown in FIG. 4.

Example 41

Synthesis of Conjugate L6

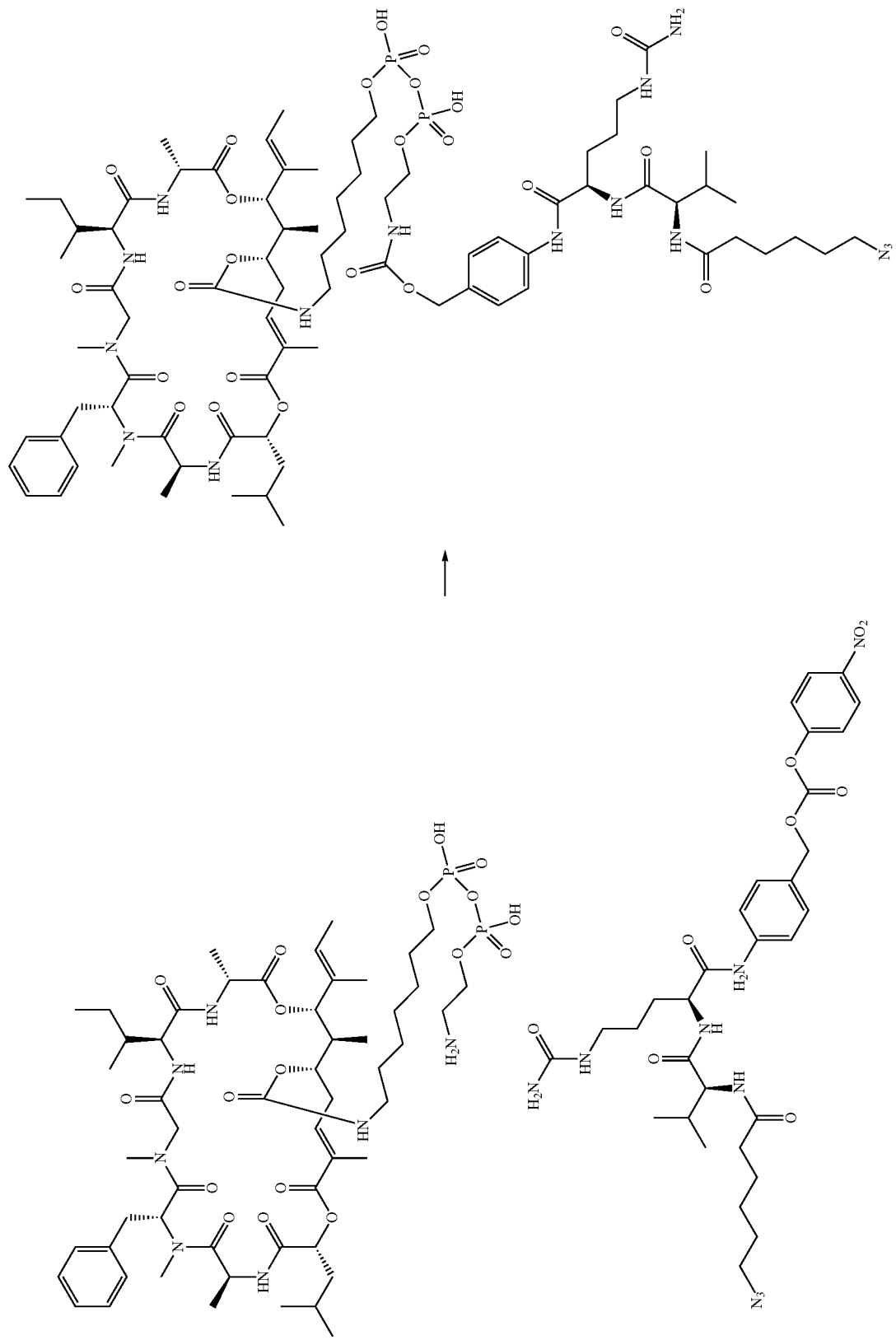

Figure 5:
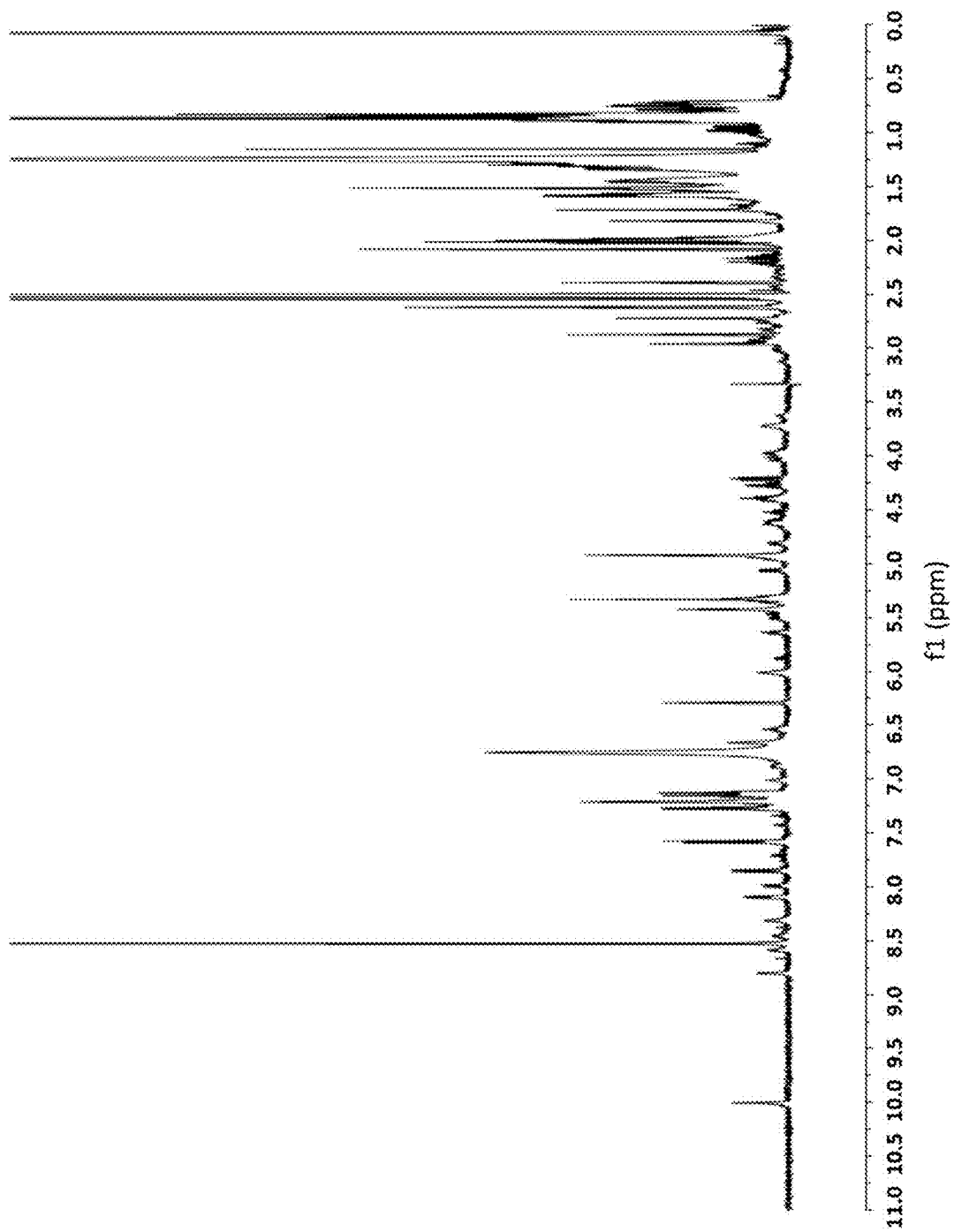
FIG. 5 is a $^1$H NMR spectrum of Conjugate L6 in DMSO-d6.

To the solution of (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (7-(((((2-aminoethoxy)(hydroxy)phosphoryl)oxy)(hydroxy)phosphoryl)oxy)heptyl)carbamate (0.674 µmol, 0.8 mg) and undefined (1.463 µmol, 1 mg) in Hünig's base (0.172 mmol, 30 µL) was added Hünig's base (0.172 mmol, 30 µL). The mixture was stirred overnight and purified with RP-flash to afford (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (7-(((((2-((((4-((R)-2-((R)-2-(6-azidohexanamido)-3-methylbutanamido)-5-ureidopentanamido)benzyl)oxy)carhonyl)amino)ethoxy)(hydroxy)phosphoryl)oxy)(hydroxy) phosphoryl)oxy)heptyl)carbamate (0.8 mg, 68.5%). Observed LRMS (ESI) m/z: 1730.9 [M+H]+. The $^1$H NMR spectrum of Conjugate L6 is shown in FIG. 5.

Example 42

Synthesis of Conjugate L7

293 294
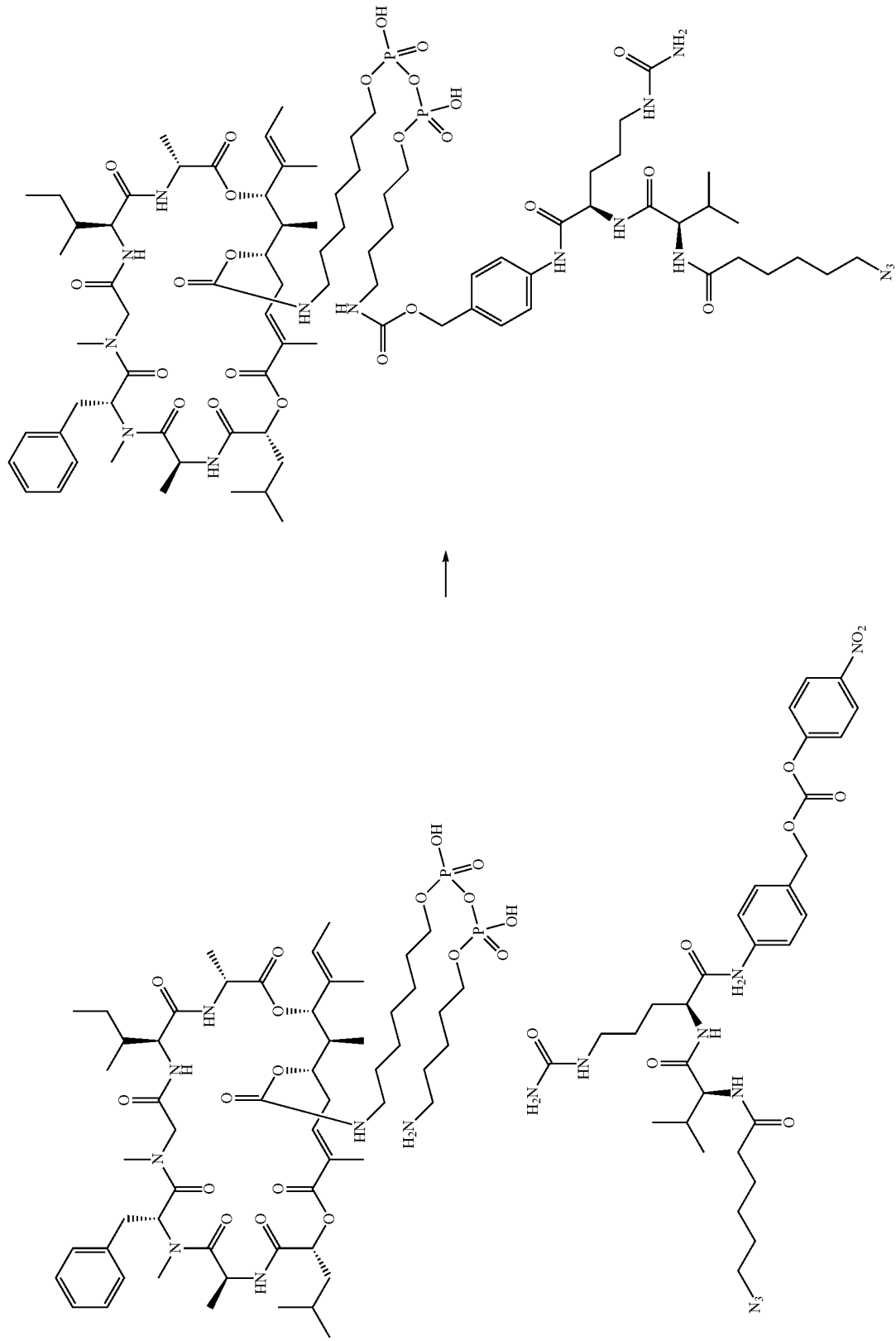

Figure 6:
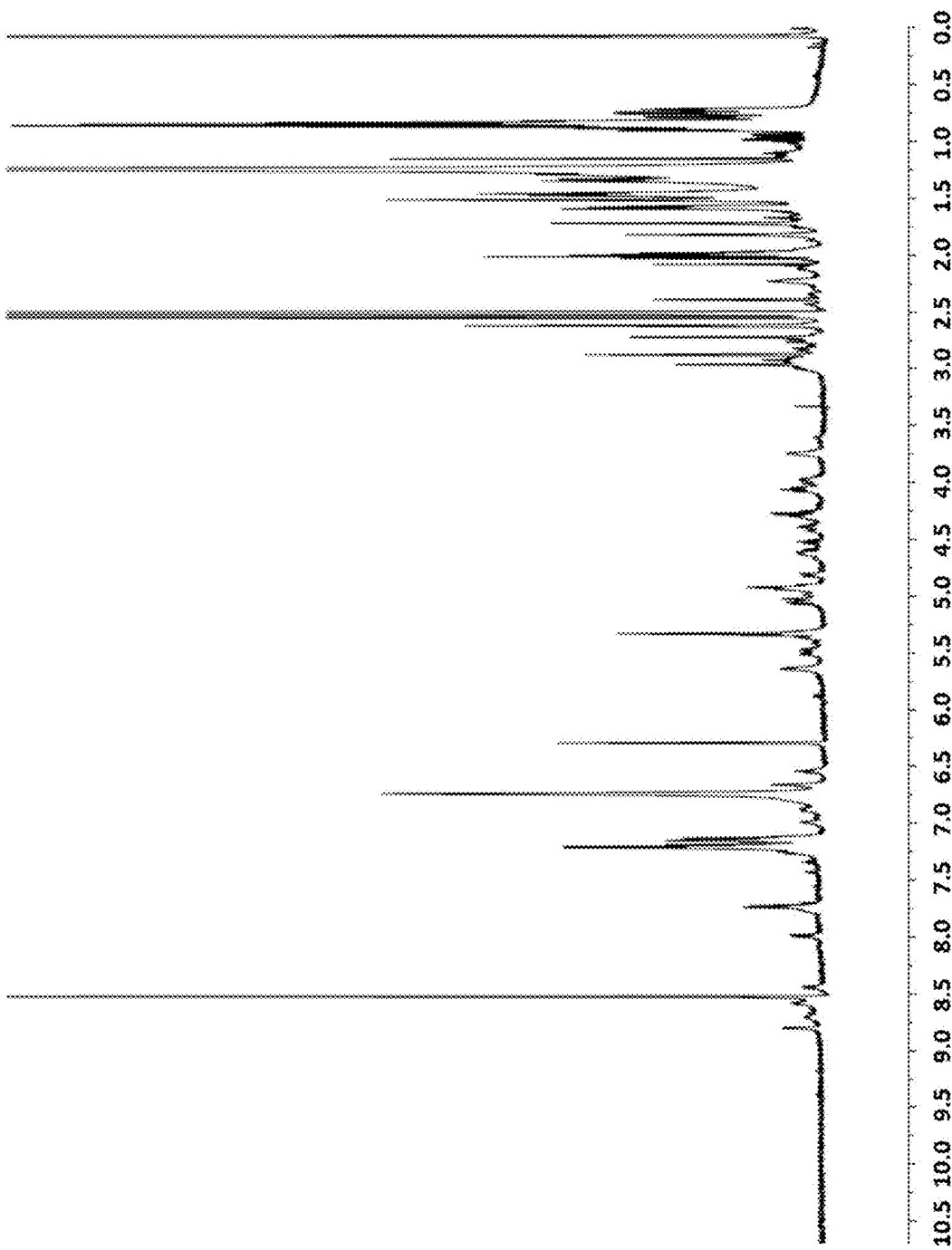
FIG. 6 is a $^1$H NMR spectrum of Conjugate L7 in DMSO-d6.

To the solution of (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (7-((((((5-aminopentyl)oxy)(hydroxy)phosphoryl)oxy)(hydroxy)phosphoryl)oxy)heptyl)carbamate (0.651 μmol, 0.8 mg) and undefined (1.463 μmol, 1 mg) in Hünig's base (0.172 mmol, 30 μL) was added Hünig's base (0.172 mmol, 30 μL). The mixture was stirred overnight and purified with RP-flash to afford (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (7-((((((5-((((4-((R)-2-((R)-2-(6-azidohexanamido)-3-methylbutanamido)-5-ureidopentanamido)benzyl)oxy)carbonyl)amino)pentyl)oxy)(hydroxy)phosphoryl)oxy)(hydroxy) phosphoryl)oxy)heptyl)carbamate (0.8 mg, 69.3%). Observed LRMS (ESI) m/z: 1772.9 [M+H]+. The $^1$H NMR spectrum of Conjugate L7 is shown in FIG. 6.

Example 43

Synthesis of Conjugate 8

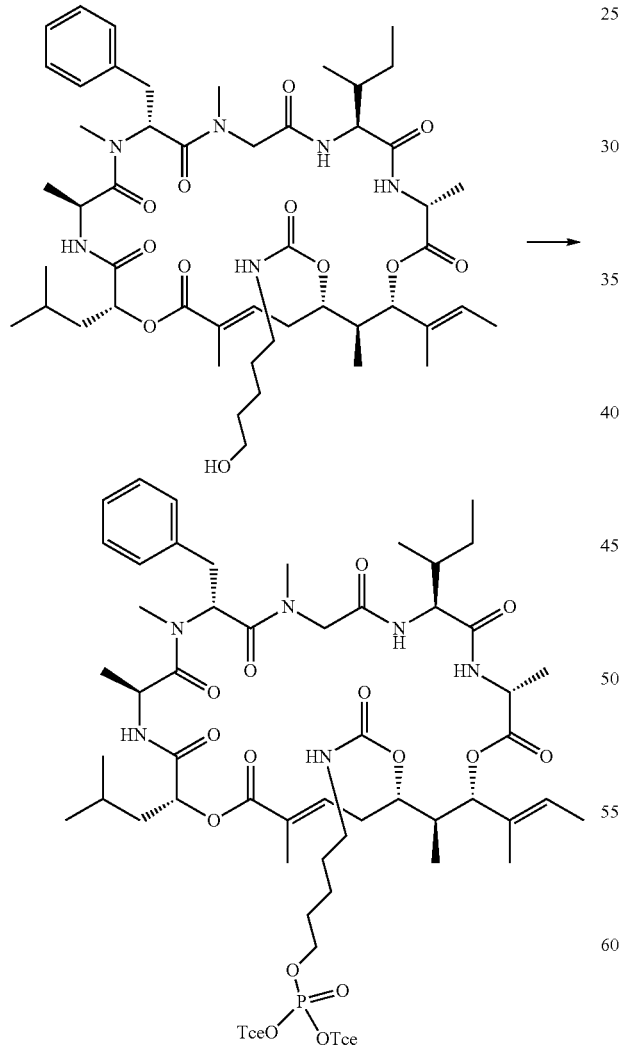

To the solution of (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (5-hydroxypentyl)carbamate (0.838 μmol, 0.8 mg) in pyridine (0.618 mmol, 50 μL) was added Bis(2,2,2-trichloroethyl) phosphorochloridate (3.35 μmol, 1.270 mg). The mixture was stirred for 4 h and purified with RP-flash to afford (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (5-((bis(2,2,2-trichloroethoxy)phosphoryl)oxy)pentyl)carbamate. Observed LRMS (ESI) m/z: 1295.1 [M+H]+

Example 44

Synthesis of Conjugate L9

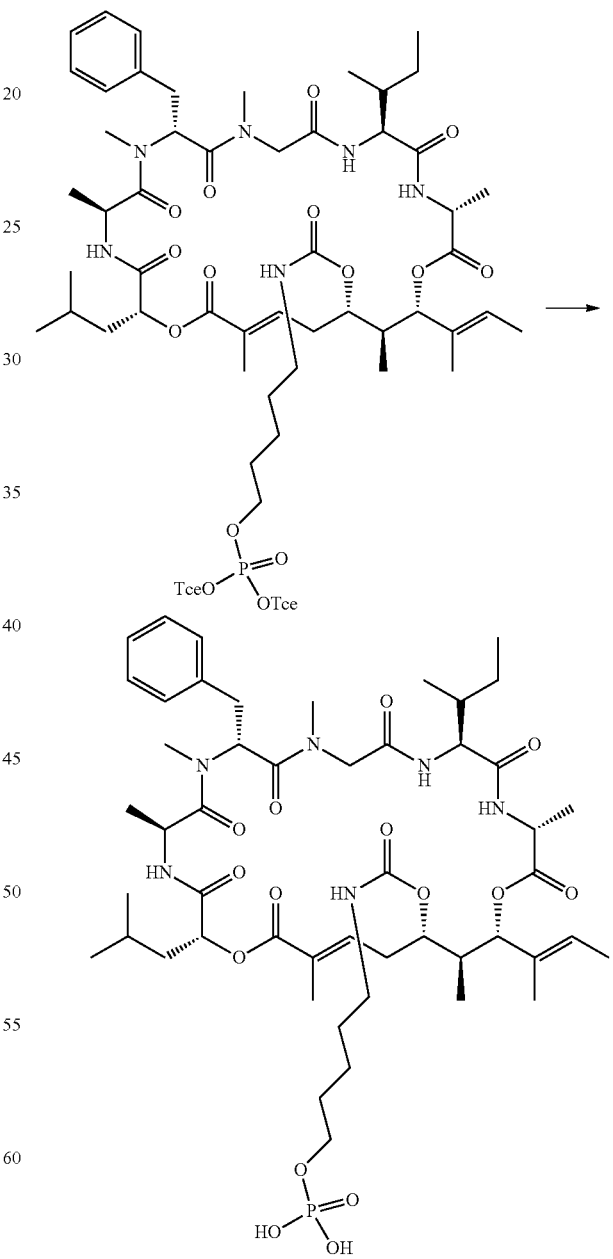

heptaoxo-1,19-dioxa-4,7,10,13,16-pentaazacyclohexacos-24-en-22-yl (5-((bis(2,2,2-trichloroethoxy)phosphoryl)oxy)pentyl)carbamate (1.541 µmol, 2 mg) in THF (6.10 mmol, 0.5 ml) and ammonium acetate (0.500 mmol, 0.5 mL) was added zinc (0.765 mmol, 50 mg). The mixture was stirred overnight and filtered over celite. The volatile was removed and the residue was purified with RP-flash to afford (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (5-(phosphonooxy)pentyl)carbamate (1 mg, 62.7%). Observed LRMS (ESI) m/z: 1035.5 [M+H]+.

Example 45

Synthesis of Conjugate L10

To the solution of (9H-fluoren-9-yl)methyl (5-(phosphonooxy)pentyl)carbamate (9.66 µmol, 3.92 mg) in DMF (6.46 mmol, 0.5 mL) was added CDI (0.019 mmol, 3.13 mg) and triethylamine (9.66 µmol, 1.346 µL). The mixture was stirred for 4 h and MeOH was added, then the volatile was removed. The residue was added DMF (6.46 mmol, 0.5 mL), (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl(5-(phosphonooxy)pentyl)carbamate (1.932 µmol, 2 mg) and zinc chloride (0.073 mmol, 10 mg) and stirred at 37 degree overnight. The mixture was purified with RP-flash to afford (9H-fluoren-9-yl)methyl (5-((((((5-(((((2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-

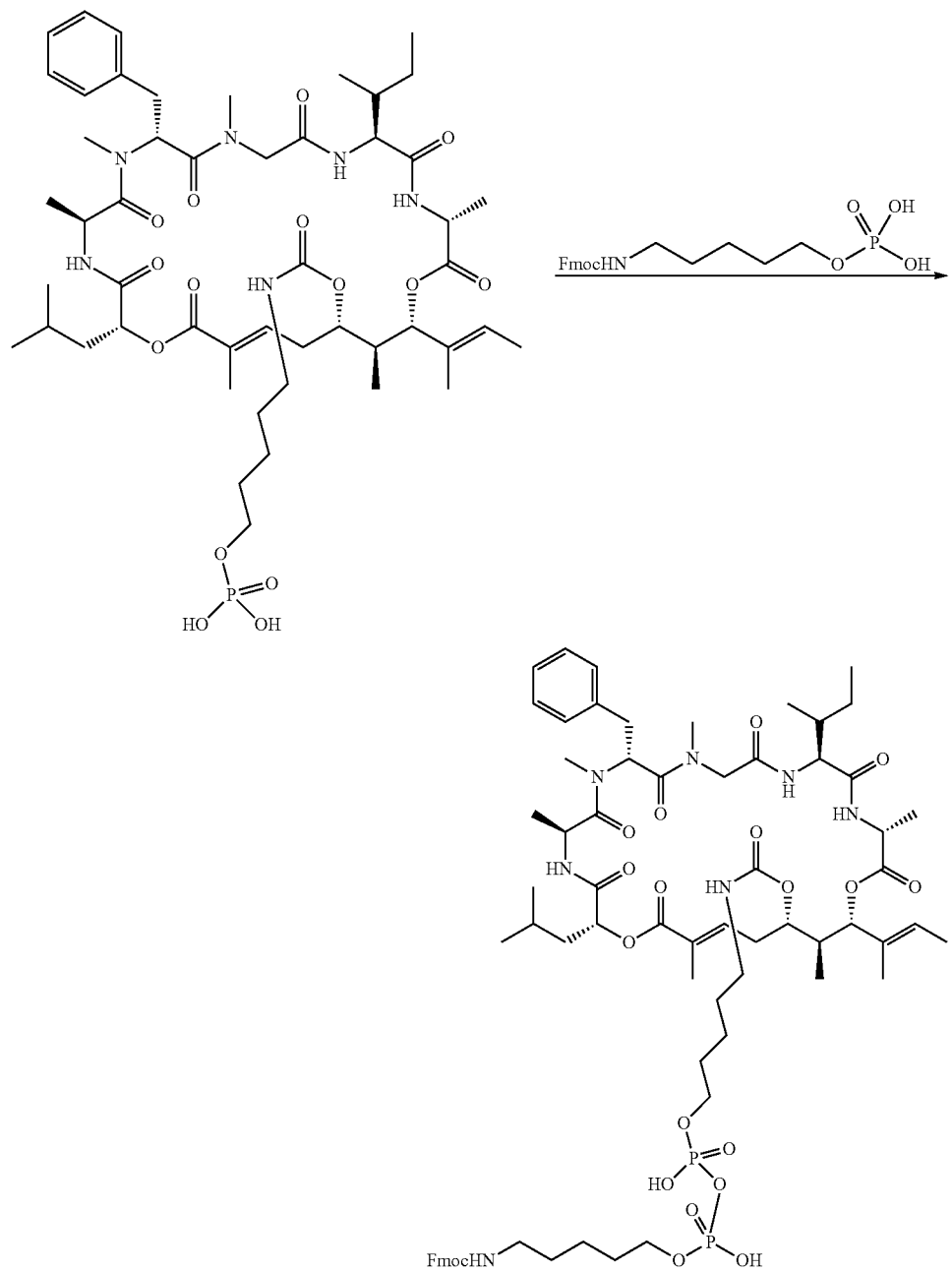

pentaazacyclohexacos-24-en-22-yl)oxy)carbonyl)amino)pentyl)oxy)(hydroxy)phosphoryl)oxy)(hydroxy)phosphoryl)oxy)pent yl)carbamate (0.5 mg, 18.19%). Observed LRMS (ESI) m/z: 1422.7 [M+H]+.

Example 46

Synthesis of Conjugate L11

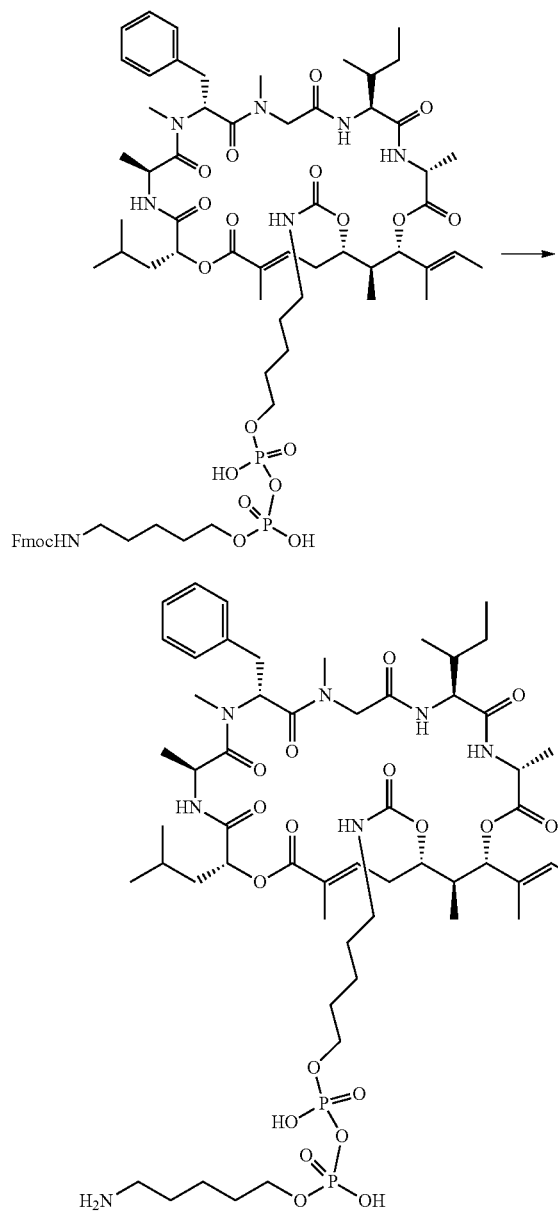

To the solution of (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (5-((((((5-((((9H-fluoren-9-yl)methoxy)carbonyl)amino)pentyl)oxy)(hydroxy)phosphoryl)oxy)(hydroxy)phosphoryl)oxy) pentyl)-14-azanecarboxylate (0.843 μmol, 1.2 mg) in MeCN (3.83 mmol, 0.2 mL) was added diethylamine (0.191 mmol, 20 μL). The mixture was stirred overnight and the volatile was removed. The residue was purified with RP-flash to afford (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (5-((((((5-aminopentyl)oxy)(hydroxy)phosphoryl)oxy)(hydroxy)phosphoryl)oxy)pentyl)-14-azanecarboxylate (0.7 mg, 69.1%). Observed HRMS (ESI) m/z: 1200.5949 [M+H]+.

Example 47

Synthesis of Conjugate L17

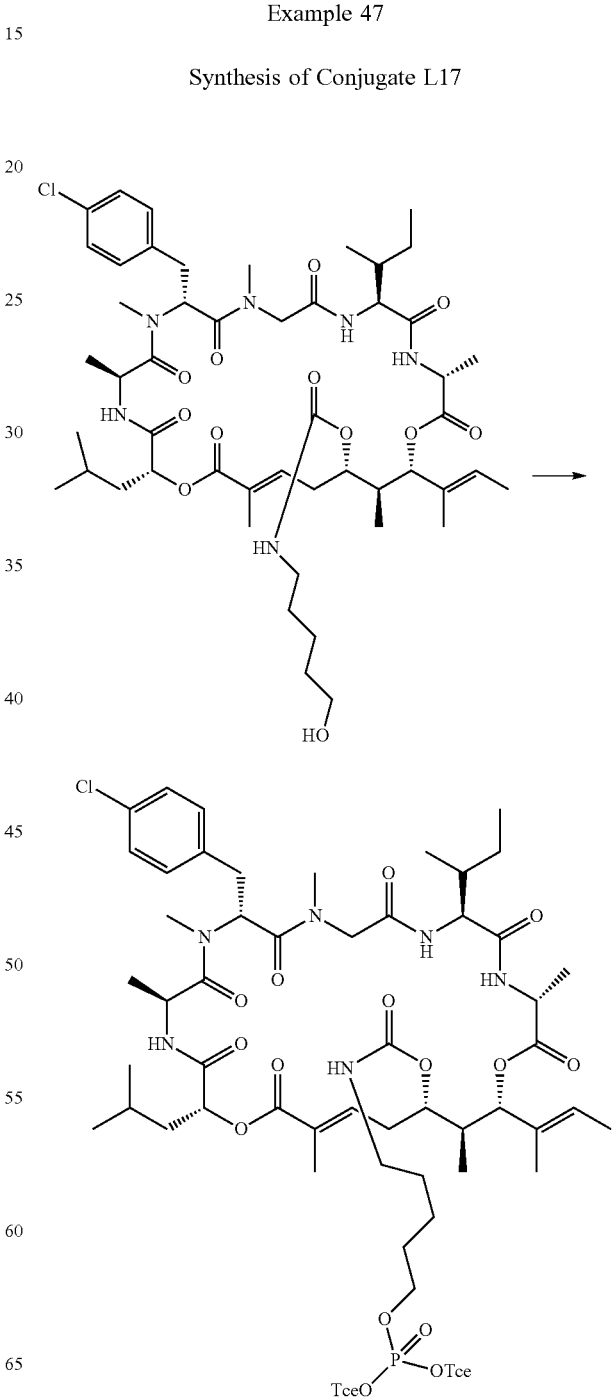

Conjugate L17 was prepared using a similar procedure as described in Example 36.
Example 48
Synthesis of Conjugate L18
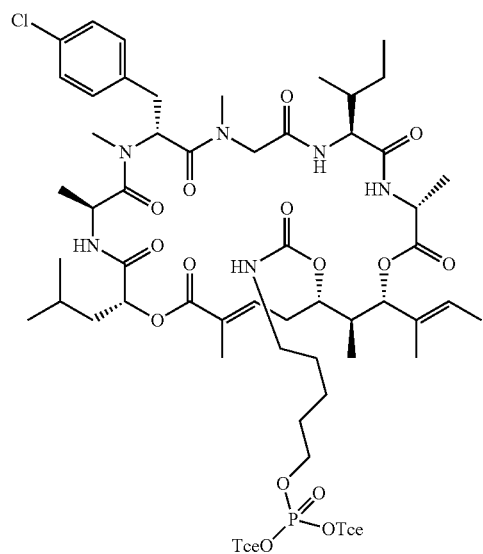
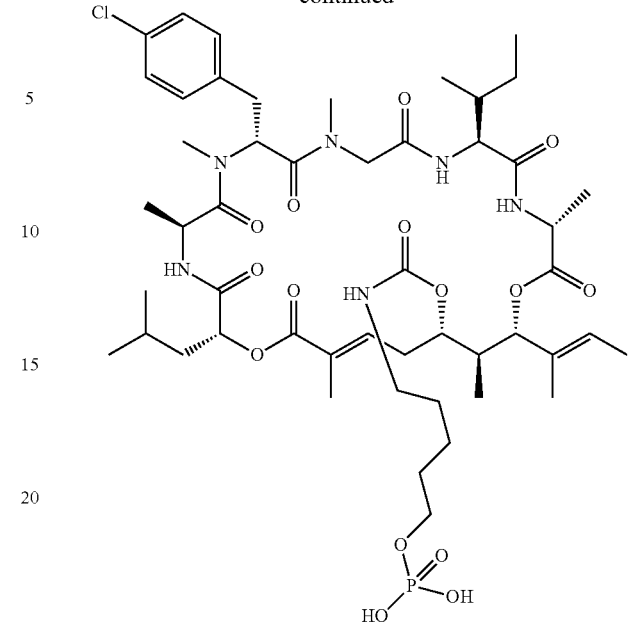
Conjugate L18 was prepared using a similar procedure as described in Example 37.
Example 49
Synthesis of Conjugate L19
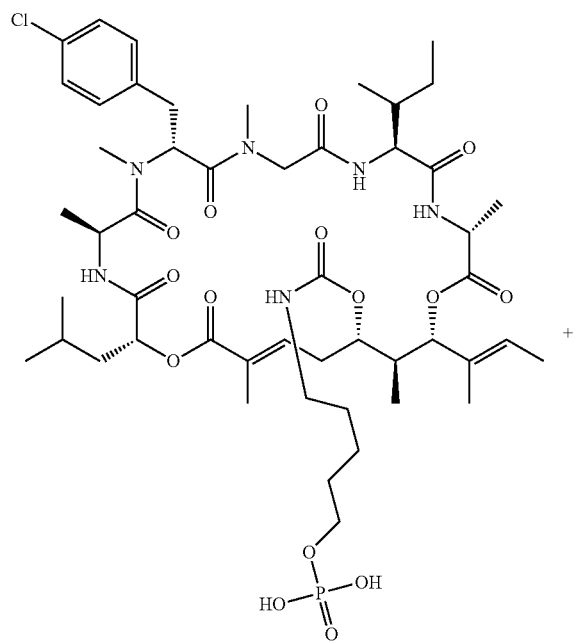

-continued

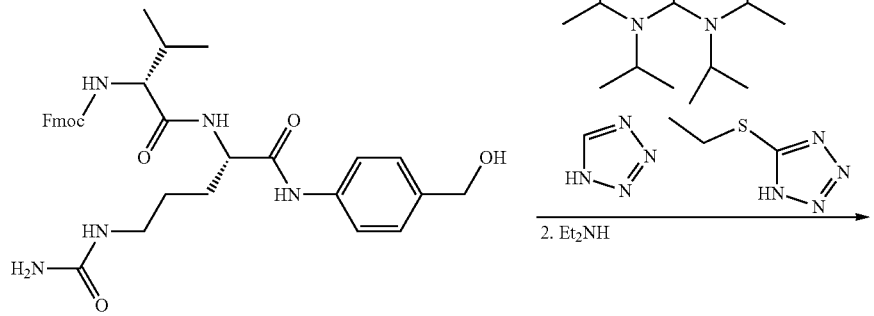

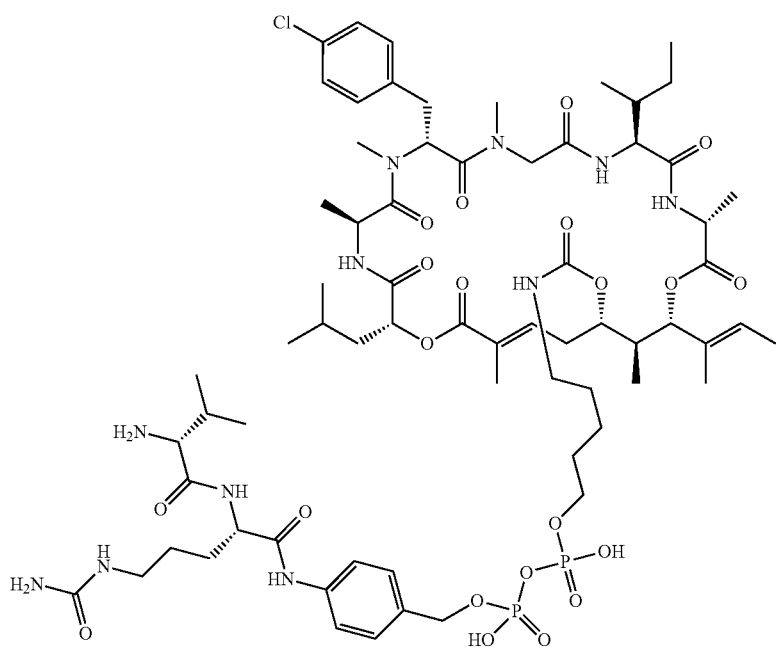

To the solution of (9H-fluoren-9-yl)methyl ((R)-1-(((S)-1-((4-hydroxymethyl)phenyl)amino)-1-oxo-5-ureidopentan-2-yl)amino)-3-methyl-1-oxobutan-2-yl)carbamate (24 mg, 0.039 mmol) in N,N-dimethylformamide (0.888 mg, 0.2 mL, 0.012 mmol) was added 3-((bis(diisopropylamino)phosphanyl)oxy)propanenitrile (14 mg, 0.046 mmol) and 1H-tetrazole (3.278 mg, 0.104 mL, 0.046 mmol). The reaction mixture was stirred for 1 h and added (2R,5S,8R,14S,17R,20S,21S,22S,E)-20-((E)-but-2-en-2-yl)-14-((R)-sec-butyl)-8-(4-chlorobenzyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (5-(phosphonooxy)pentyl)carbamate (13 mg, 0.012 mmol) and 5-(ethylthio)-1H-tetrazole (11.7 mg, 0.089 mmol). To the solution of crude mixture of (9H-fluoren-9-yl)methyl ((2R)-1-(((2S)-1-((4-((((((5-(((((2R,5S,8R,14S,17R,20S,21S,22S,E)-20-((E)-but-2-en-2-yl)-14-((R)-sec-butyl)-8-(4-chlorobenzyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl)oxy)carbonyl)amino)pentyl)oxy)(hydroxy)phosphoryl)oxy)(hydroxy)phosphoryl)oxy)meth yl)phenyl)amino)-1-oxo-5-ureidopentan-2-yl)amino)-3-methyl-1-oxobutan-2-yl)carbamate (0.020 g, 0.012 μmol) is added diethylamine (0.07 g, 0.1 mL, 0.957 mmol) and stirred for 3 h. The mixture was purified by RP flash chromatography to afford (2R,5S,8R,14S,17R,20S,21S,22S,E)-20-((E)-but-2-en-2-yl)-14-((R)-sec-butyl)-8-(4-chlorobenzyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (5-((((((4-((S)-2-((R)-2-amino-3-methylbutanamido)-5-ureidopentanamido)benzyl)oxy)(hydroxy)phosphoryl)oxy)(hydroxy)phosphoryl)oxy)pentyl) carbamate (1 mg, 5.515%). Observed LRMS (ESI) m/z: 1510.4 [M+H]$^+$.

Example 50

Synthesis of Conjugate L20

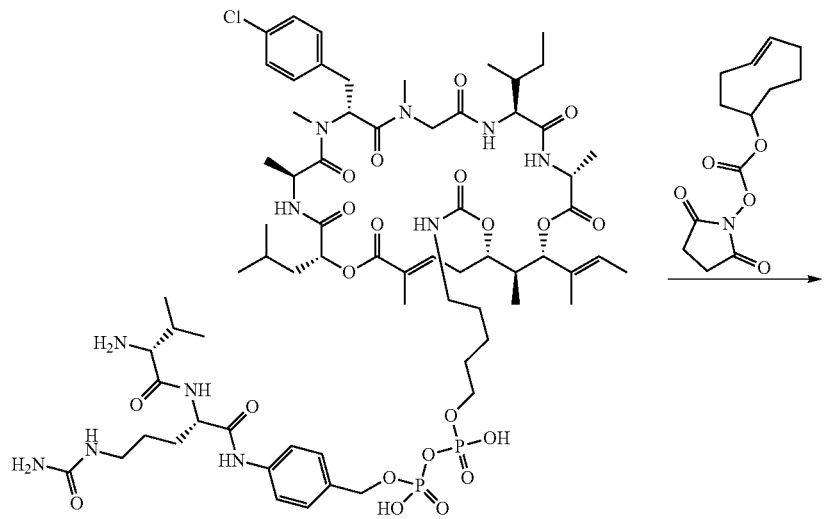

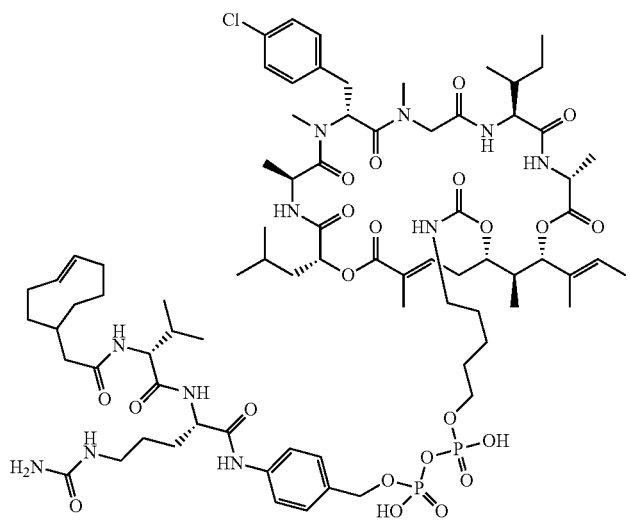

To the solution of (2R,5S,8R,14S,17R,20S,21S,22S,E)-20-((E)-but-2-en-2-yl)-14-((R)-sec-butyl)-8-(4-chlorobenzyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (5-((((((4-((S)-2-((R)-2-amino-3-methylbutanamido)-5-ureidopentanamido)benzyl)oxy)(hydroxy)phosphoryl)oxy)(hydroxy)phosphoryl)oxy)pentyl) carbamate (1 mg, 0.661 μmol), HOAt (2 mg, 0.014 mmol) and (E)-cyclooct-4-en-1-yl (2,5-dioxopyrrolidin-1-yl) carbonate (3 mg, 0.011 mmol) in DMF (0.094 g, 0.1 ml, 1.291 mmol) was added hunig's base (0.014 g, 20 μL, 0.114 mmol). The reaction was stirred overnight and purified on RP flash chromatography to afford (2R,5S,8R,14S,17R,20S,21S,22S,E)-20-((E)-but-2-en-2-yl)-14-((R)-sec-butyl)-8-(4-chlorobenzyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (5-((((((4-((2S)-2-((2R)-2-(((((E)-cyclooct-4-en-1-yl)oxy)carbonyl)amino)-3-methylbutanamido)-5-ureidopentanamido)benzyl)oxy)(hydroxy)phosphoryl)oxy)(hydroxy)phosphoryl)oxy)pentyl) carbamate (0.9 mg, 81.76%) as white solid. Observed HRMS (ESI) m/z: 1662.7589 [M+H]$^+$.

Example 51
Synthesis of Conjugate 21
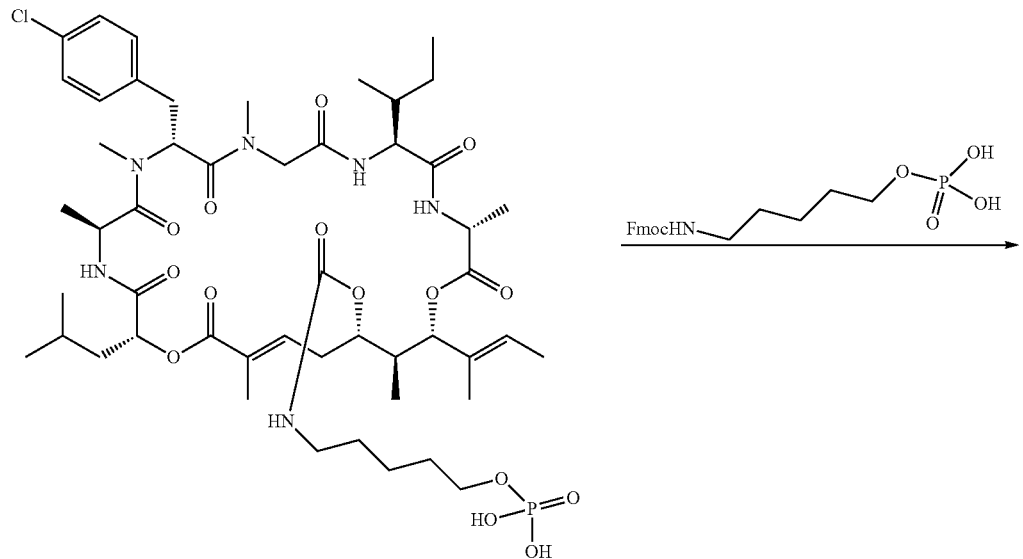
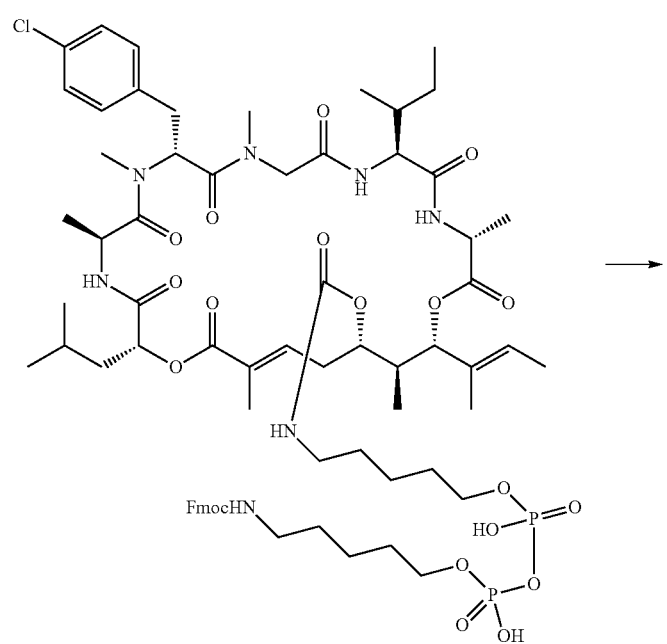

-continued

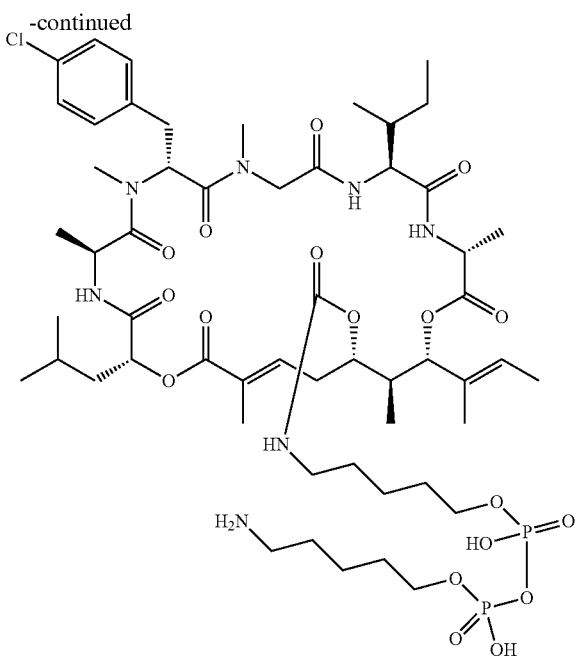

Conjugate L21 was prepared using a similar procedure as described in Examples 38 and 39.

Example 52

Synthesis of Conjugate L22

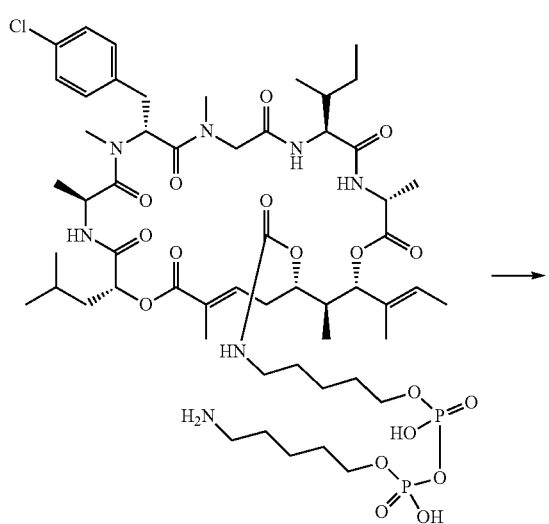

→

-continued

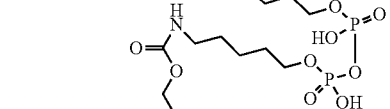

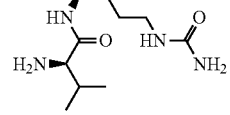

To a solution of (2R,5S,8R,14S,17R,20S,21S,22S,E)-20-((E)-but-2-en-2-yl)-14-((R)-sec-butyl)-8-(4-chlorobenzyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (5-((((((5-aminopentyl)oxy)(hydroxy)phosphoryl)oxy)(hydroxy)phosphoryl)oxy)pentyl) carbamate (0.011 g, 8.908 µmol) in DMF (0.472 g, 0.5 mL, 6.457 mmol) was added (9H-fluoren-9-yl)methyl ((S)-3-methyl-1-(((S)-1-((4-(((((4-nitrophenoxy)carbonyl)oxy)methyl)phenyl)amino)-1-oxo-5-ureidopentan-2-yl)amino)-1-oxobutan-2-yl)carbamate (0.014 g, 0.018 mmol) and DIPEA (0.011 g, 0.015 mL, 0.089 mmol). The resulting residue was dissolved in MeCN and diethylamine and stirred at RT. After 3 h the reaction was concentrated in vacuo. The residue was purified with flash chromatography to afford (2R,5S,8R,14S,17R,20S,21S,22S,E)-20-((E)-but-2-en-2-yl)-14-((R)-sec-butyl)-8-(4-chlorobenzyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (5-((((((5-((((4-((S)-2-((S)-2-((((9H-fluoren-9-yl)methoxy)carbonyl)amino)-3-methylbutanamido)-5-ureidopentanamido)benzyl)oxy)carbonyl)amino)pentyl)oxy)(hydroxy)phosphl)oxy)(hydroxy)phosphoryl)oxy)pentyl)carbamate (0.004 g, 23.53%, 9.13 μmol).

Example 53

Synthesis of Conjugate L23

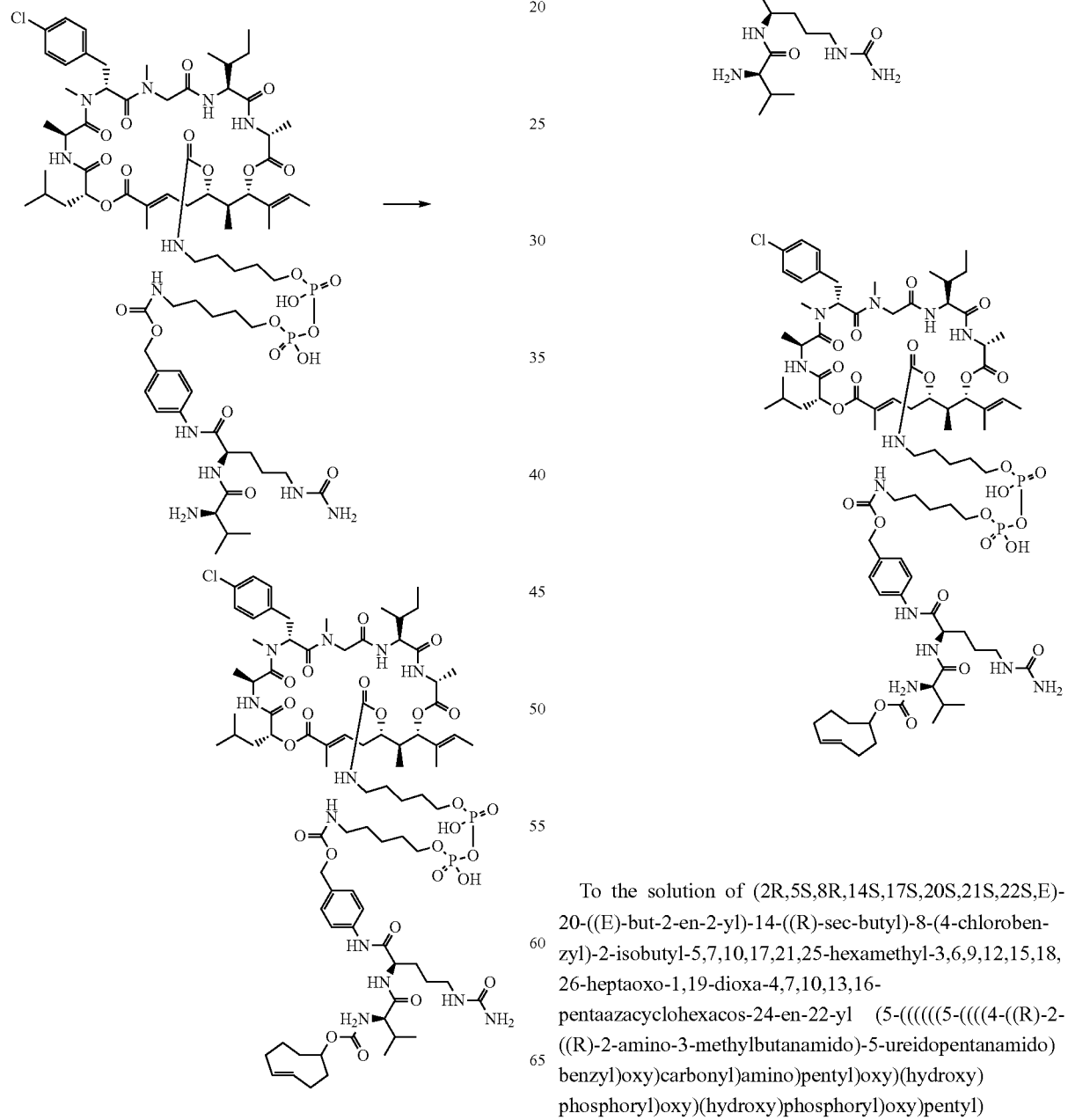

To the solution of (2R,5S,8R,14S,17S,20S,21S,22S,E)-20-((E)-but-2-en-2-yl)-14-((R)-sec-butyl)-8-(4-chlorobenzyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (5-((((((5-((((4-((R)-2-((R)-2-amino-3-methylbutanamido)-5-ureidopentanamido)benzyl)oxy)carbonyl)amino)pentyl)oxy)(hydroxy)phosphoryl)oxy)(hydroxy)phosphoryl)oxy)pentyl)

carbamate (1 mg, 0.6 μmol) was added HOAt (2 mg, 0.014 mmol), (E)-cyclooct-4-en-1-yl (2,5-dioxopyrrolidin-1-yl) carbonate (3 mg, 0.011 mmol) in DMF (0.094 g, 0.1 mL, 1.291 mmol) and hunig's base (0.014 g, 20 μL, 0.114 mmol). The reaction was stirred overnight and purified on RP flash chromatography to afford (2R,5S,8R,14S,17S,20S,21S,22S,E)-20-((E)-but-2-en-2-yl)-14-((R)-sec-butyl)-8-(4-chlorobenzyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (5-((((((5-((((4-((2R)-2-((2R)-2-(((((E)-cyclooct-4-en-1-yl)oxy)carbonyl)amino)-3-methylbutanamido)-5-ureidopentanamido)benzyl)oxy) carbonyl)amino)pentyl)oxy)(hydroxy)phosphoryl)oxy) (hydroxy)phosphoryl)oxy)pentyl)carbamate (1 mg, 0.5 μmol). Observed HRMS (ESI) m/z: 896.4223 [M+H]$^{2+}$.

Example 54

Synthesis of Conjugate L24

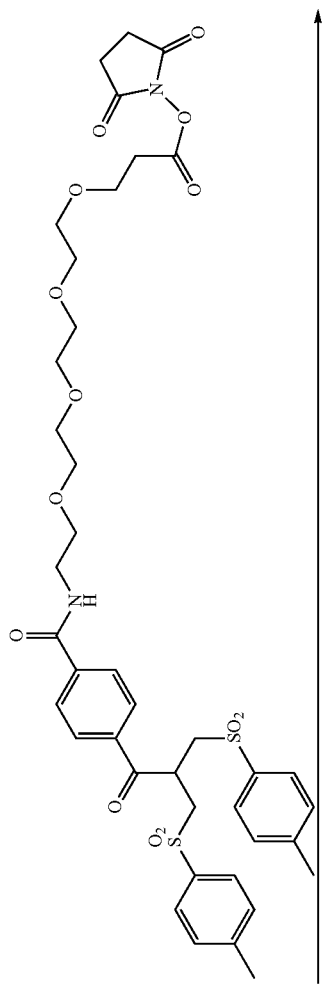
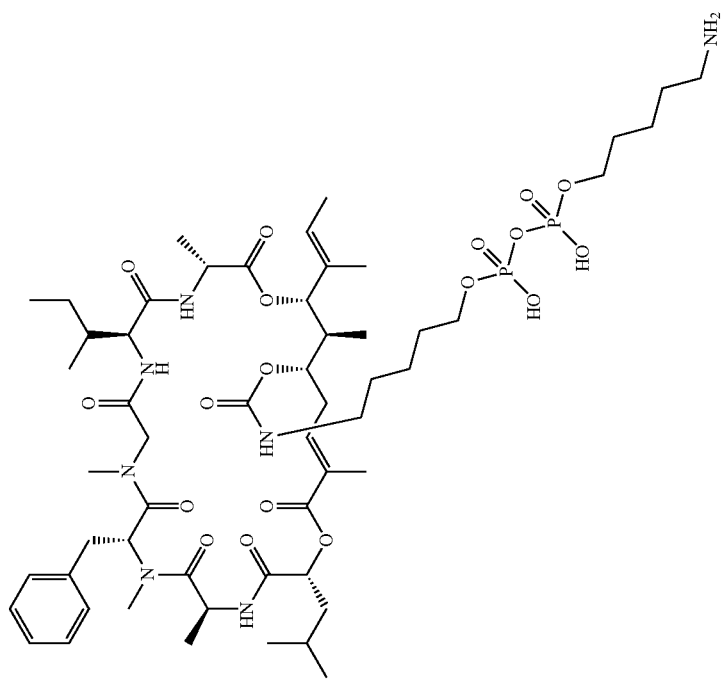

-continued
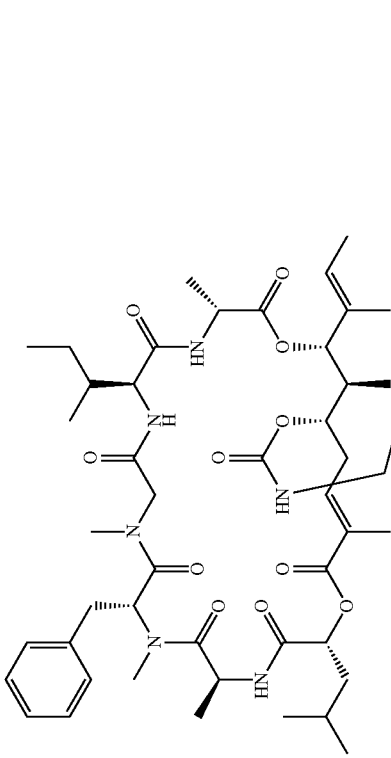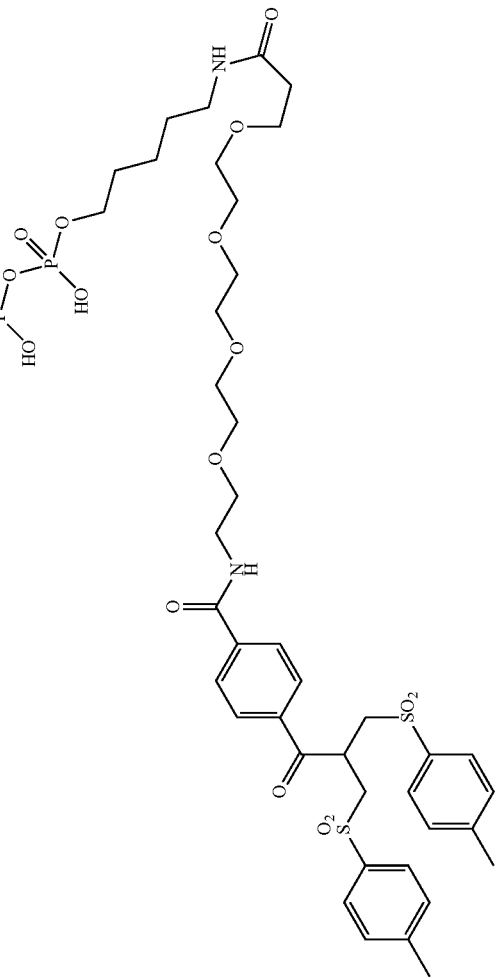

To a solution of (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (5-((((((5 aminopentyl)oxy)(hydroxy) phosphoryl)oxy)(hydroxy)phosphoryl)oxy)pentyl) carbamate (3.0 mg, 2.499 μmol, 1.0 eq; Conjugate L11 from Example 46) in DMSO (200 μL) was added 2,5-dioxopyrrolidin-1-yl 1-oxo-1-(4-(3-tosyl-2-(tosylmethyl)propanoyl)phenyl)-5,8,11,14-tetraoxa-2-azaheptadecan-17-oate (2.11 mg, 2.499 499 μmol, 1.0 eq) and N-ethyl-N-isopropylpropan-2-amine (80 μL, 0.459 mmol, 184.0 eq) and stirred at room temp for 2 h. The reaction was monitored by reverse phase HPLC. The reaction mixture was lyophilized and the crude residue obtained was washed with hexanes followed by diethyl ether leaving behind the unreacted bis-sulfone and impurities (bis-sulfone acid) in the solvent washes. The residue obtained was then taken in the ethyl acetate to which hexanes was added resulting in the precipitation of (2R,5S,8R,14S,17R,20S,21S,22S,E)-8-benzyl-20-((E)-but-2-en-2-yl)-14-((R)-sec-butyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (5-((((((1,17-dioxo-1-(4-(3-tosyl-2-(tosylmethyl)propanoyl)phenyl)-5,8,11,14-tetraoxa-2,18-diazatricosan-23-yl)oxy)(hydroxy) phosphoryl)oxy)(hydroxy)phosphoryl)oxy)pentyl) carbamate (2.68 mg, 1.38 μmol, 55.6%) as a major compound. Observed HRMS (ESI) m/z: 965.42 $[M+H]^{2+}$.

Example 55

Synthesis of Conjugate L25

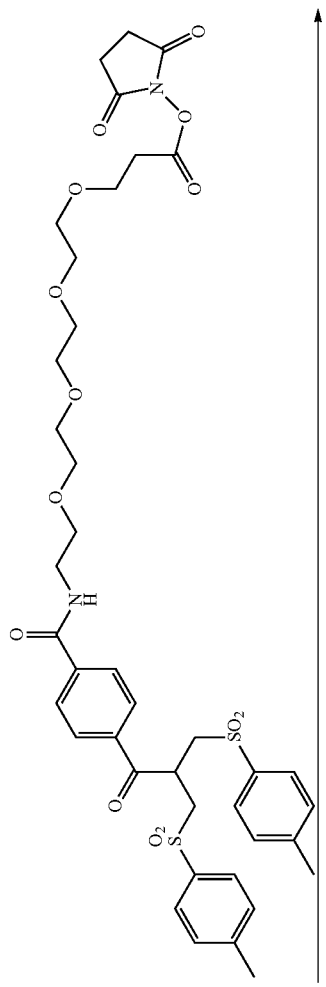
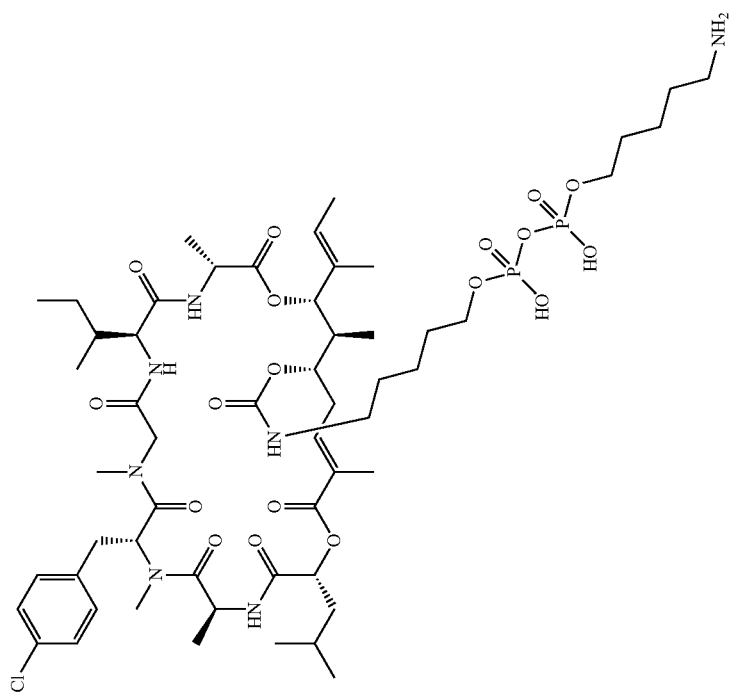

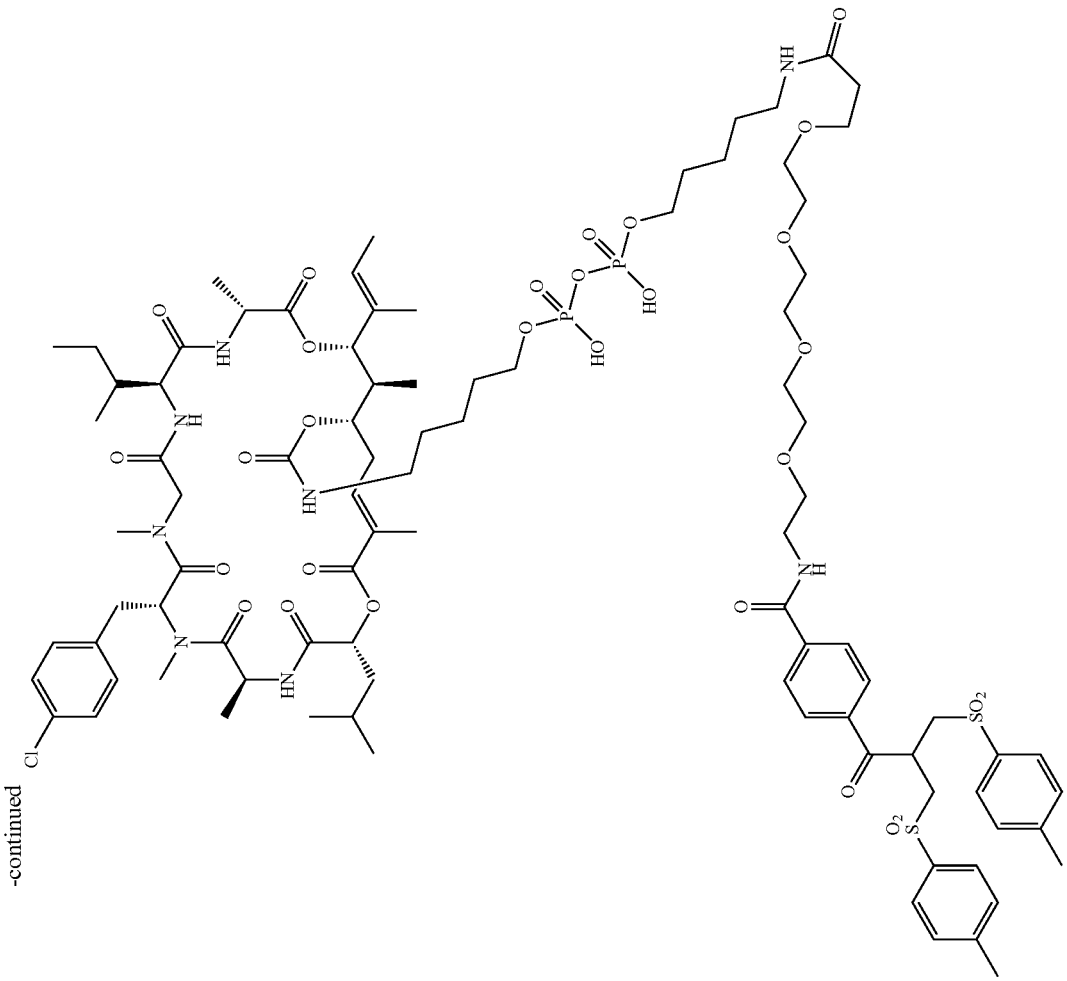

To a solution of (2R,5S,8R,14S,17R,20S,21S,22S,E)-20-((E)-but-2-en-2-yl)-14-((R)-sec-butyl)-8-(4-chlorobenzyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (5-((((((5-aminopentyl)oxy)(hydroxy) phosphoryl)oxy)(hydroxy)phosphoryl)oxy)pentyl) carbamate (3.0 mg, 2.46 µmol, 1.0 eq) in DMF (200 µL) was added 2,5-dioxopyrrolidin-1-yl 1-oxo-1-(4-(3-tosyl-2-(tosylmethyl)propanoyl)phenyl)-5,8SO11,14-tetraoxa-2-azaheptadecan-17-oate (2.46 mg, 2.92 µmol, 1.2 eq) and N-ethyl-N-isopropylpropan-2-amine (80 µL, 0.459 mmol, 184.0 eq) and stirred at room temp for 2 h. The reaction was monitored by reverse phase HPLC. The reaction mixture was lyophilized and the crude residue obtained was washed with hexanes followed by diethyl ether leaving behind the unreacted bis-sulfone in the solvent washes. The residue obtained was then taken in the ethyl acetate to which hexanes was added resulting in the precipitation of (2R,5S,8R,14S,17R,20S,21S,22S,E)-20-((E)-but-2-en-2-yl)-14-((R)-sec-butyl)-8-(4-chlorobenzyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (5-((((((1,17-dioxo-1-(4-(3-tosyl-2-(tosylmethyl)propanoyl)phenyl)-5,8,11,14-tetraoxa-2,18-diazatricosan-23-yl)oxy)(hydroxy) phosphoryl)oxy)(hydroxy)phosphoryl)oxy)pentyl) carbamate (2.2 mg, 1.12 µmol, 41.0%) as a major compound. Observed HRMS (ESI) m/z: 982.39 $[M+H]^{2+}$.

Example 56

Synthesis of Conjugate L26

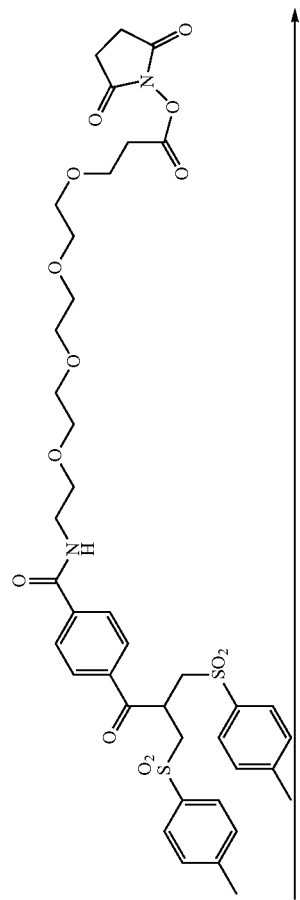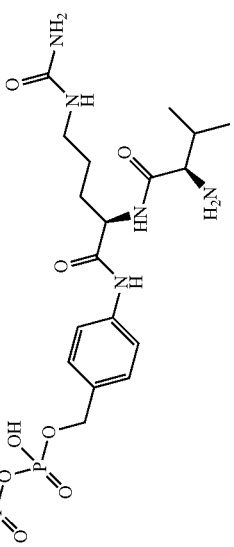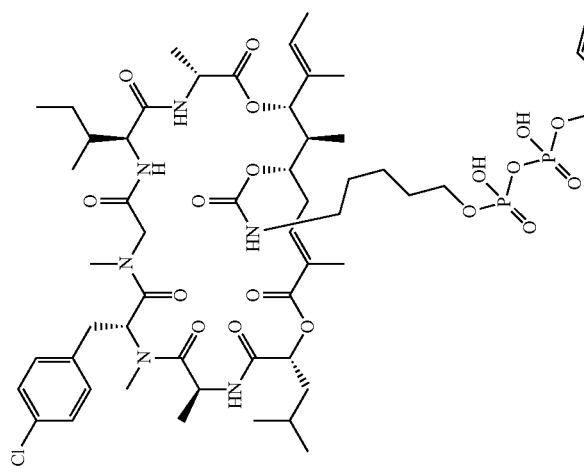

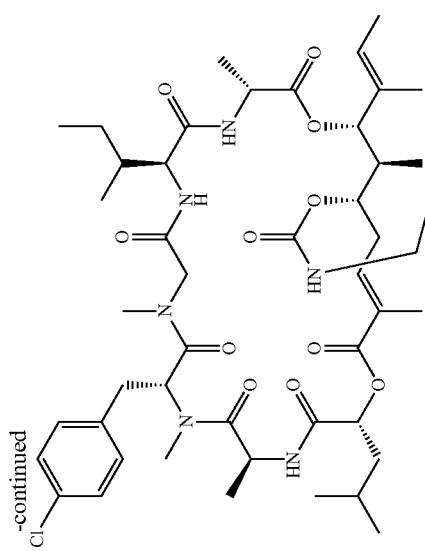
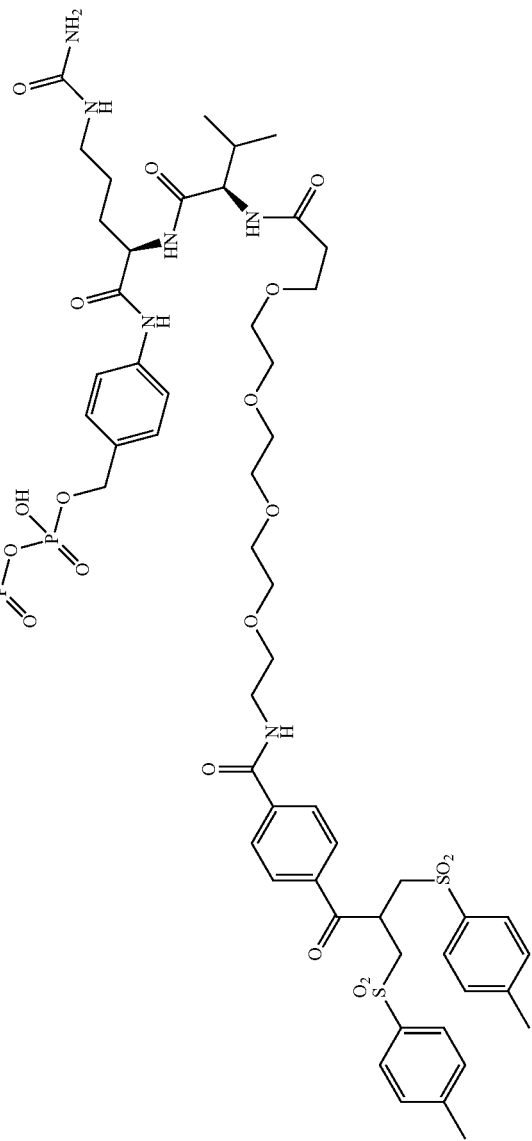

To a solution of (2R,5S,8R,14S,17R,20S,21S,22S,E)-20-((E)-but-2-en-2-yl)-14-((R)-sec-butyl)-8-(4-chlorobenzyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (5-((((((4-((R)-2-((R)-2-amino-3-methylbutanamido)-5-ureidopentanamido)benzyl)oxy)(hydroxy)phosphoryl)oxy)(hydroxy)phosphoryl)oxy)pentyl) carbamate (2.39 mg, 1.582 μmol, 1.0 eq) in DMF (400 μL) was added 2,5-dioxopyrrolidin-1-yl 1-oxo-1-(4-(3-tosyl-2-(tosylmethyl)propanoyl)phenyl)-5,8SO11,14-tetraoxa-2-azaheptadecan-17-oate (6.68 mg, 7.91 μmol, 5.0 eq), 1-Hydroxy-7-azabenzotriazole (0.21 mg, 1.582 μmol, 1.0 eq) and N-ethyl-N-isopropylpropan-2-amine (60 μL, 0.344 mmol, 218.0 eq) and stirred overnight at room temp. The reaction was monitored by reverse phase HPLC. The reaction mixture was lyophilized and the crude residue obtained was washed with hexanes followed by diethyl ether leaving behind the unreacted bis-sulfone in the solvent washes. The residue obtained was then purified by reverse phase flash chromatography (acetonitrile with 0.1% formic acid/H$_2$O with 0.1% formic acid) to afford (2R,5S,8R,14S,17R,20S,21S,22S,E)-20-((E)-but-2-en-2-yl)-14-((R)-sec-butyl)-8-(4-chlorobenzyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl(5-((hydroxy((hydroxy((4-((19R,22R)-19-isopropyl-1,17,20-trioxo-1-(4-(3-tosyl-2-(tosylmethyl)propanoyl)phenyl)-22-(3-ureidopropyl)-5,8,11,14-tetraoxa-2,18,21-triazatricosan-23-amido)benzyl)oxy)phosphoroyl)oxy)phosphoryl)oxy)pentyl)carbamate (2.0 mg, 0.89 μmol, 56.4%) as a major compound. Observed HRMS (ESI) m/z: 1120.45 [M+H]$^{2-}$.

Example 57

Synthesis of Conjugate L27

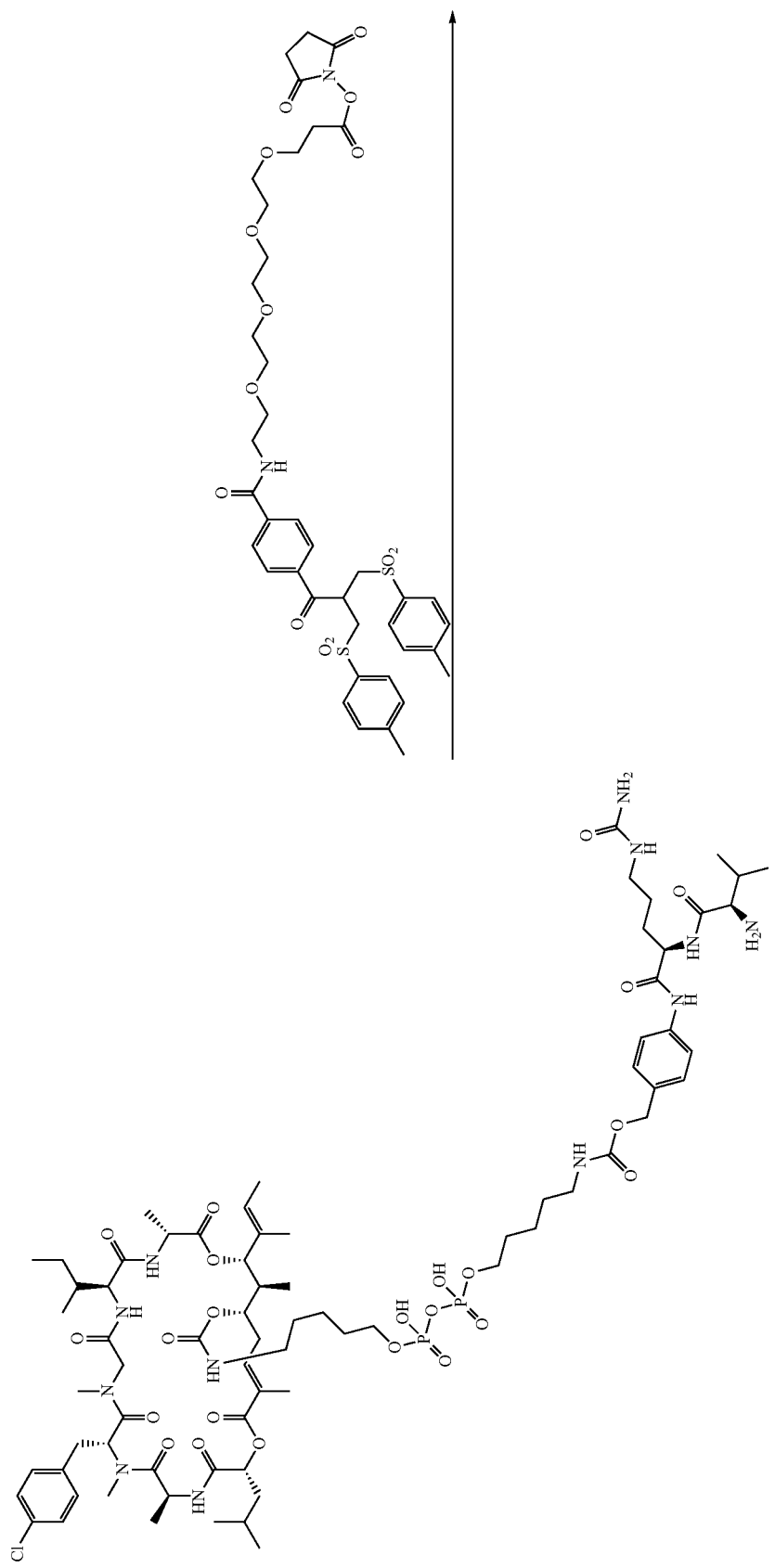

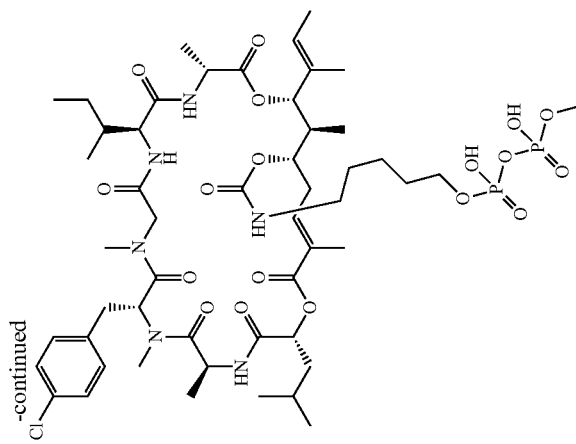
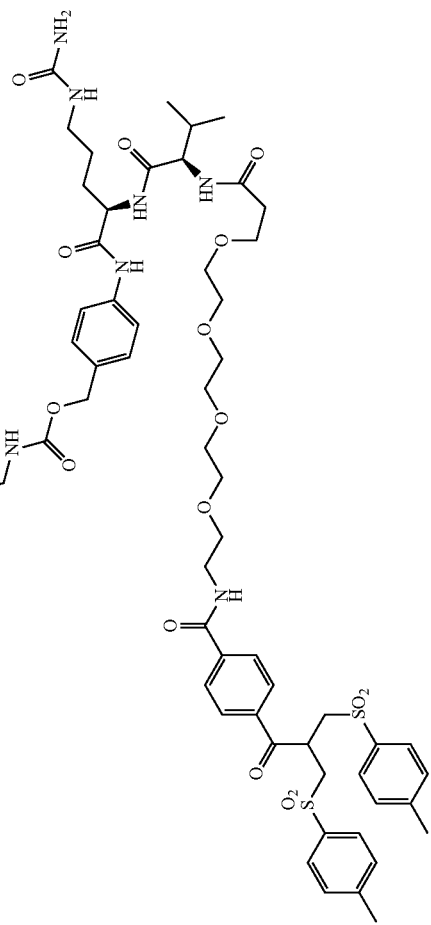

To a solution of (2R,5S,8R,14S,17R,20S,21S,22S,E)-20-((E)-but-2-en-2-yl)-14-((R)-sec-butyl)-8-(4-chlorobenzyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (5-((((((5-((((4-((R)-2-((R)-2-amino-3-methylbutanamido)-5-ureidopentanamido)benzyl)oxy)carbonyl)amino)pentyl)oxy)(hydroxy)phosphoryl)oxy)(hydroxy)phosphoryl)oxy)pentyl)carbamate (4.0 mg, 2.439 μmol, 1.0 eq) in DMSO (200 μL) was added 2,5-dioxopyrrolidin-1-yl 1-oxo-1-(4-(3-tosyl-2-(tosylmethyl)propanoyl)phenyl)-5,8SO11,14-tetraoxa-2-azaheptadecan-17-oate (4.12 mg, 4.88 μmol, 2.0 eq), 1-Hydroxy-7-azabenzotriazole (0.66 mg, 4.88 μmol, 2.0 eq) and N-ethyl-N-isopropylpropan-2-amine (100 μL, 0.574 mmol, 235.0 eq) and stirred at room temp for 3 h. The reaction was monitored by reverse phase HPLC. The reaction mixture was lyophilized and the crude residue obtained was washed with hexanes followed by diethyl ether leaving behind the unreacted bis-sulfone in the solvent washes. The residue obtained was then purified by normal phase preparative thin-layer chromatography (dichloromethane with 0.1% formic acid/methanol with 0.1% formic acid, 4:1) to afford (2R,5S,8R,14S,17R,20S,21S,22S,E)-20-((E)-but-2-en-2-yl)-14-((R)-sec-butyl)-8-(4-chlorobenzyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (5-((hydroxy((hydroxy((5-((((4-((19R,22R)-19-isopropyl-1,17,20-trioxo-1-(4-(3-tosyl-2-(tosylmethyl)propanoyl)phenyl)-22-(3-ureidopropyl)-5,8,11,14-tetraoxa-2,18,21-triazatricosan-23-amido)benzyl)oxy)carbonyl)amino)pentyl)oxy)phosphoryl)oxy)phosphoryl)oxy)pentyl)carbamate (1.79 mg, 0.755 μmol, 31.0%) as a major compound. Observed HRMS (ESI) m/z: 1185.00 [M+H]$^{2+}$.

Example 58

Synthesis of Conjugate L28

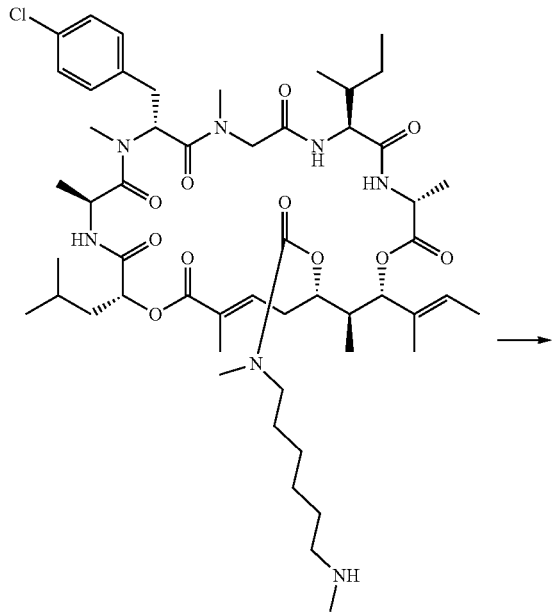

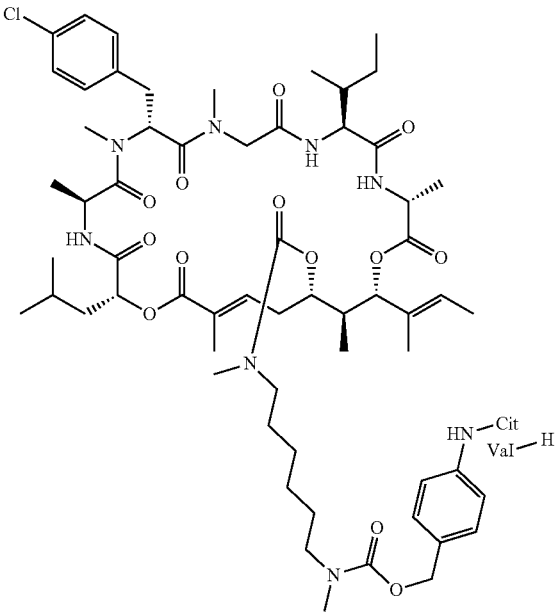

To the solution of (2R,5S,8R,14S,17R,20S,21S,22S,E)-20-((E)-but-2-en-2-yl)-14-((R)-sec-butyl)-8-(4-chlorobenzyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl methyl(6-(methylamino)hexyl)carbamate (0.006 g, 6.306 μmol) in DCM (300 μL) and DIPEA (8.150 mg, 0.011 mL, 0.063 mmol) was added 1-hydroxy-7-azabenzotriazole (0.858 mg, 6.306 μmol) and Fmoc-Val-Cit-PABC-PNP (15 mg, 19 μmol). After stirring overnight and the starting material was consumed and then added 40% Et$_2$NH/MeCN solution and the solution was stirred and purified with flash to afford 8 mg of the (2R,5S,8R,14S,17R,20S,21S,22S,E)-20-((E)-but-2-en-2-yl)-14-((R)-sec-butyl)-8-(4-chlorobenzyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (4-((S)-2-(2-((S)-3-methyl-1-oxobutan-2-yl)hydrazinyl)-5-ureidopentanamido)benzyl) hexane-1,6-diylbis(methylcarbamate).

Example 59
Synthesis of Conjugate L29
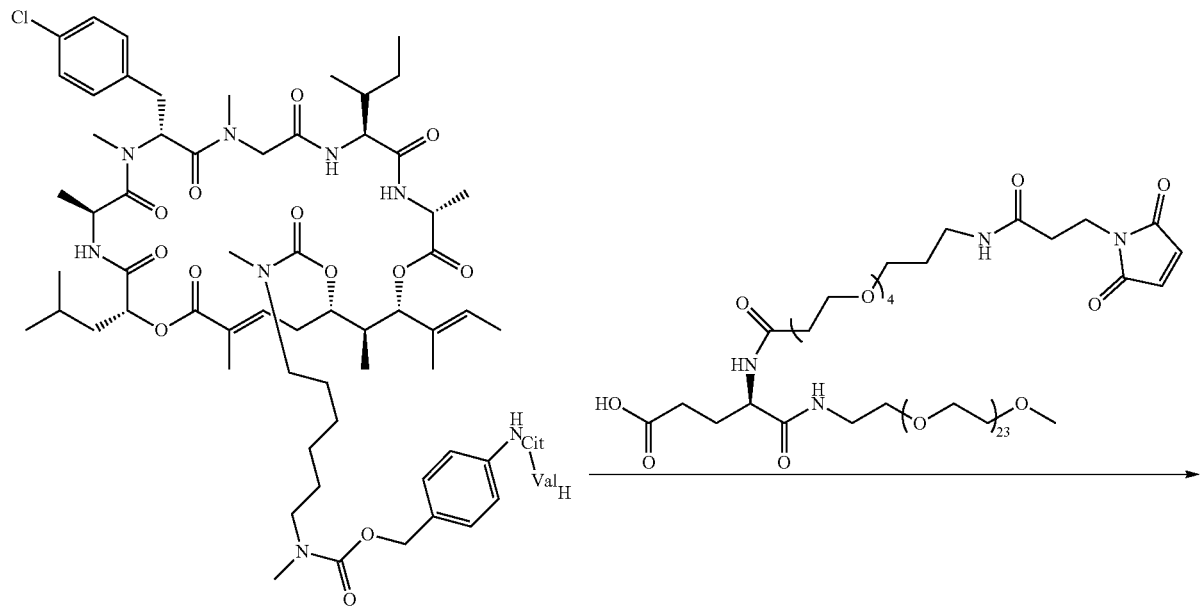
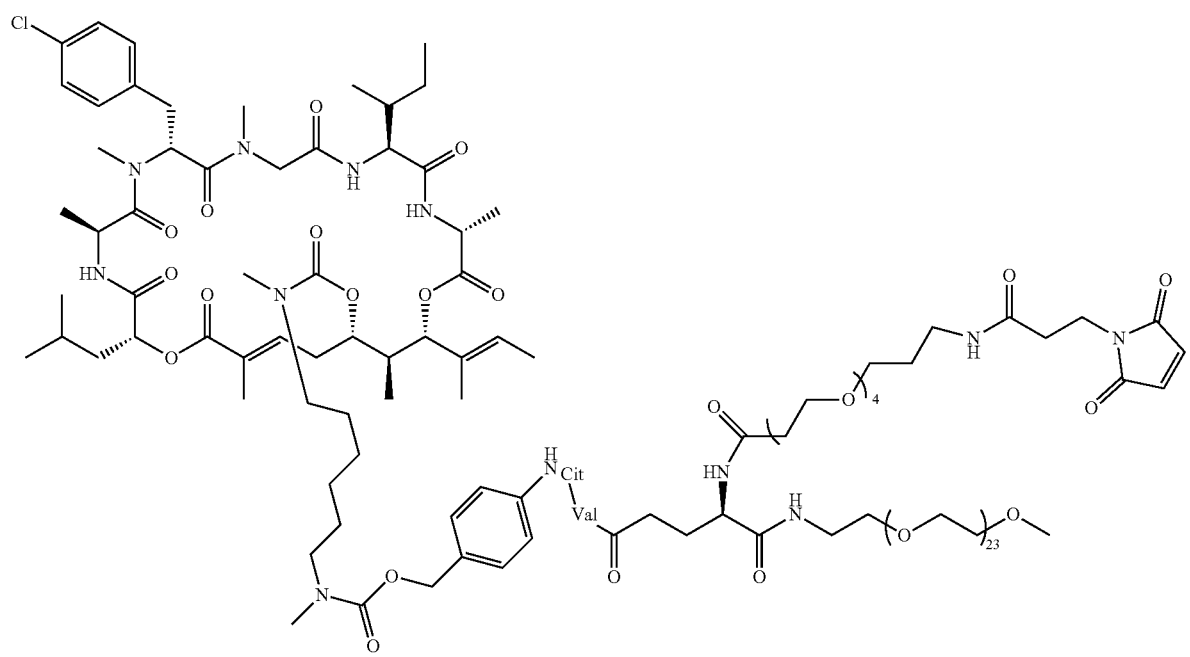
To the solution of (2R,5S,8R,14S,17R,20S,21S,22S,E)-20-((E)-but-2-en-2-yl)-14-((R)-sec-butyl)-8-(4-chlorobenzyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (4-((S)-2-(2-((S)-3-methyl-1-oxobutan-2-yl)hydrazinyl)-5-ureidopentanamido)benzyl) hexane-1,6-diylbis(methylcarbamate) (6 mg, 4.177 μmol) and 76-(1-(2,5-dioxo-2,5-dihydro-1H-pyrrol-1-yl)-3-oxo-7,10,13,16-tetraoxa-4-azanonadecan-19-amido)-75-oxo-2,5,8,11,14,17,20,23,26,29,32,35,38,41,44,47,50,53, 56,59,62,65,68,71-tetracosaoxa-74-azanonaheptacontan-79-oic acid (10 mg, 6.188 µmol) in DCM was added Hunig's base and HATU. The mixture was stirred overnight and purified with RP-flash chromatography to afford (2R,5S,8R,14S,17R,20S,21S,22S,E)-20-((E)-but-2-en-2-yl)-14-((R)-sec-butyl)-8-(4-chlorobenzyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (4-((76R,81S,84S)-76-(1-(2,5-dioxo-2,5-dihydro-1H-pyrrol-1-yl)-3-oxo-7,10,13,16-tetraoxa-4-azanonadecan-19-amido)-81-isopropyl-75,79,80-trioxo-84-(3-ureidopropyl)-2,5,8,11,14,17,20,23,26,29,32,35,38,41,44,47,50,53,56,59,62,65,68,71-tetracosaoxa-74,82,83-triazapentaoctacontan-85-amido)benzyl)hexane-1,6-diylbis(methylcarbamate) (5 mg, 39.45%). Observed HRMS (ESI) m/z: 1516.8314 $[M+H]^{2-}$.

Example 60

Synthesis of Conjugate L30

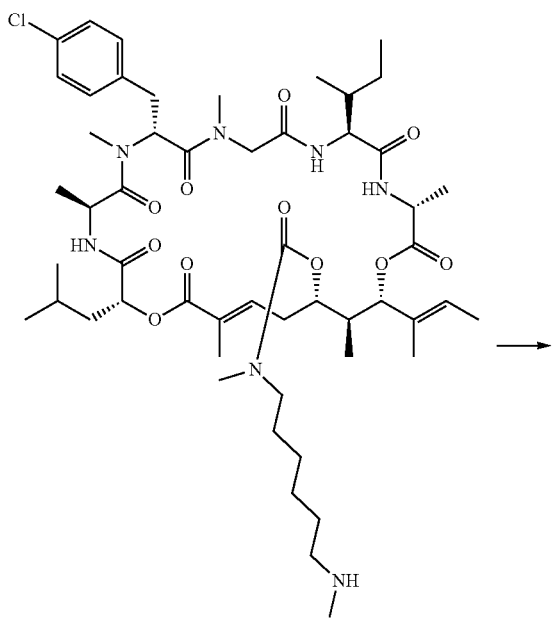

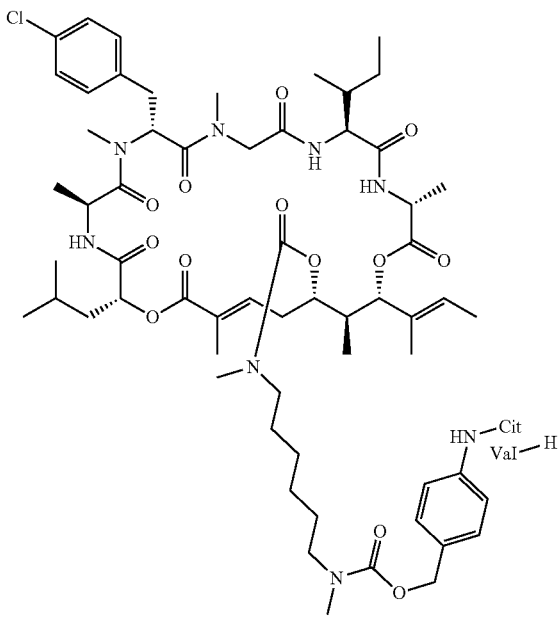

To the solution of (2R,5S,8R,14S,20S,21S,22S,E)-20-((E)-but-2-en-2-yl)-14-((R)-sec-butyl)-8-(4-chlorobenzyl)-2-isobutyl-5,7,10,17,17,21,25-heptamethyl-3,6,9,12,15,18,26-heptaoxo-1,19-dioxa-4,7,10,13,16-pentaazacyclohexacos-24-en-22-yl methyl(6-(methylamino)hexyl)carbamate (0.01 g, 9.571 µmol) in DCM (700 µL) was added DIPEA (0.012 g, 0.016 mL, 0.095 mmol), and 1-hydroxy-7-azabenzotriazole (1.302 mg, 9.571 µmol) and stirred overnight at RT. The reaction was monitored by LCMS. The resulting crude material was carried forward to Fmoc deprotection using a 40% solution of $Et_2NH$ in MeCN. The material was concentrated and loaded onto C18 column for reverse phase purification using (MeCN+0.1% FA) & ($H_2O$+0.1% FA) to afford 4-((S)-2-((S)-2-amino-3-methylbutanamido)-5-ureidopentanamido)benzyl ((2R,5S,8R,14S,20S,21S,22S,E)-20-((E)-but-2-en-2-yl)-14-((R)-sec-butyl)-8-(4-chlorobenzyl)-2-isobutyl-5,7,10,17,17,21,25-heptamethyl-3,6,9,12,15,18,26-heptaoxo-1,19-dioxa-4,7,10,13,16-pentaazacyclohexacos-24-en-22-yl) hexane-1,6-diylbis(methylcarbamate) (9.9 mg, 9.6 µmol).

Example 61

Synthesis of Conjugate L31

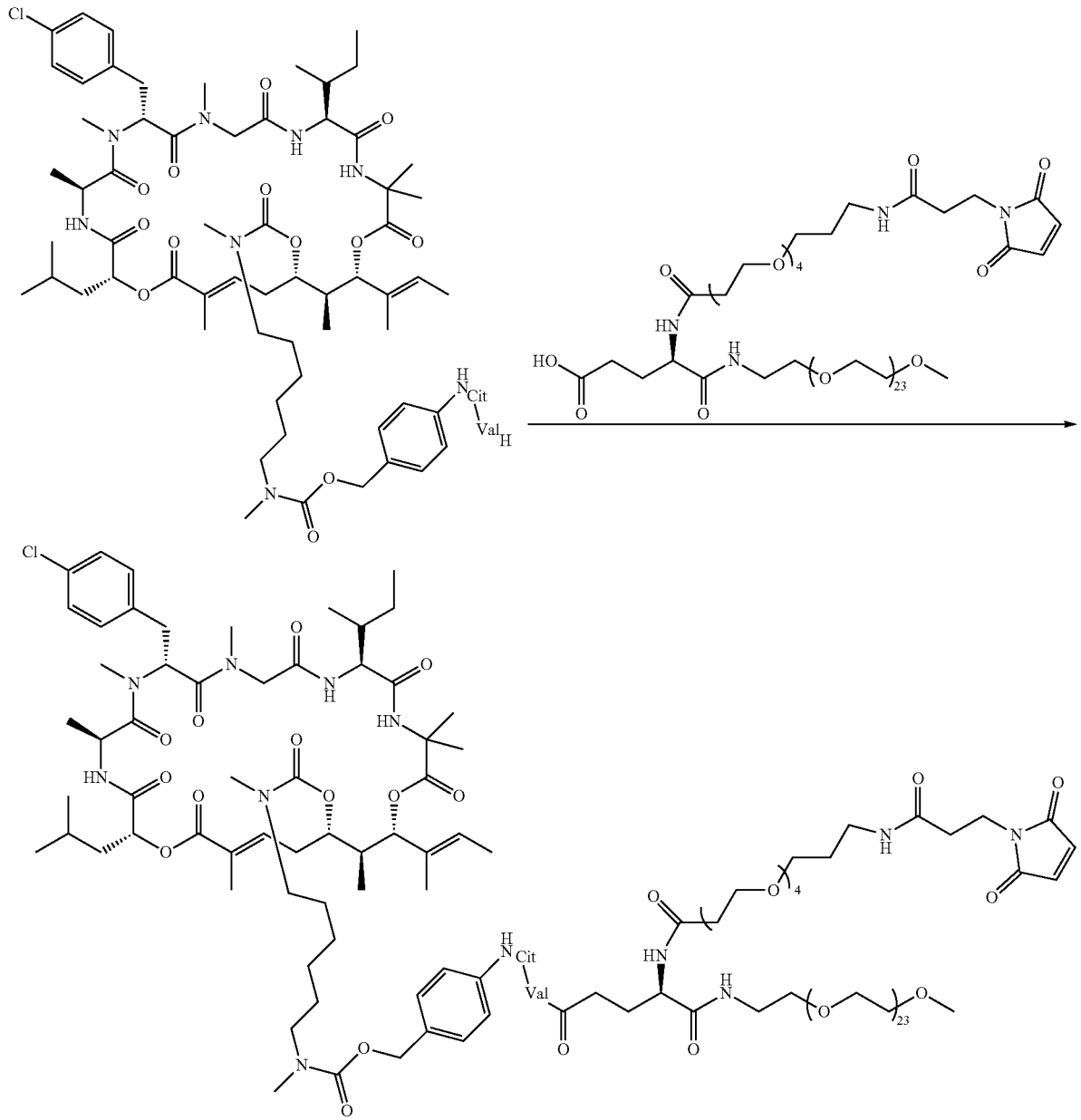

To the solution of (2R,5S,8R,14S,20S,21S,22S,E)-20-((E)-but-2-en-2-yl)-14-((R)-sec-butyl)-8-(4-chlorobenzyl)-2-isobutyl-5,7,10,17,17,21,25-heptamethyl-3,6,9,12,15,18,26-heptaoxo-1,19-dioxa-4,7,10,13,16-pentaazacyclohexacos-24-en-22-yl(4-((S)-2-(2-((S)-3-methyl-1-oxobutan-2-yl)hydrazinyl)-5-ureidopentanamido)benzyl) hexane-1,6-diylbis(methylcarbamate) (9 mg, 6.205 μmol) and 76-(1-(2,5-dioxo-2,5-dihydro-1H-pyrrol-1-yl)-3-oxo-7,10,13,16-tetraoxa-4-azanonadecan-19-amido)-75-oxo-2,5,8,11,14,17,20,23,26,29,32,35,38,41,44,47,50,53,56,59,62,65,68,71-tetracosaoxa-74-azanonaheptacontan-79-oic acid (18 mg, 0.011 mmol) in DCM was added hunigs base and HATU at 0° C. The mixture was warmed up and stirred overnight, then purified with RP-flash chromatography to afford (2R,5S,8R,14S,20S,21S,22S,E)-20-((E)-but-2-en-2-yl)-14-((R)-sec-butyl)-8-(4-chlorobenzyl)-2-isobutyl-5,7,10,17,17,21,25-heptamethyl-3,6,9,12,15,18,26-heptaoxo-1,19-dioxa-4,7,10,13,16-pentaazacyclohexacos-24-en-22-yl (4-((76R,81S,84S)-76-(1-(2,5-dioxo-2,5-dihydro-1H-pyrrol-1-yl)-3-oxo-7,10,13,16-tetraoxa-4-azanonadecan-19-amido)-81-isopropyl-75,79,80-trioxo-84-(3-ureidopropyl)-2,5,8,11,14,17,20,23,26,29,32,35,38,41,44,47,50,53,56,59,62,65,68,71-tetracosaoxa-74,82,83-triazapentaoctacontan-85-amido)benzyl) hexane-1,6-diylbis(methylcarbamate)(7 mg, 37.01%). Observed HRMS (ESI) m/z: 1523.8465 [M+H]$^{2+}$.

Example 62

Synthesis of Compound 7

This compound is prepared using a similar procedure as that described in Example 4.

Example 63

Synthesis of Conjugates L12 and L15

These compounds are prepared using similar procedures as those described in Examples 8-11 and 13 for the synthesis of Conjugate L6.

Example 64

Synthesis of Conjugates L13 and L16

Conjugates L13 and L16 are prepared from Conjugates L12 and L15, respectively, via click chemistry.

Example 65

Synthesis of Conjugate L14

This compound is prepared using a similar procedure as that described in Example 11.

Example 66

Synthesis of Intermediate 5 (Linker-1)

Step 1: To the solution of 5-(tert-butyl) 1-(2,5-dioxopyrrolidin-1-yl) (tert-butoxycarbonyl)glutamate (14 mg, 0.034 mmol) and 2,5,8,11,14,17,20,23,26,29,32,35,38,41,44,47,50,53,56,59,62,65,68,71-tetracosaoxatriheptacontan-73-amine (22 mg, 0.020 mmol) in DCM (1.32 g, 1 mL, 15.542 mmol) was added Hunig's base (0.074 g, 100 μL, 0.572 mmol). The mixture was stirred for 2 h and purified with RP-flash to afford tert-butyl 76-((tert-butoxycarbonyl)amino)-75-oxo-2,5,8,11,14,17,20,23,26,29,32,35,38,41,44,47,50,53,56,59,62,65,68,71-tetracosaoxa-74-azanonaheptacontan-79-oate (42 mg, 87.45%).

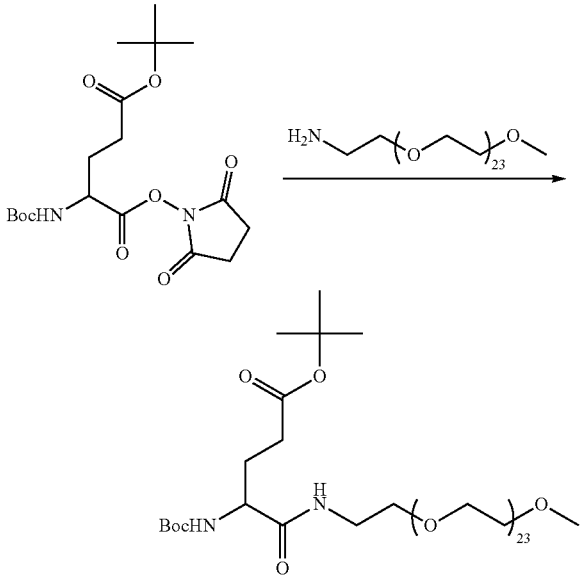

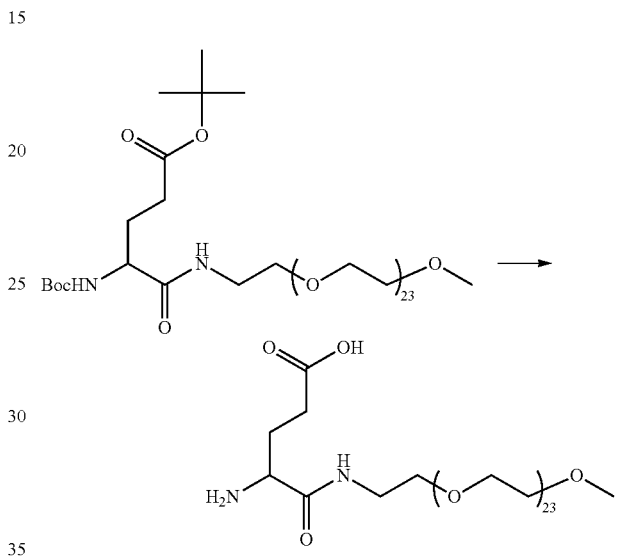

Step 2: To the solution of tert-butyl 76-((tert-butoxycarbonyl)amino)-75-oxo-2,5,8,11,14,17,20,23,26,29,32,35,38,41,44,47,50,53,56,59,62,65,68,71-tetracosaoxa-74-azanonaheptacontan-79-oate (0.035 g, 0.026 mmol) in DCM (0.66 g, 0.5 mL, 7.771 mmol) was added TFA (074 g, 0.5 ml, 6.489 mmol). The reaction mixture was stirred for 1 h and the volatile was removed. The residue was purified with RP-flash to afford 76-amino-75-oxo-2,5,8,11,14,17,20,23,26,29,32,35,38,41,44,47,50,53,56,59,62,65,68,71-tetracosaoxa-74-azanonaheptacontan-79-oic acid (32 mg, 101.1%).

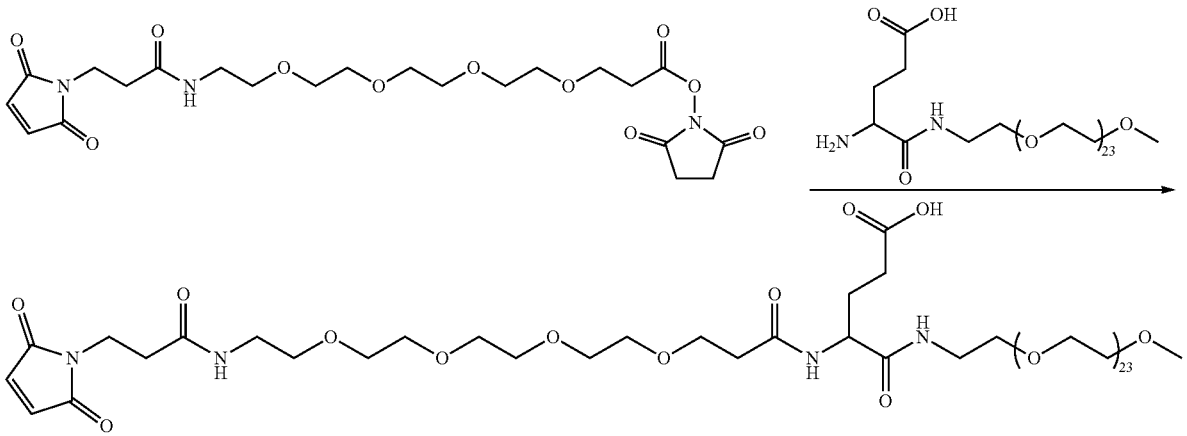

Step 3: To the solution of 2,5-dioxopyrrolidin-1-yl 1-(2,5-dioxo-2,5-dihydro-1H-pyrrol-1-yl)-3-oxo-7,10,13,16-tetraoxa-4-azanonadecan-19-oate (0.013 g, 0.026 mmol) and 76-amino-75-oxo-2,5,8,11,14,17,20,23,26,29,32,35,38,41,44,47,50,53,56,59,62,65,68,71-tetracosaoxa-74-azanonaheptacontan-79-oic acid (32 mg, 0.026 mmol) in DMF (0.472 g, 0.5 mL, 6.457 mmol) was added HOAt (3.577 mg, 0.026 mmol.). The reaction mixture was stirred for 2 h and purified with RP-flash to afford 76-(1-(2,5-dioxo-2,5-dihydro-1H-pyrrol-1-yl)-3-oxo-7,10,13,16-tetraoxa-4-azanonadecan-19-amido)-75-oxo-2,5,8,11,14,17,20,23,26,29,32,35,38,41,44,47,50,53,56,59,62,65,68,71-tetracosaoxa-74-azanonaheptacontan-79-oic acid (21 mg, 49.44%).

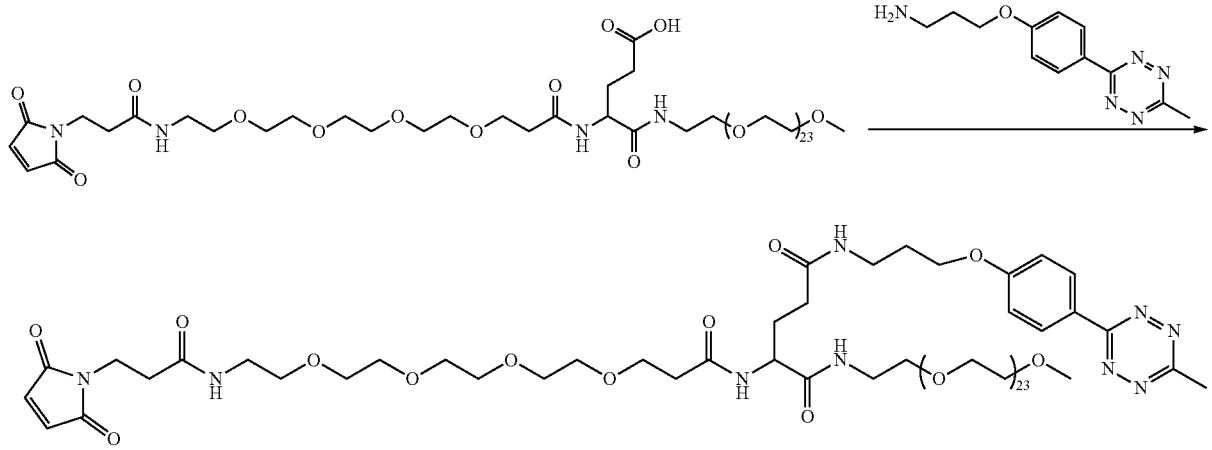

Intermediate 5 (Linker 1)

Step 4: To the solution of 76-(1-(2,5-dioxo-2,5-dihydro-1H-pyrrol-1-yl)-3-oxo-7,10,13,16-tetraoxa-4-azanonadecan-19-amido)-75-oxo-2,5,8,11,14,17,20,23,26,29,32,35,38,41,44,47,50,53,56,59,62,65,68,71-tetracosaoxa-74-azanonaheptacontan-79-oic acid (12 mg, 7.426 μmol) and 3-(4-(6-methyl-1,2,4,5-tetrazin-3-yl)phenoxy)propan-1-amine (5 mg, 0.020 mmol) in DCM (0.66 g, 0.5 mL, 7.771 mmol) and hunig's base (0.074 g, 0.1 ml, 0.572 mmol) was added HATU (10 mg, 0.026 mmol). The mixture was stirred overnight and diluted with RP-flash to afford 2-(1-(2,5-dioxo-2,5-dihydro-1H-pyrrol-1-yl)-3-oxo-7,10,13,16-tetraoxa-4-azanonadecan-19-amido)-N5-(3-(4-(6-methyl-1,2,4,5-tetrazin-3-yl)phenoxy)propyl)-N1-(2,5,8,11,14,17,20,23,26,29,32,35,38,41,44,47,50,53,56,59,62,65,68,71-tetracosaoxatriheptacontan-73-yl)pentanediamide (Linker-1, 4 mg, 29.22%).

Example 67

Synthesis of Intermediate 6 (Ab-Linker-1)

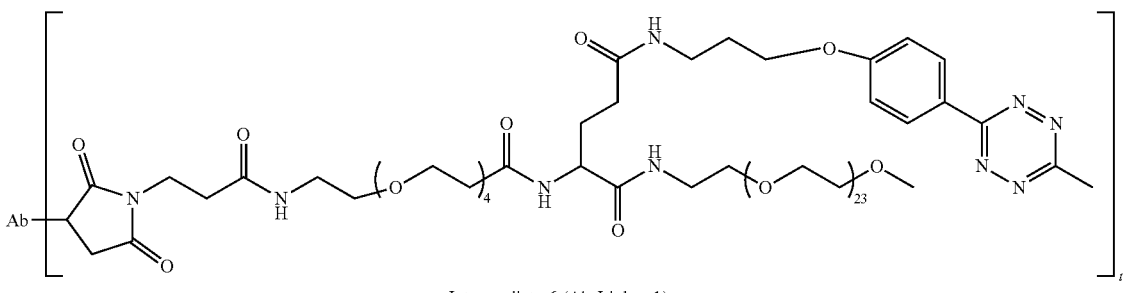

Intermediate 6 (Ab-Linker-1)

To the solution of Ab where Ab is a Trastuzumab Biosimilar (TBS, 0.991 mg, 0.099 mL, 0.006 μmol) in PBS was diluted with PBS (0.120 μg, 0.1 mL, 0.006 μmol) and added TCEP (0.033 mg, 0.026 mL, 0.134 μmol). The mixture was left at RT with mild agitation for 12 h and then added 2-(1-(2,5-dioxo-2,5-dihydro-1H-pyrrol-1-yl)-3-oxo-7,10,13,16-tetraoxa-4-azanonadecan-19-amido)-N5-(3-(4-(6-methyl-1,2,4,5-tetrazin-3-yl)phenoxy)propyl)-N1-(2,5,8,11,14,17,20,23,26,29,32,35,38,41,44,47,50,53,56,59,62,65,68,71-tetracosaoxatriheptacontan-73-yl)pentanediamide (0.098 mg, 0.010 mL, 0.053 μmol) in DMSO. The mixture was further agitated overnight and then the solution was run through a spin column (2 mL Zaba desalting spin column) to remove excess of reagents.

Example 68

Synthesis of Conjugate C20

To the solution of Intermediate-6 (Ab-Linker-1, 0.5 mg, 50 μL) in PBS (50 μL) was added (2R,5S,8R,14S,17R,20S,21S,22S,E)-20-((E)-but-2-en-2-yl)-14-((R)-sec-butyl)-8-(4-chlorobenzyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (5-((((((4-((2S)-2-((2R)-2-(((((E)-cyclooct-4-en-1-yl)oxy)carbonyl)amino)-3-methylbutanamido)-5-ureidopentanamido)benzyl)oxy)(hydroxy)phosphoryl)oxy)(hydroxy)phosphoryl)oxy)pentyl) carbamate (conjugate L20, 3.3 μmol, 1 μL) and shaken for 15 min and the solution was run through spin column to remove the excess of reagent to afford Conjugate C20.

Example 69

Synthesis of Conjugate C23

To the solution of Intermediate-6 (Ab-Linker-1, 0.5 mg, 50 μL) diluted in PBS (50 uL) was added (2R,5S,8R,14S,17S,20S,21S,22S,E)-20-((E)-but-2-en-2-yl)-14-((R)-sec-butyl)-8-(4-chlorobenzyl)-2-isobutyl-5,7,10,17,21,25-hexamethyl-3,6,9,12,15,18,26-heptaoxo-1,19-dioxa-4,7,10,13,16-pentaazacyclohexacos-24-en-22-yl (5-((((((5-((((4-((2R)-2-((2R)-2-(((((E)-cyclooct-4-en-1-yl)oxy)carbonyl)amino)-3-methylbutanamido)-5-ureidopentanamido)benzyl)oxy)carbonyl)amino)pentyl)oxy)(hydroxy)phosphoryl)oxy)(hydroxy)phosphoryl)oxy)pentyl) carbamate (conjugate L23, 3.3 μmol, 1 μL) and shaken for 15 min and the solution was run through spin column to remove the excess of reagent to afford Conjugate C23.

Example 70

Synthesis of Conjugates C24, C25, and C26

The antibody-drug conjugates C24-26, wherein Ab is Trastuzumab Biosimilar (TBS) antibody, were synthesized using protocols similar to methods described previously (Ref: Bryant, P. et al, *Mol. Pharmaceuticals*, 2015, 12, 1872-1879). Briefly, the purified antibody, Trastuzumab Biosimilar (TBS, 1-2 mg) was buffer exchanged with PBS (1× solution, pH 7.5) and EDTA (20 mM) mix and diluted to a final concentration of 2.5 mg/mL. A stock solution of TCEP (1 mM) was freshly prepared in PBS, and 6 molar equiv. (relative to the antibody concentration) was added to the antibody and left the mixture on a heat block. After 1 h, the partially reduced antibody was removed from the heat block and cooled to room temperature. A stock solution of Conjugate L24, L25, and L26 (5 mM in DMSO) was freshly prepared, and 6-8 molar equiv was added to the antibody. The reaction was incubated at RT for 15-20 h under mild agitation. Then the reaction mixture was passed through a spin column (Zeba, 2 mL) to remove small MW reagents and buffer exchanged by ultrafiltration (10 kDa MWCO) into PBS to afford the ADC, C24-C27 in PBS. The resulting ADC had an average DAR around 4 by HIC. The aggregation was measured by Size Exclusion Chromatography (SEC) and it was less than 1%.

Example 71

Synthesis of Conjugates C29 and C31

The antibody-drug conjugates C29 and C31 is synthesized from L29 and L31 respectively, using protocols similar to methods described previously (Ref Doronina, S. O. et al, *Bioconjugate Chem.* 2008, 19 (10), 1960-1963).

Example B1

Inhibitory Response of Test Compounds Against BT-474 and HCC1954 Cells

BT-474 human mammary gland ductal carcinoma cells were seeded in a clear polystyrene 96-well microculture plate (Corning® Costar® 96-well flat bottom plate, Cat. #3997) in a total volume of 90 μL/well. After 24 hours of incubation in a humidified incubator at 37° C. with 5% $CO_2$ and 95% air, 10 μL of 10×, serially diluted test agents in growth medium were added to each well (10 pt dose response curve, highest concentration 10 μM of test agent). After 72 hours of culture in a humidified incubator at 37° C., in an atmosphere of 5% $CO_2$ and 95% air, the plated cells and Cell Titer-Glo® (Protnega G7571) reagents were brought to room temperature to equilibrate for 30 minutes. 100 μL of Cell Titer-Glo® reagent was added to each well. The plate was shaken for two minutes and then left to equilibrate for ten minutes. The media/Cell Titer-Glo® reagent was transferred to a white polystyrene 96-well microculture plate (Corning® Costar® 96-well flat bottom plate, Cat. #3917) before reading luminescence on a Tecan GENios microplate reader.

Percent inhibition of cell growth was calculated relative to untreated control wells. The $IC_{50}$ value for the test agents was determined using Prism 6.05 by curve-fitting of the data using the following four parameter-logistic equation:

$$Y = \frac{\text{Top} - \text{Bottom}}{1 + (X/IC_{50})^n} + \text{Bottom},$$

where Top is the maximal % of control absorbance, Bottom is the minimal % of control absorbance at the highest agent concentration, Y is the % of control absorbance, X is the agent concentration, IC$_{50}$ is the concentration of agent that inhibits cell growth by 50% compared to the control cells, and n is the slope of the curve.

Inhibitory response of test compounds against HCC1954 cells was determined using a method analogous to that used for BT-474 cells. IC$_{50}$ values for various test agents in BT-474 and HCC1954 cells are shown in Table 4.

TABLE 4

| Compound No. | BT-474 IC$_{50}$ in nM | HCC1954 IC$_{50}$ in nM |
| --- | --- | --- |
| 1 | 0.08111 | 0.4565 |
| 2 | 3.749 | 4.947 |
| 3 | 0.0843 | 1.407 |
| 4 | 0.5231 | 3.209 |
| 5 | 0.329 | 1.11 |
| 6 | 0.9304 | 1.658 |
| 8 | 8.66 | 31.88 |
| 9 | 0.15 | 0.25 |
| 10 | — | 1.36 |
| 11 | 1.00 | 1.64 |
| 12 | — | 3.29 |
| 13 | — | 18.13 |
| 15 | 2.62 | 4.37 |
| 16 | — | 0.10 |
| 17 | — | 4.15 |
| 18 | — | 2.37 |
| 19 | — | 4.16 |
| 20 | — | 15.45 |
| 21 | — | 0.56 |
| 22 | — | 7.26 |
| 23 | — | 0.47 |
| 24 | — | 2.07 |
| 26 | — | 1.36 |
| 29 | — | 27.33 |

Example B2

Inhibitory Response of Test Conjugates Against BT-474 and HCC1954 Cells

The inhibitory responses of test conjugates against BT-474 and HCC1954 cells are determined using similar methods as described in Example B1. Serially diluted test conjugates are incubated with each type of cell in a 96-well plate for 72 hours to generate a dose response curve, as described in Example B1. The percent inhibition of cell growth is calculated relative to untreated control wells, and the IC$_{50}$ values for the test agents are determined.

While the foregoing written description of the compounds, uses, and methods described herein enables one of ordinary skill to make and use the compounds, uses, and methods described herein, those of ordinary skill will understand and appreciate the existence of variations, combinations, and equivalents of the specific embodiment, method, and examples herein. The compounds, uses, and methods provided herein should therefore not be limited by the above-described embodiments, methods, or examples, but rather encompasses all embodiments and methods within the scope and spirit of the compounds, uses, and methods provided herein.

All references disclosed herein are incorporated by reference in their entirety.

The invention claimed is:

1. A compound of Formula (I):

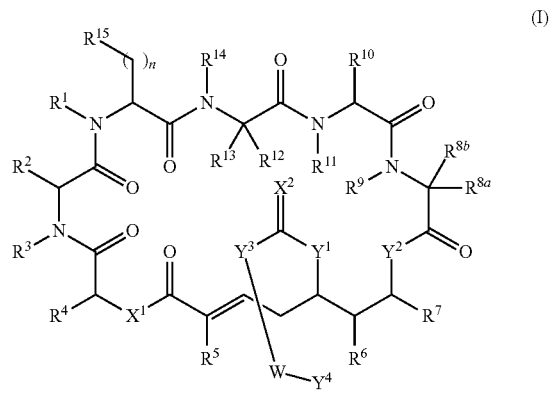

or a salt thereof, wherein $R^1$, $R^2$, $R^3$, $R^{8a}$, $R^{8b}$, $R^9$, $R^{10}$, $R^{11}$, $R^{12}$, $R^{13}$, and $R^{14}$ are each independently H, substituted or unsubstituted alkyl, substituted or unsubstituted alkenyl, substituted or unsubstituted alkynyl, substituted or unsubstituted cycloalkyl, or substituted or unsubstituted cycloalkenyl;

$R^4$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or substituted or unsubstituted heterocyclyl;

$R^5$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, halo, or perhaloalkyl;

$R^6$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclyl, halo, or perhaloalkyl;

$R^7$ is hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or substituted or unsubstituted heterocyclyl;

$R^{15}$ is substituted or unsubstituted aryl, substituted or unsubstituted heteroaryl, substituted or unsubstituted cycloalkyl, substituted or unsubstituted heterocyclyl, or substituted or unsubstituted alkyl;

n is 0, 1, or 2;

$X^1$ is —N($R^d$)— or —O—;

$X^2$ is O or S;

$Y^1$ and $Y^2$ are each independently —N($R^d$)—, —O—, or —S—;

$Y^3$ is —N($R^d$)—, —O—, —S—, or substituted or unsubstituted heterocycloalkyl;

$Y^4$ is —$OR^a$, —$NR^bR^c$, or —$SR^a$;

each $R^a$, $R^b$, $R^c$, and $R^d$ is independently H, substituted or unsubstituted alkyl, substituted or unsubstituted alkenyl, substituted or unsubstituted alkynyl, substituted or unsubstituted cycloalkyl, or substituted or unsubstituted cycloalkenyl;

W is $(CH_2)_m$—Z—$(CH_2)_p$;

Z is substituted or unsubstituted alkyl, substituted or unsubstituted substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, or $(CH_2CH_2O)_q$;

m, and p are each independently an integer from 0-12; and q is an integer from 1-12;

provided that i) when $Y^4$ is —OH, W is not —$(CH_2)_2$— or —$(CH_2CH_2O)_3(CH_2)_2$—; and ii) when $Y^4$ is —$NHR^c$ or —N($CH_3$)$R^c$, W is not —$(CH_2)_2$—, —$(CH_2)_6$—, or —$CH_2(CH_2CH_2O)_3(CH_2)_3$—.

2. The compound of claim 1, or a salt thereof, wherein $R^1$, $R^3$, $R^4$, $R^5$, $R^6$, $R^{8a}$, $R^{8b}$, $R^9$, $R^{10}$, $R^{11}$, $R^{12}$, $R^{13}$ and $R^{14}$ are each independently H or $C_1$-$C_6$ alkyl.

3. The compound of claim 1, or a salt thereof, wherein $R^2$ is H or $C_1$-$C_6$ alkyl optionally substituted with $NH_2$.

4. The compound of claim 1, or a salt thereof, wherein $R^1$, $R^5$, $R^6$, $R^8$, and $R^{14}$ are each methyl;
$R^2$ is methyl or —$(CH_2)_4NH_2$;
$R^3$, $R^{8b}$, $R^9$, $R^{11}$, $R^{12}$, and $R^{13}$ are each H;
$R^4$ is iso-butyl; and
$R^{10}$ is sec-butyl.

5. The compound of claim 1, or a salt thereof, wherein $R^{15}$ is phenyl optionally substituted with halo, hydroxy, $C_1$-$C_6$ alkoxy, $C_1$-$C_6$ alkyl, or $C_1$-$C_6$ perhaloalkyl; and n is 1.

6. The compound of claim 1, or a salt thereof, wherein $X^1$ is —O— or —N($R^d$)—, and $R^d$ is H or $C_1$-$C_6$ alkyl.

7. The compound of claim 1, or a salt thereof, wherein $R^7$ is H, $C_1$-$C_6$ alkyl, $C_1$-$C_6$ alkenyl, or $C_1$-$C_6$ alkynyl.

8. The compound of claim 1, or a salt thereof, wherein $Y^1$ is —O—.

9. The compound of claim 1, or a salt thereof, wherein $Y^2$ is —O—.

10. The compound of claim 1, or a salt thereof, wherein $X^2$ is O.

11. The compound of claim 1, or a salt thereof, wherein $Y^1$ and $Y^2$ are each —O—, $X^2$ is O and $Y^3$ is —N($R^d$)—.

12. The compound of claim 1, or a salt thereof, wherein $Y^4$ is —$OR^a$ or —$NR^bR^c$.

13. The compound of claim 1, or a salt thereof, wherein each $R^a$, $R^b$, $R^c$, and $R^d$ is independently H or —$CH_3$.

14. The compound of claim 1, or a salt thereof, wherein m and p are each 0.

15. The compound of claim 1, or a salt thereof, wherein Z is $C_3$-$C_{12}$ alkyl.

16. The compound of claim 1, or a salt thereof, wherein Z is selected from the group consisting of substituted or unsubstituted $C_3$-$C_{12}$ cycloalkyl, substituted or unsubstituted $C_3$-$C_{12}$ cycloalkenyl, substituted or unsubstituted $C_5$-$C_{12}$ aryl, substituted or unsubstituted $C_5$-$C_{12}$ heteroaryl.

17. The compound of claim 1, or a salt thereof, wherein Z is $C_3$-$C_{12}$ alkyl or $(CH_2CH_2O)_q$, wherein q is an integer from 1-8.

18. The compound of claim 1, or a salt thereof, wherein q is 1 or 2.

19. The compound of claim 1, or a salt thereof, wherein the compound is selected from the group consisting of:

| Compound No. | Structure |
|---|---|
| 1 | 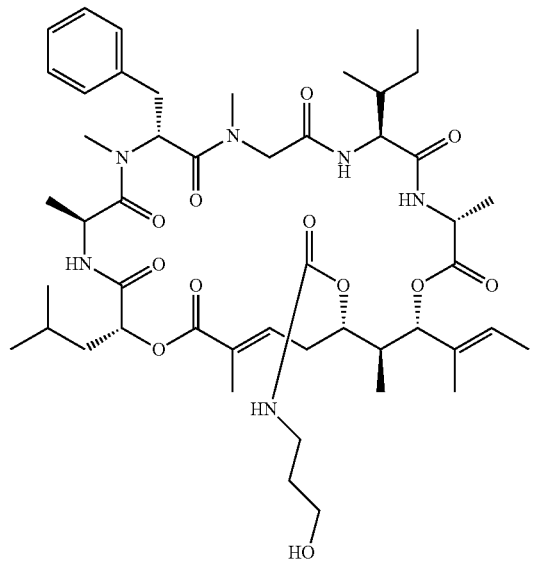 |

| Compound No. | Structure |
|---|---|
| 2 | 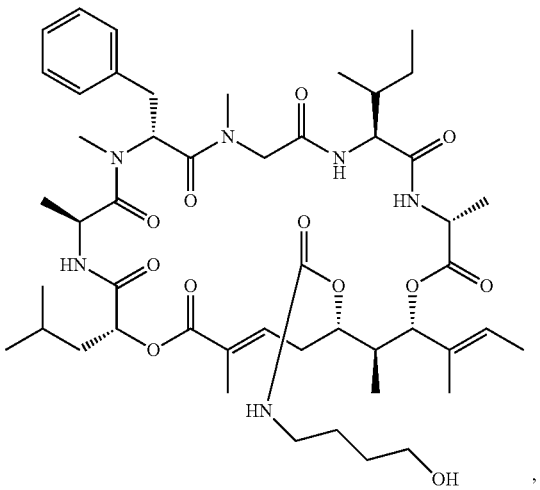 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCCO)[C@@H]1C] |
| 3 | 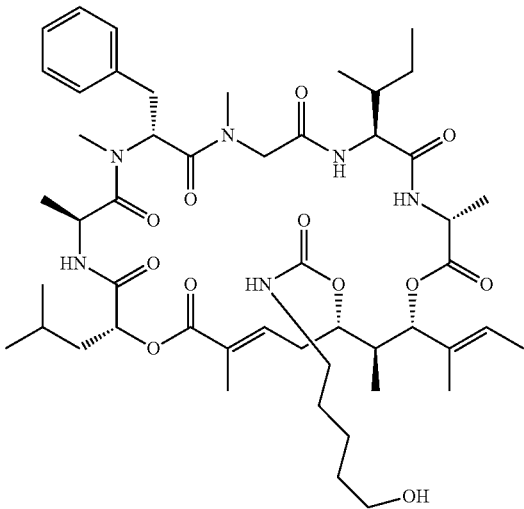 |
| 4 | 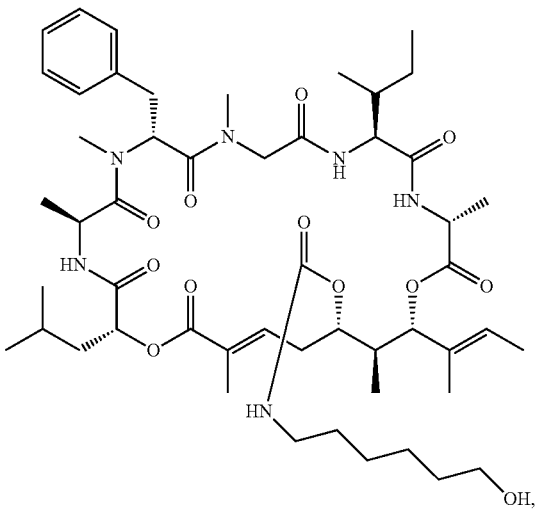 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCCCCO)[C@@H]1C] |

| Compound No. | Structure |
|---|---|
| 5 | 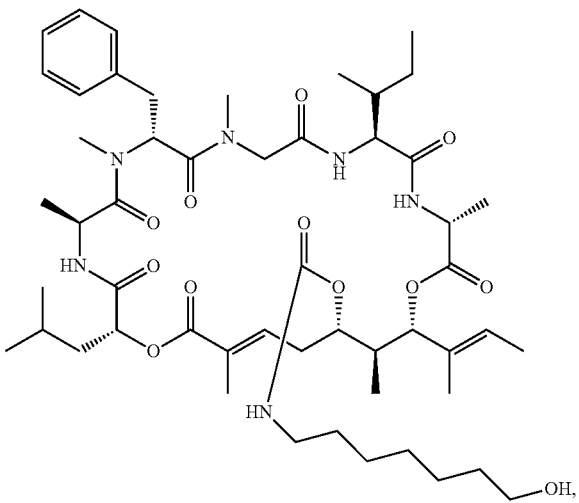 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCCCCCO)[C@@H]1C] |
| 6 | 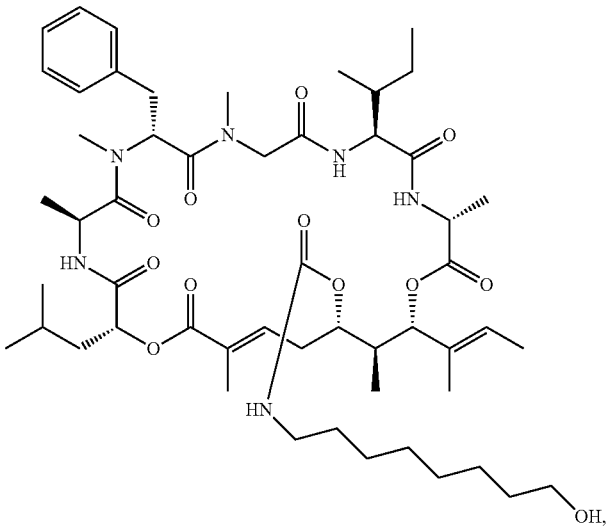 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCCCCCCO)[C@@H]1C] |

| Compound No. | Structure |
|---|---|
| 7 | 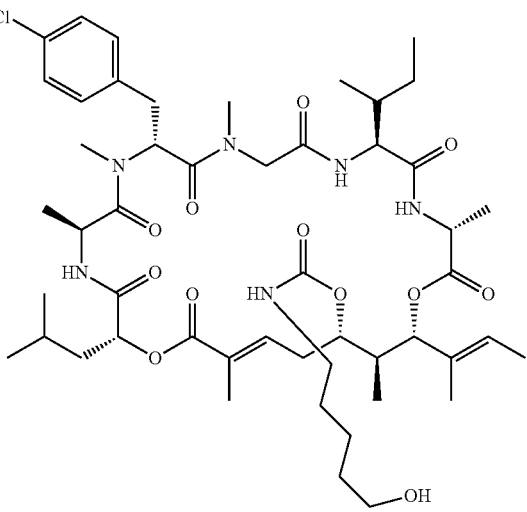 |
| 8 | 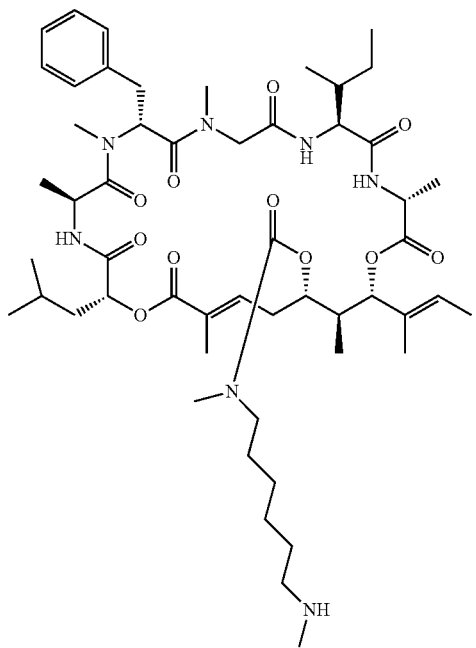 |

| Compound No. | Structure |
|---|---|
| 9 | 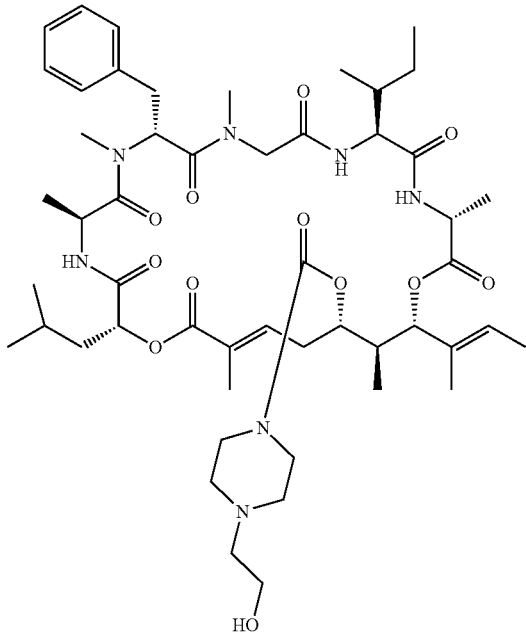 |
| 10 | 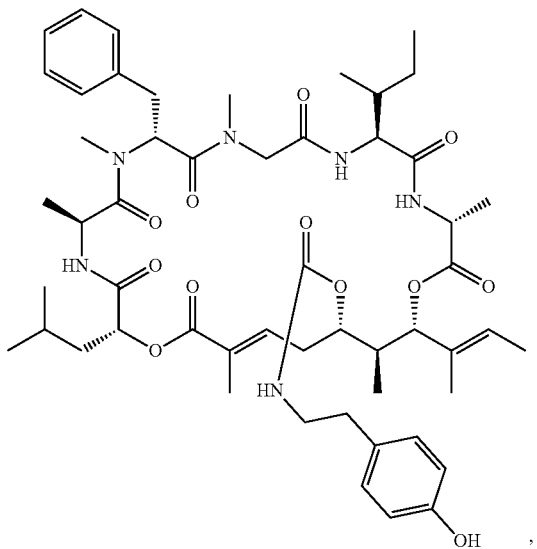 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCc2ccc(O)cc2)[C@@H]1C] |

| Compound No. | Structure |
|---|---|
| 11 | 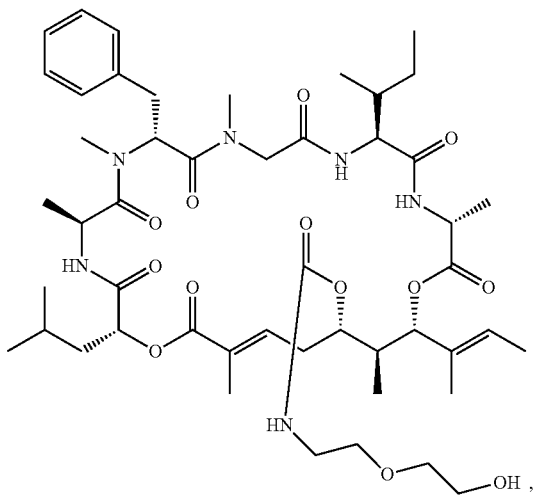 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCOCCO)[C@@H]1C] |
| 12 | 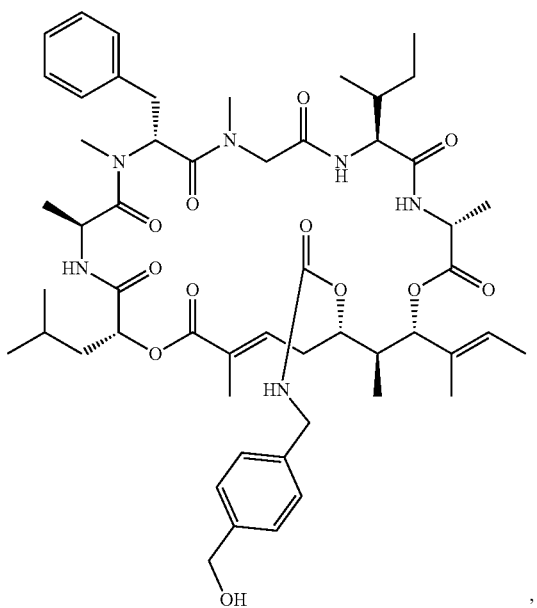 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCc2ccc(CO)cc2)[C@@H]1C] |

| Compound No. | Structure |
|---|---|
| 13 | 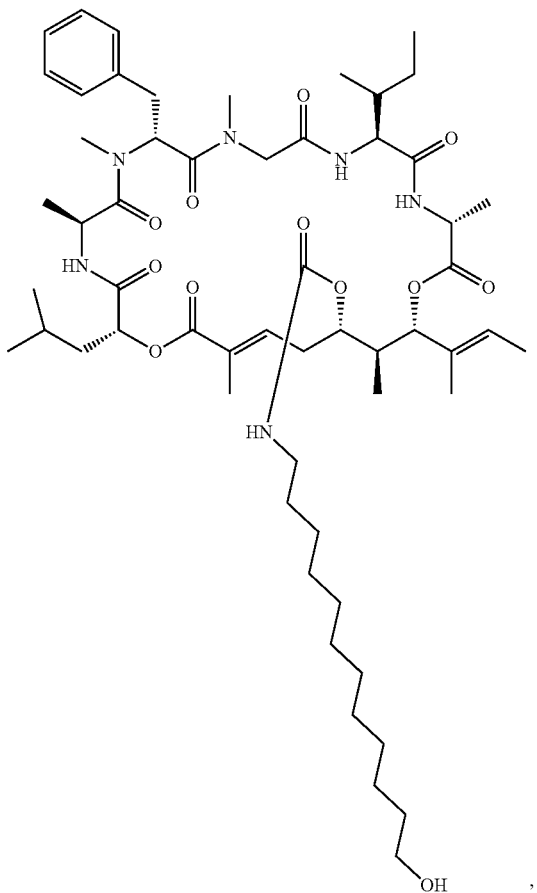 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCCCCCCCCCCO)[C@@H]1C] |
| 16 | 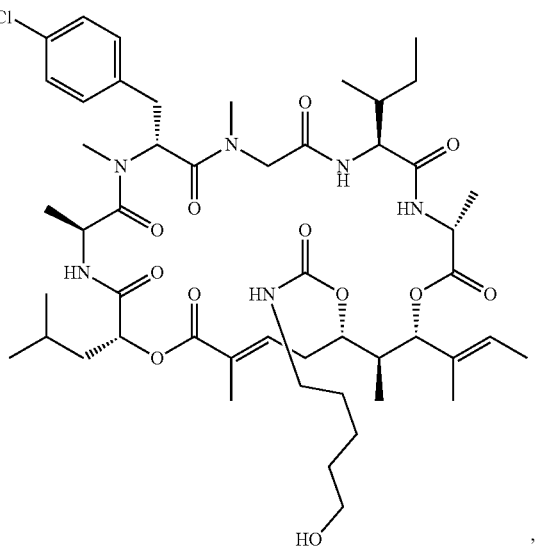 |

| Compound No. | Structure |
|---|---|
| 18 | 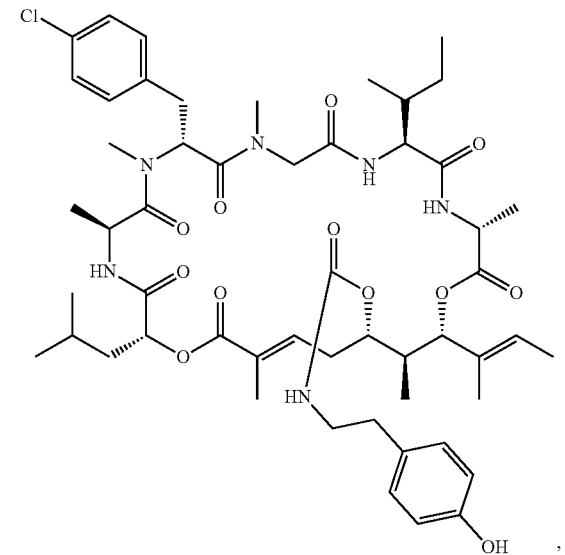 [SMILES: C/C=C(\C)[C@H]1OC(=O)[C@@H](C)NC(=O)[C@H](C(C)CC)NC(=O)CN(C)C(=O)[C@@H](Cc2ccc(Cl)cc2)N(C)C(=O)[C@H](C)NC(=O)[C@@H](CC(C)C)OC(=O)/C(C)=C/C[C@H](OC(=O)NCCc2ccc(O)cc2)[C@@H]1C] |
| 19 | 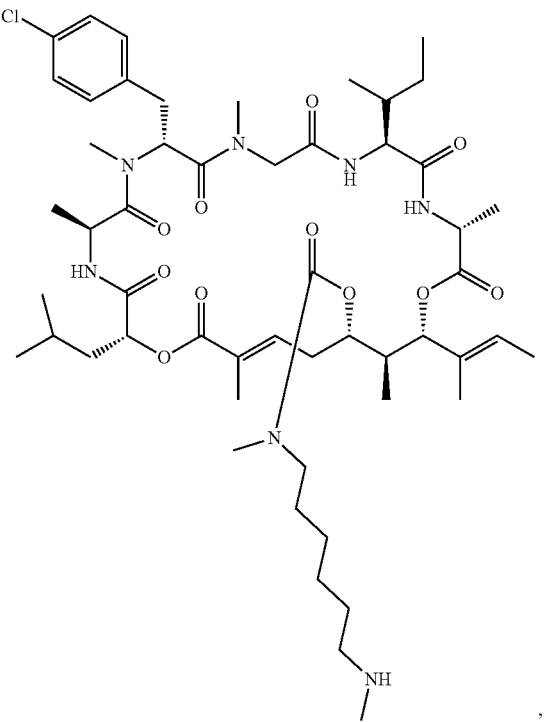 [SMILES: C/C=C(\C)[C@H]1OC(=O)[C@@H](C)NC(=O)[C@H](C(C)CC)NC(=O)CN(C)C(=O)[C@@H](Cc2ccc(Cl)cc2)N(C)C(=O)[C@H](C)NC(=O)[C@@H](CC(C)C)OC(=O)/C(C)=C/C[C@H](OC(=O)N(C)CCCCCCNC)[C@@H]1C] |

| Compound No. | Structure |
|---|---|
| 20 | 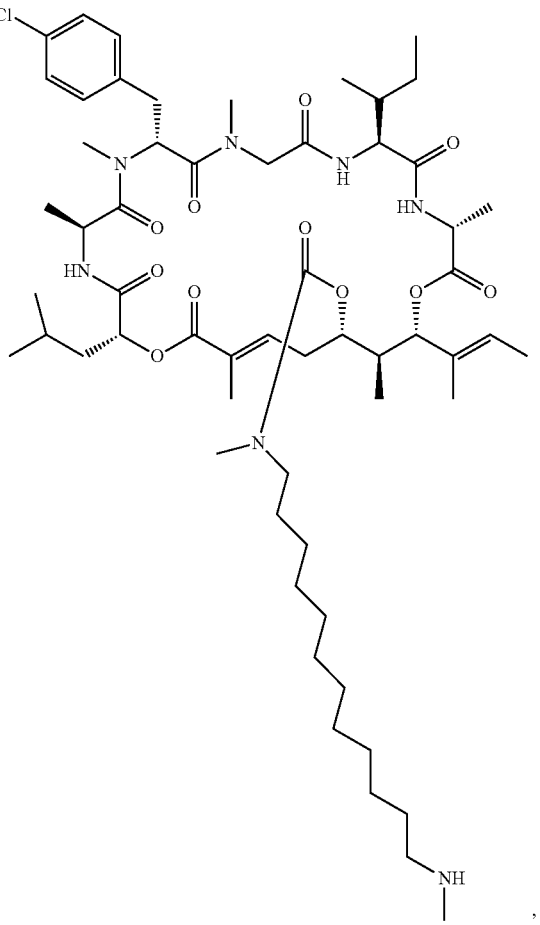 |
| 22 | 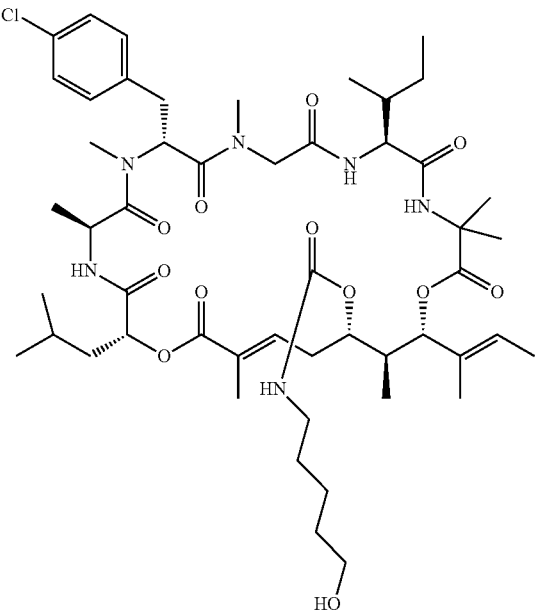 |

| Compound No. | Structure |
|---|---|
| 23 | 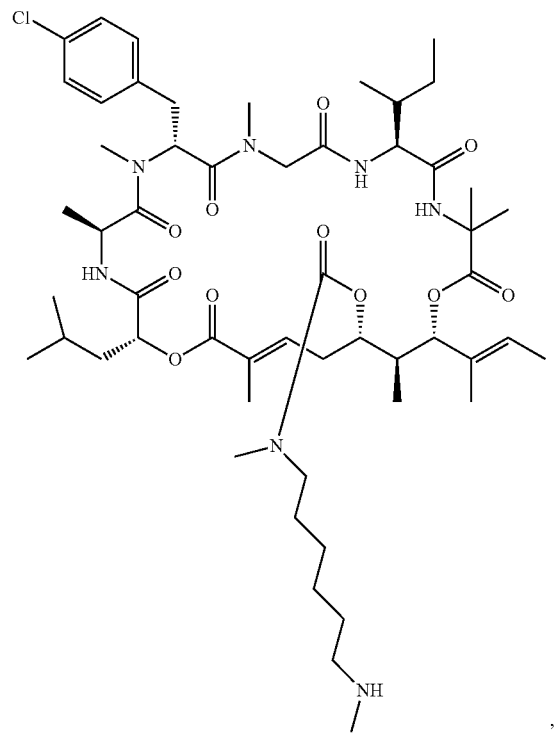 [SMILES: C/C=C(\C)[C@H]1OC(=O)C(C)(C)NC(=O)[C@H](C(C)CC)NC(=O)CN(C)C(=O)[C@@H](Cc2ccc(Cl)cc2)N(C)C(=O)[C@H](C)NC(=O)[C@@H](CC(C)C)OC(=O)/C(C)=C/C[C@H](OC(=O)N(C)CCCCCCNC)[C@@H]1C] |
| 24 | 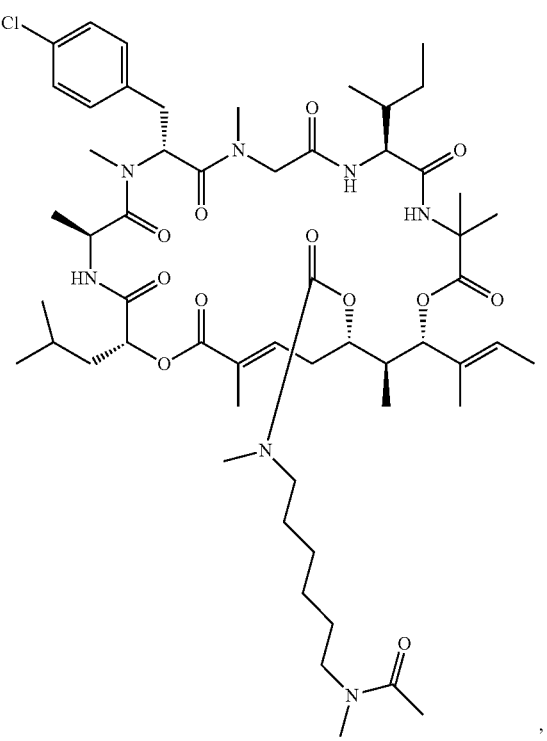 [SMILES: C/C=C(\C)[C@H]1OC(=O)C(C)(C)NC(=O)[C@H](C(C)CC)NC(=O)CN(C)C(=O)[C@@H](Cc2ccc(Cl)cc2)N(C)C(=O)[C@H](C)NC(=O)[C@@H](CC(C)C)OC(=O)/C(C)=C/C[C@H](OC(=O)N(C)CCCCCCN(C)C(C)=O)[C@@H]1C] |

| Compound No. | Structure |
|---|---|
| 25 | 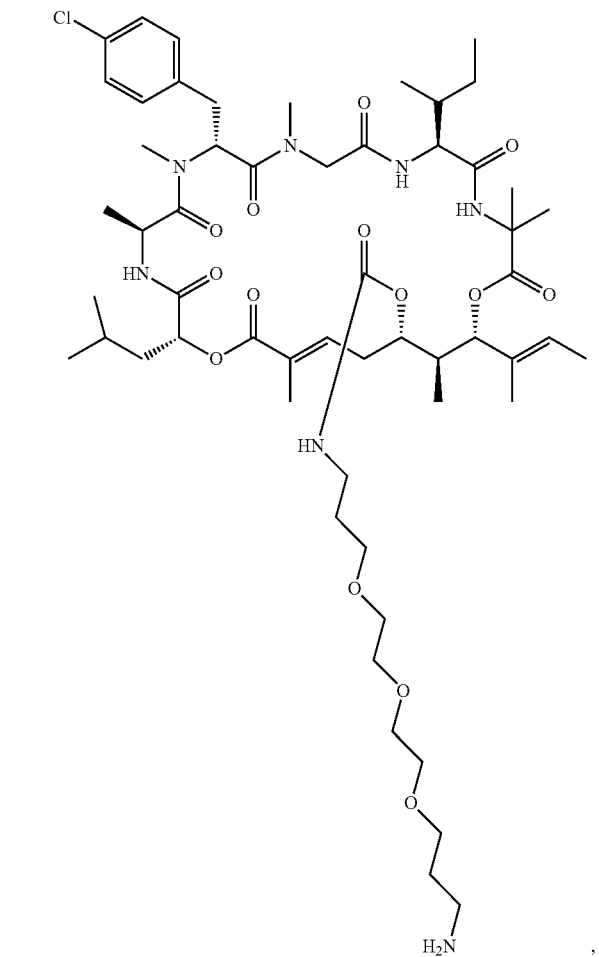 [SMILES: C/C=C(\C)[C@H]1OC(=O)C(C)(C)NC(=O)[C@H](C(C)CC)NC(=O)CN(C)C(=O)[C@@H](Cc2ccc(Cl)cc2)N(C)C(=O)[C@H](C)NC(=O)[C@@H](CC(C)C)OC(=O)/C(C)=C/C[C@H](OC(=O)NCCCOCCOCCOCCCN)[C@@H]1C] |
| 26 | 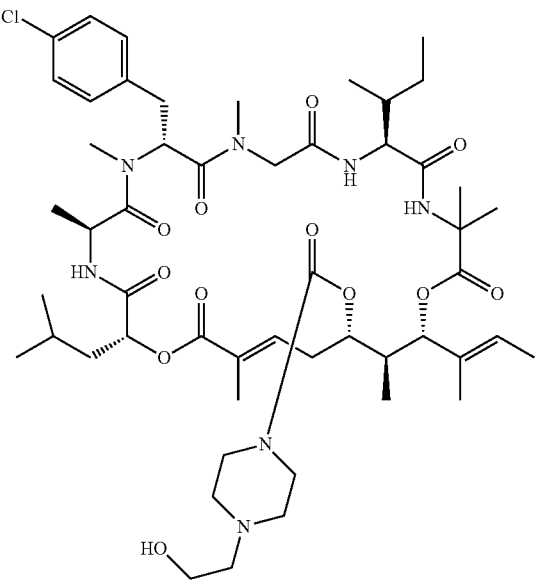 |

| Compound No. | Structure |
|---|---|
| 28 | 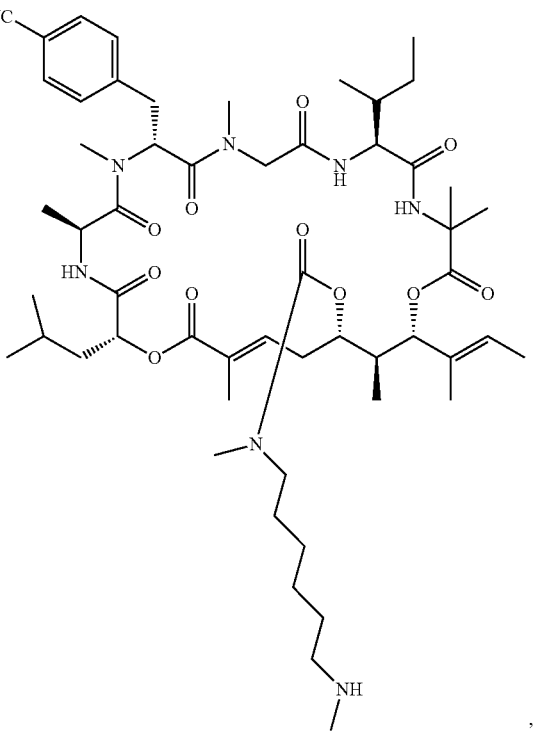 , and |
| 29 | 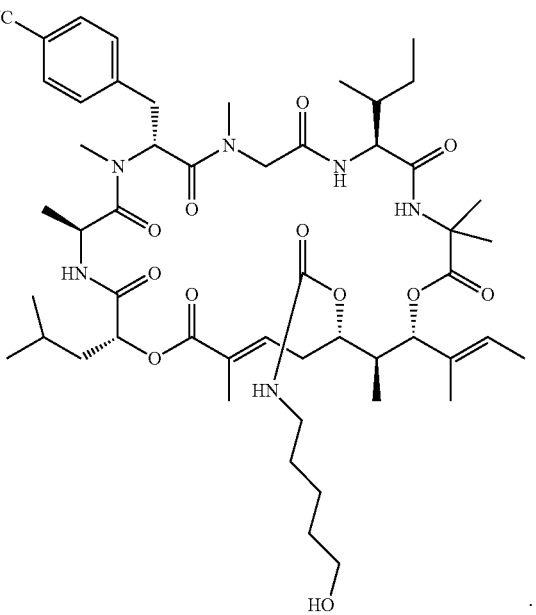 . |

20. A conjugate comprising a compound of claim 1 bonded to a ligand, wherein the ligand is a polypeptide or a nucleic acid.

21. The conjugate of claim 20, wherein the ligand is an antibody.

22. The conjugate of claim 20, wherein the compound is bonded to the ligand via a linker.

23. A conjugate comprising a compound of claim 1 bonded to a linker.

24. The conjugate of claim 22, wherein the linker is a cleavable linker.

25. The conjugate of claim 22, wherein the linker is a non-cleavable linker.

26. A pharmaceutical composition comprising a compound of claim 1, or a pharmaceutically acceptable salt thereof, and a pharmaceutically acceptable carrier.

27. A method of treating breast cancer in an individual in need thereof comprising administering to the individual a therapeutically effective amount of a compound of claim 1, or a pharmaceutically acceptable salt thereof, wherein the compound is selected from the group consisting of:
| Compound No. | Structure |
|---|---|
| 1 | 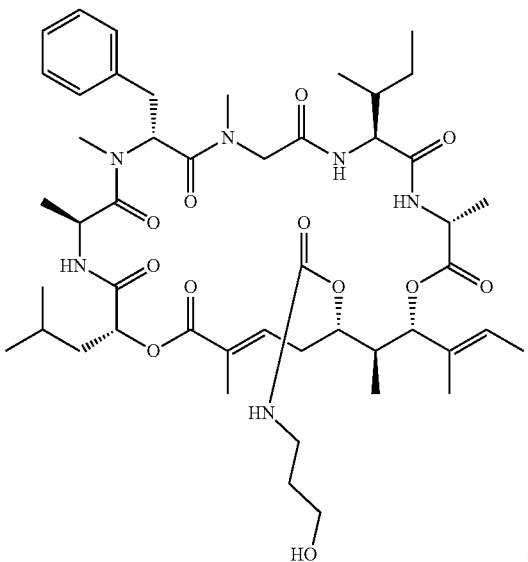 |
| 2 | 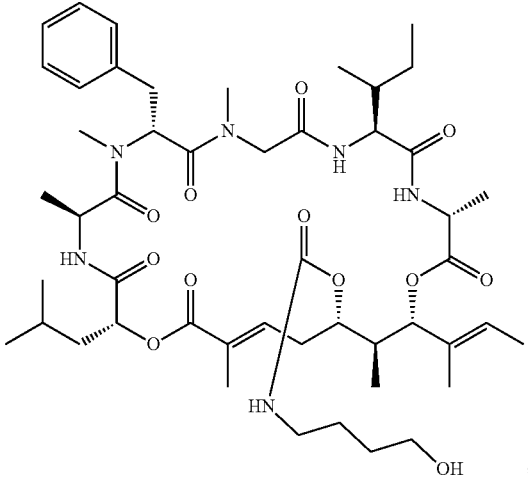 |
| 3 | 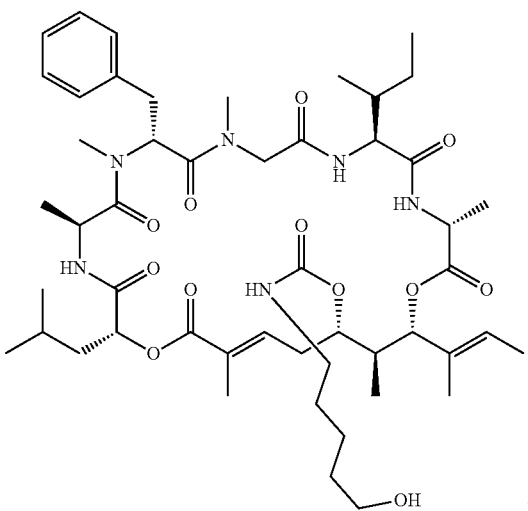 |

-continued
| Compound No. | Structure |
|---|---|
| 4 | 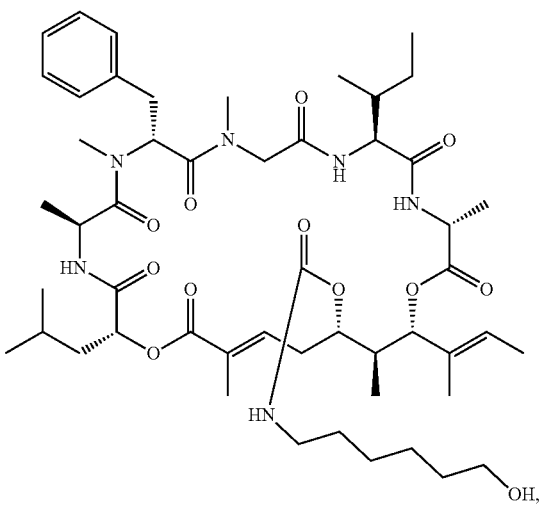 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCCCCO)[C@@H]1C] |
| 5 | 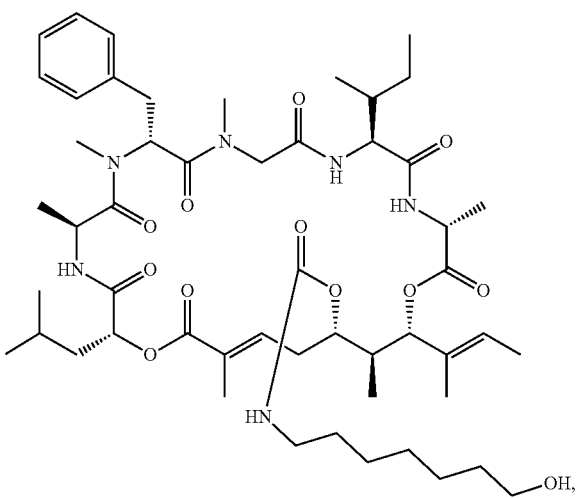 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCCCCCO)[C@@H]1C] |
| 6 | 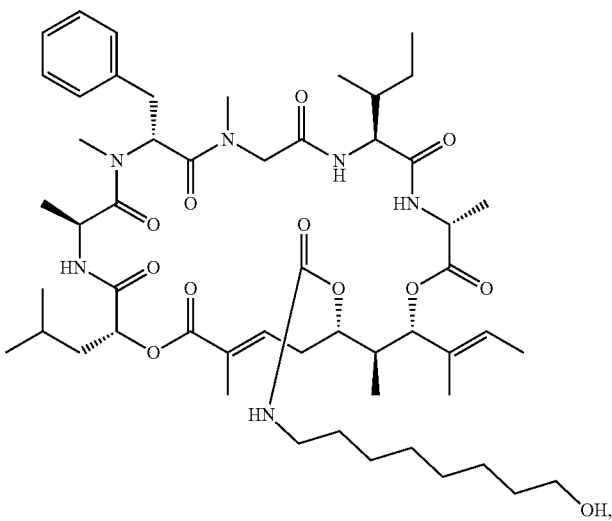 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCCCCCCO)[C@@H]1C] |

-continued
| Compound No. | Structure |
|---|---|
| 8 | 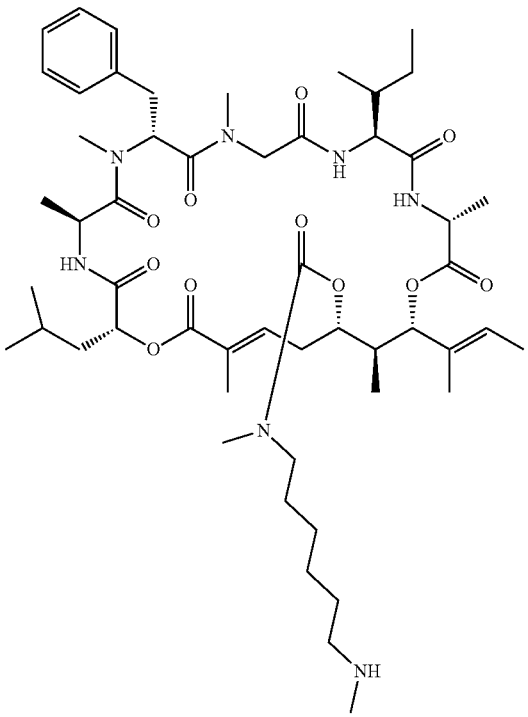 |
| 9 | 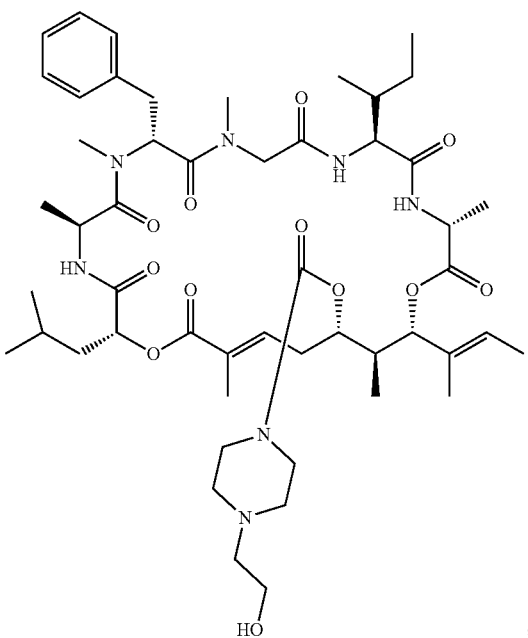 |

-continued
| Compound No. | Structure |
|---|---|
| 10 | 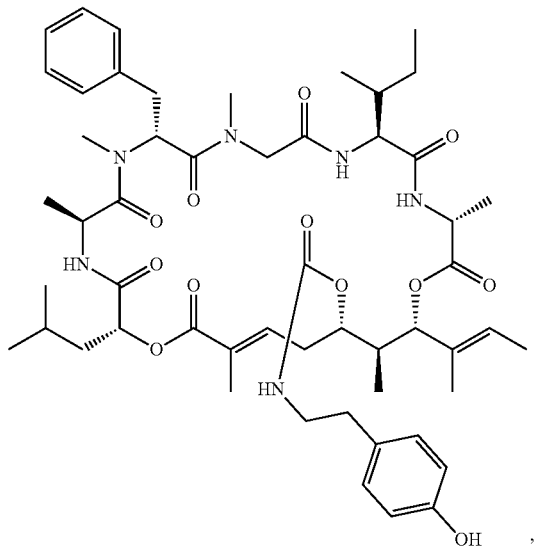 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCc2ccc(O)cc2)[C@@H]1C] |
| 11 | 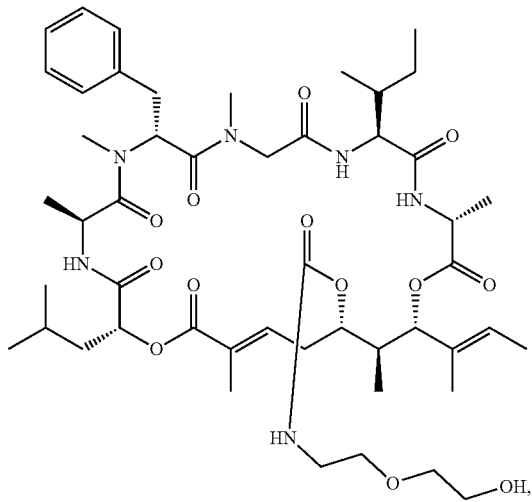 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCOCCO)[C@@H]1C] |

| Compound No. | Structure |
|---|---|
| 12 | 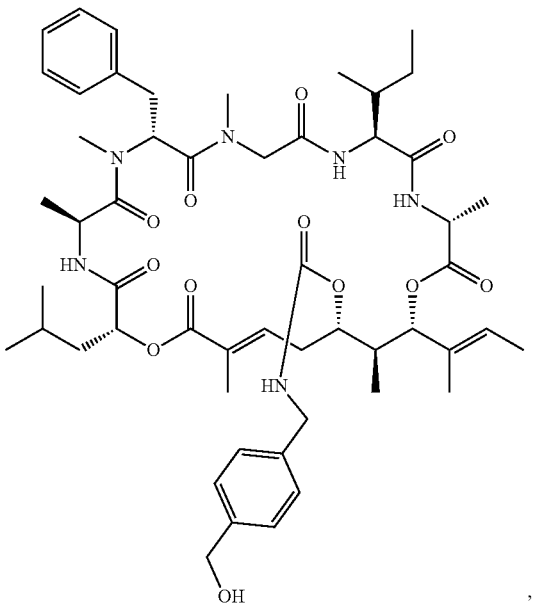 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCc2ccc(CO)cc2)[C@@H]1C] |
| 13 | 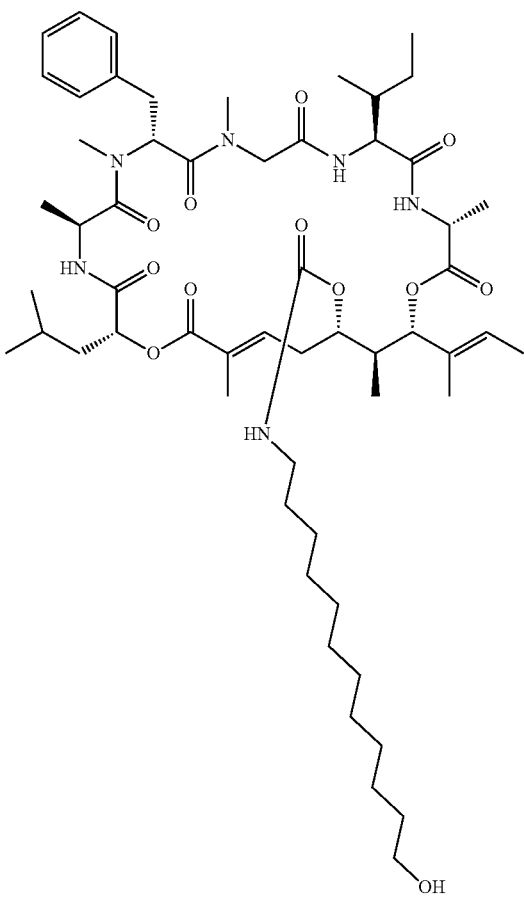 |

| Compound No. | Structure |
|---|---|
| 16 | 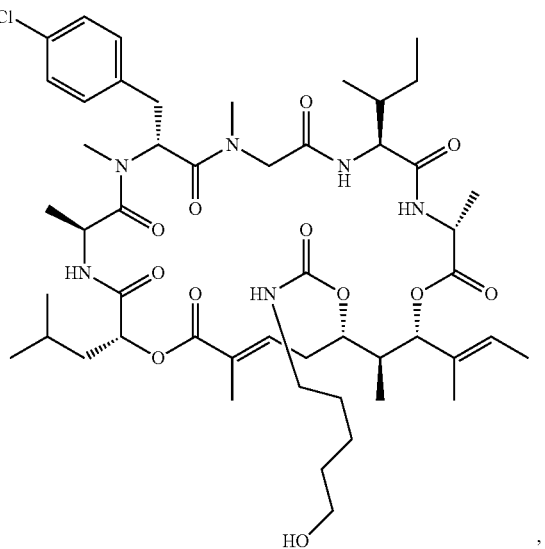 |
| 18 | 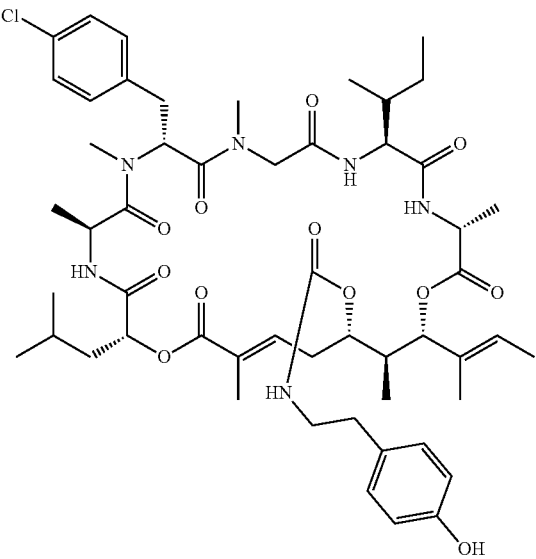 |

-continued
| Compound No. | Structure |
|---|---|
| 19 | 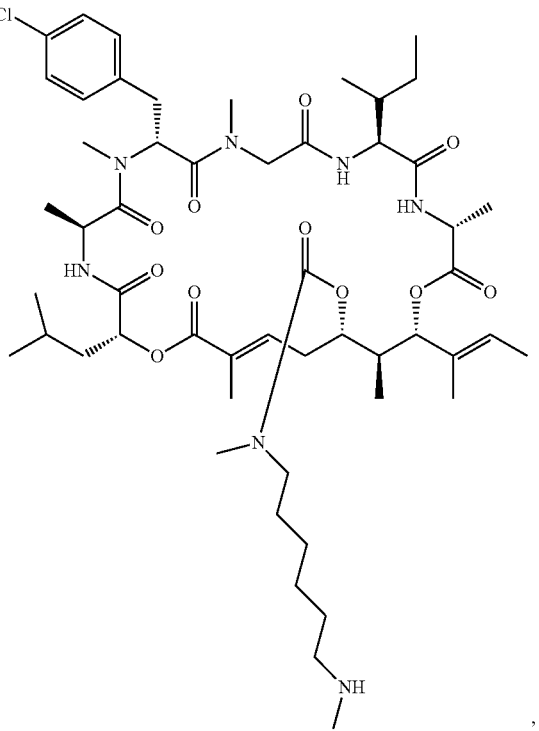 |
| 20 | 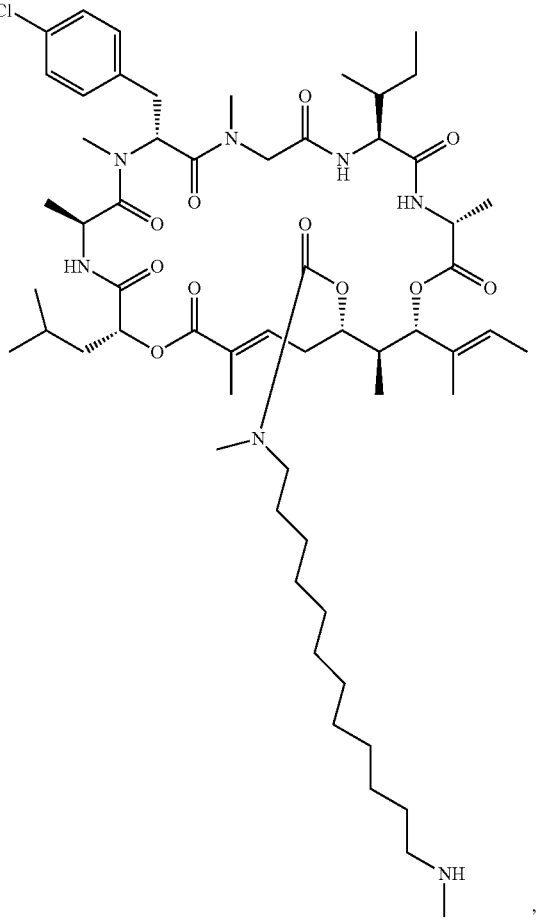 |

| Compound No. | Structure |
|---|---|
| 22 | 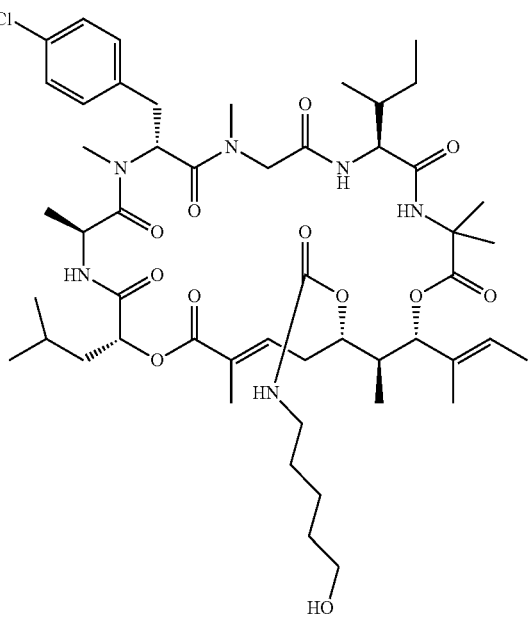 |
| 23 | 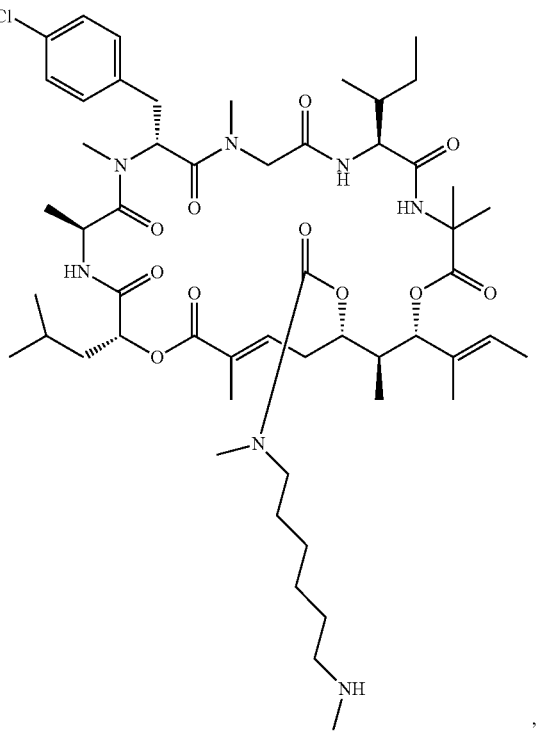 |

| Compound No. | Structure |
|---|---|
| 24 | 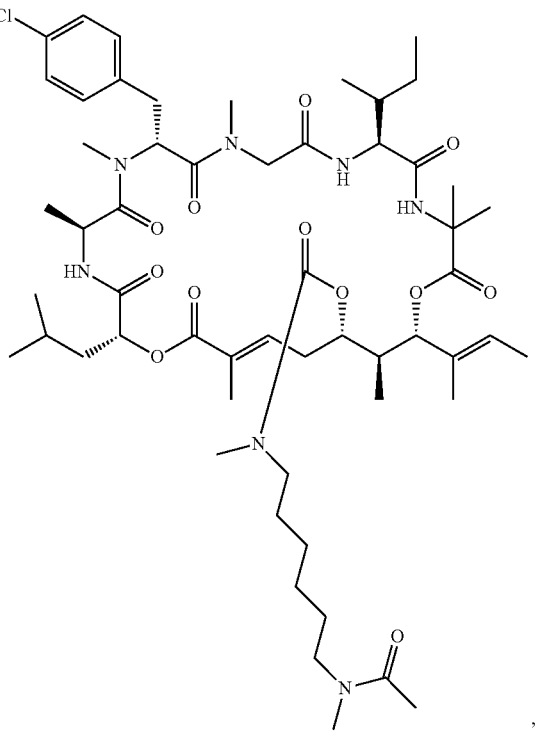 |
| 26 | 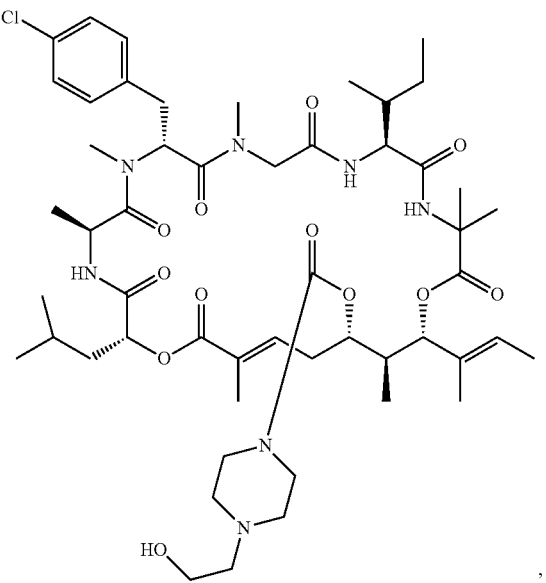, and |

| Compound No. | Structure |
|---|---|
| 29 | 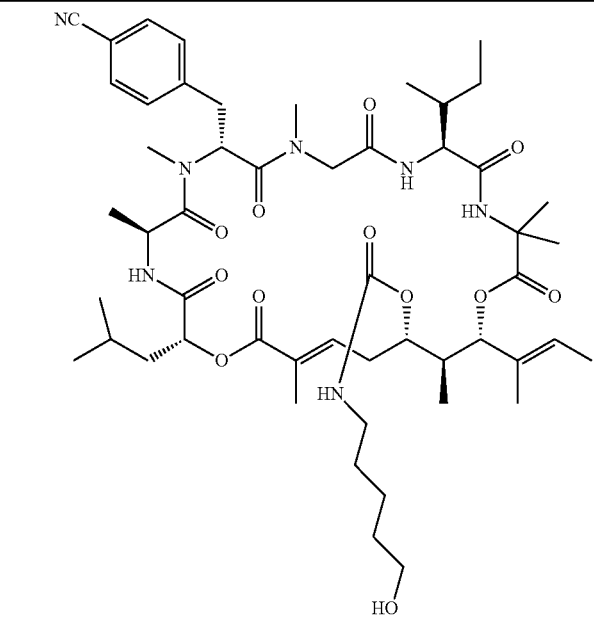 |
28. A kit comprising a compound of claim 1, or a pharmaceutically acceptable salt thereof, and instructions for use in treatment of breast cancer in an individual in need thereof, wherein the compound is selected from the group consisting of:
| Compound No. | Structure |
|---|---|
| 1 | 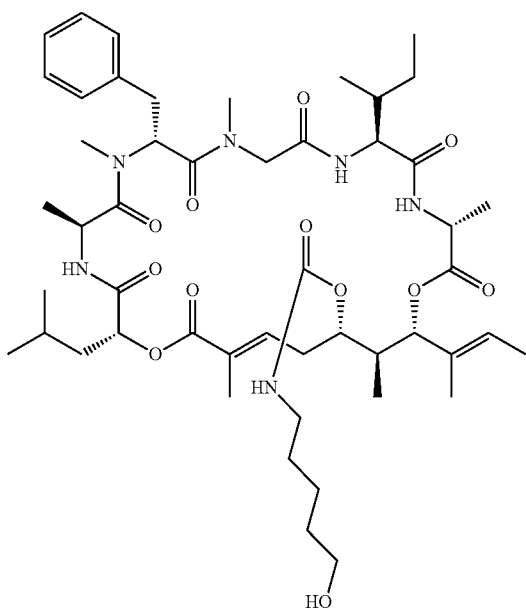 |

| Compound No. | Structure |
|---|---|
| 2 | 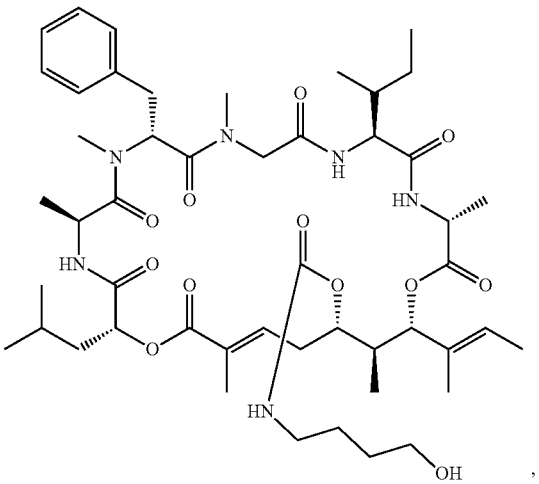 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCCO)[C@@H]1C] |
| 3 | 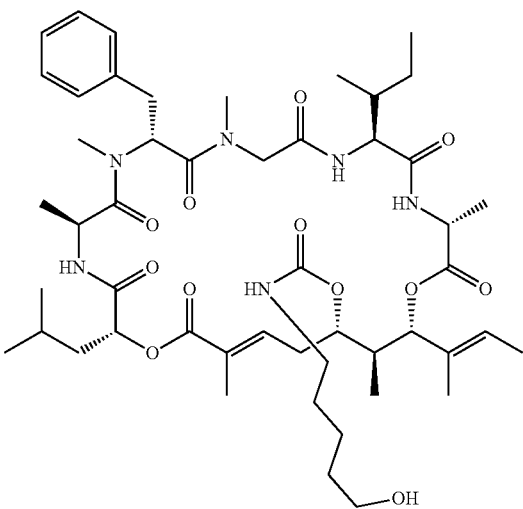 |
| 4 | 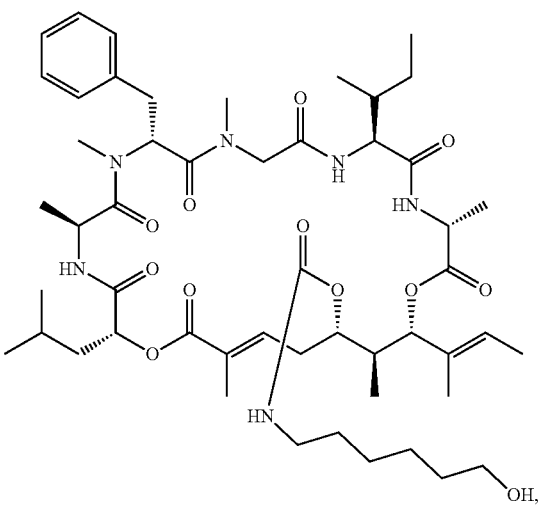 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCCCCO)[C@@H]1C] |

| Compound No. | Structure |
|---|---|
| 5 | 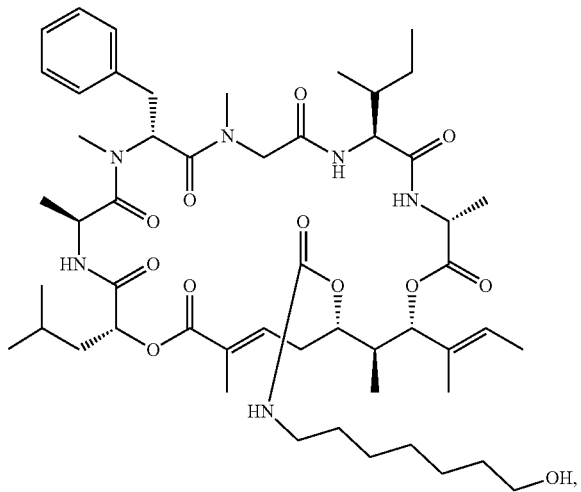 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCCCCCO)[C@@H]1C] |
| 6 | 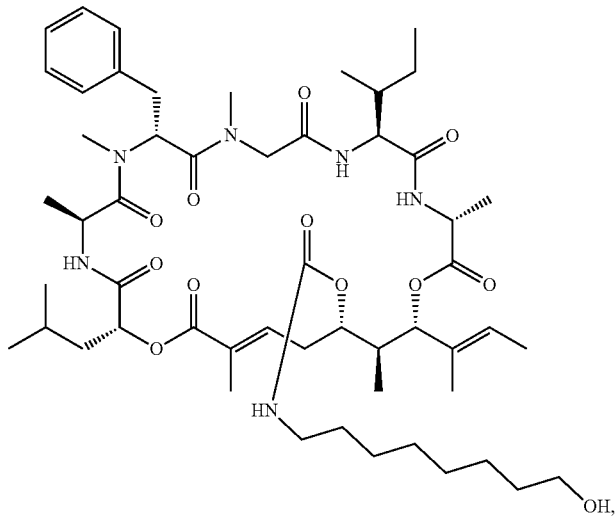 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCCCCCCCO)[C@@H]1C] |

-continued
| Compound No. | Structure |
|---|---|
| 8 | 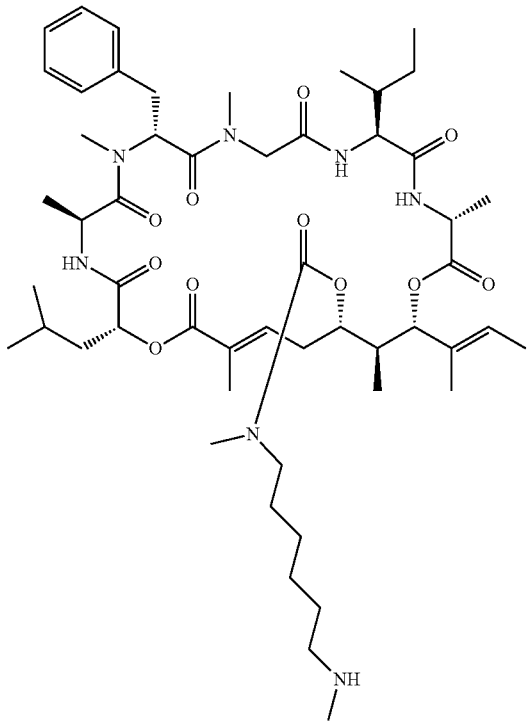 |
| 9 | 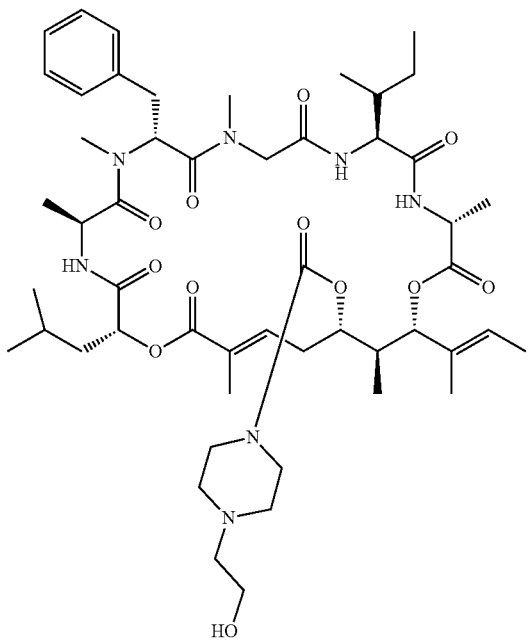 |

| Compound No. | Structure |
|---|---|
| 10 | 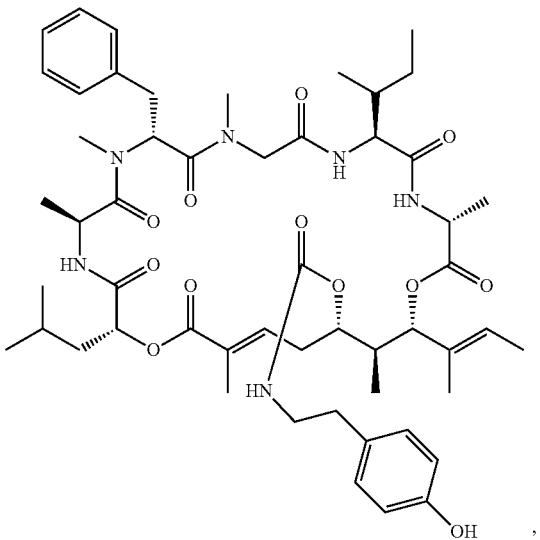 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCc2ccc(O)cc2)[C@@H]1C] |
| 11 | 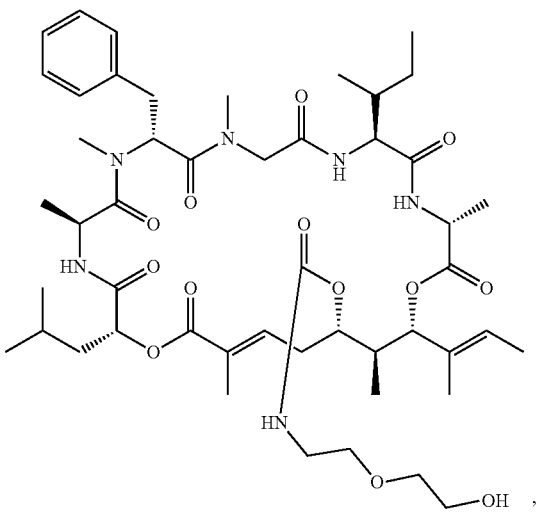 [SMILES: C/C=C(\C)[C@H]1OC(=O)[C@@H](C)NC(=O)[C@H](C(C)CC)NC(=O)CN(C)C(=O)[C@@H](Cc2ccccc2)N(C)C(=O)[C@H](C)NC(=O)[C@@H](CC(C)C)OC(=O)/C(C)=C/C[C@H](OC(=O)NCCOCCO)[C@@H]1C] |

| Compound No. | Structure |
|---|---|
| 12 | 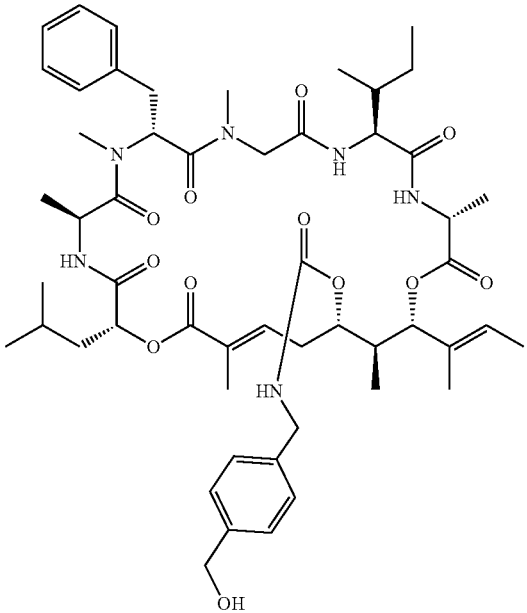 |
| 13 | 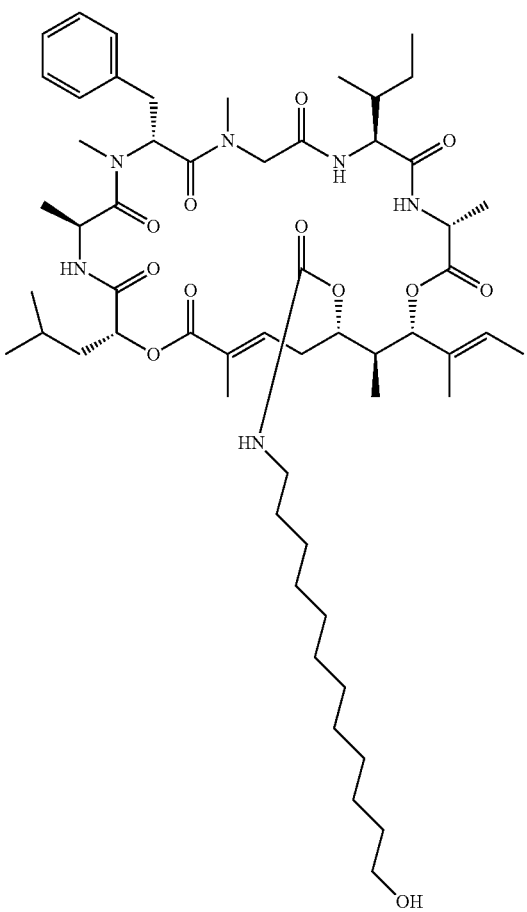 |

-continued
| Compound No. | Structure |
|---|---|
| 16 | 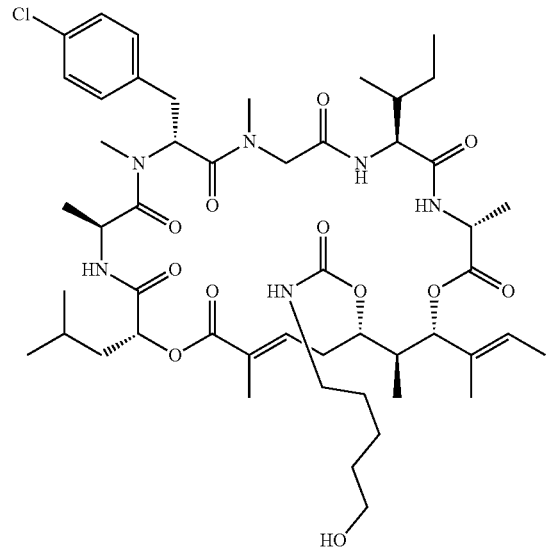 |
| 18 | 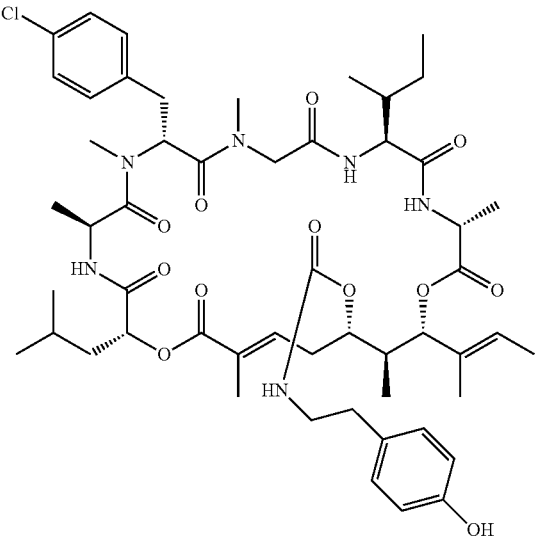 |

-continued
| Compound No. | Structure |
|---|---|
| 19 | 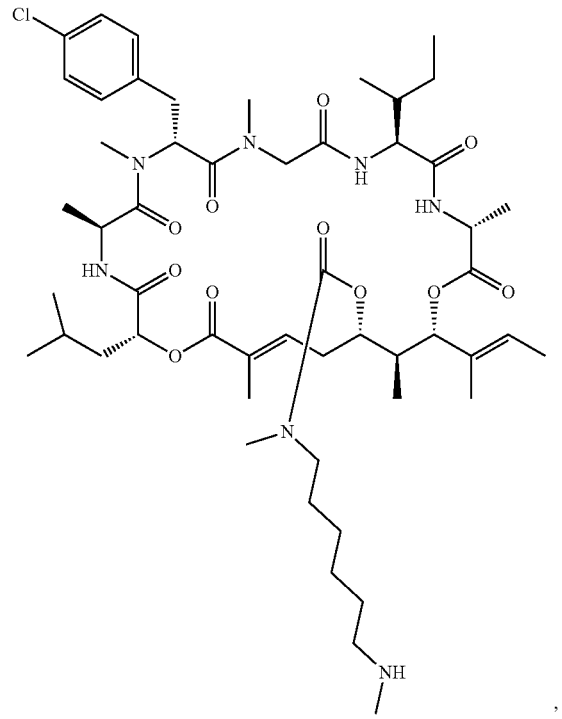 [SMILES: C/C=C(\C)[C@H]1OC(=O)[C@@H](C)NC(=O)[C@H](C(C)CC)NC(=O)CN(C)C(=O)[C@@H](Cc2ccc(Cl)cc2)N(C)C(=O)[C@H](C)NC(=O)[C@@H](CC(C)C)OC(=O)/C(C)=C/C[C@H](OC(=O)N(C)CCCCCCNC)[C@@H]1C] |
| 20 | 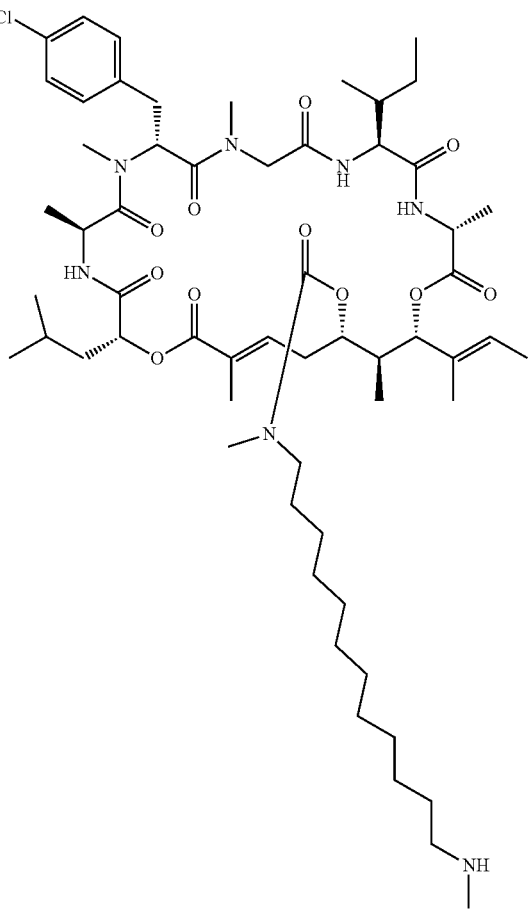 |

-continued
| Compound No. | Structure |
|---|---|
| 22 | 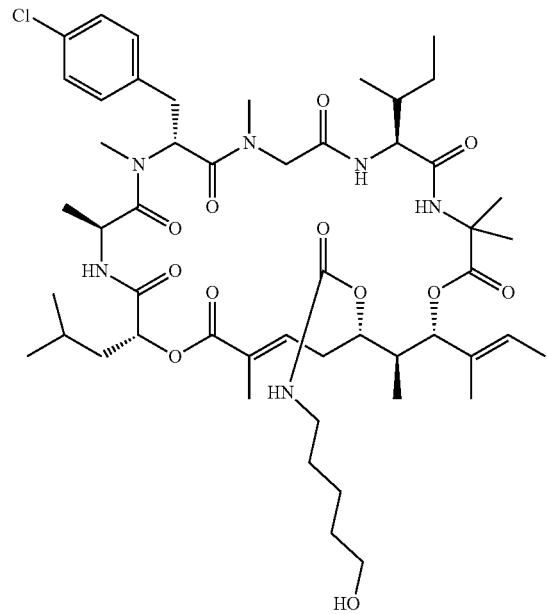 |
| 23 | 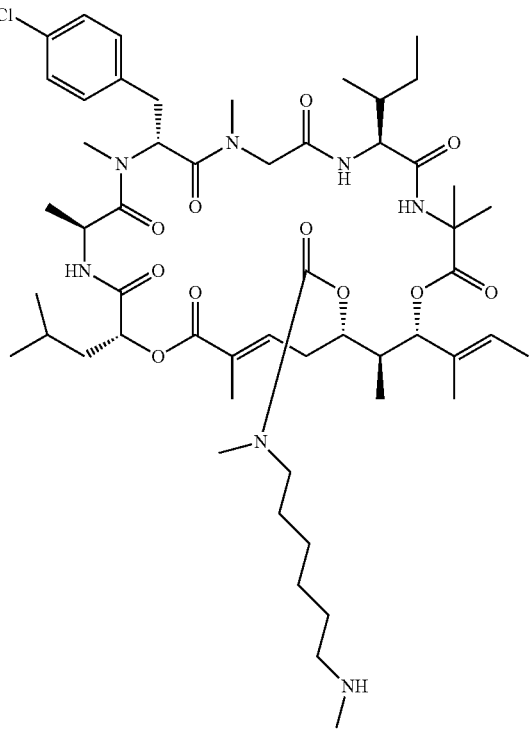 |

-continued
| Compound No. | Structure |
|---|---|
| 24 | 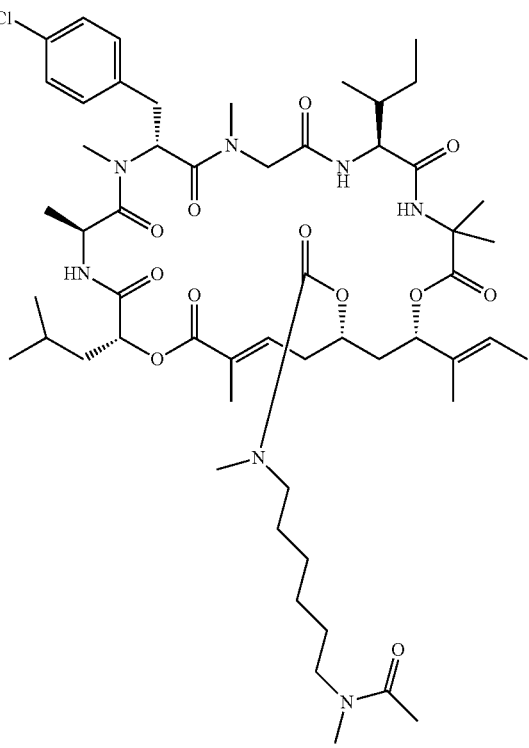 |
| 26 | 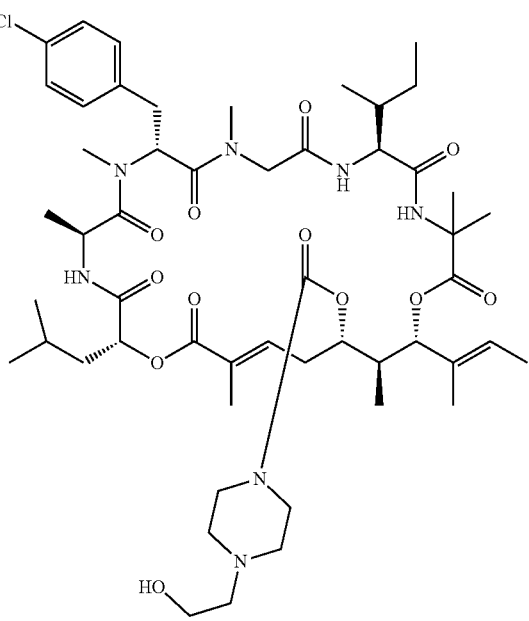, and |

-continued
| Compound No. | Structure |
|---|---|
| 29 | 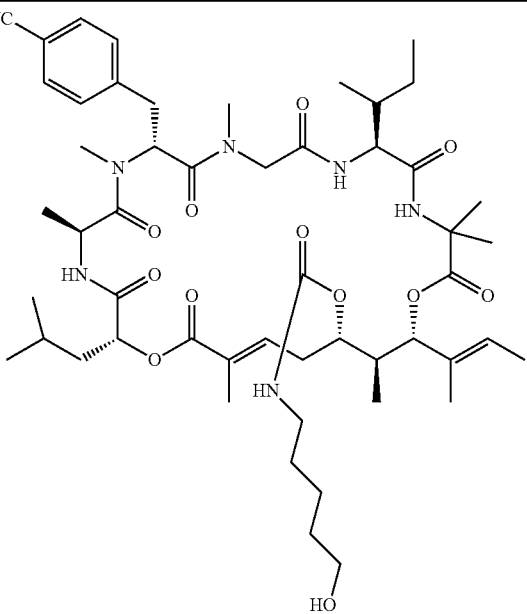 |
29. A pharmaceutical composition comprising a compound of claim 19, or a pharmaceutically acceptable salt thereof, and a pharmaceutically acceptable carrier.
* * * * *